US009066963B2

(12) United States Patent
Perou et al.

(10) Patent No.: US 9,066,963 B2
(45) Date of Patent: Jun. 30, 2015

(54) METHODS OF TREATING BREAST CANCER WITH ANTHRACYCLINE THERAPY

(75) Inventors: Charles M. Perou, Carrboro, NC (US); Matthew J. Ellis, St. Louis, MO (US); Philip S. Bernard, Salt Lake City, UT (US); Torsten O. Nielsen, North Vancouver (CA)

(73) Assignees: The University of North Carolina at Chapel Hill, Chapel Hill, NC (US); Washington University, St. Louis, MO (US); University of Utah Research Foundation, Salt Lake City, UT (US); British Columbia Cancer Agency Branch, Vancouver, British Columbia (CA)

( * ) Notice: Subject to any disclaimer, the term of this patent is extended or adjusted under 35 U.S.C. 154(b) by 0 days.

(21) Appl. No.: 13/421,367

(22) Filed: Mar. 15, 2012

(65) Prior Publication Data

US 2013/0004482 A1 Jan. 3, 2013

Related U.S. Application Data

(60) Provisional application No. 61/453,035, filed on Mar. 15, 2011.

(51) Int. Cl.

| | |
|---|---|
| ***A61K 31/704*** | (2006.01) |
| ***A61K 31/7042*** | (2006.01) |
| ***A61K 45/06*** | (2006.01) |
| ***A61K 31/513*** | (2006.01) |
| ***A61K 31/675*** | (2006.01) |
| ***C12Q 1/68*** | (2006.01) |

(52) U.S. Cl.
CPC ........... *A61K 31/704* (2013.01); *A61K 31/7042* (2013.01); *A61K 45/06* (2013.01); *A61K 31/513* (2013.01); *A61K 31/675* (2013.01); *C12Q 1/6886* (2013.01); *C12Q 2600/106* (2013.01)

(58) Field of Classification Search
None
See application file for complete search history.

(56) References Cited

U.S. PATENT DOCUMENTS

| | | | | |
|---|---|---|---|---|
| 2009/0299640 | A1 | 12/2009 | Ellis et al. | |
| 2011/0145176 | A1* | 6/2011 | Perou et al. | 706/12 |
| 2013/0337444 | A1 | 12/2013 | Ferree et al. | |
| 2013/0345161 | A1 | 12/2013 | Perou et al. | |
| 2014/0037620 | A1 | 2/2014 | Ferree et al. | |

OTHER PUBLICATIONS

Parker et al I (J of Clinical Oncology, 2009, 27:1160-1167).*
Figure A3 of Parker et al I (J of Clinical Oncology, 2009, 27:1160-1167).*
Parker et al II (Cancer Research, 2009, 69:Supp 3; abstract 2019).*
Parker et al III (Poster at 2009 San Antonio Breast Cancer Symposium, #2019).*
Pritchard et al (New England J medicine, 2006, 354:2103-2111).*
Gennari et al (Journal of National Cancer Institute, 2008, 100:14-20).*
Arriola, E. et al.: "Topoisomerase II alpha amplification may predict benefit from adjuvant anthracyclines in HER2 positive early breast cancer", Breast Cancer Res. Treat., vol. 106, No. 2, Jan. 27, 2007, pp. 181-189.

* cited by examiner

*Primary Examiner* — Laura B Goddard
(74) *Attorney, Agent, or Firm* — Cooley LLP; Ivor R. Elrifi; Matthew Pavao

(57) ABSTRACT

The application describes methods for screening subjects with breast cancer to determine if the breast cancer will be responsive to a breast cancer therapy including an anthracycline. The application also describes methods for treating subjects with breast cancer by screening them for the likelihood of the effectiveness of treating the cancer with a therapy including anthracycline and administering the therapy in subjects when it is found that anthracycline is likely to be effective.

12 Claims, 12 Drawing Sheets

SEQUENCE LISTING

```
<160> NUMBER OF SEQ ID NOS: 139

<210> SEQ ID NO 1
<211> LENGTH: 19
<212> TYPE: DNA
<213> ORGANISM: Artificial sequence
<220> FEATURE:
<223> OTHER INFORMATION: Chemically synthesized primer

<400> SEQUENCE: 1

aaagattcct gggacctga                                                19


<210> SEQ ID NO 2
<211> LENGTH: 21
<212> TYPE: DNA
<213> ORGANISM: Artificial sequence
<220> FEATURE:
<223> OTHER INFORMATION: Chemically synthesized primer

<400> SEQUENCE: 2

acagccactt tcagaagcaa g                                             21


<210> SEQ ID NO 3
<211> LENGTH: 22
<212> TYPE: DNA
<213> ORGANISM: Artificial sequence
<220> FEATURE:
<223> OTHER INFORMATION: Chemically synthesized primer

<400> SEQUENCE: 3

ctggaagagt tgaataaaga gc                                            22


<210> SEQ ID NO 4
<211> LENGTH: 18
<212> TYPE: DNA
<213> ORGANISM: Artificial sequence
<220> FEATURE:
<223> OTHER INFORMATION: Chemically synthesized primer

<400> SEQUENCE: 4

tacctgaacc ggcacctg                                                 18


<210> SEQ ID NO 5
<211> LENGTH: 17
```

<212> TYPE: DNA
<213> ORGANISM: Artificial Sequence
<220> FEATURE:
<223> OTHER INFORMATION: Chemically synthesized primer

<400> SEQUENCE: 5
gctggctgag cagaaag 17

<210> SEQ ID NO 6
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 6
ggccaaaatc gacaggac 18

<210> SEQ ID NO 7
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 7
ctgtctgagt gccgtggat 19

<210> SEQ ID NO 8
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 8
gtaaatcacc ttctgagcct 20

<210> SEQ ID NO 9
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 9
ggaggcggaa gaaaccag 18

<210> SEQ ID NO 10
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 10
gacaaggaga atcaaaagat cagc 24

<210> SEQ ID NO 11
<211> LENGTH: 17
<212> TYPE: DNA
<213> ORGANISM: Artificial sequence
<220> FEATURE:
<223> OTHER INFORMATION: Chemically synthesized primer

<400> SEQUENCE: 11
gtggcagcag atcacaa 17

<210> SEQ ID NO 12
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 12
cctcacgaat tgctgaactt 20

<210> SEQ ID NO 13
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 13
catgaaatag tgcatagttt gcc 23

<210> SEQ ID NO 14
<211> LENGTH: 25
<212> TYPE: DNA
<213> ORGANISM: Artificial Sequence
<220> FEATURE:
<223> OTHER INFORMATION: Chemically synthesized primer

<400> SEQUENCE: 14
acacagaatc tatacccacc agagt 25

<210> SEQ ID NO 15
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 15
gctggctctc acactgatag 20

<210> SEQ ID NO 16
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 16
gcagggagag gagtttgt 18

<210> SEQ ID NO 17
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 17
cccatccatg tgaggaagta taa 23

<210> SEQ ID NO 18
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 18
cttcttggac cttggcg 17

<210> SEQ ID NO 19
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 19
gctactacgc agacacg 17

<210> SEQ ID NO 20
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 20
gatgttcgag tcacagagg 19

<210> SEQ ID NO 21
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 21
ttcggctgga aggaacc 17

<210> SEQ ID NO 22
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 22
ggagatccgt caactccaaa 20

<210> SEQ ID NO 23
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 23
tgggtcgtgt caggaaac 18

<210> SEQ ID NO 24
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 24
cgcagtcatc cagagatgtg 20

-continued

<210> SEQ ID NO 25
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 25
actcagtaca agaaagaacc g 21

<210> SEQ ID NO 26
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 26
gttggaccag tcaacatctc tg 22

<210> SEQ ID NO 27
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 27
tgtggctcat taggcaac 18

<210> SEQ ID NO 28
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 28
gactccaagc gcgaaaac 18

<210> SEQ ID NO 29
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 29
ccacaaaata ttcatggttc ttg 23

<210> SEQ ID NO 30
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 30
ccagtagcat tgtccgag 18

<210> SEQ ID NO 31
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 31
gtctctggta atgcacact 19

<210> SEQ ID NO 32
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 32
gtggaatgcc tgctgacc 18

<210> SEQ ID NO 33
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 33
aggggtgccc tctgagat 18

<210> SEQ ID NO 34
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 34
cgagatcgcc aagatgtt 18

<210> SEQ ID NO 35
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 35
agcctcgaac aattgaaga 19

<210> SEQ ID NO 36
<211> LENGTH: 27
<212> TYPE: DNA
<213> ORGANISM: Artificial Sequence
<220> FEATURE:
<223> OTHER INFORMATION: Chemically synthesized primer

<400> SEQUENCE: 36
atcgactgtg taaacaacta gagaaga 27

<210> SEQ ID NO 37
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 37
tttaagaggg caatggaagg 20

<210> SEQ ID NO 38

<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 38
tgccgcagaa ctcacttg 18

<210> SEQ ID NO 39
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 39
cctcagatga tgcctatcca 20

<210> SEQ ID NO 40
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 40
cagcaagcga tggcatagt 19

<210> SEQ ID NO 41
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 41
aatgccaccg aagcctc 17

<210> SEQ ID NO 42
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 42
tcgaactgaa ggctatttac gag 23

<210> SEQ ID NO 43
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 43
gtcgaagccg caattagg 18

<210> SEQ ID NO 44
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 44
caaacgtgtg ttctggagg 19

<210> SEQ ID NO 45
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 45
tgccctgtat gatgtcagga 20

<210> SEQ ID NO 46
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 46
gtgaggggtg tcagctcagt 20

<210> SEQ ID NO 47
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 47
tggggcagtt ctgtattact tc 22

<210> SEQ ID NO 48
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 48
cgatggtttt gtacaagatt tctc 24

<210> SEQ ID NO 49
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 49
gcaaatcctt gggcaga 17

<210> SEQ ID NO 50
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 50
gccgtacagt tccacaaagg 20

<210> SEQ ID NO 51
<211> LENGTH: 22
<212> TYPE: DNA

<213> ORGANISM: Artificial Sequence
<220> FEATURE:
<223> OTHER INFORMATION: Chemically synthesized primer

<400> SEQUENCE: 51
ttcctccatc aagagttcaa ca 22

<210> SEQ ID NO 52
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 52
gggtctgcac agactgcat 19

<210> SEQ ID NO 53
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 53
tccttgtaat ggggagacca 20

<210> SEQ ID NO 54
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 54
acttgggata tgtgaataag acc 23

<210> SEQ ID NO 55
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 55
ggggaaagac aaagtttcca 20

<210> SEQ ID NO 56
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 56
actgtctggg tccatggcta 20

<210> SEQ ID NO 57
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 57
ggatttcgtg gtgggttc 18

<210> SEQ ID NO 58
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 58
ccacagtctg tgataaacgg 20

<210> SEQ ID NO 59
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 59
ccatcaacat tctctttatg aacg 24

<210> SEQ ID NO 60
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 60
atcaactccc aaacggtcac 20

<210> SEQ ID NO 61
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 61
gcccttacac atcggagaac 20

<210> SEQ ID NO 62
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 62
gacttcaggg tgctggac 18

<210> SEQ ID NO 63
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 63
tgtgaagcca gcaatatgta tc 22

<210> SEQ ID NO 64
<211> LENGTH: 21
<212> TYPE: DNA
<213> ORGANISM: Artificial Sequence
<220> FEATURE:

<223> OTHER INFORMATION: Chemically synthesized primer

<400> SEQUENCE: 64
tattgggagg caggaggttt a 21

<210> SEQ ID NO 65
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 65
ctgagttcat gttgctgacc 20

<210> SEQ ID NO 66
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 66
gacagctact attcccgtt 19

<210> SEQ ID NO 67
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 67
tatgtgagta agctcggaga c 21

<210> SEQ ID NO 68
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 68
agtggacatg cgagtggag 19

<210> SEQ ID NO 69
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 69
caccgctgga aactgaac 18

<210> SEQ ID NO 70
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 70
cgtgcacatc catgacctt 19

<210> SEQ ID NO 71
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 71
gaggagatga ccttgcc 17

<210> SEQ ID NO 72
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 72
gccatagcca ctgccact 18

<210> SEQ ID NO 73
<211> LENGTH: 17
<212> TYPE: DNA
<213> ORGANISM: Artificial Sequence
<220> FEATURE:
<223> OTHER INFORMATION: Chemically synthesized primer

<400> SEQUENCE: 73
cttcgactgg actctgt 17

<210> SEQ ID NO 74
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 74
cagacatgtt ggtattgcac att 23

<210> SEQ ID NO 75
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 75
aggcgatcct gggaaattat 20

<210> SEQ ID NO 76
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 76
cccatttgtc tgtcttcac 19

<210> SEQ ID NO 77
<211> LENGTH: 18
<212> TYPE: DNA
<213> ORGANISM: Artificial Sequence
<220> FEATURE:
<223> OTHER INFORMATION: Chemically synthesized primer

<400> SEQUENCE: 77
ctgatggttg aggctgtt 18

<210> SEQ ID NO 78
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 78
cgcactccag cacctagac 19

<210> SEQ ID NO 79
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 79
tcacagggtc aaacttccag t 21

<210> SEQ ID NO 80
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 80
gatggtagag ttccagtgat t 21

<210> SEQ ID NO 81
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 81
acacagatga tggagatgtc 20

<210> SEQ ID NO 82
<211> LENGTH: 25
<212> TYPE: DNA
<213> ORGANISM: Artificial Sequence
<220> FEATURE:
<223> OTHER INFORMATION: Chemically synthesized primer

<400> SEQUENCE: 82
agtagctaca tctccaggtt ctctg 25

<210> SEQ ID NO 83
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 83
cggattttat caacgatgca g 21

<210> SEQ ID NO 84
<211> LENGTH: 19

```
<212> TYPE: DNA
<213> ORGANISM: Artificial Sequence
<220> FEATURE:
<223> OTHER INFORMATION: Chemically synthesized primer

<400> SEQUENCE: 84

catttgccgt ccttcatcg                                                   19


<210> SEQ ID NO 85
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 85

gcaggtcaaa actctcaaag                                                  20


<210> SEQ ID NO 86
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 86

agcgggcttc tgtaatctga                                                  20


<210> SEQ ID NO 87
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 87

gcctcagatt tcaactcgt                                                   19


<210> SEQ ID NO 88
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 88

ctgctgagaa tcaaagtggg a                                                21


<210> SEQ ID NO 89
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 89

ggaacaaact gctctgcca                                                   19


<210> SEQ ID NO 90
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 90
```

-continued

```
acagctcttt agcatttgtg ga                                              22


<210> SEQ ID NO 91
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 91

gggactatca atgttgggtt ctc                                             23


<210> SEQ ID NO 92
<211> LENGTH: 21
<212> TYPE: DNA
<213> ORGANISM: Artificial Sequence
<220> FEATURE:
<223> OTHER INFORMATION: chemically synthesized primer

<400> SEQUENCE: 92

cacacagttc actgctccac a                                               21


<210> SEQ ID NO 93
<211> LENGTH: 2199
<212> TYPE: DNA
<213> ORGANISM: Homo sapiens

<400> SEQUENCE: 93

cagcggcgct gcggcggctc gcgggagacg ctgcgcgcgg ggctagcggg cggcggagcg      60

gacggcgacg gggcgctctc gggctgccgg cggggccgag cgccgcgcgt cccgagcatg     120

gcaggctccc tgcctccctg cgtggtggac tgtggcaccg ggtataccaa gcttggctac     180

gcaggcaaca ctgagcccca gttcattatt ccttcatgta ttgccatcag agagtcagca     240

aaggtagttg accaagctca aaggagagtg ttgaggggag ttgatgacct tgactttttc     300

ataggagatg aagccatcga taaacctaca tatgctacaa agtggccgat acgacatgga     360

atcattgaag actgggatct tatggaaagg ttcatggagc aagtggtttt taaatatctt     420

cgagctgaac ctgaggacca ttattttta atgacagaac ctccactcaa tacaccagaa     480

aacagagagt atcttgcaga aattatgttt gaatcattta acgtaccagg actctacatt     540

gcagttcagg cagtgctggc cttggcggca tcttggacat ctcgacaagt gggtgaacgt     600

acgttaacgg ggatagtcat tgacagcgga gatggagtca cccatgttat cccagtggca     660

gaaggttatg taattggaag ctgcatcaaa cacatcccga ttgcaggtag agatattacg     720

tatttcattc aacagctgct aagggagagg gaggtgggaa tccctcctga gcagtcactg     780

gagaccgcaa aagccattaa ggagaaatac tgttacattt gccccgatat agtcaaggaa     840

tttgccaagt atgatgtgga tccccggaag tggatcaaac agtacacggg tatcaatgcg     900

atcaaccaga agaagtttgt tatagacgtt ggttacgaaa gattcctggg acctgaaata     960

ttctttcacc cggagtttgc caacccagac tttatggagt ccatctcaga tgttgttgat    1020

gaagtaatac agaactgccc catcgatgtg cggcgcccgc tgtataagaa tgtcgtactc    1080

tcaggaggct ccaccatgtt cagggatttc ggacgccgac tgcagaggga tttgaagaga    1140

gtggtggatg ctaggctgag gctcagcgag gagctcagcg gcgggaggat caagccgaag    1200

cctgtggagg tccaggtggt cacgcatcac atgcagcgct acgccgtgtg gttcggaggc    1260

tccatgctgg cctcgactcc cgagttcttt caggtctgcc acaccaagaa ggactatgaa    1320

gagtacgggc ccagcatctg ccgccacaac cccgtctttg gagtcatgtc ctagtgtctg    1380
```

-continued cctgaacgcg tcgttcgatg gtgtcacgtt ggggaacaag tgtccttcag aacccagaga 1440
aggccgccgt tctgtaaata gcgacgtcgg tgttgctgcc cagcagcgtg cttgcattgc 1500
cggtgcatga ggcgcggcgc gggcccttca gtaaaagcca tttatccgtg tgccgaccgc 1560
tgtctgccag cctcctcctt ctcccgccct cctcaccctc gctctccctc ctcctcctcc 1620
tccgagctgc tagctgacaa atacaattct gaaggaatcc aaatgtgact ttgaaaattg 1680
ttagagaaaa caacattaga aaatggcgca aaatcgttag gtcccaggag agaatgtggg 1740
ggcgcaaacc cttttcctcc cagcctattt ttgtaaataa aatgtttaaa cttgaaatac 1800
aaatcgatgt ttatatttcc tatcattttg tattttatgg tatttggtac aactggctga 1860
tactaagcac gaatagatat tgatgttatg gagtgctgta atccaaagtt tttaattgtg 1920
aggcatgttc tgatatgttt ataggcaaac aaataaaaca gcaaactttt ttgccacatg 1980
tttgctagaa aatgattata ctttattgga gtgacatgaa gtttgaacac taaacagtaa 2040
tgtatgagaa ttactacaga tacatgtatc ttttagtttt ttttgtttga actttctgga 2100
gctgttttat agaagatgat ggtttgttgt cggtgagtgt tggatgaaat acttccttgc 2160
accattgtaa taaaagctgt tagaatattt gtaaatatc 2199

<210> SEQ ID NO 94
<211> LENGTH: 1989
<212> TYPE: DNA
<213> ORGANISM: Homo sapiens

<400> SEQUENCE: 94
cagcggcgct gcggcggctc gcgggagacg ctgcgcgcgg ggctagcggg cggcggagcg 60
gacggcgacg gggcgctctc gggctgccgg cggggccgag cgccgcgcgt cccgagcatg 120
gcaggctccc tgcctccctg cgtggtggac tgtggcaccg ggtataccaa gcttggctac 180
gcaggcaaca ctgagcccca gttcattatt ccttcatgta ttgccatcag agagtcagca 240
aaggtagttg accaagctca aaggagagtg ttgaggggag ttgatgacct tgactttttc 300
ataggagatg aagccatcga taaacctaca tatgctacaa agtggccgat acgacatgga 360
atcattgaag actgggatct tatggaaagg ttcatggagc aagtggtttt taaatatctt 420
cgagctgaac ctgaggacca ttattttta atgacagaac ctccactcaa tacaccagaa 480
aacagagagt atcttgcaga aattatgttt gaatcattta acgtaccagg actctacatt 540
gcagttcagg cagtgctggc cttggcggca tcttggacat ctcgacaagt gggtgaacgt 600
acgttaacgg ggatagtcat tgacagcgga gatggagtca cccatgttat cccagtggca 660
gaaggttatg taattggaag ctgcatcaaa cacatcccga ttgcaggtag agatattacg 720
tatttcattc aacagctgct aagggagagg gaggtgggaa tccctcctga gcagtcactg 780
gagaccgcaa aagccattaa ggagaaatac tgttacattt gccccgatat agtcaaggaa 840
tttgccaagt atgatgtgga tccccggaag tggatcaaac agtacacggg tatcaatgcg 900
atcaaccaga agaagtttgt tatagacgtt ggttacgaaa gattcctggg acctgaaata 960
ttctttcacc cggagtttgc caacccagac tttatggagt ccatctcaga tgttgttgat 1020
gaagtaatac agaactgccc catcgatgtg cggcgcccgc tgtataagcc cgagttcttt 1080
caggtctgcc acaccaagaa ggactatgaa gagtacgggc ccagcatctg ccgccacaac 1140
cccgtctttg gagtcatgtc ctagtgtctg cctgaacgcg tcgttcgatg gtgtcacgtt 1200
ggggaacaag tgtccttcag aacccagaga aggccgccgt tctgtaaata gcgacgtcgg 1260

```
tgttgctgcc cagcagcgtg cttgcattgc cggtgcatga ggcgcggcgc gggcccttca   1320

gtaaaagcca tttatccgtg tgccgaccgc tgtctgccag cctcctcctt ctcccgccct   1380

cctcaccctc gctctccctc ctcctcctcc tccgagctgc tagctgacaa atacaattct   1440

gaaggaatcc aaatgtgact ttgaaaattg ttagagaaaa caacattaga aaatggcgca   1500

aaatcgttag gtcccaggag agaatgtggg ggcgcaaacc cttttcctcc cagcctattt   1560

ttgtaaataa aatgtttaaa cttgaaatac aaatcgatgt ttatatttcc tatcattttg   1620

tattttatgg tatttggtac aactggctga tactaagcac gaatagatat tgatgttatg   1680

gagtgctgta atccaaagtt tttaattgtg aggcatgttc tgatatgttt ataggcaaac   1740

aaataaaaca gcaaactttt ttgccacatg tttgctagaa aatgattata ctttattgga   1800

gtgacatgaa gtttgaacac taaacagtaa tgtatgagaa ttactacaga tacatgtatc   1860

ttttagtttt ttttgtttga actttctgga gctgttttat agaagatgat ggtttgttgt   1920

cggtgagtgt tggatgaaat acttccttgc accattgtaa taaaagctgt tagaatattt   1980

gtaaatatc                                                           1989
```

```
<210> SEQ ID NO 95
<211> LENGTH: 4786
<212> TYPE: DNA
<213> ORGANISM: Homo sapiens

<400> SEQUENCE: 95

ctcggcgctg aaattcaaat ttgaacggct gcagaggccg agtccgtcac tggaagccga     60

gaggagagga cagctggttg tgggagagtt cccccgcctc agactcctgg tttttttccag    120

gagacacact gagctgagac tcacttttct cttcctgaat ttgaaccacc gtttccatcg    180

tctcgtagtc cgacgcctgg ggcgatggat ccgtttacgg agaaactgct ggagcgaacc    240

cgtgccaggc gagagaatct tcagagaaaa atggctgaga ggcccacagc agctccaagg    300

tctatgactc atgctaagcg agctagacag ccactttcag aagcaagtaa ccagcagccc    360

ctctctggtg gtgaagagaa atcttgtaca aaaccatcgc catcaaaaaa acgctgttct    420

gacaacactg aagtagaagt ttctaacttg gaaaataaac aaccagttga gtcgacatct    480

gcaaaatctt gttctccaag tcctgtgtct cctcaggtgc agccacaagc agcagatacc    540

atcagtgatt ctgttgctgt cccggcatca ctgctgggca tgaggagagg gctgaactca    600

agattggaag caactgcagc ctcctcagtt aaaacacgta tgcaaaaact tgcagagcaa    660

cggcgccgtt gggataatga tgatatgaca gatgacattc ctgaaagctc actcttctca    720

ccaatgccat cagaggaaaa ggctgcttcc cctcccagac ctctgctttc aaatgcctcg    780

gcaactccag ttggcagaag ggccgtctg gccaatcttg ctgcaactat ttgctcctgg    840

gaagatgatg taaatcactc atttgcaaaa caaaacagtg tacaagaaca gcctggtacc    900

gcttgtttat ccaaattttc ctctgcaagt ggagcatctg ctaggatcaa tagcagcagt    960

gttaagcagg aagctacatt ctgttcccaa agggatggcg atgcctcttt gaataaagcc   1020

ctatcctcaa gtgctgatga tgcgtctttg gttaatgcct caatttccag ctctgtgaaa   1080

gctacttctc cagtgaaatc tactacatct atcactgatg ctaaaagttg tgagggacaa   1140

aatcctgagc tacttccaaa aactcctatt agtcctctga aaacgggggt atcgaaacca   1200

attgtgaagt caactttatc ccagacagtt ccatccaagg gagaattaag tagagaaatt   1260

tgtctgcaat ctcaatctaa agacaaatct acgacaccag gaggaacagg aattaagcct   1320

ttcctggaac gctttggaga gcgttgtcaa gaacatagca aagaaagtcc agctcgtagc   1380
```

-continued

```
acaccccaca gaaccccat tattactcca aatacaaagg ccatccaaga aagattattc   1440
aagcaagaca catcttcatc tactacccat ttagcacaac agctcaagca ggaacgtcaa   1500
aaagaactag catgtcttcg tggccgattt gacaagggca atatatggag tgcagaaaaa   1560
ggcggaaact caaaaagcaa acaactagaa accaaacagg aaactcactg tcagagcact   1620
cccctcaaaa aacaccaagg tgtttcaaaa actcagtcac ttccagtaac agaaaaggtg   1680
accgaaaacc agataccagc caaaaattct agtacagaac ctaaaggttt cactgaatgc   1740
gaaatgacga aatctagccc tttgaaaata acattgtttt tagaagagga caaatcctta   1800
aaagtaacat cagacccaaa ggttgagcag aaaattgaag tgatacgtga aattgagatg   1860
agtgtggatg atgatgatat caatagttcg aaagtaatta atgacctctt cagtgatgtc   1920
ctagaggaag gtgaactaga tatggagaag agccaagagg agatggatca agcattagca   1980
gaaagcagcg aagaacagga agatgcactg aatatctcct caatgtcttt acttgcacca   2040
ttggcacaaa cagttggtgt ggtaagtcca gagagtttag tgtccacacc tagactggaa   2100
ttgaaagaca ccagcagaag tgatgaaagt ccaaaaccag gaaaattcca aagaactcgt   2160
gtccctcgag ctgaatctgg tgatagcctt ggttctgaag atcgtgatct tctttacagc   2220
attgatgcat atagatctca aagattcaaa gaaacagaac gtccatcaat aaagcaggtg   2280
attgttcgga aggaagatgt tacttcaaaa ctggatgaaa aaaataatgc ctttccttgt   2340
caagttaata tcaaacagaa aatgcaggaa ctcaataacg aaataaatat gcaacagaca   2400
gtgatctatc aagctagcca ggctcttaac tgctgtgttg atgaagaaca tggaaaaggg   2460
tccctagaag aagctgaagc agaaagactt cttctaattg caactgggaa gagaacactt   2520
ttgattgatg aattgaataa attgaagaac gaaggacctc agaggaagaa taaggctagt   2580
ccccaaagtg aatttatgcc atccaaagga tcagttactt tgtcagaaat ccgcttgcct   2640
ctaaaagcag attttgtctg cagtacggtt cagaaaccag atgcagcaaa ttactattac   2700
ttaattatac taaaagcagg agctgaaaat atggtagcca caccattagc aagtacttca   2760
aactctctta acggtgatgc tctgacattc actactacat ttactctgca agatgtatcc   2820
aatgactttg aaataaatat tgaagtttac agcttggtgc aaaagaaaga tccctcaggc   2880
cttgataaga agaaaaaaac atccaagtcc aaggctatta ctccaaagcg actcctcaca   2940
tctataacca caaaaagcaa cattcattct tcagtcatgg ccagtccagg aggtcttagt   3000
gctgtgcgaa ccagcaactt cgcccttgtt ggatcttaca cattatcatt gtcttcagta   3060
ggaaatacta agtttgttct ggacaaggtc cccttttat cttctttgga aggtcatatt   3120
tatttaaaaa taaaatgtca agtgaattcc agtgttgaag aaagaggttt tctaaccata   3180
tttgaagatg ttagtggttt tggtgcctgg catcgaagat ggtgtgttct ttctggaaac   3240
tgtatatctt attggactta tccagatgat gagaaacgca agaatcccat aggaaggata   3300
aatctggcta attgtaccag tcgtcagata gaaccagcca acagagaatt ttgtgcaaga   3360
cgcaacactt ttgaattaat tactgtccga ccacaaagag aagatgaccg agagactctt   3420
gtcagccaat gcagggacac actctgtgtt accaagaact ggctgtctgc agatactaaa   3480
gaagagcggg atctctggat gcaaaaactc aatcaagttc ttgttgatat tcgcctctgg   3540
caacctgatg cttgctacaa acctattgga aagccttaaa ccgggaaatt tccatgctat   3600
ctagaggttt ttgatgtcat cttaagaaac acacttaaga gcatcagatt tactgattgc   3660
attttatgct ttaagtacga aagggtttgt gccaatattc actacgtatt atgcagtatt   3720
```

-continued tatatctttt gtatgtaaaa ctttaactga tttctgtcat tcatcaatga gtagaagtaa 3780
atacattata gttgattttg ctaaatctta atttaaaagc ctcattttcc tagaaatcta 3840
attattcagt tattcatgac aatatttttt taaaagtaag aaattctgag ttgtcttctt 3900
ggagctgtag gtcttgaagc agcaacgtct ttcaggggtt ggagacagaa acccattctc 3960
caatctcagt agtttttcg aaaggctgtg atcatttatt gatcgtgata tgacttgtta 4020
ctagggtact gaaaaaaatg tctaaggcct ttacagaaac atttttagta atgaggatga 4080
gaactttttc aaatagcaaa tatatattgg cttaaagcat gaggctgtct tcagaaaagt 4140
gatgtggaca taggaggcaa tgtgtgagac ttgggggttc aatattttat atagaagagt 4200
taataagcac atggtttaca tttactcagc tactatatat gcagtgtggt gcacattttc 4260
acagaattct ggcttcatta agatcattat ttttgctgcg tagcttacag acttagcata 4320
ttagtttttt ctactcctac aagtgtaaat tgaaaaatct ttatattaaa aaagtaaact 4380
gttatgaagc tgctatgtac taataatact ttgcttgcca aagtgtttgg gttttgttgt 4440
tgtttgtttg tttgtttgtt tttggttcat gaacaacagt gtctagaaac ccattttgaa 4500
agtggaaaat tattaagtca cctatcacct ttaaacgcct ttttttaaaa ttataaaata 4560
ttgtaaagca gggtctcaac ttttaaatac actttgaact tcttctctga attattaaag 4620
ttctttatga cctcatttat aaacactaaa ttctgtcacc tcctgtcatt ttattttttta 4680 ttcattcaaa tgtatttttt cttgtgcata ttataaaaat atattttatg agctcttact 4740
caaataaata cctgtaaatg tctaaaggaa aaaaaaaaaa aaaaaa 4786

<210> SEQ ID NO 96
<211> LENGTH: 3885
<212> TYPE: DNA
<213> ORGANISM: Homo sapiens

<400> SEQUENCE: 96
aggccggggc ggggctggga agtagtcggg cggggttgtg agacgccgcg ctcagcttcc 60
atcgctgggc ggtcaacaag tgcgggcctg gctcagcgcg ggggggcgcg gagaccgcga 120
ggcgaccggg agcggctggg ttcccggctg cgcgcccttc ggccaggccg ggagccgcgc 180
cagtcggagc ccccggccca gcgtggtccg cctccctctc ggcgtccacc tgcccggagt 240
actgccagcg ggcatgaccg acccaccagg ggcgccgccg ccggcgctcg caggccgcgg 300
atgaagaaga aaacccggcg ccgctcgacc cggagcgagg agttgacccg gagcgaggag 360
ttgaccctga gtgaggaagc gacctggagt gaagaggcga cccagagtga ggaggcgacc 420
cagggcgaag agatgaatcg gagccaggag gtgacccggg acgaggagtc gacccggagc 480
gaggaggtga ccagggagga aatggcggca gctgggctca ccgtgactgt caccccacagc 540 aatgagaagc acgaccttca tgttacctcc cagcagggca gcagtgaacc agttgtccaa 600
gacctggccc aggttgttga agaggtcata ggggttccac agtcttttca gaaactcata 660
tttaagggaa aatctctgaa ggaaatggaa acaccgttgt cagcacttgg aatacaagat 720
ggttgccggg tcatgttaat tgggaaaaag aacagtccac aggaagaggt tgaactaaag 780
aagttgaaac atttggagaa gtctgtggag aagatagctg accagctgga agagttgaat 840
aaagagctta ctggaatcca gcagggtttt ctgcccaagg atttgcaagc tgaagctctc 900
tgcaaacttg ataggagagt aaaagccaca atagagcagt ttatgaagat cttggaggag 960
attgacacac tgatcctgcc agaaaatttc aaagacagta gattgaaaag gaaaggcttg 1020
gtaaaaaagg ttcaggcatt cctagccgag tgtgacacag tggagcagaa catctgccag 1080
gagactgagc ggctgcagtc tacaaacttt gccctggccg agtgaggtgt agcagaaaaa 1140
ggctgtgctg ccctgaagaa tggcgccacc agctctgccg tctctggagc ggaatttacc 1200
tgatttcttc agggctgctg gggcaactg gccatttgcc aattttccta ctctcacact 1260
ggttctcaat gaaaaatagt gtctttgtga ttttgagtaa agctcctatc tgttttctcc 1320
ttctgtctct gtggttgtac tgtccagcaa tccacctttt ctggagaggg ccacctctgc 1380
ccaaattttc ccagctgttt ggacctctgg gtgctttctt tgggctggtg agagctctaa 1440
tttgccttgg gccagtttca ggtttatagg ccccctcagt cttcagatac atgagggctt 1500
ctttgctctt gtgatcgtgt agtcccatag ctgtaaaacc agaatcacca ggaggttgca 1560
cctagtcagg aatattggga atggcctaga acaaggtgtt tggcacataa gtagaccact 1620
tatccctcat tgtgacctaa ttccagagca tctggctggg ttgttgggtt ctagactttg 1680
tcctcacctc ccagtgaccc tgactagcca caggccatga gataccaggg ggccgttcct 1740
tggatggagc ctgtggttga tgcaaggctt ccttgtcccc aagcaagtct tcagaaggtt 1800
agaacccagt gttgactgag tctgtgcttg aaaccaggcc agagccatgg attaggaagg 1860
gcaaagagaa ggcaccagaa tgagtaaagc aggcaggtgg tgaagccaac cataaacttc 1920
tcaggagtga catgtgcttc cttcaaaggc atttttgtta accatatcct tctgagttct 1980
atgtttcctt cacagctgtt ctatccattt tgtggactgt cccccacccc caccccatca 2040
ttgtttttaa aaaattaagg cctggcgcag cagctcatgc ctataatccc agcactttgg 2100
gaggctgagg cgggcggatc acttgaggcc aggagtttga gaccagccca ggcaacatag 2160
caaaacccca ttctgcttta aaaaaaaaaa aaaaaaaaat tagcttggcg tagtggcatg 2220
tgcctataat cccagctact ggggaggctg aggcacaaga atcatttgaa cctgggaggt 2280
agaggttgct gtgagccgag attacgcccc tgcactccag cctgggtcac agagtgagac 2340
tccatctcag aaaaaaaaaa aattgagtca ggtgcagtag ctccttcctg tagtcccagc 2400
tacttgggag gctgaggcta gaggatcact tgagcccagg agtttgagtc tagtctgggc 2460
aacatagcaa gaccccatct ctaaaattta agtaagtaaa agtagataaa taaaaagaaa 2520
aaaaaactgt ttatgtgctc atcataaagt agaagagtgg tttgcttttt tttttttttt 2580
tggattaatg aggaaatcat tctgtggctc tagtcataat ttatgcttaa taacattgat 2640
agtagccctt tgcgctataa ctctacctaa agactcacat catttggcag agagagagtc 2700
gttgaagtcc caggaattca ggactgggca ggttaagacc tcagacaagg tagtagaggt 2760
agacttgtgg acaaggctcg ggtcccagcc caccgcaccc caactttaat cagagtggtt 2820
cactattgat ctatttttgt gtgatagctg tgtggcgtgg gccacaacat ttaatgagaa 2880
gttactgtgc accaaactgc cgaacaccat tctaaactat tcatatatat tagtcattta 2940
attcttacat aacttgagag gtagacagat atccttattt tagagatgag gaaaccaaga 3000
gaacttaggt cattagcgca aggttgtaga gtaagcggca aagccaagac acaaagctgg 3060
gtggtttggt ttcagagcca gtgcttttcc cctctactgt actgcctctc aaccaacaca 3120
gggttgcaca ggcccattct ctgatttttt tcctcttgtc ctctgcctct ccctctagct 3180
cccacttcct ctctgctcta gttcattttc tttagagcag cccgagtgat catgaagtgc 3240
aaatcttgcc atgtcagtcc cctgcttaga accctccaat ggctcacttt ctctttaggc 3300
aaaagtcttt accccatgcc ttctcccatc tcatctcaac cccctcattt gttggctgtc 3360
tgctgtcagc cactcttctt tcaggtcctc agatgcactg caccctctcc tgcctggggg 3420

```
tctttgctcc tgctactacc tctgcttgaa cagctcctca ccttccttcc tccaacccta   3480

cccttgtata ggtgactttt gttcatcctt cagaattcaa ctcacatgtc tcttgcatgg   3540

agaaccctca cctactgtgt tgagaccctg tccagccccc aggtgggatc ctctctcgac   3600

ttcccataca tttctttcac agcatttaca tagtccatga tagtttactt gtgggattat   3660

ttggttaatc tttgccttta acaccagggt tccttgggtg aaggagcttc tttatcttgg   3720

taacagcatt atttcaagca taacttgtaa tatagttata ttacatatat aacatatata   3780

tatataacat aacatatata acatatataa caagcataac ttgttatata gtcttgtata   3840

tagtaagacc tcaataaata tttggagaac aaaaaaaaaa aaaaa                   3885
```

<210> SEQ ID NO 97
<211> LENGTH: 6492
<212> TYPE: DNA
<213> ORGANISM: Homo sapiens

<400> SEQUENCE: 97

```
tttctgtgaa gcagaagtct gggaatcgat ctggaaatcc tcctaatttt tactccctct     60

ccccgcgact cctgattcat tgggaagttt caaatcagct ataactggag agtgctgaag    120

attgatggga tcgttgcctt atgcatttgt tttggtttta caaaaaggaa acttgacaga    180

ggatcatgct gtacttaaaa aatacaacat cacagaggaa gtagactgat attaacaata    240

cttactaata ataacgtgcc tcatgaaata aagatccgaa aggaattgga ataaaaattt    300

cctgcatctc atgccaaggg ggaaacacca gaatcaagtg ttccgcgtga ttgaagacac    360

cccctcgtcc aagaatgcaa agcacatcca ataaaatagc tggattataa ctcctcttct    420

ttctctgggg gccgtggggt gggagctggg gcgagaggtg ccgttggccc ccgttgcttt    480

tcctctggga aggatggcgc acgctgggag aacagggtac gataaccggg agatagtgat    540

gaagtacatc cattataagc tgtcgcagag gggctacgag tgggatgcgg gagatgtggg    600

cgccgcgccc ccgggggccg cccccgcacc gggcatcttc tcctcccagc ccgggcacac    660

gccccatcca gccgcatccc gggacccggt cgccaggacc tcgccgctgc agaccccggc    720

tgcccccggc gccgccgcgg ggcctgcgct cagcccggtg ccacctgtgg tccacctgac    780

cctccgccag gccggcgacg acttctcccg ccgctaccgc cgcgacttcg ccgagatgtc    840

cagccagctg cacctgacgc ccttcaccgc gcggggacgc tttgccacgg tggtggagga    900

gctcttcagg gacggggtga actgggggag gattgtggcc ttctttgagt tcggtggggt    960

catgtgtgtg gagagcgtca accgggagat gtcgcccctg gtggacaaca tcgccctgtg   1020

gatgactgag tacctgaacc ggcacctgca cacctggatc caggataacg gaggctggga   1080

tgcctttgtg gaactgtacg gccccagcat gcggcctctg tttgatttct cctggctgtc   1140

tctgaagact ctgctcagtt tggccctggt gggagcttgc atcaccctgg gtgcctatct   1200

gggccacaag tgaagtcaac atgcctgccc caaacaaata tgcaaaaggt tcactaaagc   1260

agtagaaata atatgcattg tcagtgatgt accatgaaac aaagctgcag gctgtttaag   1320

aaaaaataac acacatataa acatcacaca cacagacaga cacacacaca cacaacaatt   1380

aacagtcttc aggcaaaacg tcgaatcagc tatttactgc caaagggaaa tatcatttat   1440

tttttacatt attaagaaaa aaagatttat ttatttaaga cagtcccatc aaaactcctg   1500

tctttggaaa tccgaccact aattgccaag caccgcttcg tgtggctcca cctggatgtt   1560

ctgtgcctgt aaacatagat tcgctttcca tgttgttggc cggatcacca tctgaagagc   1620

agacggatgg aaaaaggacc tgatcattgg ggaagctggc tttctggctg ctggaggctg   1680
```

-continued gggagaaggt gttcattcac ttgcatttct ttgccctggg ggctgtgata ttaacagagg 1740
gagggttcct gtggggggaa gtccatgcct ccctggcctg aagaagagac tctttgcata 1800
tgactcacat gatgcatacc tggtgggagg aaaagagttg ggaacttcag atggacctag 1860
tacccactga gatttccacg ccgaaggaca gcgatgggaa aaatgccctt aaatcatagg 1920
aaagtatttt tttaagctac caattgtgcc gagaaaagca ttttagcaat ttatacaata 1980
tcatccagta ccttaagccc tgattgtgta tattcatata ttttggatac gcacccccca 2040
actcccaata ctggctctgt ctgagtaaga aacagaatcc tctggaactt gaggaagtga 2100
acatttcggt gacttccgca tcaggaaggc tagagttacc cagagcatca ggccgccaca 2160
agtgcctgct tttaggagac cgaagtccgc agaacctgcc tgtgtcccag cttggaggcc 2220
tggtcctgga actgagccgg ggccctcact ggcctcctcc agggatgatc aacagggcag 2280
tgtggtctcc gaatgtctgg aagctgatgg agctcagaat tccactgtca agaaagagca 2340
gtagaggggt gtggctgggc ctgtcaccct ggggccctcc aggtaggccc gttttcacgt 2400
ggagcatggg agccacgacc cttcttaaga catgtatcac tgtagaggga aggaacagag 2460
gccctgggcc cttcctatca gaaggacatg gtgaaggctg ggaacgtgag gagaggcaat 2520
ggccacggcc catttttggct gtagcacatg gcacgttggc tgtgtggcct tggcccacct 2580
gtgagtttaa agcaaggctt taaatgactt tggagagggt cacaaatcct aaaagaagca 2640
ttgaagtgag gtgtcatgga ttaattgacc cctgtctatg gaattacatg taaaacatta 2700
tcttgtcact gtagtttggt tttatttgaa aacctgacaa aaaaaaagtt ccaggtgtgg 2760
aatatggggg ttatctgtac atcctggggc attaaaaaaa aaatcaatgg tggggaacta 2820
taaagaagta acaaaagaag tgacatcttc agcaaataaa ctaggaaatt tttttttctt 2880
ccagtttaga atcagccttg aaacattgat ggaataactc tgtggcatta ttgcattata 2940
taccatttat ctgtattaac tttggaatgt actctgttca atgtttaatg ctgtggttga 3000
tatttcgaaa gctgctttaa aaaaatacat gcatctcagc gtttttttgt ttttaattgt 3060
atttagttat ggcctataca ctatttgtga gcaaaggtga tcgttttctg tttgagattt 3120
ttatctcttg attcttcaaa agcattctga gaaggtgaga taagccctga gtctcagcta 3180
cctaagaaaa acctggatgt cactggccac tgaggagctt tgtttcaacc aagtcatgtg 3240
catttccacg tcaacagaat tgtttattgt gacagttata tctgttgtcc ctttgacctt 3300
gtttcttgaa ggtttcctcg tccctgggca attccgcatt taattcatgg tattcaggat 3360
tacatgcatg tttggttaaa cccatgagat tcattcagtt aaaaatccag atggcaaatg 3420
accagcagat tcaaatctat ggtggtttga cctttagaga gttgctttac gtggcctgtt 3480
tcaacacaga cccacccaga gccctcctgc cctccttccg cgggggcttt ctcatggctg 3540
tccttcaggg tcttcctgaa atgcagtggt gcttacgctc caccaagaaa gcaggaaacc 3600
tgtggtatga agccagacct ccccggcggg cctcagggaa cagaatgatc agacctttga 3660
atgattctaa tttttaagca aaatattatt ttatgaaagg tttacattgt caaagtgatg 3720
aatatggaat atccaatcct gtgctgctat cctgccaaaa tcattttaat ggagtcagtt 3780
tgcagtatgc tccacgtggt aagatcctcc aagctgcttt agaagtaaca atgaagaacg 3840
tggacgtttt taatataaag cctgttttgt cttttgttgt tgttcaaacg ggattcacag 3900
agtatttgaa aaatgtatat atattaagag gtcacggggg ctaattgctg gctggctgcc 3960
ttttgctgtg ggttttgtt acctggtttt aataacagta aatgtgccca gcctcttggc 4020

-continued

```
cccagaactg tacagtattg tggctgcact tgctctaaga gtagttgatg ttgcattttc   4080
cttattgtta aaaacatgtt agaagcaatg aatgtatata aaagcctcaa ctagtcattt   4140
ttttctcctc ttcttttttt tcattatatc taattatttt gcagttgggc aacagagaac   4200
catccctatt ttgtattgaa gagggattca catctgcatc ttaactgctc tttatgaatg   4260
aaaaaacagt cctctgtatg tactcctctt tacactggcc agggtcagag ttaaatagag   4320
tatatgcact ttccaaattg gggacaaggg ctctaaaaaa agccccaaaa ggagaagaac   4380
atctgagaac ctcctcggcc ctcccagtcc ctcgctgcac aaatactccg caagagaggc   4440
cagaatgaca gctgacaggg tctatggcca tcgggtcgtc tccgaagatt tggcaggggc   4500
agaaaactct ggcaggctta agatttggaa taaagtcaca gaattaagga agcacctcaa   4560
tttagttcaa acaagacgcc aacattctct ccacagctca cttacctctc tgtgttcaga   4620
tgtggccttc catttatatg tgatctttgt tttattagta aatgcttatc atctaaagat   4680
gtagctctgg cccagtggga aaaattagga agtgattata aatcgagagg agttataata   4740
atcaagatta aatgtaaata atcagggcaa tcccaacaca tgtctagctt tcacctccag   4800
gatctattga gtgaacagaa ttgcaaatag tctctatttg taattgaact tatcctaaaa   4860
caaatagttt ataaatgtga acttaaactc taattaattc caactgtact tttaaggcag   4920
tggctgtttt tagactttct tatcacttat agttagtaat gtacacctac tctatcagag   4980
aaaaacagga aaggctcgaa atacaagcca ttctaaggaa attagggagt cagttgaaat   5040
tctattctga tcttattctg tggtgtcttt tgcagcccag acaaatgtgg ttacacactt   5100
tttaagaaat acaattctac attgtcaagc ttatgaaggt tccaatcaga tctttattgt   5160
tattcaattt ggatctttca gggatttttt ttttaaatta ttatgggaca aaggacattt   5220
gttggagggg tgggagggag gaagaatttt taaatgtaaa acattcccaa gtttggatca   5280
gggagttgga agttttcaga ataaccagaa ctaagggtat gaaggacctg tattggggtc   5340
gatgtgatgc ctctgcgaag aaccttgtgt gacaaatgag aaacattttg aagtttgtgg   5400
tacgaccttt agattccaga gacatcagca tggctcaaag tgcagctccg tttggcagtg   5460
caatggtata aatttcaagc tggatatgtc taatgggtat ttaaacaata aatgtgcagt   5520
tttaactaac aggatattta atgacaacct tctggttggt agggacatct gtttctaaat   5580
gtttattatg tacaatacag aaaaaaattt tataaaatta agcaatgtga aactgaattg   5640
gagagtgata atacaagtcc tttagtctta cccagtgaat cattctgttc catgtctttg   5700
gacaaccatg accttggaca atcatgaaat atgcatctca ctggatgcaa agaaaatcag   5760
atggagcatg aatggtactg taccggttca tctggactgc cccagaaaaa taacttcaag   5820
caaacatcct atcaacaaca aggttgttct gcataccaag ctgagcacag aagatgggaa   5880
cactggtgga ggatggaaag gctcgctcaa tcaagaaaat tctgagacta ttaataaata   5940
agactgtagt gtagatactg agtaaatcca tgcacctaaa ccttttggaa aatctgccgt   6000
gggccctcca gatagctcat ttcattaagt ttttccctcc aaggtagaat ttgcaagagt   6060
gacagtggat tgcatttctt ttggggaagc tttcttttgg tggttttgtt tattatacct   6120
tcttaagttt tcaaccaagg tttgcttttg ttttgagtta ctggggttat ttttgtttta   6180
aataaaaata agtgtacaat aagtgttttt gtattgaaag cttttgttat caagattttc   6240
atacttttac cttccatggc tctttttaag attgatactt ttaagaggtg gctgatattc   6300
tgcaacactg tacacataaa aaatacggta aggatacttt acatggttaa ggtaaagtaa   6360
gtctccagtt ggccaccatt agctataatg gcactttgtt tgtgttgttg gaaaaagtca   6420
```

cattgccatt aaactttcct tgtctgtcta gttaatattg tgaagaaaaa taaagtacag 6480
tgtgagatac tg 6492

<210> SEQ ID NO 98
<211> LENGTH: 4934
<212> TYPE: DNA
<213> ORGANISM: Homo sapiens

<400> SEQUENCE: 98
aatgagggta tttataaact acttaaatta taaaaagaat gagacatcag acttacagtt 60
ttggatacta attttttca cttaacgttc attatgtgat aggagttttc catcctatta 120
taccgctgtg cgatctgatc ttgggcacgt taaccaacct cttgttgcct cgattttctc 180
acctgtaaaa gtgggggtaa tcataatgct tacttagtag gatagccctg aagaataagt 240
gacttagcga acataaatag cttacaatag ggttttcagc atgggaagga ttcagtaaat 300
gttagctgtc atcatcacca cctacaaagg aagcaatact gtgctgaaag tttttccatc 360
attaatgtaa tttctatagt acgattccca agaagatatt aaaattatgg aaataaaggt 420
attggtatat tcctaattat ttcctaaaag attgtattga taaatatgct catccttccc 480
ttaacgggat gcattccaga aaaacaagtc aaatgttaga caaagtatca gaagggaaat 540
tctgtagcca gagagctaaa aattacaata gggtctctaa ttatacttca actttttag 600 gaataattct cagtgtgttt tcccacattt catatgtaat ttttttttt ttttttttt 660 gagacagagc ctcgccctgt caccaggctg gagtacagtg gcgcgatctc ggctcactgc 720
aacttccacc tgctgggttc aagcaattct tctgacctca ggtgatccac ccgcctcggc 780
ctcccaaagt gctgggatta taacaggcgt ggcatgagtc accgcgcccg gccgatcttt 840 actttttat tctttgtacc ccctgcctat ccagttagca tgtgattaaa gtcaaagatt 900
tgccactttg ggccacatct attaatttc atctttgtta taattgtatt tagtttttga 960
tctacactgc ttattactcc cagtcatttt ttatagaact gaaaatctgg taaaatactc 1020
aaaattgcac tgacttctat gtagaggcga cactccatca gaaccgtggg ctgacaggga 1080
atcccactgt gcaggagctg cgcgcatttt catttctgat tctctttggc gtatccagga 1140
ctctgatgac atgatcatat atttatcagt agtaacaggt tgggccattt gtttttgtg 1200 gtaaatcata tatttaagat tttagaaata agttgatagc catgtatttt ggaatttgaa 1260
aaagacattg cattactcag cttcaaatta agctttaatc aaatagtgaa actttccatt 1320
aatggacagt gtatacttt ttgtgtattt aaaaaaaaaa acactgaata tagtgccttt 1380
gtgacagggg agcttggttc ctgacaatgt cctcttgagc cttttttttt tttttgagat 1440
ggagtctcac tgtgtcaccc aggctggagt gcagtggcgc catcttggct cactgcaacc 1500
tccgccccct gggttcaagt gattctcatt cctcagcttc ctaagtagct gggattacag 1560
gcacgcacca ccatgaccag ctaattttta tacttttagt agagacaggg ttttgccatg 1620
ttggctaggt tggtctcgaa ctcctgacct caagtaatcc acccaccatg gcctccccaa 1680
agtgctggga ttacaggcgt gagccatttc acccggcctc tcttccgtct ttgagctgtg 1740
aggaaatagc tacattacat gagctgctag atctgcctta tggtcagaaa tgaaggttga 1800
actctcagga acagtgacat atatacacac tgatatttcc aaagtacaat gccccaaatt 1860
gatccacaaa ggaattaagg tcatttgcaa caaaatcaca gaatagtaac aaataaatag 1920
aagataaata tggccaggga tgctgcaaac tgatatactg ccaagtttat cagttgggaa 1980

-continued

```
tcccaacagt gaaaagcata aaaatgaaag gaattttaag gagacttttt atagaagagt   2040
gggaaggatt ggaggagcca acaagtgatg gtgaggcaca cagggaagag cttcagtggg   2100
caccatcccc tctctggttt gaaggggtag ggaggggacc agagctggga ggagggggct   2160
ggaatactgc tggaggagcc actcccttcc agacctgctg tggccatcac agaatgcagc   2220
cactgccaga gcagcagccc gaggaaccag gcagggggag cacaagtacc ctagcctctc   2280
tctttctgtt tcttgcctgc cgatctcctc cactggctaa acccagctgg atgctaagag   2340
tacagtcagc ctgcctgctg aggagggacc accagggacc accatcagca agggatccaa   2400
tgtctttctg cctctgcaga atgaaggttg gggcgcgggg ggcgctctac ttcttaggga   2460
tattgtggga ataaaaggaa ataggcaaaa aatgtttttg aaaaacaaag cacatactgc   2520
gcacccgtgg gccactactg cttttgaccc ctggctctgt ttcatgaagt aatgtcgtgt   2580
cattctcttt ttaggtgcta caggatttct ttaggtttgt tttctgtcca ccatatttca   2640
actcatgtgt gctgtttgtt gtgctaaaac aaatatttgc tgatgcctga gtgaatagtt   2700
gaatatttta tataagtcaa atttatacgt aatgattttt cttgtaactt agccgtttct   2760
cttttacaaa ctcagaaaac ctcagacttt gaaaaggcct tgaagttcct cacctgaaat   2820
ctgagaactt ggagcgcctt aaaaaatcta aaggaaaaca aaacagtgaa agaacatgat   2880
atagtcagtg tagagaataa aattatttat gtaattaata ttgaggatgc agataacaca   2940
ttgtgaaatc ttgcttgtaa aaaatctcga tctgctgaag aaagatgttc tctctagaga   3000
tctttgaaag cataattatt gagcttttaa aatgttagaa acaaaagtta gacccacaca   3060
tattctggcg tgtggaagat ttgcattcct tcccctgccc gccccgcccc cacacttgtg   3120
agttgtgcct gtgtacgcag ttcctgtagc actcggctgg gcagaaatca tctttcagca   3180
ctaagggaac atagttatga tctggacctt ctgggagtgg tcagtgccca agaacaggta   3240
tgggactcca gaaagttctg ctctcaaccc tattttgaaa tagagttaca cattgttcta   3300
caattatttg agttaataag cagctctttt caaacgtgat tatgcccttc caagtttaaa   3360
tacactagac tttagtgaaa gtaattgacc tcatctcatt tctctcctgt tatattaaga   3420
tcactttcag taaaaggtag aagcttttga agtggtgagg aggaggtaga ggagggacat   3480
agagcagata ggggctggaa agtggggtga ggaagagagt ggcttctctt tggcagagta   3540
ccaaggaaaa gccctatctg tacagaacct ttgtgcctgg gaacttgatg gctgcaacct   3600
gagcctcaac ctagtttgct tgcggagcca gaagagaagc taaaaacctt cagttaacca   3660
agccagacac caagaaagtt aaaccgaaag agaacccccc accccccgca aaaaaaagaa   3720
gtaaagtggg ttaaagtgat atcatgttag cacagaaaga gaacataagg gtcatctaag   3780
ttcatctgcc ccctcttcta tttcaaggtg cagaaactaa ggcacaaggg accccgtgtc   3840
ctgctcttga tcacatagct agtgggtgcc aagccaggtc tagaactctg ttctctgggg   3900
tcacaggctg gctcttcatc cctctagaga gatagctcat ctgtgtgcac ctgagcccgt   3960
tgtgtttcgg agtcaaagca aataaaggct caaactccaa gactgttttg cagaccggct   4020
gcagtagata tggggggagg agaaacctgc tttaaattgc ttcaagcaag ttgtttctgc   4080
aaaggtgttg actttttttct ttcaactttc tagtgagtca ctgcagcctg agctgttatt   4140
tgtcattatg caataattca ggaactaact caagattctt ctttttaaat tatttgttta   4200
tttagagaca gagtcttgct ctgttgccca ggctggagtg cagtggtgtg atctcggctc   4260
actgcagcct ctgcctcctg ggttcaagca attctcatgt ctcagcctcc cgaatagctg   4320
gtattgcagg ctcgtgccac cacccccctgc taatttttgt aattttagtg gagacacggt   4380
```

-continued ttcgccatgt tggccgggct cgtcttgagc tcctggcctc aggtgatccg cccgcctcgg 4440
cctcccaaag tgctgggatt gcagccgtga gcctccacac ccggcctatt tatttatttt 4500
taaattggct gctcttagaa aggcatacca tgtttctgga tgggaaggct tattaattca 4560
ccctaattta atgtataaat ttgatgcaat catagtcaca gtcccagtgg aattttttaa 4620
cttggtaaga tgttctaaaa ttaatgagag aacttgaatt accaggtatt gaaacactgt 4680
aaagccacaa tcatgtaaac agtatgttat aaccatggga atagaggtct gtgatacagc 4740
agaaaaaagt gaaaaaaaga ataactgtat tcataaaaat ttaaatgtgg agtcactggg 4800
ggaaaggatt aaatattcga taatgtagaa acaactcaac tatttggaga aatgtaaatt 4860
tagagcctta tctcatgcca tataccaaaa tactatttag atttgattaa aaaataaaaa 4920
aaaaaaaaaa aaaa 4934

<210> SEQ ID NO 99
<211> LENGTH: 2011
<212> TYPE: DNA
<213> ORGANISM: Homo sapiens

<400> SEQUENCE: 99
gcggccgcca gcgcggtgta gggggcaggc gcggatcccg ccaccgccgc gcgctcggcc 60
cgccgactcc cggcgccgcc gccgccactg ccgtcgccgc cgccgcctgc cgggactgga 120
gcgcgccgtc cgccgcggac aagaccctgg cctcaggccg gagcagcccc atcatgccga 180
gggagcgcag ggagcgggat gcgaaggagc gggacaccat gaaggaggac ggcggcgcgg 240
agttctcggc tcgctccagg aagaggaagg caaacgtgac cgttttttttg caggatccag 300 atgaagaaat ggccaaaatc gacaggacgg cgagggacca gtgtgggagc cagccttggg 360
acaataatgc agtctgtgca gacccctgct ccctgatccc cacacctgac aaagaagatg 420
atgaccgggt ttacccaaac tcaacgtgca agcctcggat tattgcacca tccagaggct 480
ccccgctgcc tgtactgagc tgggcaaata gagaggaagt ctggaaaatc atgttaaaca 540
aggaaaagac atacttaagg gatcagcact ttcttgagca acaccctctt ctgcagccaa 600
aaatgcgagc aattcttctg gattggttaa tggaggtgtg tgaagtctat aaacttcaca 660
gggagacctt ttacttggca caagatttct ttgaccggta tatggcgaca caagaaaatg 720
ttgtaaaaac tcttttacag cttattggga tttcatcttt atttattgca gccaaacttg 780
aggaaatcta tcctccaaag ttgcaccagt ttgcgtatgt gacagatgga gcttgttcag 840
gagatgaaat tctcaccatg gaattaatga ttatgaaggc ccttaagtgg cgtttaagtc 900
ccctgactat tgtgtcctgg ctgaatgtat acatgcaggt tgcatatcta aatgacttac 960
atgaagtgct actgccgcag tatccccagc aaatctttat acagattgca gagctgttgg 1020
atctctgtgt cctggatgtt gactgccttg aatttcctta tggtatactt gctgcttcgg 1080
ccttgtatca tttctcgtca tctgaattga tgcaaaaggt ttcagggtat cagtggtgcg 1140
acatagagaa ctgtgtcaag tggatggttc catttgccat ggttataagg gagacgggga 1200
gctcaaaact gaagcacttc aggggcgtcg ctgatgaaga tgcacacaac atacagaccc 1260
acagagacag cttggatttg ctggacaaag cccgagcaaa gaaagccatg ttgtctgaac 1320
aaaatagggc ttctcctctc cccagtgggc tcctcacccc gccacagagc ggtaagaagc 1380
agagcagcgg gccggaaatg gcgtgaccac cccatccttc tccaccaaag acagttgcgc 1440
gcctgctcca cgttctcttc tgtctgttgc agcggaggcg tgcgtttgct tttacagata 1500

-continued

```
tctgaatgga agagtgtttc ttccacaaca gaagtatttc tgtggatggc atcaaacagg   1560

gcaaagtgtt ttttattgaa tgcttatagg tttttttaa ataagtgggt caagtacacc   1620

agccacctcc agacaccagt gcgtgctccc gatgctgcta tggaaggtgc tacttgacct   1680

aagggactcc cacaacaaca aaagcttgaa gctgtggagg gccacggtgg cgtggctctc   1740

ctcgcaggtg ttctgggctc cgttgtacca agtggagcag gtggttgcgg gcaagcgttg   1800

tgcagagccc atagccagct gggcaggggg ctgccctctc cacattatca gttgacagtg   1860

tacaatgcct ttgatgaact gttttgtaag tgctgctata tctatccatt ttttaataaa   1920

gataatactg tttttgaaaa aaaaaaaaaa aaaaaaaaaa aaaaaaaaaa aaaaaaaaaa   1980

aaaaaaaaaa aaaaaaaaaa aaaaaaaaaa a                                  2011
```

```
<210> SEQ ID NO 100
<211> LENGTH: 1737
<212> TYPE: DNA
<213> ORGANISM: Homo sapiens

<400> SEQUENCE: 100

gagggcacgg gctccgtagg caccaactgc aaggacccct cccccctgcgg gcgctcccat     60

ggcacagttc gcgttcgaga gtgacctgca ctcgctgctt cagctggatg cacccatccc    120

caatgcaccc cctgcgcgct ggcagcgcaa agccaaggaa gccgcaggcc cggccccctc    180

acccatgcgg gccgccaacc gatcccacag cgccggcagg actccgggcc gaactcctgg    240

caaatccagt tccaaggttc agaccactcc tagcaaacct ggcggtgacc gctatatccc    300

ccatcgcagt gctgcccaga tggaggtggc cagcttcctc ctgagcaagg agaaccagcc    360

tgaaaacagc cagacgccca ccaagaagga acatcagaaa gcctgggctt tgaacctgaa    420

cggttttgat gtagaggaag ccaagatcct tcggctcagt ggaaaaacca caaaaatgcg    480

ccagagggtt atcacgaaca gactgaaagt actctacagc caaaaggcca ctcctggctc    540

cagccggaag acctgccgtt tacattcctt ccctgccaag accgtatcct ggatgcgcct    600

gaaatcgaat gactattaac tgaacctgtg ggactggcag tccggggaat gtccgggccg    660

ggccacggcc acgaggtgtt ccgtgtggag tgcaagctgg gacacaccgt gccgcttgtg    720

cacagggcca cgcggggaaa taatcccggg gcgcgcaaag cggcactggc gagagccgca    780

cgggccggtg ctgggggtgg tacaacaggc caaaacaaca cacaaggcca acaagacata    840

cgcgcgctga caccacggtg caaagcgctc agacgagtag taaccggcac tgtggttgct    900

gcctccccac ctctcccgct ctcagcgtaa gataaaagaa agaagagcaa aaagcaaaga    960

aagaagacga gacgagacac acaggaacga acagtaaagc aagctaaagc aaacgcaaga   1020

ccagacaaca gaaatagaaa gaaccaacag agaggagaca gaacaggacg ccagcaacat   1080

agcaacaaac gaacagaaga gagcactaaa caaaagcagc agcaagacga gacaggagag   1140

aaggaggaag gagggccgag cgagcaggga gcgcgagcag cgaggcgaag cagcagacaa   1200

gggcaggcga agggcaacga gaggaggcac cacacaaaaa ggagagggga caggagaagc   1260

agcgagagaa gcggaggagc aacaagagga agaaaaggag agggagagga gggagagagc   1320

ggaaggagga agaaacagca cgaggcgacg aagggggggag acgcgggggc aggaaaagac   1380

acaggaaggc agcgcggagg aggagaaggg gaagcaggaa ggagacggaa ggagaagagg   1440

gagaggacag cgcaagagag cgcgcgcggc gacagcgagg gacggagcga gagagaggaa   1500

acggaaagcg agagggaaga ggagaggcaa cgcagcgaac caaccgaaaa cagcagaaag   1560

agaggagaag gacgcgcaaa gaggcaagcg caagacgaca ggaaacgaag cgagagacga   1620
```

gaagccggtg acgagcagga gaaagggaag gcaggagaca ggacaggcgg aagagagaca 1680
cgcgagacgc aaagagtgag cagaacgaag cgaagagcaa cgcacgagag aaacgac 1737

<210> SEQ ID NO 101
<211> LENGTH: 3053
<212> TYPE: DNA
<213> ORGANISM: Homo sapiens

<400> SEQUENCE: 101
gagcgcggct ggagtttgct gctgccgctg tgcagtttgt tcaggggctt gtggtggtga 60
gtccgagagg ctgcgtgtga gagacgtgag aaggatcctg cactgaggag gtggaaagaa 120
gaggattgct cgaggaggcc tggggtctgt gaggcagcgg agctgggtga aggctgcggg 180
ttccggcgag gcctgagctg tgctgtcgtc atgcctcaaa cccgatccca ggcacaggct 240
acaatcagtt ttccaaaaag gaagctgtct cgggcattga acaaagctaa aaactccagt 300
gatgccaaac tagaaccaac aaatgtccaa accgtaacct gttctcctcg tgtaaaagcc 360
ctgcctctca gccccaggaa acgtctgggc gatgacaacc tatgcaacac tccccattta 420
cctccttgtt ctccaccaaa gcaaggcaag aaagagaatg gtccccctca ctcacataca 480
cttaagggac gaagattggt atttgacaat cagctgacaa ttaagtctcc tagcaaaaga 540
gaactagcca aagttcacca aaacaaaata ctttcttcag ttagaaaaag tcaagagatc 600
acaacaaatt ctgagcagag atgtccactg aagaaagaat ctgcatgtgt gagactattc 660
aagcaagaag gcacttgcta ccagcaagca aagctggtcc tgaacacagc tgtcccagat 720
cggctgcctg ccagggaaag ggagatggat gtcatcagga atttcttgag ggaacacatc 780
tgtgggaaaa aagctggaag cctttacctt tctggtgctc ctggaactgg aaaaactgcc 840
tgcttaagcc ggattctgca agacctcaag aaggaactga aaggctttaa aactatcatg 900
ctgaattgca tgtccttgag gactgcccag gctgtattcc cagctattgc tcaggagatt 960
tgtcaggaag aggtatccag gccagctggg aaggacatga tgaggaaatt ggaaaaacat 1020
atgactgcag agaagggccc catgattgtg ttggtattgg acgagatgga tcaactggac 1080
agcaaaggcc aggatgtatt gtacacgcta tttgaatggc catggctaag caattctcac 1140
ttggtgctga ttggtattgc taataccctg gatctcacag atagaattct acctaggctt 1200
caagctagag aaaaatgtaa gccacagctg ttgaacttcc caccttatac cagaaatcag 1260
atagtcacta ttttgcaaga tcgacttaat caggtatcta gagatcaggt tctggacaat 1320
gctgcagttc aattctgtgc ccgcaaagtc tctgctgttt caggagatgt tcgcaaagca 1380
ctggatgttt gcaggagagc tattgaaatt gtagagtcag atgtcaaaag ccagactatt 1440
ctcaaaccac tgtctgaatg taaatcacct tctgagcctc tgattcccaa gagggttggt 1500
cttattcaca tatcccaagt catctcagaa gttgatggta acaggatgac cttgagccaa 1560
gaaggagcac aagattcctt ccctcttcag cagaagatct tggtttgctc tttgatgctc 1620
ttgatcaggc agttgaaaat caaagaggtc actctgggga agttatatga agcctacagt 1680
aaagtctgtc gcaaacagca ggtggcggct gtggaccagt cagagtgttt gtcactttca 1740
gggctcttgg aagccagggg cattttagga ttaaagagaa acaaggaaac ccgtttgaca 1800
aaggtgtttt tcaagattga agagaaagaa atagaacatg ctctgaaaga taaagcttta 1860
attggaaata tcttagctac tggattgcct taaattcttc tcttacaccc cacccgaaag 1920
tattcagctg gcatttagag agctacagtc ttcattttag tgctttacac attcgggcct 1980
gaaaacaaat atgacctttt ttacttgaag ccaatgaatt ttaatctata gattctttaa 2040
tattagcaca gaataatatc tttgggtctt actattttta cccataaaag tgaccaggta 2100 gaccettttt aattacattc actacttcta ccacttgtgt atctctagcc aatgtgcttg 2160
caagtgtaca gatctgtgta gaggaatgtg tgtatattta cctcttcgtt tgctcaaaca 2220
tgagtgggta tttttttgtt tgtttttttt gttgttgttg tttttgaggc gcgtctcacc 2280
ctgttgccca ggctggagtg caatggcgcg ttctctgctc actacagcac ccgcttccca 2340
ggttgaagtg attctcttgc ctcagcctcc cgagtagctg ggattacagg tgcccaccac 2400
cgcgcccagc taatttttta atttttagta gagacagggt tttaccatgt tggccaggct 2460
ggtcttgaac tcctgaccct caagtgatct gcccaccttg gcctccctaa gtgctgggat 2520
tataggcgtg agccaccatg ctcagccatt aaggtatttt gttaagaact ttaagtttag 2580
ggtaagaaga atgaaaatga tccagaaaaa tgcaagcaag tccacatgga gatttggagg 2640
acactggtta aagaatttat ttctttgtat agtatactat gttcatggtg cagatactac 2700
aacattgtgg cattttagac tcgttgagtt tcttgggcac tcccaagggc gttggggtca 2760
taaggagact ataactctac agattgtgaa tatatttatt ttcaagttgc attctttgtc 2820
tttttaagca atcagatttc aagagagctc aagctttcag aagtcaatgt gaaaattcct 2880
tcctaggctg tcccacagtc tttgctgccc ttagatgaag ccacttgttt caagatgact 2940
actttggggt tgggttttca tctaaacaca tttttccagt cttattagat aaattagtcc 3000
atatggttgg ttaatcaaga gccttctggg tttggtttgg tggcattaaa tgg 3053

<210> SEQ ID NO 102
<211> LENGTH: 1843
<212> TYPE: DNA
<213> ORGANISM: Homo sapiens

<400> SEQUENCE: 102
gcggaatggg gcgggacttc cagtaggagg cggcaagttt gaaaagtgat gacggttgac 60
gtttgctgat ttttgacttt gcttgtagct gctccccgaa ctcgccgtct tcctgtcggc 120
ggccggcact gtagattaac aggaaacttc caagatggaa actttgtctt tccccagata 180
taatgtagct gagattgtga ttcatattcg caataagatc ttaacaggag ctgatggtaa 240
aaacctcacc aagaatgatc tttatccaaa tccaaagcct gaagtcttgc acatgatcta 300
catgagagcc ttacaaatag tatatggaat tcgactggaa catttttaca tgatgccagt 360
gaactctgaa gtcatgtatc cacatttaat ggaaggcttc ttaccattca gcaatttagt 420
tactcatctg gactcatttt tgcctatctg ccgggtgaat gactttgaga ctgctgatat 480
tctatgtcca aaagcaaaac ggacaagtcg gtttttaagt ggcattatca actttattca 540
cttcagagaa gcatgccgtg aaacgtatat ggaatttctt tggcaatata aatcctctgc 600
ggacaaaatg caacagttaa acgccgcaca ccaggaggca ttaatgaaac tggagagact 660
tgattctgtt ccagttgaag agcaagaaga gttcaagcag ctttcagatg gaattcagga 720
gctacaacaa tcactaaatc aggattttca tcaaaaaacg atagtgctgc aagagggaaa 780
ttcccaaaag aagtcaaata tttcagagaa aaccaagcgt ttgaatgaac taaaattgtc 840
ggtggtttct ttgaaagaaa tacaagagag tttgaaaaca aaaattgtgg attctccaga 900
gaagttaaag aattataaag aaaaaatgaa agatacggtc cagaagctta aaaatgccag 960
acaagaagtg gtggagaaat atgaaatcta tggagactca gttgactgcc tgccttcatg 1020
tcagttggaa gtgcagttat atcaaaagaa aatacaggac ctttcagata atagggaaaa 1080
attagccagt atcttaaagg agagcctgaa cttggaggac caaattgaga gtgatgagtc 1140
agaactgaag aaattgaaga ctgaagaaaa ttcgttcaaa agactgatga ttgtgaagaa 1200
ggaaaaactt gccacagcac aattcaaaat aaataagaag catgaagatg ttaagcaata 1260
caaacgcaca gtaattgagg attgcaataa agttcaagaa aaaagaggtg ctgtctatga 1320
acgagtaacc acaattaatc aagaaatcca aaaaattaaa cttggaattc aacaactaaa 1380
agatgctgct gaaagggaga aactgaagtc ccaggaaata tttctaaact tgaaaactgc 1440
tttggagaaa taccacgacg gtattgaaaa ggcagcagag gactcctatg ctaagataga 1500
tgagaagaca gctgaactga agaggaagat gttcaaaatg tcaacctgat taacaaaatt 1560
acatgtcttt ttgtaaatgg cttgccatct tttaattttc tatttagaaa gaaaagttga 1620
agcgaatgga agtatcagaa gtaccaaata atgttggctt catcagtttt tatacactct 1680
cataagtagt taataagatg aatttaatgt aggcttttat taatttataa ttaaaataac 1740
ttgtgcagct attcatgtct ctactctgcc ccttgttgta aatagtttga gtaaaacaaa 1800
actagttacc tttgaaatat atatattttt ttctgttact atc 1843

<210> SEQ ID NO 103
<211> LENGTH: 3686
<212> TYPE: DNA
<213> ORGANISM: Homo sapiens

<400> SEQUENCE: 103
ggctagcgcg ggaggtggag aaagaggctt gggcggcccc gctgtagccg cgtgtgggag 60
gacgcacggg cctgcttcaa agctttggga taacagcgcc tccgggggat aatgaatgcg 120
gagcctccgt tttcagtcga cttcagatgt gtctccactt ttttccgctg tagccgcaag 180
gcaaggaaac atttctcttc ccgtactgag gaggctgagg agtgcactgg gtgttctttt 240
ctcctctaac ccagaactgc gagacagagg ctgagtccct gtaaagaaca gctccagaaa 300
agccaggaga gcgcaggagg gcatccggga ggccaggagg ggttcgctgg ggcctcaacc 360
gcacccacat cggtcccacc tgcgaggggg cgggacctcg tggcgctgga ccaatcagca 420
cccacctgcg ctcacctggc ctcctcccgc tggctcccgg gggctgcggt gctcaaaggg 480
gcaagagctg agcggaacac cggcccgccg tcgcggcagc tgcttcaccc ctctctctgc 540
agccatgggg ctccctcgtg gacctctcgc gtctctcctc cttctccagg tttgctggct 600
gcagtgcgcg gcctccgagc cgtgccgggc ggtcttcagg gaggctgaag tgaccttgga 660
ggcgggaggc gcggagcagg agcccggcca ggcgctgggg aaagtattca tgggctgccc 720
tgggcaagag ccagctctgt ttagcactga taatgatgac ttcactgtgc ggaatggcga 780
gacagtccag gaaagaaggt cactgaagga aaggaatcca ttgaagatct tcccatccaa 840
acgtatctta cgaagacaca agagagattg ggtggttgct ccaatatctg tccctgaaaa 900
tggcaagggt cccttccccc agagactgaa tcagctcaag tctaataaag atagagacac 960
caagattttc tacagcatca cggggccggg ggcagacagc ccccctgagg gtgtcttcgc 1020
tgtagagaag gagacaggct ggttgttgtt gaataagcca ctggaccggg aggagattgc 1080
caagtatgag ctctttggcc acgctgtgtc agagaatggt gcctcagtgg aggaccccat 1140
gaacatctcc atcatagtga ccgaccagaa tgaccacaag cccaagttta cccaggacac 1200
cttccgaggg agtgtcttag agggagtcct accaggtact tctgtgatgc agatgacagc 1260
cacagatgag gatgatgcca tctacaccta caatggggtg gttgcttact ccatccatag 1320

-continued ccaagaacca aaggacccac acgacctcat gttcacaatt caccggagca caggcaccat 1380
cagcgtcatc tccagtggcc tggaccggga aaaagtccct gagtacacac tgaccatcca 1440
ggccacagac atggatgggg acggctccac caccacggca gtggcagtag tggagatcct 1500
tgatgccaat gacaatgctc ccatgtttga cccccagaag tacgaggccc atgtgcctga 1560
gaatgcagtg ggccatgagg tgcagaggct gacggtcact gatctggacg cccccaactc 1620
accagcgtgg cgtgccacct accttatcat gggcggtgac gacggggacc attttaccat 1680
caccacccac cctgagagca accagggcat cctgacaacc aggaagggtt tggattttga 1740
ggccaaaaac cagcacaccc tgtacgttga agtgaccaac gaggcccctt ttgtgctgaa 1800
gctcccaacc tccacagcca ccatagtggt ccacgtggag gatgtgaatg aggcacctgt 1860
gtttgtccca ccctccaaag tcgttgaggt ccaggagggc atccccactg ggagcctgt 1920
gtgtgtctac actgcagaag accctgacaa ggagaatcaa aagatcagct accgcatcct 1980
gagagaccca gcagggtggc tagccatgga cccagacagt gggcaggtca cagctgtggg 2040
caccctcgac cgtgaggatg agcagtttgt gaggaacaac atctatgaag tcatggtctt 2100
ggccatggac aatggaagcc ctcccaccac tggcacggga acccttctgc taacactgat 2160
tgatgtcaac gaccatggcc cagtccctga gccccgtcag atcaccatct gcaaccaaag 2220
ccctgtgcgc caggtgctga acatcacgga caaggacctg tctccccaca cctcccccttt 2280
ccaggcccag ctcacagatg actcagacat ctactggacg gcagaggtca acgaggaagg 2340
tgacacagtg gtcttgtccc tgaagaagtt cctgaagcag gatacatatg acgtgcacct 2400
ttctctgtct gaccatggca acaaagagca gctgacggtg atcagggcca ctgtgtgcga 2460
ctgccatggc catgtcgaaa cctgccctgg accctggaaa ggaggtttca tcctccctgt 2520
gctgggggct gtcctggctc tgctgttcct cctgctggtg ctgcttttgt tggtgagaaa 2580
gaagcggaag atcaaggagc ccctcctact cccagaagat gacacccgtg acaacgtctt 2640
ctactatggc gaagaggggg gtggcgaaga ggaccaggac tatgacatca cccagctcca 2700
ccgaggtctg gaggccaggc cggaggtggt tctccgcaat gacgtggcac caaccatcat 2760
cccgacaccc atgtaccgtc ctaggccagc caacccagat gaaatcggca actttataat 2820
tgagaacctg aaggcggcta acacagaccc cacagccccg ccctacgaca ccctcttggt 2880
gttcgactat gagggcagcg gctccgacgc cgcgtccctg agctccctca cctcctccgc 2940
ctccgaccaa gaccaagatt acgattatct gaacgagtgg ggcagccgct tcaagaagct 3000
ggcagacatg tacggtggcg gggaggacga ctaggcggcc tgcctgcagg gctggggacc 3060
aaacgtcagg ccacagagca tctccaaggg gtctcagttc ccccttcagc tgaggacttc 3120
ggagcttgtc aggaagtggc cgtagcaact tggcggagac aggctatgag tctgacgtta 3180
gagtggttgc ttccttagcc tttcaggatg gaggaatgtg ggcagtttga cttcagcact 3240
gaaaacctct ccacctgggc cagggttgcc tcagaggcca agtttccaga agcctcttac 3300
ctgccgtaaa atgctcaacc ctgtgtcctg ggcctgggcc tgctgtgact gacctacagt 3360
ggactttctc tctggaatgg aaccttctta ggcctcctgg tgcaacttaa ttttttttt 3420
taatgctatc ttcaaaacgt tagagaaagt tcttcaaaag tgcagcccag agctgctggg 3480
cccactggcc gtcctgcatt tctggtttcc agaccccaat gcctcccatt cggatggatc 3540
tctgcgtttt tatactgagt gtgcctaggt tgccccttat tttttatttt ccctgttgcg 3600
ttgctataga tgaagggtga ggacaatcgt gtatatgtac tagaactttt ttattaaaga 3660
aacttttccc aaaaaaaaaa aaaaaa 3686

<210> SEQ ID NO 104
<211> LENGTH: 10316
<212> TYPE: DNA
<213> ORGANISM: Homo sapiens

<400> SEQUENCE: 104
gagaccagaa gcgggcgaat tgggcaccgg tggcggctgc gggcagtttg aattagactc 60
tgggctccag cccgccgaag ccgcgccaga actgtactct ccgagaggtc gttttcccgt 120
ccccgagagc aagtttattt acaaatgttg gagtaataaa gaaggcagaa caaaatgagc 180
tgggctttgg aagaatggaa agaagggctg cctacaagag ctcttcagaa aattcaagag 240
cttgaaggac agcttgacaa actgaagaag gaaaagcagc aaaggcagtt tcagcttgac 300
agtctcgagg ctgcgctgca gaagcaaaaa cagaaggttg aaaatgaaaa aaccgagggt 360
acaaacctga aaagggagaa tcaaagattg atggaaatat gtgaaagtct ggagaaaact 420
aagcagaaga tttctcatga acttcaagtc aaggagtcac aagtgaattt ccaggaagga 480
caactgaatt caggcaaaaa acaaatagaa aaactggaac aggaacttaa aaggtgtaaa 540
tctgagcttg aaagaagcca acaagctgcg cagtctgcag atgtctctct gaatccatgc 600
aatacaccac aaaaaatttt tacaactcca ctaacaccaa gtcaatatta tagtggttcc 660
aagtatgaag atctaaaaga aaaatataat aaagaggttg aagaacgaaa aagattagag 720
gcagaggtta aagccttgca ggctaaaaaa gcaagccaga ctcttccaca agccaccatg 780
aatcaccgcg acattgcccg gcatcaggct tcatcatctg tgttctcatg gcagcaagag 840
aagaccccaa gtcatctttc atctaattct caaagaactc caattaggag agatttctct 900
gcatcttact tttctgggga acaagaggtg actccaagtc gatcaacttt gcaaataggg 960
aaaagagatg ctaatagcag tttctttgac aattctagca gtcctcatct tttggatcaa 1020
ttaaaagcgc agaatcaaga gctaagaaac aagattaatg agttggaact acgcctgcaa 1080
ggacatgaaa aagaaatgaa aggccaagtg aataagtttc aagaactcca actccaactg 1140
gagaaagcaa aagtggaatt aattgaaaaa gagaaagttt tgaacaaatg tagggatgaa 1200
ctagtgagaa caacagcaca atacgaccag gcgtcaacca agtatactgc attggaacaa 1260
aaactgaaaa aattgacgga agatttgagt tgtcagcgac aaaatgcaga aagtgccaga 1320
tgttctctgg aacagaaaat taaggaaaaa gaaaaggagt ttcaagagga gctctcccgt 1380
caacagcgtt ctttccaaac actggaccag gagtgcatcc agatgaaggc cagactcacc 1440
caggagttac agcaagccaa gaatatgcac aacgtcctgc aggctgaact ggataaactc 1500
acatcagtaa agcaacagct agaaaacaat ttggaagagt ttaagcaaaa gttgtgcaga 1560
gctgaacagg cgttccaggc gagtcagatc aaggagaatg agctgaggag aagcatggag 1620
gaaatgaaga aggaaaacaa cctccttaag agtcactctg agcaaaaggc cagagaagtc 1680
tgccacctgg aggcagaact caagaacatc aaacagtgtt taaatcagag ccagaatttt 1740
gcagaagaaa tgaaagcgaa gaatacctct caggaaacca tgttaagaga tcttcaagaa 1800
aaaataaatc agcaagaaaa ctccttgact ttagaaaaac tgaagcttgc tgtggctgat 1860
ctggaaaagc agcgagattg ttctcaagac cttttgaaga aaagagaaca tcacattgaa 1920
caacttaatg ataagttaag caagacagag aaagagtcca aagccttgct gagtgcttta 1980
gagttaaaaa agaaagaata tgaagaattg aaagaagaga aaactctgtt ttcttgttgg 2040
aaaagtgaaa acgaaaaact tttaactcag atggaatcag aaaaggaaaa cttgcagagt 2100

-continued

```
aaaattaatc acttggaaac ttgtctgaag acacagcaaa taaaaagtca tgaatacaac   2160
gagagagtaa gaacgctgga gatggacaga gaaaacctaa gtgtcgagat cagaaacctt   2220
cacaacgtgt tagacagtaa gtcagtggag gtagagaccc agaaactagc ttatatggag   2280
ctacagcaga aagctgagtt ctcagatcag aaacatcaga aggaaataga aaatatgtgt   2340
ttgaagactt ctcagcttac tgggcaagtt gaagatctag aacacaagct tcagttactg   2400
tcaaatgaaa taatggacaa agaccggtgt taccaagact tgcatgccga atatgagagc   2460
ctcagggatc tgctaaaatc caaagatgct tctctggtga caaatgaaga tcatcagaga   2520
agtcttttgg cttttgatca gcagcctgcc atgcatcatt cctttgcaaa tataattgga   2580
gaacaaggaa gcatgccttc agagaggagt gaatgtcgtt tagaagcaga ccaaagtccg   2640
aaaaattctg ccatcctaca aaatagagtt gattcacttg aattttcatt agagtctcaa   2700
aaacagatga actcagacct gcaaaagcag tgtgaagagt tggtgcaaat caaaggagaa   2760
atagaagaaa atctcatgaa agcagaacag atgcatcaaa gttttgtggc tgaaacaagt   2820
cagcgcatta gtaagttaca ggaagacact tctgctcacc agaatgttgt tgctgaaacc   2880
ttaagtgccc ttgagaacaa ggaaaaagag ctgcaacttt taaatgataa ggtagaaact   2940
gagcaggcag agattcaaga attaaaaaag agcaaccatc tacttgaaga ctctctaaag   3000
gagctacaac ttttatccga aaccctaagc ttggagaaga aagaaatgag ttccatcatt   3060
tctctaaata aaagggaaat tgaagagctg acccaagaga atgggactct taaggaaatt   3120
aatgcatcct taaatcaaga gaagatgaac ttaatccaga aaagtgagag ttttgcaaac   3180
tatatagatg aaagggagaa aagcatttca gagttatctg atcagtacaa gcaagaaaaa   3240
cttattttac tacaaagatg tgaagaaacc ggaaatgcat atgaggatct tagtcaaaaa   3300
tacaaagcag cacaggaaaa gaattctaaa ttagaatgct tgctaaatga atgcactagt   3360
ctttgtgaaa ataggaaaaa tgagttggaa cagctaaagg aagcatttgc aaaggaacac   3420
caagaattct taacaaaatt agcatttgct gaagaaagaa atcagaatct gatgctagag   3480
ttggagacag tgcagcaagc tctgagatct gagatgacag ataaccaaaa caattctaag   3540
agcgaggctg gtggtttaaa gcaagaaatc atgactttaa aggaagaaca aaacaaaatg   3600
caaaaggaag ttaatgactt attacaagag aatgaacagc tgatgaaggt aatgaagact   3660
aaacatgaat gtcaaaatct agaatcagaa ccaattagga actctgtgaa agaaagagag   3720
agtgagagaa atcaatgtaa ttttaaacct cagatggatc ttgaagttaa agaaatttct   3780
ctagatagtt ataatgcgca gttggtgcaa ttagaagcta tgctaagaaa taaggaatta   3840
aaacttcagg aaagtgagaa ggagaaggag tgcctgcagc atgaattaca gacaattaga   3900
ggagatcttg aaaccagcaa tttgcaagac atgcagtcac aagaaattag tggccttaaa   3960
gactgtgaaa tagatgcgga agaaaagtat atttcagggc ctcatgagtt gtcaacaagt   4020
caaaacgaca atgcacacct tcagtgctct ctgcaaacaa caatgaacaa gctgaatgag   4080
ctagagaaaa tatgtgaaat actgcaggct gaaaagtatg aactcgtaac tgagctgaat   4140
gattcaaggt cagaatgtat cacagcaact aggaaaatgg cagaagaggt agggaaacta   4200
ctaaatgaag ttaaaatatt aaatgatgac agtggtcttc tccatggtga gttagtggaa   4260
gacataccag gaggtgaatt tggtgaacaa ccaaatgaac agcaccctgt gtctttggct   4320
ccattggacg agagtaattc ctacgagcac ttgacattgt cagacaaaga agttcaaatg   4380
cactttgccg aattgcaaga gaaattctta tctttacaaa gtgaacacaa aattttacat   4440
gatcagcact gtcagatgag ctctaaaatg tcagagctgc agacctatgt tgactcatta   4500
```

```
aaggccgaaa atttggtctt gtcaacgaat ctgagaaact ttcaaggtga cttggtgaag   4560
gagatgcagc tgggcttgga ggaggggctc gttccatccc tgtcatcctc ttgtgtgcct   4620
gacagctcta gtcttagcag tttgggagac tcctcctttt acagagctct tttagaacag   4680
acaggagata tgtctctttt gagtaattta gaaggggctg tttcagcaaa ccagtgcagt   4740
gtagatgaag tattttgcag cagtctgcag gaggagaatc tgaccaggaa agaaacccct   4800
tcggccccag cgaagggtgt tgaagagctt gagtccctct gtgaggtgta ccggcagtcc   4860
ctcgagaagc tagaagagaa aatggaaagt caagggatta tgaaaaataa ggaaattcaa   4920
gagctcgagc agttattaag ttctgaaagg caagagcttg actgccttag gaagcagtat   4980
ttgtcagaaa atgaacagtg gcaacagaag ctgacaagcg tgactctgga gatggagtcc   5040
aagttggcgg cagaaaagaa acagacggaa caactgtcac ttgagctgga agtagcacga   5100
ctccagctac aaggtctgga cttaagttct cggtctttgc ttggcatcga cacagaagat   5160
gctattcaag gccgaaatga gagctgtgac atatcaaaag aacatacttc agaaactaca   5220
gaaagaacac caaagcatga tgttcatcag atttgtgata aagatgctca gcaggacctc   5280
aatctagaca ttgagaaaat aactgagact ggtgcagtga aacccacagg agagtgctct   5340
ggggaacagt ccccagatac caattatgag cctccagggg aagataaaac ccagggctct   5400
tcagaatgca tttctgaatt gtcattttct ggtcctaatg ctttggtacc tatggatttc   5460
ctggggaatc aggaagatat ccataatctt caactgcggg taaaagagac atcaaatgag   5520
aatttgagat tacttcatgt gatagaggac cgtgacagaa aagttgaaag tttgctaaat   5580
gaaatgaaag aattagactc aaaactccat ttacaggagg tacaactaat gaccaaaatt   5640
gaagcatgca tagaattgga aaaaatagtt ggggaactta agaaagaaaa ctcagattta   5700
agtgaaaaat tggaatattt ttcttgtgat caccaggagt tactccagag agtagaaact   5760
tctgaaggcc tcaattctga tttagaaatg catgcagata aatcatcacg tgaagatatt   5820
ggagataatg tggccaaggt gaatgacagc tggaaggaga gatttcttga tgtggaaaat   5880
gagctgagta ggatcagatc ggagaaagct agcattgagc atgaagccct ctacctggag   5940
gctgacttag aggtagttca aacagagaag ctatgtttag aaaaagacaa tgaaaataag   6000
cagaaggtta ttgtctgcct tgaagaagaa ctctcagtgg tcacaagtga gagaaaccag   6060
cttcgtggag aattagatac tatgtcaaaa aaaaccacgg cactggatca gttgtctgaa   6120
aaaatgaagg agaaaacaca agagcttgag tctcatcaaa gtgagtgtct ccattgcatt   6180
caggtggcag aggcagaggt gaaggaaaag acggaactcc ttcagacttt gtcctctgat   6240
gtgagtgagc tgttaaaaga caaaactcat ctccaggaaa agctgcagag tttggaaaag   6300
gactcacagg cactgtcttt gacaaaatgt gagctggaaa accaaattgc acaactgaat   6360
aaagagaaag aattgcttgt caaggaatct gaaagcctgc aggccagact gagtgaatca   6420
gattatgaaa agctgaatgt ctccaaggcc ttggaggccg cactggtgga gaaaggtgag   6480
ttcgcattga ggctgagctc aacacaggag gaagtgcatc agctgagaag aggcatcgag   6540
aaactgagag ttcgcattga ggccgatgaa aagaagcagc tgcacatcgc agagaaactg   6600
aaagaacgcg agcgggagaa tgattcactt aaggataaag ttgagaacct tgaaagggaa   6660
ttgcagatgt cagaagaaaa ccaggagcta gtgattcttg atgccgagaa ttccaaagca   6720
gaagtagaga ctctaaaaac acaaatagaa gagatggcca gaagcctgaa agtttttgaa   6780
ttagaccttg tcacgttaag gtctgaaaaa gaaaatctga caaaacaaat acaagaaaaa   6840
```

-continued caaggtcagt tgtcagaact agacaagtta ctctcttcat ttaaaagtct gttagaagaa 6900
aaggagcaag cagagataca gatcaaagaa gaatctaaaa ctgcagtgga gatgcttcag 6960
aatcagttaa aggagctaaa tgaggcagta gcagccttgt gtggtgacca agaaattatg 7020
aaggccacag aacagagtct agacccacca atagaggaag agcatcagct gagaaatagc 7080
attgaaaagc tgagagcccg cctagaagct gatgaaaaga agcagctctg tgtcttacaa 7140
caactgaagg aaagtgagca tcatgcagat ttacttaagg gtagagtgga gaaccttgaa 7200
agagagctag agatagccag gacaaaccaa gagcatgcag ctcttgaggc agagaattcc 7260
aaaggagagg tagagaccct aaaagcaaaa atagaaggga tgacccaaag tctgagaggt 7320
ctggaattag atgttgttac tataaggtca gaaaaagaaa atctgacaaa tgaattacaa 7380
aaagagcaag agcgaatatc tgaattagaa ataataaatt catcatttga aaatattttg 7440
caagaaaaag agcaagagaa agtacagatg aaagaaaaat caagcactgc catggagatg 7500
cttcaaacac aattaaaaga gctcaatgag agagtggcag ccctgcataa tgaccaagaa 7560
gcctgtaagg ccaaagagca gaatcttagt agtcaagtag agtgtcttga acttgagaag 7620
gctcagttgc tacaaggcct tgatgaggcc aaaaataatt atattgtttt gcaatcttca 7680
gtgaatggcc tcattcaaga agtagaagat ggcaagcaga aactggagaa gaaggatgaa 7740
gaaatcagta gactgaaaaa tcaaattcaa gaccaagagc agcttgtctc taaactgtcc 7800
caggtggaag gagagcacca actttggaag gagcaaaact tagaactgag aaatctgaca 7860
gtggaattgg agcagaagat ccaagtgcta caatccaaaa atgcctcttt gcaggacaca 7920
ttagaagtgc tgcagagttc ttacaagaat ctagagaatg agcttgaatt gacaaaaatg 7980
gacaaaatgt cctttgttga aaaagtaaac aaaatgactg caaaggaaac tgagctgcag 8040
agggaaatgc atgagatggc acagaaaaca gcagagctgc aagaagaact cagtggagag 8100
aaaaataggc tagctggaga gttgcagtta ctgttggaag aaataaagag cagcaaagat 8160
caattgaagg agctcacact agaaaatagt gaattgaaga agagcctaga ttgcatgcac 8220
aaagaccagg tggaaaagga agggaaagtg agagaggaaa tagctgaata tcagctacgg 8280
cttcatgaag ctgaaaagaa acaccaggct ttgcttttgg acacaaacaa acagtatgaa 8340
gtagaaatcc agacataccg agagaaattg acttctaaag aagaatgtct cagttcacag 8400
aagctggaga tagacctttt aaagtctagt aaagaagagc tcaataattc attgaaagct 8460
actactcaga ttttggaaga attgaagaaa accaagatgg acaatctaaa atatgtaaat 8520
cagttgaaga aggaaaatga acgtgcccag gggaaaatga agttgttgat caaatcctgt 8580
aaacagctgg aagaggaaaa ggagatactg cagaaagaac tctctcaact tcaagctgca 8640
caggagaagc agaaaacagg tactgttatg gataccaagg tcgatgaatt aacaactgag 8700
atcaaagaac tgaaagaaac tcttgaagaa aaaaccaagg aggcagatga atacttggat 8760
aagtactgtt ccttgcttat aagccatgaa aagttagaga aagctaaaga gatgttagag 8820
acacaagtgg cccatctgtg ttcacagcaa tctaaacaag attcccgagg gtctcctttg 8880
ctaggtccag ttgttccagg accatctcca atcccttctg ttactgaaaa gaggttatca 8940
tctggccaaa ataaagcttc aggcaagagg caaagatcca gtggaatatg ggagaatggt 9000
agaggaccaa cacctgctac ccccagagagc ttttctaaaa aaagcaagaa agcagtcatg 9060
agtggtattc accctgcaga agacacggaa ggtactgagt ttgagccaga gggacttcca 9120
gaagttgtaa agaaagggtt tgctgacatc ccgacaggaa agactagccc atatatcctg 9180
cgaagaacaa ccatggcaac tcggaccagc ccccgcctgg ctgcacagaa gttagcgcta 9240
tccccactga gtctcggcaa agaaaatctt gcagagtcct ccaaaccaac agctggtggc 9300
agcagatcac aaaaggtcaa agttgctcag cggagcccag tagattcagg caccatcctc 9360
cgagaaccca ccacgaaatc cgtcccagtc aataatcttc ctgagagaag tccgactgac 9420
agccccagag agggcctgag ggtcaagcga ggccgacttg tccccagccc caaagctgga 9480
ctggagtcca acggcagtga gaactgtaag gtccagtgaa ggcactttgt gtgtcagtac 9540
ccctgggagg tgccagtcat tgaatagata aggctgtgcc tacaggactt ctctttagtc 9600
agggcatgct ttattagtga ggagaaaaca attccttaga agtcttaaat atattgtact 9660
ctttagatct cccatgtgta ggtattgaaa aagtttggaa gcactgatca cctgttagca 9720
ttgccattcc tctactgcaa tgtaaatagt ataaagctat gtatataaag ctttttggta 9780
atatgttaca attaaaatga caagcactat atcacaatct ctgtttgtat gtgggtttta 9840
cactaaaaaa atgcaaaaca cattttattc ttctaattaa cagctcctag gaaaatgtag 9900
acttttgctt tatgatattc tatctgtagt atgaggcatg gaatagtttt gtatcgggaa 9960
tttctcagag ctgagtaaaa tgaaggaaaa gcatgttatg tgtttttaag gaaaatgtgc 10020
acacatatac atgtaggagt gtttatcttt ctcttacaat ctgttttaga catctttgct 10080
tatgaaacct gtacatatgt gtgtgtgggt atgtgtttat ttccagtgag ggctgcaggc 10140
ttcctagagg tgtgctatac catgcgtctg tcgttgtgct tttttctgtt tttagaccaa 10200
ttttttacag ttctttggta agcattgtcg tatctggtga tggattaaca tatagccttt 10260
gttttctaat aaaatagtcg ccttcgtttt ctgtaaaaaa aaaaaaaaaa aaaaaa 10316

<210> SEQ ID NO 105
<211> LENGTH: 2639
<212> TYPE: DNA
<213> ORGANISM: Homo sapiens

<400> SEQUENCE: 105
ggcacgaggg gccgacgcga gcgccgcgct tcgcttcagc tgctagctgg cccaagggag 60
gcgaccgcgg agggtggcga ggggcggcca ggacccgcag ccccggggcc gggccggtcc 120
ggaccgccag ggagggcagg tcagtgggca gatcgcgtcc gcgggattca atctctgccc 180
gctctgataa cagtcctttt ccctggcgct cacttcgtgc ctggcacccg gctgggcgcc 240
tcaagaccgt tgtctcttcg atcgcttctt tggacttggc gaccatttca gagatgtctt 300
ccagaagtac caaagattta attaaaagta agtggggatc gaagcctagt aactccaaat 360
ccgaaactac attagaaaaa ttaaagggag aaattgcaca cttaaagaca tcagtggatg 420
aaatcacaag tgggaaagga aagctgactg ataaagagag acacagactt ttggagaaaa 480
ttcgagtcct tgaggctgag aaggagaaga atgcttatca actcacagag aaggacaaag 540
aaatacagcg actgagagac caactgaagg ccagatatag tactaccgca ttgcttgaac 600
agctggaaga gacaacgaga gaaggagaaa ggagggagca ggtgttgaaa gccttatctg 660
aagagaaaga cgtattgaaa caacagttgt ctgctgcaac ctcacgaatt gctgaacttg 720
aaagcaaaac caatacactc cgtttatcac agactgtggc tccaaactgc ttcaactcat 780
caataaataa tattcatgaa atggaaatac agctgaaaga tgctctggag aaaaatcagc 840
agtggctcgt gtatgatcag cagcgggaag tctatgtaaa aggactttta gcaaagatct 900
ttgagttgga aaagaaaacg gaaacagctg ctcattcact cccacagcag acaaaaaagc 960
ctgaatcaga aggttatctt caagaagaga agcagaaatg ttacaacgat ctcttggcaa 1020
gtgcaaaaaa agatcttgag gttgaacgac aaaccataac tcagctgagt tttgaactga 1080
gtgaatttcg aagaaaatat gaagaaaccc aaaaagaagt tcacaattta aatcagctgt 1140
tgtattcaca aagaagggca gatgtgcaac atctggaaga tgataggcat aaaacagaga 1200
agatacaaaa actcagggaa gagaatgata ttgctagggg aaaacttgaa gaagagaaga 1260
agagatccga agagctctta tctcaggtcc agtttcttta cacatctctg ctaaagcagc 1320
aagaagaaca aacaagggta gctctgttgg aacaacagat gcaggcatgt actttagact 1380
ttgaaaatga aaaactcgac cgtcaacatg tgcagcatca attgcatgta attcttaagg 1440
agctccgaaa agcaagaaat caaataacac agttggaatc cttgaaacag cttcatgagt 1500
ttgccatcac agagccatta gtcactttcc aaggagagac tgaaaacaga gaaaaagttg 1560
ccgcctcacc aaaaagtccc actgctgcac tcaatgaaag cctggtggaa tgtcccaagt 1620
gcaatataca gtatccagcc actgagcatc gcgatctgct tgtccatgtg gaatactgtt 1680
caaagtagca aaataagtat ttgttttgat attaaaagat tcaatactgt attttctgtt 1740
agcttgtggg catttttgaat tatatatttc acattttgca taaaactgcc tatctacctt 1800
tgacactcca gcatgctagt gaatcatgta tcttttaggc tgctgtgcat ttctcttggc 1860
agtgatacct ccctgacatg gttcatcatc aggctgcaat gacagaatgt ggtgagcagc 1920
gtctactgag actactaaca ttttgcactg tcaaaatact tggtgaggaa aagatagctc 1980
aggttattgc taatgggtta atgcaccagc aagcaaaata ttttatgttt tgggggtttg 2040
aaaaatcaaa gataattaac caaggatctt aactgtgttc gcattttttta tccaagcact 2100 tagaaaacct acaatcctaa ttttgatgtc cattgttaag aggtggtgat agatactatt 2160 tttttttca tattgtatag cggttattag aaaagttggg gattttcttg atctttattg 2220
ctgcttacca ttgaaactta acccagctgt gttccccaac tctgttctgc gcacgaaaca 2280
gtatctgttt gaggcataat cttaagtggc cacacacaat gttttctctt atgttatctg 2340
gcagtaactg taacttgaat tacattagca cattctgctt agctaaaatt gttaaaataa 2400
actttaataa acccatgtag ccctctcatt tgattgacag tattttagtt atttttggca 2460
ttcttaaagc tgggcaatgt aatgatcaga tctttgtttg tctgaacagg tatttttata 2520
catgcttttt gtaaaccaaa aacttttaaa tttcttcagg ttttctaaca tgcttaccac 2580
tgggctactg taaatgagaa aagaataaaa ttatttaatg ttttaaaaaa aaaaaaaaa 2639

<210> SEQ ID NO 106
<211> LENGTH: 2632
<212> TYPE: DNA
<213> ORGANISM: Homo sapiens

<400> SEQUENCE: 106
ggcggctgag cctgagcggg gatgtagagg cggcggcagc agaggcggca ctggcggcaa 60
gagcagacgc ccgagccgag cgagaagagc ggcagagcct tatcccctga agccgggccc 120
cgcgtcccag ccctgcccag cccgcgccca gccatgcgcg ccgcctgctg agtccgggcg 180
ccgcacgctg agccctccgc ccgcgagccg cgctcagctc gggggtgatt agttgctttt 240
tgttgttttt taatttgggc cgcggggagg gggaggaggg gcaggtgctg caggctcccc 300
cccctccccg cctcgggcca gccgcggcgg cgcgactcgg gctccggacc cgggcactgc 360
tggcggctgg agcggagcgc accgcggcgg tggtgcccag agcggagcgc agctccctgc 420
cccgcccctc cccctcggcc tcgcggcgac ggcggcggtg gcggcttgga cgactcggag 480
agccgagtga agacatttcc acctggacac ctgaccatgt gcctgccctg agcagcgagg 540

-continued

```
cccaccaggc atctctgttg tgggcagcag ggccaggtcc tggtctgtgg accctcggca    600

gttggcaggc tccctctgca gtggggtctg ggcctcggcc ccaccatgtc gagcctcggc    660

ggtggctccc aggatgccgg cggcagtagc agcagcagca ccaatggcag cggtggcagt    720

ggcagcagtg gcccaaaggc aggagcagca gacaagagtg cagtggtggc tgccgccgca    780

ccagcctcag tggcagatga cacaccaccc cccgagcgtc ggaacaagag cggtatcatc    840

agtgagcccc tcaacaagag cctgcgccgc tcccgcccgc tctcccacta ctcttctttt    900

ggcagcagtg gtggtagtgg cggtggcagc atgatgggcg gagagtctgc tgacaaggcc    960

actgcggctg cagccgctgc ctccctgttg gccaatgggc atgacctggc ggcggccatg   1020

gcggtggaca aaagcaaccc tacctcaaag cacaaaagtg gtgctgtggc cagcctgctg   1080

agcaaggcag agcgggccac ggagctggca gccgagggac agctgacgct gcagcagttt   1140

gcgcagtcca cagagatgct gaagcgcgtg gtgcaggagc atctcccgct gatgagcgag   1200

gcgggtgctg gcctgcctga catggaggct gtggcaggtg ccgaagccct caatggccag   1260

tccgacttcc cctacctggg cgctttcccc atcaacccag gcctcttcat tatgaccccg   1320

gcaggtgtgt tcctggccga gagcgcgctg cacatggcgg gcctggctga gtaccccatg   1380

cagggagagc tggcctctgc catcagctcc ggcaagaaga agcggaaacg ctgcggcatg   1440

tgcgcgccct gccggcggcg catcaactgc gagcagtgca gcagttgtag gaatcgaaag   1500

actggccatc agatttgcaa attcagaaaa tgtgaggaac tcaaaaagaa gccttccgct   1560

gctctggaga aggtgatgct tccgacggga gccgccttcc ggtggtttca gtgacggcgg   1620

cggaacccaa agctgccctc tccgtgcaat gtcactgctc gtgtggtctc cagcaaggga   1680

ttcgggcgaa gacaaacgga tgcacccgtc tttagaacca aaaatattct ctcacagatt   1740

tcattcctgt ttttatatat atattttttg ttgtcgtttt aacatctcca cgtccctagc   1800

ataaaaagaa aaagaaaaaa atttaaactg ctttttcgga agaacaacaa caaaaaagag   1860

gtaaagacga atctataaag taccgagact tcctgggcaa agaatggaca atcagtttcc   1920

ttcctgtgtc gatgtcgatg ttgtctgtgc aggagatgca gtttttgtgt agagaatgta   1980

aattttctgt aacctttga aatctagtta ctaataagca ctactgtaat ttagcacagt    2040

ttaactccac cctcatttaa acttcctttg attctttccg accatgaaat agtgcatagt   2100

ttgcctggag aatccactca cgttcataaa gagaatgttg atggcgccgt gtagaagccg   2160

ctctgtatcc atccacgcgt gcagagctgc cagcagggag ctcacagaag gggagggagc   2220

accaggccag ctgagctgca cccacagtcc cgagactggg atcccccacc ccaacagtga   2280

ttttggaaaa aaaaatgaaa gttctgttcg tttatccatt gcgatctggg gagccccatc   2340

tcgatatttc caatcctggc tacttttctt agagaaaata agtccttttt ttctggcctt   2400

gctaatggca acagaagaaa gggcttcttt gcgtggtccc ctgctggtgg gggtgggtcc   2460

ccaggggggcc ccctgcggcc tgggcccccc tgcccacggc cagcttcctg ctgatgaaca  2520

tgctgtttgt attgttttag gaaaccaggc tgttttgtga ataaaacgaa tgcatgtttg   2580

tgtcacgaaa aaaaaaaaaa aaaaaaaaaa aaaaaaaaaa aaaaaaaaaa aa           2632
```

<210> SEQ ID NO 107
<211> LENGTH: 5616
<212> TYPE: DNA
<213> ORGANISM: Homo sapiens

<400> SEQUENCE: 107

-continued

```
ccccggcgca gcgcggccgc agcagcctcc gccccccgca cggtgtgagc gcccgacgcg     60
gccgaggcgg ccggagtccc gagctagccc cggcggccgc cgccgcccag accggacgac    120
aggccacctc gtcggcgtcc gcccgagtcc ccgcctcgcc gccaacgcca caaccaccgc    180
gcacggcccc ctgactccgt ccagtattga tcgggagagc cggagcgagc tcttcgggga    240
gcagcgatgc gaccctccgg gacggccggg gcagcgctcc tggcgctgct ggctgcgctc    300
tgcccggcga gtcgggctct ggaggaaaag aaagtttgcc aaggcacgag taacaagctc    360
acgcagttgg gcacttttga agatcatttt ctcagcctcc agaggatgtt caataactgt    420
gaggtggtcc ttgggaattt ggaaattacc tatgtgcaga ggaattatga tctttccttc    480
ttaaagacca tccaggaggt ggctggttat gtcctcattg ccctcaacac agtggagcga    540
attcctttgg aaaacctgca gatcatcaga ggaaatatgt actacgaaaa ttcctatgcc    600
ttagcagtct tatctaacta tgatgcaaat aaaaccggac tgaaggagct gcccatgaga    660
aatttacagg aaatcctgca tggcgccgtg cggttcagca acaaccctgc cctgtgcaac    720
gtggagagca tccagtggcg ggacatagtc agcagtgact ttctcagcaa catgtcgatg    780
gacttccaga accacctggg cagctgccaa aagtgtgatc caagctgtcc caatgggagc    840
tgctggggtg caggagagga gaactgccag aaactgacca aaatcatctg tgcccagcag    900
tgctccgggc gctgccgtgg caagtccccc agtgactgct gccacaacca gtgtgctgca    960
ggctgcacag gcccccggga gagcgactgc ctggtctgcc gcaaattccg agacgaagcc   1020
acgtgcaagg acacctgccc cccactcatg ctctacaacc ccaccacgta ccagatggat   1080
gtgaaccccg agggcaaata cagctttggt gccacctgcg tgaagaagtg tccccgtaat   1140
tatgtggtga cagatcacgg ctcgtgcgtc cgagcctgtg gggccgacag ctatgagatg   1200
gaggaagacg gcgtccgcaa gtgtaagaag tgcgaagggc cttgccgcaa agtgtgtaac   1260
ggaataggta ttggtgaatt taaagactca ctctccataa atgctacgaa tattaaacac   1320
ttcaaaaact gcacctccat cagtggcgat ctccacatcc tgccggtggc atttaggggt   1380
gactccttca cacatactcc tcctctggat ccacaggaac tggatattct gaaaaccgta   1440
aaggaaatca cagggttttt gctgattcag gcttggcctg aaaacaggac ggacctccat   1500
gcctttgaga acctagaaat catacgcggc aggaccaagc aacatggtca gttttctctt   1560
gcagtcgtca gcctgaacat aacatccttg ggattacgct ccctcaagga gataagtgat   1620
ggagatgtga taatttcagg aaacaaaaat ttgtgctatg caaatacaat aaactggaaa   1680
aaactgtttg ggacctccgg tcagaaaacc aaaattataa gcaacagagg tgaaaacagc   1740
tgcaaggcca caggccaggt ctgccatgcc ttgtgctccc ccgagggctg ctggggcccg   1800
gagcccaggg actgcgtctc ttgccggaat gtcagccgag gcagggaatg cgtggacaag   1860
tgcaaccttc tggagggtga gccaagggag tttgtggaga actctgagtg catacagtgc   1920
cacccagagt gcctgcctca ggccatgaac atcacctgca caggacgggg accagacaac   1980
tgtatccagt gtgcccacta cattgacggc ccccactgcg tcaagacctg cccggcagga   2040
gtcatgggag aaaacaacac cctggtctgg aagtacgcag acgccggcca tgtgtgccac   2100
ctgtgccatc caaactgcac ctacggatgc actgggccag gtcttgaagg ctgtccaacg   2160
aatgggccta agatcccgtc catcgccact gggatggtgg gggccctcct cttgctgctg   2220
gtggtggccc tggggatcgg cctcttcatg cgaaggcgcc acatcgttcg gaagcgcacg   2280
ctgcggaggc tgctgcagga gagggagctt gtggagcctc ttacacccag tggagaagct   2340
cccaaccaag ctctcttgag gatcttgaag gaaactgaat tcaaaaagat caaagtgctg   2400
```

-continued

```
ggctccggtg cgttcggcac ggtgtataag ggactctgga tcccagaagg tgagaaagtt   2460
aaaattcccg tcgctatcaa ggaattaaga gaagcaacat ctccgaaagc caacaaggaa   2520
atcctcgatg aagcctacgt gatggccagc gtggacaacc cccacgtgtg ccgcctgctg   2580
ggcatctgcc tcacctccac cgtgcagctc atcacgcagc tcatgccctt cggctgcctc   2640
ctggactatg tccgggaaca caaagacaat attggctccc agtacctgct caactggtgt   2700
gtgcagatcg caaagggcat gaactacttg gaggaccgtc gcttggtgca ccgcgacctg   2760
gcagccagga acgtactggt gaaaacaccg cagcatgtca agatcacaga ttttgggctg   2820
gccaaactgc tgggtgcgga agagaaagaa taccatgcag aaggaggcaa agtgcctatc   2880
aagtggatgg cattggaatc aattttacac agaatctata cccaccagag tgatgtctgg   2940
agctacgggg tgaccgtttg ggagttgatg acctttggat ccaagccata tgacggaatc   3000
cctgccagcg agatctcctc catcctggag aaaggagaac gcctccctca gccaccccata   3060
tgtaccatcg atgtctacat gatcatggtc aagtgctgga tgatagacgc agatagtcgc   3120
ccaaagttcc gtgagttgat catcgaattc tccaaaatgg cccgagaccc ccagcgctac   3180
cttgtcattc agggggatga aagaatgcat ttgccaagtc ctacagactc caacttctac   3240
cgtgccctga tggatgaaga agacatggac gacgtggtgg atgccgacga gtacctcatc   3300
ccacagcagg gcttcttcag cagcccctcc acgtcacgga ctcccctcct gagctctctg   3360
agtgcaacca gcaacaattc caccgtggct tgcattgata gaaatgggct gcaaagctgt   3420
cccatcaagg aagacagctt cttgcagcga tacagctcag accccacagg cgccttgact   3480
gaggacagca tagacgacac cttcctccca gtgcctgaat acataaacca gtccgttccc   3540
aaaaggcccg ctggctctgt gcagaatcct gtctatcaca atcagcctct gaaccccgcg   3600
cccagcagag acccacacta ccaggacccc cacagcactg cagtgggcaa ccccgagtat   3660
ctcaacactg tccagcccac ctgtgtcaac agcacattcg acagccctgc ccactgggcc   3720
cagaaaggca gccaccaaat tagcctggac aaccctgact accagcagga cttctttccc   3780
aaggaagcca agccaaatgg catctttaag ggctccacag ctgaaaatgc agaataccta   3840
agggtcgcgc cacaaagcag tgaatttatt ggagcatgac cacggaggat agtatgagcc   3900
ctaaaaatcc agactctttc gatacccagg accaagccac agcaggtcct ccatcccaac   3960
agccatgccc gcattagctc ttagacccac agactggttt tgcaacgttt acaccgacta   4020
gccaggaagt acttccacct cgggcacatt ttgggaagtt gcattccttt gtcttcaaac   4080
tgtgaagcat ttacagaaac gcatccagca agaatattgt ccctttgagc agaaatttat   4140
ctttcaaaga ggtatatttg aaaaaaaaaa aaagtatatg tgaggatttt tattgattgg   4200
ggatcttgga gtttttcatt gtcgctattg atttttactt caatgggctc ttccaacaag   4260
gaagaagctt gctggtagca cttgctaccc tgagttcatc caggcccaac tgtgagcaag   4320
gagcacaagc cacaagtctt ccagaggatg cttgattcca gtggttctgc ttcaaggctt   4380
ccactgcaaa acactaaaga tccaagaagg ccttcatggc cccagcaggc cggatcggta   4440
ctgtatcaag tcatggcagg tacagtagga taagccactc tgtcccttcc tgggcaaaga   4500
agaaacggag gggatggaat tcttccttag acttactttt gtaaaaatgt ccccacggta   4560
cttactcccc actgatggac cagtggtttc cagtcatgag cgttagactg acttgtttgt   4620
cttccattcc attgttttga aactcagtat gctgcccctg tcttgctgtc atgaaatcag   4680
caagagagga tgacacatca aataataact cggattccag cccacattgg attcatcagc   4740
```

```
atttggacca atagcccaca gctgagaatg tggaatacct aaggatagca ccgcttttgt   4800
tctcgcaaaa acgtatctcc taatttgagg ctcagatgaa atgcatcagg tcctttgggg   4860
catagatcag aagactacaa aaatgaagct gctctgaaat ctcctttagc catcacccca   4920
accccccaaa attagtttgt gttacttatg gaagatagtt ttctcctttt acttcacttc   4980
aaaagctttt tactcaaaga gtatatgttc cctccaggtc agctgccccc aaacccccctc  5040
cttacgcttt gtcacacaaa aagtgtctct gccttgagtc atctattcaa gcacttacag   5100
ctctggccac aacagggcat tttacaggtg cgaatgacag tagcattatg agtagtgtgg   5160
aattcaggta gtaaatatga aactagggtt tgaaattgat aatgctttca caacatttgc   5220
agatgtttta gaaggaaaaa agttccttcc taaaataatt tctctacaat tggaagattg   5280
gaagattcag ctagttagga gcccaccttt tttcctaatc tgtgtgtgcc ctgtaacctg   5340
actggttaac agcagtcctt tgtaaacagt gttttaaact ctcctagtca atatccaccc   5400
catccaattt atcaaggaag aaatggttca gaaaatattt tcagcctaca gttatgttca   5460
gtcacacaca catacaaaat gttccttttg cttttaaagt aatttttgac tcccagatca   5520
gtcagagccc ctacagcatt gttaagaaag tatttgattt ttgtctcaat gaaaataaaa   5580
ctatattcat ttccactcta aaaaaaaaaa aaaaaa                             5616
```

<210> SEQ ID NO 108
<211> LENGTH: 4816
<212> TYPE: DNA
<213> ORGANISM: Homo sapiens

<400> SEQUENCE: 108

```
gttcccggat ttttgtgggc gcctgccccg cccctcgtcc ccctgctgtg tccatatatc     60
gaggcgatag ggttaaggga aggcggacgc ctgatgggtt aatgagcaaa ctgaagtgtt    120
ttccatgatc ttttttgagt cgcaattgaa gtaccacctc ccgagggtga ttgcttcccc    180
atgcggggta gaacctttgc tgtcctgttc accactctac ctccagcaca gaatttggct    240
tatgcctact caatgtgaag atgatgagga tgaaaacctt tgtgatgatc cacttccact    300
taatgaatgg tggcaaagca aagctatatt caagaccaca tgcaaagcta ctccctgagc    360
aaagagtcac agataaaacg ggggcaccag tagaatggcc aggacaaacg cagtgcagca    420
cagagactca gaccctggca gccatgcctg cgcaggcagt gatgagagtg acatgtactg    480
ttgtggacat gcacaaaagt gagtgtgcac cggcacagac atgaagctgc ggctccctgc    540
cagtcccgag acccacctgg acatgctccg ccacctctac cagggctgcc aggtggtgca    600
gggaaacctg gaactcacct acctgcccac caatgccagc ctgtccttcc tgcaggatat    660
ccaggaggtg cagggctacg tgctcatcgc tcacaaccaa gtgaggcagg tcccactgca    720
gaggctgcgg attgtgcgag gcacccagct ctttgaggac aactatgccc tggccgtgct    780
agacaatgga gacccgctga acaataccac ccctgtcaca ggggcctccc caggaggcct    840
gcgggagctg cagcttcgaa gcctcacaga gatcttgaaa ggaggggtct tgatccagcg    900
gaacccccag ctctgctacc aggacacgat tttgtggaag gacatcttcc acaagaacaa    960
ccagctggct ctcacactga tagacaccaa ccgctctcgg gcctgccacc cctgttctcc   1020
gatgtgtaag ggctcccgct gctggggaga gagttctgag gattgtcaga gcctgacgcg   1080
cactgtctgt gccggtggct gtgcccgctg caaggggcca ctgcccactg actgctgcca   1140
tgagcagtgt gctgccggct gcacgggccc caagcactct gactgcctgg cctgcctcca   1200
cttcaaccac agtggcatct gtgagctgca ctgcccagcc ctggtcacct acaacacaga   1260
```

-continued cacgtttgag tccatgccca atcccgaggg ccggtataca ttcggcgcca gctgtgtgac 1320
tgcctgtccc tacaactacc tttctacgga cgtgggatcc tgcaccctcg tctgccccct 1380
gcacaaccaa gaggtgacag cagaggatgg aacacagcgg tgtgagaagt gcagcaagcc 1440
ctgtgcccga gtgtgctatg gtctgggcat ggagcacttg cgagaggtga gggcagttac 1500
cagtgccaat atccaggagt ttgctggctg caagaagatc tttgggagcc tggcatttct 1560
gccggagagc tttgatgggg acccagcctc caacactgcc ccgctccagc cagagcagct 1620
ccaagtgttt gagactctgg aagagatcac aggttaccta tacatctcag catggccgga 1680
cagcctgcct gacctcagcg tcttccagaa cctgcaagta atccggggac gaattctgca 1740
caatggcgcc tactcgctga ccctgcaagg gctgggcatc agctggctgg ggctgcgctc 1800
actgagggaa ctgggcagtg gactggccct catccaccat aacacccacc tctgcttcgt 1860
gcacacggtg ccctgggacc agctctttcg gaacccgcac caagctctgc tccacactgc 1920
caaccggcca gaggacgagt gtgtgggcga gggcctggcc tgccaccagc tgtgcgcccg 1980
agggcactgc tggggtccag ggcccaccca gtgtgtcaac tgcagccagt tccttcgggg 2040
ccaggagtgc gtggaggaat gccgagtact gcaggggctc cccagggagt atgtgaatgc 2100
caggcactgt ttgccgtgcc accctgagtg tcagccccag aatggctcag tgacctgttt 2160
tggaccggag gctgaccagt gtgtggcctg tgcccactat aaggaccctc ccttctgcgt 2220
ggcccgctgc cccagcggtg tgaaacctga cctctcctac atgcccatct ggaagtttcc 2280
agatgaggag ggcgcatgcc agccttgccc catcaactgc acccactcct gtgtggacct 2340
ggatgacaag ggctgccccg ccgagcagag agccagccct ctgacgtcca tcatctctgc 2400
ggtggttggc attctgctgg tcgtggtctt gggggtggtc tttgggatcc tcatcaagcg 2460
acggcagcag aagatccgga agtacacgat gcggagactg ctgcaggaaa cggagctggt 2520
ggagccgctg acacctagcg gagcgatgcc caaccaggcg cagatgcgga tcctgaaaga 2580
gacggagctg aggaaggtga aggtgcttgg atctggcgct tttggcacag tctacaaggg 2640
catctggatc cctgatgggg agaatgtgaa aattccagtg gccatcaaag tgttgaggga 2700
aaacacatcc cccaaagcca acaaagaaat cttagacgaa gcatacgtga tggctggtgt 2760
gggctcccca tatgtctccc gccttctggg catctgcctg acatccacgg tgcagctggt 2820
gacacagctt atgccctatg gctgcctctt agaccatgtc cgggaaaacc gcggacgcct 2880
gggctcccag gacctgctga actggtgtat gcagattgcc aaggggatga gctacctgga 2940
ggatgtgcgg ctcgtacaca gggacttggc cgctcggaac gtgctggtca agagtcccaa 3000
ccatgtcaaa attacagact tcgggctggc tcggctgctg gacattgacg agacagagta 3060
ccatgcagat gggggcaagg tgcccatcaa gtggatggcg ctggagtcca ttctccgccg 3120
gcggttcacc caccagagtg atgtgtggag ttatggtgtg actgtgtggg agctgatgac 3180
ttttggggcc aaaccttacg atgggatccc agcccgggag atccctgacc tgctggaaaa 3240
gggggagcgg ctgccccagc cccccatctg caccattgat gtctacatga tcatggtcaa 3300
atgttggatg attgactctg aatgtcggcc aagattccgg gagttggtgt ctgaattctc 3360
ccgcatggcc agggaccccc agcgctttgt ggtcatccag aatgaggact tgggcccagc 3420
cagtcccttg gacagcacct tctaccgctc actgctggag gacgatgaca tgggggacct 3480
ggtggatgct gaggagtatc tggtacccca gcagggcttc ttctgtccag accctgcccc 3540
gggcgctggg ggcatggtcc accacaggca ccgcagctca tctaccagga gtggcggtgg 3600
ggacctgaca ctagggctgg agccctctga agaggaggcc cccaggtctc cactggcacc 3660
ctccgaaggg gctggctccg atgtatttga tggtgacctg ggaatggggg cagccaaggg 3720
gctgcaaagc ctccccacac atgaccccag ccctctacag cggtacagtg aggaccccac 3780
agtacccctg ccctctgaga ctgatggcta cgttgccccc ctgacctgca gcccccagcc 3840
tgaatatgtg aaccagccag atgttcggcc ccagccccct tcgccccgag agggccctct 3900
gcctgctgcc cgacctgctg gtgccactct ggaaaggccc aagactctct ccccagggaa 3960
gaatggggtc gtcaaagacg tttttgcctt tgggggtgcc gtggagaacc ccgagtactt 4020
gacaccccag ggaggagctg cccctcagcc ccaccctcct cctgccttca gcccagcctt 4080
cgacaacctc tattactggg accaggaccc accagagcgg ggggctccac ccagcacctt 4140
caaagggaca cctacggcag agaacccaga gtacctgggt ctggacgtgc cagtgtgaac 4200
cagaaggcca agtccgcaga agccctgatg tgtcctcagg gagcagggaa ggcctgactt 4260
ctgctggcat caagaggtgg gagggccctc cgaccacttc caggggaacc tgccatgcca 4320
ggaacctgtc ctaaggaacc ttccttcctg cttgagttcc cagatggctg gaaggggtcc 4380
agcctcgttg gaagaggaac agcactgggg agtctttgtg gattctgagg ccctgcccaa 4440
tgagactcta gggtccagtg gatgccacag cccagcttgg ccctttcctt ccagatcctg 4500
ggtactgaaa gccttaggga agctggcctg agaggggaag cggccctaag ggagtgtcta 4560
agaacaaaag cgacccattc agagactgtc cctgaaacct agtactgccc cccatgagga 4620
aggaacagca atggtgtcag tatccaggct ttgtacagag tgcttttctg tttagttttt 4680
actttttttg ttttgttttt ttaaagatga aataaagacc caggggggaga atgggtgttg 4740 tatggggagg caagtgtggg gggtccttct ccacacccac tttgtccatt tgcaaatata 4800
ttttggaaaa cagcta 4816

<210> SEQ ID NO 109
<211> LENGTH: 6466
<212> TYPE: DNA
<213> ORGANISM: Homo sapiens

<400> SEQUENCE: 109
atggtcataa cagcctcctg tctaccgact cagaacggat tttaccaaaa ctgaaaatgc 60
aggctccatg ctcagaagct ctttaacagg ctcgaaaggt ccatgctcct ttctcctgcc 120
cattctatag cataagaaga cagtctctga gtgataatct tctcttcaag aagaagaaaa 180
ctaggaagga gtaagcacaa agatctcttc acattctccg ggactgcggt accaaatatc 240
agcacagcac ttcttgaaaa aggatgtaga ttttaatctg aactttgaac catcactgag 300
gtggcccgcc ggtttctgag ccttctgccc tgcggggaca cggtctgcac cctgcccgcg 360
gccacggacc atgaccatga ccctccacac caaagcatct gggatggccc tactgcatca 420
gatccaaggg aacgagctgg agcccctgaa ccgtccgcag ctcaagatcc ccctggagcg 480
gcccctgggc gaggtgtacc tggacagcag caagcccgcc gtgtacaact accccgaggg 540
cgccgcctac gagttcaacg ccgcggccgc cgccaacgcg caggtctacg gtcagaccgg 600
cctcccctac ggcccccgggt ctgaggctgc ggcgttcggc tccaacggcc tggggggttt 660
ccccccactc aacagcgtgt ctccgagccc gctgatgcta ctgcacccgc cgccgcagct 720
gtcgcctttc ctgcagcccc acggccagca ggtgccctac tacctggaga acgagcccag 780
cggctacacg gtgcgcgagg ccggcccgcc ggcattctac aggccaaatt cagataatcg 840
acgccagggt ggcagagaaa gattggccag taccaatgac aagggaagta tggctatgga 900

-continued

```
atctgccaag gagactcgct actgtgcagt gtgcaatgac tatgcttcag gctaccatta    960
tggagtctgg tcctgtgagg gctgcaaggc cttcttcaag agaagtattc aaggacataa   1020
cgactatatg tgtccagcca ccaaccagtg caccattgat aaaaacagga ggaagagctg   1080
ccaggcctgc cggctccgca aatgctacga agtgggaatg atgaaaggtg ggatacgaaa   1140
agaccgaaga ggagggagaa tgttgaaaca caagcgccag agagatgatg gggagggcag   1200
gggtgaagtg gggtctgctg gagacatgag agctgccaac ctttggccaa gcccgctcat   1260
gatcaaacgc tctaagaaga acagcctggc cttgtccctg acggccgacc agatggtcag   1320
tgccttgttg gatgctgagc cccccatact ctattccgag tatgatccta ccagaccctt   1380
cagtgaagct tcgatgatgg gcttactgac caacctggca gacagggagc tggttcacat   1440
gatcaactgg gcgaagaggg tgccaggctt tgtggatttg accctccatg atcaggtcca   1500
ccttctagaa tgtgcctggc tagagatcct gatgattggt ctcgtctggc gctccatgga   1560
gcacccaggg aagctactgt ttgctcctaa cttgctcttg gacaggaacc agggaaaatg   1620
tgtagagggc atggtggaga tcttcgacat gctgctggct acatcatctc ggttccgcat   1680
gatgaatctg cagggagagg agtttgtgtg cctcaaatct attattttgc ttaattctgg   1740
agtgtacaca tttctgtcca gcaccctgaa gtctctggaa gagaaggacc atatccaccg   1800
agtcctggac aagatcacag acactttgat ccacctgatg gccaaggcag gcctgaccct   1860
gcagcagcag caccagcggc tggcccagct cctcctcatc ctctcccaca tcaggcacat   1920
gagtaacaaa ggcatggagc atctgtacag catgaagtgc aagaacgtgg tgcccctcta   1980
tgacctgctg ctggagatgc tggacgccca ccgcctacat gcgcccacta gccgtggagg   2040
ggcatccgtg gaggagacgg accaaagcca cttggccact gcgggctcta cttcatcgca   2100
ttccttgcaa aagtattaca tcacggggga ggcagagggt ttccctgcca cggtctgaga   2160
gctccctggc tcccacacgg ttcagataat ccctgctgca ttttaccctc atcatgcacc   2220
actttagcca aattctgtct cctgcataca ctccggcatg catccaacac caatggcttt   2280
ctagatgagt ggccattcat ttgcttgctc agttcttagt ggcacatctt ctgtcttctg   2340
ttgggaacag ccaaagggat tccaaggcta aatctttgta acagctctct ttcccccttg   2400
ctatgttact aagcgtgagg attcccgtag ctcttcacag ctgaactcag tctatgggtt   2460
ggggctcaga taactctgtg catttaagct acttgtagag acccaggcct ggagagtaga   2520
cattttgcct ctgataagca ctttttaaat ggctctaaga ataagccaca gcaaagaatt   2580
taaagtggct cctttaattg gtgacttgga gaaagctagg tcaagggttt attatagcac   2640
cctcttgtat tcctatggca atgcatcctt ttatgaaagt ggtacacctt aaagctttta   2700
tatgactgta gcagagtatc tggtgattgt caattcattc cccctatagg aatacaaggg   2760
gcacacaggg aaggcagatc ccctagttgg caagactatt ttaacttgat acactgcaga   2820
ttcagatgtg ctgaaagctc tgcctctggc tttccggtca tgggttccag ttaattcatg   2880
cctcccatgg acctatggag agcagcaagt tgatcttagt taagtctccc tatatgaggg   2940
ataagttcct gatttttgtt tttatttttg tgttacaaaa gaaagccctc cctccctgaa   3000
cttgcagtaa ggtcagcttc aggacctgtt ccagtgggca ctgtacttgg atcttcccgg   3060
cgtgtgtgtg ccttacacag ggtgaactg ttcactgtgg tgatgcatga tgagggtaaa    3120
tggtagttga aaggagcagg ggccctggtg ttgcatttag ccctggggca tggagctgaa   3180
cagtacttgt gcaggattgt tgtggctact agagaacaag agggaaagta gggcagaaac   3240
```

-continued

```
tggatacagt tctgaggcac agccagactt gctcagggtg gccctgccac aggctgcagc   3300
tacctaggaa cattccttgc agaccccgca ttgccctttg ggggtgccct gggatccctg   3360
gggtagtcca gctcttcttc atttcccagc gtggccctgg ttggaagaag cagctgtcac   3420
agctgctgta gacagctgtg ttcctacaat tggcccagca ccctggggca cgggagaagg   3480
gtggggaccg ttgctgtcac tactcaggct gactggggcc tggtcagatt acgtatgccc   3540
ttggtggttt agagataatc caaaatcagg gtttggtttg gggaagaaaa tcctccccct   3600
tcctccccg ccccgttccc taccgcctcc actcctgcca gctcatttcc ttcaatttcc   3660
tttgacctat aggctaaaaa agaaaggctc attccagcca cagggcagcc ttccctgggc   3720
ctttgcttct ctagcacaat tatgggttac ttcctttttc ttaacaaaaa agaatgtttg   3780
atttcctctg ggtgacctta ttgtctgtaa ttgaaaccct attgagaggt gatgtctgtg   3840
ttagccaatg acccaggtga gctgctcggg cttctcttgg tatgtcttgt ttggaaaagt   3900
ggatttcatt catttctgat tgtccagtta agtgatcacc aaaggactga gaatctggga   3960
gggcaaaaaa aaaaaaaaag tttttatgtg cacttaaatt tggggacaat tttatgtatc   4020
tgtgttaagg atatgtttaa gaacataatt cttttgttgc tgtttgttta agaagcacct   4080
tagtttgttt aagaagcacc ttatatagta taatatatat ttttttgaaa ttacattgct   4140
tgtttatcag acaattgaat gtagtaattc tgttctggat ttaatttgac tgggttaaca   4200
tgcaaaaacc aaggaaaaat atttagtttt tttttttttt tttgtatact tttcaagcta   4260
ccttgtcatg tatacagtca tttatgccta aagcctggtg attattcatt taaatgaaga   4320
tcacatttca tatcaacttt tgtatccaca gtagacaaaa tagcactaat ccagatgcct   4380
attgttggat actgaatgac agacaatctt atgtagcaaa gattatgcct gaaaaggaaa   4440
attattcagg gcagctaatt ttgcttttac caaaatatca gtagtaatat ttttggacag   4500
tagctaatgg gtcagtgggt tctttttaat gtttatactt agattttctt ttaaaaaaat   4560
taaaataaaa caaaaaaaaa tttctaggac tagacgatgt aataccagct aaagccaaac   4620
aattatacag tggaaggttt tacattattc atccaatgtg tttctattca tgttaagata   4680
ctactacatt tgaagtgggc agagaacatc agatgattga aatgttcgcc caggggtctc   4740
cagcaacttt ggaaatctct ttgtattttt acttgaagtg ccactaatgg acagcagata   4800
ttttctggct gatgttggta ttgggtgtag gaacatgatt taaaaaaaaa ctcttgcctc   4860
tgctttcccc cactctgagg caagttaaaa tgtaaaagat gtgatttatc tggggggctc   4920
aggtatggtg gggaagtgga ttcaggaatc tggggaatgg caaatatatt aagaagagta   4980
ttgaaagtat ttggaggaaa atggttaatt ctgggtgtgc accagggttc agtagagtcc   5040
acttctgccc tggagaccac aaatcaacta gctccattta cagccatttc taaaatggca   5100
gcttcagttc tagagaagaa agaacaacat cagcagtaaa gtccatggaa tagctagtgg   5160
tctgtgtttc ttttcgccat tgcctagctt gccgtaatga ttctataatg ccatcatgca   5220
gcaattatga gaggctaggt catccaaaga gaagacccta tcaatgtagg ttgcaaaatc   5280
taacccctaa ggaagtgcag tctttgattt gatttcccta gtaaccttgc agatatgttt   5340
aaccaagcca tagcccatgc cttttgaggg ctgaacaaat aagggactta ctgataattt   5400
acttttgatc acattaaggt gttctcacct tgaaatctta tacactgaaa tggccattga   5460
tttaggccac tggcttagag tactccttcc cctgcatgac actgattaca aatactttcc   5520
tattcatact ttccaattat gagatggact gtgggtactg ggagtgatca ctaacaccat   5580
agtaatgtct aatattcaca ggcagatctg cttggggaag ctagttatgt gaaaggcaaa   5640
```

-continued

```
tagagtcata cagtagctca aaaggcaacc ataattctct ttggtgcagg tcttgggagc   5700
gtgatctaga ttacactgca ccattcccaa gttaatcccc tgaaaactta ctctcaactg   5760
gagcaaatga actttggtcc caaatatcca tcttttcagt agcgttaatt atgctctgtt   5820
tccaactgca tttcctttcc aattgaatta aagtgtggcc tcgtttttag tcatttaaaa   5880
ttgttttcta agtaattgct gcctctatta tggcacttca attttgcact gtcttttgag   5940
attcaagaaa aatttctatt cttttttttg catccaattg tgcctgaact tttaaaatat   6000
gtaaatgctg ccatgttcca aacccatcgt cagtgtgtgt gtttagagct gtgcacccta   6060
gaaacaacat attgtcccat gagcaggtgc ctgagacaca gacccctttg cattcacaga   6120
gaggtcattg gttatagaga cttgaattaa taagtgacat tatgccagtt tctgttctct   6180
cacaggtgat aaacaatgct ttttgtgcac tacatactct tcagtgtaga gctcttgttt   6240
tatgggaaaa ggctcaaatg ccaaattgtg tttgatggat taatatgccc ttttgccgat   6300
gcatactatt actgatgtga ctcggttttg tcgcagcttt gctttgttta atgaaacaca   6360
cttgtaaacc tcttttgcac tttgaaaaag aatccagcgg gatgctcgag cacctgtaaa   6420
caattttctc aacctatttg atgttcaaat aaagaattaa actaaa                 6466
```

<210> SEQ ID NO 110
<211> LENGTH: 3478
<212> TYPE: DNA
<213> ORGANISM: Homo sapiens

<400> SEQUENCE: 110

```
aaattgaaag gtcagccttt cgcgcgctgt gtaggcaagt tacccgtgtt ctgcgttgcc     60
ggccgtgggt gctctggcca cagtgagtta ggggcgtcgg agcgggtttc tccaaccgca    120
atcggctccg ctcaagggga ggaggagagt cccttctcgg aaggcctaag gaaacgtgtc    180
gtctggaatg ggcttggggg ccacgcctgc acatctccgc gagacagagg gataaagtga    240
agatggtgct gttattgtta cctcgagtgc cacatgcgac ctctgagata tgtacacagt    300
cattcttact atcgcactca gccattctta ctacgctaaa gaagaaataa ttattcgagg    360
atatttgcct ggcccagaag aaacttatgt aaatttcatg aactattata tccgttttcc    420
tcggagtgag agaaaactct ttttagatat catctgagag aactagtgaa tcccagtcac    480
tgagtggagt tgagagtcta agaacctctg aaatttgaga actgctggac cagagccttt    540
agagctctga taaggtgtca acagggtagt taatttggca ccatggggat acagggattg    600
ctacaattta tcaaagaagc ttcagaaccc atccatgtga ggaagtataa agggcaggta    660
gtagctgtgg atacatattg ctggcttcac aaaggagcta ttgcttgtgc tgaaaaacta    720
gccaaaggtg aacctactga taggtatgta ggattttgta tgaaatttgt aaatatgtta    780
ctatctcatg ggatcaagcc tattctcgta tttgatggat gtactttacc ttctaaaaag    840
gaagtagaga gatctagaag agaaagacga caagccaatc ttcttaaggg aaagcaactt    900
cttcgtgagg ggaaagtctc ggaagctcga gagtgtttca cccggtctat caatatcaca    960
catgccatgg cccacaaagt aattaaagct gcccggtctc agggggtaga ttgcctcgtg   1020
gctccctatg aagctgatgc gcagttggcc tatcttaaca aagcgggaat tgtgcaagcc   1080
ataattacag aggactcgga tctcctagct tttggctgta aaaaggtaat tttaaagatg   1140
gaccagtttg gaaatggact tgaaattgat caagctcggc taggaatgtg cagacagctt   1200
ggggatgtat tcacggaaga gaagtttcgt tacatgtgta ttctttcagg ttgtgactac   1260
```

-continued

```
ctgtcatcac tgcgtgggat tggattagca aaggcatgca aagtcctaag actagccaat   1320

aatccagata tagtaaaggt tatcaagaaa attggacatt atctcaagat gaatatcacg   1380

gtaccagagg attacatcaa cgggtttatt cgggccaaca ataccttcct ctatcagcta   1440

gtttttgatc ccatcaaaag gaaacttatt cctctgaacg cctatgaaga tgatgttgat   1500

cctgaaacac taagctacgc tgggcaatat gttgatgatt ccatagctct tcaaatagca   1560

cttggaaata aagatataaa tacttttgaa cagatcgatg actacaatcc agacactgct   1620

atgcctgccc attcaagaag tcatagttgg gatgacaaaa catgtcaaaa gtcagctaat   1680

gttagcagca tttggcatag gaattactct cccagaccag agtcgggtac tgtttcagat   1740

gccccacaat tgaaggaaaa tccaagtact gtgggagtgg aacgagtgat tagtactaaa   1800

gggttaaatc tcccaaggaa atcatccatt gtgaaaagac caagaagtgc agagctgtca   1860

gaagatgacc tgttgagtca gtattctctt tcatttacga agaagaccaa gaaaaatagc   1920

tctgaaggca ataaatcatt gagcttttct gaagtgtttg tgcctgacct ggtaaatgga   1980

cctactaaca aaaagagtgt aagcactcca cctaggacga gaaataaatt tgcaacattt   2040

ttacaaagga aaaatgaaga aagtggtgca gttgtggttc cagggaccag aagcaggttt   2100

ttttgcagtt cagattctac tgactgtgta tcaaacaaag tgagcatcca gcctctggat   2160

gaaactgctg tcacagataa agagaacaat ctgcatgaat cagagtatgg agaccaagaa   2220

ggcaagagac tggttgacac agatgtagca cgtaattcaa gtgatgacat tccgaataat   2280

catattccag gtgatcatat tccagacaag gcaacagtgt ttacagatga agagtcctac   2340

tcttttgaga gcagcaaatt tacaaggacc atttcaccac ccactttggg aacactaaga   2400

agttgtttta gttggtctgg aggtcttgga gatttttcaa gaacgccgag cccctctcca   2460

agcacagcat tgcagcagtt ccgaagaaag agcgattccc ccacctcttt gcctgagaat   2520

aatatgtctg atgtgtcgca gttaaagagc gaggagtcca gtgacgatga gtctcatccc   2580

ttacgagaag aggcatgttc ttcacagtcc caggaaagtg gagaattctc actgcagagt   2640

tcaaatgcat caaagctttc tcagtgctct agtaaggact ctgattcaga ggaatctgat   2700

tgcaatatta agttacttga cagtcaaagt gaccagacct ccaagctacg tttatctcat   2760

ttctcaaaaa aagacacacc tctaaggaac aaggttcctg ggctatataa gtccagttct   2820

gcagactctc tttctacaac caagatcaaa cctctaggac ctgccagagc cagtgggctg   2880

agcaagaagc cggcaagcat ccagaagaga aagcatcata atgccgagaa caagccgggg   2940

ttacagatca aactcaatga gctctggaaa aactttggat ttaaaaaaga ttctgaaaag   3000

cttcctcctt gtaagaaacc cctgtcccca gtcagagata acatccaact aactccagaa   3060

gcggaagagg atatatttaa caaacctgaa tgtggccgtg ttcaaagagc aatattccag   3120

taaatgcaga ctgctgcaaa gcttttgcct gcaagagaat ctgatcaatt tgaagtccct   3180

gtttgggaat gaggcactta tcagcatgaa gaatttttc tcattctgtg ccattttaaa   3240

aatagaatac attttgtata ttaactttat aattgggttg tggttttttt gctcagcttt   3300

ttatattttt ataagaagct aaatagaaga ataattgtat ctctgacagg tttttggagg   3360

ttttagtgtt aattgggaaa atcctctgga gtttataaaa gtctactcta aatatttctg   3420

taatgttgtc aagtagaaag atagtaaatg gagaaactac aaaaaaaaaa aaaaaaaa     3478
```

<210> SEQ ID NO 111
<211> LENGTH: 5192
<212> TYPE: DNA
<213> ORGANISM: Homo sapiens

<400> SEQUENCE: 111
ccatgacctg ccttgagaag gggcagggga agccagatgg actggaagtg gagtggcagt 60
gaccaaggag gaggaggtgt gataggcttc ccacgcaggg tagatccaga gacaccagtg 120
ccacccatag gcccctagga ctgcagtggt caccccgattc ctttgtccca gctgagactc 180
agttctgagt gttctatttt ggggaacaga ggcgtccttg gtagcatttg gaagaggata 240
gccagctggg gtgtgtgtac atcacagcct gacagtaaca gcatccgaac cagaggtgac 300
tggctaaggg cagacccagg gcaacaggtt aaccgttcta gggccgggca cagggaggag 360
aacattccaa cactctgtgt gcccagtgcc gacgcacgtt ctctctttta tcctcaaaac 420
agtcctatga ggatataagc cagagagaga cagagacaag gaattacaag ttggtgagag 480
tcaggatttg aacttggctc tggcagatgg aaaattaggg tctgtattct ttacaaaacc 540
gtgtgtgcct cagatggagt tggtgcataa caagcagagg tatccagggt cgcggtcctg 600
cttgccacgg aaggggccgc cttgtcagtt gtgaccaccc agccctggaa atgtcagtaa 660
tgctgtaagg agtggggatc ggatcagatg ccatccagat gctgaagttt gaccttgtgt 720
catttttcac tttctttttt ggctcttctg caatcaattc atttatttag caaaaaagaa 780
attatgtgtg ccgagagcat gcagaagata tgtctccgtt ctctgcttcc ctccaaaaaa 840
gaatcccaaa actgctttct gtgaacgtgt gccagggtcc cagcaggact cagggagagc 900
aggaagccca gcccagaccc cttgcacaac ctaccgtggg gaggccttag gctctggcta 960
ctacagagct ggttccagtc tgcactgcca cagcctggcc agggacttgg acacatctgc 1020
tggccacttc ctgtctcagt ttccttatct gcaaaataag ggaaaagccc ccacaaaggt 1080
gcacgtgtag caggagctct tttccctccc tattttagga aggcagttgg tgggaagtcc 1140
agcttgggtc cctgagagct gtgagaagga gatgcggctg ctgctggccc tgttgggggt 1200
cctgctgagt gtgcctgggc ctccagtctt gtccctggag gcctctgagg aagtggagct 1260
tggtatggct tctgaggtgg gagagggtgg caggggtggg aagagtgggc accaggaggg 1320
ggctgctggg ctgagcaaag ctggaaagga tccttgccca ggccctgaga aggtggcggc 1380
agggcagggc tcaaccactg agactcagtc agtgcctggc ttccagcaag cattcatcta 1440
tcactgtgtc tgcgagagag gactggcctt gcagggcgca gggccctaag ctgggctgca 1500
gagctggtgg tgagctcctt gcctgggtgt gtgtgcgtgt gtgtgtgtgt tctgtgcact 1560
gggtgtgtga cctaggaggt ccaggcagca tgtgtggtat aagcattatg agggtgatat 1620
gccccggtgc agcatgaccc tgtatgtggc accaacagca tgtgccttgt gtgtgtgtgt 1680
gtccgtatgt gtgtgtgtgt atgcgtgtgt gtgtgtgtgt gtgtgtgtct tggccactgt 1740
catgtgcact aaatgctgtg tgtgtgacat gccccaagag tgtggcattt gccctgggtg 1800
tggcatccgc agcatgtggc tgtgtgggtg tcaaggagtg gtggctcctt cagcatgcgt 1860
tgcgaagtgc ttgtgccctg catgtgcggt gtgttctctg tacacaggag gctgcctcag 1920
atggggctgc ggggtctgct gacctctgcc ctctgcccac agagccctgc ctggctccca 1980
gcctggagca gcaagagcag gagctgacag tagcccttgg gcagcctgtg cggctgtgct 2040
gtgggcgggc tgagcgtggt ggccactggt acaaggaggg cagtcgcctg gcacctgctg 2100
gccgtgtacg gggctggagg ggccgcctag agattgccag cttcctacct gaggatgctg 2160
gccgctacct ctgcctggca cgaggctcca tgatcgtcct gcagaatctc accttgatta 2220
caggtgactc cttgacctcc agcaacgatg atgaggaccc caagtcccat agggacctct 2280

-continued

```
cgaataggca cagttacccc cagcaaggtc agtaggtctc caaggacttg tgtccccgct   2340
gctgctcatc tgatcactga gaagaggagg cctgtgtggg aacacacggt cattctaggg   2400
gccttcccct gccctccagc accctactgg acacaccccc agcgcatgga gaagaaactg   2460
catgcagtac ctgcggggaa caccgtcaag ttccgctgtc cagctgcagg caaccccacg   2520
cccaccatcc gctggcttaa ggatggacag gcctttcatg ggagaaccg cattggaggc    2580
attcggctgc gccatcagca ctggagtctc gtgatggaga gcgtggtgcc ctcggaccgc   2640
ggcacataca cctgcctggt agagaacgct gtgggcagca tccgttataa ctacctgcta   2700
gatgtgctgg agcggtcccc gcaccggccc atcctgcagg ccgggctccc ggccaacacc   2760
acagccgtgg tgggcagcga cgtggagctg ctgtgcaagg tgtacagcga tgcccagccc   2820
cacatccagt ggctgaagca catcgtcatc aacggcagca gcttcggagc cgacggtttc   2880
ccctatgtgc aagtcctaaa gactgcagac atcaatagct cagaggtgga ggtcctgtac   2940
ctgcggaacg tgtcagccga ggacgcaggc gagtacacct gcctcgcagg caattccatc   3000
ggcctctcct accagtctgc ctggctcacg gtgctgccag gtgagcacct gaagggccag   3060
gagatgctgc gagatgcccc tctgggccag cagtgggggc tgtggcctgt tgggtggtca   3120
gtctctgttg gcctgtgggg tctggcctgg ggggcagtgt gtggatttgt gggtttgagc   3180
tgtatgacag cccctctgtg cctctccaca cgtggccgtc catgtgaccg tctgctgagg   3240
tgtgggtgcc tgggactggg cataactaca gcttcctccg tgtgtgtccc cacatatgtt   3300
gggagctggg agggactgag ttagggtgca cggggcggcc agtctcacca ctgaccagtt   3360
tgtctgtctg tgtgtgtcca tgtgcgaggg cagaggagga ccccacatgg accgcagcag   3420
cgcccgaggc caggtatacg gacatcatcc tgtacgcgtc gggctccctg gccttggctg   3480
tgctcctgct gctggccagg ctgtatcgag ggcaggcgct ccacggccgg cacccccgcc   3540
cgcccgccac tgtgcagaag ctctcccgct tccctctggc ccgacagttc tccctggagt   3600
caggctcttc cggcaagtca agctcatccc tggtacgagg cgtgcgtctc tcctccagcg   3660
gccccgcctt gctcgccggc ctcgtgagtc tagatctacc tctcgaccca ctatgggagt   3720
tcccccggga caggctggtg cttgggaagc ccctaggcga gggctgcttt ggccaggtag   3780
tacgtgcaga ggcctttggc atggaccctg cccggcctga ccaagccagc actgtggccg   3840
tcaagatgct caaagacaac gcctctgaca aggacctggc cgacctggtc tcggagatgg   3900
aggtgatgaa gctgatcggc cgacacaaga acatcatcaa cctgcttggt gtctgcaccc   3960
aggaagggcc cctgtacgtg atcgtggagt gcgccgccaa gggaaacctg cgggagttcc   4020
tgcgggcccg gcgcccccca ggccccgacc tcagccccga cggtcctcgg agcagtgagg   4080
ggccgctctc cttcccagtc ctggtctcct gcgcctacca ggtggcccga ggcatgcagt   4140
atctggagtc ccggaagtgt atccaccggg acctggctgc ccgcaatgtg ctggtgactg   4200
aggacaatgt gatgaagatt gctgactttg ggctggcccg cggcgtccac cacattgact   4260
actataagaa aaccagcaac ggccgcctgc ctgtgaagtg gatggcgccc gaggccttgt   4320
ttgaccgggt gtacacacac cagagtgacg tgtggtcttt tgggatcctg ctatgggaga   4380
tcttcaccct cgggggctcc ccgtatcctg gcatcccggt ggaggagctg ttctcgctgc   4440
tgcgggaggg acatcggatg gaccgacccc cacactgccc cccagagctg tacgggctga   4500
tgcgtgagtg ctggcacgca gcgccctccc agaggcctac cttcaagcag ctggtggagg   4560
cgctggacaa ggtcctgctg gccgtctctg aggagtacct cgacctccgc ctgaccttcg   4620
gaccctattc cccctctggt ggggacgcca gcagcacctg ctcctccagc gattctgtct   4680
```

```
tcagccacga cccccctgcca ttgggatcca gctccttccc cttcgggtct ggggtgcaga   4740
catgagcaag gctcaaggct gtgcaggcac ataggctggt ggccttgggc cttggggctc   4800
agccacagcc tgacacagtg ctcgaccttg atagcatggg gcccctggcc cagagttgct   4860
gtgccgtgtc caagggccgt gcccttgccc ttggagctgc cgtgcctgtg tcctgatggc   4920
ccaaatgtca gggttctgct cggcttcttg gaccttggcg cttagtcccc atcccgggtt   4980
tggctgagcc tggctggaga gctgctatgc taaacctcct gcctcccaat accagcagga   5040
ggttctgggc ctctgaaccc cctttcccca cacctccccc tgctgctgct gccccagcgt   5100
cttgacggga gcattggccc ctgagcccag agaagctgga agcctgccga aaacaggagc   5160
aaatggcgtt ttataaatta ttttttgaa at                                  5192
```

<210> SEQ ID NO 112
<211> LENGTH: 3124
<212> TYPE: DNA
<213> ORGANISM: Homo sapiens

<400> SEQUENCE: 112

```
taagatccac atcagctcaa ctgcacttgc ctcgcagagg cagcccgctc acttcccgcg     60
gaggcgctcc ccggcgccgc gctccgcggc agccgcctgc ccccggcgct gcccccgccc    120
gccgcgccgc cgccgccgcc gcgcacgccg cgccccgcag ctctgggctt cctcttcgcc    180
cgggtggcgt tgggcccgcg cgggcgctcg ggtgactgca gctgctcagc tcccctcccc    240
cgccccgcgc cgcgcggccg cccgtcgctt cgcacagggc tggatggttg tattgggcag    300
ggtggctcca ggatgttagg aactgtgaag atggaagggc atgaaaccag cgactggaac    360
agctactacg cagacacgca ggaggcctac tcctccgtcc cggtcagcaa catgaactca    420
ggcctgggct ccatgaactc catgaacacc tacatgacca tgaacaccat gactacgagc    480
ggcaacatga ccccggcgtc cttcaacatg tcctatgcca acccgggcct aggggccggc    540
ctgagtcccg gcgcagtagc cggcatgccg gggggctcgg cgggcgccat gaacagcatg    600
actgcggccg gcgtgacggc catgggtacg gcgctgagcc cgagcggcat gggcgccatg    660
ggtgcgcagc aggcggcctc catgaatggc ctgggcccct acgcggccgc catgaacccg    720
tgcatgagcc ccatggcgta cgcgccgtcc aacctgggcc gcagccgcgc gggcggcggc    780
ggcgacgcca agacgttcaa gcgcagctac ccgcacgcca agccgcccta ctcgtacatc    840
tcgctcatca ccatggccat ccagcaggcg cccagcaaga tgctcacgct gagcgagatc    900
taccagtgga tcatggacct cttcccctat taccggcaga accagcagcg ctggcagaac    960
tccatccgcc actcgctgtc cttcaatgac tgcttcgtca aggtggcacg ctccccggac   1020
aagccgggca agggctccta ctggacgctg cacccggact ccggcaacat gttcgagaac   1080
ggctgctact tgcgccgcca gaagcgcttc aagtgcgaga agcagccggg ggccggcggc   1140
gggggcggga gcggaagcgg gggcagcggc gccaagggcg gccctgagag ccgcaaggac   1200
ccctctggcg cctctaaccc cagcgccgac tcgcccctcc atcggggtgt gcacgggaag   1260
accggccagc tagagggcgc gccggccccc gggcccgccg ccagccccca gactctggac   1320
cacagtgggg cgacggcgac agggggcgcc tcggagttga agactccagc ctcctcaact   1380
gcgccccccca taagctccgg gcccggggcg ctggcctctg tgcccgcctc tcacccggca   1440
cacggcttgg caccccacga gtcccagctg cacctgaaag gggaccccca ctactccttc   1500
aaccacccgt tctccatcaa caacctcatg tcctcctcgg agcagcagca taagctggac   1560
```

-continued ttcaaggcat acgaacaggc actgcaatac tcgccttacg gctctacgtt gcccgccagc 1620
ctgcctctag gcagcgcctc ggtgaccacc aggagcccca tcgagccctc agccctggag 1680
ccggcgtact accaaggtgt gtattccaga cccgtcctaa acacttccta gctcccggga 1740
ctggggggtt tgtctggcat agccatgctg gtagcaagag agaaaaaatc aacagcaaac 1800
aaaaccacac aaaccaaacc gtcaacagca taataaaatc ccaacaacta tttttatttc 1860
atttttcatg cacaaccttt cccccagtgc aaaagactgt tactttatta ttgtattcaa 1920
aattcattgt gtatattact acaaagacaa ccccaaacca atttttttcc tgcgaagttt 1980
aatgatccac aagtgtatat atgaaattct cctccttcct tgcccccctc tctttcttcc 2040
ctctttcccc tccagacatt ctagtttgtg gagggttatt taaaaaaaca aaaaaggaag 2100
atggtcaagt ttgtaaaata tttgtttgtg ctttttcccc ctccttacct gaccccctac 2160
gagtttacag gtctgtggca atactcttaa ccataagaat tgaaatggtg aagaaacaag 2220
tatacactag aggctcttaa aagtattgaa agacaatact gctgttatat agcaagacat 2280
aaacagatta taaacatcag agccatttgc ttctcagttt acatttctga tacatgcaga 2340
tagcagatgt ctttaaatga aatacatgta tattgtgtat ggacttaatt atgcacatgc 2400
tcagatgtgt agacatcctc cgtatattta cataacatat agaggtaata gataggtgat 2460
atacatgata cattctcaag agttgcttga ccgaaagtta caaggacccc aaccccttg 2520 tcctctctac ccacagatgg ccctgggaat caattcctca ggaattgccc tcaagaactc 2580
tgcttcttgc tttgcagagt gccatggtca tgtcattctg aggtcacata acacataaaa 2640
ttagtttcta tgagtgtata ccatttaaag aatttttttt tcagtaaaag ggaatattac 2700
aatgttggag gagagataag ttatagggag ctggatttca aaacgtggtc caagattcaa 2760
aaatcctatt gatagtggcc attttaatca ttgccatcgt gtgcttgttt catccagtgt 2820
tatgcacttt ccacagttgg acatggtgtt agtatagcca gacgggtttc attattattt 2880
ctctttgctt tctcaatgtt aatttattgc atggtttatt ctttttcttt acagctgaaa 2940
ttgctttaaa tgatggttaa aattacaaat taaattgtta atttttatca atgtgattgt 3000
aattaaaaat attttgattt aaataacaaa aataatacca gattttaagc cgtggaaaat 3060
gttcttgatc atttgcagtt aaggacttta aataaatcaa atgttaacaa aaaaaaaaaa 3120
aaaa 3124

<210> SEQ ID NO 113
<211> LENGTH: 3452
<212> TYPE: DNA
<213> ORGANISM: Homo sapiens

<400> SEQUENCE: 113
atgcaggcgc gctactccgt gtccagcccc aactccctgg gagtggtgcc ctacctcggc 60
ggcgagcaga gctactaccg cgcggcggcc gcggcggccg ggggcggcta caccgccatg 120
ccggccccca tgagcgtgta ctcgcaccct gcgcacgccg agcagtaccc gggcggcatg 180
gcccgcgcct acgggcccta cacgccgcag ccgcagccca aggacatggt gaagccgccc 240
tatagctaca tcgcgctcat caccatggcc atccagaacg ccccggacaa gaagatcacc 300
ctgaacggca tctaccagtt catcatggac cgcttcccct tctaccggga caacaagcag 360
ggctggcaga acagcatccg ccacaacctc tcgctcaacg agtgcttcgt caaggtgccg 420
cgcgacgaca agaagccggg caagggcagc tactggacgc tggacccgga ctcctacaac 480
atgttcgaga acggcagctt cctgcggcgg cggcggcgct tcaagaagaa ggacgcggtg 540

-continued

```
aaggacaagg aggagaagga caggctgcac ctcaaggagc cgcccccgcc cggccgccag    600
cccccgcccg cgccgccgga gcaggccgac ggcaacgcgc ccggtccgca gccgccgccc    660
gtgcgcatcc aggacatcaa gaccgagaac ggtacgtgcc cctcgccgcc ccagcccctg    720
tccccggccg ccgccctggg cagcggcagc gccgccgcgg tgcccaagat cgagagcccc    780
gacagcagca gcagcagcct gtccagcggg agcagccccc cgggcagcct gccgtcggcg    840
cggccgctca gcctggacgg tgcggattcc gcgccgccgc cgcccgcgcc ctccgccccg    900
ccgccgcacc atagccaggg cttcagcgtg gacaacatca tgacgtcgct gcgggggtcg    960
ccgcagagcg cggccgcgga gctcagctcc ggccttctgg cctcggcggc cgcgtcctcg   1020
cgcgcgggga tcgcaccccc gctggcgctc ggcgcctact cgcccggcca gagctccctc   1080
tacagctccc cctgcagcca gacctccagc gcgggcagct cgggcggcgg cggcggcggc   1140
gcgggggccg cgggggcgc gggcggcgcc gggacctacc actgcaacct gcaagccatg   1200
agcctgtacg cggccggcga gcgcgggggc cacttgcagg gcgcgcccgg gggcgcgggc   1260
ggctcggccg tggacgaccc cctgcccgac tactctctgc ctccggtcac cagcagcagc   1320
tcgtcgtccc tgagtcacgg cggcggcggc ggcggcggcg ggggaggcca ggaggccggc   1380
caccaccctg cggcccacca aggccgcctc acctcgtggt acctgaacca ggcgggcgga   1440
gacctgggcc acttggcgag cgcggcggcg gcggcggcgg ccgcaggcta cccgggccag   1500
cagcagaact tccactcggt gcgggagatg ttcgagtcac agaggatcgg cttgaacaac   1560
tctccagtga acgggaatag tagctgtcaa atggccttcc cttccagcca gtctctgtac   1620
cgcacgtccg gagctttcgt ctacgactgt agcaagtttt gacacaccct caaagccgaa   1680
ctaaatcgaa ccccaaagca ggaaaagcta aaggaaccca tcaaggcaaa atcgaaacta   1740
aaaaaaaaaa atccaattaa aaaaaacccc tgagaatatt caccacacca gcgaacagaa   1800
tatccctcca aaaattcagc tcaccagcac cagcacgaag aaaactctat tttcttaacc   1860
gattaattca gagccacctc cactttgcct tgtctaaata aacaaacccg taaactgttt   1920
tatacagaga cagcaaaatc ttggtttatt aaaggacagt gttactccag ataacacgta   1980
agtttcttct tgcttttcag agacctgctt tcccctcctc ccgtctcccc tctcttgcct   2040
tcttccttgc ctctcacctg taagatatta ttttatccta tgttgaaggg agggggaaag   2100
tccccgttta tgaaagtcgc tttcttttta ttcatggact tgttttaaaa tgtaaattgc   2160
aacatagtaa tttattttta atttgtagtt ggatgtcgtg gaccaaacgc cagaaagtgt   2220
tcccaaaacc tgacgttaaa ttgcctgaaa ctttaaattg tgcttttttt ctcattataa   2280
aaagggaaac tgtattaatc ttattctatc ctcttttctt tctttttgtt gaacatattc   2340
attgtttgtt tattaataaa ttaccattca gtttgaatga gacctatatg tctggatact   2400
ttaatagagc tttaattatt acgaaaaaag atttcagaga taaaacacta gaagttacct   2460
attctccacc taaatctctg aaaaatggag aaaccctctg actagtccat gtcaaatttt   2520
actaaaagtc tttttgttta gatttatttt cctgcagcat cttctgcaaa atgtactata   2580
tagtcagctt gctttgaggc tagtaaaaag atatttttct aaacagattg gagttggcat   2640
ataaacaaat acgttttctc actaatgaca gtccatgatt cggaaatttt aagcccatga   2700
atcagccgcg gtcttaccac ggtgatgcct gtgtgccgag agatgggact gtgcggccag   2760
atatgcacag ataaatattt ggcttgtgta ttccatataa aattgcagtg catattatac   2820
atccctgtga gccagatgct gaatagatat tttcctatta tttcagtcct ttataaaagg   2880
```

```
aaaaataaac cagtttttaa atgtatgtat ataattctcc cccatttaca atccttcatg   2940
tattacatag aaggattgct tttttaaaaa tatactgcgg gttggaaagg gatatttaat   3000
ctttgagaaa ctattttaga aaatatgttt gtagaacaat tatttttgaa aaagatttaa   3060
agcaataaca agaaggaagg cgagaggagc agaacatttt ggtctagggt ggtttctttt   3120
taaaccattt tttcttgtta atttacagtt aaacctaggg gacaatccgg attggccctc   3180
ccccttttgt aaataaccca ggaaatgtaa taaattcatt atcttagggt gatctgccct   3240
gccaatcaga ctttggggag atggcgattt gattacagac gttcgggggg gtggggggct   3300
tgcagtttgt tttggagata atacagtttc ctgctatctg ccgctcctat ctagaggcaa   3360
cacttaagca gtaattgctg ttgcttgttg tcaaaatttg atcattgtta aaggattgct   3420
gcaaataaat acactttaat ttcagtcaaa aa                                 3452
```

<210> SEQ ID NO 114
<211> LENGTH: 1749
<212> TYPE: DNA
<213> ORGANISM: Homo sapiens

<400> SEQUENCE: 114

```
gtggcctcga ggtggtggca gggccgcccc ctgcagtccg gagacgaacg cacggaccgg     60
gcctccggag gcaggttcgg ctggaaggaa ccgctctcgc ttcgtcctac acttgcgcaa    120
atgtctccga gcttactcac atagcatatt ggtatatcaa aatgaaatgc aaggaaccaa    180
aaataacata attgaaggca gtaaaagtga aattaaatag gaagatcatc agtcaaggaa    240
gacccactgg agaggacaga aaatgaagca gtgttttatc atgtgtattt cagcaggtct    300
tcttgaaatt taactaaaaa tatgactgct ctctcttcag agaactgctc ttttcagtac    360
cagttacgtc aaacaaacca gcccctagac gttaactatc tgctattctt gatcatactt    420
gggaaaatat tattaaatat ccttacacta ggaatgagaa gaaaaaacac ctgtcaaaat    480
tttatggaat atttttgcat ttcactagca ttcgttgatc ttttactttt ggtaaacatt    540
tccattatat tgtatttcag ggattttgta cttttaagca ttaggttcac taaataccac    600
atctgcctat ttactcaaat tatttccttt acttatggct ttttgcatta tccagttttc    660
ctgacagctt gtatagatta ttgcctgaat ttctctaaaa caaccaagct ttcatttaag    720
tgtcaaaaat tattttattt ctttacagta attttaattt ggatttcagt ccttgcttat    780
gttttgggag acccagccat ctaccaaagc ctgaaggcac agaatgctta ttctcgtcac    840
tgtcctttct atgtcagcat tcagagttac tggctgtcat ttttcatggt gatgatttta    900
tttgtagctt tcataacctg ttgggaagaa gttactactt tggtacaggc tatcaggata    960
acttcctata tgaatgaaac tatcttatat tttccttttt catcccactc cagttatact   1020
gtgagatcta aaaaaatatt cttatccaag ctcattgtct gttttctcag tacctggtta   1080
ccatttgtac tacttcaggt aatcattgtt ttacttaaag ttcagattcc agcatatatt   1140
gagatgaata ttccctggtt atactttgtc aatagttttc tcattgctac agtgtattgg   1200
tttaattgtc acaagcttaa tttaaaagac attggattac ctttggatcc atttgtcaac   1260
tggaagtgct gcttcattcc acttacaatt cctaatcttg agcaaattga aaagcctata   1320
tcaataatga tttgttaata ttattaatta aaagttacag ctgtcataag atcataattt   1380
tatgaacaga aagaactcag gacatattaa aaaataaact gaactaaaac aacttttgcc   1440
ccctgactga tagcatttca gaatgtgtct tttgaagggc tataccagtt attaaatagt   1500
gttttatttt aaaaacaaaa taattccaag aagtttttat agttattcag ggacactata   1560
```

ttacaaatat tactttgtta ttaacacaaa aagtgataag agttaacatt tggctatact 1620
gatgtttgtg ttactcaaaa aaactactgg atgcaaactg ttatgtaaat ctgagatttc 1680
actgacaact ttaagatatc aacctaaaca tttttattaa atgttcaaat gtaagcaaga 1740
aaaaaaaaa 1749

<210> SEQ ID NO 115
<211> LENGTH: 935
<212> TYPE: DNA
<213> ORGANISM: Homo sapiens

<400> SEQUENCE: 115
agtcagaggt cgcgcaggcg ctggtacccc gttggtccgc gcgttgctgc gttgtgaggg 60
gtgtcagctc agtgcatccc aggcagctct tagtgtggag cagtgaactg tgtgtggttc 120
cttctacttg ggatcatgc agagagcttc acgtctgaag agagagctgc acatgttagc 180
cacagagcca cccccaggca tcacatgttg gcaagataaa gaccaaatgg atgacctgcg 240
agctcaaata ttaggtggag ccaacacacc ttatgagaaa ggtgttttta agctagaagt 300
tatcattcct gagaggtacc catttgaacc tcctcagatc cgatttctca ctccaattta 360
tcatccaaac attgattctg ctggaaggat ttgtctggat gttctcaaat tgccaccaaa 420
aggtgcttgg agaccatccc tcaacatcgc aactgtgttg acctctattc agctgctcat 480
gtcagaaccc aaccctgatg acccgctcat ggctgacata tcctcagaat ttaaatataa 540
taagccagcc ttcctcaaga atgccagaca gtggacagag aagcatgcaa gacagaaaca 600
aaaggctgat gaggaagaga tgcttgataa tctaccagag gctggtgact ccagagtaca 660
caactcaaca cagaaaagga aggccagtca gctagtaggc atagaaaaga aatttcatcc 720
tgatgtttag gggacttgtc ctggttcatc ttagttaatg tgttctttgc caaggtgatc 780
taagttgcct accttgaatt ttttttaaa tatatttgat gacataattt ttgtgtagtt 840
tatttatctt gtacatatgt attttgaaat cttttaaacc tgaaaaataa atagtcattt 900
aatgttgaaa aaaaaaaaaa aaaaaaaaaa aaaaa 935

<210> SEQ ID NO 116
<211> LENGTH: 2896
<212> TYPE: DNA
<213> ORGANISM: Homo sapiens

<400> SEQUENCE: 116
acgcttgcgc gcgggattta aactgcggcg gtttacgcgg cgttaagact tcgtagggtt 60
agcgaaattg aggtttcttg gtattgcgcg tttctcttcc ttgctgactc tccgaatggc 120
catggactcg tcgcttcagg cccgcctgtt tcccggtctc gctatcaaga tccaacgcag 180
taatggttta attcacagtg ccaatgtaag gactgtgaac ttggagaaat cctgtgtttc 240
agtggaatgg gcagaaggag gtgccacaaa gggcaaagag attgattttg atgatgtggc 300
tgcaataaac ccagaactct tacagcttct tcccttacat ccgaaggaca atctgccctt 360
gcaggaaaat gtaacaatcc agaaacaaaa acggagatcc gtcaactcca aaattcctgc 420
tccaaaagaa agtcttcgaa gccgctccac tcgcatgtcc actgtctcag agcttcgcat 480
cacggctcag gagaatgaca tggaggtgga gctgcctgca gctgcaaact cccgcaagca 540
gttttcagtt cctcctgccc ccactaggcc ttcctgccct gcagtggctg aaataccatt 600
gaggatggtc agcgaggaga tggaagagca agtccattcc atccgaggca gctcttctgc 660

-continued

```
aaaccctgtg aactcagttc ggaggaaatc atgtcttgtg aaggaagtgg aaaaaatgaa    720

gaacaagcga gaagagaaga aggcccagaa ctctgaaatg agaatgaaga gagctcagga    780

gtatgacagt agttttccaa actgggaatt tgcccgaatg attaaagaat ttcgggctac    840

tttggaatgt catccactta ctatgactga tcctatcgaa gagcacagaa tatgtgtctg    900

tgttaggaaa cgcccactga ataagcaaga attggccaag aaagaaattg atgtgatttc    960

cattcctagc aagtgtctcc tcttggtaca tgaacccaag ttgaaagtgg acttaacaaa   1020

gtatctggag aaccaagcat tctgctttga ctttgcattt gatgaaacag cttcgaatga   1080

agttgtctac aggttcacag caaggccact ggtacagaca atctttgaag gtggaaaagc   1140

aacttgtttt gcatatggcc agacaggaag tggcaagaca catactatgg gcggagacct   1200

ctctgggaaa gcccagaatg catccaaagg gatctatgcc atggcctccc gggacgtctt   1260

cctcctgaag aatcaaccct gctaccggaa gttgggcctg gaagtctatg tgacattctt   1320

cgagatctac aatgggaagc tgtttgacct gctcaacaag aaggccaagc tgcgcgtgct   1380

ggaggacggc aagcaacagg tgcaagtggt ggggctgcag gagcatctgg ttaactctgc   1440

tgatgatgtc atcaagatga tcgacatggg cagcgcctgc agaacctctg ggcagacatt   1500

tgccaactcc aattcctccc gctcccacgc gtgcttccaa attattcttc gagctaaagg   1560

gagaatgcat ggcaagttct ctttggtaga tctggcaggg aatgagcgag gcgcggacac   1620

ttccagtgct gaccggcaga cccgcatgga gggcgcagaa atcaacaaga gtctcttagc   1680

cctgaaggag tgcatcaggg ccctgggaca gaacaaggct cacacccggt tccgtgagag   1740

caagctgaca caggtgctga gggactcctt cattggggag aactctagga cttgcatgat   1800

tgccacgatc tcaccaggca taagctcctg tgaatatact ttaaacaccc tgagatatgc   1860

agacagggtc aaggagctga gcccccacag tgggcccagt ggagagcagt tgattcaaat   1920

ggaaacagaa gagatggaag cctgctctaa cggggcgctg attccaggca atttatccaa   1980

ggaagaggag gaactgtctt cccagatgtc cagctttaac gaagccatga ctcagatcag   2040

ggagctggag gagaaggcta tggaagagct caaggagatc atacagcaag gaccagactg   2100

gcttgagctc tctgagatga ccgagcagcc agactatgac ctggagacct ttgtgaacaa   2160

agcggaatct gctctggccc agcaagccaa gcatttctca gccctgcgag atgtcatcaa   2220

ggccttgcgc ctggccatgc agctggaaga gcaggctagc agacaaataa gcagcaagaa   2280

acggccccag tgacgactgc aaataaaaat ctgtttggtt tgacacccag cctcttccct   2340

ggccctcccc agagaacttt gggtacctgg tgggtctagg cagggtctga gctgggacag   2400

gttctggtaa atgccaagta tgggggcatc tgggcccagg gcagctgggg agggggtcag   2460

agtgacatgg gacactcctt ttctgttcct cagttgtcgc cctcacgaga ggaaggagct   2520

cttagttacc cttttgtgtt gcccttcttt ccatcaaggg gaatgttctc agcatagagc   2580

tttctccgca gcatcctgcc tgcgtggact ggctgctaat ggagagctcc ctggggttgt   2640

cctggctctg gggagagaga cggagccttt agtacagcta tctgctggct ctaaaccttc   2700

tacgcctttg ggccgagcac tgaatgtctt gtactttaaa aaaatgtttc tgagacctct   2760

ttctacttta ctgtctccct agagatccta gaggatccct actgttttct gttttatgtg   2820

tttatacatt gtatgtaaca ataaagagaa aaaataaatc agctgtttaa gtgtgtggaa   2880

aaaaaaaaaa aaaaaa                                                   2896
```

<210> SEQ ID NO 117
<211> LENGTH: 2209

<212> TYPE: DNA
<213> ORGANISM: Homo sapiens

<400> SEQUENCE: 117
actgcgcgcg tcgtgcgtaa tgacgtcagc gccggcggag aatttcaaat tcgaacggct 60
ttggcgggcc gaggaaggac ctggtgtttt gatgaccgct gtcctgtcta gcagatactt 120
gcacggttta cagaaattcg gtccctgggt cgtgtcagga aactggaaaa aaggtcataa 180
gcatgaagcg cagttcagtt tccagcggtg gtgctggccg cctctccatg caggagttaa 240
gatcccagga tgtaaataaa caaggcctct ataccccctca aaccaaagag aaaccaacct 300
ttggaaagtt gagtataaac aaaccgacat ctgaaagaaa agtctcgcta tttggcaaaa 360
gaactagtgg acatggatcc cggaatagtc aacttggtat attttccagt tctgagaaaa 420
tcaaggaccc gagaccactt aatgacaaag cattcattca gcagtgtatt cgacaactct 480
gtgagtttct tacagaaaat ggttatgcac ataatgtgtc catgaaatct ctacaagctc 540
cctctgttaa agacttcctg aagatcttca catttcttta tggcttcctg tgcccctcat 600
acgaacttcc tgacacaaag tttgaagaag aggttccaag aatctttaaa gaccttgggt 660
atccttttgc actatccaaa agctccatgt acacagtggg ggctcctcat acatggcctc 720
acattgtggc agccttagtt tggctaatag actgcatcaa gatacatact gccatgaaag 780
aaagctcacc tttatttgat gatgggcagc cttggggaga agaaactgaa gatggaatta 840
tgcataataa gttgtttttg gactacacca taaaatgcta tgagagtttt atgagtggtg 900
ccgacagctt tgatgagatg aatgcagagc tgcagtcaaa actgaaggat ttatttaatg 960
tggatgcttt taagctggaa tcattagaag caaaaaacag agcattgaat gaacagattg 1020
caagattgga acaagaaaga gaaaaagaac cgaatcgtct agagtcgttg agaaaactga 1080
aggcttcctt acaaggagat gttcaaaagt atcaggcata catgagcaat ttggagtctc 1140
attcagccat tcttgaccag aaattaaatg gtctcaatga ggaaattgct agagtagaac 1200
tagaatgtga aacaataaaa caggagaaca ctcgactaca gaatatcatt gacaaccaga 1260
agtactcagt tgcagacatt gagcgaataa atcatgaaag aaatgaattg cagcagacta 1320
ttaataaatt aaccaaggac ctggaagctg aacaacagaa gttgtggaat gaggagttaa 1380
aatatgccag aggcaaagaa gcgattgaaa cacaattagc agagtatcac aaattggcta 1440
gaaaattaaa acttattcct aaaggtgctg agaattccaa aggttatgac tttgaaatta 1500
agtttaatcc cgaggctggt gccaactgcc ttgtcaaata cagggctcaa gtttatgtac 1560
ctcttaagga actcctgaat gaaactgaag aagaaattaa taaagcccta aataaaaaaa 1620
tgggtttgga ggatacttta gaacaattga atgcaatgat aacagaaagc aagagaagtg 1680
tgagaactct gaaagaagaa gttcaaaagc tggatgatct ttaccaacaa aaaattaagg 1740
aagcagagga agaggatgaa aaatgtgcca gtgagcttga gtccttggag aaacacaagc 1800
acctgctaga aagtactgtt aaccaggggc tcagtgaagc tatgaatgaa ttagatgctg 1860
ttcagcggga ataccaacta gttgtgcaaa ccacgactga agaaagacga aaagtgggaa 1920
ataacttgca acgtctgtta gagatggttg ctacacatgt tgggtctgta gagaaacatc 1980
ttgaggagca gattgctaaa gttgatagag aatatgaaga atgcatgtca gaagatctct 2040
cggaaaatat taaagagatt agagataagt atgagaagaa agctactcta attaagtctt 2100
ctgaagaatg aagataaaat gttgatcatg tatatatatc catagtgaat aaaattgtct 2160
cagtaaagtg taaaaaaaaa aaaaaaaaaa aaaaaaaaaa aaaaaaaaa 2209

<210> SEQ ID NO 118
<211> LENGTH: 1740
<212> TYPE: DNA
<213> ORGANISM: Homo sapiens

<400> SEQUENCE: 118
ctccctcctc tgcaccatga ctacctgcag ccgccagttc acctcctcca gctccatgaa 60
gggctcctgc ggcatcgggg gcggcatcgg gggcggctcc agccgcatct cctccgtcct 120
ggccggaggg tcctgccgcg cccccagcac ctacgggggc ggcctgtctg tctcatcctc 180
ccgcttctcc tctgggggag cctatgggtt gggggggcggc tatggcggtg gcttcagcag 240
cagcagcagc agctttggta gtggctttgg gggaggatat ggtggtggcc ttggtgctgg 300
cttgggtggt ggctttggtg gtggctttgc tggtggtgat gggcttctgg tgggcagtga 360
gaaggtgacc atgcagaacc tcaacgaccg cctggcctcc tacctggaca aggtgcgtgc 420
tctggaggag gccaacgccg acctggaagt gaagatccgt gactggtacc agaggcagcg 480
gcctgctgag atcaaagact acagtcccta cttcaagacc attgaggacc tgaggaacaa 540
gattctcaca gccacagtgg acaatgccaa tgtccttctg cagattgaca atgcccgtct 600
ggccgcggat gacttccgca ccaagtatga gacagagttg aacctgcgca tgagtgtgga 660
agccgacatc aatggcctgc gcagggtgct ggacgaactg accctggcca gagctgacct 720
ggagatgcag attgagagcc tgaaggagga gctggcctac ctgaagaaga accacgagga 780
ggagatgaat gccctgagag gccaggtggg tggagatgtc aatgtggaga tggacgctgc 840
acctggcgtg gacctgagcc gcattctgaa cgagatgcgt gaccagtatg agaagatggc 900
agagaagaac cgcaaggatg ccgaggaatg gttcttcacc aagacagagg agctgaaccg 960
cgaggtggcc accaacagcg agctggtgca gagcggcaag agcgagatct cggagctccg 1020
gcgcaccatg cagaacctgg agattgagct gcagtcccag ctcagcatga aagcatccct 1080
ggagaacagc ctggaggaga ccaaaggtcg ctactgcatg cagctggccc agatccagga 1140
gatgattggc agcgtggagg agcagctggc ccagctccgc tgcgagatgg agcagcagaa 1200
ccaggagtac aagatcctgc tggacgtgaa gacgcggctg gagcaggaga tcgccaccta 1260
ccgccgcctg ctggagggcg aggacgccca cctctcctcc tcccagttct cctctggatc 1320
gcagtcatcc agagatgtga cctcctccag ccgccaaatc cgcaccaagg tcatggatgt 1380
gcacgatggc aaggtggtgt ccacccacga gcaggtcctt cgcaccaaga actgaggctg 1440
cccagccccg ctcaggccta ggaggccccc cgtgtggaca cagatcccac tggaagatcc 1500
cctctcctgc ccaagcactt cacagctgga ccctgcttca ccctcacccc ctcctggcaa 1560
tcaatacagc ttcattatct gagttgcata aaaaaaaaaa aaaaaaaaaa aaaaaaaaaa 1620
aaaaaaaaaa aaaaaaaaaa aaaaaaaaaa aaaaaaaaaa aaaaaaaaaa aaaaaaaaaa 1680
aaaaaaaaaa aaaaaaaaaa aaaaaaaaaa aaaaaaaaaa aaaaaaaaaa aaaaaaaaaa 1740

<210> SEQ ID NO 119
<211> LENGTH: 2895
<212> TYPE: DNA
<213> ORGANISM: Homo sapiens

<400> SEQUENCE: 119
ctcttttgca ggggccgttc ctcggggcat gacgctggct cctgcacaga tcctgctcct 60
ctgtggcctt cctgggctgc cctcccctcc tccgggactg ctctggactg acactgctca 120
ggttcggatt ccctcaaaga ctttgggaga caagacttgg tccccctttt acaaacaagg 180
gaacggaggc tctagaactg acttcctgaa aggcttggat ccaaagctcc ctcagttcag 240
cggccacgtc tatttccctc agacacaggg atccttgaac ctgtgggctg tatctccccg 300
cggacttgga agaatcccaa gagagtgggg ctcccacagg ctggagtgca atggtgtgat 360
ctcggctcac tgcaacctcc acctcccagg ttcaagctat tctcctgcct cagcctcctg 420
agtagctggg attacagatc ctggtggctg tggtcggtaa ttccagcttc gtgctggcta 480
caggtggatg atgcccacct ggctgccgat gacctctgca ccaagtgagg ctgggtctct 540
ggagctgccc caggggctgg acaagctgac cctggccggg gccaacctgg agatgcagat 600
tgagaacctc aaggaggacc tggtctacct gaagaagaac cacaagcagg aaatgaacgt 660
cctttgaggt caggtggatg aggatgtcag tgtgaagatg gacactgtgc ctggagtgaa 720
cctgagctgc atcctgaatg agatgcgtga ccaggacaag acattggtgg agaagagctg 780
caaggatgcc gagggctggt tcttcagcat ggtgggtggc cgtgcgtaag caggtgtgta 840
cacgtgtggg cacatgtgct gcatgctggt gcagctggag cactggcaga tccacaggct 900
gtcccagttg gaaggacttt tggaaaccag ttggaccagc ccctcatgtt ttagatgtaa 960
aacgtgaggc tcagagagga ctcaagctca cacagccctt cactgtggcc tgcaaaatag 1020
atccaggtct ctacaagtct ggtcttgggt ttccaccaca gctgtttaca ggatgtgcgt 1080
atttgaatac atatgtatac ccttggcaag cacaggctga gtatctccgg tatcctaggg 1140
acagcaacag gcgcaaaaga ataacaccca gtgcctgtct ttgaggtgct gcagttcagt 1200
aggaaaaaga aatgcaaatg accgcagagc aggctgaatt cctccaagtt ccaatgtggg 1260
tgcagaggct ctctgtgtgc agaaagaggg gctgaactgc gaggtggcca ccaacacaga 1320
ggccctgcag agtggctgga tagagatatg gagctctacg tctctgtgca gaacctgagc 1380
cgtcccagct cagcaagaaa gcatcgctgg agggcagcct ggtggagatg gaggtgtgtt 1440
acaggaccct gccggcccag ctgcaggggc ttaacagaag catggagcag cagctgtgcg 1500
agctctgctg cgacacggag caccaggacc acaagcacag gtccttctgg acgtgaagac 1560
gtggctggag caggagatcg ccacctaccg ccgcttgctg gaggttgagg acgcccagag 1620
gtgatactga cgatgcaggc tggagtctgg ctgaggagcc ttgaatgcca agttaaagcg 1680
tctggactag atcacgtagg caatggggag ccatggaggg atttggagca ggagagtgaa 1740
atgaacatca agagatttta gaacattcac tctggctgca gagggagaaa tggatcagag 1800
gggtcagggc ggggccagag agatgtgtca gggggctgga gcagggagtc tggccagaga 1860
agtcccgtgc ggtggtgggt agtggggcag gggaaggaag gtggtgcacg cagaagagag 1920
gttatagctc aaaacagcgg gactggatgc ctggatctcg gggtaagcat ggctcacagt 1980
caggactcag taagtgtcgg gagaacacat gaaggagcag gcattgatgg ccctgggttt 2040
ctggttctga tgactgtgtg agtggtgaag agcaaggtgg gtggtggttg ggtttgcagt 2100
tgggaagggt gatcaggcct tcagctgaga gtgtcccgga gtctccatgc ttagtcacac 2160
gttgcagctt tttgctcccc ggaaatggtg aagtccatct atagtctaac aacagtctct 2220
cctgctttaa ttgggtctat ttgttgggcc ctctgggtta tggaaaaacc acttgctcag 2280
cttctccttg taaattcctg gtgagtagcc acagagtgcc gccagaccta ctgctgtgct 2340
gtttcttttt cttcttcctg ctgtgctgaa cccctgccct ttcattcttg ggcctgcgct 2400
aatttctgtg cattcccaac tgtgattttt caccaattta ggggaacctc ctctgccagg 2460
gcctacttct ccccagcagt gcttgcaggt gcctgggctg gctggcatcc ctgggctgat 2520

```
gggtgcttct ctccctgcag gctggccact cagtactcct tgtccctggc ctcgcagccc   2580

acccgggaag ccacagtgac cagccaccag gtgtgccatc gtggaggaag tccaggttgg   2640

agaggtggtc ttcttctgtg agcaggtcca cttctccacc cactgagacc cctttctgtc   2700

tgcgacagcc ccacctcgag ggccacggca cagccatcag ctccagctcc cagcatgcta   2760

ctgccacgcc ccgagtgtcc gtctgggccc cggtgcatgg cctgttgtct ttctgtatct   2820

actttctgca gcccctcact gaggaggcct cctgggtttg tccagtgcct actattaaag   2880

ctttgctcca agttc                                                    2895
```

```
<210> SEQ ID NO 120
<211> LENGTH: 2529
<212> TYPE: DNA
<213> ORGANISM: Homo sapiens

<400> SEQUENCE: 120

gcatcctttt tgggctgctc acagccccca gcctctatgg tgaagacata cttgctagca     60

gcgtcaccaa cttgctgcca agagatcagt gctgcaaggc aaggttattt ctaactgagc    120

agagcctgcc aggaagaaag cgtttgcacc ccacaccact gtgcaggtgt gaccggtgag    180

ctcacagctg ccccccaggc atgcccagcc cacttaatca ttcacagctc gacagctctc    240

tcgcccagcc cagttctgga agggataaaa agggggcatc accgttcctg ggtaacagag    300

ccaccttctg cgtcctgctg agctctgttc tctccagcac ctcccaaccc actagtgcct    360

ggttctcttg ctccaccagg aacaagccac catgtctcgc cagtcaagtg tgtccttccg    420

gagcgggggc agtcgtagct tcagcaccgc ctctgccatc accccgtctg tctcccgcac    480

cagcttcacc tccgtgtccc ggtccggggg tggcggtggt ggtggcttcg gcagggtcag    540

ccttgcgggt gcttgtggag tgggtggcta tggcagccgg agcctctaca acctgggggg    600

ctccaagagg atatccatca gcactagagg aggcagcttc aggaaccggt ttggtgctgg    660

tgctggaggc ggctatggct ttggaggtgg tgccggtagt ggatttggtt tcggcggtgg    720

agctggtggt ggctttgggc tcggtggcgg agctggcttt ggaggtggct tcggtggccc    780

tggctttcct gtctgccctc ctggaggtat ccaagaggtc actgtcaacc agagtctcct    840

gactcccctc aacctgcaaa tcgaccccag catccagagg gtgaggaccg aggagcgcga    900

gcagatcaag accctcaaca ataagtttgc ctccttcatc gacaaggtgc ggttcctgga    960

gcagcagaac aaggttctgg acaccaagtg gaccctgctg caggagcagg gcaccaagac   1020

tgtgaggcag aacctggagc cgttgttcga gcagtacatc aacaacctca ggaggcagct   1080

ggacagcatc gtgggggaac ggggccgcct ggactcagag ctgagaaaca tgcaggacct   1140

ggtggaagac ttcaagaaca agtatgagga tgaaatcaac aagcgtacca ctgctgagaa   1200

tgagtttgtg atgctgaaga aggatgtaga tgctgcctac atgaacaagg tggagctgga   1260

ggccaaggtt gatgcactga tggatgagat taacttcatg aagatgttct ttgatgcgga   1320

gctgtcccag atgcagacgc atgtctctga cacctcagtg gtcctctcca tggacaacaa   1380

ccgcaacctg gacctggata gcatcatcgc tgaggtcaag gcccagtatg aggagattgc   1440

caaccgcagc cggacagaag ccgagtcctg gtatcagacc aagtatgagg agctgcagca   1500

gacagctggc cggcatggcg atgacctccg caacaccaag catgagatca cagagatgaa   1560

ccggatgatc cagaggctga gagccgagat tgacaatgtc aagaaacagt gcgccaatct   1620

gcagaacgcc attgcggatg ccgagcagcg tggggagctg gccctcaagg atgccaggaa   1680

caagctggcc gagctggagg aggccctgca gaaggccaag caggacatgg cccggctgct   1740
```

gcgtgagtac caggagctca tgaacaccaa gctggccctg gacgtggaga tcgccactta 1800
ccgcaagctg ctggagggcg aggaatgcag actcagtgga gaaggagttg gaccagtcaa 1860
catctctgtt gtcacaagca gtgtttcctc tggatatggc agtggcagtg gctatggcgg 1920
tggcctcggt ggaggtcttg gcggcggcct cggtggaggt cttgccggag gtagcagtgg 1980
aagctactac tccagcagca gtgggggtgt cggcctaggt ggtgggctca gtgtgggggg 2040
ctctggcttc agtgcaagca gtggccgagg gctgggggtg ggctttggca gtggcggggg 2100
tagcagctcc agcgtcaaat ttgtctccac cacctcctcc tcccggaaga gcttcaagag 2160
ctaagaacct gctgcaagtc actgccttcc aagtgcagca acccagccca tggagattgc 2220
ctcttctagg cagttgctca agccatgttt tatccttttc tggagagtag tctagaccaa 2280
gccaattgca gaaccacatt ctttggttcc caggagagcc ccattcccag cccctggtct 2340
cccgtgccgc agttctatat tctgcttcaa atcagccttc aggtttccca cagcatggcc 2400
cctgctgaca cgagaaccca aagttttccc aaatctaaat catcaaaaca gaatccccac 2460
cccaatccca aattttgttt tggttctaac tacctccaga atgtgttcaa taaaatgctt 2520
ttataatat 2529

<210> SEQ ID NO 121
<211> LENGTH: 6816
<212> TYPE: DNA
<213> ORGANISM: Homo sapiens

<400> SEQUENCE: 121
ggacggccga gcggcagggc gctcgcgcgc gcccactagt ggccggagga gaaggctccc 60
gcggaggccg cgctgcccgc cccctcccct ggggaggctc gcgttcccgc tgctcgcgcc 120
tgcgccgccc gccggcctca ggaacgcgcc ctcttcgccg gcgcgcgccc tcgcagtcac 180
cgccacccac cagctccggc accaacagca gcgccgctgc caccgcccac cttctgccgc 240
cgccaccaca gccaccttct cctcctccgc tgtcctctcc cgtcctcgcc tctgtcgact 300
atcaggtgaa ctttgaacca ggatggctga gccccgccag gagttcgaag tgatggaaga 360
tcacgctggg acgtacgggt tgggggacag gaaagatcag gggggctaca ccatgcacca 420
agaccaagag ggtgacacgg acgctggcct gaaagaatct cccctgcaga cccccactga 480
ggacggatct gaggaaccgg gctctgaaac ctctgatgct aagagcactc caacagcgga 540
agatgtgaca gcacccttag tggatgaggg agctcccggc aagcaggctg ccgcgcagcc 600
ccacacggag atcccagaag gaaccacagc tgaagaagca ggcattggag acacccccag 660
cctggaagac gaagctgctg gtcacgtgac ccaagagcct gaaagtggta aggtggtcca 720
ggaaggcttc ctccgagagc caggcccccc aggtctgagc caccagctca tgtccggcat 780
gcctggggct cccctcctgc ctgagggccc cagagaggcc acacgccaac cttcggggac 840
aggacctgag gacacagagg gcggccgcca cgcccctgag ctgctcaagc accagcttct 900
aggagacctg caccaggagg ggccgccgct gaagggggca gggggcaaag agaggccggg 960
gagcaaggag gaggtggatg aagaccgcga cgtcgatgag tcctccccc aagactcccc 1020 tccctccaag gcctccccag cccaagatgg gcggcctccc cagacagccg ccagagaagc 1080
caccagcatc ccaggcttcc cagcggaggg tgccatcccc ctccctgtgg atttcctctc 1140
caaagtttcc acagagatcc cagcctcaga gcccgacggg cccagtgtag ggcgggccaa 1200
agggcaggat gccccccctgg agttcacgtt tcacgtggaa atcacaccca acgtgcagaa 1260

-continued

```
ggagcaggcg cactcggagg agcatttggg aagggctgca tttccagggg cccctggaga   1320
ggggccagag gcccggggcc cctctttggg agaggacaca aaagaggctg accttccaga   1380
gccctctgaa aagcagcctg ctgctgctcc gcgggggaag cccgtcagcc gggtccctca   1440
actcaaagct cgcatggtca gtaaaagcaa agacgggact ggaagcgatg acaaaaaagc   1500
caagacatcc acacgttcct ctgctaaaac cttgaaaaat aggccttgcc ttagccccaa   1560
acaccccact cctggtagct cagaccctct gatccaaccc tccagccctg ctgtgtgccc   1620
agagccacct tcctctccta aatacgtctc ttctgtcact tcccgaactg gcagttctgg   1680
agcaaaggag atgaaactca agggggctga tggtaaaacg aagatcgcca caccgcgggg   1740
agcagcccct ccaggccaga agggccaggc caacgccacc aggattccag caaaaacccc   1800
gcccgctcca aagacaccac ccagctctgc gactaagcaa gtccagagaa gaccaccccc   1860
tgcagggccc agatctgaga gaggtgaacc tccaaaatca ggggatcgca gcggctacag   1920
cagccccggc tccccaggca ctcccggcag ccgctcccgc accccgtccc ttccaacccc   1980
acccacccgg gagcccaaga aggtggcagt ggtccgtact ccacccaagt cgccgtcttc   2040
cgccaagagc cgcctgcaga cagcccccgt gcccatgcca gacctgaaga atgtcaagtc   2100
caagatcggc tccactgaga acctgaagca ccagccggga ggcgggaagg tgcagataat   2160
taataagaag ctggatctta gcaacgtcca gtccaagtgt ggctcaaagg ataatatcaa   2220
acacgtcccg ggaggcggca gtgtgcaaat agtctacaaa ccagttgacc tgagcaaggt   2280
gacctccaag tgtggctcat taggcaacat ccatcataaa ccaggaggtg gccaggtgga   2340
agtaaaatct gagaagcttg acttcaagga cagagtccag tcgaagattg ggtccctgga   2400
caatatcacc cacgtccctg gcggaggaaa taaaaagatt gaaacccaca agctgacctt   2460
ccgcgagaac gccaaagcca agacagacca cggggcggag atcgtgtaca agtcgccagt   2520
ggtgtctggg gacacgtctc cacggcatct cagcaatgtc tcctccaccg gcagcatcga   2580
catggtagac tcgccccagc tcgccacgct agctgacgag gtgtctgcct ccctggccaa   2640
gcagggtttg tgatcaggcc cctggggcgg tcaataattg tggagaggag agaatgagag   2700
agtgtggaaa aaaaaagaat aatgacccgg cccccgccct ctgcccccag ctgctcctcg   2760
cagttcggtt aattggttaa tcacttaacc tgcttttgtc actcggcttt ggctcgggac   2820
ttcaaaatca gtgatgggag taagagcaaa tttcatcttt ccaaattgat gggtgggcta   2880
gtaataaaat atttaaaaaa aaacattcaa aaacatggcc acatccaaca tttcctcagg   2940
caattccttt tgattctttt ttcttccccc tccatgtaga agagggagaa ggagaggctc   3000
tgaaagctgc ttctggggga tttcaaggga ctgggggtgc caaccacctc tggccctgtt   3060
gtgggggtgt cacagaggca gtggcagcaa caaaggattt gaaacttggt gtgttcgtgg   3120
agccacaggc agacgatgtc aaccttgtgt gagtgtgacg gggggttgggg tggggcggga   3180
ggccacgggg gaggccgagg caggggctgg gcagaggggga gaggaagcac aagaagtggg   3240
agtgggagag gaagccacgt gctggagagt agacatcccc ctccttgccg ctgggagagc   3300
caaggcctat gccacctgca gcgtctgagc ggccgcctgt ccttggtggc cgggggtggg   3360
ggcctgctgt gggtcagtgt gccaccctct gcagggcagc ctgtgggaga agggacagcg   3420
ggtaaaaaga gaaggcaagc tggcaggagg gtggcacttc gtggatgacc tccttagaaa   3480
agactgacct tgatgtcttg agagcgctgg cctcttcctc cctccctgca gggtaggggg   3540
cctgagttga ggggcttccc tctgctccac agaaaccctg ttttattgag ttctgaaggt   3600
tggaactgct gccatgattt tggccacttt gcagacctgg gactttaggg ctaaccagtt   3660
```

-continued

```
ctctttgtaa ggacttgtgc ctcttgggag acgtccaccc gtttccaagc ctgggccact   3720
ggcatctctg gagtgtgtgg gggtctggga ggcaggtccc gagcccccctg tccttcccac   3780
ggccactgca gtcaccccgt ctgcgccgct gtgctgttgt ctgccgtgag agcccaatca   3840
ctgcctatac ccctcatcac acgtcacaat gtcccgaatt cccagcctca ccaccccttc   3900
tcagtaatga ccctggttgg ttgcaggagg tacctactcc atactgaggg tgaaattaag   3960
ggaaggcaaa gtccaggcac aagagtggga ccccagcctc tcactctcag ttccactcat   4020
ccaactggga ccctcaccac gaatctcatg atctgattcg gttccctgtc tcctcctccc   4080
gtcacagatg tgagccaggg cactgctcag ctgtgaccct aggtgtttct gccttgttga   4140
catggagaga gccctttccc ctgagaaggc ctggcccctt cctgtgctga gcccacagca   4200
gcaggctggg tgtcttggtt gtcagtggtg gcaccaggat ggaagggcaa ggcacccagg   4260
gcaggcccac agtcccgctg tcccccactt gcaccctagc ttgtagctgc caacctccca   4320
gacagcccag cccgctgctc agctccacat gcatagtatc agccctccac acccgacaaa   4380
ggggaacaca ccccccttgga aatggttctt ttcccccagt cccagctgga agccatgctg   4440
tctgttctgc tggagcagct gaacatatac atagatgttg ccctgccctc cccatctgca   4500
ccctgttgag ttgtagttgg atttgtctgt ttatgcttgg attcaccaga gtgactatga   4560
tagtgaaaag aaaaaaaaaa aaaaaaaagg acgcatgtat cttgaaatgc ttgtaaagag   4620
gtttctaacc caccctcacg aggtgtctct cacccccaca ctgggactcg tgtggcctgt   4680
gtggtgccac cctgctgggg cctcccaagt tttgaaaggc tttcctcagc acctgggacc   4740
caacagagac cagcttctag cagctaagga ggccgttcag ctgtgacgaa ggcctgaagc   4800
acaggattag gactgaagcg atgatgtccc cttccctact tccccttggg gctccctgtg   4860
tcagggcaca gactaggtct tgtggctggt ctggcttgcg gcgcgaggat ggttctctct   4920
ggtcatagcc cgaagtctca tggcagtccc aaaggaggct tacaactcct gcatcacaag   4980
aaaaaggaag ccactgccag ctggggggat ctgcagctcc cagaagctcc gtgagcctca   5040
gccacccctc agactgggtt cctctccaag ctcgccctct ggaggggcag cgcagcctcc   5100
caccaagggc cctgcgacca cagcagggat tgggatgaat tgcctgtcct ggatctgctc   5160
tagaggccca agctgcctgc ctgaggaagg atgacttgac aagtcaggag acactgttcc   5220
caaagccttg accagagcac ctcagcccgc tgaccttgca caaactccat ctgctgccat   5280
gagaaaaggg aagccgcctt tgcaaaacat tgctgcctaa agaaactcag cagcctcagg   5340
cccaattctg ccacttctgg tttgggtaca gttaaaggca accctgaggg acttggcagt   5400
agaaatccag ggcctcccct ggggctggca gcttcgtgtg cagctagagc tttacctgaa   5460
aggaagtctc tgggcccaga actctccacc aagagcctcc ctgccgttcg ctgagtccca   5520
gcaattctcc taagttgaag ggatctgaga aggagaagga aatgtggggt agatttggtg   5580
gtggttagag atatgccccc ctcattactg ccaacagttt cggctgcatt tcttcacgca   5640
cctcggttcc tcttcctgaa gttcttgtgc cctgctcttc agcaccatgg gccttcttat   5700
acggaaggct ctgggatctc ccccttgtgg ggcaggctct tggggccagc ctaagatcat   5760
ggtttagggt gatcagtgct ggcagataaa ttgaaaaggc acgctggctt gtgatcttaa   5820
atgaggacaa tccccccagg gctgggcact cctcccctcc cctcacttct cccacctgca   5880
gagccagtgt ccttgggtgg gctagatagg atatactgta tgccggctcc ttcaagctgc   5940
tgactcactt tatcaatagt tccatttaaa ttgacttcag tggtgagact gtatcctgtt   6000
```

-continued tgctattgct tgttgtgcta tggggggagg ggggaggaat gtgtaagata gttaacatgg 6060
gcaaagggag atcttggggt gcagcactta aactgcctcg taaccctttt catgatttca 6120
accacatttg ctagagggag ggagcagcca cggagttaga ggcccttggg gtttctcttt 6180
tccactgaca ggctttccca ggcagctggc tagttcattc cctccccagc caggtgcagg 6240
cgtaggaata tggacatctg gttgctttgg cctgctgccc tctttcaggg gtcctaagcc 6300
cacaatcatg cctccctaag accttggcat ccttccctct aagccgttgg cacctctgtg 6360
ccacctctca cactggctcc agacacacag cctgtgcttt tggagctgag atcactcgct 6420
tcaccctcct catctttgtt ctccaagtaa agccacgagg tcggggcgag ggcagaggtg 6480
atcacctgcg tgtcccatct acagacctgc agcttcataa aacttctgat ttctcttcag 6540
ctttgaaaag ggttaccctg ggcactggcc tagagcctca cctcctaata gacttagccc 6600
catgagtttg ccatgttgag caggactatt tctggcactt gcaagtccca tgatttcttc 6660
ggtaattctg agggtggggg gagggacatg aaatcatctt agcttagctt tctgtctgtg 6720
aatgtctata tagtgtattg tgtgttttaa caaatgattt acactgactg ttgctgtaaa 6780
agtgaatttg gaaataaagt tattactctg attaaa 6816

<210> SEQ ID NO 122
<211> LENGTH: 2372
<212> TYPE: DNA
<213> ORGANISM: Homo sapiens

<400> SEQUENCE: 122
gcaccgcgcg agcttggctg cttctggggc ctgtgtggcc ctgtgtgtcg gaaagatgga 60
gcaagaagcc gagcccgagg ggcggccgcg acccctctga ccgagatcct gctgctttcg 120
cagccaggag caccgtccct ccccggatta gtgcgtacga gcgcccagtg ccctggcccg 180
gagagtggaa tgatccccga ggcccagggc gtcgtgcttc cgcagtagtc agtccccgtg 240
aaggaaactg gggagtcttg agggaccccc gactccaagc gcgaaaaccc cggatggtga 300
ggagcaggca aatgtgcaat accaacatgt ctgtacctac tgatggtgct gtaaccacct 360
cacagattcc agcttcggaa caagagaccc tggttagacc aaagccattg cttttgaagt 420
tattaaagtc tgttggtgca caaaaagaca cttatactat gaaagaggtt ctttttttatc 480 ttggccagta tattatgact aaacgattat atgatgagaa gcaacaacat attgtatatt 540
gttcaaatga tcttctagga gatttgtttg gcgtgccaag cttctctgtg aaagagcaca 600
ggaaaatata taccatgatc tacaggaact tggtagtagt caatcagcag gaatcatcgg 660
actcaggtac atctgtgagt gagaacaggt gtcaccttga aggtgggagt gatcaaaagg 720
accttgtaca agagcttcag gaagagaaac cttcatcttc acatttggtt tctagaccat 780
ctacctcatc tagaaggaga gcaattagtg agacagaaga aaattcagat gaattatctg 840
gtgaacgaca aagaaaacgc cacaaatctg atagtatttc cctttccttt gatgaaagcc 900
tggctctgtg tgtaataagg gagatatgtt gtgaaagaag cagtagcagt gaatctacag 960
ggacgccatc gaatccggat cttgatgctg gtgtaagtga acattcaggt gattggttgg 1020
atcaggattc agtttcagat cagtttagtg tagaatttga agttgaatct ctcgactcag 1080
aagattatag ccttagtgaa gaaggacaag aactctcaga tgaagatgat gaggtatatc 1140
aagttactgt gtatcaggca ggggagagtg atacagattc atttgaagaa gatcctgaaa 1200
tttccttagc tgactattgg aaatgcactt catgcaatga aatgaatccc ccccttccat 1260
cacattgcaa cagatgttgg gcccttcgtg agaattggct tcctgaagat aaagggaaag 1320
ataaagggga aatctctgag aaagccaaac tggaaaactc aacacaagct gaagagggct 1380
ttgatgttcc tgattgtaaa aaaactatag tgaatgattc cagagagtca tgtgttgagg 1440
aaaatgatga taaaattaca caagcttcac aatcacaaga aagtgaagac tattctcagc 1500
catcaacttc tagtagcatt atttatagca gccaagaaga tgtgaaagag tttgaaaggg 1560
aagaaaccca agacaaagaa gagagtgtgg aatctagttt gcccccttaat gccattgaac 1620 cttgtgtgat ttgtcaaggt cgacctaaaa atggttgcat tgtccatggc aaaacaggac 1680
atcttatggc ctgctttaca tgtgcaaaga agctaaagaa aaggaataag ccctgcccag 1740
tatgtagaca accaattcaa atgattgtgc taacttattt cccctagttg acctgtctat 1800
aagagaatta tatatttcta actatataac cctaggaatt tagacaacct gaaatttatt 1860
cacatatatc aaagtgagaa aatgcctcaa ttcacataga tttcttctct ttagtataat 1920
tgacctactt tggtagtgga atagtgaata cttactataa tttgacttga atatgtagct 1980
catcctttac accaactcct aattttaaat aatttctact ctgtcttaaa tgagaagtac 2040
ttggtttttt ttttcttaaa tatgtatatg acatttaaat gtaacttatt attttttttg 2100
agaccgagtc ttgctctgtt acccaggctg gagtgcagtg ggtgatcttg gctcactgca 2160
agctctgccc tccccgggtt cgcaccattc tcctgcctca gcctcccaat tagcttggcc 2220
tacagtcatc tgccaccaca cctggctaat tttttgtact tttagtagag acagggtttc 2280
accgtgttag ccaggatggt ctcgatctcc tgacctcgtg atccgcccac ctcggcctcc 2340
caaagtgctg ggattacagg catgagccac cg 2372

<210> SEQ ID NO 123
<211> LENGTH: 2486
<212> TYPE: DNA
<213> ORGANISM: Homo sapiens

<400> SEQUENCE: 123
gagatttgat tcccttggcg ggcggaagcg gccacaaccc ggcgatcgaa aagattctta 60
ggaacgccgt accagccgcg tctctcagga cagcaggccc ctgtccttct gtcgggcgcc 120
gctcagccgt gccctccgcc cctcaggttc tttttctaat tccaaataaa cttgcaagag 180
gactatgaaa gattatgatg aacttctcaa atattatgaa ttacatgaaa ctattgggac 240
aggtggcttt gcaaaggtca aacttgcctg ccatatcctt actggagaga tggtagctat 300
aaaaatcatg gataaaaaca cactagggag tgatttgccc cggatcaaaa cggagattga 360
ggccttgaag aacctgagac atcagcatat atgtcaactc taccatgtgc tagagacagc 420
caacaaaata ttcatggttc ttgagtactg ccctggagga gagctgtttg actatataat 480
ttcccaggat cgcctgtcag aagaggagac ccgggttgtc ttccgtcaga tagtatctgc 540
tgttgcttat gtgcacagcc agggctatgc tcacagggac ctcaagccag aaaatttgct 600
gtttgatgaa tatcataaat taaagctgat tgactttggt ctctgtgcaa aacccaaggg 660
taacaaggat taccatctac agacatgctg tgggagtctg gcttatgcag cacctgagtt 720
aatacaaggc aaatcatatc ttggatcaga ggcagatgtt tggagcatgg gcatactgtt 780
atatgttctt atgtgtggat ttctaccatt tgatgatgat aatgtaatgg ctttatacaa 840
gaagattatg agaggaaaat atgatgttcc caagtggctc tctcccagta gcattctgct 900
tcttcaacaa atgctgcagg tggacccaaa gaaacggatt tctatgaaaa atctattgaa 960
ccatccctgg atcatgcaag attacaacta tcctgttgag tggcaaagca agaatccttt 1020

-continued tattcacctc gatgatgatt gcgtaacaga actttctgta catcacagaa acaacaggca 1080
aacaatggag gatttaattt cactgtggca gtatgatcac ctcacggcta cctatcttct 1140
gcttctagcc aagaaggctc ggggaaaacc agttcgttta aggctttctt ctttctcctg 1200
tggacaagcc agtgctaccc cattcacaga catcaagtca aataattgga gtctggaaga 1260
tgtgaccgca agtgataaaa attatgtggc gggattaata gactatgatt ggtgtgaaga 1320
tgatttatca acaggtgctg ctactccccg aacatcacag tttaccaagt actggacaga 1380
atcaaatggg gtggaatcta aatcattaac tccagcctta tgcagaacac ctgcaaataa 1440
attaaagaac aaagaaaatg tatatactcc taagtctgct gtaaagaatg aagagtactt 1500
tatgtttcct gagccaaaga ctccagttaa taagaaccag cataagagag aaatactcac 1560
tacgccaaat cgttacacta caccctcaaa agctagaaac cagtgcctga aagaaactcc 1620
aattaaaata ccagtaaatt caacaggaac agacaagtta atgacaggtg tcattagccc 1680
tgagaggcgg tgccgctcag tggaattgga tctcaaccaa gcacatatgg aggagactcc 1740
aaaaagaaag ggagccaaag tgtttgggag ccttgaaagg gggttggata aggttatcac 1800
tgtgctcacc aggagcaaaa ggaagggttc tgccagagac gggcccagaa gactaaagct 1860
tcactataac gtgactacaa ctagattagt gaatccagat caactgttga atgaaataat 1920
gtctattctt ccaaagaagc atgttgactt tgtacaaaag ggttatacac tgaagtgtca 1980
aacacagtca gattttggga aagtgacaat gcaatttgaa ttagaagtgt gccagcttca 2040
aaaacccgat gtggtgggta tcaggaggca gcggcttaag ggcgatgcct gggtttacaa 2100
aagattagtg gaagacatcc tatctagctg caaggtataa ttgatggatt cttccatcct 2160
gccggatgag tgtgggtgtg atacagccta cataaagact gttatgatcg ctttgatttt 2220
aaagttcatt ggaactacca acttgtttct aaagagctat cttaagacca atatctcttt 2280
gtttttaaac aaaagatatt attttgtgta tgaatctaaa tcaagcccat ctgtcattat 2340
gttactgtct tttttaatca tgtggttttg tatattaata attgttgact ttcttagatt 2400
cacttccata tgtgaatgta agctcttaac tatgtctctt tgtaatgtgt aatttctttc 2460
tgaaataaaa ccatttgtga atatag 2486

<210> SEQ ID NO 124
<211> LENGTH: 1140
<212> TYPE: DNA
<213> ORGANISM: Homo sapiens
<220> FEATURE:
<221> NAME/KEY: misc_feature
<222> LOCATION: (1140)..(1140)
<223> OTHER INFORMATION: n is a, c, g, t or u

<400> SEQUENCE: 124
gcagcggagg agcccagtcc acgatggccc ggtccctggt gtgccttggt gtcatcatct 60
tgctgtctgc cttctccgga cctggtgtca ggggtggtcc tatgcccaag ctggctgacc 120
ggaagctgtg tgcggaccag gagtgcagcc accctatctc catggctgtg gcccttcagg 180
actacatggc cccccgactgc cgattcctga ccattcaccg ggccaagtg gtgtatgtct 240 tctccaagct gaagggccgt gggcggctct tctggggagg cagcgttcag ggagattact 300
atggagatct ggctgctcgc ctgggctatt tccccagtag cattgtccga gaggaccaga 360
ccctgaaacc tggcaaagtc gatgtgaaga cagacaaatg ggatttctac tgccagtgag 420
ctcagcctac cgctggccct gccgtttccc ctccttgggt ttatgcaaat acaatcagcc 480
cagtgcaaaa aaaaaaaaaa aaaaaaaaaa cttcggagaa gagatagcaa caaaaggccg 540

-continued cttgtgtgaa ggcgccaaaa gttttcgccc aagagacctt cggcctcccc cagggcgcgc 600
gcaaaggcgc cttgttttga caacctcttg gacaaccgga ggggctaccg cccggagacc 660
cctgtggtgg accccccggg caacccggtg tgacagggta ctcaccccca cggctttgtc 720
gggggtccca ccaaaggccc caaagaggct ctttcaaggc actattcctt gttgtagacc 780
ttgtgtgtgc cacaggcgcc aaagaaacct cggggggcta acaaacgcac gtgcttggca 840
gctccgagaa ggctctctcc cacccgaggg gtggacgcaa cagggggaat gggccatcat 900
attgttgccc ccggtgggca ccaactcttt ttcccccata gagaggcctt agcacactat 960
gtggggcacg ttattgccgc ctagagaaac cgagcgccag aaaatttcga aggggggggc 1020
gcttctcatc attttgcgca aaaccccctt gtgggagtat gccccgaact cctctggaac 1080
acacaagcga cacttgcgcg gggtctgcaa aaaacctcct gttgggaagc cggcttcacn 1140

<210> SEQ ID NO 125
<211> LENGTH: 12507
<212> TYPE: DNA
<213> ORGANISM: Homo sapiens

<400> SEQUENCE: 125
taccgggcgg aggtgagcgc ggcgccggct cctcctgcgg cggactttgg gtgcgacttg 60
acgagcggtg gttcgacaag tggccttgcg ggccggatcg tcccagtgga agagttgtaa 120
atttgcttct ggccttcccc tacggattat acctggcctt cccctacgga ttatactcaa 180
cttactgttt agaaaatgtg gcccacgaga cgcctggtta ctatcaaaag gagcggggtc 240
gacggtcccc actttcccct gagcctcagc acctgcttgt ttggaagggg tattgaatgt 300
gacatccgta tccagcttcc tgttgtgtca aaacaacatt gcaaaattga aatccatgag 360
caggaggcaa tattacataa tttcagttcc acaaatccaa cacaagtaaa tgggtctgtt 420
attgatgagc ctgtacggct aaaacatgga gatgtaataa ctattattga tcgttccttc 480
aggtatgaaa atgaaagtct tcagaatgga aggaagtcaa ctgaatttcc aagaaaaata 540
cgtgaacagg agccagcacg tcgtgtctca agatctagct tctcttctga ccctgatgag 600
aaagctcaag attccaaggc ctattcaaaa atcactgaag gaaaagtttc aggaaatcct 660
caggtacata tcaagaatgt caaagaagac agtaccgcag atgactcaaa agacagtgtt 720
gctcagggaa caactaatgt tcattcctca gaacatgctg gacgtaatgg cagaaatgca 780
gctgatccca tttctgggga ttttaaagaa atttccagcg ttaaattagt gagccgttat 840
ggagaattga agtctgttcc cactacacaa tgtcttgaca atagcaaaaa aaatgaatct 900 ccctttttgga agctttatga gtcagtgaag aaagagttgg atgtaaaatc acaaaaagaa 960
aatgtcctac agtattgtag aaaatctgga ttacaaactg attacgcaac agagaaagaa 1020
agtgctgatg gtttacaggg ggagacccaa ctgttggtct cgcgtaagtc aagaccaaaa 1080
tctggtggga gcggccacgc tgtggcagag cctgcttcac ctgaacaaga gcttgaccag 1140
aacaagggga agggaagaga cgtggagtct gttcagactc ccagcaaggc tgtgggcgcc 1200
agctttcctc tctatgagcc ggctaaaatg aagacccctg tacaatattc acagcaacaa 1260
aattctccac aaaaacataa gaacaaagac ctgtatacta ctggtagaag agaatctgtg 1320
aatctgggta aaagtgaagg cttcaaggct ggtgataaaa ctcttactcc caggaagctt 1380
tcaactagaa atcgaacacc agctaaagtt gaagatgcag ctgactctgc cactaagcca 1440
gaaaatctct cttccaaaac cagaggaagt attcctacag atgtggaagt tctgcctacg 1500

-continued

```
gaaactgaaa ttcacaatga gccattttta actctgtggc tcactcaagt tgagaggaag   1560
atccaaaagg attccctcag caagcctgag aaattgggca ctacagctgg acagatgtgc   1620
tctgggttac ctggtcttag ttcagttgat atcaacaact ttggtgattc cattaatgag   1680
agtgagggaa tacctttgaa aagaaggcgt gtgtcctttg gtgggcacct aagacctgaa   1740
ctatttgatg aaaacttgcc tcctaatacg cctctcaaaa ggggagaagc cccaaccaaa   1800
agaaagtctc tggtaatgca cactccacct gtcctgaaga aaatcatcaa ggaacagcct   1860
caaccatcag gaaaacaaga gtcaggttca gaaatccatg tggaagtgaa ggcacaaagc   1920
ttggttataa gccctccagc tcctagtcct aggaaaactc cagttgccag tgatcaacgc   1980
cgtaggtcct gcaaaacagc ccctgcttcc agcagcaaat ctcagacaga ggttcctaag   2040
agaggaggga gaaagagtgg caacctgcct tcaaagagag tgtctatcag ccgaagtcaa   2100
catgatattt tacagatgat atgttccaaa agaagaagtg gtgcttcgga agcaaatctg   2160
attgttgcaa aatcatgggc agatgtagta aaacttggtg caaaacaaac acaaactaaa   2220
gtcataaaac atggtcctca aaggtcaatg aacaaaaggc aaagaagacc tgctactcca   2280
aagaagcctg tgggcgaagt tcacagtcaa tttagtacag gccacgcaaa ctctccttgt   2340
accataataa tagggaaagc tcatactgaa aaagtacatg tgcctgctcg accctacaga   2400
gtgctcaaca acttcatttc caaccaaaaa atggacttta aggaagatct ttcaggaata   2460
gctgaaatgt tcaagacccc agtgaaggag caaccgcagt tgacaagcac atgtcacatc   2520
gctatttcaa attcagagaa tttgcttgga aaacagtttc aaggaactga ttcaggagaa   2580
gaacctctgc tccccacctc agagagtttt ggaggaaatg tgttcttcag tgcacagaat   2640
gcagcaaaac agccatctga taaatgctct gcaagccctc ccttaagacg gcagtgtatt   2700
agagaaaatg gaaacgtagc aaaaacgccc aggaacacct acaaaatgac ttctctggag   2760
acaaaaactt cagatactga gacagagcct tcaaaaacag tatccactgc aaacaggtca   2820
ggaaggtcta cagagttcag gaatatacag aagctacctg tggaaagtaa gagtgaagaa   2880
acaaatacag aaattgttga gtgcatccta aaaagaggtc agaaggcaac actactacaa   2940
caaaggagag aaggagagat gaaggaaata gaaagacctt ttgagacata taaggaaaat   3000
attgaattaa aagaaaacga tgaaaagatg aaagcaatga agagatcaag aacttggggg   3060
cagaaatgtg caccaatgtc tgacctgaca gacctcaaga gcttgcctga tacagaactc   3120
atgaaagaca cggcacgtgg ccagaatctc ctccaaaccc aagatcatgc caaggcacca   3180
aagagtgaga aaggcaaaat cactaaaatg ccctgccagt cattacaacc agaaccaata   3240
aacaccccaa cacacacaaa acaacagttg aaggcatccc tggggaaagt aggtgtgaaa   3300
gaagagctcc tagcagtcgg caagttcaca cggacgtcag gggagaccac gcacacgcac   3360
agagagccag caggagatgg caagagcatc agaacgttta aggagtctcc aaagcagatc   3420
ctggacccag cagcccgtgt aactggaatg aagaagtggc caagaacgcc taaggaagag   3480
gcccagtcac tagaagacct ggctggcttc aaagagctct tccagacacc aggtccctct   3540
gaggaatcaa tgactgatga gaaaactacc aaaatagcct gcaaatctcc accaccagaa   3600
tcagtggaca ctccaacaag cacaaagcaa tggcctaaga gaagtctcag gaaagcagat   3660
gtagaggaag aattcttagc actcaggaaa ctaacaccat cagcagggaa agccatgctt   3720
acgcccaaac cagcaggagg tgatgagaaa gacattaaag catttatggg aactccagtg   3780
cagaaactgg acctggcagg aactttacct ggcagcaaaa gacagctaca gactcctaag   3840
gaaaaggccc aggctctaga agacctggct ggctttaaag agctcttcca gactcctggt   3900
```

-continued

```
cacaccgagg aattagtggc tgctggtaaa accactaaaa taccctgcga ctctccacag   3960
tcagacccag tggacacccc aacaagcaca aagcaacgac ccaagagaag tatcaggaaa   4020
gcagatgtag agggagaact cttagcgtgc aggaatctaa tgccatcagc aggcaaagcc   4080
atgcacacgc ctaaaccatc agtaggtgaa gagaaagaca tcatcatatt tgtgggaact   4140
ccagtgcaga aactggacct gacagagaac ttaaccggca gcaagagacg gccacaaact   4200
cctaaggaag aggcccaggc tctggaagac ctgactggct ttaaagagct cttccagacc   4260
cctggtcata ctgaagaagc agtggctgct ggcaaaacta ctaaaatgcc ctgcgaatct   4320
tctccaccag aatcagcaga caccccaaca agcacaagaa ggcagcccaa gacacctttg   4380
gagaaaaggg acgtacagaa ggagctctca gccctgaaga agctcacaca gacatcaggg   4440
gaaaccacac acacagataa agtaccagga ggtgaggata aaagcatcaa cgcgtttagg   4500
gaaactgcaa aacagaaact ggacccagca gcaagtgtaa ctggtagcaa gaggcaccca   4560
aaaactaagg aaaaggccca acccctagaa gacctggctg gcttgaaaga gctcttccag   4620
acaccagtat gcactgacaa gcccacgact cacgagaaaa ctaccaaaat agcctgcaga   4680
tcacaaccag acccagtgga cacaccaaca agctccaagc cacagtccaa gagaagtctc   4740
aggaaagtgg acgtagaaga agaattcttc gcactcagga aacgaacacc atcagcaggc   4800
aaagccatgc acacacccaa accagcagta agtggtgaga aaaacatcta cgcatttatg   4860
ggaactccag tgcagaaact ggacctgaca gagaacttaa ctggcagcaa gagacggcta   4920
caaactccta aggaaaaggc ccaggctcta gaagacctgg ctggctttaa agagctcttc   4980
cagacacgag gtcacactga ggaatcaatg actaacgata aaactgccaa agtagcctgc   5040
aaatcttcac aaccagaccc agacaaaaac ccagcaagct ccaagcgacg gctcaagaca   5100
tccctgggga aagtgggcgt gaaagaagag ctcctagcag ttggcaagct cacacagaca   5160
tcaggagaga ctacacacac acacacagag ccaacaggag atggtaagag catgaaagca   5220
tttatggagt ctccaaagca gatcttagac tcagcagcaa gtctaactgg cagcaagagg   5280
cagctgagaa ctcctaaggg aaagtctgaa gtccctgaag acctggccgg cttcatcgag   5340
ctcttccaga caccaagtca cactaaggaa tcaatgacta acgaaaaaac taccaaagta   5400
tcctacagag cttcacagcc agacctagtg gacaccccaa caagctccaa gccacagccc   5460
aagagaagtc tcaggaaagc agacactgaa gaagaatttt tagcatttag gaaacaaacg   5520
ccatcagcag gcaaagccat gcacacaccc aaaccagcag taggtgaaga gaaagacatc   5580
aacacgtttt tgggaactcc agtgcagaaa ctggaccagc caggaaattt acctggcagc   5640
aatagacggc tacaaactcg taaggaaaag gcccaggctc tagaagaact gactggcttc   5700
agagagcttt tccagacacc atgcactgat aaccccacga ctgatgagaa aactaccaaa   5760
aaaatactct gcaaatctcc gcaatcagac ccagcggaca ccccaacaaa cacaaagcaa   5820
cggcccaaga gaagcctcaa gaaagcagac gtagaggaag aatttttagc attcaggaaa   5880
ctaacaccat cagcaggcaa agccatgcac acgcctaaag cagcagtagg tgaagagaaa   5940
gacatcaaca catttgtggg gactccagtg gagaaactgg acctgctagg aaatttacct   6000
ggcagcaaga gacggccaca aactcctaaa gaaaaggcca aggctctaga agatctggct   6060
ggcttcaaag agctcttcca gacaccaggt cacactgagg aatcaatgac cgatgacaaa   6120
atcacagaag tatcctgcaa atctccacaa ccagacccag tcaaaacccc aacaagctcc   6180
aagcaacgac tcaagatatc cttggggaaa gtaggtgtga aagaagaggt cctaccagtc   6240
```

-continued

```
ggcaagctca cacagacgtc agggaagacc acacagacac acagagagac agcaggagat   6300
ggaaagagca tcaaagcgtt taaggaatct gcaaagcaga tgctggaccc agcaaactat   6360
ggaactggga tggagaggtg gccaagaaca cctaaggaag aggcccaatc actagaagac   6420
ctggccggct tcaaagagct cttccagaca ccagaccaca ctgaggaatc aacaactgat   6480
gacaaaacta ccaaaatagc ctgcaaatct ccaccaccag aatcaatgga cactccaaca   6540
agcacaagga ggcggcccaa aacacctttg ggaaaaggg atatagtgga agagctctca   6600
gccctgaagc agctcacaca gaccacacac acagacaaag taccaggaga tgaggataaa   6660
ggcatcaacg tgttcaggga aactgcaaaa cagaaactgg acccagcagc aagtgtaact   6720
ggtagcaaga ggcagccaag aactcctaag ggaaaagccc aacccctaga agacttggct   6780
ggcttgaaag agctcttcca gacaccaata tgcactgaca agcccacgac tcatgagaaa   6840
actaccaaaa tagcctgcag atctccacaa ccagacccag tgggtacccc aacaatcttc   6900
aagccacagt ccaagagaag tctcaggaaa gcagacgtag aggaagaatc cttagcactc   6960
aggaaacgaa caccatcagt agggaaagct atggacacac ccaaaccagc aggaggtgat   7020
gagaaagaca tgaaagcatt tatgggaact ccagtgcaga aattggacct gccaggaaat   7080
ttacctggca gcaaaagatg gccacaaact cctaaggaaa aggcccaggc tctagaagac   7140
ctggctggct tcaaagagct cttccagaca ccaggcactg acaagcccac gactgatgag   7200
aaaactacca aaatagcctg caaatctcca caaccagacc cagtggacac cccagcaagc   7260
acaaagcaac ggcccaagag aaacctcagg aaagcagacg tagaggaaga atttttagca   7320
ctcaggaaac gaacaccatc agcaggcaaa gccatggaca caccaaaacc agcagtaagt   7380
gatgagaaaa atatcaacac atttgtggaa actccagtgc agaaactgga cctgctagga   7440
aatttacctg gcagcaagag acagccacag actcctaagg aaaaggctga ggctctagag   7500
gacctggttg gcttcaaaga actcttccag acaccaggtc acactgagga atcaatgact   7560
gatgacaaaa tcacagaagt atcctgtaaa tctccacagc cagagtcatt caaaacctca   7620
agaagctcca agcaaaggct caagataccc ctggtgaaag tggacatgaa agaagagccc   7680
ctagcagtca gcaagctcac acggacatca ggggagacta cgcaaacaca cacagagcca   7740
acaggagata gtaagagcat caaagcgttt aaggagtctc caaagcagat cctggaccca   7800
gcagcaagtg taactggtag caggaggcag ctgagaactc gtaaggaaaa ggcccgtgct   7860
ctagaagacc tggttgactt caaagagctc ttctcagcac caggtcacac tgaagagtca   7920
atgactattg acaaaaacac aaaaattccc tgcaaatctc cccccaccaga actaacagac   7980
actgccacga gcacaaagag atgccccaag acacgtccca ggaaagaagt aaaagaggag   8040
ctctcagcag ttgagaggct cacgcaaaca tcagggcaaa gcacacacac acacaaagaa   8100
ccagcaagcg gtgatgaggg catcaaagta ttgaagcaac gtgcaaagaa gaaaccaaac   8160
ccagtagaag aggaacccag caggagaagg ccaagagcac ctaaggaaaa ggcccaaccc   8220
ctggaagacc tggccggctt cacagagctc tctgaaacat caggtcacac tcaggaatca   8280
ctgactgctg gcaaagccac taaaataccc tgcgaatctc ccccactaga agtggtagac   8340
accacagcaa gcacaaagag gcatctcagg acacgtgtgc agaaggtaca agtaaaagaa   8400
gagccttcag cagtcaagtt cacacaaaca tcaggggaaa ccacggatgc agacaaagaa   8460
ccagcaggtg aagataaagg catcaaagca ttgaaggaat ctgcaaaaca gacaccggct   8520
ccagcagcaa gtgtaactgg cagcaggaga cggccaagag cacccaggga aagtgcccaa   8580
gccatagaag acctagctgg cttcaaagac ccagcagcag gtcacactga agaatcaatg   8640
```

-continued

```
actgatgaca aaaccactaa aataccctgc aaatcatcac cagaactaga agacaccgca   8700
acaagctcaa agagacggcc caggacacgt gcccagaaag tagaagtgaa ggaggagctg   8760
ttagcagttg gcaagctcac acaaacctca ggggagacca cgcacaccga caaagagccg   8820
gtaggtgagg gcaaaggcac gaaagcattt aagcaacctg caaagcggaa gctggacgca   8880
gaagatgtaa ttggcagcag gagacagcca agagcaccta aggaaaaggc ccaacccctg   8940
gaagatctgg ccagcttcca agagctctct caaacaccag gccacactga ggaactggca   9000
aatggtgctg ctgatagctt tacaagcgct ccaaagcaaa cacctgacag tggaaaacct   9060
ctaaaaatat ccagaagagt tcttcgggcc cctaaagtag aacccgtggg agacgtggta   9120
agcaccagag accctgtaaa atcacaaagc aaaagcaaca cttccctgcc cccactgccc   9180
ttcaagaggg gaggtggcaa agatggaagc gtcacgggaa ccaagaggct gcgctgcatg   9240
ccagcaccag aggaaattgt ggaggagctg ccagccagca agaagcagag ggttgctccc   9300
agggcaagag gcaaatcatc cgaacccgtg gtcatcatga agagaagttt gaggacttct   9360
gcaaaaagaa ttgaacctgc ggaagagctg aacagcaacg acatgaaaac caacaaagag   9420
gaacacaaat tacaagactc ggtccctgaa aataagggaa tatccctgcg ctccagacgc   9480
caaaataaga ctgaggcaga acagcaaata actgaggtct ttgtattagc agaaagaata   9540
gaaataaaca gaaatgaaaa gaagcccatg aagacctccc cagagatgga cattcagaat   9600
ccagatgatg gagcccggaa acccatacct agagacaaag tcactgagaa caaaaggtgc   9660
ttgaggtctg ctagacagaa tgagagctcc cagcctaagg tggcagagga gagcggaggg   9720
cagaagagtg cgaaggttct catgcagaat cagaaaggga aaggagaagc aggaaattca   9780
gactccatgt gcctgagatc aagaaagaca aaaagccagc ctgcagcaag cactttggag   9840
agcaaatctg tgcagagagt aacgcggagt gtcaagaggt gtgcagaaaa tccaaagaag   9900
gctgaggaca atgtgtgtgt caagaaaata agaaccagaa gtcataggga cagtgaagat   9960
atttgacaga aaaatcgaac tgggaaaaat ataataaagt tagttttgtg ataagttcta  10020
gtgcagtttt tgtcataaat tacaagtgaa ttctgtaagt aaggctgtca gtctgcttaa  10080
gggaagaaaa ctttggattt gctgggtctg aatcggcttc ataaactcca ctgggagcac  10140
tgctgggctc ctggactgag aatagttgaa caccgggggc tttgtgaagg agtctgggcc  10200
aaggtttgcc ctcagctttg cagaatgaag ccttgaggtc tgtcaccacc cacagccacc  10260
ctacagcagc cttaactgtg acacttgcca cactgtgtcg tcgtttgttt gcctatgtcc  10320
tccagggcac ggtggcagga acaactatcc tcgtctgtcc caacactgag caggcactcg  10380
gtaaacacga atgaatggat gagcgcacgg atgaatggag cttacaagat ctgtctttcc  10440
aatggccggg ggcatttggt ccccaaatta aggctattgg acatctgcac aggacagtcc  10500
tatttttgat gtcctttcct ttctgaaaat aaagttttgt gctttggaga atgactcgtg  10560
agcacatctt tagggaccaa gagtgacttt ctgtaaggag tgactcgtgg cttgccttgg  10620
tctcttggga atacttttct aactagggtt gctctcacct gagacattct ccacccgcgg  10680
aatctcaggg tcccaggctg tgggccatca cgacctcaaa ctggctccta atctccagct  10740
ttcctgtcat tgaaagcttc ggaagtttac tggctctgct cccgcctgtt ttctttctga  10800
ctctatctgg cagcccgatg ccacccagta caggaagtga caccagtact ctgtaaagca  10860
tcatcatcct tggagagact gagcactcag caccttcagc cacgatttca ggatcgcttc  10920
cttgtgagcc gctgcctccg aaatctcctt tgaagcccag acatctttct ccagcttcag  10980
```

-continued acttgtagat ataactcgtt catcttcatt tactttccac tttgcccccct gtcctctctg 11040 tgttccccaa atcagagaat agcccgccat cccccaggtc acctgtctgg attcctcccc 11100
attcacccac cttgccaggt gcaggtgagg atggtgcacc agacagggta gctgtccccc 11160
aaaatgtgcc ctgtgcgggc agtgccctgt ctccacgttt gtttccccag tgtctggcgg 11220
ggagccaggt gacatcataa atacttgctg aatgaatgca gaaatcagcg gtactgactt 11280
gtactatatt ggctgccatg atagggttct cacagcgtca tccatgatcg taagggagaa 11340
tgacattctg cttgagggag ggaatagaaa ggggcaggga ggggacatct gagggcttca 11400
cagggctgca aagggtacag ggattgcacc agggcagaac aggggagggt gttcaaggaa 11460
gagtggctct tagcagaggc actttggaag gtgtgaggca taaatgcttc cttctacgta 11520
ggccaacctc aaaactttca gtaggaatgt tgctatgatc aagttgttct aacactttag 11580
acttagtagt aattatgaac ctcacataga aaaatttcat ccagccatat gcctgtggag 11640
tggaatattc tgtttagtag aaaaatcctt tagagttcag ctctaaccag aaatcttgct 11700
gaagtatgtc agcacctttt ctcaccctgg taagtacagt atttcaagag cacgctaagg 11760
gtggttttca ttttacaggg ctgttgatga tgggttaaaa atgttcattt aagggctacc 11820
cccgtgttta atagatgaac accacttcta cacaaccctc cttggtactg ggggagggag 11880
agatctgaca aatactgccc attcccctag gctgactgga tttgagaaca aatacccacc 11940
catttccacc atggtatggt aacttctctg agcttcagtt tccaagtgaa tttccatgta 12000
ataggacatt cccattaaat acaagctgtt tttacttttt cgcctcccag ggcctgtggg 12060
atctggtccc ccagcctctc ttgggctttc ttacactaac tctgtaccta ccatctcctg 12120
cctcccttag gcaggcacct ccaaccacca cacactccct gctgttttcc ctgcctggaa 12180
ctttccctcc tgccccacca agatcatttc atccagtcct gagctcagct taagggaggc 12240
ttcttgcctg tgggttccct cacccccatg cctgtcctcc aggctggggc aggttcttag 12300
tttgcctgga attgttctgt acctctttgt agcacgtagt gttgtggaaa ctaagccact 12360
aattgagttt ctggctcccc tcctggggtt gtaagttttg ttcattcatg agggccgact 12420
gcatttcctg gttactctat cccagtgacc agccacagga gatgtccaat aaagtatgtg 12480
atgaaatggt cttaaaaaaa aaaaaaa 12507

<210> SEQ ID NO 126
<211> LENGTH: 3771
<212> TYPE: DNA
<213> ORGANISM: Homo sapiens

<400> SEQUENCE: 126
gcgccgggac gtggccagtt gcccgcctgc cccggagagc caggcgctaa ccagccgctc 60
tgcgccccgc gccctgcttg cccccattat ccagccttgc cccggcgccc tgacctgacg 120
ccctggcctg acgccctgct tcgtcgcctc ctttctctcc caggtgctgg accagggact 180
gagcgtcccc cggagagggt ccggtgtgac cccgacaaga agcagaaatg ggaagaaac 240 tggatctttc caagctcact gatgaagagg cccagcatgt cttggaagtt gttcaacgag 300
attttgacct ccgaaggaaa gaagaggaac ggctagaggc gttgaagggc aagattaaga 360
aggaaagctc caagagggag ctgctttccg acactgccca tctgaacgag acccactgcg 420
cccgctgcct gcagccctac cagctgcttg tgaatagcaa aaggcagtgc ctggaatgtg 480
gcctcttcac ctgcaaaagc tgtggccgcg tccacccgga ggagcagggc tggatctgtg 540
acccctgcca tctggccaga gtcgtgaaga tcggctcact ggagtggtac tatgagcatg 600

-continued

```
tgaaagcccg cttcaagagg ttcggaagtg ccaaggtcat ccggtccctc cacgggcggc    660
tgcagggtgg agctgggcct gaactgatat ctgaagagag aagtggagac agcgaccaga    720
cagatgagga tggagaacct ggctcagagg cccaggccca ggcccagccc tttggcagca    780
aaaaaaagcg cctcctctcc gtccacgact tcgacttcga gggagactca gatgactcca    840
ctcagcctca aggtcactcc ctgcacctgt cctcagtccc tgaggccagg gacagcccac    900
agtccctcac agatgagtcc tgctcagaga aggcagcccc tcacaaggct gagggcctgg    960
aggaggctga tactggggcc tctgggtgcc actcccatcc ggaagagcag ccgaccagca   1020
tctcaccttc cagacacggc gccctggctg agctctgccc gcctggaggc tcccacagga   1080
tggccctggg gactgctgct gcactcgggt cgaatgtcat caggaatgag cagctgcccc   1140
tgcagtactt ggccgatgtg gacacctctg atgaggaaag catccgggct cacgtgatgg   1200
cctcccacca ttccaagcgg agaggccggg cgtcttctga gagtcagatc tttgagctga   1260
ataagcatat ttcagctgtg gaatgcctgc tgacctacct ggagaacaca gttgtgcctc   1320
ccttggccaa gggtctaggt gctggagtgc gcacggaggc cgatgtagag gaggaggccc   1380
tgaggaggaa gctggaggag ctgaccagca acgtcagtga ccaggagacc tcgtccgagg   1440
aggaggaagc caaggacgaa aaggcagagc ccaacaggga caaatcagtt gggcctctcc   1500
cccaggcgga cccggaggtg ggcacggctg cccatcaaac caacagacag gaaaaaagcc   1560
cccaggaccc tggggacccc gtccagtaca acaggaccac agatgaggag ctgtcagagc   1620
tggaggacag agtggcagtg acggcctcag aagtccagca ggcagagagc gaggtttcag   1680
acattgaatc caggattgca gccctgaggg ccgcagggct cacggtgaag ccctcgggaa   1740
agccccggag gaagtcaaac ctcccgatat ttctccctcg agtggctggg aaacttggca   1800
agagaccaga ggacccaaat gcagaccctt caagtgaggc caaggcaatg gctgtgccct   1860
atcttctgag aagaaagttc agtaattccc tgaaaagtca aggtaaagat gatgattctt   1920
ttgatcggaa atcagtgtac cgaggctcgc tgacacagag aaaccccaac gcgaggaaag   1980
gaatggccag ccacaccttc gcgaaacctg tggtggccca ccagtcctaa cgggacagga   2040
cagagagaca gagcagccct gcactgtttt ccctccacca cagccatcct gtccctcatt   2100
ggctctgtgc tttccactat acacagtcac cgtcccaatg agaaacaaga aggagcaccc   2160
tccacatgga ctcccacctg caagtggaca gcgacattca gtcctgcact gctcacctgg   2220
gtttactgat gactcctggc tgccccacca tcctctctga tctgtgagaa acagctaagc   2280
tgctgtgact tccctttagg acaatgttgt gtaaatcttt gaaggacaca ccgaagacct   2340
ttatactgtg atcttttacc cctttcactc ttggctttct tatgttgctt tcatgaatgg   2400
aatggaaaaa agatgactca gttaaggcac cagccatatg tgtattcttg atggtctata   2460
tcggggtgtg agcagatgtt tgcgtatttc ttgtgggtgt gactggatat tagacatccg   2520
gacaagtgac tgaactaatg atctgctgaa taatgaagga ggaatagaca ccccagtccc   2580
caccctacgt gcacccgctc tgcaagttcc catgtgatct gtagaccagg ggaaattaca   2640
ctgcggtcaa gggcagagcc tgcacatgac agcaagtgag catttgatag atgctcagat   2700
gctagtgcag agagcctgct gggagacgaa gagacagcag gcagagctcc agatgggcaa   2760
ggaagaggct tggttctagc ctggctctgc ccctcactgc agtggatcca gtggggcaga   2820
ggacagaggg tcacaaccaa tgagggatgt ctgccaagga tgggggtgca gaggccacag   2880
gagtcagctt gccactcgcc cattggttac atagatgatc tctcagacag gctgggactc   2940
```

-continued agagttattt cctagtatcg gtgtgcccca tccagtttta agtggagccc tccaagactc 3000
tccagagctg cctttgaaca tcctaacagt aatcacatct caccctccct gaggttcact 3060
ttagacagga cccaatggct gcactgcctt tgtcagaggg ggtgctgaga ggagtggctt 3120
cttttagaat caaacagtag agacaagagt caagccttgt gtcttcaagc attgaccaag 3180
ttaagtgttt ccttccctct ctcaataaga cacttccagg agctttccaa tctctcactt 3240
aaaactaagg tttgaatctc aaagtgttgc tgggaggctg atactcctgc aacttcagga 3300
gacctgtgag cacacattag cagctgtttc tctgactcct tgtggcatca gataaaaacg 3360
tgggagtttt tccatataat tcccagcctt acttataaat tctattcttt gaaaaaatta 3420
ttcaggctag gtaaggtggc tcatacctat aatcccagcc ctttgagagg ccaaggtggg 3480
agaattgctt gaggccagga gtttgagacc tcctgggcaa catagtgaga tcccatctct 3540
acaaaaaaca aaacaaaaaa attacccaag catgatggta tatgcctgta gtcgtaccta 3600
cttacttagg aggctgaggc aggaggatca cttgagccct ggaggttggg gctgcagtga 3660
gccatgatcg catcactata ctcgagcctg ggcaacagag tgagaccttg tctcttaaaa 3720
aaattaataa taaataaatg aaaataattc ttcagaaaaa aaaaaaaaaa a 3771

<210> SEQ ID NO 127
<211> LENGTH: 2240
<212> TYPE: DNA
<213> ORGANISM: Homo sapiens

<400> SEQUENCE: 127
aagcccagca gccccggggc ggatggctcc ggccgcctgg ctccgcagcg cggccgcgcg 60
cgccctcctg cccccgatgc tgctgctgct gctccagccg ccgccgctgc tggcccgggc 120
tctgccgccg gacgcccacc acctccatgc cgagaggagg gggccacagc cctggcatgc 180
agccctgccc agtagcccgg cacctgcccc tgccacgcag gaagcccccc ggcctgccag 240
cagcctcagg cctccccgct gtggcgtgcc cgacccatct gatgggctga gtgcccgcaa 300
ccgacagaag aggttcgtgc tttctggcgg gcgctgggag aagacggacc tcacctacag 360
gatccttcgg ttcccatggc agttggtgca ggagcaggtg cggcagacga tggcagaggc 420
cctaaaggta tggagcgatg tgacgccact cacctttact gaggtgcacg agggccgtgc 480
tgacatcatg atcgacttcg ccaggtactg gcatggggac gacctgccgt ttgatgggcc 540
tgggggcatc ctggcccatg ccttcttccc caagactcac cgagaagggg atgtccactt 600
cgactatgat gagacctgga ctatcgggga tgaccagggc acagacctgc tgcaggtggc 660
agcccatgaa tttggccacg tgctggggct gcagcacaca acagcagcca aggccctgat 720
gtccgccttc tacacctttc gctacccact gagtctcagc ccagatgact gcaggggcgt 780
tcaacaccta tatggccagc cctggcccac tgtcacctcc aggaccccag ccctgggccc 840
ccaggctggg atagacacca atgagattgc accgctggag ccagacgccc cgccagatgc 900
ctgtgaggcc tcctttgacg cggtctccac catccgaggc gagctctttt tcttcaaagc 960
gggctttgtg tggcgcctcc gtgggggcca gctgcagccc ggctacccag cattggcctc 1020
tcgccactgg cagggactgc ccagccctgt ggacgctgcc ttcgaggatg cccagggcca 1080
catttggttc ttccaaggtg ctcagtactg ggtgtacgac ggtgaaaagc cagtcctggg 1140
ccccgcaccc ctcaccgagc tgggcctggt gaggttcccg gtccatgctg ccttggtctg 1200
gggtcccgag aagaacaaga tctacttctt ccgaggcagg gactactggc gtttccaccc 1260
cagcacccgg cgtgtagaca gtcccgtgcc ccgcagggcc actgactgga gaggggtgcc 1320

```
ctctgagatc gacgctgcct tccaggatgc tgatggctat gcctacttcc tgcgcggccg   1380

cctctactgg aagtttgacc ctgtgaaggt gaaggctctg gaaggcttcc cccgtctcgt   1440

gggtcctgac ttctttggct gtgccgagcc tgccaacact ttcctctgac catggcttgg   1500

atgccctcag ggtgctgac ccctgccagg ccacgaatat caggctagag acccatggcc    1560

atctttgtgg ctgtgggcac caggcatggg actgagccca tgtctcctca gggggatggg   1620

gtggggtaca accaccatga caactgccgg gagggccacg caggtcgtgg tcacctgcca   1680

gcgactgtct cagactgggc agggaggctt tggcatgact taagaggaag ggcagtcttg   1740

ggcccgctat gcaggtcctg gcaaacctgg ctgccctgtc tccatccctg tccctcaggg   1800

tagcaccatg gcaggactgg gggaactgga gtgtccttgc tgtatccctg ttgtgaggtt   1860

ccttccaggg gctggcactg aagcaagggt gctggggccc catggccttc agccctggct   1920

gagcaactgg gctgtagggc agggccactt cctgaggtca ggtcttggta ggtgcctgca   1980

tctgtctgcc ttctggctga caatcctgga aatctgttct ccagaatcca ggccaaaaag   2040

ttcacagtca aatggggagg ggtattcttc atgcaggaga ccccaggccc tggaggctgc   2100

aacatacctc aatcctgtcc caggccggat cctcctgaag ccctttttcgc agcactgcta  2160

tcctccaaag ccattgtaaa tgtgtgtaca gtgtgtataa accttcttct tcttttttt   2220

tttttaaact gaggattgtc                                               2240
```

<210> SEQ ID NO 128
<211> LENGTH: 2379
<212> TYPE: DNA
<213> ORGANISM: Homo sapiens

<400> SEQUENCE: 128

```
gacccccgag ctgtgctgct cgcggccgcc accgccgggc cccggccgtc cctggctccc     60

ctcctgcctc gagaagggca gggcttctca gaggcttggc gggaaaaaga acggagggag    120

ggatcgcgct gagtataaaa gccggttttc ggggctttat ctaactcgct gtagtaattc    180

cagcgagagg cagagggagc gagcgggcgg ccggctaggg tggaagagcc gggcgagcag    240

agctgcgctg cgggcgtcct gggaagggag atccggagcg aatagggggc ttcgcctctg    300

gcccagccct cccgctgatc ccccagccag cggtccgcaa cccttgccgc atccacgaaa    360

ctttgcccat agcagcgggc gggcactttg cactggaact tacaacaccc gagcaaggac    420

gcgactctcc cgacgcgggg aggctattct gcccatttgg ggacacttcc ccgccgctgc    480

caggacccgc ttctctgaaa ggctctcctt gcagctgctt agacgctgga tttttttcgg    540

gtagtggaaa accagcagcc tcccgcgacg atgcccctca acgttagctt caccaacagg    600

aactatgacc tcgactacga ctcggtgcag ccgtatttct actgcgacga ggaggagaac    660

ttctaccagc agcagcagca gagcgagctg cagcccccgg cgcccagcga ggatatctgg    720

aagaaattcg agctgctgcc cacccccgccc ctgtccccta gccgccgctc cgggctctgc   780

tcgccctcct acgttgcggt cacacccttc tcccttcggg gagacaacga cggcggtggc    840

gggagcttct ccacggccga ccagctggag atggtgaccg agctgctggg aggagacatg    900

gtgaaccaga gtttcatctg cgacccggac gacgagacct tcatcaaaaa catcatcatc    960

caggactgta tgtggagcgg cttctcggcc gccgccaagc tcgtctcaga gaagctggcc   1020

tcctaccagg ctgcgcgcaa agacagcggc agcccgaacc ccgcccgcgg ccacagcgtc   1080

tgctccacct ccagcttgta cctgcaggat ctgagcgccg ccgcctcaga gtgcatcgac   1140
```

-continued ccctcggtgg tcttccccta ccctctcaac gacagcagct cgcccaagtc ctgcgcctcg 1200
caagactcca gcgccttctc tccgtcctcg gattctctgc tctcctcgac ggagtcctcc 1260
ccgcagggca gccccgagcc cctggtgctc catgaggaga caccgcccac caccagcagc 1320
gactctgagg aggaacaaga agatgaggaa gaaatcgatg ttgtttctgt ggaaaagagg 1380
caggctcctg gcaaaaggtc agagtctgga tcaccttctg ctggaggcca cagcaaacct 1440
cctcacagcc cactggtcct caagaggtgc cacgtctcca cacatcagca caactacgca 1500
gcgcctccct ccactcggaa ggactatcct gctgccaaga gggtcaagtt ggacagtgtc 1560
agagtcctga gacagatcag caacaaccga aaatgcacca gccccaggtc ctcggacacc 1620
gaggagaatg tcaagaggcg aacacacaac gtcttggagc gccagaggag gaacgagcta 1680
aaacggagct tttttgccct gcgtgaccag atcccggagt tggaaaacaa tgaaaaggcc 1740
cccaaggtag ttatccttaa aaaagccaca gcatacatcc tgtccgtcca agcagaggag 1800
caaaagctca tttctgaaga ggacttgttg cggaaacgac gagaacagtt gaaacacaaa 1860
cttgaacagc tacggaactc ttgtgcgtaa ggaaaagtaa ggaaaacgat tccttctaac 1920
agaaatgtcc tgagcaatca cctatgaact tgtttcaaat gcatgatcaa atgcaacctc 1980
acaaccttgg ctgagtcttg agactgaaag atttagccat aatgtaaact gcctcaaatt 2040
ggactttggg cataaaagaa ctttttttatg cttaccatct tttttttttc tttaacagat 2100
ttgtatttaa gaattgtttt taaaaaattt taagatttac acaatgtttc tctgtaaata 2160
ttgccattaa atgtaaataa ctttaataaa acgtttatag cagttacaca gaatttcaat 2220
cctagtatat agtacctagt attataggta ctataaaccc taattttttt tatttaagta 2280
cattttgctt tttaaagttg atttttttct attgttttta gaaaaaataa aataactggc 2340
aaatatatca ttgagccaaa tcttaaaaaa aaaaaaaaa 2379

<210> SEQ ID NO 129
<211> LENGTH: 1799
<212> TYPE: DNA
<213> ORGANISM: Homo sapiens

<400> SEQUENCE: 129
gtgggaggat tgcattcagt ctagttcctg gttgccggct gaaataacct gctctccaaa 60
atgtccacaa aagtgactta agtcaggttc ccccaaacca gacaccaaga caagaatcca 120
tgtgtgtgtg actgaaggaa gtgctgggag agccccagct gcagcctgga tgtgaactgc 180
aactccaaag tgtgtccaga ctcaaggcaa gggcactagg ctttccagac ctcctactaa 240
gtcattgatc cagcactgcc ctgccaggac ataaatccct ggcacctctt gctctctgca 300
aaggagggca aagcagcttc aggagccctt gggagtcctc caaagagagt ctagggtaca 360
ggtccgaaag tagaagaaca cagaaggcag gccaggggca ctgtgagatg gtaaaagaga 420
tctgaaggga tccagaattc aagccaggaa gaagcagcaa tctgtcttct ggattaaaac 480
tgaagatcaa cctactttca acttactaag aaaggggatc atggacattg aagcatatct 540
tgaaagaatt ggctataaga agtctaggaa caaattggac ttggaaacat taactgatat 600
tcttcaacac cagatccgag ctgttccctt tgagaacctt aacatccatt gtggggatgc 660
catggactta ggcttagagg ccatttttga tcaagttgtg agaagaaatc ggggtggatg 720
gtgtctccag gtcaatcatc ttctgtactg ggctctgacc actattggtt ttgagaccac 780
gatgttggga gggtatgttt acagcactcc agccaaaaaa tacagcactg gcatgattca 840
ccttctcctg caggtgacca ttgatggcag gaactacatt gtcgatgctg ggtttggacg 900

```
ctcataccag atgtggcagc ctctggagtt aatttctggg aaggatcagc ctcaggtgcc    960

ttgtgtcttc cgtttgacgg aagagaatgg attctggtat ctagaccaaa tcagaaggga   1020

acagtacatt ccaaatgaag aatttcttca ttctgatctc ctagaagaca gcaaataccg   1080

aaaaatctac tcctttactc ttaagcctcg aacaattgaa gattttgagt ctatgaatac   1140

atacctgcag acatctccat catctgtgtt tactagtaaa tcattttgtt ccttgcagac   1200

cccagatggg gttcactgtt tggtgggctt caccctcacc cataggagat tcaattataa   1260

ggacaataca gatctaatag agttcaagac tctgagtgag gaagaaatag aaaaagtgct   1320

gaaaaatata tttaatattt ccttgcagag aaagcttgtg cccaaacatg gtgatagatt   1380

ttttactatt tagaataagg agtaaaacaa tcttgtctat ttgtcatcca gctcaccagt   1440

tatcaactga cgacctatca tgtatcttct gtacccttac cttattttga agaaaatcct   1500

agacatcaaa tcatttcacc tataaaaatg tcatcatata taattaaaca gctttttaaa   1560

gaaacataac cacaaacctt ttcaaataat aataataata ataataataa atgtctttta   1620

aagatggcct gtggttatct tggaaattgg tgatttatgc tagaaagctt ttaatgttgg   1680

tttattgttg aattcctaga aaagttttat gggtagatga gtaaataaaa tattgtaaaa   1740

aaacttattg tctataaagt atattaaaac attgttggct aatataaaaa aaaaaaaaa    1799
```

<210> SEQ ID NO 130
<211> LENGTH: 1644
<212> TYPE: DNA
<213> ORGANISM: Homo sapiens

<400> SEQUENCE: 130

```
gcgcgcgggt ttcgttgacc cgcggcgttc acgggaattg ttcgctttag tgccggcgcc     60

atggggtcgg agctgatcgg gcgcctagcc ccgcgcctgg gcctcgccga gcccgacatg    120

ctgaggaaag cagaggagta cttgcgcctg tcccgggtga agtgtgtcgg cctctccgca    180

cgcaccacgg agaccagcag tgcagtcatg tgcctggacc ttgcagcttc ctggatgaag    240

tgccccttgg acagggctta tttaattaaa ctttctggtt tgaacaagga gacatatcag    300

agctgtctta aatcttttga gtgtttactg ggcctgaatt caaatattgg aataagagac    360

ctagctgtac agtttagctg tatagaagca gtgaacatgg cttcaaagat actaaaaagc    420

tatgagtcca gtcttcccca gacacagcaa gtggatcttg acttatccag gccacttttc    480

acttctgctg cactgctttc agcatgcaag attctaaagc tgaaagtgga taaaaacaaa    540

atggtagcca catccggtgt aaaaaaagct atatttgatc gactgtgtaa acaactagag    600

aagattggac agcaggtcga cagagaacct ggagatgtag ctactccacc acggaagaga    660

aagaagatag tggttgaagc cccagcaaag gaaatggaga aggtagagga gatgccacat    720

aaaccacaga aagatgaaga tctgacacag gattatgaag aatggaaaag aaaaattttg    780

gaaaatgctg ccagtgctca aaaggctaca gcagagtgat ttcagcttcc aaactggtat    840

acattccaaa ctgatagtac attgccatct ccaggaagac ttgacggctt tgggattttg    900

tttaaacttt tataataagg atcctaagac tgttgccttt aaatagcaaa gcagcctacc    960

tggaggctaa gtctgggcag tgggctggcc cctggtgtga gcattagacc agccacagtg   1020

cctgattggt atagccttat gtgctttcct acaaaatgga attggaggcc gggcgcagtg   1080

gctcacgcct gtaatcccag cactttggga ggccaaggtg ggtggatcac ctgaggtcag   1140

gagctcgaga ccagcctggc caacatggtg aaaccccatc tctactaaaa atacaaaaat   1200
```

-continued

```
tagccaggtg tgatggtgca tgcctgtaat cccagctcct cagtaggctg agacaggagc   1260

atcacttgaa cgtgggaggc agaggttgca gtgagccgag attgcaccac cgcactccag   1320

cctgggtgac agagcgagac ttatctcata aataaataga tagatactcc agcctgggtg   1380

acagagcgag acttatagat agatagatag atagatggat agatagatag atagatagat   1440

agatagataa acggaattgg agccattttg ctttaagtga atggcagtcc cttgtcttat   1500

tcagaatata aaattcagtc tgaatggcat cttacagatt ttacttcaat ttttgtgtac   1560

ggtatttttt atttgactaa atcaatatat tgtacagcct aagttaataa atgttattta   1620

tatatgcaaa aaaaaaaaaa aaaa                                          1644
```

<210> SEQ ID NO 131
<211> LENGTH: 13037
<212> TYPE: DNA
<213> ORGANISM: Homo sapiens

<400> SEQUENCE: 131

```
agtccacagc tgtcactaat cggggtaagc cttgttgtat ttgtgcgtgt gggtggcatt     60

ctcaatgaga actagcttca cttgtcattt gagtgaaatc tacaacccga ggcggctagt    120

gctcccgcac tactgggatc tgagatcttc ggagatgact gtcgcccgca gtacggagcc    180

agcagaagtc cgacccttcc tgggaatggg ctgtaccgag aggtccgact agccccaggg    240

ttttagtgag ggggcagtgg aactcagcga gggactgaga gcttcacagc atgcacgagt    300

ttgatgccag agaaaaagtc gggagataaa ggagccgcgt gtcactaaat tgccgtcgca    360

gccgcagcca ctcaagtgcc ggacttgtga gtactctgcg tctccagtcc tcggacagaa    420

gttggagaac tctcttggag aactccccga gttaggagac gagatctcct aacaattact    480

actttttctt gcgctcccca cttgccgctc gctgggacaa acgacagcca cagttcccct    540

gacgacagga tggaggccaa gggcaggagc tgaccagcgc cgccctcccc cgccccccgac    600

ccaggaggtg gagatccctc cggtccagcc acattcaaca cccactttct cctccctctg    660

cccctatatt cccgaaaccc cctcctcctt cccttttccc tcctcctgga gacgggggag    720

gagaaaaggg gagtccagtc gtcatgactg agctgaaggc aaagggtccc cgggctcccc    780

acgtggcggg cggcccgccc tcccccgagg tcggatcccc actgctgtgt cgcccagccg    840

caggtccgtt cccggggagc cagacctcgg acaccttgcc tgaagtttcg gccataccta    900

tctccctgga cgggctactc ttccctcggc cctgccaggg acaggacccc tccgacgaaa    960

agacgcagga ccagcagtcg ctgtcggacg tggagggcgc atattccaga gctgaagcta   1020

caaggggtgc tggaggcagc agttctagtc ccccagaaaa ggacagcgga ctgctggaca   1080

gtgtcttgga cactctgttg gcgccctcag gtcccgggca gagccaaccc agccctcccg   1140

cctgcgaggt caccagctct tggtgcctgt ttggccccga acttcccgaa gatccaccgg   1200

ctgcccccgc cacccagcgg gtgttgtccc cgctcatgag ccggtccggg tgcaaggttg   1260

gagacagctc cgggacggca gctgcccata aagtgctgcc ccggggcctg tcaccagccc   1320

ggcagctgct gctcccggcc tctgagagcc ctcactggtc cggggcccca gtgaagccgt   1380

ctccgcaggc cgctgcggtg gaggttgagg aggaggatgg ctctgagtcc gaggagtctg   1440

cgggtccgct tctgaagggc aaacctcggg ctctgggtgg cgcggcggct ggaggaggag   1500

ccgcggctgt cccgccgggg gcggcagcag gaggcgtcgc cctggtcccc aaggaagatt   1560

cccgcttctc agcgcccagg gtcgccctgg tggagcagga cgcgccgatg gcgcccgggc   1620

gctccccgct ggccaccacg gtgatggatt tcatccacgt gcctatcctg cctctcaatc   1680
```

acgccttatt ggcagcccgc actcggcagc tgctggaaga cgaaagttac gacggcgggg 1740
ccggggctgc cagcgccttt gccccgccgc ggagttcacc ctgtgcctcg tccaccccgg 1800
tcgctgtagg cgacttcccc gactgcgcgt acccgcccga cgccgagccc aaggacgacg 1860
cgtaccctct ctatagcgac ttccagccgc ccgctctaaa gataaaggag gaggaggaag 1920
gcgcggaggc ctccgcgcgc tccccgcgtt cctaccttgt ggccggtgcc aaccccgcag 1980
ccttcccgga tttcccgttg gggccaccgc ccccgctgcc gccgcgagcg accccatcca 2040
gacccgggga agcggcggtg acggccgcac ccgccagtgc ctcagtctcg tctgcgtcct 2100
cctcggggtc gaccctggag tgcatcctgt acaaagcgga gggcgcgccg ccccagcagg 2160
gcccgttcgc gccgccgccc tgcaaggcgc cgggcgcgag cggctgcctg ctcccgcggg 2220
acggcctgcc ctccacctcc gcctctgccg ccgccgccgg ggcggccccc gcgctctacc 2280
ctgcactcgg cctcaacggg ctcccgcagc tcggctacca ggccgccgtg ctcaaggagg 2340
gcctgccgca ggtctacccg ccctatctca actacctgag gccggattca gaagccagcc 2400
agagcccaca atacagcttc gagtcattac ctcagaagat ttgtttaatc tgtggggatg 2460
aagcatcagg ctgtcattat ggtgtcctta cctgtgggag ctgtaaggtc ttctttaaga 2520
gggcaatgga agggcagcac aactacttat gtgctggaag aaatgactgc atcgttgata 2580
aaatccgcag aaaaaactgc ccagcatgtc gccttagaaa gtgctgtcag gctggcatgg 2640
tccttggagg tcgaaaattt aaaaagttca ataaagtcag agttgtgaga gcactggatg 2700
ctgttgctct cccacagcca gtgggcgttc caaatgaaag ccaagcccta agccagagat 2760
tcactttttc accaggtcaa gacatacagt tgattccacc actgatcaac ctgttaatga 2820
gcattgaacc agatgtgatc tatgcaggac atgacaacac aaaacctgac acctccagtt 2880
ctttgctgac aagtcttaat caactaggcg agaggcaact tctttcagta gtcaagtggt 2940
ctaaatcatt gccaggtttt cgaaacttac atattgatga ccagataact ctcattcagt 3000
attcttggat gagcttaatg gtgtttggtc taggatggag atcctacaaa cacgtcagtg 3060
ggcagatgct gtattttgca cctgatctaa tactaaatga acagcggatg aaagaatcat 3120
cattctattc attatgcctt accatgtggc agatcccaca ggagtttgtc aagcttcaag 3180
ttagccaaga agagttcctc tgtatgaaag tattgttact tcttaataca attcctttgg 3240
aagggctacg aagtcaaacc cagtttgagg agatgaggtc aagctacatt agagagctca 3300
tcaaggcaat tggtttgagg caaaaaggag ttgtgtcgag ctcacagcgt ttctatcaac 3360
ttacaaaact tcttgataac ttgcatgatc ttgtcaaaca acttcatctg tactgcttga 3420
atacatttat ccagtcccgg gcactgagtg ttgaatttcc agaaatgatg tctgaagtta 3480
ttgctgcaca attacccaag atattggcag ggatggtgaa accccttctc tttcataaaa 3540
agtgaatgtc atcttttcct tttaaagaat taaattttgt ggtatgtctt tttgttttgg 3600
tcaggattat gaggtcttga gtttttataa tgttcttctg aaagccttac atttataaca 3660
tcatagtgtg taaatttaaa agaaaaattg tgaggttcta attattttct tttataaagt 3720
ataattagaa tgtttaactg ttttgtttac ccatattttc ttgaagaatt tacaagattg 3780
aaaaagtact aaaattgtta aagtaaacta tcttatccat attatttcat accatgtagg 3840
tgaggatttt taacttttgc atctaacaaa tcatcgactt aagagaaaaa atcttacatg 3900
taataacaca aagctattat atgttatttc taggtaactc cctttgtgtc aattatattt 3960
ccaaaaatga acctttaaaa tggtatgcaa aattttgtct atatatattt gtgtgaggag 4020

-continued gaaattcata actttcctca gattttcaaa agtattttta atgcaaaaaa tgtagaaaga 4080
gtttaaaacc actaaaatag attgatgttc ttcaaactag gcaaaacaac tcatatgtta 4140
agaccatttt ccagattgga aacacaaatc tcttaggaag ttaataagta gattcatatc 4200
attatgcaaa tagtattgtg ggttttgtag gtttttaaaa taaccttttt tggggagaga 4260
attgtcctct aatgaggtat tgcgagtgga cataagaaat cagaagatta tggcctaact 4320
gtactcctta ccaactgtgg catgctgaaa gttagtcact cttactgatt ctcaattctc 4380
tcacctttga aagtagtaaa atatctttcc tgccaattgc tcctttgggt cagagcttat 4440
taacatcttt tcaaatcaaa ggaaagaaga aagggagagg aggaggaggg aggtatcaat 4500
tcacatacct ttctcctctt tatcctccac tatcatgaat tcatattatg tttcagccat 4560
gcaaatcttt ttaccatgaa atttcttcca gaattttccc cctttgacac aaattccatg 4620
catgtttcaa ccttcgagac tcagccaaat gtcatttctg taaaatcttc cctgagtctt 4680
ccaagcagta atttgccttc tcctagagtt tacctgccat tttgtgcaca tttgagttac 4740
agtagcatgt tattttacaa ttgtgactct cctgggagtc tgggagccat ataaagtggt 4800
caatagtgtt tgctgactga gagttgaatg acattttctc tctgtcttgg tattactgta 4860
gatttcgatc attctttggt tacatttctg catatttctg tacccatgac tttatcactt 4920
tcttctccca tgctttatct ccatcaatta tcttcattac ttttaaattt tccacctttg 4980
cttcctactt tgtgagatct ctccctttac tgactataac atagaagaat agaagtgtat 5040
tttatgtgtc ttaaggacaa tactttagat tccttgttct aagtttttaa actgaatgaa 5100
tggaatatta tttctctccc taagcaaaat tccacaaaac aattatttct tatgtttatg 5160
tagccttaaa ttgttttgta ctgtaaacct cagcataaaa actttcttca tttctaattt 5220
cattcaacaa atattgattg aatacctggt attagcacaa gaaaaatgtg ctaataagcc 5280
ttatgagaat ttggagctga agaaagacat ataactcagg aaagttacag tccagtagta 5340
ggtataaatt acagtgcctg ataaataggc attttaatat ttgtacactc aacgtatact 5400
aggtaggtgc aaaacattta catataattt tactgatacc catgcagcac aaaggtacta 5460
actttaaata ttaaataaca cctttatgtg tcagtaattc atttgcatta aatcttattg 5520
aaaaggcttt caatatattt tccccacaaa tgtcatccca agaaaaaagt atttttaaca 5580
tctcccaaat ataatagtta caggaaatct acctctgtga gagtgacacc tctcagaatg 5640
aactgtgtga cacaagaaaa tgaatgtagg tctatccaaa aaaaacccca agaaacaaaa 5700
acaatattat tagcccttta tgcttaagtg atggactcag ggaacagttg atgttgtgat 5760
cattttatta tctgattctt gttactttga attaaaccaa tattttgatg atataaatca 5820
tttccaccag catatattta atttccataa taactttaaa attttctaat ttcactcaac 5880
tatgagggaa tagaatgtgg tggccacagg tttggctttt gttaaaatgt ttgatatctt 5940
cgatgttgat ctctgtctgc aatgtagatg tctaaacact aggatttaat atttaaggct 6000
aagctttaaa aataaagtac ctttttaaaa agaatatggc ttcaccaaat ggaaaatacc 6060
taatttctaa atcttttttct ctacaaagtc ctatctacta atgtctccat tactatttag 6120
tcatcataac cattatcttc attttacatg tcgtgttctt tctggtagct ctaaaatgac 6180
actaaatcat aagaagacag gttacatatc aggaaatact tgaaggttac tgaaatagat 6240
tcttgagtta atgaaaatat tttctgtaaa aaggtttgaa aagccatttg agtctaaagc 6300
attatacctc cattatcagt agttatgtga caattgtgtg tgtgtttaat gtttaaagat 6360
gtggcacttt ttaataaggc aatgctatgc tattttttcc catttaacat taagataatt 6420

-continued

```
tattgctata cagatgatat ggaaatatga tgaacaatat ttttttgcc aaaactatgc   6480
cttgtaagta gccatggaat gtcaacctgt aacttaaatt atccacagat agtcatgtgt   6540
ttgatgatgg gcactgtgga gataactgac ataggactgt gcccccttc tctgccactt   6600
actagctgga tgagattaag caagtcattt aactgctctg attaaacctg cctttcccaa   6660
gtgctttgta atgaatagaa atggaaacca aaaaaaacgt atacaggcct tcagaaatag   6720
taattgctac tattttgttt tcattaagcc atagttctgg ctataatttt atcaaactca   6780
ccagctatat tctacagtga aagcaggatt ctagaaagtc tcactgtttt atttatgtca   6840
ccatgtgcta tgatatattt ggttgaattc atttgaaatt agggctggaa gtattcaagt   6900
aatttcttct gctgaaaaaa tacagtgttt tgagtttagg gcctgtttta tcaaagttct   6960
aaagagccta tcactcttcc attgtagaca ttttaaaata atgacactga ttttaacatt   7020
tttaagtgtc tttttagaac agagagcctg actagaacac agccccctcca aaaacccatg   7080
ctcaaattat ttttactatg gcagcaattc cacaaaaggg aacaatgggt ttagaaatta   7140
caatgaagtc atcaacccaa aaaacatccc tatccctaag aaggttatga tataaaatgc   7200
ccacaagaaa tctatgtctg ctttaatctg tcttttattg ctttggaagg atggctatta   7260
catttttagt ttttgctgtg aatacctgag cagtttctct catccatact tatccttcac   7320
acatcagaag tcaggataga atatgaatca ttttaaaaac ttttacaact ccagagccat   7380
gtgcataaga agcattcaaa acttgccaaa acatacattt tttttcaaat ttaaagatac   7440
tctatttttg tattcaatag ctcaacaact gtggtcccca ctgataaagt gaagtggaca   7500
aggagacaag taatggcata agtttgtttt tcccaaagta tgcctgttca atagccattg   7560
gatgtgggaa atttctacat ctcttaaaat tttacagaaa atacatagcc agatagtcta   7620
gcaaaagttc accaagtcct aaattgctta tccttacttc actaagtcat gaaatcattt   7680
taatgaaaag aacatcacct aggttttgtg gtttcttttt ttcttattca tggctgagtg   7740
aaaacaacaa tctctgtttc tccctagcat ctgtggacta tttaatgtac cattattcca   7800
cactctatgg tccttactaa atacaaaatt gaacaaaaag cagtaaaaca actgactctt   7860
cacccatatt ataaaatata atccaagcca gattagtcaa catccataag atgaatccaa   7920
gctgaactgg gcctagatta ttgagttcag gttggatcac atccctattt attaataaac   7980
ttaggaaaga aggccttaca gaccatcagt tagctggagc taatagaacc tacacttcta   8040
aagttcggcc tagaatcaat gtggccttaa aagctgaaaa gaagcaggaa agaacagttt   8100
tcttcaataa tttgtccacc ctgtcactgg agaaaattta agaatttggg ggtgttggta   8160
gtaagttaaa cacagcagct gttcatggca gaaattattc aatacatacc ttctctgaat   8220
atcctataac caaagcaaag aaaaacacca aggggtttgt tctcctcctt ggagttgacc   8280
tcattccaag gcagagctca ggtcacaggc acaggggctg cgcccaagct tgtccgcagc   8340
cttatgcagc tgtggagtct ggaagactgt tgcaggactg ctggcctagt cccagaatgt   8400
cagcctcatt ttcgatttac tggctcttgt tgctgtatgt catgctgacc ttattgttaa   8460
acacaggttt gtttgctttt tttccactca tggagacatg ggagaggcat tatttttaag   8520
ctggttgaaa gctttaaccg ataaagcatt tttagagaaa tgtgaatcag gcagctaaga   8580
aagcatactc tgtccattac ggtaaagaaa atgcacagat tattaactct gcagtgtggc   8640
attagtgtcc tggtcaatat tcggatagat atgaataaaa tatttaaatg gtattgtaaa   8700
tagttttcag gacatatgct atagcttatt tttattatct tttgaaattg ctcttaatac   8760
```

-continued

```
atcaaatcct gatgtattca atttatcaga tataaattat tctaaatgaa gcccagttaa   8820
atgtttttgt cttgtcagtt atatgttaag tttctgatct ctttgtctat gacgtttact   8880
aatctgcatt tttactgtta tgaattattt tagacagcag tggtttcaag ctttttgcca   8940
ctaaaaatac cttttatttt ctcctccccc agaaaagtct ataccttgaa gtatctatcc   9000
accaaactgt acttctatta agaaatagtt attgtgtttt cttaatgttt tgttattcaa   9060
agacatatca atgaaagctg ctgagcagca tgaataacaa ttatatccac acagatttga   9120
tatattttgt gcagccttaa cttgatagta taaaatgtca ttgcttttta aataatagtt   9180
agtcaatgga cttctatcat agctttccta aactaggtta agatccagag ctttggggtc   9240
ataatatatt acatacaatt aagttatctt tttctaaggg ctttaaaatt catgagaata   9300
accaaaaaag gtatgtggag agttaataca aacataccat attcttgttg aaacagagat   9360
gtggctctgc ttgttctcca taaggtagaa atactttcca gaatttgcct aaactagtaa   9420
gccctgaatt tgctatgatt agggatagga agagattttc acatggcaga ctttagaatt   9480
cttcacttta gccagtaaag tatctccttt tgatcttagt attctgtgta ttttaacttt   9540
tctgagttgt gcatgtttat aagaaaaatc agcacaaagg gtttaagtta aagccttttt   9600
actgaaattt gaaagaaaca gaagaaaata tcaaagttct ttgtattttg agaggattaa   9660
atatgattta caaaagttac atggagggct ctctaaaaca ttaaattaat tatttttttgt  9720
tgaaaagtct tactttaggc atcattttat tcctcagcaa ctagctgtga agcctttact   9780
gtgctgtatg ccagtcactc tgctagattg tggagattac cagtgttccc gtcttctccg   9840
agcttagagt tggatgggga ataaagacag gtaaacagat agctacaata ttgtactgtg   9900
aatgcttatg ctggaggaag tacagggaac tattggagca cctaagagga gcacctacct   9960
tgaatttagg ggttagcaga ggcatcctga aaaaagtcaa agctaagcca caatctataa  10020
gcagtttagg aattagcaga acgtgcgtgg tgaggagatg ccaaaggcaa gaagagaaga  10080
gtattccaaa caggagggat tccaaagaga gaagagtatc ccaaacaaca tttgcacaaa  10140
cctgatgggg agagagaatg tggggtgggg atggatgatg agactgaaga agaaagccag  10200
gtctagataa tcagtggcct tgtacaccat gttaaagagt gtagacttga ttctgttgta  10260
aacaggaaag cagcacaatt catatgaata ttttagaaga ctcccactgg aatatggaga  10320
ataaagttgg agatgactaa tcctggaagc agggagaaca tttttgagga agttgcacta  10380
ttttggtgaa aatgatgatc ataaacatga agaattgtag gtgatcatga cctcctctct  10440
aattttccag aagggttttg gaagatataa cataggaaca ttgacaggac tgacgaaagg  10500
agatgaaata caccatataa attgtcaaac acaaggccag atgtctaatt attttgctta  10560
tgtgttgaaa ttacaaattt ttcatcagga aaccaaaaac tacaaaactt agttttccca  10620
agtcccagaa ttctatctgt ccaaacaatc tgtaccactc cacctatatc cctacctttg  10680
catgtctgtc caacctcaaa gtccaggtct atacacacgg gtaagactag agcagttcaa  10740
gtttcagaaa atgagaaaga ggaactgagt tgtgctgaac ccatacaaaa taaacacatt  10800
ctttgtatag attcttggaa cctcgagagg aattcaccta actcataggt atttgatggt  10860
atgaatccat ggctgggctc ggcttttaaa aagccttatc tgggattcct tctatggaac  10920
caagttccat caaagcccat ttaaaagcct acattaaaaa caaaattctt gctgcattgt  10980
atacaaataa tgatgtcatg atcaaataat cagatgccat tatcaagtgg aattacaaaa  11040
tggtataccc actccaaaaa aaaaaaaaaa gctaaattct cagtagaaca ttgtgacttc  11100
atgagccctc cacagccttg gagctgagga gggagcactg gtgagcagta ggttgaagag  11160
```

```
aaaacttggc gcttaataat ctatccatgt tttttcatct aaaagagcct tctttttgga  11220

ttaccttatt caatttccat caaggaaatt gttagttcca ctaaccagac agcagctggg  11280

aaggcagaag cttactgtat gtacatggta gctgtgggaa ggaggtttct ttctccaggt  11340

cctcactggc catacaccag tcccttgtta gttatgcctg gtcatagacc cccgttgcta  11400

tcatctcata tttaagtctt tggcttgtga atttatctat tctttcagct tcagcactgc  11460

agagtgctgg gactttgcta acttccattt cttgctggct tagcacattc ctcataggcc  11520

cagctctttt ctcatctggc cctgctgtgg agtcaccttg ccccttcagg agagccatgg  11580

cttaccactg cctgctaagc ctccactcag ctgccaccac actaaatcca agcttctcta  11640

agatgttgca gactttacag gcaagcataa aaggcttgat cttcctggac ttccctttac  11700

ttgtctgaat ctcacctcct tcaactttca gtctcagaat gtaggcattt gtcctctttg  11760

ccctacatct tccttcttct gaatcatgaa agcctctcac ttcctcttgc tatgtgctgg  11820

aggcttctgt caggttttag aatgagttct catctagtcc tagtagcttt tgatgcttaa  11880

gtccaccttt taaggatacc tttgagattt agaccatgtt tttcgcttga gaaagcccta  11940

atctccagac ttgcctttct gtggatttca aagaccaact gaggaagtca aaagctgaat  12000

gttgactttc tttgaacatt tccgctataa caattccaat tctcctcaga gcaatatgcc  12060

tgcctccaac tgaccaggag aaaggtccag tgccaaagag aaaaacacaa agattaatta  12120

tttcagttga gcacatactt tcaaagtggt ttgggtattc atatgaggtt ttctgtcaag  12180

agggtgagac tcttcatcta tccatgtgtg cctgacagtt ctcctggcac tggctggtaa  12240

cagatgcaaa actgtaaaaa ttaagtgatc atgtatttta acgatatcat cacatactta  12300

ttttctatgt aatgttttaa atttccccta acatactttg actgttttgc acatggtaga  12360

tattcacatt tttttgtgtt gaagttgatg caatcttcaa agttatctac cccgttgctt  12420

attagtaaaa ctagtgttaa tacttggcaa gagatgcagg gaatctttct catgactcac  12480

gccctattta gttattaatg ctactaccct attttgagta agtagtaggt ccctaagtac  12540

attgtccaga gttatacttt taaagatatt tagccccata tacttcttga atctaaagtc  12600

atacaccttg ctcctcattt ctgagtggga aagacatttg agagtatgtt gacaattgtt  12660

ctgaaggttt ttgccaagaa ggtgaaactg tcctttcatc tgtgtatgcc tggggctggg  12720

tccctggcag tgatggggtg acaatgcaaa gctgtaaaaa ctaggtgcta gtgggcacct  12780

aatatcatca tcatatactt attttcaagc taatatgcaa aatcccatct ctgtttttaa  12840

actaagtgta gatttcagag aaaatatttt gtggttcaca taagaaaaca gtctactcag  12900

cttgacaagt gttttatgtt aaattggctg gtggtttgaa atgaatcatc ttcacataat  12960

gttttcttta aaaatattgt gaatttaact ctaattcttg ttattctgtg tgataataaa  13020

gaataaacta atttcta                                                 13037
```

<210> SEQ ID NO 132
<211> LENGTH: 3180
<212> TYPE: DNA
<213> ORGANISM: Homo sapiens

<400> SEQUENCE: 132

```
attctatgct gcagcctaag catcattcct cttctcttct tagtggagat aaaattaccc     60

actgctctcc ttacatttac tttgtccata tttgctccta tgctctaggc tcgtgcacaa    120

caaacacagt gtgggccctt accctagaag ccaacttctc atgacctttc tctatctcca    180
```

-continued

```
gaatccatgc agtgggaatg aaggtaaaag aaggttttca tgggatccag ctgagagctc    240
tacggggaaa atggatctga ggagccatgt gctccatctc ttttatttta caggtagaga    300
ctaggggtat agagtgaggt gaattaccgc agtgacccac acattgttgg cagacctagg    360
attagaactc tgtcttcctg gttcccagct tggtgctttt gaaagcatac ttgctgcttt    420
cttaccggcc tggtgtctgc cactttggga cagagtgtgg acttgctcac ctgccccatt    480
tcttagggat tctcattctg tgtttgagca agaatattct tattctggaa agaaccacat    540
accacaggat tctgggtgag cataaggaag attgtcttgg ggatctgact tagctcacgt    600
atagtggcta tgatgaattc agtgtcttat tttttgcata tgtatatttt tagtctaata    660
ttgcctgggt gtctgagcaa gtctagatga atttaattgc tctcattttt cccctgcccc    720
tcttcctttg gtctctcttt taggaaatgt ttttctttca acattcgttt cattcattat    780
ttactcattc ggccaaccaa catttattga gtgccttccc tgtatcaggg acaggggctt    840
acaaagtaga atttgatccc acctctgccc tcagtagctc agtgtctaat ggaggtagtg    900
atgttcatta agcgtcgcca gatactgtgc taggtgctgt gcctgttctc tctcgcttgt    960
tcctcacaca cttgagaagg ccgaagctga ttcatagctt ggaaggcagg ggccttggat   1020
ttgaacccag gcctgaccaa tggcagaacc tatcagatgt gtggacagat gacattgcct   1080
ttctttcttt ggatatatca aaatcagcca gcaggcagga actcccattt tgagcaagca   1140
atgtgcagga atgatagggt atacagagag gaacaggaga tggcccctga cttccagcat   1200
gtgtctgatg gacatccagg ctgcaggcat catggtgctg tctagagaga tgagccaggt   1260
gcccagagcc catgggccaa tgctgccctt tcttgagcat gccaaacaaa gcggttggtg   1320
tgttagaggc acagtctcct ccactctaag taaaaatcag catgagtcct agcccacatt   1380
tccctagtga gtacaccaaa gatatctatg aactggcagt catcagtgac ttcctaaggt   1440
tccggaaatg catctcttac tcaggagtaa gcaatgatgt gcctgcggct ttacgagttc   1500
tcacagaatg actttctgga cccaaatgtt ttttctgctt caggactgtg aaggccttat   1560
tgttcgctct gccaccaagg tgaccgctga tgtcatcaac gcagctgaga aactccaggt   1620
ggtgggcagg gctggcacag gtgtggacaa tgtggatctg gaggccgcaa caaggaaggg   1680
catcttggtt atgaacaccc ccaatgggaa cagcctcagt gccgcagaac tcacttgtgg   1740
aatgatcatg tgcctggcca ggcagattcc ccaggcgacg gcttcgatga aggacggcaa   1800
atgggagcgg aagaagttca tgggaacaga gctgaatgga aagaccctgg gaattcttgg   1860
cctgggcagg attgggagag aggtagctac ccggatgcag tcctttggga tgaagactat   1920
agggtatgac cccatcattt ccccagaggt ctcggcctcc tttggtgttc agcagctgcc   1980
cctggaggag atctggcctc tctgtgattt catcactgtg cacactcctc tcctgccctc   2040
cacgacaggc ttgctgaatg acaacacctt tgcccagtgc aagaaggggg tgcgtgtggt   2100
gaactgtgcc cgtggaggga tcgtggacga aggcgccctg ctccgggccc tgcagtctgg   2160
ccagtgtgcc ggggctgcac tggacgtgtt tacggaagag ccgccacggg accgggcctt   2220
ggtggaccat gagaatgtca tcagctgtcc ccacctgggt gccagcacca aggaggctca   2280
gagccgctgt ggggaggaaa ttgctgttca gttcgtggac atggtgaagg ggaaatctct   2340
cacgggggtt gtgaatgccc aggcccttac cagtgccttc tctccacaca ccaagccttg   2400
gattggtctg gcagaagctc tggggacact gatgcgagcc tgggctgggt cccccaaagg   2460
gaccatccag gtgataacac agggaacatc cctgaagaat gctgggaact gcctaagccc   2520
cgcagtcatt gtcggcctcc tgaaagaggc ttccaagcag gcggatgtga acttggtgaa   2580
```

cgctaagctg ctggtgaaag aggctggcct caatgtcacc acctcccaca gccctgctgc 2640
accagggggg caaggcttcg gggaatgcct cctggccgtg gccctggcag gcgcccctta 2700
ccaggctgtg ggcttggtcc aaggcactac acctgtactg caggggctca atggagctgt 2760
cttcaggcca gaagtgcctc tccgcaggga cctgcccctg ctcctattcc ggactcagac 2820
ctctgaccct gcaatgctgc ctaccatgat tggcctcctg gcagaggcag gcgtgcggct 2880
gctgtcctac cagacttcac tggtgtcaga tggggagacc tggcacgtca tgggcatctc 2940
ctccttgctg cccagcctgg aagcgtggaa gcagcatgtg actgaagcct tccagttcca 3000
cttctaacct tggagctcac tggtccctgc ctctggggct tttctgaaga aacccaccca 3060
ctgtgatcaa tagggagaga aaatccacat tcttgggctg aacgcgagcc tctgacactg 3120
cttacactgc actctgaccc tgtagtacag caataaccgt ctaataaaga gcctaccccc 3180

<210> SEQ ID NO 133
<211> LENGTH: 1301
<212> TYPE: DNA
<213> ORGANISM: Homo sapiens
<220> FEATURE:
<221> NAME/KEY: misc_feature
<222> LOCATION: (1301)..(1301)
<223> OTHER INFORMATION: n is a, c, g, t or u

<400> SEQUENCE: 133
caaacaaaaa cagccaagct tttctgccaa aaagatgact gagaagactg ttaaagcaaa 60
aagctctgtt cctgcctcag atgatgccta tccagaaata gaaaaattct ttcccttcaa 120
tcctctagac tttgagagtt ttgacctgcc tgaagagcac cagattgcgc acctcccctt 180
gagtggagtg cctctcatga tccttgacga ggagagagag cttgaaaagc tgtttcagct 240 gggccccccct tcacctgtga agatgccctc tccaccatgg gaatccaatc tgttgcagtc 300
tccttcaagc attctgtcga ccctggatgt tgaattgcca cctgtttgct gtgacataga 360
tatttaaatt tcttagtgct tcagagtctg tgtgtatttg tattaataaa gcattcttta 420
acagaaaaaa aaaaaaaaaa aaaaaaaaaa aaaaaaaaaa aaaaaaaaaa agggggggga 480
gacacaaaaa gaattcccca agagggggcc acaagataat cagaggatat cacacaagat 540
ctctcggcgc accaacgacg gggccccaa ataagggaga gacccagaat cacaacagcc 600
aagacacggt ggacacgacg gaaacaaaca cacagcccag acacgggggc aaacacgcgc 660
gcacaccgcg gacaccatgg gacaaagcag acaccaccca caaaacaaca ccgcggaggg 720
ggaagaacaa caaaacaagt gcgcaaacag aacacaacca cagaaagaga aaaattaaaa 780
cggcccccaa gacggcgaca acacaacaaa acaaccacta cagagcgctc aacagccgag 840
taaaaacaca acaacggaca actaacacac aaaggaatga aacaaagcgg ggccacacac 900
cgacaccgga aatccggcga acaactcaca ccgagcgagg gtcccagaca acaaatacac 960
agacaacgaa accgagaaac aagaccagca agacgagcag gcaaaagaca aacaagacag 1020
aggagacgac gacgaacgca aaggacaaga ggacacaacg acgcgaggag cgagagcgag 1080
aggaagagac aacaaaaaga cacaaaagaa caacaagcaa gcagcgaaga acgacacaca 1140
accacacgag acagcaggag cagaggcgga gaaaacacaa cgagcaagcc aagaccaaga 1200
gaggagaaca aaataaaaaa atacgagagc aggcggacga gagcacgaga cgaacagaca 1260
aacgggaatc agaagcataa cgatccgcga cgcgaacaac n 1301

<210> SEQ ID NO 134

<211> LENGTH: 3203
<212> TYPE: DNA
<213> ORGANISM: Homo sapiens

<400> SEQUENCE: 134

```
gtgcaccctg tcccagccgt cctgtcctgg ctgctcgctc tgcttcgctg cgcctccact     60
atgctctccc tccgtgtccc gctcgcgccc atcacggacc cgcagcagct gcagctctcg    120
ccgctgaagg ggctcagctt ggtcgacaag gagaacacgc cgccggccct gagcgggacc    180
cgcgtcctgg ccagcaagac cgcgaggagg atcttccagg agaaaacccc cgccgctttg    240
tcatcttccc catcgagtac catgatatct ggcagatgta taagaaggca gaggcttcct    300
tttggaccgc cgaggaggtg gacctctcca aggacattca gcactgggaa tccctgaaac    360
ccgaggagag atattttata tcccatgttc tggctttctt tgcagcaagc gatggcatag    420
taaatgaaaa cttggtggag cgatttagcc aagaagttca gattacagaa gcccgctgtt    480
tctatggctt ccaaattgcc atggaaaaca tacattctga aatgtatagt cttcttattg    540
acacttacat aaaagatccc aaagaaaggg aatttctctt caatgccatt gaaacgatgc    600
cttgtgtcaa gaagaaggca gactgggcct tgcgctggat tggggacaaa gaggctacct    660
atggtgaacg tgttgtagcc tttgctgcag tggaaggcat tttcttttcc ggttcttttg    720
cgtcgatatt ctggctcaag aaacgaggac tgatgcctgg cctcacattt tctaatgaac    780
ttattagcag agatgagggt ttacactgtg attttgcttg cctgatgttc aaacacctgg    840
tacacaaacc atcggaggag agagtaagag aaataattat caatgctgtt cggatagaac    900
aggagttcct cactgaggcc ttgcctgtga agctcattgg gatgaattgc actctaatga    960
agcaatacat tgagtttgtg gcagacagac ttatgctgga actgggtttt agcaaggttt   1020
tcagagtaga gaacccattt gactttatgg agaatatttc actggaagga aagactaact   1080
tctttgagaa gagagtaggc gagtatcaga ggatgggagt gatgtcaagt ccaacagaga   1140
attcttttac cttggatgct gacttctaaa tgaactgaag atgtgccctt acttggctga   1200
tttttttttt tccatctcat aagaaaaatc agctgaagtg ttaccaacta gccacaccat   1260
gaattgtccg taatgttcat taacagcatc tttaaaactg tgtagctacc tcacaaccag   1320
tcctgtctgt ttatagtgct ggtagtatca ccttttgcca gaaggcctgg ctggctgtga   1380
cttaccatag cagtgacaat ggcagtcttg gctttaaagt gaggggtgac cctttagtga   1440
gcttagcaca gcgggattaa acagtccttt aaccagcaca gccagttaaa agatgcagcc   1500
tcactgcttc aacgcagatt ttaatgttta cttaaatata aacctggcac tttacaaaca   1560
aataaacatt gtttgtactc acaaggcgat aatagcttga tttatttggt ttctacacca   1620
aatacattct cctgaccact aatgggagcc aattcacaat tcactaagtg actaaagtaa   1680
gttaaacttg tgtagactaa gcatgtaatt tttaagtttt attttaatga attaaaatat   1740
ttgttaacca actttaaagt cagtcctgtg tatacctaga tattagtcag ttggtgccag   1800
atagaagaca ggttgtgttt ttatcctgtg gcttgtgtag tgtcctggga ttctctgccc   1860
cctctgagta gagtgttgtg ggataaagga atctctcagg gcaaggagct tcttaagtta   1920
aatcactaga aatttagggg tgatctgggc cttcatatgt gtgagaagcc gtttcatttt   1980
atttctcact gtattttcct caacgtctgg ttgatgagaa aaaattcttg aagagttttc   2040
atatgtggga gctaaggtag tattgtaaaa tttcaagtca tccttaaaca aaatgatcca   2100
cctaagatct tgcccctgtt aagtggtgaa atcaactaga ggtggttcct acaagttgtt   2160
cattctagtt ttgtttggtg taagtaggtt gtgtgagtta attcatttat atttactatg   2220
```

tctgttaaat cagaaatttt ttattatcta tgttcttcta gattttacct gtagttcata 2280
cttcagtcac ccagtgtctt attctggcat tgtctaaatc tgagcattgt ctagggggat 2340
cttaaacttt agtaggaaac catgagctgt taatacagtt tccattcaaa tattaatttc 2400
agaatgaaac ataatttttt tttttttttt ttgagatgga gtctcgctct gttgcccagg 2460
ctggagtgca gtggcgcgat tttggctcac tgtaacctcc atctcctggg ttcaagcaat 2520
tctcctgtct cagcctccct agtagctggg actgcaggta tgtgctacca cacctggcta 2580
atttttgtat ttttagtaga gatggagttt caccatattg gtcaggctgg tcttgaactc 2640
ctgacctcag gtgatccacc cacctcggcc tcccaaagtg ctgggattgc aggcgtgata 2700
aacaaatatt cttaataggg ctactttgaa ttaatctgcc tttatgtttg ggagaagaaa 2760
gctgagacat tgcatgaaag atgatgagag ataaatgttg atcttttggc cccatttgtt 2820
aattgtattc agtatttgaa cgtcgtcctg tttattgtta gttttcttca tcatttattg 2880
tatagacaat ttttaaatct ctgtaatatg atacattttc ctatctttta agttattgtt 2940
acctaaagtt aatccagatt atatggtcct tatatgtgta caacattaaa atgaaaggct 3000
ttgtcttgca ttgtgaggta caggcggaag ttggaatcag gttttaggat tctgtctctc 3060
attagctgaa taatgtgagg attaacttct gccagctcag accatttcct aatcagttga 3120
aagggaaaca agtatttcag tctcaaaatt gaataatgca caagtcttaa gtgattaaaa 3180
taaaactgtt cttatgtcag ttt 3203

<210> SEQ ID NO 135
<211> LENGTH: 4482
<212> TYPE: DNA
<213> ORGANISM: Homo sapiens

<400> SEQUENCE: 135
agcgggggca ctccagccct gcagcctccg gagtcagtgc cgcgcgcccg ccgccccgcg 60
ccttcctgct cgccgcacct ccgggagccg gggcgcaccc agcccgcagc gccgcctccc 120
cgcccgcgcc gcctccgacc gcaggccgag ggccgccact ggccgggggg accgggcagc 180
agcttgcggc cgcggagccg ggcaacgctg gggactgcgc cttttgtccc cggaggtccc 240
tggaagtttg cggcaggacg cgcgcgggga ggcggcggag gcagccccga cgtcgcggag 300
aacagggcgc agagccggca tgggcatcgg gcgcagcgag gggggccgcc gcggggcagc 360
cctgggcgtg ctgctggcgc tgggcgcggc gcttctggcc gtgggctcgg ccagcgagta 420
cgactacgtg agcttccagt cggacatcgg cccgtaccag agcgggcgct tctacaccaa 480
gccacctcag tgcgtggaca tccccgcgga cctgcggctg tgccacaacg tgggctacaa 540
gaagatggtg ctgcccaacc tgctggagca cgagaccatg gcggaggtga agcagcaggc 600
cagcagctgg gtgcccctgc tcaacaagaa ctgccacgcc ggcacccagg tcttcctctg 660
ctcgctcttc gcgcccgtct gcctggaccg gcccatctac ccgtgtcgct ggctctgcga 720
ggccgtgcgc gactcgtgcg agccggtcat gcagttcttc ggcttctact ggcccgagat 780
gcttaagtgt gacaagttcc ccgaggggga cgtctgcatc gccatgacgc cgcccaatgc 840
caccgaagcc tccaagcccc aaggcacaac ggtgtgtcct ccctgtgaca acgagttgaa 900
atctgaggcc atcattgaac atctctgtgc cagcgagttt gcactgagga tgaaaataaa 960
agaagtgaaa aaagaaaatg gcgacaagaa gattgtcccc aagaagaaga agcccctgaa 1020
gttggggccc atcaagaaga aggacctgaa gaagcttgtg ctgtacctga agaatggggc 1080

```
tgactgtccc tgccaccagc tggacaacct cagccaccac ttcctcatca tgggccgcaa   1140
ggtgaagagc cagtacttgc tgacggccat ccacaagtgg gacaagaaaa acaaggagtt   1200
caaaaacttc atgaagaaaa tgaaaaacca tgagtgcccc acctttcagt ccgtgtttaa   1260
gtgattctcc cgggggcagg gtggggaggg agcctcgggt ggggtgggag cggggggggac  1320
agtgccccgg gaacccggtg ggtcacacac acgcactgcg cctgtcagta gtggacattt   1380
aatccagtcg gcttgttctt gcagcattcc cgctcccttc cctccatagc cacgctccaa   1440
accccagggt agccatggcc gggtaaagca agggccattt agattaggaa ggtttttaag   1500
atccgcaatg tggagcagca gccactgcac aggaggaggt gacaaaccat ttccaacagc   1560
aacacagcca ctaaaacaca aaaaggggga ttgggcggaa agtgagagcc agcagcaaaa   1620
actacatttt gcaacttgtt ggtgtggatc tattggctga tctatgcctt tcaactagaa   1680
aattctaatg attggcaagt cacgttgttt tcaggtccag agtagtttct ttctgtctgc   1740
tttaaatgga aacagactca taccacactt acaattaagg tcaagcccag aaagtgataa   1800
gtgcagggag gaaaagtgca agtccattat gtaatagtga cagcaaaggg accaggggag   1860
aggcattgcc ttctctgccc acagtctttc cgtgtgattg tctttgaatc tgaatcagcc   1920
agtctcagat gccccaaagt ttcggttcct atgagcccgg ggcatgatct gatccccaag   1980
acatgtggag gggcagcctg tgcctgcctt tgtgtcagaa aaaggaaacc acagtgagcc   2040
tgagagagac ggcgattttc gggctgagaa ggcagtagtt ttcaaaacac atagttaaaa   2100
aagaaacaaa tgaaaaaaat tttagaacag tccagcaaat tgctagtcag ggtgaattgt   2160
gaaattgggt gaagagctta cgattctaat ctcatgtttt ttccttttca catttttaaa   2220
agaacaatga caaacaccca cttatttttc aaggttttaa aacagtctac attgagcatt   2280
tgaaaggtgt gctagaacaa ggtctcctga tccgtccgag gctgcttccc agaggagcag   2340
ctctccccag gcatttgcca agggaggcgg atttccctgg tagtgtagct gtgtggcttt   2400
ccttcctgaa gagtccgtgg ttgccctaga acctaacacc ccctagcaaa actcacagag   2460
ctttccgttt ttttctttcc tgtaaagaaa catttccttt gaacttgatt gcctatggat   2520
caaagaaatt cagaacagcc tgcctgtccc cccgcacttt ttacatatat ttgtttcatt   2580
tctgcagatg gaaagttgac atgggtgggg tgtccccatc cagcgagaga gtttaaaaag   2640
caaaacatct ctgcagtttt tcccaagtgc cctgagatac ttcccaaagc ccttatgttt   2700
aatcagcgat gtatataagc cagttcactt agacaacttt acccttcttg tccaatgtac   2760
aggaagtagt tctaaaaaaa atgcatatta atttcttccc ccaaagccgg attcttaatt   2820
ctctgcaaca ctttgaggac atttatgatt gtccctctgg gccaatgctt atacccagtg   2880
aggatgctgc agtgaggctg taaagtggcc ccctgcggcc ctagcctgac ccggaggaaa   2940
ggatggtaga ttctgttaac tcttgaagac tccagtatga aaatcagcat gcccgcctag   3000
ttacctaccg gagagttatc ctgataaatt aacctctcac agttagtgat cctgtccttt   3060
taacaccttt tttgtggggt tctctctgac ctttcatcgt aaagtgctgg ggaccttaag   3120
tgatttgcct gtaattttgg atgattaaaa aatgtgtata tatattagct aattagaaat   3180
attctacttc tctgttgtca aactgaaatt cagagcaagt tcctgagtgc gtggatctgg   3240
gtcttagttc tggttgattc actcaagagt tcagtgctca tacgtatctg ctcattttga   3300
caaagtgcct catgcaaccg ggccctctct ctgcggcaga gtccttagtg gaggggttta   3360
cctggaacat tagtagttac cacagaatac ggaagagcag gtgactgtgc tgtgcagctc   3420
tctaaatggg aattctcagg taggaagcaa cagcttcaga aagagctcaa aataaattgg   3480
```

aaatgtgaat cgcagctgtg ggttttacca ccgtctgtct cagagtccca ggaccttgag 3540
tgtcattagt tactttattg aaggttttag acccatagca gctttgtctc tgtcacatca 3600
gcaatttcag aaccaaaagg gaggctctct gtaggcacag agctgcacta tcacgagcct 3660
ttgtttttct ccacaaagta tctaacaaaa ccaatgtgca gactgattgg cctggtcatt 3720
ggtctccgag agaggaggtt tgcctgtgat ttcctaatta tcgctagggc caaggtggga 3780
tttgtaaagc tttacaataa tcattctgga tagagtcctg ggaggtcctt ggcagaactc 3840
agttaaatct ttgaagaata tttgtagtta tcttagaaga tagcatggga ggtgaggatt 3900
ccaaaaacat tttattttta aaatatcctg tgtaacactt ggctcttggt acctgtgggt 3960
tagcatcaag ttctccccag ggtagaattc aatcagagct ccagtttgca tttggatgtg 4020
taaattacag taatcccatt tcccaaacct aaaatctgtt tttctcatca gactctgagt 4080
aactggttgc tgtgtcataa cttcatagat gcaggaggct caggtgatct gtttgagcag 4140
agcaccctag gcagcctgca gggaataaca tactggccgt tctgacctgt tgccagcaga 4200
tacacaggac atggatgaaa ttcccgtttc ctctagtttc ttcctgtagt actcctcttt 4260
tagatcctaa gtctcttaca aaagctttga atactgtgaa aatgttttac attccatttc 4320
atttgtgttg ttttttttaac tgcattttac cagatgtttt gatgttatcg cttatgttaa 4380
tagtaattcc cgtacgtgtt cattttattt tcatgctttt tcagccatgt atcaatattc 4440
acttgactaa aatcactcaa ttaatcaaaa aaaaaaaaaa aa 4482

<210> SEQ ID NO 136
<211> LENGTH: 3637
<212> TYPE: DNA
<213> ORGANISM: Homo sapiens

<400> SEQUENCE: 136
agtcctgggc gaagggggcg gtggttcccc gcggcgctgc gcgcggcggt aattagtgat 60
tgtcttccag cttcgcgaag gctaggggcg cggctgccgg gtggctgcgc ggcgctgccc 120
ccggaccgag ggcagccaa cccaatgaaa ccaccgcgtg ttcgcgcctg gtagagattt 180
ctcgaagaca ccagtgggcc cgttccgagc cctctggacc gcccgtgtgg aaccaaacct 240
gcgcgcgtgg ccgggccgtg ggacaacgag gccgcggaga cgaaggcgca atggcgagga 300
agttatctgt aatcttgatc ctgacctttg ccctctctgt cacaaatccc cttcatgaac 360
taaaagcagc tgctttcccc cagaccactg agaaaattag tccgaattgg gaatctggca 420
ttaatgttga cttggcaatt tccacacggc aatatcatct acaacagctt ttctaccgct 480
atggagaaaa taattctttg tcagttgaag ggttcagaaa attacttcaa aatataggca 540
tagataagat taaaagaatc catatacacc atgaccacga ccatcactca gaccacgagc 600
atcactcaga ccatgagcgt cactcagacc atgagcatca ctcagaccac gagcatcact 660
ctgaccatga tcatcactct caccataatc atgctgcttc tggtaaaaat aagcgaaaag 720
ctctttgccc agaccatgac tcagatagtt caggtaaaga tcctagaaac agccagggga 780
aaggagctca ccgaccagaa catgccagtg gtagaaggaa tgtcaaggac agtgttagtg 840
ctagtgaagt gacctcaact gtgtacaaca ctgtctctga aggaactcac tttctagaga 900
caatagagac tccaagacct ggaaaactct tccccaaaga tgtaagcagc tccactccac 960
ccagtgtcac atcaaagagc cgggtgagcc ggctggctgg taggaaaaca aatgaatctg 1020
tgagtgagcc ccgaaaaggc tttatgtatt ccagaaacac aaatgaaaat cctcaggagt 1080

-continued

```
gtttcaatgc atcaaagcta ctgacatctc atggcatggg catccaggtt ccgctgaatg   1140
caacagagtt caactatctc tgtccagcca tcatcaacca aattgatgct agatcttgtc   1200
tgattcatac aagtgaaaag aaggctgaaa tccctccaaa gacctattca ttacaaatag   1260
cctgggttgg tggttttata gccatttcca tcatcagttt cctgtctctg ctgggggtta   1320
tcttagtgcc tctcatgaat cgggtgtttt tcaaatttct cctgagtttc cttgtggcac   1380
tggccgttgg gactttgagt ggtgatgctt ttttacacct tcttccacat tctcatgcaa   1440
gtcaccacca tagtcatagc catgaagaac cagcaatgga aatgaaaaga ggaccacttt   1500
tcagtcatct gtcttctcaa aacatagaag aaagtgccta ttttgattcc acgtggaagg   1560
gtctaacagc tctaggaggc ctgtatttca tgtttcttgt tgaacatgtc ctcacattga   1620
tcaaacaatt taaagataag aagaaaaaga atcagaagaa acctgaaaat gatgatgatg   1680
tggagattaa gaagcagttg tccaagtatg aatctcaact ttcaacaaat gaggagaaag   1740
tagatacaga tgatcgaact gaaggctatt tacgagcaga ctcacaagag ccctccccact   1800
ttgattctca gcagcctgca gtcttggaag aagaagaggt catgatagct catgctcatc   1860
cacaggaagt ctacaatgaa tatgtaccca gagggtgcaa gaataaatgc cattcacatt   1920
tccacgatac actcggccag tcagacgatc tcattcacca ccatcatgac taccatcata   1980
ttctccatca tcaccaccac caaaaccacc atcctcacag tcacagccag cgctactctc   2040
gggaggagct gaaagatgcc ggcgtcgcca ctctggcctg gatggtgata atgggtgatg   2100
gcctgcacaa tttcagcgat ggcctagcaa ttggtgctgc ttttactgaa ggcttatcaa   2160
gtggtttaag tacttctgtt gctgtgttct gtcatgagtt gcctcatgaa ttaggtgact   2220
ttgctgttct actaaaggct ggcatgaccg ttaagcaggc tgtcctttat aatgcattgt   2280
cagccatgct ggcgtatctt ggaatggcaa caggaatttt cattggtcat tatgctgaaa   2340
atgtttctat gtggatattt gcacttactg ctggcttatt catgtatgtt gctctggttg   2400
atatggtacc tgaaatgctg cacaatgatg ctagtgacca tggatgtagc cgctgggggt   2460
atttcttttt acagaatgct gggatgcttt tgggttttgg aattatgtta cttatttcca   2520
tatttgaaca taaaatcgtg tttcgtataa atttctagtt aaggtttaaa tgctagagta   2580
gcttaaaaag ttgtcatagt ttcagtaggt catagggaga tgagtttgta tgctgtacta   2640
tgcagcgttt aaagttagtg ggttttgtga tttttgtatt gaatattgct gtctgttaca   2700
aagtcagtta aaggtacgtt ttaatattta agttattcta tcttggagat aaaatctgta   2760
tgtgcaattc accggtatta ccagtttatt atgtaaacaa gagatttggc atgacatgtt   2820
ctgtatgttt cagggaaaaa tgtctttaat gctttttcaa gaactaacac agttattcct   2880
atactggatt ttaggtctct gaagaactgc tggtgtttag gaataagaat gtgcatgaag   2940
cctaaaatac caagaaagct tatactgaat ttaagcaaag aaataaagga gaaaagagaa   3000
gaatctgaga attggggagg catagattct tataaaaatc acaaaatttg ttgtaaatta   3060
gaggggagaa atttagaatt aagtataaaa aggcagaatt agtatagagt acattcatta   3120
aacatttttg tcaggattat ttcccgtaaa aacgtagtga gcacttttca tatactaatt   3180
tagttgtaca tttaactttg tataatacag aaatctaaat atatttaatg aattcaagca   3240
atatatcact tgaccaagaa attggaattt caaaatgttc gtgcgggtat ataccagatg   3300
agtacagtga gtagttttat gtatcaccag actgggttat tgccaagtta tatatcacca   3360
aaagctgtat gactggatgt tctggttacc tggtttacaa aattatcaga gtagtaaaac   3420
tttgatatat atgaggatat taaaactaca ctaagtatca tttgattcga ttcagaaagt   3480
```

```
actttgatat ctctcagtgc ttcagtgcta tcattgtgag caattgtctt ttatatacgg   3540

tactgtagcc atactaggcc tgtctgtggc attctctaga tgtttctttt ttacacaata   3600

aattccttat atcagcttga aaaaaaaaaa aaaaaaa                            3637


<210> SEQ ID NO 137
<211> LENGTH: 2208
<212> TYPE: DNA
<213> ORGANISM: Homo sapiens

<400> SEQUENCE: 137

aacgcacttg gcgcgcggcg cgggctgcag acggctgcga ggcgctgggc acaggtgtcc     60

tgatggcaaa tttcaagggc cacgcgcttc cagggagttt cttcctgatc attgggctgt    120

gttggtcagt gaagtacccg ctgaagtact ttagccacac gcggaagaac agcccactac    180

attactatca gcgtctcgag atcgtcgaag ccgcaattag gactttgttt tccgtcactg    240

ggatcctggc agagcagttt gttccggatg ggccccacct gcacctctac catgagaacc    300

actggataaa gttaatgaat tggcagcaca gcaccatgta cctattcttt gcagtctcag    360

gaattgttga catgctcacc tatctggtca gccacgttcc cttgggggtg gacagactgg    420

ttatggctgt ggcagtattc atggaaggtt tcctcttcta ctaccacgtc cacaaccggc    480

ctccgctgga ccagcacatc cactcactcc tgctgtatgc tctgttcgga gggtgtgtta    540

gtatctccct agaggtgatc ttccgggacc acattgtgct ggaacttttc cgaaccagtc    600

tcatcattct tcagggaacc tggttctggc agattgggtt tgtgctgttc ccaccttttg    660

gaacacccga atgggaccag aaggatgatg ccaacctcat gttcatcacc atgtgcttct    720

gctggcacta cctggctgcc ctcagcattg tggccgtcaa ctattctctt gtttactgcc    780

ttttgactcg gatgaagaga cacggaaggg gagaaatcat tggaattcag aagctgaatt    840

cagatgacac ttaccagacc gccctcttga gtggctcaga tgaggaatga gccgagatgc    900

ggagggcgca gatgtcccac tgcacagctg gaatgaatgg agttcatccc ctccacctga    960

atgcctgctg tggtctgatc ttaagggtct atatatttgc acctcctcat tcaacacagg   1020

gctggaggtt ctacaacagg aaatcaggcc tacagcatcc tgtgtatctt gcagttggga   1080

tttttaaaca tactataaag tctgtgttgg tatagtaccc ttcataagga aaaatgaagt   1140

aatgcctata agtagcaggc ctttgtgcct cagtgtcaag agaaatcaag agatgctaaa   1200

agctttacaa tggaagtggc ctcatggatg aatccggggt atgagcccag gagaacgtgc   1260

tgcttttggt aacttatccc tttttctctt aagaaagcag gtactttctt attagaaata   1320

tgttagaatg tgtaagcaaa cgacagtgcc tttagaatta caattctaac ttacatattt   1380

tttgaaagta aaataattca caagctttgg tattttaaaa ttattgttaa acatatcata   1440

actaatcata ccagggtact gcaataccac tgtttataag tgacaaaatt aggccaaagg   1500

tgattttttt ttaaatcagg aagctggtta ctggctctac tgagagttgg agccctgatg   1560

ttctgattct tcaaagtcac cctaaaagaa gatctgacag gaaagctgta taatgagata   1620

gaaaaacgtc aggtatggaa ggctttcagt tttaatatgg ctgaaagcaa aggataacga   1680

attcagaatt agtaatgtaa aatcttgata ccctaatctt gcttctggat ctgttctttt   1740

tttaaaaaaa cttccttcac cgcgcctata atcctagcac tttgggaggc cgaggcaggc   1800

agatcacggg gtcaggagat caagaccatc ctggctaaca tggtgaaacc ccgtctctac   1860

tgaaaataca aaaaattagc cgggtgtggt ggcgggcgcc tgtagttcca gctactcggg   1920
```

aggctgaggc aagagaatgg catgaacccg gtaggggagc ttgcagtgag cccagatcat 1980
gccactgtac tccagcctag gtgacagagc aagactctgt ctcaaaaaca agcaaacaga 2040
cttccttcaa caaatattta ttaaatatcc actttgcaac agcactgaaa tggctgtaag 2100
gactcctgag atatgtgtcc agcaaggagt ttacagtcaa acaggagaga catgcctgta 2160
gttacatcca gtgtgatggg tgctgagagg caagtacaaa ccacgatg 2208

<210> SEQ ID NO 138
<211> LENGTH: 1678
<212> TYPE: DNA
<213> ORGANISM: Homo sapiens
<220> FEATURE:
<221> NAME/KEY: misc_feature
<222> LOCATION: (523)..(523)
<223> OTHER INFORMATION: n is a, c, g, t or u
<220> FEATURE:
<221> NAME/KEY: misc_feature
<222> LOCATION: (569)..(569)
<223> OTHER INFORMATION: n is a, c, g, t or u
<220> FEATURE:
<221> NAME/KEY: misc_feature
<222> LOCATION: (961)..(961)
<223> OTHER INFORMATION: n is a, c, g, t or u
<220> FEATURE:
<221> NAME/KEY: misc_feature
<222> LOCATION: (1021)..(1021)
<223> OTHER INFORMATION: n is a, c, g, t or u
<220> FEATURE:
<221> NAME/KEY: misc_feature
<222> LOCATION: (1066)..(1066)
<223> OTHER INFORMATION: n is a, c, g, t or u
<220> FEATURE:
<221> NAME/KEY: misc_feature
<222> LOCATION: (1069)..(1069)
<223> OTHER INFORMATION: n is a, c, g, t or u
<220> FEATURE:
<221> NAME/KEY: misc_feature
<222> LOCATION: (1194)..(1194)
<223> OTHER INFORMATION: n is a, c, g, t or u
<220> FEATURE:
<221> NAME/KEY: misc_feature
<222> LOCATION: (1202)..(1202)
<223> OTHER INFORMATION: n is a, c, g, t or u
<220> FEATURE:
<221> NAME/KEY: misc_feature
<222> LOCATION: (1287)..(1287)
<223> OTHER INFORMATION: n is a, c, g, t or u
<220> FEATURE:
<221> NAME/KEY: misc_feature
<222> LOCATION: (1472)..(1472)
<223> OTHER INFORMATION: n is a, c, g, t or u

<400> SEQUENCE: 138
tcccgccgcg ccacttcgcc tgcctccgtc ccccgcccgc cgcgccatgc ctgtggccgg 60
ctcggagctg ccgcgccggc ccttgccccc cgccgcacag gagcgggacg ccgagccgcg 120
tccgccgcac ggggagctgc agtacctggg gcagatccaa cacatcctcc gctgcggcgt 180
caggaaggac gcccgcccgg gcaccggtac cctgccggta ttcggcatgc aggcgcgcta 240
cagcctgaga gatgaattcc ctctgctgac aaccaaacgt gtgttctgga acggtgcttc 300
ggaggagctg ctgtggctta tcaagggatc cacaaacgct atagacctgt cttccccggc 360
agcgaaaatc tcgggatgcc actggatccc gacactctct ggacaccctg ggattctcca 420
ccagagaaga acgcgacttg ggcccagttt gtggctctca gcggaggcct cctgtggcag 480
aatacataca tttccaatca gatcacttcc cggacacgga ccntgaccag cctgccaaaa 540
agtggatttc cccccacccc agaacccanc ccctgacgca cagaaaccaa cccattcgtt 600
gttgccgcct tgcgaacccc aaccagaatc tctcccccct ggccggcgcg cctgccgctg 660

-continued ccaatgcccc tatggcggcc tcttggcccg caccttccaa ttggtcgccc tgcgcaacca 720
gcgagaaaac actggcccgc ccgtctcccc cccgctccgc ctaccccact taatgcgcct 780
ccgtggcatg acgcacgcgt ttggtgtccg ccgccgtctc atgtccgcgc ggtgtggacc 840 ccctttttctc tcgcggcaca tccccccctat tcccttgccc tttggggggc accccctcta 900
gacccgcgct tctcttctcg tccggtgggg gacattggtt tgcctgccgc ggcgggggcg 960
ntaaaaataa aaacagcctg ttagcccggc ccagtacccc cccccggccg gggccgcctt 1020
ncgtttgcat ttatacccca acccataaag ccgcgcccct ttagcnccnt aacttttgtg 1080
gtgtggcctc ccccctttt cccggggagc agcaacggac atctgtacac taatgctggc 1140
cccgaccttt cccaaaaacc ccccgcccgt gtcccgtata aatttggtgc caancctgac 1200
gngttctccc ccgccctcgc cccgttggcc gcccgtttaa agcccccccg gtggttgcgc 1260
cgcccaacga gtccacctat agttaantcc accaacaccc ccaccttttc ctccccgccg 1320
catcttcccc acgtacccc ttttgtcgcg agatggccac tccccccccc ctgtttgttt 1380
aaaacaacga gaatggtgct gccaacgctg gtcttttccc cccccggacc gcgaccgcca 1440
gggggaatac gtaccataag cccccgcgcc cncctttttt ccccccctccc cgccaatcaa 1500 gatccgccgt ccattagacg tattattttt cccgcgatac acgaaaaaac agggccgccc 1560
atttataact aaattcccgt cgccgccgcg cggatatgtt tcccaaaata ccaccccccc 1620
ccccccattt tctttgcccc caactcctgc gcaccggtgt tcaccagcct cgcgccgc 1678

<210> SEQ ID NO 139
<211> LENGTH: 1611
<212> TYPE: DNA
<213> ORGANISM: Homo sapiens

<400> SEQUENCE: 139
ggacgcgtgg gtcgacccac gcgtccggac ccacgcgtcc ggtcgtgttc tccgagttcc 60
tgtctctctg ccaacgccgc ccggatggct tcccaaaacc gcgacccagc cgccactagc 120
gtcgccgccg cccgtaaagg agctgagccg agcgggggcg ccgcccgggg tccggtgggc 180
aaaaggctac agcaggagct gatgaccctc atggtgagtg attaagtgcc cagaacccca 240
gccttccatc caattttcag tagcctcctt ttttccgtca gctttttttgc tagacatagg 300 ggtaatgtaa tttgctccct cctgggaaag aagttcatac accccaccta caccatttct 360
tccagcagtc cctcctccca attccatccc cccacacgaa gttatctcga acacttccct 420
gaagtcatac aagaccctcc ctatccagtg tgtccctact tcctagcccc aaccaagctt 480
tacccacacc caactccccg cccttcttgg tatttctagc ctatgaattt ggttgcttta 540
ttttggatca gagtgatgag attaagggga ggctgggcgc ggtagctcac accttataat 600
cccaaagtgc tgggattaca ggcgtgagcc accgcgcccg gccagcaact aatattctaa 660
ttgaactaaa gcacaggatg ccaatttaca atccttagac caaagagtca ctgatgtctc 720
caccagataa gaggaaagca tcaggctagg catagtggct cacacctgta atctcagcac 780
tttgggaggc tgaggcaggc agatcacatg agcccaggag tttgagactg gcctgggcaa 840
catggtgaaa ccctgtctct aaaataaaaa ctaaactaaa aaaacttttt aaaaaggcag 900
tggggagcat cagaaccagc tcaacagttt gtctactgtc cggtcccaga gaaactcaag 960
attctagcaa gcccctttgtg tggggcttgg gttgggacat gaggctgctg ctggagctta 1020
ctctgcaact gtttctccaa atgccaggta tatgaagacc tgaggtataa gctctcgcta 1080

-continued

```
gagttcccca gtggctaccc ttacaatgcg cccacagtga agttcctcac gccctgctat   1140

caccccaacg tggacaccca gggtaacata tgcctggaca tcctgaagga aaagtggtct   1200

gccctgtatg atgtcaggac cattctgctc tccatccaga gccttctagg agaacccaac   1260

attgatagtc ccttgaacac acatgctgcc gagctctgga aaaaccccac agcttttaag   1320

aagtacctgc aagaaaccta ctcaaagcag gtcaccagcc aggagccctg acccaggctg   1380

cccagcctgt ccttgtgtcg tctttttaat ttttccttag atggtctgtc ctttttgtga   1440

tttctgtata ggactcttta tcttgagctg tggtattttt gttttgtttt tgtcttttaa   1500

attaagcctc ggttgagccc ttgtatatta aataaatgca tttttgtcct tttttaaaaa   1560

aaaaataaaa aaaaaaaaaa aaaaaaaaaa aaaaaaaaaa aaaaaaaaaa a            1611
```

METHODS OF TREATING BREAST CANCER WITH ANTHRACYCLINE THERAPY

CROSS-REFERENCE TO RELATED APPLICATIONS

This application claims the benefit of U.S. Provisional Application No. 61/453,035, filed Mar. 15, 2011, the contents of which are incorporated herein by reference in its entirety.

INCORPORATION-BY-REFERENCE OF SEQUENCE LISTING

The contents of the text file named "40448-510001US_ST25.txt", which was created on May 15, 2012 and is 241 KB in size, is hereby incorporated by reference in their entirety.

FIELD OF THE INVENTION

This disclosure relates generally to the field of cancer biology, and specifically, to the fields of detection and identification of specific cancer cell phenotypes and correlation with appropriate therapies.

BACKGROUND OF THE INVENTION

Anthracycline therapy has proven to be effective against many types of tumors. However, the side effects associated with anthracycline therapy, including cardiotoxicity, secondary leukemia and vomiting are severe. Alternative therapies with less severe side effects are known. Thus, there is a need in the art to determine types of cancer that respond best to anthracycline based therapy and which types of cancer would be better to treat with non-anthracycline based therapy. The present invention addresses these needs.

SUMMARY OF THE INVENTION

The present invention provides a method of treating breast cancer in a subject in need thereof. This method includes the steps of providing a biological sample from the subject; assaying the biological sample to determine whether the biological sample is classified as a Her2+ subtype; assaying the biological sample to determine whether the biological sample is classified as a Her-2-E subtype; and administering a breast cancer treatment to the subject. If the biological sample is classified as both a Her2+ subtype and a Her-2-E subtype, the subject is administered a breast cancer treatment including anthracycline. If the biological sample is not both a Her2+ subtype and a Her-2-E subtype, the subject is administered a breast cancer treatment without anthracycline.

The assaying of the biological sample to determine whether the biological sample is classified as a Her2+ subtype is performed using fluorescence in situ hybridization (FISH) or immunohistochemistry (IHC). The assaying the biological sample to determine whether the biological sample is classified as a Her-2-E subtype is performed by detecting at least 10, at least 15, at least 20, at least 25 or all 50 of the intrinsic genes listed in Table 1. Preferably, detection is of all 50 of the intrinsic genes listed in Table 1. The expression of the members of the intrinsic gene list of Table 1 can be determined using the nanoreporter code system (nCounter® Analysis system).

The anthracycline is selected from the group consisting of daunorubicin, doxorubicin, epirubicin, idarubicin, valrubicin and mitoxantrone. Preferably, the anthracycline is epirubicin.

The breast cancer treatment that includes anthracycline can also include cyclophosphamide, fluorouracil (or 5-fluorouracil or 5-FU), methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb or bevacizumab, or combinations thereof. Preferably, the treatment that includes anthracyclines also includes one or more anti-cancer agents of the group consisting of cyclophosphamide and/or 5-fluorouracil. The breast cancer treatment not comprising an anthracycline includes cyclophosphamide, fluorouracil (or 5-fluorouracil or 5-FU), methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb or bevacizumab, or combinations thereof. Preferably, the treatment that does not include anthracycline includes one or more anti-cancer agents of the group consisting of cyclophosphamide, 5-fluorouracil and methotrexate.

The biological sample can be a cell, a tissue or a bodily fluid. The tissue can be sampled from a biopsy or smear. The sample can also be a sampling of bodily fluids. These bodily fluids can include blood, lymph, urine, saliva, nipple aspirates and gynecological fluids.

The present invention also provides a method of screening for the likelihood of the effectiveness of a breast cancer treatment including an anthracycline in a subject in need thereof. This method includes the steps of providing a biological sample from the subject; assaying the biological sample to determine whether the biological sample is classified as a Her2+ subtype; and assaying the biological sample to determine whether the biological sample is classified as a Her-2-E subtype. If the biological sample is classified as both a Her2+ subtype and a Her-2-E subtype, the breast cancer treatment including the anthracycline is more likely to be effective in the subject.

The assaying of the biological sample to determine whether the biological sample is classified as a Her2+ subtype is performed using fluorescence in situ hybridization (FISH) or immunohistochemistry (IHC). The assaying the biological sample to determine whether the biological sample is classified as a Her-2-E subtype is performed by detecting at least 10, at least 15, at least 20, at least 25 or all 50 of the intrinsic genes listed in Table 1. Preferably, detection is of all 50 of the intrinsic genes listed in Table 1. The expression of the members of the intrinsic gene list of Table 1 can be determined using the nanoreporter code system (nCounter® Analysis system).

The anthracycline is selected from the group consisting of daunorubicin, doxorubicin, epirubicin, idarubicin, valrubicin and mitoxantrone. Preferably, the anthracycline is epirubicin.

The breast cancer treatment that includes anthracycline can also include cyclophosphamide, fluorouracil (or 5-fluorouracil or 5-FU), methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb or bevacizumab, or combinations thereof. Preferably, the treatment that includes anthracyclines also includes one or more anti-cancer agents of the group consisting of cyclophosphamide and/or 5-fluorouracil.

The biological sample can be a cell, a tissue or a bodily fluid. The tissues can be sampled from a tumor biopsy or surgical specimen. The sample can also be a sampling of bodily fluids. These bodily fluids can include blood, lymph, urine, saliva and nipple aspirates.

The present invention also provides a kit for screening for the likelihood of the effectiveness of a breast cancer treatment including reagents sufficient for the detection of at least 10, at least 15, at least 20, at least 25 or all 50 of the intrinsic genes and a reagent sufficient for the detection of the amount of expression of Her2. Preferably, the kit includes reagents sufficient for the detection of all 50 of the intrinsic genes listed in Table 1. The reagent sufficient for the detection of the at least 10, at least 15, at least 20, at least 25 or all 50 of the intrinsic genes listed in Table 1 can include a microarray. The reagent sufficient for the detection of the amount of expression of Her2 can be a Her2 antibody.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In the case of conflict, the present specification, including definitions, will control. In addition, the materials, methods, and examples are illustrative only and are not intended to be limiting. Other features and advantages of the invention will be apparent from the following detailed description and claim

DETAILED DESCRIPTION OF THE INVENTION

Figure 1:
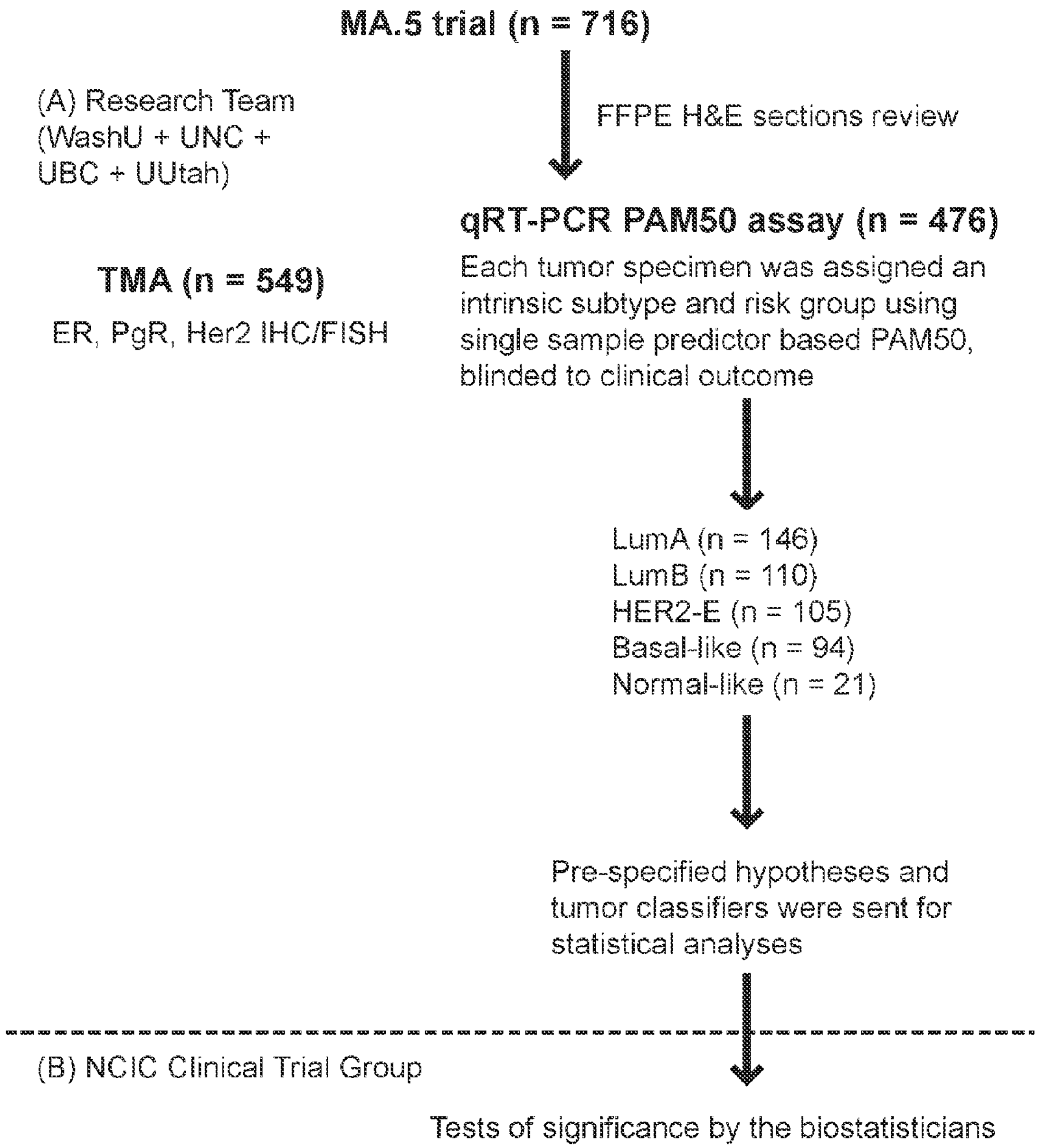
FIG. 1 is a schematic showing a REMARK Diagram of study design.

The present invention provides a method of determining whether a breast cancer treatment comprising an anthracycline is optimal for administration to a patient suffering from breast cancer. Determining whether a breast cancer patient should receive a treatment including anthracycline includes determining the subtype of the breast cancer using an intrinsic gene expression set and determining the Her2 status of the breast cancer by using fluorescence in situ hybridization analysis (FISH) or immunohistochemistry (IHC). The disclosure also provides a method of treating breast cancer by determining whether a breast cancer patient should receive a treatment including anthracycline and then administering the optimal breast cancer treatment to the patient based on that determination.

Intrinsic genes, as described in Perou et al. (2000) Nature 406:747-752, are statistically selected to have low variation in expression between biological sample replicates from the same individual and high variation in expression across samples from different individuals. Thus, intrinsic genes are used as classifier genes for breast cancer classification. Although clinical information was not used to derive the breast cancer intrinsic subtypes, this classification has proved to have prognostic significance. Intrinsic gene screening can be used to classify breast cancers into various subtypes. The major intrinsic subtypes of breast cancer are referred to as Luminal A (LumA), Luminal B (LumB), HER2-enriched (Her-2-E), Basal-like, and Normal-like (Perou et al. Nature, 406(6797):747-52 (2000); Sorlie et al. PNAS, 98(19):10869-74 (2001)).

The PAM50 gene expression assay (Parker et al. J Clin Oncol., 27(8):1160-7 (2009) and U.S. Patent Application Publication No. 2011/0145176, both incorporated herein, by reference, in their entireties) is able to identify intrinsic subtype from standard formalin fixed paraffin embedded tumor tissue. The methods utilize a supervised algorithm to classify subject samples according to breast cancer intrinsic subtype.

This algorithm, referred to herein as the PAM50 classification model, is based on the gene expression profile of a defined subset of intrinsic genes that has been identified herein as superior for classifying breast cancer intrinsic subtypes. The subset of genes, along with primers specific for their detection, is provided in Table 1.

TABLE 1

PAM50 Intrinsic Gene List

| GENE | REPRESENTATIVE GENBANK ACCESSION NUMBER | FORWARD PRIMER | SEQ ID NO: | REVERSE PRIMER | SEQ ID NO: |
|---|---|---|---|---|---|
| ACTR3B | NM_020445\| NM_001040135 | AAAGATTCCTGGG ACCTGA | 1 | TGGGGCAGTTCTGTA TTACTTC | 51 |
| ANLN | NM_018685 | ACAGCCACTTTCA GAAGCAAG | 2 | CGATGGTTTTGTACA AGATTTCTC | 52 |
| BAG1 | NM_004323 | CTGGAAGAGTTGA ATAAAGAGC | 3 | GCAAATCCTTGGGCA GA | 53 |
| BCL2 | NM_000633 | TACCTGAACCGGC ACCTG | 4 | GCCGTACAGTTCCAC AAAGG | 54 |
| BIRC5 | NM_001012271 | GCACAAAGCCATT CTAAGTC | 5 | GACGCTTCCTATCAC TCTATTC | 55 |
| BLVRA | BX647539 | GCTGGCTGAGCAG AAAG | 6 | TTCCTCCATCAAGAG TTCAACA | 56 |
| CCNB1 | NM_031966 | CTTTCGCCTGAGCC TATTT | 7 | GGGCACATCCAGAT GTTT | 57 |
| CCNE1 | BC035498 | GGCCAAAATCGAC AGGAC | 8 | GGGTCTGCACAGACT GCAT | 58 |
| CDC20 | BG256659 | CTGTCTGAGTGCC GTGGAT | 9 | TCCTTGTAATGGGGA GACCA | 59 |
| CDC6 | NM_001254 | GTAAATCACCTTCT GAGCCT | 10 | ACTTGGGATATGTGA ATAAGACC | 60 |
| CDCA1 | NM_031423 | GGAGGCGGAAGAA ACCAG | 11 | GGGGAAAGACAAAG TTTCCA | 61 |
| CDH3 | BC041846 | GACAAGGAGAATC AAAAGATCAGC | 12 | ACTGTCTGGGTCCAT GGCTA | 62 |
| CENPF | NM_016343 | GTGGCAGCAGATC ACAA | 13 | GGATTTCGTGGTGGG TTC | 63 |
| CEP55 | AB091343 | CCTCACGAATTGCT GAACTT | 14 | CCACAGTCTGTGATA AACGG | 64 |
| CXXC5 | BC006428 | CATGAAATAGTGC ATAGTTTGCC | 15 | CCATCAACATTCTCT TTATGAACG | 65 |
| EGFR | NM_005228 | ACACAGAATCTAT ACCCACCAGAGT | 16 | ATCAACTCCCAAACG GTCAC | 66 |
| ERBB2 | NM_001005862 | GCTGGCTCTCACA CTGATAG | 17 | GCCCTTACACATCGG AGAAC | 67 |
| ESR1 | NM_001122742 | GCAGGGAGAGGAG TTTGT | 18 | GACTTCAGGGTGCTG GAC | 68 |
| EXO1 | NM_130398 | CCCATCCATGTGA GGAAGTATAA | 19 | TGTGAAGCCAGCAA TATGTATC | 69 |
| FGFR4 | AB209631 | CTTCTTGGACCTTG GCG | 20 | TATTGGGAGGCAGG AGGTTTA | 70 |
| FOXA1 | NM_004496 | GCTACTACGCAGA CACG | 21 | CTGAGTTCATGTTGC TGACC | 71 |

TABLE 1-continued

PAM50 Intrinsic Gene List

| GENE | REPRESENTATIVE GENBANK ACCESSION NUMBER | FORWARD PRIMER | SEQ ID NO: | REVERSE PRIMER | SEQ ID NO: |
|---|---|---|---|---|---|
| FOXC1 | NM_001453 | GATGTTCGAGTCACAGAGG | 22 | GACAGCTACTATTCCCGTT | 72 |
| GPR160 | AJ249248 | TTCGGCTGGAAGGAACC | 23 | TATGTGAGTAAGCTCGGAGAC | 73 |
| GRB7 | NM_005310 | CGTGGCAGATGTGAACGA | 24 | AGTGGGCATCCCGTAGA | 74 |
| HSPC150 (UBE2T) | NM_014176 | GGAGATCCGTCAACTCCAAA | 25 | AGTGGACATGCGAGTGGAG | 75 |
| KIF2C | NM_006845 | TGGGTCGTGTCAGGAAAC | 26 | CACCGCTGGAAACTGAAC | 76 |
| KNTC2 | NM_006101 | CGCAGTCATCCAGAGATGTG | 27 | CGTGCACATCCATGACCTT | 77 |
| KRT14 | BC042437 | ACTCAGTACAAGAAAGAACCG | 28 | GAGGAGATGACCTTGCC | 78 |
| KRT17 | AK095281 | GTTGGACCAGTCAACATCTCTG | 29 | GCCATAGCCACTGCCACT | 79 |
| KRT5 | M21389 | TGTGGCTCATTAGGCAAC | 30 | CTTCGACTGGACTCTGT | 80 |
| MAPT | NM_001123066 | GACTCCAAGCGCGAAAAC | 31 | CAGACATGTTGGTATTGCACATT | 81 |
| MDM2 | M92424 | CCAACAAAATATTCATGGTTCTTG | 32 | AGGCGATCCTGGGAAATTAT | 82 |
| MELK | NM_014791 | CCAGTAGCATTGTCCGAG | 33 | CCCATTTGTCTGTCTTCAC | 83 |
| MIA | BG765502 | GTCTCTGGTAATGCACACT | 34 | CTGATGGTTGAGGCTGTT | 84 |
| MKI67 | NM_002417 | GTGGAATGCCTGCTGACC | 35 | CGCACTCCAGCACCTAGAC | 85 |
| MLPH | NM_024101 | AGGGGTGCCCTCTGAGAT | 36 | TCACAGGGTCAAACTTCCAGT | 86 |
| MMP11 | NM_005940 | CGAGATCGCCAAGATGTT | 37 | GATGGTAGAGTTCCAGTGATT | 87 |
| MYBL2 | BX647151 | AGGCGAACACACAACGTC | 38 | TCTGGTCACGCAGGGCAA | 88 |
| MYC | NM_002467 | AGCCTCGAACAATTGAAGA | 39 | ACACAGATGATGGAGATGTC | 89 |
| NAT1 | BC013732 | ATCGACTGTGTAAACAACTAGAGAAGA | 40 | AGTAGCTACATCTCCAGGTTCTCTG | 90 |
| ORC6L | NM_014321 | TTTAAGAGGGCAATGGAAGG | 41 | CGGATTTTATCAACGATGCAG | 91 |
| PGR | NM_000926 | TGCCGCAGAACTCACTTG | 42 | CATTTGCCGTCCTTCATCG | 92 |
| PHGDH | AK093306 | CCTCAGATGATGCCTATCCA | 43 | GCAGGTCAAAACTCTCAAAG | 93 |
| PTTG1 | BE904476 | CAGCAAGCGATGGCATAGT | 44 | AGCGGGCTTCTGTAATCTGA | 94 |
| RRM2 | AK123010 | AATGCCACCGAAGCCTC | 45 | GCCTCAGATTTCAACTCGT | 95 |

TABLE 1-continued

PAM50 Intrinsic Gene List

| GENE | REPRESENTATIVE GENBANK ACCESSION NUMBER | FORWARD PRIMER | SEQ ID NO: | REVERSE PRIMER | SEQ ID NO: |
|---|---|---|---|---|---|
| SFRP1 | BC036503 | TCGAACTGAAGGC TATTTACGAG | 46 | CTGCTGAGAATCAA AGTGGGA | 96 |
| SLC39A6 | NM_012319 | GTCGAAGCCGCAA TTAGG | 47 | GGAACAAACTGCTCT GCCA | 97 |
| TMEM45B | AK098106 | CAAACGTGTGTTCT GGAAGG | 48 | ACAGCTCTTTAGCAT TTGTGGA | 98 |
| TYMS | BQ056428 | TGCCCTGTATGATG TCAGGA | 49 | GGGACTATCAATGTT GGGTTCTC | 99 |
| UBE2C | BC032677 | GTGAGGGGTGTCA GCTCAGT | 50 | CACACAGTTCACTGC TCCACA | 100 |

Table 2 provides select sequences for the PAM50 genes of Table 1.

TABLE 2

| GENBANK ACCESSION NUMBER | SEQUENCE | SEQ ID NO: |
|---|---|---|
| NM_020445 | CAGCGGCGCTGCGGCGGCTCGCGGGAGACGCTGCGCGCGGGGCTAGCGGGCGGCGGAGCGGACGGCGACG<br>GGGCGCTCTCGGGCTGCCGGCGGGGCCGAGCGCCGCGCGTCCCGAGCATGGCAGGCTCCCTGCCTCCCTG<br>CGTGGTGGACTGTGGCACCGGGTATACCAAGCTTGGCTACGCAGGCAACACTGAGCCCCAGTTCATTATT<br>CCTTCATGTATTGCCATCAGAGAGTCAGCAAAGGTAGTTGACCAAGCTCAAAGGAGAGTGTTGAGGGGAG<br>TTGATGACCTTGACTTTTTCATAGGAGATGAAGCCATCGATAAACCTACATATGCTACAAAGTGGCCGAT<br>ACGACATGGAATCATTGAAGACTGGGATCTTATGGAAAGGTTCATGGAGCAAGTGGTTTTTAAATATCTT<br>CGAGCTGAACCTGAGGACCATTATTTTTTAATGACAGAACCTCCACTCAATACACCAGAAAACAGAGAGT<br>ATCTTGCAGAAATTATGTTTGAATCATTTAACGTACCAGGACTCTACATTGCAGTTCAGGCAGTGCTGGC<br>CTTGGCGGCATCTTGGACATCTCGACAAGTGGGTGAACGTACGTTAACGGGGATAGTCATTGACAGCGGA<br>GATGGAGTCACCCATGTTATCCCAGTGGCAGAAGGTTATGTAATTGGAAGCTGCATCAAACACATCCCGA<br>TTGCAGGTAGAGATATTACGTATTTCATTCAACAGCTGCTAAGGGAGAGGGAGGTGGGAATCCCTCCTGA<br>GCAGTCACTGGAGACCGCAAAAGCCATTAAGGAGAAATACTGTTACATTTGCCCCGATATAGTCAAGGAA<br>TTTGCCAAGTATGATGTGGATCCCCGGAAGTGGATCAAACAGTACACGGGTATCAATGCGATCAACCAGA<br>AGAAGTTTGTTATAGACGTTGGTTACGAAAGATTCCTGGGACCTGAAATATTCTTTCACCCGGAGTTTGC<br>CAACCCAGACTTTATGGAGTCCATCTCAGATGTTGTTGATGAAGTAATACAGAACTGCCCCATCGATGTG<br>CGGCGCCCGCTGTATAAGAATGTCGTACTCTCAGGAGGCTCCACCATGTTCAGGGATTTCGGACGCCGAC<br>TGCAGAGGGATTTGAAGAGAGTGGTGGATGCTAGGCTGAGGCTCAGCGAGGAGCTCAGCGGCGGGAGGAT<br>CAAGCCGAAGCCTGTGGAGGTCCAGGTGGTCACGCATCACATGCAGCGCTACGCCGTGTGGTTCGGAGGC<br>TCCATGCTGGCCTCGACTCCCGAGTTCTTTCAGGTCTGCCACACCAAGAAGGACTATGAAGAGTACGGGC<br>CCAGCATCTGCCGCCACAACCCCGTCTTTGGAGTCATGTCCTAGTGTCTGCCTGAACGCGTCGTTCGATG<br>GTGTCACGTTGGGGAACAAGTGTCCTTCAGAACCCAGAGAAGGCCGCCGTTCTGTAAATAGCGACGTCGG<br>TGTTGCTGCCCAGCAGCGTGCTTGCATTGCCGGTGCATGAGGCGCGGCGCGGGCCCTTCAGTAAAAGCCA<br>TTTATCCGTGTGCCGACCGCTGTCTGCCAGCCTCCTCCTTCTCCCGCCCTCCTCACCCTCGCTCTCCCTC<br>CTCCTCCTCCTCCGAGCTGCTAGCTGACAAATACAATTCTGAAGGAATCCAAATGTGACTTTGAAAATTG<br>TTAGAGAAAACAACATTAGAAAATGGCGCAAAATCGTTAGGTCCCAGGAGAGAATGTGGGGGCGCAAACC<br>CTTTTCCTCCCAGCCTATTTTTGTAAATAAAATGTTTAAACTTGAAATACAAATCGATGTTTATATTTCC<br>TATCATTTTGTATTTTATGGTATTTGGTACAACTGGCTGATACTAAGCACGAATAGATATTGATGTTATG<br>GAGTGCTGTAATCCAAAGTTTTTAATTGTGAGGCATGTTCTGATATGTTTATAGGCAAACAAATAAAACA<br>GCAAACTTTTTTGCCACATGTTTGCTAGAAAATGATTATACTTTATTGGAGTGACATGAAGTTTGAACAC<br>TAAACAGTAATGTATGAGAATTACTACAGATACATGTATCTTTTAGTTTTTTTTGTTTGAACTTTCTGGA<br>GCTGTTTTATAGAAGATGATGGTTTGTTGTCGGTGAGTGTTGGATGAAATACTTCCTTGCACCATTGTAA<br>TAAAAGCTGTTAGAATATTTGTAAATATC | 101 |
| NM_001040135 | CAGCGGCGCTGCGGCGGCTCGCGGGAGACGCTGCGCGCGGGGCTAGCGGGCGGCGGAGCGGACGGCGACG<br>GGGCGCTCTCGGGCTGCCGGCGGGGCCGAGCGCCGCGCGTCCCGAGCATGGCAGGCTCCCTGCCTCCCTG<br>CGTGGTGGACTGTGGCACCGGGTATACCAAGCTTGGCTACGCAGGCAACACTGAGCCCCAGTTCATTATT<br>CCTTCATGTATTGCCATCAGAGAGTCAGCAAAGGTAGTTGACCAAGCTCAAAGGAGAGTGTTGAGGGGAG<br>TTGATGACCTTGACTTTTTCATAGGAGATGAAGCCATCGATAAACCTACATATGCTACAAAGTGGCCGAT<br>ACGACATGGAATCATTGAAGACTGGGATCTTATGGAAAGGTTCATGGAGCAAGTGGTTTTTAAATATCTT<br>CGAGCTGAACCTGAGGACCATTATTTTTTAATGACAGAACCTCCACTCAATACACCAGAAAACAGAGAGT<br>ATCTTGCAGAAATTATGTTTGAATCATTTAACGTACCAGGACTCTACATTGCAGTTCAGGCAGTGCTGGC<br>CTTGGCGGCATCTTGGACATCTCGACAAGTGGGTGAACGTACGTTAACGGGGATAGTCATTGACAGCGGA<br>GATGGAGTCACCCATGTTATCCCAGTGGCAGAAGGTTATGTAATTGGAAGCTGCATCAAACACATCCCGA<br>TTGCAGGTAGAGATATTACGTATTTCATTCAACAGCTGCTAAGGGAGAGGGAGGTGGGAATCCCTCCTGA<br>GCAGTCACTGGAGACCGCAAAAGCCATTAAGGAGAAATACTGTTACATTTGCCCCGATATAGTCAAGGAA<br>TTTGCCAAGTATGATGTGGATCCCCGGAAGTGGATCAAACAGTACACGGGTATCAATGCGATCAACCAGA | 102 |

TABLE 2-continued

| GENBANK ACCESSION NUMBER | SEQUENCE | SEQ ID NO: |
|---|---|---|
| | AGAAGTTTGTTATAGACGTTGGTTACGAAAGATTCCTGGGACCTGAAATATTCTTTCACCCGGAGTTTGC<br>CAACCCAGACTTTATGGAGTCCATCTCAGATGTTGTTGATGAAGTAATACAGAACTGCCCCATCGATGTG<br>CGGCGCCCGCTGTATAAGCCCGAGTTCTTTCAGGTCTGCCACACCAAGAAGGACTATGAAGAGTACGGGC<br>CCAGCATCTGCCGCCACAACCCCGTCTTTGGAGTCATGTCCTAGTGTCTGCCTGAACGCGTCGTTCGATG<br>GTGTCACGTTGGGGAACAAGTGTCCTTCAGAACCCAGAGAAGGCCGCCGTTCTGTAAATAGCGACGTCGG<br>TGTTGCTGCCCAGCAGCGTGCTTGCATTGCCGGTGCATGAGGCGCGGCGCGGGCCCTTCAGTAAAAGCCA<br>TTTATCCGTGTGCCGACCGCTGTCTGCCAGCCTCCTCCTTCTCCCGCCCTCCTCACCCTCGCTCTCCCTC<br>CTCCTCCTCCTCCGAGCTGCTAGCTGACAAATACAATTCTGAAGGAATCCAAATGTGACTTTGAAAATTG<br>TTAGAGAAAACAACATTAGAAAATGGCGCAAAATCGTTAGGTCCCAGGAGAGAATGTGGGGGCGCAAACC<br>CTTTTCCTCCCAGCCTATTTTTGTAAATAAAATGTTTAAACTTGAAATACAAATCGATGTTTATATTTCC<br>TATCATTTTGTATTTTATGGTATTTGGTACAACTGGCTGATACTAAGCACGAATAGATATTGATGTTATG<br>GAGTGCTGTAATCCAAAGTTTTTAATTGTGAGGCATGTTCTGATATGTTTATAGGCAAACAAATAAAACA<br>GCAAACTTTTTTGCCACATGTTTGCTAGAAAATGATTATACTTTATTGGAGTGACATGAAGTTTGAACAC<br>TAAACAGTAATGTATGAGAATTACTACAGATACATGTATCTTTTAGTTTTTTTTGTTTGAACTTTCTGGA<br>GCTGTTTTATAGAAGATGATGGTTTGTTGTCGGTGAGTGTTGGATGAAATACTTCCTTGCACCATTGTAA<br>TAAAAGCTGTTAGAATATTTGTAAATATC | |
| NM_018685 | CTCGGCGCTGAAATTCAAATTTGAACGGCTGCAGAGGCCGAGTCCGTCACTGGAAGCCGAGAGGAGAGGA<br>CAGCTGGTTGTGGGAGAGTTCCCCCGCCTCAGACTCCTGGTTTTTTCCAGGAGACACACTGAGCTGAGAC<br>TCACTTTTCTCTTCCTGAATTTGAACCACCGTTTCCATCGTCTCGTAGTCCGACGCCTGGGGCGATGGAT<br>CCGTTTACGGAGAAACTGCTGGAGCGAACCCGTGCCAGGCGAGAGAATCTTCAGAGAAAAATGGCTGAGA<br>GGCCCACAGCAGCTCCAAGGTCTATGACTCATGCTAAGCGAGCTAGACAGCCACTTTCAGAAGCAAGTAA<br>CCAGCAGCCCCTCTCTGGTGGTGAAGAGAAATCTTGTACAAAACCATCGCCATCAAAAAAACGCTGTTCT<br>GACAACACTGAAGTAGAAGTTTCTAACTTGGAAAATAAACAACCAGTTGAGTCGACATCTGCAAAATCTT<br>GTTCTCCAAGTCCTGTGTCTCCTCAGGTGCAGCCACAAGCAGCAGATACCATCAGTGATTCTGTTGCTGT<br>CCCGGCATCACTGCTGGGCATGAGGAGAGGGCTGAACTCAAGATTGGAAGCAACTGCAGCCTCCTCAGTT<br>AAAACACGTATGCAAAAACTTGCAGAGCAACGGCGCCGTTGGGATAATGATGATATGACAGATGACATTC<br>CTGAAAGCTCACTCTTCTCACCAATGCCATCAGAGGAAAAGGCTGCTTCCCCTCCCAGACCTCTGCTTTC<br>AAATGCCTCGGCAACTCCAGTTGGCAGAAGGGGCCGTCTGGCCAATCTTGCTGCAACTATTTGCTCCTGG<br>GAAGATGATGTAAATCACTCATTTGCAAAACAAAACAGTGTACAAGAACAGCCTGGTACCGCTTGTTTAT<br>CCAAATTTTCCTCTGCAAGTGGAGCATCTGCTAGGATCAATAGCAGCAGTGTTAAGCAGGAAGCTACATT<br>CTGTTCCCAAAGGGATGGCGATGCCTCTTTGAATAAAGCCCTATCCTCAAGTGCTGATGATGCGTCTTTG<br>GTTAATGCCTCAATTTCCAGCTCTGTGAAAGCTACTTCTCCAGTGAAATCTACTACATCTATCACTGATG<br>CTAAAAGTTGTGAGGGACAAAATCCTGAGCTACTTCCAAAAACTCCTATTAGTCCTCTGAAAACGGGGGT<br>ATCGAAACCAATTGTGAAGTCAACTTTATCCCAGACAGTTCCATCCAAGGGAGAATTAAGTAGAGAAATT<br>TGTCTGCAATCTCAATCTAAAGACAAATCTACGACACCAGGAGGAACAGGAATTAAGCCTTTCCTGGAAC<br>GCTTTGGAGAGCGTTGTCAAGAACATAGCAAAGAAAGTCCAGCTCGTAGCACACCCCACAGAACCCCCAT<br>TATTACTCCAAATACAAAGGCCATCCAAGAAAGATTATTCAAGCAAGACACATCTTCATCTACTACCCAT<br>TTAGCACAACAGCTCAAGCAGGAACGTCAAAAAGAACTAGCATGTCTTCGTGGCCGATTTGACAAGGGCA<br>ATATATGGAGTGCAGAAAAAGGCGGAAACTCAAAAAGCAAACAACTAGAAACCAAACAGGAAACTCACTG<br>TCAGAGCACTCCCCTCAAAAAACACCAAGGTGTTTCAAAAACTCAGTCACTTCCAGTAACAGAAAAGGTG<br>ACCGAAAACCAGATACCAGCCAAAAATTCTAGTACAGAACCTAAAGGTTTCACTGAATGCGAAATGACGA<br>AATCTAGCCCTTTGAAAATAACATTGTTTTTAGAAGAGGACAAATCCTTAAAAGTAACATCAGACCCAAA<br>GGTTGAGCAGAAAATTGAAGTGATACGTGAAATTGAGATGAGTGTGGATGATGATGATATCAATAGTTCG<br>AAAGTAATTAATGACCTCTTCAGTGATGTCCTAGAGGAAGGTGAACTAGATATGGAGAAGAGCCAAGAGG<br>AGATGGATCAAGCATTAGCAGAAAGCAGCGAAGAACAGGAAGATGCACTGAATATCTCCTCAATGTCTTT<br>ACTTGCACCATTGGCACAAACAGTTGGTGTGGTAAGTCCAGAGAGTTTAGTGTCCACACCTAGACTGGAA<br>TTGAAAGACACCAGCAGAAGTGATGAAAGTCCAAAACCAGGAAAATTCCAAAGAACTCGTGTCCCTCGAG<br>CTGAATCTGGTGATAGCCTTGGTTCTGAAGATCGTGATCTTCTTTACAGCATTGATGCATATAGATCTCA<br>AAGATTCAAAGAAACAGAACGTCCATCAATAAAGCAGGTGATTGTTCGGAAGGAAGATGTTACTTCAAAA<br>CTGGATGAAAAAAATAATGCCTTTCCTTGTCAAGTTAATATCAAACAGAAAATGCAGGAACTCAATAACG<br>AAATAAATATGCAACAGACAGTGATCTATCAAGCTAGCCAGGCTCTTAACTGCTGTGTTGATGAAGAACA<br>TGGAAAAGGGTCCCTAGAAGAAGCTGAAGCAGAAAGACTTCTTCTAATTGCAACTGGGAAGAGAACACTT<br>TTGATTGATGAATTGAATAAATTGAAGAACGAAGGACCTCAGAGGAAGAATAAGGCTAGTCCCCAAAGTG<br>AATTTATGCCATCCAAAGGATCAGTTACTTTGTCAGAAATCCGCTTGCCTCTAAAAGCAGATTTTGTCTG<br>CAGTACGGTTCAGAAACCAGATGCAGCAAATTACTATTACTTAATTATACTAAAAGCAGGAGCTGAAAAT<br>ATGGTAGCCACACCATTAGCAAGTACTTCAAACTCTCTTAACGGTGATGCTCTGACATTCACTACTACAT<br>TTACTCTGCAAGATGTATCCAATGACTTTGAAATAAATATTGAAGTTTACAGCTTGGTGCAAAAGAAAGA<br>TCCCTCAGGCCTTGATAAGAAGAAAAAAACATCCAAGTCCAAGGCTATTACTCCAAAGCGACTCCTCACA<br>TCTATAACCACAAAAAGCAACATTCATTCTTCAGTCATGGCCAGTCCAGGAGGTCTTAGTGCTGTGCGAA<br>CCAGCAACTTCGCCCTTGTTGGATCTTACACATTATCATTGTCTTCAGTAGGAAATACTAAGTTTGTTCT<br>GGACAAGGTCCCCTTTTTATCTTCTTTGGAAGGTCATATTTATTTAAAAATAAAATGTCAAGTGAATTCC<br>AGTGTTGAAGAAAGAGGTTTTCTAACCATATTTGAAGATGTTAGTGGTTTTGGTGCCTGGCATCGAAGAT<br>GGTGTGTTCTTTCTGGAAACTGTATATCTTATTGGACTTATCCAGATGATGAGAAACGCAAGAATCCCAT<br>AGGAAGGATAAATCTGGCTAATTGTACCAGTCGTCAGATAGAACCAGCCAACAGAGAATTTTGTGCAAGA<br>CGCAACACTTTTGAATTAATTACTGTCCGACCACAAAGAGAAGATGACCGAGAGACTCTTGTCAGCCAAT<br>GCAGGGACACACTCTGTGTTACCAAGAACTGGCTGTCTGCAGATACTAAAGAAGAGCGGGATCTCTGGAT<br>GCAAAAACTCAATCAAGTTCTTGTTGATATTCGCCTCTGGCAACCTGATGCTTGCTACAAACCTATTGGA<br>AAGCCTTAAACCGGGAAATTTCCATGCTATCTAGAGGTTTTTGATGTCATCTTAAGAAACACACTTAAGA<br>GCATCAGATTTACTGATTGCATTTTATGCTTTAAGTACGAAAGGGTTTGTGCCAATATTCACTACGTATT<br>ATGCAGTATTTATATCTTTTGTATGTAAAACTTTAACTGATTTCTGTCATTCATCAATGAGTAGAAGTAA<br>ATACATTATAGTTGATTTTGCTAAATCTTAATTTAAAAGCCTCATTTTCCTAGAAATCTAATTATTCAGT<br>TATTCATGACAATATTTTTTTAAAAGTAAGAAATTCTGAGTTGTCTTCTTGGAGCTGTAGGTCTTGAAGC<br>AGCAACGTCTTTCAGGGGTTGGAGACAGAAACCCATTCTCCAATCTCAGTAGTTTTTTCGAAAGGCTGTG<br>ATCATTTATTGATCGTGATATGACTTGTTACTAGGGTACTGAAAAAAATGTCTAAGGCCTTTACAGAAAC<br>ATTTTTAGTAATGAGGATGAGAACTTTTTCAAATAGCAAATATATATTGGCTTAAAGCATGAGGCTGTCT | 103 |

TABLE 2-continued

| GENBANK ACCESSION NUMBER | SEQUENCE | SEQ ID NO: |
|---|---|---|
| | TCAGAAAAGTGATGTGGACATAGGAGGCAATGTGTGAGACTTGGGGGTTCAATATTTTATATAGAAGAGT<br>TAATAAGCACATGGTTTACATTTACTCAGCTACTATATATGCAGTGTGGTGCACATTTTCACAGAATTCT<br>GGCTTCATTAAGATCATTATTTTTGCTGCGTAGCTTACAGACTTAGCATATTAGTTTTTTCTACTCCTAC<br>AAGTGTAAATTGAAAAATCTTTATATTAAAAAAGTAAACTGTTATGAAGCTGCTATGTACTAATAATACT<br>TTGCTTGCCAAAGTGTTTGGGTTTTGTTGTTGTTTGTTTGTTTGTTTGTTTTTGGTTCATGAACAACAGT<br>GTCTAGAAACCCATTTTGAAAGTGGAAAATTATTAAGTCACCTATCACCTTTAAACGCCTTTTTTTAAAA<br>TTATAAAATATTGTAAAGCAGGGTCTCAACTTTTAAATACACTTTGAACTTCTTCTCTGAATTATTAAAG<br>TTCTTTATGACCTCATTTATAAACACTAAATTCTGTCACCTCCTGTCATTTTATTTTTTATTCATTCAAA<br>TGTATTTTTTCTTGTGCATATTATAAAAATATATTTTATGAGCTCTTACTCAAATAAATACCTGTAAATG<br>TCTAAAGGAAAAAAAAAAAAAAAAAA | |
| NM_004323 | AGGCCGGGGCGGGGCTGGGAAGTAGTCGGGCGGGGTTGTGAGACGCCGCGCTCAGCTTCCATCGCTGGGC<br>GGTCAACAAGTGCGGGCCTGGCTCAGCGCGGGGGGGCGCGGAGACCGCGAGGCGACCGGGAGCGGCTGGG<br>TTCCCGGCTGCGCGCCCTTCGGCCAGGCCGGGAGCCGCGCCAGTCGGAGCCCCCGGCCCAGCGTGGTCCG<br>CCTCCCTCTCGGCGTCCACCTGCCCGGAGTACTGCCAGCGGGCATGACCGACCCACCAGGGGCGCCGCCG<br>CCGGCGCTCGCAGGCCGCGGATGAAGAAGAAAACCCGGCGCCGCTCGACCCGGAGCGAGGAGTTGACCCG<br>GAGCGAGGAGTTGACCCTGAGTGAGGAAGCGACCTGGAGTGAAGAGGCGACCCAGAGTGAGGAGGCGACC<br>CAGGGCGAAGAGATGAATCGGAGCCAGGAGGTGACCCGGGACGAGGAGTCGACCCGGAGCGAGGAGGTGA<br>CCAGGGAGGAAATGGCGGCAGCTGGGCTCACCGTGACTGTCACCCACAGCAATGAGAAGCACGACCTTCA<br>TGTTACCTCCCAGCAGGGCAGCAGTGAACCAGTTGTCCAAGACCTGGCCCAGGTTGTTGAAGAGGTCATA<br>GGGGTTCCACAGTCTTTTCAGAAACTCATATTTAAGGGAAAATCTCTGAAGGAAATGGAAACACCGTTGT<br>CAGCACTTGGAATACAAGATGGTTGCCGGGTCATGTTAATTGGGAAAAAGAACAGTCCACAGGAAGAGGT<br>TGAACTAAAGAAGTTGAAACATTTGGAGAAGTCTGTGGAGAAGATAGCTGACCAGCTGGAAGAGTTGAAT<br>AAAGAGCTTACTGGAATCCAGCAGGGTTTTCTGCCCAAGGATTTGCAAGCTGAAGCTCTCTGCAAACTTG<br>ATAGGAGAGTAAAAGCCACAATAGAGCAGTTTATGAAGATCTTGGAGGAGATTGACACACTGATCCTGCC<br>AGAAAATTTCAAAGACAGTAGATTGAAAAGGAAAGGCTTGGTAAAAAAGGTTCAGGCATTCCTAGCCGAG<br>TGTGACACAGTGGAGCAGAACATCTGCCAGGAGACTGAGCGGCTGCAGTCTACAAACTTTGCCCTGGCCG<br>AGTGAGGTGTAGCAGAAAAAGGCTGTGCTGCCCTGAAGAATGGCGCCACCAGCTCTGCCGTCTCTGGAGC<br>GGAATTTACCTGATTTCTTCAGGGCTGCTGGGGGCAACTGGCCATTTGCCAATTTTCCTACTCTCACACT<br>GGTTCTCAATGAAAAATAGTGTCTTTGTGATTTTGAGTAAAGCTCCTATCTGTTTTCTCCTTCTGTCTCT<br>GTGGTTGTACTGTCCAGCAATCCACCTTTTCTGGAGAGGGCCACCTCTGCCCAAATTTTCCCAGCTGTTT<br>GGACCTCTGGGTGCTTTCTTTGGGCTGGTGAGAGCTCTAATTTGCCTTGGGCCAGTTTCAGGTTTATAGG<br>CCCCCTCAGTCTTCAGATACATGAGGGCTTCTTTGCTCTTGTGATCGTGTAGTCCCATAGCTGTAAAACC<br>AGAATCACCAGGAGGTTGCACCTAGTCAGGAATATTGGGAATGGCCTAGAACAAGGTGTTTGGCACATAA<br>GTAGACCACTTATCCCTCATTGTGACCTAATTCCAGAGCATCTGGCTGGGTTGTTGGGTTCTAGACTTTG<br>TCCTCACCTCCCAGTGACCCTGACTAGCCACAGGCCATGAGATACCAGGGGGCCGTTCCTTGGATGGAGC<br>CTGTGGTTGATGCAAGGCTTCCTTGTCCCCAAGCAAGTCTTCAGAAGGTTAGAACCCAGTGTTGACTGAG<br>TCTGTGCTTGAAACCAGGCCAGAGCCATGGATTAGGAAGGGCAAAGAGAAGGCACCAGAATGAGTAAAGC<br>AGGCAGGTGGTGAAGCCAACCATAAACTTCTCAGGAGTGACATGTGCTTCCTTCAAAGGCATTTTTGTTA<br>ACCATATCCTTCTGAGTTCTATGTTTCCTTCACAGCTGTTCTATCCATTTTGTGGACTGTCCCCCACCCC<br>CACCCCATCATTGTTTTTAAAAAATTAAGGCCTGGCGCAGCAGCTCATGCCTATAATCCCAGCACTTTGG<br>GAGGCTGAGGCGGGCGGATCACTTGAGGCCAGGAGTTTGAGACCAGCCCAGGCAACATAGCAAAACCCCA<br>TTCTGCTTTAAAAAAAAAAAAAAAAAAAAATTAGCTTGGCGTAGTGGCATGTGCCTATAATCCCAGCTACT<br>GGGGAGGCTGAGGCACAAGAATCATTTGAACCTGGGAGGTAGAGGTTGCTGTGAGCCGAGATTACGCCCC<br>TGCACTCCAGCCTGGGTCACAGAGTGAGACTCCATCTCAGAAAAAAAAAAAAATTGAGTCAGGTGCAGTAG<br>CTCCTTCCTGTAGTCCCAGCTACTTGGGAGGCTGAGGCTAGAGGATCACTTGAGCCCAGGAGTTTGAGTC<br>TAGTCTGGGCAACATAGCAAGACCCCATCTCTAAAATTTAAGTAAGTAAAAGTAGATAAATAAAAAGAAA<br>AAAAAACTGTTTATGTGCTCATCATAAAGTAGAAGAGTGGTTTGCTTTTTTTTTTTTTTTTTGGATTAATG<br>AGGAAATCATTCTGTGGCTCTAGTCATAATTTATGCTTAATAACATTGATAGTAGCCCTTTGCGCTATAA<br>CTCTACCTAAAGACTCACATCATTTGGCAGAGAGAGAGTCGTTGAAGTCCCAGGAATTCAGGACTGGGCA<br>GGTTAAGACCTCAGACAAGGTAGTAGAGGTAGACTTGTGGACAAGGCTCGGGTCCCAGCCCACCGCACCC<br>CAACTTTAATCAGAGTGGTTCACTATTGATCTATTTTTGTGTGATAGCTGTGTGGCGTGGGCCACAACAT<br>TTAATGAGAAGTTACTGTGCACCAAACTGCCGAACACCATTCTAAACTATTCATATATATTAGTCATTTA<br>ATTCTTACATAACTTGAGAGGTAGACAGATATCCTTATTTTAGAGATGAGGAAACCAAGAGAACTTAGGT<br>CATTAGCGCAAGGTTGTAGAGTAAGCGGCAAAGCCAAGACACAAAGCTGGGTGGTTTGGTTTCAGAGCCA<br>GTGCTTTTCCCCTCTACTGTACTGCCTCTCAACCAACACAGGGTTGCACAGGCCCATTCTCTGATTTTTT<br>TCCTCTTGTCCTCTGCCTCTCCCTCTAGCTCCCACTTCCTCTCTGCTCTAGTTCATTTTCTTTAGAGCAG<br>CCCGAGTGATCATGAAGTGCAAATCTTGCCATGTCAGTCCCCTGCTTAGAACCCTCCAATGGCTCACTTT<br>CTCTTTAGGCAAAAGTCTTTACCCCATGCCTTCTCCCATCTCATCTCAACCCCCCTCATTTGTTGGCTGTC<br>TGCTGTCAGCCACTCTTCTTTCAGGTCCTCAGATGCACTGCACCCTCTCCTGCCTGGGGGTCTTTGCTCC<br>TGCTACTACCTCTGCTTGAACAGCTCCTCACCTTCCTTCCTCCAACCCTACCCTTGTATAGGTGACTTTT<br>GTTCATCCTTCAGAATTCAACTCACATGTCTCTTGCATGGAGAACCCTCACCTACTGTGTTGAGACCCTG<br>TCCAGCCCCCAGGTGGGATCCTCTCTCGACTTCCCATACATTTCTTTCACAGCATTTACATAGTCCATGA<br>TAGTTTACTTGTGGGATTATTTGGTTAATCTTTGCCTTTAACACCAGGGTTCCTTGGGTGAAGGAGCTTC<br>TTTATCTTGGTAACAGCATTATTTCAAGCATAACTTGTAATATAGTTATATTACATATATAACATATATA<br>TATATAACATAACATATATAACATATATAACAAGCATAACTTGTTATATAGTCTTGTATATAGTAAGACC<br>TCAATAAATATTTGGAGAACAAAAAAAAAAAAAAA | 104 |
| NM_000633 | TTTCTGTGAAGCAGAAGTCTGGGAATCGATCTGGAAATCCTCCTAATTTTTACTCCCTCTCCCCGCGACT<br>CCTGATTCATTGGGAAGTTTCAAATCAGCTATAACTGGAGAGTGCTGAAGATTGATGGGATCGTTGCCTT<br>ATGCATTTGTTTTGGTTTTACAAAAAGGAAACTTGACAGAGGATCATGCTGTACTTAAAAAATACAACAT<br>CACAGAGGAAGTAGACTGATATTAACAATACTTACTAATAATAACGTGCCTCATGAAATAAAGATCCGAA<br>AGGAATTGGAATAAAAATTTCCTGCATCTCATGCCAAGGGGGAAACACCAGAATCAAGTGTTCCGCGTGA<br>TTGAAGACACCCCCTCGTCCAAGAATGCAAAGCACATCCAATAAAATAGCTGGATTATAACTCCTCTTCT<br>TTCTCTGGGGGCCGTGGGGTGGGAGCTGGGGCGAGAGGTGCCGTTGGCCCCCGTTGCTTTTCCTCTGGGA<br>AGGATGGCGCACGCTGGGAGAACAGGGTACGATAACCGGGAGATAGTGATGAAGTACATCCATTATAAGC | 105 |

TABLE 2-continued

| GENBANK ACCESSION NUMBER | SEQUENCE | SEQ ID NO: |
|---|---|---|
| | TGTCGCAGAGGGGCTACGAGTGGGATGCGGGAGATGTGGGCGCCGCGCCCCCGGGGGCCGCCCCCGCACC | |
| | GGGCATCTTCTCCTCCCAGCCCGGGCACACGCCCCATCCAGCCGCATCCCGGGACCCGGTCGCCAGGACC | |
| | TCGCCGCTGCAGACCCCGGCTGCCCCCGGCGCCGCCGCGGGGCCTGCGCTCAGCCCGGTGCCACCTGTGG | |
| | TCCACCTGACCCTCCGCCAGGCCGGCGACGACTTCTCCCGCCGCTACCGCCGCGACTTCGCCGAGATGTC | |
| | CAGCCAGCTGCACCTGACGCCCTTCACCGCGCGGGGACGCTTTGCCACGGTGGTGGAGGAGCTCTTCAGG | |
| | GACGGGGTGAACTGGGGGAGGATTGTGGCCTTCTTTGAGTTCGGTGGGGTCATGTGTGTGGAGAGCGTCA | |
| | ACCGGGAGATGTCGCCCCTGGTGGACAACATCGCCCTGTGGATGACTGAGTACCTGAACCGGCACCTGCA | |
| | CACCTGGATCCAGGATAACGGAGGCTGGGATGCCTTTGTGGAACTGTACGGCCCCAGCATGCGGCCTCTG | |
| | TTTGATTTCTCCTGGCTGTCTCTGAAGACTCTGCTCAGTTTGGCCCTGGTGGGAGCTTGCATCACCCTGG | |
| | GTGCCTATCTGGGCCACAAGTGAAGTCAACATGCCTGCCCCAAACAAATATGCAAAAGGTTCACTAAAGC | |
| | AGTAGAAATAATATGCATTGTCAGTGATGTACCATGAAACAAAGCTGCAGGCTGTTTAAGAAAAAATAAC | |
| | ACACATATAAACATCACACACACAGACAGACACACACACACACAACAATTAACAGTCTTCAGGCAAAACG | |
| | TCGAATCAGCTATTTACTGCCAAAGGGAAATATCATTTATTTTTTACATTATTAAGAAAAAAAGATTTAT | |
| | TTATTTAAGACAGTCCCATCAAAACTCCTGTCTTTGGAAATCCGACCACTAATTGCCAAGCACCGCTTCG | |
| | TGTGGCTCCACCTGGATGTTCTGTGCCTGTAAACATAGATTCGCTTTCCATGTTGTTGGCCGGATCACCA | |
| | TCTGAAGAGCAGACGGATGGAAAAAGGACCTGATCATTGGGGAAGCTGGCTTTCTGGCTGCTGGAGGCTG | |
| | GGGAGAAGGTGTTCATTCACTTGCATTTCTTTGCCCTGGGGGCTGTGATATTAACAGAGGGAGGGTTCCT | |
| | GTGGGGGGAAGTCCATGCCTCCCTGGCCTGAAGAAGAGACTCTTTGCATATGACTCACATGATGCATACC | |
| | TGGTGGGAGGAAAAGAGTTGGGAACTTCAGATGGACCTAGTACCCACTGAGATTTCCACGCCGAAGGACA | |
| | GCGATGGGAAAAATGCCCTTAAATCATAGGAAAGTATTTTTTTAAGCTACCAATTGTGCCGAGAAAAGCA | |
| | TTTTAGCAATTTATACAATATCATCCAGTACCTTAAGCCCTGATTGTGTATATTCATATATTTTGGATAC | |
| | GCACCCCCCAACTCCCAATACTGGCTCTGTCTGAGTAAGAAACAGAATCCTCTGGAACTTGAGGAAGTGA | |
| | ACATTTCGGTGACTTCCGCATCAGGAAGGCTAGAGTTACCCAGAGCATCAGGCCGCCACAAGTGCCTGCT | |
| | TTTAGGAGACCGAAGTCCGCAGAACCTGCCTGTGTCCCAGCTTGGAGGCCTGGTCCTGGAACTGAGCCGG | |
| | GGCCCTCACTGGCCTCCTCCAGGGATGATCAACAGGGCAGTGTGGTCTCCGAATGTCTGGAAGCTGATGG | |
| | AGCTCAGAATTCCACTGTCAAGAAAGAGCAGTAGAGGGGTGTGGCTGGGCCTGTCACCCTGGGGCCCTCC | |
| | AGGTAGGCCCGTTTTCACGTGGAGCATGGGAGCCACGACCCTTCTTAAGACATGTATCACTGTAGAGGGA | |
| | AGGAACAGAGGCCCTGGGCCCTTCCTATCAGAAGGACATGGTGAAGGCTGGGAACGTGAGGAGAGGCAAT | |
| | GGCCACGGCCCATTTTGGCTGTAGCACATGGCACGTTGGCTGTGTGGCCTTGGCCCACCTGTGAGTTTAA | |
| | AGCAAGGCTTTAAATGACTTTGGAGAGGGTCACAAATCCTAAAAGAAGCATTGAAGTGAGGTGTCATGGA | |
| | TTAATTGACCCCTGTCTATGGAATTACATGTAAAACATTATCTTGTCACTGTAGTTTGGTTTTATTTGAA | |
| | AACCTGACAAAAAAAAAGTTCCAGGTGTGGAATATGGGGGTTATCTGTACATCCTGGGGCATTAAAAAAA | |
| | AAATCAATGGTGGGGAACTATAAAGAAGTAACAAAAGAAGTGACATCTTCAGCAAATAAACTAGGAAATT | |
| | TTTTTTTCTTCCAGTTTAGAATCAGCCTTGAAACATTGATGGAATAACTCTGTGGCATTATTGCATTATA | |
| | TACCATTTATCTGTATTAACTTTGGAATGTACTCTGTTCAATGTTTAATGCTGTGGTTGATATTTCGAAA | |
| | GCTGCTTTAAAAAAATACATGCATCTCAGCGTTTTTTTGTTTTTAATTGTATTTAGTTATGGCCTATACA | |
| | CTATTTGTGAGCAAAGGTGATCGTTTTCTGTTTGAGATTTTTATCTCTTGATTCTTCAAAAGCATTCTGA | |
| | GAAGGTGAGATAAGCCCTGAGTCTCAGCTACCTAAGAAAAACCTGGATGTCACTGGCCACTGAGGAGCTT | |
| | TGTTTCAACCAAGTCATGTGCATTTCCACGTCAACAGAATTGTTTATTGTGACAGTTATATCTGTTGTCC | |
| | CTTTGACCTTGTTTCTTGAAGGTTTCCTCGTCCCTGGGCAATTCCGCATTTAATTCATGGTATTCAGGAT | |
| | TACATGCATGTTTGGTTAAACCCATGAGATTCATTCAGTTAAAAATCCAGATGGCAAATGACCAGCAGAT | |
| | TCAAATCTATGGTGGTTTGACCTTTAGAGAGTTGCTTTACGTGGCCTGTTTCAACACAGACCCACCCAGA | |
| | GCCCTCCTGCCCTCCTTCCGCGGGGGCTTTCTCATGGCTGTCCTTCAGGGTCTTCCTGAAATGCAGTGGT | |
| | GCTTACGCTCCACCAAGAAAGCAGGAAACCTGTGGTATGAAGCCAGACCTCCCCGGCGGGCCTCAGGGAA | |
| | CAGAATGATCAGACCTTTGAATGATTCTAATTTTTAAGCAAAATATTATTTTATGAAAGGTTTACATTGT | |
| | CAAAGTGATGAATATGGAATATCCAATCCTGTGCTGCTATCCTGCCAAAATCATTTTAATGGAGTCAGTT | |
| | TGCAGTATGCTCCACGTGGTAAGATCCTCCAAGCTGCTTTAGAAGTAACAATGAAGAACGTGGACGTTTT | |
| | TAATATAAAGCCTGTTTTGTCTTTTGTTGTTGTTCAAACGGGATTCACAGAGTATTTGAAAAATGTATAT | |
| | ATATTAAGAGGTCACGGGGGCTAATTGCTGGCTGGCTGCCTTTTGCTGTGGGGTTTTGTTACCTGGTTTT | |
| | AATAACAGTAAATGTGCCCAGCCTCTTGGCCCCAGAACTGTACAGTATTGTGGCTGCACTTGCTCTAAGA | |
| | GTAGTTGATGTTGCATTTTCCTTATTGTTAAAAACATGTTAGAAGCAATGAATGTATATAAAAGCCTCAA | |
| | CTAGTCATTTTTTTCTCCTCTTCTTTTTTTTCATTATATCTAATTATTTTGCAGTTGGGCAACAGAGAAC | |
| | CATCCCTATTTTGTATTGAAGAGGGATTCACATCTGCATCTTAACTGCTCTTTATGAATGAAAAAACAGT | |
| | CCTCTGTATGTACTCCTCTTTACACTGGCCAGGGTCAGAGTTAAATAGAGTATATGCACTTTCCAAATTG | |
| | GGGACAAGGGCTCTAAAAAAAGCCCCAAAAGGAGAAGAACATCTGAGAACCTCCTCGGCCCTCCCAGTCC | |
| | CTCGCTGCACAAATACTCCGCAAGAGAGGCCAGAATGACAGCTGACAGGGTCTATGGCCATCGGGTCGTC | |
| | TCCGAAGATTTGGCAGGGGCAGAAAACTCTGGCAGGCTTAAGATTTGGAATAAAGTCACAGAATTAAGGA | |
| | AGCACCTCAATTTAGTTCAAACAAGACGCCAACATTCTCTCCACAGCTCACTTACCTCTCTGTGTTCAGA | |
| | TGTGGCCTTCCATTTATATGTGATCTTTGTTTTATTAGTAAATGCTTATCATCTAAAGATGTAGCTCTGG | |
| | CCCAGTGGGAAAAATTAGGAAGTGATTATAAATCGAGAGGAGTTATAATAATCAAGATTAAATGTAAATA | |
| | ATCAGGGCAATCCCAACACATGTCTAGCTTTCACCTCCAGGATCTATTGAGTGAACAGAATTGCAAATAG | |
| | TCTCTATTTGTAATTGAACTTATCCTAAAACAAATAGTTTATAAATGTGAACTTAAACTCTAATTAATTC | |
| | CAACTGTACTTTTAAGGCAGTGGCTGTTTTTAGACTTTCTTATCACTTATAGTTAGTAATGTACACCTAC | |
| | TCTATCAGAGAAAAACAGGAAAGGCTCGAAATACAAGCCATTCTAAGGAAATTAGGGAGTCAGTTGAAAT | |
| | TCTATTCTGATCTTATTCTGTGGTGTCTTTTGCAGCCCAGACAAATGTGGTTACACACTTTTTAAGAAAT | |
| | ACAATTCTACATTGTCAAGCTTATGAAGGTTCCAATCAGATCTTTATTGTTATTCAATTTGGATCTTTCA | |
| | GGGATTTTTTTTTAAATTATTATGGGACAAAGGACATTTGTTGGAGGGGTGGAGGGAGGAAGAATTTT | |
| | TAAATGTAAAACATTCCCAAGTTTGGATCAGGGAGTTGGAAGTTTTCAGAATAACCAGAACTAAGGGTAT | |
| | GAAGGACCTGTATTGGGGTCGATGTGATGCCTCTGCGAAGAACCTTGTGTGACAAATGAGAAACATTTTG | |
| | AAGTTTGTGGTACGACCTTTAGATTCCAGAGACATCAGCATGGCTCAAAGTGCAGCTCCGTTTGGCAGTG | |
| | CAATGGTATAAATTTCAAGCTGGATATGTCTAATGGGTATTTAAACAATAAATGTGCAGTTTTAACTAAC | |
| | AGGATATTTAATGACAACCTTCTGGTTGGTAGGGACATCTGTTTCTAAATGTTTATTATGTACAATACAG | |
| | AAAAAAATTTTATAAAATTAAGCAATGTGAAACTGAATTGGAGAGTGATAATACAAGTCCTTTAGTCTTA | |
| | CCCAGTGAATCATTCTGTTCCATGTCTTTGGACAACCATGACCTTGGACAATCATGAAATATGCATCTCA | |
| | CTGGATGCAAAGAAAATCAGATGGAGCATGAATGGTACTGTACCGGTTCATCTGGACTGCCCCAGAAAAA | |
| | TAACTTCAAGCAAACATCCTATCAACAACAAGGTTGTTCTGCATACCAAGCTGAGCACAGAAGATGGGAA | |

TABLE 2-continued

| GENBANK ACCESSION NUMBER | SEQUENCE | SEQ ID NO: |
|---|---|---|
| | CACTGGTGGAGGATGGAAAGGCTCGCTCAATCAAGAAAATTCTGAGACTATTAATAAATAAGACTGTAGT<br>GTAGATACTGAGTAAATCCATGCACCTAAACCTTTTGGAAAATCTGCCGTGGGCCCTCCAGATAGCTCAT<br>TTCATTAAGTTTTTCCCTCCAAGGTAGAATTTGCAAGAGTGACAGTGGATTGCATTTCTTTTGGGGAAGC<br>TTTCTTTTGGTGGTTTTGTTTATTATACCTTCTTAAGTTTTCAACCAAGGTTTGCTTTTGTTTTGAGTTA<br>CTGGGGTTATTTTTGTTTTAAATAAAAATAAGTGTACAATAAGTGTTTTTGTATTGAAAGCTTTTGTTAT<br>CAAGATTTTCATACTTTTACCTTCCATGGCTCTTTTTAAGATTGATACTTTTAAGAGGTGGCTGATATTC<br>TGCAACACTGTACACATAAAAAATACGGTAAGGATACTTTACATGGTTAAGGTAAAGTAAGTCTCCAGTT<br>GGCCACCATTAGCTATAATGGCACTTTGTTTGTGTTGTTGGAAAAAGTCACATTGCCATTAAACTTTCCT<br>TGTCTGTCTAGTTAATATTGTGAAGAAAAATAAAGTACAGTGTGAGATACTG | |
| NM_001012271 | CCCAGAAGGCCGCGGGGGGTGGACCGCCTAAGAGGGCGTGCGCTCCCGACATGCCCCGCGGCGCGCCATT<br>AACCGCCAGATTTGAATCGCGGACCCGTTGGCAGAGGTGGCGGCGGCGGCATGGGTGCCCCGACGTTGC<br>CCCCTGCCTGGCAGCCCTTTCTCAAGGACCACCGCATCTCTACATTCAAGAACTGGCCCTTCTTGGAGGG<br>CTGCGCCTGCACCCCGGAGCGGATGGCCGAGGCTGGCTTCATCCACTGCCCCACTGAGAACGAGCCAGAC<br>TTGGCCCAGTGTTTCTTCTGCTTCAAGGAGCTGGAAGGCTGGGAGCCAGATGACGACCCCATTGGGCCGG<br>GCACGGTGGCTTACGCCTGTAATACCAGCACTTTGGGAGGCCGAGGCGGGCGGATCACGAGAGAGGAACA<br>TAAAAAGCATTCGTCCGGTTGCGCTTTCCTTTCTGTCAAGAAGCAGTTTGAAGAATTAACCCTTGGTGAA<br>TTTTTGAAACTGGACAGAGAAAGAGCCAAGAACAAAATTGCAAAGGAAACCAACAATAAGAAGAAAGAAT<br>TTGAGGAAACTGCGGAGAAAGTGCGCCGTGCCATCGAGCAGCTGGCTGCCATGGATTGAGGCCTCTGGCC<br>GGAGCTGCCTGGTCCCAGAGTGGCTGCACCACTTCCAGGGTTTATTCCCTGGTGCCACCAGCCTTCCTGT<br>GGGCCCCTTAGCAATGTCTTAGGAAAGGAGATCAACATTTTCAAATTAGATGTTTCAACTGTGCTCTTGT<br>TTTGTCTTGAAAGTGGCACCAGAGGTGCTTCTGCCTGTGCAGCGGGTGCTGCTGGTAACAGTGGCTGCTT<br>CTCTCTCTCTCTCTCTTTTTTGGGGGCTCATTTTTGCTGTTTTGATTCCCGGGCTTACCAGGTGAGAAGT<br>GAGGGAGGAAGAAGGCAGTGTCCCTTTTGCTAGAGCTGACAGCTTTGTTCGCGTGGGCAGAGCCTTCCAC<br>AGTGAATGTGTCTGGACCTCATGTTGTTGAGGCTGTCACAGTCCTGAGTGTGGACTTGGCAGGTGCCTGT<br>TGAATCTGAGCTGCAGGTTCCTTATCTGTCACACCTGTGCCTCCTCAGAGGACAGTTTTTTTGTTGTTGT<br>GTTTTTTTGTTTTTTTTTTTTTGGTAGATGCATGACTTGTGTGTGATGAGAGAATGGAGACAGAGTCCCT<br>GGCTCCTCTACTGTTTAACAACATGGCTTTCTTATTTTGTTTGAATTGTTAATTCACAGAATAGCACAAA<br>CTACAATTAAAACTAAGCACAAAGCCATTCTAAGTCATTGGGGAAACGGGGTGAACTTCAGGTGGATGAG<br>GAGACAGAATAGAGTGATAGGAAGCGTCTGGCAGATACTCCTTTTGCCACTGCTGTGTGATTAGACAGGC<br>CCAGTGAGCCGCGGGGCACATGCTGGCCGCTCCTCCCTCAGAAAAAGGCAGTGGCCTAAATCCTTTTTAA<br>ATGACTTGGCTCGATGCTGTGGGGGACTGGCTGGGCTGCTGCAGGCCGTGTGTCTGTCAGCCCAACCTTC<br>ACATCTGTCACGTTCTCCACACGGGGGAGAGACGCAGTCCGCCCAGGTCCCCGCTTTCTTTGGAGGCAGC<br>AGCTCCCGCAGGGCTGAAGTCTGGCGTAAGATGATGGATTTGATTCGCCCTCCTCCCTGTCATAGAGCTG<br>CAGGGTGGATTGTTACAGCTTCGCTGGAAACCTCTGGAGGTCATCTCGGCTGTTCCTGAGAAATAAAAAG<br>CCTGTCATTTCAAACACTGCTGTGGACCCTACTGGGTTTTTAAAATATTGTCAGTTTTTCATCGTCGTCC<br>CTAGCCTGCCAACAGCCATCTGCCCAGACAGCCGCAGTGAGGATGAGCGTCCTGGCAGAGACGCAGTTGT<br>CTCTGGGCGCTTGCCAGAGCCACGAACCCCAGACCTGTTTGTATCATCCGGGCTCCTTCCGGGCAGAAAC<br>AACTGAAAATGCACTTCAGACCCACTTATTTCTGCCACATCTGAGTCGGCCTGAGATAGACTTTTCCCTC<br>TAAACTGGGAGAATATCACAGTGGTTTTTGTTAGCAGAAAATGCACTCCAGCCTCTGTACTCATCTAAGC<br>TGCTTATTTTTGATATTTGTGTCAGTCTGTAAATGGATACTTCACTTTAATAACTGTTGCTTAGTAATTG<br>GCTTTGTAGAGAAGCTGGAAAAAAATGGTTTTGTCTTCAACTCCTTTGCATGCCAGGCGGTGATGTGGAT<br>CTCGGCTTCTGTGAGCCTGTGCTGTGGGCAGGGCTGAGCTGGAGCCGCCCCTCTCAGCCCGCCTGCCACG<br>GCCTTTCCTTAAAGGCCATCCTTAAAACCAGACCCTCATGGCTACCAGCACCTGAAAGCTTCCTCGACAT<br>CTGTTAATAAAGCCGTAGGCCCTTGTCTAAGTGCAACCGCCTAGACTTTCTTTCAGATACATGTCCACAT<br>GTCCATTTTTCAGGTTCTCTAAGTTGGAGTGGAGTCTGGGAAGGGTTGTGAATGAGGCTTCTGGGCTATG<br>GGTGAGGTTCCAATGGCAGGTTAGAGCCCCTCGGGCCAACTGCCATCCTGGAAAGTAGAGACAGCAGTGC<br>CCGCTGCCCAGAAGAGACCAGCAAGCCAAACTGGAGCCCCCATTGCAGGCTGTCGCCATGTGGAAAGAGT<br>AACTCACAATTGCCAATAAAGTCTCATGTGGTTTTATCTAAAAAAAAAAAAAAAAAAAAAAAAA | 106 |
| BX647539 | AATGAGGGTATTTATAAACTACTTAAATTATAAAAAGAATGAGACATCAGACTTACAGTTTTGGATACTA<br>ATTTTTTTCACTTAACGTTCATTATGTGATAGGAGTTTTCCATCCTATTATACCGCTGTGCGATCTGATC<br>TTGGGCACGTTAACCAACCTCTTGTTGCCTCGATTTTCTCACCTGTAAAAGTGGGGGTAATCATAATGCT<br>TACTTAGTAGGATAGCCCTGAAGAATAAGTGACTTAGCGAACATAAATAGCTTACAATAGGGTTTTCAGC<br>ATGGGAAGGATTCAGTAAATGTTAGCTGTCATCATCACCACCTACAAAGGAAGCAATACTGTGCTGAAAG<br>TTTTTCCATCATTAATGTAATTTCTATAGTACGATTCCCAAGAAGATATTAAAATTATGGAAATAAAGGT<br>ATTGGTATATTCCTAATTATTTCCTAAAAGATTGTATTGATAAATATGCTCATCCTTCCCTTAACGGGAT<br>GCATTCCAGAAAAACAAGTCAAATGTTAGACAAAGTATCAGAAGGGAAATTCTGTAGCCAGAGAGCTAAA<br>AATTACAATAGGGTCTCTAATTATACTTCAACTTTTTTAGGAATAATTCTCAGTGTGTTTTCCCACATTT<br>CATATGTAATTTTTTTTTTTTTTTTTTTTTTGAGACAGAGCCTCGCCCTGTCACCAGGCTGGAGTACAGTG<br>GCGCGATCTCGGCTCACTGCAACTTCCACCTGCTGGGTTCAAGCAATTCTTCTGACCTCAGGTGATCCAC<br>CCGCCTCGGCCTCCCAAAGTGCTGGGATTATAACAGGCGTGGCATGAGTCACCGCGCCCGGCCGATCTTT<br>ACTTTTTTATTCTTTGTACCCCCTGCCTATCCAGTTAGCATGTGATTAAAGTCAAAGATTTGCCACTTTG<br>GGCCACATCTATTAATTTTCATCTTTGTTATAATTGTATTTAGTTTTTGATCTACACTGCTTATTACTCC<br>CAGTCATTTTTTATAGAACTGAAAATCTGGTAAAATACTCAAAATTGCACTGACTTCTATGTAGAGGCGA<br>CACTCCATCAGAACCGTGGGCTGACAGGGAATCCCACTGTGCAGGAGCTGCGCGCATTTTCATTTCTGAT<br>TCTCTTTGGCGTATCCAGGACTCTGATGACATGATCATATATTTATCAGTAGTAACAGGTTGGGCCATTT<br>GTTTTTTGTGGTAAATCATATATTTAAGATTTTAGAAATAAGTTGATAGCCATGTATTTTGGAATTTGAA<br>AAAGACATTGCATTACTCAGCTTCAAATTAAGCTTTAATCAAATAGTGAAACTTTCCATTAATGGACAGT<br>GTATACCTTTTTGTGTATTTAAAAAAAAAAACACTGAATATAGTGCCTTTGTGACAGGGGAGCTTGGTTC<br>CTGACAATGTCCTCTTGAGCCTTTTTTTTTTTTTTGAGATGGAGTCTCACTGTGTCACCCAGGCTGGAGT<br>GCAGTGGCGCCATCTTGGCTCACTGCAACCTCCGCCCCCTGGGTTCAAGTGATTCTCATTCCTCAGCTTC<br>CTAAGTAGCTGGGATTACAGGCACGCACCACCATGACCAGCTAATTTTTATACTTTTAGTAGAGACAGGG<br>TTTTGCCATGTTGGCTAGGTTGGTCTCGAACTCCTGACCTCAAGTAATCCACCCACCATGGCCTCCCCAA<br>AGTGCTGGGATTACAGGCGTGAGCCATTTCACCCGGCCTCTCTTCCGTCTTTGAGCTGTGAGGAAATAGC<br>TACATTACATGAGCTGCTAGATCTGCCTTATGGTCAGAAATGAAGGTTGAACTCTCAGGAACAGTGACAT | 107 |

TABLE 2-continued

| GENBANK ACCESSION NUMBER | SEQUENCE | SEQ ID NO: |
|---|---|---|
| | ATATACACACTGATATTTCCAAAGTACAATGCCCCAAATTGATCCACAAAGGAATTAAGGTCATTTGCAA | |
| | CAAAATCACAGAATAGTAACAAATAAATAGAAGATAAATATGGCCAGGGATGCTGCAAACTGATATACTG | |
| | CCAAGTTTATCAGTTGGGAATCCCAACAGTGAAAAGCATAAAAATGAAAGGAATTTTAAGGAGACTTTTT | |
| | ATAGAAGAGTGGGAAGGATTGGAGGAGCCAACAAGTGATGGTGAGGCACACAGGGAAGAGCTTCAGTGGG | |
| | CACCATCCCCTCTCTGGTTTGAAGGGGTAGGGAGGGGACCAGAGCTGGGAGGAGGGGGCTGGAATACTGC | |
| | TGGAGGAGCCACTCCCTTCCAGACCTGCTGTGGCCATCACAGAATGCAGCCACTGCCAGAGCAGCAGCCC | |
| | GAGGAACCAGGCAGGGGGAGCACAAGTACCCTAGCCTCTCTCTTTCTGTTTCTTGCCTGCCGATCTCCTC | |
| | CACTGGCTAAACCCAGCTGGATGCTAAGAGTACAGTCAGCCTGCCTGCTGAGGAGGGACCACCAGGGACC | |
| | ACCATCAGCAAGGGATCCAATGTCTTTCTGCCTCTGCAGAATGAAGGTTGGGGCGCGGGGGGCGCTCTAC | |
| | TTCTTAGGGATATTGTGGGAATAAAAGGAAATAGGCAAAAAATGTTTTTGAAAAACAAAGCACATACTGC | |
| | GCACCCGTGGGCCACTACTGCTTTTGACCCCTGGCTCTGTTTCATGAAGTAATGTCGTGTCATTCTCTTT | |
| | TTAGGTGCTACAGGATTTCTTTAGGTTTGTTTTCTGTCCACCATATTTCAACTCATGTGTGCTGTTTGTT | |
| | GTGCTAAAACAAATATTTGCTGATGCCTGAGTGAATAGTTGAATATTTTATATAAGTCAAATTTATACGT | |
| | AATGATTTTTCTTGTAACTTAGCCGTTTCTCTTTTACAAACTCAGAAAACCTCAGACTTTGAAAAGGCCT | |
| | TGAAGTTCCTCACCTGAAATCTGAGAACTTGGAGCGCCTTAAAAAATCTAAAGGAAAACAAAACAGTGAA | |
| | AGAACATGATATAGTCAGTGTAGAGAATAAAATTATTTATGTAATTAATATTGAGGATGCAGATAACACA | |
| | TTGTGAAATCTTGCTTGTAAAAAATCTCGATCTGCTGAAGAAAGATGTTCTCTCTAGAGATCTTTGAAAG | |
| | CATAATTATTGAGCTTTTAAAATGTTAGAAACAAAAGTTAGACCCACACATATTCTGGCGTGTGGAAGAT | |
| | TTGCATTCCTTCCCCTGCCCGCCCCGCCCCCACACTTGTGAGTTGTGCCTGTGTACGCAGTTCCTGTAGC | |
| | ACTCGGCTGGGCAGAAATCATCTTTCAGCACTAAGGGAACATAGTTATGATCTGGACCTTCTGGGAGTGG | |
| | TCAGTGCCCAAGAACAGGTATGGGACTCCAGAAAGTTCTGCTCTCAACCCTATTTTGAAATAGAGTTACA | |
| | CATTGTTCTACAATTATTTGAGTTAATAAGCAGCTCTTTTCAAACGTGATTATGCCCTTCCAAGTTTAAA | |
| | TACACTAGACTTTAGTGAAAGTAATTGACCTCATCTCATTTCTCTCCTGTTATATTAAGATCACTTTCAG | |
| | TAAAAGGTAGAAGCTTTTGAAGTGGTGAGGAGGAGGTAGAGGAGGGACATAGAGCAGATAGGGGCTGGAA | |
| | AGTGGGGTGAGGAAGAGAGTGGCTTCTCTTTGGCAGAGTACCAAGGAAAAGCCCTATCTGTACAGAACCT | |
| | TTGTGCCTGGGAACTTGATGGCTGCAACCTGAGCCTCAACCTAGTTTGCTTGCGGAGCCAGAAGAGAAGC | |
| | TAAAAACCTTCAGTTAACCAAGCCAGACACCAAGAAAGTTAAACCGAAAGAGAACCCCCCACCCCCCGCA | |
| | AAAAAAAGAAGTAAAGTGGGTTAAAGTGATATCATGTTAGCACAGAAAGAGAACATAAGGGTCATCTAAG | |
| | TTCATCTGCCCCCTCTTCTATTTCAAGGTGCAGAAACTAAGGCACAAGGGACCCCGTGTCCTGCTCTTGA | |
| | TCACATAGCTAGTGGGTGCCAAGCCAGGTCTAGAACTCTGTTCTCTGGGGTCACAGGCTGGCTCTTCATC | |
| | CCTCTAGAGAGATAGCTCATCTGTGTGCACCTGAGCCCGTTGTGTTTCGGAGTCAAAGCAAATAAAGGCT | |
| | CAAACTCCAAGACTGTTTTGCAGACCGGCTGCAGTAGATATGGGGGGAGGAGAAACCTGCTTTAAATTGC | |
| | TTCAAGCAAGTTGTTTCTGCAAAGGTGTTGACTTTTTTCTTTCAACTTTCTAGTGAGTCACTGCAGCCTG | |
| | AGCTGTTATTTGTCATTATGCAATAATTCAGGAACTAACTCAAGATTCTTCTTTTTAAATTATTTGTTTA | |
| | TTTAGAGACAGAGTCTTGCTCTGTTGCCCAGGCTGGAGTGCAGTGGTGTGATCTCGGCTCACTGCAGCCT | |
| | CTGCCTCCTGGGTTCAAGCAATTCTCATGTCTCAGCCTCCCGAATAGCTGGTATTGCAGGCTCGTGCCAC | |
| | CACCCCCTGCTAATTTTTGTAATTTTAGTGGAGACACGGTTTCGCCATGTTGGCCGGGCTCGTCTTGAGC | |
| | TCCTGGCCTCAGGTGATCCGCCCGCCTCGGCCTCCCAAAGTGCTGGGATTGCAGCCGTGAGCCTCCACAC | |
| | CCGGCCTATTTATTTATTTTTAAATTGGCTGCTCTTAGAAAGGCATACCATGTTTCTGGATGGGAAGGCT | |
| | TATTAATTCACCCTAATTTAATGTATAAATTTGATGCAATCATAGTCACAGTCCCAGTGGAATTTTTTAA | |
| | CTTGGTAAGATGTTCTAAAATTAATGAGAGAACTTGAATTACCAGGTATTGAAACACTGTAAAGCCACAA | |
| | TCATGTAAACAGTATGTTATAACCATGGGAATAGAGGTCTGTGATACAGCAGAAAAAAGTGAAAAAAAGA | |
| | ATAACTGTATTCATAAAAAATTTAAATGTGGAGTCACTGGGGGAAAGGATTAAATATTCGATAATGTAGAA | |
| | ACAACTCAACTATTTGGAGAAATGTAAATTTAGAGCCTTATCTCATGCCATATACCAAAATACTATTTAG | |
| | ATTTGATTAAAAAATAAAAAAAAAAAAAAAAAA | |
| NM_031966 | CGAACGCCTTCGCGCGATCGCCCTGGAAACGCATTCTCTGCGACCGGCAGCCGCCAATGGGAAGGGAGTG | 108 |
| | AGTGCCACGAACAGGCCAATAAGGAGGGAGCAGTGCGGGGTTTAAATCTGAGGCTAGGCTGGCTCTTCTC | |
| | GGCGTGCTGCGGCGGAACGGCTGTTGGTTTCTGCTGGGTGTAGGTCCTTGGCTGGTCGGGCCTCCGGTGT | |
| | TCTGCTTCTCCCCGCTGAGCTGCTGCCTGGTGAAGAGGAAGCCATGGCGCTCCGAGTCACCAGGAACTCG | |
| | AAAATTAATGCTGAAAATAAGGCGAAGATCAACATGGCAGGCGCAAAGCGCGTTCCTACGGCCCCTGCTG | |
| | CAACCTCCAAGCCCGGACTGAGGCCAAGAACAGCTCTTGGGGACATTGGTAACAAAGTCAGTGAACAACT | |
| | GCAGGCCAAAATGCCTATGAAGAAGGAAGCAAAACCTTCAGCTACTGGAAAAGTCATTGATAAAAAACTA | |
| | CCAAAACCTCTTGAAAAGGTACCTATGCTGGTGCCAGTGCCAGTGTCTGAGCCAGTGCCAGAGCCAGAAC | |
| | CTGAGCCAGAACCTGAGCCTGTTAAAGAAGAAAAACTTTCGCCTGAGCCTATTTTGGTTGATACTGCCTC | |
| | TCCAAGCCCAATGGAAACATCTGGATGTGCCCCTGCAGAAGAAGACCTGTGTCAGGCTTTCTCTGATGTA | |
| | ATTCTTGCAGTAAATGATGTGGATGCAGAAGATGGAGCTGATCCAAACCTTTGTAGTGAATATGTGAAAG | |
| | ATATTTATGCTTATCTGAGACAACTTGAGGAAGAGCAAGCAGTCAGACCAAAATACCTACTGGGTCGGGA | |
| | AGTCACTGGAAACATGAGAGCCATCCTAATTGACTGGCTAGTACAGGTTCAAATGAAATTCAGGTTGTTG | |
| | CAGGAGACCATGTACATGACTGTCTCCATTATTGATCGGTTCATGCAGAATAATTGTGTGCCCAAGAAGA | |
| | TGCTGCAGCTGGTTGGTGTCACTGCCATGTTTATTGCAAGCAAATATGAAGAAATGTACCCTCCAGAAAT | |
| | TGGTGACTTTGCTTTTGTGACTGACAACACTTATACTAAGCACCAAATCAGACAGATGGAAATGAAGATT | |
| | CTAAGAGCTTTAAACTTTGGTCTGGGTCGGCCTCTACCTTTGCACTTCCTTCGGAGAGCATCTAAGATTG | |
| | GAGAGGTTGATGTCGAGCAACATACTTTGGCCAAATACCTGATGGAACTAACTATGTTGGACTATGACAT | |
| | GGTGCACTTTCCTCCTTCTCAAATTGCAGCAGGAGCTTTTTGCTTAGCACTGAAAATTCTGGATAATGGT | |
| | GAATGGACACCAACTCTACAACATTACCTGTCATATACTGAAGAATCTCTTCTTCCAGTTATGCAGCACC | |
| | TGGCTAAGAATGTAGTCATGGTAAATCAAGGACTTACAAAGCACATGACTGTCAAGAACAAGTATGCCAC | |
| | ATCGAAGCATGCTAAGATCAGCACTCTACCACAGCTGAATTCTGCACTAGTTCAAGATTTAGCCAAGGCT | |
| | GTGGCAAAGGTGTAACTTGTAAACTTGAGTTGGAGTACTATATTTACAAATAAAATTGGCACCATGTGCC | |
| | ATCTGTACATATTACTGTTGCATTTACTTTTAATAAAGCTTGTGGCCCCTTTTACTTTTTTATAGCTTAA | |
| | CTAATTTGAATGTGGTTACTTCCTACTGTAGGGTAGCGGAAAAGTTGTCTTAAAAGGTATGGTGGGGATA | |
| | TTTTTAAAAACTCCTTTTGGTTTACCTGGGGATCCAATTGATGTATATGTTTATATACTGGGTTCTTGTT | |
| | TTATATACCTGGCTTTTACTTTATTAATATGAGTTACTGAAGGTGATGGAGGTATTTGAAAATTTTACTT | |
| | CCATAGGACATACTGCATGTAAGCCAAGTCATGGAGAATCTGCTGCATAGCTCTATTTTAAAGTAAAAGT | |
| | CTACCACCGAATCCCTAGTCCCCCTGTTTTCTGTTTCTTCTTGTGATTGCTGCCATAATTCTAAGTTATT | |
| | TACTTTTACCACTATTTAAGTTATCAACTTTAGCTAGTATCTTCAAACTTTCACTTTGAAAAATGAGAAT | |

TABLE 2-continued

| GENBANK ACCESSION NUMBER | SEQUENCE | SEQ ID NO: |
|---|---|---|
| | TTTATATTCTAAGCCAGTTTTCATTTTGGTTTTGTGTTTTGGTTAATAAAACAATACTCAAATACAAAAA AAAAAAA | |
| BC035498 | GCGGCCGCCAGCGCGGTGTAGGGGGCAGGCGCGGATCCCGCCACCGCCGCGCGCTCGGCCCGCCGACTCC CGGCGCCGCCGCCGCCACTGCCGTCGCCGCCGCCGCCTGCCGGGACTGGAGCGCGCCGTCCGCCGCGGAC AAGACCCTGGCCTCAGGCCGGAGCAGCCCCATCATGCCGAGGGAGCGCAGGGAGCGGGATGCGAAGGAGC GGGACACCATGAAGGAGGACGGCGGCGCGGAGTTCTCGGCTCGCTCCAGGAAGAGGAAGGCAAACGTGAC CGTTTTTTTGCAGGATCCAGATGAAGAAATGGCCAAAATCGACAGGACGGCGAGGGACCAGTGTGGGAGC CAGCCTTGGGACAATAATGCAGTCTGTGCAGACCCCTGCTCCCTGATCCCCACACCTGACAAAGAAGATG ATGACCGGGTTTACCCAAACTCAACGTGCAAGCCTCGGATTATTGCACCATCCAGAGGCTCCCCGCTGCC TGTACTGAGCTGGGCAAATAGAGAGGAAGTCTGGAAAATCATGTTAAACAAGGAAAAGACATACTTAAGG GATCAGCACTTTCTTGAGCAACACCCTCTTCTGCAGCCAAAAATGCGAGCAATTCTTCTGGATTGGTTAA TGGAGGTGTGTGAAGTCTATAAACTTCACAGGGAGACCTTTTACTTGGCACAAGATTTCTTTGACCGGTA TATGGCGACACAAGAAAATGTTGTAAAAACTCTTTTACAGCTTATTGGGATTTCATCTTTATTTATTGCA GCCAAACTTGAGGAAATCTATCCTCCAAAGTTGCACCAGTTTGCGTATGTGACAGATGGAGCTTGTTCAG GAGATGAAATTCTCACCATGGAATTAATGATTATGAAGGCCCTTAAGTGGCGTTTAAGTCCCCTGACTAT TGTGTCCTGGCTGAATGTATACATGCAGGTTGCATATCTAAATGACTTACATGAAGTGCTACTGCCGCAG TATCCCCAGCAAATCTTTATACAGATTGCAGAGCTGTTGGATCTCTGTGTCCTGGATGTTGACTGCCTTG AATTTCCTTATGGTATACTTGCTGCTTCGGCCTTGTATCATTTCTCGTCATCTGAATTGATGCAAAAGGT TTCAGGGTATCAGTGGTGCGACATAGAGAACTGTGTCAAGTGGATGGTTCCATTTGCCATGGTTATAAGG GAGACGGGGAGCTCAAAACTGAAGCACTTCAGGGGCGTCGCTGATGAAGATGCACACAACATACAGACCC ACAGAGACAGCTTGGATTTGCTGGACAAAGCCCGAGCAAAGAAAGCCATGTTGTCTGAACAAAATAGGGC TTCTCCTCTCCCCAGTGGGCTCCTCACCCCGCCACAGAGCGGTAAGAAGCAGAGCAGCGGGCCGGAAATG GCGTGACCACCCCATCCTTCTCCACCAAAGACAGTTGCGCGCCTGCTCCACGTTCTCTTCTGTCTGTTGC AGCGGAGGCGTGCGTTTGCTTTTACAGATATCTGAATGGAAGAGTGTTTCTTCCACAACAGAAGTATTTC TGTGGATGGCATCAAACAGGGCAAAGTGTTTTTTATTGAATGCTTATAGGTTTTTTTTAAATAAGTGGGT CAAGTACACCAGCCACCTCCAGACACCAGTGCGTGCTCCCGATGCTGCTATGGAAGGTGCTACTTGACCT AAGGGACTCCCACAACAACAAAAGCTTGAAGCTGTGGAGGGCCACGGTGGCGTGGCTCTCCTCGCAGGTG TTCTGGGCTCCGTTGTACCAAGTGGAGCAGGTGGTTGCGGGCAAGCGTTGTGCAGAGCCCATAGCCAGCT GGGCAGGGGGCTGCCCTCTCCACATTATCAGTTGACAGTGTACAATGCCTTTGATGAACTGTTTTGTAAG TGCTGCTATATCTATCCATTTTTTAATAAAGATAATACTGTTTTTGAAAAAAAAAAAAAAAAAAAAAAAA AAAAAAAAAAAAAAAAAAAAAAAAAAAAAAAAAAAAAAAAAAAAAAAAAA | 110 |
| BG256659 | GAGGGCACGGGCTCCGTAGGCACCAACTGCAAGGACCCCTCCCCCTGCGGGCGCTCCCATGGCACAGTTC GCGTTCGAGAGTGACCTGCACTCGCTGCTTCAGCTGGATGCACCCATCCCCAATGCACCCCCTGCGCGCT GGCAGCGCAAAGCCAAGGAAGCCGCAGGCCCGGCCCCCTCACCCATGCGGGCCGCCAACCGATCCCACAG CGCCGGCAGGACTCCGGGCCGAACTCCTGGCAAATCCAGTTCCAAGGTTCAGACCACTCCTAGCAAACCT GGCGGTGACCGCTATATCCCCCATCGCAGTGCTGCCCAGATGGAGGTGGCCAGCTTCCTCCTGAGCAAGG AGAACCAGCCTGAAAACAGCCAGACGCCCACCAAGAAGGAACATCAGAAAGCCTGGGCTTTGAACCTGAA CGGTTTTGATGTAGAGGAAGCCAAGATCCTTCGGCTCAGTGGAAAACCACAAAAATGCGCCAGAGGGTT ATCACGAACAGACTGAAAGTACTCTACAGCCAAAAGGCCACTCCTGGCTCCAGCCGGAAGACCTGCCGTT TACATTCCTTCCCTGCCAAGACCGTATCCTGGATGCGCCTGAAATCGAATGACTATTAACTGAACCTGTG GGACTGGCAGTCCGGGGAATGTCCGGGCCGGGCCACGGCCACGAGGTGTTCCGTGTGGAGTGCAAGCTGG GACACACCGTGCCGCTTGTGCACAGGGCCACGCGGGGAAATAATCCCGGGGCGCGCAAAGCGGCACTGGC GAGAGCCGCACGGGCCGGTGCTGGGGGTGGTACAACAGGCCAAAACAACACACAAGGCCAACAAGACATA CGCGCGCTGACACCACGGTGCAAAGCGCTCAGACGAGTAGTAACCGGCACTGTGGTTGCTGCCTCCCCAC CTCTCCCGCTCTCAGCGTAAGATAAAAGAAAGAAGAGCAAAAAGCAAAGAAAGAAGACGAGACGAGACAC ACAGGAACGAACAGTAAAGCAAGCTAAAGCAAACGCAAGACCAGACAACAGAAATAGAAAGAACCAACAG AGAGGAGACAGAACAGGACGCCAGCAACATAGCAACAAACGAACAGAAGAGAGCACTAAACAAAAGCAGC AGCAAGACGAGACAGGAGAGAAGGAGGAAGGAGGGCCGAGCGAGCAGGGAGCGCGAGCAGCGAGGCGAAG CAGCAGACAAGGGCAGGCGAAGGGCAACGAGAGGAGGCACCACACAAAAAGGAGAGGGGACAGGAGAAGC AGCGAGAGAAGCGGAGGAGCAACAAGAGGAAGAAAAGGAGAGGGAGAGGAGGGAGAGAGCGGAAGGAGGA AGAAACAGCACGAGGCGACGAAGGGGGGAGACGCGGGGGCAGGAAAAGACACAGGAAGGCAGCGCGGAGG AGGAGAAGGGGAAGCAGGAAGGAGACGGAAGGAGAAGAGGGAGAGGACAGCGCAAGAGAGCGCGCGCGGC GACAGCGAGGGACGGAGCGAGAGAGAGGAAACGGAAAGCGAGAGGGAAGAGGAGAGGCAACGCAGCGAAC CAACCGAAAACAGCAGAAAGAGAGGAGAAGGACGCGCAAAGAGGCAAGCGCAAGACGACAGGAAACGAAG CGAGAGACGAGAAGCCGGTGACGAGCAGGAGAAAGGGAAGGCAGGAGACAGGACAGGCGGAAGAGAGACA CGCGAGACGCAAAGAGTGAGCAGAACGAAGCGAAGAGCAACGCACGAGAGAAACGAC | 111 |
| NM_001254 | GAGCGCGGCTGGAGTTTGCTGCTGCCGCTGTGCAGTTTGTTCAGGGGCTTGTGGTGGTGAGTCCGAGAGG CTGCGTGTGAGAGACGTGAGAAGGATCCTGCACTGAGGAGGTGGAAAGAAGAGGATTGCTCGAGGAGGCC TGGGGTCTGTGAGGCAGCGGAGCTGGGTGAAGGCTGCGGGTTCCGGCGAGGCCTGAGCTGTGCTGTCGTC ATGCCTCAAACCCGATCCCAGGCACAGGCTACAATCAGTTTTCCAAAAAGGAAGCTGTCTCGGGCATTGA ACAAAGCTAAAAACTCCAGTGATGCCAAACTAGAACCAACAAATGTCCAAACCGTAACCTGTTCTCCTCG TGTAAAAGCCCTGCCTCTCAGCCCCAGGAAACGTCTGGGCGATGACAACCTATGCAACACTCCCCATTTA CCTCCTTGTTCTCCACCAAAGCAAGGCAAGAAAGAGAATGGTCCCCCTCACTCACATACACTTAAGGGAC GAAGATTGGTATTTGACAATCAGCTGACAATTAAGTCTCCTAGCAAAAGAGAACTAGCCAAAGTTCACCA AAACAAAATACTTTCTTCAGTTAGAAAAAGTCAAGAGATCACAACAAATTCTGAGCAGAGATGTCCACTG AAGAAAGAATCTGCATGTGTGAGACTATTCAAGCAAGAAGGCACTTGCTACCAGCAAGCAAAGCTGGTCC TGAACACAGCTGTCCCAGATCGGCTGCCTGCCAGGGAAAGGGAGATGGATGTCATCAGGAATTTCTTGAG GGAACACATCTGTGGGAAAAAAGCTGGAAGCCTTTACCTTTCTGGTGCTCCTGGAACTGGAAAAACTGCC TGCTTAAGCCGGATTCTGCAAGACCTCAAGAAGGAACTGAAAGGCTTTAAAACTATCATGCTGAATTGCA TGTCCTTGAGGACTGCCCAGGCTGTATTCCCAGCTATTGCTCAGGAGATTTGTCAGGAAGAGGTATCCAG GCCAGCTGGGAAGGACATGATGAGGAAATTGGAAAAACATATGACTGCAGAGAAGGGCCCCATGATTGTG TTGGTATTGGACGAGATGGATCAACTGGACAGCAAAGGCCAGGATGTATTGTACACGCTATTTGAATGGC CATGGCTAAGCAATTCTCACTTGGTGCTGATTGGTATTGCTAATACCCTGGATCTCACAGATAGAATTCT | 112 |

TABLE 2-continued

| GENBANK ACCESSION NUMBER | SEQUENCE | SEQ ID NO: |
|---|---|---|
| | ACCTAGGCTTCAAGCTAGAGAAAAATGTAAGCCACAGCTGTTGAACTTCCCACCTTATACCAGAAATCAG<br>ATAGTCACTATTTTGCAAGATCGACTTAATCAGGTATCTAGAGATCAGGTTCTGGACAATGCTGCAGTTC<br>AATTCTGTGCCCGCAAAGTCTCTGCTGTTTCAGGAGATGTTCGCAAAGCACTGGATGTTTGCAGGAGAGC<br>TATTGAAATTGTAGAGTCAGATGTCAAAAGCCAGACTATTCTCAAACCACTGTCTGAATGTAAATCACCT<br>TCTGAGCCTCTGATTCCCAAGAGGGTTGGTCTTATTCACATATCCCAAGTCATCTCAGAAGTTGATGGTA<br>ACAGGATGACCTTGAGCCAAGAAGGAGCACAAGATTCCTTCCCTCTTCAGCAGAAGATCTTGGTTTGCTC<br>TTTGATGCTCTTGATCAGGCAGTTGAAAATCAAAGAGGTCACTCTGGGGAAGTTATATGAAGCCTACAGT<br>AAAGTCTGTCGCAAACAGCAGGTGGCGGCTGTGGACCAGTCAGAGTGTTTGTCACTTTCAGGGCTCTTGG<br>AAGCCAGGGGCATTTTAGGATTAAAGAGAAACAAGGAAACCCGTTTGACAAAGGTGTTTTTCAAGATTGA<br>AGAGAAAGAAATAGAACATGCTCTGAAAGATAAAGCTTTAATTGGAAATATCTTAGCTACTGGATTGCCT<br>TAAATTCTTCTCTTACACCCCACCCGAAAGTATTCAGCTGGCATTTAGAGAGCTACAGTCTTCATTTTAG<br>TGCTTTACACATTCGGGCCTGAAAACAAATATGACCTTTTTTACTTGAAGCCAATGAATTTTAATCTATA<br>GATTCTTTAATATTAGCACAGAATAATATCTTTGGGTCTTACTATTTTTACCCATAAAAGTGACCAGGTA<br>GACCCTTTTTAATTACATTCACTACTTCTACCACTTGTGTATCTCTAGCCAATGTGCTTGCAAGTGTACA<br>GATCTGTGTAGAGGAATGTGTGTATATTTACCTCTTCGTTTGCTCAAACATGAGTGGGTATTTTTTTGTT<br>TGTTTTTTTTGTTGTTGTTGTTTTTGAGGCGCGTCTCACCCTGTTGCCCAGGCTGGAGTGCAATGGCGCG<br>TTCTCTGCTCACTACAGCACCCGCTTCCCAGGTTGAAGTGATTCTCTTGCCTCAGCCTCCCGAGTAGCTG<br>GGATTACAGGTGCCCACCACCGCGCCCAGCTAATTTTTTAATTTTTAGTAGAGACAGGGTTTTACCATGT<br>TGGCCAGGCTGGTCTTGAACTCCTGACCCTCAAGTGATCTGCCCACCTTGGCCTCCCTAAGTGCTGGGAT<br>TATAGGCGTGAGCCACCATGCTCAGCCATTAAGGTATTTTGTTAAGAACTTTAAGTTTAGGGTAAGAAGA<br>ATGAAAATGATCCAGAAAAATGCAAGCAAGTCCACATGGAGATTTGGAGGACACTGGTTAAAGAATTTAT<br>TTCTTTGTATAGTATACTATGTTCATGGTGCAGATACTACAACATTGTGGCATTTTAGACTCGTTGAGTT<br>TCTTGGGCACTCCCAAGGGCGTTGGGGTCATAAGGAGACTATAACTCTACAGATTGTGAATATATTTATT<br>TTCAAGTTGCATTCTTTGTCTTTTTAAGCAATCAGATTTCAAGAGAGCTCAAGCTTTCAGAAGTCAATGT<br>GAAAATTCCTTCCTAGGCTGTCCCACAGTCTTTGCTGCCCTTAGATGAAGCCACTTGTTTCAAGATGACT<br>ACTTTGGGGTTGGGTTTTCATCTAAACACATTTTTCCAGTCTTATTAGATAAATTAGTCCATATGGTTGG<br>TTAATCAAGAGCCTTCTGGGTTTGGTTTGGTGGCATTAAATGG | |
| NM_031423 | GCGGAATGGGGCGGGACTTCCAGTAGGAGGCGGCAAGTTTGAAAAGTGATGACGGTTGACGTTTGCTGAT<br>TTTTGACTTTGCTTGTAGCTGCTCCCCGAACTCGCCGTCTTCCTGTCGGCGGCCGGCACTGTAGATTAAC<br>AGGAAACTTCCAAGATGGAAACTTTGTCTTTCCCCAGATATAATGTAGCTGAGATTGTGATTCATATTCG<br>CAATAAGATCTTAACAGGAGCTGATGGTAAAAACCTCACCAAGAATGATCTTTATCCAAATCCAAAGCCT<br>GAAGTCTTGCACATGATCTACATGAGAGCCTTACAAATAGTATATGGAATTCGACTGGAACATTTTTACA<br>TGATGCCAGTGAACTCTGAAGTCATGTATCCACATTTAATGGAAGGCTTCTTACCATTCAGCAATTTAGT<br>TACTCATCTGGACTCATTTTTGCCTATCTGCCGGGTGAATGACTTTGAGACTGCTGATATTCTATGTCCA<br>AAAGCAAAACGGACAAGTCGGTTTTTAAGTGGCATTATCAACTTTATTCACTTCAGAGAAGCATGCCGTG<br>AAACGTATATGGAATTTCTTTGGCAATATAAATCCTCTGCGGACAAAATGCAACAGTTAAACGCCGCACA<br>CCAGGAGGCATTAATGAAACTGGAGAGACTTGATTCTGTTCCAGTTGAAGAGCAAGAAGAGTTCAAGCAG<br>CTTTCAGATGGAATTCAGGAGCTACAACAATCACTAAATCAGGATTTTCATCAAAAAACGATAGTGCTGC<br>AAGAGGGAAATTCCCAAAAGAAGTCAAATATTTCAGAGAAAACCAAGCGTTTGAATGAACTAAAATTGTC<br>GGTGGTTTCTTTGAAAGAAATACAAGAGAGTTTGAAAACAAAAATTGTGGATTCTCCAGAGAAGTTAAAG<br>AATTATAAAGAAAAAATGAAAGATACGGTCCAGAAGCTTAAAAATGCCAGACAAGAAGTGGTGGAGAAAT<br>ATGAAATCTATGGAGACTCAGTTGACTGCCTGCCTTCATGTCAGTTGGAAGTGCAGTTATATCAAAAGAA<br>AATACAGGACCTTTCAGATAATAGGGAAAAATTAGCCAGTATCTTAAAGGAGAGCCTGAACTTGGAGGAC<br>CAAATTGAGAGTGATGAGTCAGAACTGAAGAAATTGAAGACTGAAGAAAATTCGTTCAAAAGACTGATGA<br>TTGTGAAGAAGGAAAAACTTGCCACAGCACAATTCAAAATAAATAAGAAGCATGAAGATGTTAAGCAATA<br>CAAACGCACAGTAATTGAGGATTGCAATAAAGTTCAAGAAAAAAGAGGTGCTGTCTATGAACGAGTAACC<br>ACAATTAATCAAGAAATCCAAAAAATTAAACTTGGAATTCAACAACTAAAAGATGCTGCTGAAAGGGAGA<br>AACTGAAGTCCCAGGAAATATTTCTAAACTTGAAAACTGCTTTGGAGAAATACCACGACGGTATTGAAAA<br>GGCAGCAGAGGACTCCTATGCTAAGATAGATGAGAAGACAGCTGAACTGAAGAGGAAGATGTTCAAAATG<br>TCAACCTGATTAACAAAATTACATGTCTTTTTGTAAATGGCTTGCCATCTTTTAATTTTCTATTTAGAAA<br>GAAAAGTTGAAGCGAATGGAAGTATCAGAAGTACCAAATAATGTTGGCTTCATCAGTTTTTATACACTCT<br>CATAAGTAGTTAATAAGATGAATTTAATGTAGGCTTTTATTAATTTATAATTAAAATAACTTGTGCAGCT<br>ATTCATGTCTCTACTCTGCCCCTTGTTGTAAATAGTTTGAGTAAAACAAAACTAGTTACCTTTGAAATAT<br>ATATATTTTTTTCTGTTACTATC | 113 |
| BC041846 | GGCTAGCGCGGGAGGTGGAGAAAGAGGCTTGGGCGGCCCCGCTGTAGCCGCGTGTGGGAGGACGCACGGG<br>CCTGCTTCAAAGCTTTGGGATAACAGCGCCTCCGGGGGATAATGAATGCGGAGCCTCCGTTTTCAGTCGA<br>CTTCAGATGTGTCTCCACTTTTTTCCGCTGTAGCCGCAAGGCAAGGAAACATTTCTCTTCCCGTACTGAG<br>GAGGCTGAGGAGTGCACTGGGTGTTCTTTTCTCCTCTAACCCAGAACTGCGAGACAGAGGCTGAGTCCCT<br>GTAAAGAACAGCTCCAGAAAAGCCAGGAGAGCGCAGGAGGGCATCCGGGAGGCCAGGAGGGGTTCGCTGG<br>GGCCTCAACCGCACCCACATCGGTCCCACCTGCGAGGGGGCGGGACCTCGTGGCGCTGGACCAATCAGCA<br>CCCACCTGCGCTCACCTGGCCTCCTCCCGCTGGCTCCCGGGGGCTGCGGTGCTCAAAGGGGCAAGAGCTG<br>AGCGGAACACCGGCCCGCCGTCGCGGCAGCTGCTTCACCCCTCTCTCTGCAGCCATGGGGCTCCCTCGTG<br>GACCTCTCGCGTCTCTCCTCCTTCTCCAGGTTTGCTGGCTGCAGTGCGCGGCCTCCGAGCCGTGCCGGGC<br>GGTCTTCAGGGAGGCTGAAGTGACCTTGGAGGCGGGAGGCGCGGAGCAGGAGCCCGGCCAGGCGCTGGGG<br>AAAGTATTCATGGGCTGCCCTGGGCAAGAGCCAGCTCTGTTTAGCACTGATAATGATGACTTCACTGTGC<br>GGAATGGCGAGACAGTCCAGGAAAGAAGGTCACTGAAGGAAAGGAATCCATTGAAGATCTTCCCATCCAA<br>ACGTATCTTACGAAGACACAAGAGAGATTGGGTGGTTGCTCCAATATCTGTCCCTGAAAATGGCAAGGGT<br>CCCTTCCCCCAGAGACTGAATCAGCTCAAGTCTAATAAAGATAGAGACACCAAGATTTTCTACAGCATCA<br>CGGGGCCGGGGGCAGACAGCCCCCCTGAGGGTGTCTTCGCTGTAGAGAAGGAGACAGGCTGGTTGTTGTT<br>GAATAAGCCACTGGACCGGGAGGAGATTGCCAAGTATGAGCTCTTTGGCCACGCTGTGTCAGAGAATGGT<br>GCCTCAGTGGAGGACCCCATGAACATCTCCATCATAGTGACCGACCAGAATGACCACAAGCCCAAGTTTA<br>CCCAGGACACCTTCCGAGGGAGTGTCTTAGAGGGAGTCCTACCAGGTACTTCTGTGATGCAGATGACAGC<br>CACAGATGAGGATGATGCCATCTACACCTACAATGGGGTGGTTGCTTACTCCATCCATAGCCAAGAACCA<br>AAGGACCCACACGACCTCATGTTCACAATTCACCGGAGCACAGGCACCATCAGCGTCATCTCCAGTGGCC | 114 |

TABLE 2-continued

| GENBANK ACCESSION NUMBER | SEQUENCE | SEQ ID NO: |
|---|---|---|
| | TGGACCGGGAAAAAGTCCCTGAGTACACACTGACCATCCAGGCCACAGACATGGATGGGGACGGCTCCAC | |
| | CACCACGGCAGTGGCAGTAGTGGAGATCCTTGATGCCAATGACAATGCTCCCATGTTTGACCCCCAGAAG | |
| | TACGAGGCCCATGTGCCTGAGAATGCAGTGGGCCATGAGGTGCAGAGGCTGACGGTCACTGATCTGGACG | |
| | CCCCCAACTCACCAGCGTGGCGTGCCACCTACCTTATCATGGGCGGTGACGACGGGGACCATTTTACCAT | |
| | CACCACCCACCCTGAGAGCAACCAGGGCATCCTGACAACCAGGAAGGGTTTGGATTTTGAGGCCAAAAAC | |
| | CAGCACACCCTGTACGTTGAAGTGACCAACGAGGCCCCTTTTGTGCTGAAGCTCCCAACCTCCACAGCCA | |
| | CCATAGTGGTCCACGTGGAGGATGTGAATGAGGCACCTGTGTTTGTCCCACCCTCCAAAGTCGTTGAGGT | |
| | CCAGGAGGGCATCCCCACTGGGGAGCCTGTGTGTGTCTACACTGCAGAAGACCCTGACAAGGAGAATCAA | |
| | AAGATCAGCTACCGCATCCTGAGAGACCCAGCAGGGTGGCTAGCCATGGACCCAGACAGTGGGCAGGTCA | |
| | CAGCTGTGGGCACCCTCGACCGTGAGGATGAGCAGTTTGTGAGGAACAACATCTATGAAGTCATGGTCTT | |
| | GGCCATGGACAATGGAAGCCCTCCCACCACTGGCACGGGAACCCTTCTGCTAACACTGATTGATGTCAAC | |
| | GACCATGGCCCAGTCCCTGAGCCCCGTCAGATCACCATCTGCAACCAAAGCCCTGTGCGCCAGGTGCTGA | |
| | ACATCACGGACAAGGACCTGTCTCCCCACACCTCCCCTTTCCAGGCCCAGCTCACAGATGACTCAGACAT | |
| | CTACTGGACGGCAGAGGTCAACGAGGAAGGTGACACAGTGGTCTTGTCCCTGAAGAAGTTCCTGAAGCAG | |
| | GATACATATGACGTGCACCTTTCTCTGTCTGACCATGGCAACAAAGAGCAGCTGACGGTGATCAGGGCCA | |
| | CTGTGTGCGACTGCCATGGCCATGTCGAAACCTGCCCTGGACCCTGGAAAGGAGGTTTCATCCTCCCTGT | |
| | GCTGGGGGCTGTCCTGGCTCTGCTGTTCCTCCTGCTGGTGCTGCTTTTGTTGGTGAGAAAGAAGCGGAAG | |
| | ATCAAGGAGCCCCTCCTACTCCCAGAAGATGACACCCGTGACAACGTCTTCTACTATGGCGAAGAGGGGG | |
| | GTGGCGAAGAGGACCAGGACTATGACATCACCCAGCTCCACCGAGGTCTGGAGGCCAGGCCGGAGGTGGT | |
| | TCTCCGCAATGACGTGGCACCAACCATCATCCCGACACCCATGTACCGTCCTAGGCCAGCCAACCCAGAT | |
| | GAAATCGGCAACTTTATAATTGAGAACCTGAAGGCGGCTAACACAGACCCCACAGCCCCGCCCTACGACA | |
| | CCCTCTTGGTGTTCGACTATGAGGGCAGCGGCTCCGACGCCGCGTCCCTGAGCTCCCTCACCTCCTCCGC | |
| | CTCCGACCAAGACCAAGATTACGATTATCTGAACGAGTGGGGCAGCCGCTTCAAGAAGCTGGCAGACATG | |
| | TACGGTGGCGGGGAGGACGACTAGGCGGCCTGCCTGCAGGGCTGGGGACCAAACGTCAGGCCACAGAGCA | |
| | TCTCCAAGGGGTCTCAGTTCCCCCTTCAGCTGAGGACTTCGGAGCTTGTCAGGAAGTGGCCGTAGCAACT | |
| | TGGCGGAGACAGGCTATGAGTCTGACGTTAGAGTGGTTGCTTCCTTAGCCTTTCAGGATGGAGGAATGTG | |
| | GGCAGTTTGACTTCAGCACTGAAAACCTCTCCACCTGGGCCAGGGTTGCCTCAGAGGCCAAGTTTCCAGA | |
| | AGCCTCTTACCTGCCGTAAAATGCTCAACCCTGTGTCCTGGGCCTGGGCCTGCTGTGACTGACCTACAGT | |
| | GGACTTTCTCTCTGGAATGGAACCTTCTTAGGCCTCCTGGTGCAACTTAATTTTTTTTTTTAATGCTATC | |
| | TTCAAAACGTTAGAGAAAGTTCTTCAAAAGTGCAGCCCAGAGCTGCTGGGCCCACTGGCCGTCCTGCATT | |
| | TCTGGTTTCCAGACCCCAATGCCTCCCATTCGGATGGATCTCTGCGTTTTTATACTGAGTGTGCCTAGGT | |
| | TGCCCCTTATTTTTTATTTTCCCTGTTGCGTTGCTATAGATGAAGGGTGAGGACAATCGTGTATATGTAC | |
| | TAGAACTTTTTTATTAAAGAAACTTTTCCCAAAAAAAAAAAAAAAA | |
| NM_016343 | GAGACCAGAAGCGGGCGAATTGGGCACCGGTGGCGGCTGCGGGCAGTTTGAATTAGACTCTGGGCTCCAG | 115 |
| | CCCGCCGAAGCCGCGCCAGAACTGTACTCTCCGAGAGGTCGTTTTCCCGTCCCCGAGAGCAAGTTTATTT | |
| | ACAAATGTTGGAGTAATAAAGAAGGCAGAACAAAATGAGCTGGGCTTTGGAAGAATGGAAAGAAGGGCTG | |
| | CCTACAAGAGCTCTTCAGAAAATTCAAGAGCTTGAAGGACAGCTTGACAAACTGAAGAAGGAAAAGCAGC | |
| | AAAGGCAGTTTCAGCTTGACAGTCTCGAGGCTGCGCTGCAGAAGCAAAAACAGAAGGTTGAAAATGAAAA | |
| | AACCGAGGGTACAAACCTGAAAAGGGAGAATCAAAGATTGATGGAAATATGTGAAAGTCTGGAGAAAACT | |
| | AAGCAGAAGATTTCTCATGAACTTCAAGTCAAGGAGTCACAAGTGAATTTCCAGGAAGGACAACTGAATT | |
| | CAGGCAAAAAACAAATAGAAAAACTGGAACAGGAACTTAAAAGGTGTAAATCTGAGCTTGAAAGAAGCCA | |
| | ACAAGCTGCGCAGTCTGCAGATGTCTCTCTGAATCCATGCAATACACCACAAAAAATTTTTACAACTCCA | |
| | CTAACACCAAGTCAATATTATAGTGGTTCCAAGTATGAAGATCTAAAAGAAAAATATAATAAAGAGGTTG | |
| | AAGAACGAAAAAGATTAGAGGCAGAGGTTAAAGCCTTGCAGGCTAAAAAAGCAAGCCAGACTCTTCCACA | |
| | AGCCACCATGAATCACCGCGACATTGCCCGGCATCAGGCTTCATCATCTGTGTTCTCATGGCAGCAAGAG | |
| | AAGACCCCAAGTCATCTTTCATCTAATTCTCAAAGAACTCCAATTAGGAGAGATTTCTCTGCATCTTACT | |
| | TTTCTGGGGAACAAGAGGTGACTCCAAGTCGATCAACTTTGCAAATAGGGAAAAGAGATGCTAATAGCAG | |
| | TTTCTTTGACAATTCTAGCAGTCCTCATCTTTTGGATCAATTAAAAGCGCAGAATCAAGAGCTAAGAAAC | |
| | AAGATTAATGAGTTGGAACTACGCCTGCAAGGACATGAAAAAGAAATGAAAGGCCAAGTGAATAAGTTTC | |
| | AAGAACTCCAACTCCAACTGGAGAAAGCAAAAGTGGAATTAATTGAAAAAGAGAAAGTTTTGAACAAATG | |
| | TAGGGATGAACTAGTGAGAACAACAGCACAATACGACCAGGCGTCAACCAAGTATACTGCATTGGAACAA | |
| | AAACTGAAAAAATTGACGGAAGATTTGAGTTGTCAGCGACAAAATGCAGAAAGTGCCAGATGTTCTCTGG | |
| | AACAGAAAATTAAGGAAAAAGAAAAGGAGTTTCAAGAGGAGCTCTCCCGTCAACAGCGTTCTTTCCAAAC | |
| | ACTGGACCAGGAGTGCATCCAGATGAAGGCCAGACTCACCCAGGAGTTACAGCAAGCCAAGAATATGCAC | |
| | AACGTCCTGCAGGCTGAACTGGATAAACTCACATCAGTAAAGCAACAGCTAGAAAACAATTTGGAAGAGT | |
| | TTAAGCAAAAGTTGTGCAGAGCTGAACAGGCGTTCCAGGCGAGTCAGATCAAGGAGAATGAGCTGAGGAG | |
| | AAGCATGGAGGAAATGAAGAAGGAAAACAACCTCCTTAAGAGTCACTCTGAGCAAAAGGCCAGAGAAGTC | |
| | TGCCACCTGGAGGCAGAACTCAAGAACATCAAACAGTGTTTAAATCAGAGCCAGAATTTTGCAGAAGAAA | |
| | TGAAAGCGAAGAATACCTCTCAGGAAACCATGTTAAGAGATCTTCAAGAAAAAATAAATCAGCAAGAAAA | |
| | CTCCTTGACTTTAGAAAAACTGAAGCTTGCTGTGGCTGATCTGGAAAAGCAGCGAGATTGTTCTCAAGAC | |
| | CTTTTGAAGAAAAGAGAACATCACATTGAACAACTTAATGATAAGTTAAGCAAGACAGAGAAAGAGTCCA | |
| | AAGCCTTGCTGAGTGCTTTAGAGTTAAAAAAGAAAGAATATGAAGAATTGAAAGAAGAGAAAACTCTGTT | |
| | TTCTTGTTGGAAAAGTGAAAACGAAAAACTTTTAACTCAGATGGAATCAGAAAAGGAAAACTTGCAGAGT | |
| | AAAATTAATCACTTGGAAACTTGTCTGAAGACACAGCAAATAAAAAGTCATGAATACAACGAGAGAGTAA | |
| | GAACGCTGGAGATGGACAGAGAAAACCTAAGTGTCGAGATCAGAAACCTTCACAACGTGTTAGACAGTAA | |
| | GTCAGTGGAGGTAGAGACCCAGAAACTAGCTTATATGGAGCTACAGCAGAAAGCTGAGTTCTCAGATCAG | |
| | AAACATCAGAAGGAAATAGAAAATATGTGTTTGAAGACTTCTCAGCTTACTGGGCAAGTTGAAGATCTAG | |
| | AACACAAGCTTCAGTTACTGTCAAATGAAATAATGGACAAAGACCGGTGTTACCAAGACTTGCATGCCGA | |
| | ATATGAGAGCCTCAGGGATCTGCTAAAATCCAAAGATGCTTCTCTGGTGACAAATGAAGATCATCAGAGA | |
| | AGTCTTTTGGCTTTTGATCAGCAGCCTGCCATGCATCATTCCTTTGCAAATATAATTGGAGAACAAGGAA | |
| | GCATGCCTTCAGAGAGGAGTGAATGTCGTTTAGAAGCAGACCAAAGTCCGAAAAATTCTGCCATCCTACA | |
| | AAATAGAGTTGATTCACTTGAATTTTCATTAGAGTCTCAAAAACAGATGAACTCAGACCTGCAAAAGCAG | |
| | TGTGAAGAGTTGGTGCAAATCAAAGGAGAAATAGAAGAAAATCTCATGAAAGCAGAACAGATGCATCAAA | |
| | GTTTTGTGGCTGAAACAAGTCAGCGCATTAGTAAGTTACAGGAAGACACTTCTGCTCACCAGAATGTTGT | |
| | TGCTGAAACCTTAAGTGCCCTTGAGAACAAGGAAAAAGAGCTGCAACTTTTAAATGATAAGGTAGAAACT | |

TABLE 2-continued

| GENBANK ACCESSION NUMBER | SEQUENCE | SEQ ID NO: |
|---|---|---|
| | GAGCAGGCAGAGATTCAAGAATTAAAAAGAGCAACCATCTACTTGAAGACTCTCTAAAGGAGCTACAAC | |
| | TTTTATCCGAAACCCTAAGCTTGGAGAAGAAAGAAATGAGTTCCATCATTTCTCTAAATAAAAGGGAAAT | |
| | TGAAGAGCTGACCCAAGAGAATGGGACTCTTAAGGAAATTAATGCATCCTTAAATCAAGAGAAGATGAAC | |
| | TTAATCCAGAAAAGTGAGAGTTTTGCAAACTATATAGATGAAAGGGAGAAAAGCATTTCAGAGTTATCTG | |
| | ATCAGTACAAGCAAGAAAAACTTATTTTACTACAAAGATGTGAAGAAACCGGAAATGCATATGAGGATCT | |
| | TAGTCAAAAATACAAAGCAGCACAGGAAAAGAATTCTAAATTAGAATGCTTGCTAAATGAATGCACTAGT | |
| | CTTTGTGAAAATAGGAAAAATGAGTTGGAACAGCTAAAGGAAGCATTTGCAAAGGAACACCAAGAATTCT | |
| | TAACAAAATTAGCATTTGCTGAAGAAAGAAATCAGAATCTGATGCTAGAGTTGGAGACAGTGCAGCAAGC | |
| | TCTGAGATCTGAGATGACAGATAACCAAAACAATTCTAAGAGCGAGGCTGGTGGTTTAAAGCAAGAAATC | |
| | ATGACTTTAAAGGAAGAACAAAACAAAATGCAAAAGGAAGTTAATGACTTATTACAAGAGAATGAACAGC | |
| | TGATGAAGGTAATGAAGACTAAACATGAATGTCAAAATCTAGAATCAGAACCAATTAGGAACTCTGTGAA | |
| | AGAAAGAGAGAGTGAGAGAAATCAATGTAATTTTAAACCTCAGATGGATCTTGAAGTTAAAGAAATTTCT | |
| | CTAGATAGTTATAATGCGCAGTTGGTGCAATTAGAAGCTATGCTAAGAAATAAGGAATTAAAACTTCAGG | |
| | AAAGTGAGAAGGAGAAGGAGTGCCTGCAGCATGAATTACAGACAATTAGAGGAGATCTTGAAACCAGCAA | |
| | TTTGCAAGACATGCAGTCACAAGAAATTAGTGGCCTTAAAGACTGTGAAATAGATGCGGAAGAAAAGTAT | |
| | ATTTCAGGGCCTCATGAGTTGTCAACAAGTCAAAACGACAATGCACACCTTCAGTGCTCTCTGCAAACAA | |
| | CAATGAACAAGCTGAATGAGCTAGAGAAAATATGTGAAATACTGCAGGCTGAAAAGTATGAACTCGTAAC | |
| | TGAGCTGAATGATTCAAGGTCAGAATGTATCACAGCAACTAGGAAAATGGCAGAAGAGGTAGGGAAACTA | |
| | CTAAATGAAGTTAAAATATTAAATGATGACAGTGGTCTTCTCCATGGTGAGTTAGTGGAAGACATACCAG | |
| | GAGGTGAATTTGGTGAACAACCAAATGAACAGCACCCTGTGTCTTTGGCTCCATTGGACGAGAGTAATTC | |
| | CTACGAGCACTTGACATTGTCAGACAAAGAAGTTCAAATGCACTTTGCCGAATTGCAAGAGAAATTCTTA | |
| | TCTTTACAAAGTGAACACAAAATTTTACATGATCAGCACTGTCAGATGAGCTCTAAAATGTCAGAGCTGC | |
| | AGACCTATGTTGACTCATTAAAGGCCGAAAATTTGGTCTTGTCAACGAATCTGAGAAACTTTCAAGGTGA | |
| | CTTGGTGAAGGAGATGCAGCTGGGCTTGGAGGAGGGGCTCGTTCCATCCCTGTCATCCTCTTGTGTGCCT | |
| | GACAGCTCTAGTCTTAGCAGTTTGGGAGACTCCTCCTTTTACAGAGCTCTTTTAGAACAGACAGGAGATA | |
| | TGTCTCTTTTGAGTAATTTAGAAGGGGCTGTTTCAGCAAACCAGTGCAGTGTAGATGAAGTATTTTGCAG | |
| | CAGTCTGCAGGAGGAGAATCTGACCAGGAAAGAAACCCCTTCGGCCCCAGCGAAGGGTGTTGAAGAGCTT | |
| | GAGTCCCTCTGTGAGGTGTACCGGCAGTCCCTCGAGAAGCTAGAAGAGAAAATGGAAAGTCAAGGGATTA | |
| | TGAAAAATAAGGAAATTCAAGAGCTCGAGCAGTTATTAAGTTCTGAAAGGCAAGAGCTTGACTGCCTTAG | |
| | GAAGCAGTATTTGTCAGAAAATGAACAGTGGCAACAGAAGCTGACAAGCGTGACTCTGGAGATGGAGTCC | |
| | AAGTTGGCGGCAGAAAAGAAACAGACGGAACAACTGTCACTTGAGCTGGAAGTAGCACGACTCCAGCTAC | |
| | AAGGTCTGGACTTAAGTTCTCGGTCTTTGCTTGGCATCGACACAGAAGATGCTATTCAAGGCCGAAATGA | |
| | GAGCTGTGACATATCAAAAGAACATACTTCAGAAACTACAGAAAGAACACCAAAGCATGATGTTCATCAG | |
| | ATTTGTGATAAAGATGCTCAGCAGGACCTCAATCTAGACATTGAGAAAATAACTGAGACTGGTGCAGTGA | |
| | AACCCACAGGAGAGTGCTCTGGGGAACAGTCCCCAGATACCAATTATGAGCCTCCAGGGGAAGATAAAAC | |
| | CCAGGGCTCTTCAGAATGCATTTCTGAATTGTCATTTTCTGGTCCTAATGCTTTGGTACCTATGGATTTC | |
| | CTGGGGAATCAGGAAGATATCCATAATCTTCAACTGCGGGTAAAAGAGACATCAAATGAGAATTTGAGAT | |
| | TACTTCATGTGATAGAGGACCGTGACAGAAAAGTTGAAAGTTTGCTAAATGAAATGAAAGAATTAGACTC | |
| | AAAACTCCATTTACAGGAGGTACAACTAATGACCAAAATTGAAGCATGCATAGAATTGGAAAAAATAGTT | |
| | GGGGAACTTAAGAAAGAAAACTCAGATTTAAGTGAAAAATTGGAATATTTTTCTTGTGATCACCAGGAGT | |
| | TACTCCAGAGAGTAGAAACTTCTGAAGGCCTCAATTCTGATTTAGAAATGCATGCAGATAAATCATCACG | |
| | TGAAGATATTGGAGATAATGTGGCCAAGGTGAATGACAGCTGGAAGGAGAGATTTCTTGATGTGGAAAAT | |
| | GAGCTGAGTAGGATCAGATCGGAGAAAGCTAGCATTGAGCATGAAGCCCTCTACCTGGAGGCTGACTTAG | |
| | AGGTAGTTCAAACAGAGAAGCTATGTTTAGAAAAAGACAATGAAAATAAGCAGAAGGTTATTGTCTGCCT | |
| | TGAAGAAGAACTCTCAGTGGTCACAAGTGAGAGAAACCAGCTTCGTGGAGAATTAGATACTATGTCAAAA | |
| | AAAACCACGGCACTGGATCAGTTGTCTGAAAAAATGAAGGAGAAAACACAAGAGCTTGAGTCTCATCAAA | |
| | GTGAGTGTCTCCATTGCATTCAGGTGGCAGAGGCAGAGGTGAAGGAAAAGACGGAACTCCTTCAGACTTT | |
| | GTCCTCTGATGTGAGTGAGCTGTTAAAAGACAAAACTCATCTCCAGGAAAAGCTGCAGAGTTTGGAAAAG | |
| | GACTCACAGGCACTGTCTTTGACAAAATGTGAGCTGGAAAACCAAATTGCACAACTGAATAAAGAGAAAG | |
| | AATTGCTTGTCAAGGAATCTGAAAGCCTGCAGGCCAGACTGAGTGAATCAGATTATGAAAAGCTGAATGT | |
| | CTCCAAGGCCTTGGAGGCCGCACTGGTGGAGAAAGGTGAGTTCGCATTGAGGCTGAGCTCAACACAGGAG | |
| | GAAGTGCATCAGCTGAGAAGAGGCATCGAGAAACTGAGAGTTCGCATTGAGGCCGATGAAAAGAAGCAGC | |
| | TGCACATCGCAGAGAAACTGAAAGAACGCGAGCGGGAGAATGATTCACTTAAGGATAAAGTTGAGAACCT | |
| | TGAAAGGGAATTGCAGATGTCAGAAGAAAACCAGGAGCTAGTGATTCTTGATGCCGAGAATTCCAAAGCA | |
| | GAAGTAGAGACTCTAAAAACACAAATAGAAGAGATGGCCAGAAGCCTGAAAGTTTTTGAATTAGACCTTG | |
| | TCACGTTAAGGTCTGAAAAAGAAAATCTGACAAAACAAATACAAGAAAAACAAGGTCAGTTGTCAGAACT | |
| | AGACAAGTTACTCTCTTCATTTAAAAGTCTGTTAGAAGAAAAGGAGCAAGCAGAGATACAGATCAAAGAA | |
| | GAATCTAAAACTGCAGTGGAGATGCTTCAGAATCAGTTAAAGGAGCTAAATGAGGCAGTAGCAGCCTTGT | |
| | GTGGTGACCAAGAAATTATGAAGGCCACAGAACAGAGTCTAGACCCACCAATAGAGGAAGAGCATCAGCT | |
| | GAGAAATAGCATTGAAAAGCTGAGAGCCCGCCTAGAAGCTGATGAAAAGAAGCAGCTCTGTGTCTTACAA | |
| | CAACTGAAGGAAAGTGAGCATCATGCAGATTTACTTAAGGGTAGAGTGGAGAACCTTGAAAGAGAGCTAG | |
| | AGATAGCCAGGACAAACCAAGAGCATGCAGCTCTTGAGGCAGAGAATTCCAAAGGAGAGGTAGAGACCCT | |
| | AAAAGCAAAAATAGAAGGGATGACCCAAAGTCTGAGAGGTCTGGAATTAGATGTTGTTACTATAAGGTCA | |
| | GAAAAAGAAAATCTGACAAATGAATTACAAAAAGAGCAAGAGCGAATATCTGAATTAGAAATAATAAATT | |
| | CATCATTTGAAAATATTTTGCAAGAAAAAGAGCAAGAGAAAGTACAGATGAAAGAAAAATCAAGCACTGC | |
| | CATGGAGATGCTTCAAACACAATTAAAAGAGCTCAATGAGAGAGTGGCAGCCCTGCATAATGACCAAGAA | |
| | GCCTGTAAGGCCAAAGAGCAGAATCTTAGTAGTCAAGTAGAGTGTCTTGAACTTGAGAAGGCTCAGTTGC | |
| | TACAAGGCCTTGATGAGGCCAAAAATAATTATATTGTTTTGCAATCTTCAGTGAATGGCCTCATTCAAGA | |
| | AGTAGAAGATGGCAAGCAGAAACTGGAGAAGAAGGATGAAGAAATCAGTAGACTGAAAAATCAAATTCAA | |
| | GACCAAGAGCAGCTTGTCTCTAAACTGTCCCAGGTGGAAGGAGAGCACCAACTTTGGAAGGAGCAAAACT | |
| | TAGAACTGAGAAATCTGACAGTGGAATTGGAGCAGAAGATCCAAGTGCTACAATCCAAAAATGCCTCTTT | |
| | GCAGGACACATTAGAAGTGCTGCAGAGTTCTTACAAGAATCTAGAGAATGAGCTTGAATTGACAAAAATG | |
| | GACAAAATGTCCTTTGTTGAAAAAGTAAACAAAATGACTGCAAAGGAAACTGAGCTGCAGAGGGAAATGC | |
| | ATGAGATGGCACAGAAAACAGCAGAGCTGCAAGAAGAACTCAGTGGAGAGAAAAATAGGCTAGCTGGAGA | |
| | GTTGCAGTTACTGTTGGAAGAAATAAAGAGCAGCAAAGATCAATTGAAGGAGCTCACACTAGAAAATAGT | |
| | GAATTGAAGAAGAGCCTAGATTGCATGCACAAAGACCAGGTGGAAAAGGAAGGGAAAGTGAGAGAGGAAA | |

TABLE 2-continued

| GENBANK ACCESSION NUMBER | SEQUENCE | SEQ ID NO: |
|---|---|---|
| | TAGCTGAATATCAGCTACGGCTTCATGAAGCTGAAAAGAAACACCAGGCTTTGCTTTTGGACACAAACAA<br>ACAGTATGAAGTAGAAATCCAGACATACCGAGAGAAATTGACTTCTAAAGAAGAATGTCTCAGTTCACAG<br>AAGCTGGAGATAGACCTTTTAAAGTCTAGTAAAGAAGAGCTCAATAATTCATTGAAAGCTACTACTCAGA<br>TTTTGGAAGAATTGAAGAAAACCAAGATGGACAATCTAAAATATGTAAATCAGTTGAAGAAGGAAAATGA<br>ACGTGCCCAGGGGAAAATGAAGTTGTTGATCAAATCCTGTAAACAGCTGGAAGAGGAAAAGGAGATACTG<br>CAGAAAGAACTCTCTCAACTTCAAGCTGCACAGGAGAAGCAGAAAACAGGTACTGTTATGGATACCAAGG<br>TCGATGAATTAACAACTGAGATCAAAGAACTGAAAGAAACTCTTGAAGAAAAAACCAAGGAGGCAGATGA<br>ATACTTGGATAAGTACTGTTCCTTGCTTATAAGCCATGAAAAGTTAGAGAAAGCTAAAGAGATGTTAGAG<br>ACACAAGTGGCCCATCTGTGTTCACAGCAATCTAAACAAGATTCCCGAGGGTCTCCTTTGCTAGGTCCAG<br>TTGTTCCAGGACCATCTCCAATCCCTTCTGTTACTGAAAAGAGGTTATCATCTGGCCAAAATAAAGCTTC<br>AGGCAAGAGGCAAAGATCCAGTGGAATATGGGAGAATGGTAGAGGACCAACACCTGCTACCCCAGAGAGC<br>TTTTCTAAAAAAAGCAAGAAAGCAGTCATGAGTGGTATTCACCCTGCAGAAGACACGGAAGGTACTGAGT<br>TTGAGCCAGAGGGACTTCCAGAAGTTGTAAAGAAAGGGTTTGCTGACATCCCGACAGGAAAGACTAGCCC<br>ATATATCCTGCGAAGAACAACCATGGCAACTCGGACCAGCCCCCGCCTGGCTGCACAGAAGTTAGCGCTA<br>TCCCCACTGAGTCTCGGCAAAGAAAATCTTGCAGAGTCCTCCAAACCAACAGCTGGTGGCAGCAGATCAC<br>AAAAGGTCAAAGTTGCTCAGCGGAGCCCAGTAGATTCAGGCACCATCCTCCGAGAACCCACCACGAAATC<br>CGTCCCAGTCAATAATCTTCCTGAGAGAAGTCCGACTGACAGCCCCAGAGAGGGCCTGAGGGTCAAGCGA<br>GGCCGACTTGTCCCCAGCCCCAAAGCTGGACTGGAGTCCAACGGCAGTGAGAACTGTAAGGTCCAGTGAA<br>GGCACTTTGTGTGTCAGTACCCCTGGGAGGTGCCAGTCATTGAATAGATAAGGCTGTGCCTACAGGACTT<br>CTCTTTAGTCAGGGCATGCTTTATTAGTGAGGAGAAAACAATTCCTTAGAAGTCTTAAATATATTGTACT<br>CTTTAGATCTCCCATGTGTAGGTATTGAAAAAGTTTGGAAGCACTGATCACCTGTTAGCATTGCCATTCC<br>TCTACTGCAATGTAAATAGTATAAAGCTATGTATATAAAGCTTTTTGGTAATATGTTACAATTAAAATGA<br>CAAGCACTATATCACAATCTCTGTTTGTATGTGGGTTTTACACTAAAAAAATGCAAAACACATTTTATTC<br>TTCTAATTAACAGCTCCTAGGAAAATGTAGACTTTTGCTTTATGATATTCTATCTGTAGTATGAGGCATG<br>GAATAGTTTTGTATCGGGAATTTCTCAGAGCTGAGTAAAATGAAGGAAAAGCATGTTATGTGTTTTTAAG<br>GAAAATGTGCACACATATACATGTAGGAGTGTTTATCTTTCTCTTACAATCTGTTTTAGACATCTTTGCT<br>TATGAAACCTGTACATATGTGTGTGTGGGTATGTGTTTATTTCCAGTGAGGGCTGCAGGCTTCCTAGAGG<br>TGTGCTATACCATGCGTCTGTCGTTGTGCTTTTTTCTGTTTTTAGACCAATTTTTTACAGTTCTTTGGTA<br>AGCATTGTCGTATCTGGTGATGGATTAACATATAGCCTTTGTTTTCTAATAAAATAGTCGCCTTCGTTTT<br>CTGTAAAAAAAAAAAAAAAAAAAAA | |
| AB091343 | GGCACGAGGGGCCGACGCGAGCGCCGCGCTTCGCTTCAGCTGCTAGCTGGCCCAAGGGAGGCGACCGCGG<br>AGGGTGGCGAGGGGCGGCCAGGACCCGCAGCCCCGGGGCCGGGCCGGTCCGGACCGCCAGGGAGGGCAGG<br>TCAGTGGGCAGATCGCGTCCGCGGGATTCAATCTCTGCCCGCTCTGATAACAGTCCTTTTCCCTGGCGCT<br>CACTTCGTGCCTGGCACCCGGCTGGGCGCCTCAAGACCGTTGTCTCTTCGATCGCTTCTTTGGACTTGGC<br>GACCATTTCAGAGATGTCTTCCAGAAGTACCAAAGATTTAATTAAAAGTAAGTGGGGATCGAAGCCTAGT<br>AACTCCAAATCCGAAACTACATTAGAAAAATTAAAGGGAGAAATTGCACACTTAAAGACATCAGTGGATG<br>AAATCACAAGTGGGAAAGGAAAGCTGACTGATAAAGAGAGACACAGACTTTTGGAGAAAATTCGAGTCCT<br>TGAGGCTGAGAAGGAGAAGAATGCTTATCAACTCACAGAGAAGGACAAAGAAATACAGCGACTGAGAGAC<br>CAACTGAAGGCCAGATATAGTACTACCGCATTGCTTGAACAGCTGGAAGAGACAACGAGAGAAGGAGAAA<br>GGAGGGAGCAGGTGTTGAAAGCCTTATCTGAAGAGAAAGACGTATTGAAACAACAGTTGTCTGCTGCAAC<br>CTCACGAATTGCTGAACTTGAAAGCAAAACCAATACACTCCGTTTATCACAGACTGTGGCTCCAAACTGC<br>TTCAACTCATCAATAAATAATATTCATGAAATGGAAATACAGCTGAAAGATGCTCTGGAGAAAAATCAGC<br>AGTGGCTCGTGTATGATCAGCAGCGGGAAGTCTATGTAAAAGGACTTTTAGCAAAGATCTTTGAGTTGGA<br>AAAGAAAACGGAAACAGCTGCTCATTCACTCCCACAGCAGACAAAAAAGCCTGAATCAGAAGGTTATCTT<br>CAAGAAGAGAAGCAGAAATGTTACAACGATCTCTTGGCAAGTGCAAAAAAAGATCTTGAGGTTGAACGAC<br>AAACCATAACTCAGCTGAGTTTTGAACTGAGTGAATTTCGAAGAAAATATGAAGAAACCCAAAAAGAAGT<br>TCACAATTTAAATCAGCTGTTGTATTCACAAAGAAGGGCAGATGTGCAACATCTGGAAGATGATAGGCAT<br>AAAACAGAGAAGATACAAAAACTCAGGGAAGAGAATGATATTGCTAGGGGAAAACTTGAAGAAGAGAAGA<br>AGAGATCCGAAGAGCTCTTATCTCAGGTCCAGTTTCTTTACACATCTCTGCTAAAGCAGCAAGAAGAACA<br>AACAAGGGTAGCTCTGTTGGAACAACAGATGCAGGCATGTACTTTAGACTTTGAAAATGAAAAACTCGAC<br>CGTCAACATGTGCAGCATCAATTGCATGTAATTCTTAAGGAGCTCCGAAAAGCAAGAAATCAAATAACAC<br>AGTTGGAATCCTTGAAACAGCTTCATGAGTTTGCCATCACAGAGCCATTAGTCACTTTCCAAGGAGAGAC<br>TGAAAACAGAGAAAAAGTTGCCGCCTCACCAAAAAGTCCCACTGCTGCACTCAATGAAAGCCTGGTGGAA<br>TGTCCCAAGTGCAATATACAGTATCCAGCCACTGAGCATCGCGATCTGCTTGTCCATGTGGAATACTGTT<br>CAAAGTAGCAAAATAAGTATTTGTTTTGATATTAAAAGATTCAATACTGTATTTTCTGTTAGCTTGTGGG<br>CATTTTGAATTATATATTTCACATTTTGCATAAAACTGCCTATCTACCTTTGACACTCCAGCATGCTAGT<br>GAATCATGTATCTTTTAGGCTGCTGTGCATTTCTCTTGGCAGTGATACCTCCCTGACATGGTTCATCATC<br>AGGCTGCAATGACAGAATGTGGTGAGCAGCGTCTACTGAGACTACTAACATTTTGCACTGTCAAAATACT<br>TGGTGAGGAAAAGATAGCTCAGGTTATTGCTAATGGGTTAATGCACCAGCAAGCAAAATATTTTATGTTT<br>TGGGGGTTTGAAAAATCAAAGATAATTAACCAAGGATCTTAACTGTGTTCGCATTTTTTATCCAAGCACT<br>TAGAAAACCTACAATCCTAATTTTGATGTCCATTGTTAAGAGGTGGTGATAGATACTATTTTTTTTTTCA<br>TATTGTATAGCGGTTATTAGAAAAGTTGGGGATTTTCTTGATCTTTATTGCTGCTTACCATTGAAACTTA<br>ACCCAGCTGTGTTCCCCAACTCTGTTCTGCGCACGAAACAGTATCTGTTTGAGGCATAATCTTAAGTGGC<br>CACACACAATGTTTTCTCTTATGTTATCTGGCAGTAACTGTAACTTGAATTACATTAGCACATTCTGCTT<br>AGCTAAAATTGTTAAAATAAACTTTAATAAACCCATGTAGCCCTCTCATTTGATTGACAGTATTTTAGTT<br>ATTTTTGGCATTCTTAAAGCTGGGCAATGTAATGATCAGATCTTTGTTTGTCTGAACAGGTATTTTTATA<br>CATGCTTTTTGTAAACCAAAAACTTTTAAATTTCTTCAGGTTTTCTAACATGCTTACCACTGGGCTACTG<br>TAAATGAGAAAAGAATAAAATTATTTAATGTTTTAAAAAAAAAAAAAAA | 116 |
| BC006428 | GGCGGCTGAGCCTGAGCGGGGATGTAGAGGCGGCGGCAGCAGAGGCGGCACTGGCGGCAAGAGCAGACGC<br>CCGAGCCGAGCGAGAAGAGCGGCAGAGCCTTATCCCCTGAAGCCGGGCCCCGCGTCCCAGCCCTGCCCAG<br>CCCGCGCCCAGCCATGCGCGCCGCCTGCTGAGTCCGGGCGCCGCACGCTGAGCCCTCCGCCCGCGAGCCG<br>CGCTCAGCTCGGGGGTGATTAGTTGCTTTTTGTTGTTTTTTAATTTGGGCCGCGGGGAGGGGGAGGAGGG<br>GCAGGTGCTGCAGGCTCCCCCCCCTCCCCGCCTCGGGCCAGCCGCGGCGGCGCGACTCGGGCTCCGGACC<br>CGGGCACTGCTGGCGGCTGGAGCGGAGCGCACCGCGGCGGTGGTGCCCAGAGCGGAGCGCAGCTCCCTGC | 117 |

TABLE 2-continued

| GENBANK ACCESSION NUMBER | SEQUENCE | SEQ ID NO: |
|---|---|---|
| | CCCGCCCCTCCCCCTCGGCCTCGCGGCGACGGCGGCGGTGGCGGCTTGGACGACTCGGAGAGCCGAGTGA | |
| | AGACATTTCCACCTGGACACCTGACCATGTGCCTGCCCTGAGCAGCGAGGCCCACCAGGCATCTCTGTTG | |
| | TGGGCAGCAGGGCCAGGTCCTGGTCTGTGGACCCTCGGCAGTTGGCAGGCTCCCTCTGCAGTGGGGTCTG | |
| | GGCCTCGGCCCCACCATGTCGAGCCTCGGCGGTGGCTCCCAGGATGCCGGCGGCAGTAGCAGCAGCAGCA | |
| | CCAATGGCAGCGGTGGCAGTGGCAGCAGTGGCCCAAAGGCAGGAGCAGCAGACAAGAGTGCAGTGGTGGC | |
| | TGCCGCCGCACCAGCCTCAGTGGCAGATGACACACCACCCCCCGAGCGTCGGAACAAGAGCGGTATCATC | |
| | AGTGAGCCCCTCAACAAGAGCCTGCGCCGCTCCCGCCCGCTCTCCCACTACTCTTCTTTTGGCAGCAGTG | |
| | GTGGTAGTGGCGGTGGCAGCATGATGGGCGGAGAGTCTGCTGACAAGGCCACTGCGGCTGCAGCCGCTGC | |
| | CTCCCTGTTGGCCAATGGGCATGACCTGGCGGCGGCCATGGCGGTGGACAAAAGCAACCCTACCTCAAAG | |
| | CACAAAAGTGGTGCTGTGGCCAGCCTGCTGAGCAAGGCAGAGCGGGCCACGGAGCTGGCAGCCGAGGGAC | |
| | AGCTGACGCTGCAGCAGTTTGCGCAGTCCACAGAGATGCTGAAGCGCGTGGTGCAGGAGCATCTCCCGCT | |
| | GATGAGCGAGGCGGGTGCTGGCCTGCCTGACATGGAGGCTGTGGCAGGTGCCGAAGCCCTCAATGGCCAG | |
| | TCCGACTTCCCCTACCTGGGCGCTTTCCCCATCAACCCAGGCCTCTTCATTATGACCCCGGCAGGTGTGT | |
| | TCCTGGCCGAGAGCGCGCTGCACATGGCGGGCCTGGCTGAGTACCCCATGCAGGGAGAGCTGGCCTCTGC | |
| | CATCAGCTCCGGCAAGAAGAAGCGGAAACGCTGCGGCATGTGCGCGCCCTGCCGGCGGCGCATCAACTGC | |
| | GAGCAGTGCAGCAGTTGTAGGAATCGAAAGACTGGCCATCAGATTTGCAAATTCAGAAAATGTGAGGAAC | |
| | TCAAAAAGAAGCCTTCCGCTGCTCTGGAGAAGGTGATGCTTCCGACGGGAGCCGCCTTCCGGTGGTTTCA | |
| | GTGACGGCGGCGGAACCCAAAGCTGCCCTCTCCGTGCAATGTCACTGCTCGTGTGGTCTCCAGCAAGGGA | |
| | TTCGGGCGAAGACAAACGGATGCACCCGTCTTTAGAACCAAAAATATTCTCTCACAGATTTCATTCCTGT | |
| | TTTTATATATATATTTTTTGTTGTCGTTTTAACATCTCCACGTCCCTAGCATAAAAAGAAAAAGAAAAAA | |
| | ATTTAAACTGCTTTTTCGGAAGAACAACAACAAAAAAGAGGTAAAGACGAATCTATAAAGTACCGAGACT | |
| | TCCTGGGCAAAGAATGGACAATCAGTTTCCTTCCTGTGTCGATGTCGATGTTGTCTGTGCAGGAGATGCA | |
| | GTTTTTGTGTAGAGAATGTAAATTTTCTGTAACCTTTTGAAATCTAGTTACTAATAAGCACTACTGTAAT | |
| | TTAGCACAGTTTAACTCCACCCTCATTTAAACTTCCTTTGATTCTTTCCGACCATGAAATAGTGCATAGT | |
| | TTGCCTGGAGAATCCACTCACGTTCATAAAGAGAATGTTGATGGCGCCGTGTAGAAGCCGCTCTGTATCC | |
| | ATCCACGCGTGCAGAGCTGCCAGCAGGGAGCTCACAGAAGGGGAGGGAGCACCAGGCCAGCTGAGCTGCA | |
| | CCCACAGTCCCGAGACTGGGATCCCCCACCCCAACAGTGATTTTGGAAAAAAAAAATGAAAGTTCTGTTCG | |
| | TTTATCCATTGCGATCTGGGGAGCCCCATCTCGATATTTCCAATCCTGGCTACTTTTCTTAGAGAAAATA | |
| | AGTCCTTTTTTTCTGGCCTTGCTAATGGCAACAGAAGAAAGGGCTTCTTTGCGTGGTCCCCTGCTGGTGG | |
| | GGGTGGGTCCCCAGGGGGCCCCCTGCGGCCTGGGCCCCCCTGCCCACGGCCAGCTTCCTGCTGATGAACA | |
| | TGCTGTTTGTATTGTTTTAGGAAACCAGGCTGTTTTGTGAATAAAACGAATGCATGTTTGTGTCACGAAA | |
| | AAAAAAAAAAAAAAAAAAAAAAAAAAAAAAAAAAAAAAAAAAA | |
| NM_005228 | CCCCGGCGCAGCGCGGCCGCAGCAGCCTCCGCCCCCCGCACGGTGTGAGCGCCCGACGCGGCCGAGGCGG | 118 |
| | CCGGAGTCCCGAGCTAGCCCCGGCGGCCGCCGCCGCCCAGACCGGACGACAGGCCACCTCGTCGGCGTCC | |
| | GCCCGAGTCCCCGCCTCGCCGCCAACGCCACAACCACCGCGCACGGCCCCCTGACTCCGTCCAGTATTGA | |
| | TCGGGAGAGCCGGAGCGAGCTCTTCGGGGAGCAGCGATGCGACCCTCCGGGACGGCCGGGGCAGCGCTCC | |
| | TGGCGCTGCTGGCTGCGCTCTGCCCGGCGAGTCGGGCTCTGGAGGAAAAGAAAGTTTGCCAAGGCACGAG | |
| | TAACAAGCTCACGCAGTTGGGCACTTTTGAAGATCATTTTCTCAGCCTCCAGAGGATGTTCAATAACTGT | |
| | GAGGTGGTCCTTGGGAATTTGGAAATTACCTATGTGCAGAGGAATTATGATCTTTCCTTCTTAAAGACCA | |
| | TCCAGGAGGTGGCTGGTTATGTCCTCATTGCCCTCAACACAGTGGAGCGAATTCCTTTGGAAAACCTGCA | |
| | GATCATCAGAGGAAATATGTACTACGAAAATTCCTATGCCTTAGCAGTCTTATCTAACTATGATGCAAAT | |
| | AAAACCGGACTGAAGGAGCTGCCCATGAGAAATTTACAGGAAATCCTGCATGGCGCCGTGCGGTTCAGCA | |
| | ACAACCCTGCCCTGTGCAACGTGGAGAGCATCCAGTGGCGGGACATAGTCAGCAGTGACTTTCTCAGCAA | |
| | CATGTCGATGGACTTCCAGAACCACCTGGGCAGCTGCCAAAAGTGTGATCCAAGCTGTCCCAATGGGAGC | |
| | TGCTGGGGTGCAGGAGAGGAGAACTGCCAGAAACTGACCAAAATCATCTGTGCCCAGCAGTGCTCCGGGC | |
| | GCTGCCGTGGCAAGTCCCCCAGTGACTGCTGCCACAACCAGTGTGCTGCAGGCTGCACAGGCCCCCGGGA | |
| | GAGCGACTGCCTGGTCTGCCGCAAATTCCGAGACGAAGCCACGTGCAAGGACACCTGCCCCCCACTCATG | |
| | CTCTACAACCCCACCACGTACCAGATGGATGTGAACCCCGAGGGCAAATACAGCTTTGGTGCCACCTGCG | |
| | TGAAGAAGTGTCCCCGTAATTATGTGGTGACAGATCACGGCTCGTGCGTCCGAGCCTGTGGGGCCGACAG | |
| | CTATGAGATGGAGGAAGACGGCGTCCGCAAGTGTAAGAAGTGCGAAGGGCCTTGCCGCAAAGTGTGTAAC | |
| | GGAATAGGTATTGGTGAATTTAAAGACTCACTCTCCATAAATGCTACGAATATTAAACACTTCAAAAACT | |
| | GCACCTCCATCAGTGGCGATCTCCACATCCTGCCGGTGGCATTTAGGGGTGACTCCTTCACACATACTCC | |
| | TCCTCTGGATCCACAGGAACTGGATATTCTGAAAACCGTAAAGGAAATCACAGGGTTTTTGCTGATTCAG | |
| | GCTTGGCCTGAAAACAGGACGGACCTCCATGCCTTTGAGAACCTAGAAATCATACGCGGCAGGACCAAGC | |
| | AACATGGTCAGTTTTCTCTTGCAGTCGTCAGCCTGAACATAACATCCTTGGGATTACGCTCCCTCAAGGA | |
| | GATAAGTGATGGAGATGTGATAATTTCAGGAAACAAAAATTTGTGCTATGCAAATACAATAAACTGGAAA | |
| | AAACTGTTTGGGACCTCCGGTCAGAAAACCAAAATTATAAGCAACAGAGGTGAAAACAGCTGCAAGGCCA | |
| | CAGGCCAGGTCTGCCATGCCTTGTGCTCCCCCGAGGGCTGCTGGGGCCCGGAGCCCAGGGACTGCGTCTC | |
| | TTGCCGGAATGTCAGCCGAGGCAGGGAATGCGTGGACAAGTGCAACCTTCTGGAGGGTGAGCCAAGGGAG | |
| | TTTGTGGAGAACTCTGAGTGCATACAGTGCCACCCAGAGTGCCTGCCTCAGGCCATGAACATCACCTGCA | |
| | CAGGACGGGGACCAGACAACTGTATCCAGTGTGCCCACTACATTGACGGCCCCCACTGCGTCAAGACCTG | |
| | CCCGGCAGGAGTCATGGGAGAAAACAACACCCTGGTCTGGAAGTACGCAGACGCCGGCCATGTGTGCCAC | |
| | CTGTGCCATCCAAACTGCACCTACGGATGCACTGGGCCAGGTCTTGAAGGCTGTCCAACGAATGGGCCTA | |
| | AGATCCCGTCCATCGCCACTGGGATGGTGGGGGCCCTCCTCTTGCTGCTGGTGGTGGCCCTGGGGATCGG | |
| | CCTCTTCATGCGAAGGCGCCACATCGTTCGGAAGCGCACGCTGCGGAGGCTGCTGCAGGAGAGGGAGCTT | |
| | GTGGAGCCTCTTACACCCAGTGGAGAAGCTCCCAACCAAGCTCTCTTGAGGATCTTGAAGGAAACTGAAT | |
| | TCAAAAAGATCAAAGTGCTGGGCTCCGGTGCGTTCGGCACGGTGTATAAGGGACTCTGGATCCCAGAAGG | |
| | TGAGAAAGTTAAAATTCCCGTCGCTATCAAGGAATTAAGAGAAGCAACATCTCCGAAAGCCAACAAGGAA | |
| | ATCCTCGATGAAGCCTACGTGATGGCCAGCGTGGACAACCCCCACGTGTGCCGCCTGCTGGGCATCTGCC | |
| | TCACCTCCACCGTGCAGCTCATCACGCAGCTCATGCCCTTCGGCTGCCTCCTGGACTATGTCCGGGAACA | |
| | CAAAGACAATATTGGCTCCCAGTACCTGCTCAACTGGTGTGTGCAGATCGCAAAGGGCATGAACTACTTG | |
| | GAGGACCGTCGCTTGGTGCACCGCGACCTGGCAGCCAGGAACGTACTGGTGAAAACACCGCAGCATGTCA | |
| | AGATCACAGATTTTGGGCTGGCCAAACTGCTGGGTGCGGAAGAGAAAGAATACCATGCAGAAGGAGGCAA | |
| | AGTGCCTATCAAGTGGATGGCATTGGAATCAATTTTACACAGAATCTATACCCACCAGAGTGATGTCTGG | |
| | AGCTACGGGGTGACCGTTTGGGAGTTGATGACCTTTGGATCCAAGCCATATGACGGAATCCCTGCCAGCG | |

TABLE 2-continued

| GENBANK ACCESSION NUMBER | SEQUENCE | SEQ ID NO: |
|---|---|---|
| | AGATCTCCTCCATCCTGGAGAAAGGAGAACGCCTCCCTCAGCCACCCATATGTACCATCGATGTCTACAT<br>GATCATGGTCAAGTGCTGGATGATAGACGCAGATAGTCGCCCAAAGTTCCGTGAGTTGATCATCGAATTC<br>TCCAAAATGGCCCGAGACCCCCAGCGCTACCTTGTCATTCAGGGGGATGAAAGAATGCATTTGCCAAGTC<br>CTACAGACTCCAACTTCTACCGTGCCCTGATGGATGAAGAAGACATGGACGACGTGGTGGATGCCGACGA<br>GTACCTCATCCCACAGCAGGGCTTCTTCAGCAGCCCCTCCACGTCACGGACTCCCCTCCTGAGCTCTCTG<br>AGTGCAACCAGCAACAATTCCACCGTGGCTTGCATTGATAGAAATGGGCTGCAAAGCTGTCCCATCAAGG<br>AAGACAGCTTCTTGCAGCGATACAGCTCAGACCCCACAGGCGCCTTGACTGAGGACAGCATAGACGACAC<br>CTTCCTCCCAGTGCCTGAATACATAAACCAGTCCGTTCCCAAAAGGCCCGCTGGCTCTGTGCAGAATCCT<br>GTCTATCACAATCAGCCTCTGAACCCCGCGCCCAGCAGAGACCCACACTACCAGGACCCCCACAGCACTG<br>CAGTGGGCAACCCCGAGTATCTCAACACTGTCCAGCCCACCTGTGTCAACAGCACATTCGACAGCCCTGC<br>CCACTGGGCCCAGAAAGGCAGCCACCAAATTAGCCTGGACAACCCTGACTACCAGCAGGACTTCTTTCCC<br>AAGGAAGCCAAGCCAAATGGCATCTTTAAGGGCTCCACAGCTGAAAATGCAGAATACCTAAGGGTCGCGC<br>CACAAAGCAGTGAATTTATTGGAGCATGACCACGGAGGATAGTATGAGCCCTAAAAATCCAGACTCTTTC<br>GATACCCAGGACCAAGCCACAGCAGGTCCTCCATCCCAACAGCCATGCCCGCATTAGCTCTTAGACCCAC<br>AGACTGGTTTTGCAACGTTTACACCGACTAGCCAGGAAGTACTTCCACCTCGGGCACATTTTGGGAAGTT<br>GCATTCCTTTGTCTTCAAACTGTGAAGCATTTACAGAAACGCATCCAGCAAGAATATTGTCCCTTTGAGC<br>AGAAATTTATCTTTCAAAGAGGTATATTTGAAAAAAAAAAAAAGTATATGTGAGGATTTTTATTGATTGG<br>GGATCTTGGAGTTTTTCATTGTCGCTATTGATTTTTACTTCAATGGGCTCTTCCAACAAGGAAGAAGCTT<br>GCTGGTAGCACTTGCTACCCTGAGTTCATCCAGGCCCAACTGTGAGCAAGGAGCACAAGCCACAAGTCTT<br>CCAGAGGATGCTTGATTCCAGTGGTTCTGCTTCAAGGCTTCCACTGCAAAACACTAAAGATCCAAGAAGG<br>CCTTCATGGCCCCAGCAGGCCGGATCGGTACTGTATCAAGTCATGGCAGGTACAGTAGGATAAGCCACTC<br>TGTCCCTTCCTGGGCAAAGAAGAAACGGAGGGGATGGAATTCTTCCTTAGACTTACTTTTGTAAAAATGT<br>CCCCACGGTACTTACTCCCCACTGATGGACCAGTGGTTTCCAGTCATGAGCGTTAGACTGACTTGTTTGT<br>CTTCCATTCCATTGTTTTGAAACTCAGTATGCTGCCCCTGTCTTGCTGTCATGAAATCAGCAAGAGAGGA<br>TGACACATCAAATAATAACTCGGATTCCAGCCCACATTGGATTCATCAGCATTTGGACCAATAGCCCACA<br>GCTGAGAATGTGGAATACCTAAGGATAGCACCGCTTTTGTTCTCGCAAAAACGTATCTCCTAATTTGAGG<br>CTCAGATGAAATGCATCAGGTCCTTTGGGGCATAGATCAGAAGACTACAAAAATGAAGCTGCTCTGAAAT<br>CTCCTTTAGCCATCACCCCAACCCCCCAAAATTAGTTTGTGTTACTTATGGAAGATAGTTTTCTCCTTTT<br>ACTTCACTTCAAAAGCTTTTTACTCAAAGAGTATATGTTCCCTCCAGGTCAGCTGCCCCCAAACCCCCTC<br>CTTACGCTTTGTCACACAAAAAGTGTCTCTGCCTTGAGTCATCTATTCAAGCACTTACAGCTCTGGCCAC<br>AACAGGGCATTTTACAGGTGCGAATGACAGTAGCATTATGAGTAGTGTGGAATTCAGGTAGTAAATATGA<br>AACTAGGGTTTGAAATTGATAATGCTTTCACAACATTTGCAGATGTTTTAGAAGGAAAAAAGTTCCTTCC<br>TAAAATAATTTCTCTACAATTGGAAGATTGGAAGATTCAGCTAGTTAGGAGCCCACCTTTTTTCCTAATC<br>TGTGTGTGCCCTGTAACCTGACTGGTTAACAGCAGTCCTTTGTAAACAGTGTTTTAAACTCTCCTAGTCA<br>ATATCCACCCCATCCAATTTATCAAGGAAGAAATGGTTCAGAAAATATTTTCAGCCTACAGTTATGTTCA<br>GTCACACACACATACAAAATGTTCCTTTTGCTTTTAAAGTAATTTTTGACTCCCAGATCAGTCAGAGCCC<br>CTACAGCATTGTTAAGAAAGTATTTGATTTTTGTCTCAATGAAAATAAAACTATATTCATTTCCACTCTA<br>AAAAAAAAAAAAAAAA | |
| NM_001005862 | GTTCCCGGATTTTTGTGGGCGCCTGCCCCGCCCCTCGTCCCCCTGCTGTGTCCATATATCGAGGCGATAG<br>GGTTAAGGGAAGGCGGACGCCTGATGGGTTAATGAGCAAACTGAAGTGTTTTCCATGATCTTTTTTGAGT<br>CGCAATTGAAGTACCACCTCCCGAGGGTGATTGCTTCCCCATGCGGGGTAGAACCTTTGCTGTCCTGTTC<br>ACCACTCTACCTCCAGCACAGAATTTGGCTTATGCCTACTCAATGTGAAGATGATGAGGATGAAAACCTT<br>TGTGATGATCCACTTCCACTTAATGAATGGTGGCAAAGCAAAGCTATATTCAAGACCACATGCAAAGCTA<br>CTCCCTGAGCAAAGAGTCACAGATAAAACGGGGGCACCAGTAGAATGGCCAGGACAAACGCAGTGCAGCA<br>CAGAGACTCAGACCCTGGCAGCCATGCCTGCGCAGGCAGTGATGAGAGTGACATGTACTGTTGTGGACAT<br>GCACAAAAGTGAGTGTGCACCGGCACAGACATGAAGCTGCGGCTCCCTGCCAGTCCCGAGACCCACCTGG<br>ACATGCTCCGCCACCTCTACCAGGGCTGCCAGGTGGTGCAGGGAAACCTGGAACTCACCTACCTGCCCAC<br>CAATGCCAGCCTGTCCTTCCTGCAGGATATCCAGGAGGTGCAGGGCTACGTGCTCATCGCTCACAACCAA<br>GTGAGGCAGGTCCCACTGCAGAGGCTGCGGATTGTGCGAGGCACCCAGCTCTTTGAGGACAACTATGCCC<br>TGGCCGTGCTAGACAATGGAGACCCGCTGAACAATACCACCCCTGTCACAGGGGCCTCCCCAGGAGGCCT<br>GCGGGAGCTGCAGCTTCGAAGCCTCACAGAGATCTTGAAAGGAGGGGTCTTGATCCAGCGGAACCCCCAG<br>CTCTGCTACCAGGACACGATTTTGTGGAAGGACATCTTCCACAAGAACAACCAGCTGGCTCTCACACTGA<br>TAGACACCAACCGCTCTCGGGCCTGCCACCCCTGTTCTCCGATGTGTAAGGGCTCCCGCTGCTGGGGAGA<br>GAGTTCTGAGGATTGTCAGAGCCTGACGCGCACTGTCTGTGCCGGTGGCTGTGCCCGCTGCAAGGGGCCA<br>CTGCCCACTGACTGCTGCCATGAGCAGTGTGCTGCCGGCTGCACGGGCCCCAAGCACTCTGACTGCCTGG<br>CCTGCCTCCACTTCAACCACAGTGGCATCTGTGAGCTGCACTGCCCAGCCCTGGTCACCTACAACACAGA<br>CACGTTTGAGTCCATGCCCAATCCCGAGGGCCGGTATACATTCGGCGCCAGCTGTGTGACTGCCTGTCCC<br>TACAACTACCTTTCTACGGACGTGGGATCCTGCACCCTCGTCTGCCCCCTGCACAACCAAGAGGTGACAG<br>CAGAGGATGGAACACAGCGGTGTGAGAAGTGCAGCAAGCCCTGTGCCCGAGTGTGCTATGGTCTGGGCAT<br>GGAGCACTTGCGAGAGGTGAGGGCAGTTACCAGTGCCAATATCCAGGAGTTTGCTGGCTGCAAGAAGATC<br>TTTGGGAGCCTGGCATTTCTGCCGGAGAGCTTTGATGGGGACCCAGCCTCCAACACTGCCCCGCTCCAGC<br>CAGAGCAGCTCCAAGTGTTTGAGACTCTGGAAGAGATCACAGGTTACCTATACATCTCAGCATGGCCGGA<br>CAGCCTGCCTGACCTCAGCGTCTTCCAGAACCTGCAAGTAATCCGGGGACGAATTCTGCACAATGGCGCC<br>TACTCGCTGACCCTGCAAGGGCTGGGCATCAGCTGGCTGGGGCTGCGCTCACTGAGGGAACTGGGCAGTG<br>GACTGGCCCTCATCCACCATAACACCCACCTCTGCTTCGTGCACACGGTGCCCTGGGACCAGCTCTTTCG<br>GAACCCGCACCAAGCTCTGCTCCACACTGCCAACCGGCCAGAGGACGAGTGTGTGGGCGAGGGCCTGGCC<br>TGCCACCAGCTGTGCGCCCGAGGGCACTGCTGGGGTCCAGGGCCCACCCAGTGTGTCAACTGCAGCCAGT<br>TCCTTCGGGGCCAGGAGTGCGTGGAGGAATGCCGAGTACTGCAGGGGCTCCCCAGGGAGTATGTGAATGC<br>CAGGCACTGTTTGCCGTGCCACCCTGAGTGTCAGCCCCAGAATGGCTCAGTGACCTGTTTTGGACCGGAG<br>GCTGACCAGTGTGTGGCCTGTGCCCACTATAAGGACCCTCCCTTCTGCGTGGCCCGCTGCCCCAGCGGTG<br>TGAAACCTGACCTCTCCTACATGCCCATCTGGAAGTTTCCAGATGAGGAGGGCGCATGCCAGCCTTGCCC<br>CATCAACTGCACCCACTCCTGTGTGGACCTGGATGACAAGGGCTGCCCCGCCGAGCAGAGAGCCAGCCCT<br>CTGACGTCCATCATCTCTGCGGTGGTTGGCATTCTGCTGGTCGTGGTCTTGGGGGTGGTCTTTGGGATCC<br>TCATCAAGCGACGGCAGCAGAAGATCCGGAAGTACACGATGCGGAGACTGCTGCAGGAAACGGAGCTGGT<br>GGAGCCGCTGACACCTAGCGGAGCGATGCCCAACCAGGCGCAGATGCGGATCCTGAAAGAGACGGAGCTG | 119 |

TABLE 2-continued

| GENBANK ACCESSION NUMBER | SEQUENCE | SEQ ID NO: |
|---|---|---|
| | AGGAAGGTGAAGGTGCTTGGATCTGGCGCTTTTGGCACAGTCTACAAGGGCATCTGGATCCCTGATGGGG | |
| | AGAATGTGAAAATTCCAGTGGCCATCAAAGTGTTGAGGGAAAACACATCCCCCAAAGCCAACAAAGAAAT | |
| | CTTAGACGAAGCATACGTGATGGCTGGTGTGGGCTCCCCATATGTCTCCCGCCTTCTGGGCATCTGCCTG | |
| | ACATCCACGGTGCAGCTGGTGACACAGCTTATGCCCTATGGCTGCCTCTTAGACCATGTCCGGGAAAACC | |
| | GCGGACGCCTGGGCTCCCAGGACCTGCTGAACTGGTGTATGCAGATTGCCAAGGGGATGAGCTACCTGGA | |
| | GGATGTGCGGCTCGTACACAGGGACTTGGCCGCTCGGAACGTGCTGGTCAAGAGTCCCAACCATGTCAAA | |
| | ATTACAGACTTCGGGCTGGCTCGGCTGCTGGACATTGACGAGACAGAGTACCATGCAGATGGGGGCAAGG | |
| | TGCCCATCAAGTGGATGGCGCTGGAGTCCATTCTCCGCCGGCGGTTCACCCACCAGAGTGATGTGTGGAG | |
| | TTATGGTGTGACTGTGTGGGAGCTGATGACTTTTGGGGCCAAACCTTACGATGGGATCCCAGCCCGGGAG | |
| | ATCCCTGACCTGCTGGAAAAGGGGGAGCGGCTGCCCCAGCCCCCCATCTGCACCATTGATGTCTACATGA | |
| | TCATGGTCAAATGTTGGATGATTGACTCTGAATGTCGGCCAAGATTCCGGGAGTTGGTGTCTGAATTCTC | |
| | CCGCATGGCCAGGGACCCCCAGCGCTTTGTGGTCATCCAGAATGAGGACTTGGGCCCAGCCAGTCCCTTG | |
| | GACAGCACCTTCTACCGCTCACTGCTGGAGGACGATGACATGGGGGACCTGGTGGATGCTGAGGAGTATC | |
| | TGGTACCCCAGCAGGGCTTCTTCTGTCCAGACCCTGCCCCGGGCGCTGGGGGCATGGTCCACCACAGGCA | |
| | CCGCAGCTCATCTACCAGGAGTGGCGGTGGGGACCTGACACTAGGGCTGGAGCCCTCTGAAGAGGAGGCC | |
| | CCCAGGTCTCCACTGGCACCCTCCGAAGGGGCTGGCTCCGATGTATTTGATGGTGACCTGGGAATGGGGG | |
| | CAGCCAAGGGGCTGCAAAGCCTCCCCACACATGACCCCAGCCCTCTACAGCGGTACAGTGAGGACCCCAC | |
| | AGTACCCCTGCCCTCTGAGACTGATGGCTACGTTGCCCCCCTGACCTGCAGCCCCCAGCCTGAATATGTG | |
| | AACCAGCCAGATGTTCGGCCCCAGCCCCCTTCGCCCCGAGAGGGCCCTCTGCCTGCTGCCCGACCTGCTG | |
| | GTGCCACTCTGGAAAGGCCCAAGACTCTCTCCCCAGGGAAGAATGGGGTCGTCAAAGACGTTTTTGCCTT | |
| | TGGGGGTGCCGTGGAGAACCCCGAGTACTTGACACCCCAGGGAGGAGCTGCCCCTCAGCCCCACCCTCCT | |
| | CCTGCCTTCAGCCCAGCCTTCGACAACCTCTATTACTGGGACCAGGACCCACCAGAGCGGGGGGCTCCAC | |
| | CCAGCACCTTCAAAGGGACACCTACGGCAGAGAACCCAGAGTACCTGGGTCTGGACGTGCCAGTGTGAAC | |
| | CAGAAGGCCAAGTCCGCAGAAGCCCTGATGTGTCCTCAGGGAGCAGGGAAGGCCTGACTTCTGCTGGCAT | |
| | CAAGAGGTGGGAGGGCCCTCCGACCACTTCCAGGGGAACCTGCCATGCCAGGAACCTGTCCTAAGGAACC | |
| | TTCCTTCCTGCTTGAGTTCCCAGATGGCTGGAAGGGGTCCAGCCTCGTTGGAAGAGGAACAGCACTGGGG | |
| | AGTCTTTGTGGATTCTGAGGCCCTGCCCAATGAGACTCTAGGGTCCAGTGGATGCCACAGCCCAGCTTGG | |
| | CCCTTTCCTTCCAGATCCTGGGTACTGAAAGCCTTAGGGAAGCTGGCCTGAGAGGGGAAGCGGCCCTAAG | |
| | GGAGTGTCTAAGAACAAAAGCGACCCATTCAGAGACTGTCCCTGAAACCTAGTACTGCCCCCCATGAGGA | |
| | AGGAACAGCAATGGTGTCAGTATCCAGGCTTTGTACAGAGTGCTTTTCTGTTTAGTTTTTACTTTTTTTG | |
| | TTTTGTTTTTTTAAAGATGAAATAAAGACCCAGGGGGAGAATGGGTGTTGTATGGGGAGGCAAGTGTGGG | |
| | GGGTCCTTCTCCACACCCACTTTGTCCATTTGCAAATATATTTTGGAAAACAGCTA | |
| NM_001122742 | ATGGTCATAACAGCCTCCTGTCTACCGACTCAGAACGGATTTTACCAAAACTGAAAATGCAGGCTCCATG | 120 |
| | CTCAGAAGCTCTTTAACAGGCTCGAAAGGTCCATGCTCCTTTCTCCTGCCCATTCTATAGCATAAGAAGA | |
| | CAGTCTCTGAGTGATAATCTTCTCTTCAAGAAGAAGAAAACTAGGAAGGAGTAAGCACAAAGATCTCTTC | |
| | ACATTCTCCGGGACTGCGGTACCAAATATCAGCACAGCACTTCTTGAAAAAGGATGTAGATTTTAATCTG | |
| | AACTTTGAACCATCACTGAGGTGGCCCGCCGGTTTCTGAGCCTTCTGCCCTGCGGGGACACGGTCTGCAC | |
| | CCTGCCCGCGGCCACGGACCATGACCATGACCCTCCACACCAAAGCATCTGGGATGGCCCTACTGCATCA | |
| | GATCCAAGGGAACGAGCTGGAGCCCCTGAACCGTCCGCAGCTCAAGATCCCCCTGGAGCGGCCCCTGGGC | |
| | GAGGTGTACCTGGACAGCAGCAAGCCCGCCGTGTACAACTACCCCGAGGGCGCCGCCTACGAGTTCAACG | |
| | CCGCGGCCGCCGCCAACGCGCAGGTCTACGGTCAGACCGGCCTCCCCTACGGCCCCGGGTCTGAGGCTGC | |
| | GGCGTTCGGCTCCAACGGCCTGGGGGGTTTCCCCCCACTCAACAGCGTGTCTCCGAGCCCGCTGATGCTA | |
| | CTGCACCCGCCGCCGCAGCTGTCGCCTTTCCTGCAGCCCCACGGCCAGCAGGTGCCCTACTACCTGGAGA | |
| | ACGAGCCCAGCGGCTACACGGTGCGCGAGGCCGGCCCGCCGGCATTCTACAGGCCAAATTCAGATAATCG | |
| | ACGCCAGGGTGGCAGAGAAAGATTGGCCAGTACCAATGACAAGGGAAGTATGGCTATGGAATCTGCCAAG | |
| | GAGACTCGCTACTGTGCAGTGTGCAATGACTATGCTTCAGGCTACCATTATGGAGTCTGGTCCTGTGAGG | |
| | GCTGCAAGGCCTTCTTCAAGAGAAGTATTCAAGGACATAACGACTATATGTGTCCAGCCACCAACCAGTG | |
| | CACCATTGATAAAAACAGGAGGAAGAGCTGCCAGGCCTGCCGGCTCCGCAAATGCTACGAAGTGGGAATG | |
| | ATGAAAGGTGGGATACGAAAAGACCGAAGAGGAGGGAGAATGTTGAAACACAAGCGCCAGAGAGATGATG | |
| | GGGAGGGCAGGGGTGAAGTGGGGTCTGCTGGAGACATGAGAGCTGCCAACCTTTGGCCAAGCCCGCTCAT | |
| | GATCAAACGCTCTAAGAAGAACAGCCTGGCCTTGTCCCTGACGGCCGACCAGATGGTCAGTGCCTTGTTG | |
| | GATGCTGAGCCCCCCATACTCTATTCCGAGTATGATCCTACCAGACCCTTCAGTGAAGCTTCGATGATGG | |
| | GCTTACTGACCAACCTGGCAGACAGGGAGCTGGTTCACATGATCAACTGGGCGAAGAGGGTGCCAGGCTT | |
| | TGTGGATTTGACCCTCCATGATCAGGTCCACCTTCTAGAATGTGCCTGGCTAGAGATCCTGATGATTGGT | |
| | CTCGTCTGGCGCTCCATGGAGCACCCAGGGAAGCTACTGTTTGCTCCTAACTTGCTCTTGGACAGGAACC | |
| | AGGGAAAATGTGTAGAGGGCATGGTGGAGATCTTCGACATGCTGCTGGCTACATCATCTCGGTTCCGCAT | |
| | GATGAATCTGCAGGGAGAGGAGTTTGTGTGCCTCAAATCTATTATTTTGCTTAATTCTGGAGTGTACACA | |
| | TTTCTGTCCAGCACCCTGAAGTCTCTGGAAGAGAAGGACCATATCCACCGAGTCCTGGACAAGATCACAG | |
| | ACACTTTGATCCACCTGATGGCCAAGGCAGGCCTGACCCTGCAGCAGCAGCACCAGCGGCTGGCCCAGCT | |
| | CCTCCTCATCCTCTCCCACATCAGGCACATGAGTAACAAAGGCATGGAGCATCTGTACAGCATGAAGTGC | |
| | AAGAACGTGGTGCCCCTCTATGACCTGCTGCTGGAGATGCTGGACGCCCACCGCCTACATGCGCCCACTA | |
| | GCCGTGGAGGGGCATCCGTGGAGGAGACGGACCAAAGCCACTTGGCCACTGCGGGCTCTACTTCATCGCA | |
| | TTCCTTGCAAAAGTATTACATCACGGGGGAGGCAGAGGGTTTCCCTGCCACGGTCTGAGAGCTCCCTGGC | |
| | TCCCACACGGTTCAGATAATCCCTGCTGCATTTTACCCTCATCATGCACCACTTTAGCCAAATTCTGTCT | |
| | CCTGCATACACTCCGGCATGCATCCAACACCAATGGCTTTCTAGATGAGTGGCCATTCATTTGCTTGCTC | |
| | AGTTCTTAGTGGCACATCTTCTGTCTTCTGTTGGGAACAGCCAAAGGGATTCCAAGGCTAAATCTTTGTA | |
| | ACAGCTCTCTTTCCCCCTTGCTATGTTACTAAGCGTGAGGATTCCCGTAGCTCTTCACAGCTGAACTCAG | |
| | TCTATGGGTTGGGGCTCAGATAACTCTGTGCATTTAAGCTACTTGTAGAGACCCAGGCCTGGAGAGTAGA | |
| | CATTTTGCCTCTGATAAGCACTTTTTAAATGGCTCTAAGAATAAGCCACAGCAAAGAATTTAAAGTGGCT | |
| | CCTTTAATTGGTGACTTGGAGAAAGCTAGGTCAAGGGTTTATTATAGCACCCTCTTGTATTCCTATGGCA | |
| | ATGCATCCTTTTATGAAAGTGGTACACCTTAAAGCTTTTATATGACTGTAGCAGAGTATCTGGTGATTGT | |
| | CAATTCATTCCCCCTATAGGAATACAAGGGGCACACAGGGAAGGCAGATCCCCTAGTTGGCAAGACTATT | |
| | TTAACTTGATACACTGCAGATTCAGATGTGCTGAAAGCTCTGCCTCTGGCTTTCCGGTCATGGGTTCCAG | |
| | TTAATTCATGCCTCCCATGGACCTATGGAGAGCAGCAAGTTGATCTTAGTTAAGTCTCCCTATATGAGGG | |
| | ATAAGTTCCTGATTTTTGTTTTTATTTTTGTGTTACAAAAGAAAGCCCTCCCTCCCTGAACTTGCAGTAA | |

TABLE 2-continued

| GENBANK ACCESSION NUMBER | SEQUENCE | SEQ ID NO: |
|---|---|---|
| | GGTCAGCTTCAGGACCTGTTCCAGTGGGCACTGTACTTGGATCTTCCCGGCGTGTGTGTGCCTTACACAG<br>GGGTGAACTGTTCACTGTGGTGATGCATGATGAGGGTAAATGGTAGTTGAAAGGAGCAGGGGCCCTGGTG<br>TTGCATTTAGCCCTGGGGCATGGAGCTGAACAGTACTTGTGCAGGATTGTTGTGGCTACTAGAGAACAAG<br>AGGGAAAGTAGGGCAGAAACTGGATACAGTTCTGAGGCACAGCCAGACTTGCTCAGGGTGGCCCTGCCAC<br>AGGCTGCAGCTACCTAGGAACATTCCTTGCAGACCCCGCATTGCCCTTTGGGGGTGCCCTGGGATCCCTG<br>GGGTAGTCCAGCTCTTCTTCATTTCCCAGCGTGGCCCTGGTTGGAAGAAGCAGCTGTCACAGCTGCTGTA<br>GACAGCTGTGTTCCTACAATTGGCCCAGCACCCTGGGGCACGGGAGAAGGGTGGGGACCGTTGCTGTCAC<br>TACTCAGGCTGACTGGGGCCTGGTCAGATTACGTATGCCCTTGGTGGTTTAGAGATAATCCAAAATCAGG<br>GTTTGGTTTGGGGAAGAAAATCCTCCCCCTTCCTCCCCCGCCCCGTTCCCTACCGCCTCCACTCCTGCCA<br>GCTCATTTCCTTCAATTTCCTTTGACCTATAGGCTAAAAAAGAAAGGCTCATTCCAGCCACAGGGCAGCC<br>TTCCCTGGGCCTTTGCTTCTCTAGCACAATTATGGGTTACTTCCTTTTTCTTAACAAAAAAGAATGTTTG<br>ATTTCCTCTGGGTGACCTTATTGTCTGTAATTGAAACCCTATTGAGAGGTGATGTCTGTGTTAGCCAATG<br>ACCCAGGTGAGCTGCTCGGGCTTCTCTTGGTATGTCTTGTTTGGAAAAGTGGATTTCATTCATTTCTGAT<br>TGTCCAGTTAAGTGATCACCAAAGGACTGAGAATCTGGGAGGGCAAAAAAAAAAAAAAAGTTTTTATGTG<br>CACTTAAATTTGGGGACAATTTTATGTATCTGTGTTAAGGATATGTTTAAGAACATAATTCTTTTGTTGC<br>TGTTTGTTTAAGAAGCACCTTAGTTTGTTTAAGAAGCACCTTATATAGTATAATATATATTTTTTTGAAA<br>TTACATTGCTTGTTTATCAGACAATTGAATGTAGTAATTCTGTTCTGGATTTAATTTGACTGGGTTAACA<br>TGCAAAAACCAAGGAAAAATATTTAGTTTTTTTTTTTTTTTTTGTATACTTTTCAAGCTACCTTGTCATG<br>TATACAGTCATTTATGCCTAAAGCCTGGTGATTATTCATTTAAATGAAGATCACATTTCATATCAACTTT<br>TGTATCCACAGTAGACAAAATAGCACTAATCCAGATGCCTATTGTTGGATACTGAATGACAGACAATCTT<br>ATGTAGCAAAGATTATGCCTGAAAAGGAAAATTATTCAGGGCAGCTAATTTTGCTTTTACCAAAATATCA<br>GTAGTAATATTTTTGGACAGTAGCTAATGGGTCAGTGGGTTCTTTTTAATGTTTATACTTAGATTTTCTT<br>TTAAAAAAATTAAAATAAAACAAAAAAAAATTTCTAGGACTAGACGATGTAATACCAGCTAAAGCCAAAC<br>AATTATACAGTGGAAGGTTTTACATTATTCATCCAATGTGTTTCTATTCATGTTAAGATACTACTACATT<br>TGAAGTGGGCAGAGAACATCAGATGATTGAAATGTTCGCCCAGGGGTCTCCAGCAACTTTGGAAATCTCT<br>TTGTATTTTTACTTGAAGTGCCACTAATGGACAGCAGATATTTTCTGGCTGATGTTGGTATTGGGTGTAG<br>GAACATGATTTAAAAAAAAACTCTTGCCTCTGCTTTCCCCCACTCTGAGGCAAGTTAAAATGTAAAAGAT<br>GTGATTTATCTGGGGGGCTCAGGTATGGTGGGGAAGTGGATTCAGGAATCTGGGGAATGGCAAATATATT<br>AAGAAGAGTATTGAAAGTATTTGGAGGAAAATGGTTAATTCTGGGTGTGCACCAGGGTTCAGTAGAGTCC<br>ACTTCTGCCCTGGAGACCACAAATCAACTAGCTCCATTTACAGCCATTTCTAAAATGGCAGCTTCAGTTC<br>TAGAGAAGAAAGAACAACATCAGCAGTAAAGTCCATGGAATAGCTAGTGGTCTGTGTTTCTTTTCGCCAT<br>TGCCTAGCTTGCCGTAATGATTCTATAATGCCATCATGCAGCAATTATGAGAGGCTAGGTCATCCAAAGA<br>GAAGACCCTATCAATGTAGGTTGCAAAATCTAACCCCTAAGGAAGTGCAGTCTTTGATTTGATTTCCCTA<br>GTAACCTTGCAGATATGTTTAACCAAGCCATAGCCCATGCCTTTTGAGGGCTGAACAAATAAGGGACTTA<br>CTGATAATTTACTTTTGATCACATTAAGGTGTTCTCACCTTGAAATCTTATACACTGAAATGGCCATTGA<br>TTTAGGCCACTGGCTTAGAGTACTCCTTCCCCTGCATGACACTGATTACAAATACTTTCCTATTCATACT<br>TTCCAATTATGAGATGGACTGTGGGTACTGGGAGTGATCACTAACACCATAGTAATGTCTAATATTCACA<br>GGCAGATCTGCTTGGGGAAGCTAGTTATGTGAAAGGCAAATAGAGTCATACAGTAGCTCAAAAGGCAACC<br>ATAATTCTCTTTGGTGCAGGTCTTGGGAGCGTGATCTAGATTACACTGCACCATTCCCAAGTTAATCCCC<br>TGAAAACTTACTCTCAACTGGAGCAAATGAACTTTGGTCCCAAATATCCATCTTTTCAGTAGCGTTAATT<br>ATGCTCTGTTTCCAACTGCATTTCCTTTCCAATTGAATTAAAGTGTGGCCTCGTTTTTAGTCATTTAAAA<br>TTGTTTTCTAAGTAATTGCTGCCTCTATTATGGCACTTCAATTTTGCACTGTCTTTTGAGATTCAAGAAA<br>AATTTCTATTCTTTTTTTTGCATCCAATTGTGCCTGAACTTTTAAAATATGTAAATGCTGCCATGTTCCA<br>AACCCATCGTCAGTGTGTGTGTTTAGAGCTGTGCACCCTAGAAACAACATATTGTCCCATGAGCAGGTGC<br>CTGAGACACAGACCCCTTTGCATTCACAGAGAGGTCATTGGTTATAGAGACTTGAATTAATAAGTGACAT<br>TATGCCAGTTTCTGTTCTCTCACAGGTGATAAACAATGCTTTTTGTGCACTACATACTCTTCAGTGTAGA<br>GCTCTTGTTTTATGGGAAAAGGCTCAAATGCCAAATTGTGTTTGATGGATTAATATGCCCTTTTGCCGAT<br>GCATACTATTACTGATGTGACTCGGTTTTGTCGCAGCTTTGCTTTGTTTAATGAAACACACTTGTAAACC<br>TCTTTTGCACTTTGAAAAAGAATCCAGCGGGATGCTCGAGCACCTGTAAACAATTTTCTCAACCTATTTG<br>ATGTTCAAATAAAGAATTAAACTAAA | |
| NM_130398 | AAATTGAAAGGTCAGCCTTTCGCGCGCTGTGTAGGCAAGTTACCCGTGTTCTGCGTTGCCGGCCGTGGGT<br>GCTCTGGCCACAGTGAGTTAGGGGCGTCGGAGCGGGTTTCTCCAACCGCAATCGGCTCCGCTCAAGGGGA<br>GGAGGAGAGTCCCTTCTCGGAAGGCCTAAGGAAACGTGTCGTCTGGAATGGGCTTGGGGGCCACGCCTGC<br>ACATCTCCGCGAGACAGAGGGATAAAGTGAAGATGGTGCTGTTATTGTTACCTCGAGTGCCACATGCGAC<br>CTCTGAGATATGTACACAGTCATTCTTACTATCGCACTCAGCCATTCTTACTACGCTAAAGAAGAAATAA<br>TTATTCGAGGATATTTGCCTGGCCCAGAAGAAACTTATGTAAATTTCATGAACTATTATATCCGTTTTCC<br>TCGGAGTGAGAGAAAACTCTTTTTAGATATCATCTGAGAGAACTAGTGAATCCCAGTCACTGAGTGGAGT<br>TGAGAGTCTAAGAACCTCTGAAATTTGAGAACTGCTGGACCAGAGCCTTTAGAGCTCTGATAAGGTGTCA<br>ACAGGGTAGTTAATTTGGCACCATGGGGATACAGGGATTGCTACAATTTATCAAAGAAGCTTCAGAACCC<br>ATCCATGTGAGGAAGTATAAAGGGCAGGTAGTAGCTGTGGATACATATTGCTGGCTTCACAAAGGAGCTA<br>TTGCTTGTGCTGAAAAACTAGCCAAAGGTGAACCTACTGATAGGTATGTAGGATTTTGTATGAAATTTGT<br>AAATATGTTACTATCTCATGGGATCAAGCCTATTCTCGTATTTGATGGATGTACTTTACCTTCTAAAAAG<br>GAAGTAGAGAGATCTAGAAGAGAAAGACGACAAGCCAATCTTCTTAAGGGAAAGCAACTTCTTCGTGAGG<br>GGAAAGTCTCGGAAGCTCGAGAGTGTTTCACCCGGTCTATCAATATCACACATGCCATGGCCCACAAAGT<br>AATTAAAGCTGCCCGGTCTCAGGGGGTAGATTGCCTCGTGGCTCCCTATGAAGCTGATGCGCAGTTGGCC<br>TATCTTAACAAAGCGGGAATTGTGCAAGCCATAATTACAGAGGACTCGGATCTCCTAGCTTTTGGCTGTA<br>AAAAGGTAATTTTAAAGATGGACCAGTTTGGAAATGGACTTGAAATTGATCAAGCTCGGCTAGGAATGTG<br>CAGACAGCTTGGGGATGTATTCACGGAAGAGAAGTTTCGTTACATGTGTATTCTTTCAGGTTGTGACTAC<br>CTGTCATCACTGCGTGGGATTGGATTAGCAAAGGCATGCAAAGTCCTAAGACTAGCCAATAATCCAGATA<br>TAGTAAAGGTTATCAAGAAAATTGGACATTATCTCAAGATGAATATCACGGTACCAGAGGATTACATCAA<br>CGGGTTTATTCGGGCCAACAATACCTTCCTCTATCAGCTAGTTTTTGATCCCATCAAAAGGAAACTTATT<br>CCTCTGAACGCCTATGAAGATGATGTTGATCCTGAAACACTAAGCTACGCTGGGCAATATGTTGATGATT<br>CCATAGCTCTTCAAATAGCACTTGGAAATAAAGATATAAATACTTTTGAACAGATCGATGACTACAATCC<br>AGACACTGCTATGCCTGCCCATTCAAGAAGTCATAGTTGGGATGACAAAACATGTCAAAAGTCAGCTAAT<br>GTTAGCAGCATTTGGCATAGGAATTACTCTCCCAGACCAGAGTCGGGTACTGTTTCAGATGCCCCACAAT | 121 |

TABLE 2-continued

| GENBANK ACCESSION NUMBER | SEQUENCE | SEQ ID NO: |
|---|---|---|
| | TGAAGGAAAATCCAAGTACTGTGGGAGTGGAACGAGTGATTAGTACTAAAGGGTTAAATCTCCCAAGGAA | |
| | ATCATCCATTGTGAAAAGACCAAGAAGTGCAGAGCTGTCAGAAGATGACCTGTTGAGTCAGTATTCTCTT | |
| | TCATTTACGAAGAAGACCAAGAAAAATAGCTCTGAAGGCAATAAATCATTGAGCTTTTCTGAAGTGTTTG | |
| | TGCCTGACCTGGTAAATGGACCTACTAACAAAAAGAGTGTAAGCACTCCACCTAGGACGAGAAATAAATT | |
| | TGCAACATTTTTACAAAGGAAAAATGAAGAAAGTGGTGCAGTTGTGGTTCCAGGGACCAGAAGCAGGTTT | |
| | TTTTGCAGTTCAGATTCTACTGACTGTGTATCAAACAAAGTGAGCATCCAGCCTCTGGATGAAACTGCTG | |
| | TCACAGATAAAGAGAACAATCTGCATGAATCAGAGTATGGAGACCAAGAAGGCAAGAGACTGGTTGACAC | |
| | AGATGTAGCACGTAATTCAAGTGATGACATTCCGAATAATCATATTCCAGGTGATCATATTCCAGACAAG | |
| | GCAACAGTGTTTACAGATGAAGAGTCCTACTCTTTTGAGAGCAGCAAATTTACAAGGACCATTTCACCAC | |
| | CCACTTTGGGAACACTAAGAAGTTGTTTTAGTTGGTCTGGAGGTCTTGGAGATTTTTCAAGAACGCCGAG | |
| | CCCCTCTCCAAGCACAGCATTGCAGCAGTTCCGAAGAAAGAGCGATTCCCCCACCTCTTTGCCTGAGAAT | |
| | AATATGTCTGATGTGTCGCAGTTAAAGAGCGAGGAGTCCAGTGACGATGAGTCTCATCCCTTACGAGAAG | |
| | AGGCATGTTCTTCACAGTCCCAGGAAAGTGGAGAATTCTCACTGCAGAGTTCAAATGCATCAAAGCTTTC | |
| | TCAGTGCTCTAGTAAGGACTCTGATTCAGAGGAATCTGATTGCAATATTAAGTTACTTGACAGTCAAAGT | |
| | GACCAGACCTCCAAGCTACGTTTATCTCATTTCTCAAAAAAAGACACACCTCTAAGGAACAAGGTTCCTG | |
| | GGCTATATAAGTCCAGTTCTGCAGACTCTCTTTCTACAACCAAGATCAAACCTCTAGGACCTGCCAGAGC | |
| | CAGTGGGCTGAGCAAGAAGCCGGCAAGCATCCAGAAGAGAAAGCATCATAATGCCGAGAACAAGCCGGGG | |
| | TTACAGATCAAACTCAATGAGCTCTGGAAAAACTTTGGATTTAAAAAAGATTCTGAAAAGCTTCCTCCTT | |
| | GTAAGAAACCCCTGTCCCCAGTCAGAGATAACATCCAACTAACTCCAGAAGCGGAAGAGGATATATTTAA | |
| | CAAACCTGAATGTGGCCGTGTTCAAAGAGCAATATTCCAGTAAATGCAGACTGCTGCAAAGCTTTTGCCT | |
| | GCAAGAGAATCTGATCAATTTGAAGTCCCTGTTTGGGAATGAGGCACTTATCAGCATGAAGAATTTTTTC | |
| | TCATTCTGTGCCATTTTAAAAATAGAATACATTTTGTATATTAACTTTATAATTGGGTTGTGGTTTTTTT | |
| | GCTCAGCTTTTTATATTTTTATAAGAAGCTAAATAGAAGAATAATTGTATCTCTGACAGGTTTTTGGAGG | |
| | TTTTAGTGTTAATTGGGAAAATCCTCTGGAGTTTATAAAAGTCTACTCTAAATATTTCTGTAATGTTGTC | |
| | AAGTAGAAAGATAGTAAATGGAGAAACTACAAAAAAAAAAAAAAAAAA | |
| AB209631 | CCATGACCTGCCTTGAGAAGGGGCAGGGGAAGCCAGATGGACTGGAAGTGGAGTGGCAGTGACCAAGGAG | 122 |
| | GAGGAGGTGTGATAGGCTTCCCACGCAGGGTAGATCCAGAGACACCAGTGCCACCCATAGGCCCCTAGGA | |
| | CTGCAGTGGTCACCCGATTCCTTTGTCCCAGCTGAGACTCAGTTCTGAGTGTTCTATTTTGGGGAACAGA | |
| | GGCGTCCTTGGTAGCATTTGGAAGAGGATAGCCAGCTGGGGTGTGTACATCACAGCCTGACAGTAACA | |
| | GCATCCGAACCAGAGGTGACTGGCTAAGGGCAGACCCAGGGCAACAGGTTAACCGTTCTAGGGCCGGGCA | |
| | CAGGGAGGAGAACATTCCAACACTCTGTGTGCCCAGTGCCGACGCACGTTCTCTCTTTTATCCTCAAAAC | |
| | AGTCCTATGAGGATATAAGCCAGAGAGAGACAGAGACAAGGAATTACAAGTTGGTGAGAGTCAGGATTTG | |
| | AACTTGGCTCTGGCAGATGGAAAATTAGGGTCTGTATTCTTTACAAAACCGTGTGTGCCTCAGATGGAGT | |
| | TGGTGCATAACAAGCAGAGGTATCCAGGGTCGCGGTCCTGCTTGCCACGGAAGGGGCCGCCTTGTCAGTT | |
| | GTGACCACCCAGCCCTGGAAATGTCAGTAATGCTGTAAGGAGTGGGGATCGGATCAGATGCCATCCAGAT | |
| | GCTGAAGTTTGACCTTGTGTCATTTTTCACTTTCTTTTTGGCTCTTCTGCAATCAATTCATTTATTTAG | |
| | CAAAAAAGAAATTATGTGTGCCGAGAGCATGCAGAAGATATGTCTCCGTTCTCTGCTTCCCTCCAAAAAA | |
| | GAATCCCAAAACTGCTTTCTGTGAACGTGTGCCAGGGTCCCAGCAGGACTCAGGGAGAGCAGGAAGCCCA | |
| | GCCCAGACCCCTTGCACAACCTACCGTGGGGAGGCCTTAGGCTCTGGCTACTACAGAGCTGGTTCCAGTC | |
| | TGCACTGCCACAGCCTGGCCAGGGACTTGGACACATCTGCTGGCCACTTCCTGTCTCAGTTTCCTTATCT | |
| | GCAAAATAAGGGAAAAGCCCCCACAAAGGTGCACGTGTAGCAGGAGCTCTTTTCCCTCCCTATTTTAGGA | |
| | AGGCAGTTGGTGGGAAGTCCAGCTTGGGTCCCTGAGAGCTGTGAGAAGGAGATGCGGCTGCTGCTGGCCC | |
| | TGTTGGGGGTCCTGCTGAGTGTGCCTGGGCCTCCAGTCTTGTCCCTGGAGGCCTCTGAGGAAGTGGAGCT | |
| | TGGTATGGCTTCTGAGGTGGGAGAGGGTGGCAGGGGTGGGAAGAGTGGGCACCAGGAGGGGGCTGCTGGG | |
| | CTGAGCAAAGCTGGAAAGGATCCTTGCCCAGGCCCTGAGAAGGTGGCGGCAGGGCAGGGCTCAACCACTG | |
| | AGACTCAGTCAGTGCCTGGCTTCCAGCAAGCATTCATCTATCACTGTGTCTGCGAGAGAGGACTGGCCTT | |
| | GCAGGGCGCAGGGCCCTAAGCTGGGCTGCAGAGCTGGTGGTGAGCTCCTTGCCTGGGTGTGTGTGCGTGT | |
| | GTGTGTGTGTTCTGTGCACTGGGTGTGTGACCTAGGAGGTCCAGGCAGCATGTGTGGTATAAGCATTATG | |
| | AGGGTGATATGCCCCGGTGCAGCATGACCCTGTATGTGGCACCAACAGCATGTGCCTTGTGTGTGTGTGT | |
| | GTCCGTATGTGTGTGTGTGTATGCGTGTGTGTGTGTGTGTGTGTGTGTCTTGGCCACTGTCATGTGCACT | |
| | AAATGCTGTGTGTGTGACATGCCCCAAGAGTGTGGCATTTGCCCTGGGTGTGGCATCCGCAGCATGTGGC | |
| | TGTGTGGGTGTCAAGGAGTGGTGGCTCCTTCAGCATGCGTTGCGAAGTGCTTGTGCCCTGCATGTGCGGT | |
| | GTGTTCTCTGTACACAGGAGGCTGCCTCAGATGGGGCTGCGGGGTCTGCTGACCTCTGCCCTCTGCCCAC | |
| | AGAGCCCTGCCTGGCTCCCAGCCTGGAGCAGCAAGAGCAGGAGCTGACAGTAGCCCTTGGGCAGCCTGTG | |
| | CGGCTGTGCTGTGGGCGGGCTGAGCGTGGTGGCCACTGGTACAAGGAGGGCAGTCGCCTGGCACCTGCTG | |
| | GCCGTGTACGGGGCTGGAGGGGCCGCCTAGAGATTGCCAGCTTCCTACCTGAGGATGCTGGCCGCTACCT | |
| | CTGCCTGGCACGAGGCTCCATGATCGTCCTGCAGAATCTCACCTTGATTACAGGTGACTCCTTGACCTCC | |
| | AGCAACGATGATGAGGACCCCAAGTCCCATAGGGACCTCTCGAATAGGCACAGTTACCCCCAGCAAGGTC | |
| | AGTAGGTCTCCAAGGACTTGTGTCCCCGCTGCTGCTCATCTGATCACTGAGAAGAGGAGGCCTGTGTGGG | |
| | AACACACGGTCATTCTAGGGGCCTTCCCCTGCCCTCCAGCACCCTACTGGACACACCCCCAGCGCATGGA | |
| | GAAGAAACTGCATGCAGTACCTGCGGGGAACACCGTCAAGTTCCGCTGTCCAGCTGCAGGCAACCCCACG | |
| | CCCACCATCCGCTGGCTTAAGGATGGACAGGCCTTTCATGGGGAGAACCGCATTGGAGGCATTCGGCTGC | |
| | GCCATCAGCACTGGAGTCTCGTGATGGAGAGCGTGGTGCCCTCGGACCGCGGCACATACACCTGCCTGGT | |
| | AGAGAACGCTGTGGGCAGCATCCGTTATAACTACCTGCTAGATGTGCTGGAGCGGTCCCCGCACCGGCCC | |
| | ATCCTGCAGGCCGGGCTCCCGGCCAACACCACAGCCGTGGTGGGCAGCGACGTGGAGCTGCTGTGCAAGG | |
| | TGTACAGCGATGCCCAGCCCCACATCCAGTGGCTGAAGCACATCGTCATCAACGGCAGCAGCTTCGGAGC | |
| | CGACGGTTTCCCCTATGTGCAAGTCCTAAAGACTGCAGACATCAATAGCTCAGAGGTGGAGGTCCTGTAC | |
| | CTGCGGAACGTGTCAGCCGAGGACGCAGGCGAGTACACCTGCCTCGCAGGCAATTCCATCGGCCTCTCCT | |
| | ACCAGTCTGCCTGGCTCACGGTGCTGCCAGGTGAGCACCTGAAGGGCCAGGAGATGCTGCGAGATGCCCC | |
| | TCTGGGCCAGCAGTGGGGGCTGTGGCCTGTTGGGTGGTCAGTCTCTGTTGGCCTGTGGGGTCTGGCCTGG | |
| | GGGGCAGTGTGTGGATTTGTGGGTTTGAGCTGTATGACAGCCCCTCTGTGCCTCTCCACACGTGGCCGTC | |
| | CATGTGACCGTCTGCTGAGGTGTGGGTGCCTGGGACTGGGCATAACTACAGCTTCCTCCGTGTGTGTCCC | |
| | CACATATGTTGGGAGCTGGGAGGGACTGAGTTAGGGTGCACGGGGCGGCCAGTCTCACCACTGACCAGTT | |
| | TGTCTGTCTGTGTGTGTCCATGTGCGAGGGCAGAGGAGGACCCCACATGGACCGCAGCAGCGCCCGAGGC | |
| | CAGGTATACGGACATCATCCTGTACGCGTCGGGCTCCCTGGCCTTGGCTGTGCTCCTGCTGCTGGCCAGG | |

TABLE 2-continued

| GENBANK ACCESSION NUMBER | SEQUENCE | SEQ ID NO: |
|---|---|---|
| | CTGTATCGAGGGCAGGCGCTCCACGGCCGGCACCCCCGCCCGCCCGCCACTGTGCAGAAGCTCTCCCGCT<br>TCCCTCTGGCCCGACAGTTCTCCCTGGAGTCAGGCTCTTCCGGCAAGTCAAGCTCATCCCTGGTACGAGG<br>CGTGCGTCTCTCCTCCAGCGGCCCCGCCTTGCTCGCCGGCCTCGTGAGTCTAGATCTACCTCTCGACCCA<br>CTATGGGAGTTCCCCCGGGACAGGCTGGTGCTTGGGAAGCCCCTAGGCGAGGGCTGCTTTGGCCAGGTAG<br>TACGTGCAGAGGCCTTTGGCATGGACCCTGCCCGGCCTGACCAAGCCAGCACTGTGGCCGTCAAGATGCT<br>CAAAGACAACGCCTCTGACAAGGACCTGGCCGACCTGGTCTCGGAGATGGAGGTGATGAAGCTGATCGGC<br>CGACACAAGAACATCATCAACCTGCTTGGTGTCTGCACCCAGGAAGGGCCCCTGTACGTGATCGTGGAGT<br>GCGCCGCCAAGGGAAACCTGCGGGAGTTCCTGCGGGCCCGGCGCCCCCCAGGCCCCGACCTCAGCCCCGA<br>CGGTCCTCGGAGCAGTGAGGGGCCGCTCTCCTTCCCAGTCCTGGTCTCCTGCGCCTACCAGGTGGCCCGA<br>GGCATGCAGTATCTGGAGTCCCGGAAGTGTATCCACCGGGACCTGGCTGCCCGCAATGTGCTGGTGACTG<br>AGGACAATGTGATGAAGATTGCTGACTTTGGGCTGGCCCGCGGCGTCCACCACATTGACTACTATAAGAA<br>AACCAGCAACGGCCGCCTGCCTGTGAAGTGGATGGCGCCCGAGGCCTTGTTTGACCGGGTGTACACACAC<br>CAGAGTGACGTGTGGTCTTTTGGGATCCTGCTATGGGAGATCTTCACCCTCGGGGGCTCCCCGTATCCTG<br>GCATCCCGGTGGAGGAGCTGTTCTCGCTGCTGCGGGAGGGACATCGGATGGACCGACCCCCACACTGCCC<br>CCCAGAGCTGTACGGGCTGATGCGTGAGTGCTGGCACGCAGCGCCCTCCCAGAGGCCTACCTTCAAGCAG<br>CTGGTGGAGGCGCTGGACAAGGTCCTGCTGGCCGTCTCTGAGGAGTACCTCGACCTCCGCCTGACCTTCG<br>GACCCTATTCCCCCTCTGGTGGGGACGCCAGCAGCACCTGCTCCTCCAGCGATTCTGTCTTCAGCCACGA<br>CCCCCTGCCATTGGGATCCAGCTCCTTCCCCTTCGGGTCTGGGGTGCAGACATGAGCAAGGCTCAAGGCT<br>GTGCAGGCACATAGGCTGGTGGCCTTGGGCCTTGGGGCTCAGCCACAGCCTGACACAGTGCTCGACCTTG<br>ATAGCATGGGGCCCCTGGCCCAGAGTTGCTGTGCCGTGTCCAAGGGCCGTGCCCTTGCCCTTGGAGCTGC<br>CGTGCCTGTGTCCTGATGGCCCAAATGTCAGGGTTCTGCTCGGCTTCTTGGACCTTGGCGCTTAGTCCCC<br>ATCCCGGGTTTGGCTGAGCCTGGCTGGAGAGCTGCTATGCTAAACCTCCTGCCTCCCAATACCAGCAGGA<br>GGTTCTGGGCCTCTGAACCCCCTTTCCCCACACCTCCCCCTGCTGCTGCTGCCCCAGCGTCTTGACGGGA<br>GCATTGGCCCCTGAGCCCAGAGAAGCTGGAAGCCTGCCGAAAACAGGAGCAAATGGCGTTTTATAAATTA<br>TTTTTTTGAAAT | |
| NM_004496 | TAAGATCCACATCAGCTCAACTGCACTTGCCTCGCAGAGGCAGCCCGCTCACTTCCCGCGGAGGCGCTCC<br>CCGGCGCCGCGCTCCGCGGCAGCCGCCTGCCCCCGGCGCTGCCCCCGCCCGCCGCGCCGCCGCCGCCGCC<br>GCGCACGCCGCGCCCCGCAGCTCTGGGCTTCCTCTTCGCCCGGGTGGCGTTGGGCCCGCGCGGGCGCTCG<br>GGTGACTGCAGCTGCTCAGCTCCCCTCCCCCGCCCCGCGCCGCGCGGCCGCCCGTCGCTTCGCACAGGGC<br>TGGATGGTTGTATTGGGCAGGGTGGCTCCAGGATGTTAGGAACTGTGAAGATGGAAGGGCATGAAACCAG<br>CGACTGGAACAGCTACTACGCAGACACGCAGGAGGCCTACTCCTCCGTCCCGGTCAGCAACATGAACTCA<br>GGCCTGGGCTCCATGAACTCCATGAACACCTACATGACCATGAACACCATGACTACGAGCGGCAACATGA<br>CCCCGGCGTCCTTCAACATGTCCTATGCCAACCCGGGCCTAGGGGCCGGCCTGAGTCCCGGCGCAGTAGC<br>CGGCATGCCGGGGGGCTCGGCGGGCGCCATGAACAGCATGACTGCGGCCGGCGTGACGGCCATGGGTACG<br>GCGCTGAGCCCGAGCGGCATGGGCGCCATGGGTGCGCAGCAGGCGGCCTCCATGAATGGCCTGGGCCCCT<br>ACGCGGCCGCCATGAACCCGTGCATGAGCCCCATGGCGTACGCGCCGTCCAACCTGGGCCGCAGCCGCGC<br>GGGCGGCGGCGGCGACGCCAAGACGTTCAAGCGCAGCTACCCGCACGCCAAGCCGCCCTACTCGTACATC<br>TCGCTCATCACCATGGCCATCCAGCAGGCGCCCAGCAAGATGCTCACGCTGAGCGAGATCTACCAGTGGA<br>TCATGGACCTCTTCCCCTATTACCGGCAGAACCAGCAGCGCTGGCAGAACTCCATCCGCCACTCGCTGTC<br>CTTCAATGACTGCTTCGTCAAGGTGGCACGCTCCCCGGACAAGCCGGGCAAGGGCTCCTACTGGACGCTG<br>CACCCGGACTCCGGCAACATGTTCGAGAACGGCTGCTACTTGCGCCGCCAGAAGCGCTTCAAGTGCGAGA<br>AGCAGCCGGGGGCCGGCGGCGGGGGCGGGAGCGGAAGCGGGGGCAGCGGCGCCAAGGGCGGCCCTGAGAG<br>CCGCAAGGACCCCTCTGGCGCCTCTAACCCCAGCGCCGACTCGCCCCTCCATCGGGGTGTGCACGGGAAG<br>ACCGGCCAGCTAGAGGGCGCGCCGGCCCCCGGGCCCGCCGCCAGCCCCCAGACTCTGGACCACAGTGGGG<br>CGACGGCGACAGGGGGCGCCTCGGAGTTGAAGACTCCAGCCTCCTCAACTGCGCCCCCCATAAGCTCCGG<br>GCCCGGGGCGCTGGCCTCTGTGCCCGCCTCTCACCCGGCACACGGCTTGGCACCCCACGAGTCCCAGCTG<br>CACCTGAAAGGGGACCCCCACTACTCCTTCAACCACCCGTTCTCCATCAACAACCTCATGTCCTCCTCGG<br>AGCAGCAGCATAAGCTGGACTTCAAGGCATACGAACAGGCACTGCAATACTCGCCTTACGGCTCTACGTT<br>GCCCGCCAGCCTGCCTCTAGGCAGCGCCTCGGTGACCACCAGGAGCCCCATCGAGCCCTCAGCCCTGGAG<br>CCGGCGTACTACCAAGGTGTGTATTCCAGACCCGTCCTAAACACTTCCTAGCTCCCGGGACTGGGGGGTT<br>TGTCTGGCATAGCCATGCTGGTAGCAAGAGAGAAAAAATCAACAGCAAACAAAACCACACAAACCAAACC<br>GTCAACAGCATAATAAAATCCCAACAACTATTTTTATTTCATTTTTCATGCACAACCTTTCCCCCAGTGC<br>AAAAGACTGTTACTTTATTATTGTATTCAAAATTCATTGTGTATATTACTACAAAGACAACCCCAAACCA<br>ATTTTTTTCCTGCGAAGTTTAATGATCCACAAGTGTATATATGAAATTCTCCTCCTTCCTTGCCCCCCTC<br>TCTTTCTTCCCTCTTTCCCCTCCAGACATTCTAGTTTGTGGAGGGTTATTTAAAAAAACAAAAAAGGAAG<br>ATGGTCAAGTTTGTAAAATATTTGTTTGTGCTTTTTCCCCCTCCTTACCTGACCCCCTACGAGTTTACAG<br>GTCTGTGGCAATACTCTTAACCATAAGAATTGAAATGGTGAAGAAACAAGTATACACTAGAGGCTCTTAA<br>AAGTATTGAAAGACAATACTGCTGTTATATAGCAAGACATAAACAGATTATAAACATCAGAGCCATTTGC<br>TTCTCAGTTTACATTTCTGATACATGCAGATAGCAGATGTCTTTAAATGAAATACATGTATATTGTGTAT<br>GGACTTAATTATGCACATGCTCAGATGTGTAGACATCCTCCGTATATTTACATAACATATAGAGGTAATA<br>GATAGGTGATATACATGATACATTCTCAAGAGTTGCTTGACCGAAAGTTACAAGGACCCCAACCCCTTTG<br>TCCTCTCTACCCACAGATGGCCCTGGGAATCAATTCCTCAGGAATTGCCCTCAAGAACTCTGCTTCTTGC<br>TTTGCAGAGTGCCATGGTCATGTCATTCTGAGGTCACATAACACATAAAATTAGTTTCTATGAGTGTATA<br>CCATTTAAAGAATTTTTTTTCAGTAAAAGGGAATATTACAATGTTGGAGGAGAGATAAGTTATAGGGAG<br>CTGGATTTCAAAACGTGGTCCAAGATTCAAAAATCCTATTGATAGTGGCCATTTTAATCATTGCCATCGT<br>GTGCTTGTTTCATCCAGTGTTATGCACTTTCCACAGTTGGACATGGTGTTAGTATAGCCAGACGGGTTTC<br>ATTATTATTTCTCTTTGCTTTCTCAATGTTAATTTATTGCATGGTTTATTCTTTTTCTTTACAGCTGAAA<br>TTGCTTTAAATGATGGTTAAAATTACAAATTAAATTGTTAATTTTTATCAATGTGATTGTAATTAAAAAT<br>ATTTTGATTTAAATAACAAAAATAATACCAGATTTTAAGCCGTGGAAAATGTTCTTGATCATTTGCAGTT<br>AAGGACTTTAAATAAATCAAATGTTAACAAAAAAAAAAAAAAAA | 123 |
| NM_001453 | ATGCAGGCGCGCTACTCCGTGTCCAGCCCCAACTCCCTGGGAGTGGTGCCCTACCTCGGCGGCGAGCAGA<br>GCTACTACCGCGCGGCGGCCGCGGCGGCCGGGGGCGGCTACACCGCCATGCCGGCCCCCATGAGCGTGTA<br>CTCGCACCCTGCGCACGCCGAGCAGTACCCGGGCGGCATGGCCCGCGCCTACGGGCCCTACACGCCGCAG<br>CCGCAGCCCAAGGACATGGTGAAGCCGCCCTATAGCTACATCGCGCTCATCACCATGGCCATCCAGAACG | 124 |

TABLE 2-continued

| GENBANK ACCESSION NUMBER | SEQUENCE | SEQ ID NO: |
|---|---|---|
| | CCCCGGACAAGAAGATCACCCTGAACGGCATCTACCAGTTCATCATGGACCGCTTCCCCTTCTACCGGGA<br>CAACAAGCAGGGCTGGCAGAACAGCATCCGCCACAACCTCTCGCTCAACGAGTGCTTCGTCAAGGTGCCG<br>CGCGACGACAAGAAGCCGGGCAAGGGCAGCTACTGGACGCTGGACCCGGACTCCTACAACATGTTCGAGA<br>ACGGCAGCTTCCTGCGGCGGCGGCGGCGCTTCAAGAAGAAGGACGCGGTGAAGGACAAGGAGGAGAAGGA<br>CAGGCTGCACCTCAAGGAGCCGCCCCCGCCCGGCCGCCAGCCCCCGCCCGCGCCGCCGGAGCAGGCCGAC<br>GGCAACGCGCCCGGTCCGCAGCCGCCGCCCGTGCGCATCCAGGACATCAAGACCGAGAACGGTACGTGCC<br>CCTCGCCGCCCCAGCCCCTGTCCCCGGCCGCCGCCCTGGGCAGCGGCAGCGCCGCCGCGGTGCCCAAGAT<br>CGAGAGCCCCGACAGCAGCAGCAGCAGCCTGTCCAGCGGGAGCAGCCCCCGGGCAGCCTGCCGTCGGCG<br>CGGCCGCTCAGCCTGGACGGTGCGGATTCCGCGCCGCCGCCGCCCGCGCCCTCCGCCCCGCCGCCGCACC<br>ATAGCCAGGGCTTCAGCGTGGACAACATCATGACGTCGCTGCGGGGGTCGCCGCAGAGCGCGGCCGCGGA<br>GCTCAGCTCCGGCCTTCTGGCCTCGGCGGCCGCGTCCTCGCGCGCGGGGATCGCACCCCCGCTGGCGCTC<br>GGCGCCTACTCGCCCGGCCAGAGCTCCCTCTACAGCTCCCCCTGCAGCCAGACCTCCAGCGCGGGCAGCT<br>CGGGCGGCGGCGGCGGCGGCGCGGGGGCCGCGGGGGGCGCGGGCGGCGCCGGGACCTACCACTGCAACCT<br>GCAAGCCATGAGCCTGTACGCGGCCGGCGAGCGCGGGGGCCACTTGCAGGGCGCGCCCGGGGGCGCGGGC<br>GGCTCGGCCGTGGACGACCCCCTGCCCGACTACTCTCTGCCTCCGGTCACCAGCAGCAGCTCGTCGTCCC<br>TGAGTCACGGCGGCGGCGGCGGCGGCGGCGGGGGAGGCCAGGAGGCCGGCCACCACCCTGCGGCCCACCA<br>AGGCCGCCTCACCTCGTGGTACCTGAACCAGGCGGGCGGAGACCTGGGCCACTTGGCGAGCGCGGCGGCG<br>GCGGCGGCGGCCGCAGGCTACCCGGGCCAGCAGCAGAACTTCCACTCGGTGCGGGAGATGTTCGAGTCAC<br>AGAGGATCGGCTTGAACAACTCTCCAGTGAACGGGAATAGTAGCTGTCAAATGGCCTTCCCTTCCAGCCA<br>GTCTCTGTACCGCACGTCCGGAGCTTTCGTCTACGACTGTAGCAAGTTTTGACACACCCTCAAAGCCGAA<br>CTAAATCGAACCCCAAAGCAGGAAAAGCTAAAGGAACCCATCAAGGCAAAATCGAAACTAAAAAAAAAAA<br>ATCCAATTAAAAAAAACCCCTGAGAATATTCACCACACCAGCGAACAGAATATCCCTCCAAAAATTCAGC<br>TCACCAGCACCAGCACGAAGAAAACTCTATTTTCTTAACCGATTAATTCAGAGCCACCTCCACTTTGCCT<br>TGTCTAAATAAACAAACCCGTAAACTGTTTATACAGAGACAGCAAAATCTTGGTTTATTAAAGGACAGT<br>GTTACTCCAGATAACACGTAAGTTTCTTCTTGCTTTTCAGAGACCTGCTTTCCCCTCCTCCCGTCTCCCC<br>TCTCTTGCCTTCTTCCTTGCCTCTCACCTGTAAGATATTATTTTATCCTATGTTGAAGGGAGGGGGAAAG<br>TCCCCGTTTATGAAAGTCGCTTTCTTTTTATTCATGGACTTGTTTTAAAATGTAAATTGCAACATAGTAA<br>TTTATTTTTAATTTGTAGTTGGATGTCGTGGACCAAACGCCAGAAAGTGTTCCCAAAACCTGACGTTAAA<br>TTGCCTGAAACTTTAAATTGTGCTTTTTTTCTCATTATAAAAAGGGAAACTGTATTAATCTTATTCTATC<br>CTCTTTTCTTTCTTTTTGTTGAACATATTCATTGTTTGTTTATTAATAAATTACCATTCAGTTTGAATGA<br>GACCTATATGTCTGGATACTTTAATAGAGCTTTAATTATTACGAAAAAAGATTTCAGAGATAAAACACTA<br>GAAGTTACCTATTCTCCACCTAAATCTCTGAAAAATGGAGAAACCCTCTGACTAGTCCATGTCAAATTTT<br>ACTAAAAGTCTTTTTGTTTAGATTTATTTTCCTGCAGCATCTTCTGCAAAATGTACTATATAGTCAGCTT<br>GCTTTGAGGCTAGTAAAAAGATATTTTTCTAAACAGATTGGAGTTGGCATATAAACAAATACGTTTTCTC<br>ACTAATGACAGTCCATGATTCGGAAATTTTAAGCCCATGAATCAGCCGCGGTCTTACCACGGTGATGCCT<br>GTGTGCCGAGAGATGGGACTGTGCGGCCAGATATGCACAGATAAATATTTGGCTTGTGTATTCCATATAA<br>AATTGCAGTGCATATTATACATCCCTGTGAGCCAGATGCTGAATAGATATTTTCCTATTATTTCAGTCCT<br>TTATAAAAGGAAAAATAAACCAGTTTTTAAATGTATGTATATAATTCTCCCCCATTTACAATCCTTCATG<br>TATTACATAGAAGGATTGCTTTTTTAAAAATATACTGCGGGTTGGAAAGGGATATTTAATCTTTGAGAAA<br>CTATTTTAGAAAATATGTTTGTAGAACAATTATTTTTGAAAAAGATTTAAAGCAATAACAAGAAGGAAGG<br>CGAGAGGAGCAGAACATTTTGGTCTAGGGTGGTTTCTTTTTAAACCATTTTTTCTTGTTAATTTACAGTT<br>AAACCTAGGGGACAATCCGGATTGGCCCTCCCCCTTTTGTAAATAACCCAGGAAATGTAATAAATTCATT<br>ATCTTAGGGTGATCTGCCCTGCCAATCAGACTTTGGGGAGATGGCGATTTGATTACAGACGTTCGGGGGG<br>GTGGGGGGCTTGCAGTTTGTTTTGGAGATAATACAGTTTCCTGCTATCTGCCGCTCCTATCTAGAGGCAA<br>CACTTAAGCAGTAATTGCTGTTGCTTGTTGTCAAAATTTGATCATTGTTAAAGGATTGCTGCAAATAAAT<br>ACACTTTAATTTCAGTCAAAAA | |
| AJ249248 | GTGGCCTCGAGGTGGTGGCAGGGCCGCCCCCTGCAGTCCGGAGACGAACGCACGGACCGGGCCTCCGGAG<br>GCAGGTTCGGCTGGAAGGAACCGCTCTCGCTTCGTCCTACACTTGCGCAAATGTCTCCGAGCTTACTCAC<br>ATAGCATATTGGTATATCAAAATGAAATGCAAGGAACCAAAAATAACATAATTGAAGGCAGTAAAAGTGA<br>AATTAAATAGGAAGATCATCAGTCAAGGAAGACCCACTGGAGAGGACAGAAAATGAAGCAGTGTTTTATC<br>ATGTGTATTTCAGCAGGTCTTCTTGAAATTTAACTAAAAATATGACTGCTCTCTCTTCAGAGAACTGCTC<br>TTTTCAGTACCAGTTACGTCAAACAAACCAGCCCCTAGACGTTAACTATCTGCTATTCTTGATCATACTT<br>GGGAAAATATTATTAAATATCCTTACACTAGGAATGAGAAGAAAAAACACCTGTCAAAATTTTATGGAAT<br>ATTTTTGCATTTCACTAGCATTCGTTGATCTTTTACTTTTGGTAAACATTTCCATTATATTGTATTTCAG<br>GGATTTTGTACTTTTAAGCATTAGGTTCACTAAATACCACATCTGCCTATTTACTCAAATTATTTCCTTT<br>ACTTATGGCTTTTTGCATTATCCAGTTTTCCTGACAGCTTGTATAGATTATTGCCTGAATTTCTCTAAAA<br>CAACCAAGCTTTCATTTAAGTGTCAAAAATTATTTTATTTCTTTACAGTAATTTTAATTTGGATTTCAGT<br>CCTTGCTTATGTTTTGGGAGACCCAGCCATCTACCAAAGCCTGAAGGCACAGAATGCTTATTCTCGTCAC<br>TGTCCTTTCTATGTCAGCATTCAGAGTTACTGGCTGTCATTTTTCATGGTGATGATTTTATTTGTAGCTT<br>TCATAACCTGTTGGGAAGAAGTTACTACTTTGGTACAGGCTATCAGGATAACTTCCTATATGAATGAAAC<br>TATCTTATATTTTCCTTTTTCATCCCACTCCAGTTATACTGTGAGATCTAAAAAAATATTCTTATCCAAG<br>CTCATTGTCTGTTTTCTCAGTACCTGGTTACCATTTGTACTACTTCAGGTAATCATTGTTTTACTTAAAG<br>TTCAGATTCCAGCATATATTGAGATGAATATTCCCTGGTTATACTTTGTCAATAGTTTTCTCATTGCTAC<br>AGTGTATTGGTTTAATTGTCACAAGCTTAATTTAAAAGACATTGGATTACCTTTGGATCCATTTGTCAAC<br>TGGAAGTGCTGCTTCATTCCACTTACAATTCCTAATCTTGAGCAAATTGAAAAGCCTATATCAATAATGA<br>TTTGTTAATATTATTAATTAAAAGTTACAGCTGTCATAAGATCATAATTTTATGAACAGAAAGAACTCAG<br>GACATATTAAAAAATAAACTGAACTAAAACAACTTTTGCCCCCTGACTGATAGCATTTCAGAATGTGTCT<br>TTTGAAGGGCTATACCAGTTATTAAATAGTGTTTTATTTTAAAAACAAAATAATTCCAAGAAGTTTTTAT<br>AGTTATTCAGGGACACTATATTACAAATATTACTTTGTTATTAACACAAAAAGTGATAAGAGTTAACATT<br>TGGCTATACTGATGTTTGTGTTACTCAAAAAAACTACTGGATGCAAACTGTTATGTAAATCTGAGATTTC<br>ACTGACAACTTTAAGATATCAACCTAAACATTTTTATTAAATGTTCAAATGTAAGCAAGAAAAAAAAAA | 125 |
| NM_005310 | ACCCGCCCCCATCTGCCCAAGATAATTTTAGTTTCCTTGGGCCTGGAATCTGGACACACAGGGCTCCCCC<br>CCGCCTCTGACTTCTCTGTCCGAAGTCGGGACACCCTCCTACCACCTGTAGAGAAGCGGGAGTGGATCTG<br>AAATAAAATCCAGGAATCTGGGGGTTCCTAGACGGAGCCAGACTTCGGAACGGGTGTCCTGCTACTCCTG | 126 |

TABLE 2-continued

| GENBANK ACCESSION NUMBER | SEQUENCE | SEQ ID NO: |
|---|---|---|
| | CTGGGGCTCCTCCAGGACAAGGGCACACAACTGGTTCCGTTAAGCCCCTCTCTCGCTCAGACGCCATGGA<br>GCTGGATCTGTCTCCACCTCATCTTAGCAGCTCTCCGGAAGACCTTTGCCCAGCCCCTGGGACCCCTCCT<br>GGGACTCCCCGGCCCCCTGATACCCCTCTGCCTGAGGAGGTAAAGAGGTCCCAGCCTCTCCTCATCCCAA<br>CCACCGGCAGGAAACTTCGAGAGGAGGAGAGGCGTGCCACCTCCCTCCCCTCTATCCCCAACCCCTTCCC<br>TGAGCTCTGCAGTCCTCCCTCACAGAGCCCAATTCTCGGGGGCCCCTCCAGTGCAAGGGGGCTGCTCCCC<br>CGCGATGCCAGCCGCCCCCATGTAGTAAAGGTGTACAGTGAGGATGGGGCCTGCAGGTCTGTGGAGGTGG<br>CAGCAGGTGCCACAGCTCGCCACGTGTGTGAAATGCTGGTGCAGCGAGCTCACGCCTTGAGCGACGAGAC<br>CTGGGGGCTGGTGGAGTGCCACCCCCACCTAGCACTGGAGCGGGGTTTGGAGGACCACGAGTCCGTGGTG<br>GAAGTGCAGGCTGCCTGGCCCGTGGGCGGAGATAGCCGCTTCGTCTTCCGGAAAAACTTCGCCAAGTACG<br>AACTGTTCAAGAGCTCCCCACACTCCCTGTTCCCAGAAAAAATGGTCTCCAGCTGTCTCGATGCACACAC<br>TGGTATATCCCATGAAGACCTCATCCAGAACTTCCTGAATGCTGGCAGCTTTCCTGAGATCCAGGGCTTT<br>CTGCAGCTGCGGGGTTCAGGACGGAAGCTTTGGAAACGCTTTTTCTGCTTCTTGCGCCGATCTGGCCTCT<br>ATTACTCCACCAAGGGCACCTCTAAGGATCCGAGGCACCTGCAGTACGTGGCAGATGTGAACGAGTCCAA<br>CGTGTACGTGGTGACGCAGGGCCGCAAGCTCTACGGGATGCCCACTGACTTCGGTTTCTGTGTCAAGCCC<br>AACAAGCTTCGAAATGGCCACAAGGGGCTTCGGATCTTCTGCAGTGAAGATGAGCAGAGCCGCACCTGCT<br>GGCTGGCTGCCTTCCGCCTCTTCAAGTACGGGGTGCAGCTGTACAAGAATTACCAGCAGGCACAGTCTCG<br>CCATCTGCATCCATCTTGTTTGGGCTCCCCACCCTTGAGAAGTGCCTCAGATAATACCCTGGTGGCCATG<br>GACTTCTCTGGCCATGCTGGGCGTGTCATTGAGAACCCCCGGGAGGCTCTGAGTGTGGCCCTGGAGGAGG<br>CCCAGGCCTGGAGGAAGAAGACAAACCACCGCCTCAGCCTGCCCATGCCAGCCTCCGGCACGAGCCTCAG<br>TGCAGCCATCCACCGCACCCAACTCTGGTTCCACGGGCGCATTTCCCGTGAGGAGAGCCAGCGGCTTATT<br>GGACAGCAGGGCTTGGTAGACGGCCTGTTCCTGGTCCGGGAGAGTCAGCGGAACCCCCAGGGCTTTGTCC<br>TCTCTTTGTGCCACCTGCAGAAAGTGAAGCATTATCTCATCCTGCCGAGCGAGGAGGAGGGCCGCCTGTA<br>CTTCAGCATGGATGATGGCCAGACCCGCTTCACTGACCTGCTGCAGCTCGTGGAGTTCCACCAGCTGAAC<br>CGCGGCATCCTGCCGTGCTTGCTGCGCCATTGCTGCACGCGGGTGGCCCTCTGACCAGGCCGTGGACTGG<br>CTCATGCCTCAGCCCGCCTTCAGGCTGCCCGCCGCCCCTCCACCCATCCAGTGGACTCTGGGGCGCGGCC<br>ACAGGGGACGGGATGAGGAGCGGGAGGGTTCCGCCACTCCAGTTTTCTCCTCTGCTTCTTTGCCTCCCTC<br>AGATAGAAAACAGCCCCCACTCCAGTCCACTCCTGACCCCTCTCCTCAAGGGAAGGCCTTGGGTGGCCCC<br>CTCTCCTTCTCCTAGCTCTGGAGGTGCTGCTCTAGGGCAGGGAATTATGGGAGAAGTGGGGGCAGCCCAG<br>GCGGTTTCACGCCCCACACTTTGTACAGACCGAGAGGCCAGTTGATCTGCTCTGTTTTATACTAGTGACA<br>ATAAAGATTATTTTTTGATACAAAAAAAAAAAAAAAAAAAAAAA | |
| NM_014176 | AGTCAGAGGTCGCGCAGGCGCTGGTACCCCGTTGGTCCGCGCGTTGCTGCGTTGTGAGGGGTGTCAGCTC<br>AGTGCATCCCAGGCAGCTCTTAGTGTGGAGCAGTGAACTGTGTGTGGTTCCTTCTACTTGGGGATCATGC<br>AGAGAGCTTCACGTCTGAAGAGAGAGCTGCACATGTTAGCCACAGAGCCACCCCCAGGCATCACATGTTG<br>GCAAGATAAAGACCAAATGGATGACCTGCGAGCTCAAATATTAGGTGGAGCCAACACACCTTATGAGAAA<br>GGTGTTTTTAAGCTAGAAGTTATCATTCCTGAGAGGTACCCATTTGAACCTCCTCAGATCCGATTTCTCA<br>CTCCAATTTATCATCCAAACATTGATTCTGCTGGAAGGATTTGTCTGGATGTTCTCAAATTGCCACCAAA<br>AGGTGCTTGGAGACCATCCCTCAACATCGCAACTGTGTTGACCTCTATTCAGCTGCTCATGTCAGAACCC<br>AACCCTGATGACCCGCTCATGGCTGACATATCCTCAGAATTTAAATATAATAAGCCAGCCTTCCTCAAGA<br>ATGCCAGACAGTGGACAGAGAAGCATGCAAGACAGAAACAAAAGGCTGATGAGGAAGAGATGCTTGATAA<br>TCTACCAGAGGCTGGTGACTCCAGAGTACACAACTCAACACAGAAAAGGAAGGCCAGTCAGCTAGTAGGC<br>ATAGAAAAGAAATTTCATCCTGATGTTTAGGGGACTTGTCCTGGTTCATCTTAGTTAATGTGTTCTTTGC<br>CAAGGTGATCTAAGTTGCCTACCTTGAATTTTTTTTAAATATATTTGATGACATAATTTTTGTGTAGTT<br>TATTTATCTTGTACATATGTATTTTGAAATCTTTTAAACCTGAAAAATAAATAGTCATTTAATGTTGAAA<br>AAAAAAAAAAAAAAAAAAAAAAAA | 127 |
| NM_006845 | ACGCTTGCGCGCGGGATTTAAACTGCGGCGGTTTACGCGGCGTTAAGACTTCGTAGGGTTAGCGAAATTG<br>AGGTTTCTTGGTATTGCGCGTTTCTCTTCCTTGCTGACTCTCCGAATGGCCATGGACTCGTCGCTTCAGG<br>CCCGCCTGTTTCCCGGTCTCGCTATCAAGATCCAACGCAGTAATGGTTTAATTCACAGTGCCAATGTAAG<br>GACTGTGAACTTGGAGAAATCCTGTGTTTCAGTGGAATGGGCAGAAGGAGGTGCCACAAAGGGCAAAGAG<br>ATTGATTTTGATGATGTGGCTGCAATAAACCCAGAACTCTTACAGCTTCTTCCCTTACATCCGAAGGACA<br>ATCTGCCCTTGCAGGAAAATGTAACAATCCAGAAACAAAAACGGAGATCCGTCAACTCCAAAATTCCTGC<br>TCCAAAAGAAAGTCTTCGAAGCCGCTCCACTCGCATGTCCACTGTCTCAGAGCTTCGCATCACGGCTCAG<br>GAGAATGACATGGAGGTGGAGCTGCCTGCAGCTGCAAACTCCCGCAAGCAGTTTTCAGTTCCTCCTGCCC<br>CCACTAGGCCTTCCTGCCCTGCAGTGGCTGAAATACCATTGAGGATGGTCAGCGAGGAGATGGAAGAGCA<br>AGTCCATTCCATCCGAGGCAGCTCTTCTGCAAACCCTGTGAACTCAGTTCGGAGGAAATCATGTCTTGTG<br>AAGGAAGTGGAAAAAATGAAGAACAAGCGAGAAGAGAAGAAGGCCCAGAACTCTGAAATGAGAATGAAGA<br>GAGCTCAGGAGTATGACAGTAGTTTTCCAAACTGGGAATTTGCCCGAATGATTAAAGAATTTCGGGCTAC<br>TTTGGAATGTCATCCACTTACTATGACTGATCCTATCGAAGAGCACAGAATATGTGTCTGTGTTAGGAAA<br>CGCCCACTGAATAAGCAAGAATTGGCCAAGAAAGAAATTGATGTGATTTCCATTCCTAGCAAGTGTCTCC<br>TCTTGGTACATGAACCCAAGTTGAAAGTGGACTTAACAAAGTATCTGGAGAACCAAGCATTCTGCTTTGA<br>CTTTGCATTTGATGAAACAGCTTCGAATGAAGTTGTCTACAGGTTCACAGCAAGGCCACTGGTACAGACA<br>ATCTTTGAAGGTGGAAAAGCAACTTGTTTTGCATATGGCCAGACAGGAAGTGGCAAGACACATACTATGG<br>GCGGAGACCTCTCTGGGAAAGCCCAGAATGCATCCAAAGGGATCTATGCCATGGCCTCCCGGGACGTCTT<br>CCTCCTGAAGAATCAACCCTGCTACCGGAAGTTGGGCCTGGAAGTCTATGTGACATTCTTCGAGATCTAC<br>AATGGGAAGCTGTTTGACCTGCTCAACAAGAAGGCCAAGCTGCGCGTGCTGGAGGACGGCAAGCAACAGG<br>TGCAAGTGGTGGGGCTGCAGGAGCATCTGGTTAACTCTGCTGATGATGTCATCAAGATGATCGACATGGG<br>CAGCGCCTGCAGAACCTCTGGGCAGACATTTGCCAACTCCAATTCCTCCCGCTCCCACGCGTGCTTCCAA<br>ATTATTCTTCGAGCTAAAGGGAGAATGCATGGCAAGTTCTCTTTGGTAGATCTGGCAGGGAATGAGCGAG<br>GCGCGGACACTTCCAGTGCTGACCGGCAGACCCGCATGGAGGGCGCAGAAATCAACAAGAGTCTCTTAGC<br>CCTGAAGGAGTGCATCAGGGCCCTGGGACAGAACAAGGCTCACACCCCGTTCCGTGAGAGCAAGCTGACA<br>CAGGTGCTGAGGGACTCCTTCATTGGGGAGAACTCTAGGACTTGCATGATTGCCACGATCTCACCAGGCA<br>TAAGCTCCTGTGAATATACTTTAAACACCCTGAGATATGCAGACAGGGTCAAGGAGCTGAGCCCCCACAG<br>TGGGCCCAGTGGAGAGCAGTTGATTCAAATGGAAACAGAAGAGATGGAAGCCTGCTCTAACGGGGCGCTG<br>ATTCCAGGCAATTTATCCAAGGAAGAGGAGGAACTGTCTTCCCAGATGTCCAGCTTTAACGAAGCCATGA<br>CTCAGATCAGGGAGCTGGAGGAGAAGGCTATGGAAGAGCTCAAGGAGATCATACAGCAAGGACCAGACTG | 128 |

TABLE 2-continued

| GENBANK ACCESSION NUMBER | SEQUENCE | SEQ ID NO: |
|---|---|---|
| | GCTTGAGCTCTCTGAGATGACCGAGCAGCCAGACTATGACCTGGAGACCTTTGTGAACAAAGCGGAATCT GCTCTGGCCCAGCAAGCCAAGCATTTCTCAGCCCTGCGAGATGTCATCAAGGCCTTGCGCCTGGCCATGC AGCTGGAAGAGCAGGCTAGCAGACAAATAAGCAGCAAGAAACGGCCCCAGTGACGACTGCAAATAAAAAT CTGTTTGGTTTGACACCCAGCCTCTTCCCTGGCCCTCCCCAGAGAACTTTGGGTACCTGGTGGGTCTAGG CAGGGTCTGAGCTGGGACAGGTTCTGGTAAATGCCAAGTATGGGGGCATCTGGGCCCAGGGCAGCTGGGG AGGGGGTCAGAGTGACATGGGACACTCCTTTTCTGTTCCTCAGTTGTCGCCCTCACGAGAGGAAGGAGCT CTTAGTTACCCTTTTGTGTTGCCCTTCTTTCCATCAAGGGGAATGTTCTCAGCATAGAGCTTTCTCCGCA GCATCCTGCCTGCGTGGACTGGCTGCTAATGGAGAGCTCCCTGGGGTTGTCCTGGCTCTGGGGAGAGAGA CGGAGCCTTTAGTACAGCTATCTGCTGGCTCTAAACCTTCTACGCCTTTGGGCCGAGCACTGAATGTCTT GTACTTTAAAAAAATGTTTCTGAGACCTCTTTCTACTTTACTGTCTCCCTAGAGATCCTAGAGGATCCCT ACTGTTTTCTGTTTTATGTGTTTATACATTGTATGTAACAATAAAGAGAAAAAATAAATCAGCTGTTTAA GTGTGTGGAAAAAAAAAAAAAAAAAAA | |
| NM_006101 | ACTGCGCGCGTCGTGCGTAATGACGTCAGCGCCGGCGGAGAATTTCAAATTCGAACGGCTTTGGCGGGCC GAGGAAGGACCTGGTGTTTTGATGACCGCTGTCCTGTCTAGCAGATACTTGCACGGTTTACAGAAATTCG GTCCCTGGGTCGTGTCAGGAAACTGGAAAAAAGGTCATAAGCATGAAGCGCAGTTCAGTTTCCAGCGGTG GTGCTGGCCGCCTCTCCATGCAGGAGTTAAGATCCCAGGATGTAAATAAACAAGGCCTCTATACCCCTCA AACCAAAGAGAAACCAACCTTTGGAAAGTTGAGTATAAACAAACCGACATCTGAAAGAAAAGTCTCGCTA TTTGGCAAAAGAACTAGTGGACATGGATCCCGGAATAGTCAACTTGGTATATTTTCCAGTTCTGAGAAAA TCAAGGACCCGAGACCACTTAATGACAAAGCATTCATTCAGCAGTGTATTCGACAACTCTGTGAGTTTCT TACAGAAAATGGTTATGCACATAATGTGTCCATGAAATCTCTACAAGCTCCCTCTGTTAAAGACTTCCTG AAGATCTTCACATTTCTTTATGGCTTCCTGTGCCCCTCATACGAACTTCCTGACACAAAGTTTGAAGAAG AGGTTCCAAGAATCTTTAAAGACCTTGGGTATCCTTTTGCACTATCCAAAAGCTCCATGTACACAGTGGG GGCTCCTCATACATGGCCTCACATTGTGGCAGCCTTAGTTTGGCTAATAGACTGCATCAAGATACATACT GCCATGAAAGAAAGCTCACCTTTATTTGATGATGGGCAGCCTTGGGGAGAAGAAACTGAAGATGGAATTA TGCATAATAAGTTGTTTTTGGACTACACCATAAAATGCTATGAGAGTTTTATGAGTGGTGCCGACAGCTT TGATGAGATGAATGCAGAGCTGCAGTCAAAACTGAAGGATTTATTTAATGTGGATGCTTTTAAGCTGGAA TCATTAGAAGCAAAAAACAGAGCATTGAATGAACAGATTGCAAGATTGGAACAAGAAAGAGAAAAAGAAC CGAATCGTCTAGAGTCGTTGAGAAAACTGAAGGCTTCCTTACAAGGAGATGTTCAAAAGTATCAGGCATA CATGAGCAATTTGGAGTCTCATTCAGCCATTCTTGACCAGAAATTAAATGGTCTCAATGAGGAAATTGCT AGAGTAGAACTAGAATGTGAAACAATAAAACAGGAGAACACTCGACTACAGAATATCATTGACAACCAGA AGTACTCAGTTGCAGACATTGAGCGAATAAATCATGAAAGAAATGAATTGCAGCAGACTATTAATAAATT AACCAAGGACCTGGAAGCTGAACAACAGAAGTTGTGGAATGAGGAGTTAAAATATGCCAGAGGCAAAGAA GCGATTGAAACACAATTAGCAGAGTATCACAAATTGGCTAGAAAATTAAAACTTATTCCTAAAGGTGCTG AGAATTCCAAAGGTTATGACTTTGAAATTAAGTTTAATCCCGAGGCTGGTGCCAACTGCCTTGTCAAATA CAGGGCTCAAGTTTATGTACCTCTTAAGGAACTCCTGAATGAAACTGAAGAAGAAATTAATAAAGCCCTA AATAAAAAAATGGGTTTGGAGGATACTTTAGAACAATTGAATGCAATGATAACAGAAAGCAAGAGAAGTG TGAGAACTCTGAAAGAAGAAGTTCAAAAGCTGGATGATCTTTACCAACAAAAAATTAAGGAAGCAGAGGA AGAGGATGAAAAATGTGCCAGTGAGCTTGAGTCCTTGGAGAAACACAAGCACCTGCTAGAAAGTACTGTT AACCAGGGGCTCAGTGAAGCTATGAATGAATTAGATGCTGTTCAGCGGGAATACCAACTAGTTGTGCAAA CCACGACTGAAGAAAGACGAAAAGTGGGAAATAACTTGCAACGTCTGTTAGAGATGGTTGCTACACATGT TGGGTCTGTAGAGAAACATCTTGAGGAGCAGATTGCTAAAGTTGATAGAGAATATGAAGAATGCATGTCA GAAGATCTCTCGGAAAATATTAAAGAGATTAGAGATAAGTATGAGAAGAAAGCTACTCTAATTAAGTCTT CTGAAGAATGAAGATAAAATGTTGATCATGTATATATATCCATAGTGAATAAAATTGTCTCAGTAAAGTG TAAAAAAAAAAAAAAAAAAAAAAAAAAAAAAAAAAAAAAA | 129 |
| BC042437 | CTCCCTCCTCTGCACCATGACTACCTGCAGCCGCCAGTTCACCTCCTCCAGCTCCATGAAGGGCTCCTGC GGCATCGGGGGCGGCATCGGGGGCGGCTCCAGCCGCATCTCCTCCGTCCTGGCCGGAGGGTCCTGCCGCG CCCCCAGCACCTACGGGGGCGGCCTGTCTGTCTCATCCTCCCGCTTCTCCTCTGGGGGAGCCTATGGGTT GGGGGGCGGCTATGGCGGTGGCTTCAGCAGCAGCAGCAGCAGCTTTGGTAGTGGCTTTGGGGGAGGATAT GGTGGTGGCCTTGGTGCTGGCTTGGGTGGTGGCTTTGGTGGTGGCTTTGCTGGTGGTGATGGGCTTCTGG TGGGCAGTGAGAAGGTGACCATGCAGAACCTCAACGACCGCCTGGCCTCCTACCTGGACAAGGTGCGTGC TCTGGAGGAGGCCAACGCCGACCTGGAAGTGAAGATCCGTGACTGGTACCAGAGGCAGCGGCCTGCTGAG ATCAAAGACTACAGTCCCTACTTCAAGACCATTGAGGACCTGAGGAACAAGATTCTCACAGCCACAGTGG ACAATGCCAATGTCCTTCTGCAGATTGACAATGCCCGTCTGGCCGCGGATGACTTCCGCACCAAGTATGA GACAGAGTTGAACCTGCGCATGAGTGTGGAAGCCGACATCAATGGCCTGCGCAGGGTGCTGGACGAACTG ACCCTGGCCAGAGCTGACCTGGAGATGCAGATTGAGAGCCTGAAGGAGGAGCTGGCCTACCTGAAGAAGA ACCACGAGGAGGAGATGAATGCCCTGAGAGGCCAGGTGGGTGGAGATGTCAATGTGGAGATGGACGCTGC ACCTGGCGTGGACCTGAGCCGCATTCTGAACGAGATGCGTGACCAGTATGAGAAGATGGCAGAGAAGAAC CGCAAGGATGCCGAGGAATGGTTCTTCACCAAGACAGAGGAGCTGAACCGCGAGGTGGCCACCAACAGCG AGCTGGTGCAGAGCGGCAAGAGCGAGATCTCGGAGCTCCGGCGCACCATGCAGAACCTGGAGATTGAGCT GCAGTCCCAGCTCAGCATGAAAGCATCCCTGGAGAACAGCCTGGAGGAGACCAAAGGTCGCTACTGCATG CAGCTGGCCCAGATCCAGGAGATGATTGGCAGCGTGGAGGAGCAGCTGGCCCAGCTCCGCTGCGAGATGG AGCAGCAGAACCAGGAGTACAAGATCCTGCTGGACGTGAAGACGCGGCTGGAGCAGGAGATCGCCACCTA CCGCCGCCTGCTGGAGGGCGAGGACGCCCACCTCTCCTCCTCCCAGTTCTCCTCTGGATCGCAGTCATCC AGAGATGTGACCTCCTCCAGCCGCCAAATCCGCACCAAGGTCATGGATGTGCACGATGGCAAGGTGGTGT CCACCCACGAGCAGGTCCTTCGCACCAAGAACTGAGGCTGCCCAGCCCCGCTCAGGCCTAGGAGGCCCCC CGTGTGGACACAGATCCCACTGGAAGATCCCCTCTCCTGCCCAAGCACTTCACAGCTGGACCCTGCTTCA CCCTCACCCCCTCCTGGCAATCAATACAGCTTCATTATCTGAGTTGCATAAAAAAAAAAAAAAAAAAAAA AAAAAAAAAAAAAAAAAAAAAAAAAAAAAAAAAAAAAAAAAAAAAAAAAAAAAAAAAAAAAAAAAAAAAA AAAAAAAAAAAAAAAAAAAAAAAAAAAAAAAAAAAAAAAAAAAAAAAAAAAAAAAAAAAA | 130 |
| AK095281 | CTCTTTTGCAGGGGCCGTTCCTCGGGGCATGACGCTGGCTCCTGCACAGATCCTGCTCCTCTGTGGCCTT CCTGGGCTGCCCTCCCCTCCTCCGGGACTGCTCTGGACTGACACTGCTCAGGTTCGGATTCCCTCAAAGA CTTTGGGAGACAAGACTTGGTCCCCCTTTTACAAACAAGGGAACGGAGGCTCTAGAACTGACTTCCTGAA AGGCTTGGATCCAAAGCTCCCTCAGTTCAGCGGCCACGTCTATTTCCCTCAGACACAGGGATCCTTGAAC | 131 |

TABLE 2-continued

| GENBANK ACCESSION NUMBER | SEQUENCE | SEQ ID NO: |
|---|---|---|
| | CTGTGGGCTGTATCTCCCCGCGGACTTGGAAGAATCCCAAGAGAGTGGGGCTCCCACAGGCTGGAGTGCA<br>ATGGTGTGATCTCGGCTCACTGCAACCTCCACCTCCCAGGTTCAAGCTATTCTCCTGCCTCAGCCTCCTG<br>AGTAGCTGGGATTACAGATCCTGGTGGCTGTGGTCGGTAATTCCAGCTTCGTGCTGGCTACAGGTGGATG<br>ATGCCCACCTGGCTGCCGATGACCTCTGCACCAAGTGAGGCTGGGTCTCTGGAGCTGCCCCAGGGGCTGG<br>ACAAGCTGACCCTGGCCGGGGCCAACCTGGAGATGCAGATTGAGAACCTCAAGGAGGACCTGGTCTACCT<br>GAAGAAGAACCACAAGCAGGAAATGAACGTCCTTTGAGGTCAGGTGGATGAGGATGTCAGTGTGAAGATG<br>GACACTGTGCCTGGAGTGAACCTGAGCTGCATCCTGAATGAGATGCGTGACCAGGACAAGACATTGGTGG<br>AGAAGAGCTGCAAGGATGCCGAGGGCTGGTTCTTCAGCATGGTGGGTGGCCGTGCGTAAGCAGGTGTGTA<br>CACGTGTGGGCACATGTGCTGCATGCTGGTGCAGCTGGAGCACTGGCAGATCCACAGGCTGTCCCAGTTG<br>GAAGGACTTTTGGAAACCAGTTGGACCAGCCCCTCATGTTTTAGATGTAAAACGTGAGGCTCAGAGAGGA<br>CTCAAGCTCACACAGCCCTTCACTGTGGCCTGCAAAATAGATCCAGGTCTCTACAAGTCTGGTCTTGGGT<br>TTCCACCACAGCTGTTTACAGGATGTGCGTATTTGAATACATATGTATACCCTTGGCAAGCACAGGCTGA<br>GTATCTCCGGTATCCTAGGGACAGCAACAGGCGCAAAAGAATAACACCCAGTGCCTGTCTTTGAGGTGCT<br>GCAGTTCAGTAGGAAAAAGAAATGCAAATGACCGCAGAGCAGGCTGAATTCCTCCAAGTTCCAATGTGGG<br>TGCAGAGGCTCTCTGTGTGCAGAAAGAGGGGCTGAACTGCGAGGTGGCCACCAACACAGAGGCCCTGCAG<br>AGTGGCTGGATAGAGATATGGAGCTCTACGTCTCTGTGCAGAACCTGAGCCGTCCCAGCTCAGCAAGAAA<br>GCATCGCTGGAGGGCAGCCTGGTGGAGATGGAGGTGTGTTACAGGACCCTGCCGGCCCAGCTGCAGGGGC<br>TTAACAGAAGCATGGAGCAGCAGCTGTGCGAGCTCTGCTGCGACACGGAGCACCAGGACCACAAGCACAG<br>GTCCTTCTGGACGTGAAGACGTGGCTGGAGCAGGAGATCGCCACCTACCGCCGCTTGCTGGAGGTTGAGG<br>ACGCCCAGAGGTGATACTGACGATGCAGGCTGGAGTCTGGCTGAGGAGCCTTGAATGCCAAGTTAAAGCG<br>TCTGGACTAGATCACGTAGGCAATGGGGAGCCATGGAGGGATTTGGAGCAGGAGAGTGAAATGAACATCA<br>AGAGATTTTAGAACATTCACTCTGGCTGCAGAGGGAGAAATGGATCAGAGGGGTCAGGGCGGGGCCAGAG<br>AGATGTGTCAGGGGGCTGGAGCAGGGAGTCTGGCCAGAGAAGTCCCGTGCGGTGGTGGGTAGTGGGGCAG<br>GGGAAGGAAGGTGGTGCACGCAGAAGAGAGGTTATAGCTCAAAACAGCGGGACTGGATGCCTGGATCTCG<br>GGGTAAGCATGGCTCACAGTCAGGACTCAGTAAGTGTCGGGAGAACACATGAAGGAGCAGGCATTGATGG<br>CCCTGGGTTTCTGGTTCTGATGACTGTGTGAGTGGTGAAGAGCAAGGTGGGTGGTGGTTGGGTTTGCAGT<br>TGGGAAGGGTGATCAGGCCTTCAGCTGAGAGTGTCCCGGAGTCTCCATGCTTAGTCACACGTTGCAGCTT<br>TTTGCTCCCCGGAAATGGTGAAGTCCATCTATAGTCTAACAACAGTCTCTCCTGCTTTAATTGGGTCTAT<br>TTGTTGGGCCCTCTGGGTTATGGAAAAACCACTTGCTCAGCTTCTCCTTGTAAATTCCTGGTGAGTAGCC<br>ACAGAGTGCCGCCAGACCTACTGCTGTGCTGTTTCTTTTTCTTCTTCCTGCTGTGCTGAACCCCTGCCCT<br>TTCATTCTTGGGCCTGCGCTAATTTCTGTGCATTCCCAACTGTGATTTTTCACCAATTTAGGGGAACCTC<br>CTCTGCCAGGGCCTACTTCTCCCCAGCAGTGCTTGCAGGTGCCTGGGCTGGCTGGCATCCCTGGGCTGAT<br>GGGTGCTTCTCTCCCTGCAGGCTGGCCACTCAGTACTCCTTGTCCCTGGCCTCGCAGCCCACCCGGGAAG<br>CCACAGTGACCAGCCACCAGGTGTGCCATCGTGGAGGAAGTCCAGGTTGGAGAGGTGGTCTTCTTCTGTG<br>AGCAGGTCCACTTCTCCACCCACTGAGACCCCTTTCTGTCTGCGACAGCCCCACCTCGAGGGCCACGGCA<br>CAGCCATCAGCTCCAGCTCCCAGCATGCTACTGCCACGCCCCGAGTGTCCGTCTGGGCCCCGGTGCATGG<br>CCTGTTGTCTTTCTGTATCTACTTTCTGCAGCCCCTCACTGAGGAGGCCTCCTGGGTTTGTCCAGTGCCT<br>ACTATTAAAGCTTTGCTCCAAGTTC | |
| M21389 | GCATCCTTTTTGGGCTGCTCACAGCCCCCAGCCTCTATGGTGAAGACATACTTGCTAGCAGCGTCACCAA<br>CTTGCTGCCAAGAGATCAGTGCTGCAAGGCAAGGTTATTTCTAACTGAGCAGAGCCTGCCAGGAAGAAAG<br>CGTTTGCACCCCACACCACTGTGCAGGTGTGACCGGTGAGCTCACAGCTGCCCCCCAGGCATGCCCAGCC<br>CACTTAATCATTCACAGCTCGACAGCTCTCTCGCCCAGCCCAGTTCTGGAAGGGATAAAAAGGGGGCATC<br>ACCGTTCCTGGGTAACAGAGCCACCTTCTGCGTCCTGCTGAGCTCTGTTCTCTCCAGCACCTCCCAACCC<br>ACTAGTGCCTGGTTCTCTTGCTCCACCAGGAACAAGCCACCATGTCTCGCCAGTCAAGTGTGTCCTTCCG<br>GAGCGGGGGCAGTCGTAGCTTCAGCACCGCCTCTGCCATCACCCCGTCTGTCTCCCGCACCAGCTTCACC<br>TCCGTGTCCCGGTCCGGGGGTGGCGGTGGTGGTGGCTTCGGCAGGGTCAGCCTTGCGGGTGCTTGTGGAG<br>TGGGTGGCTATGGCAGCCGGAGCCTCTACAACCTGGGGGGCTCCAAGAGGATATCCATCAGCACTAGAGG<br>AGGCAGCTTCAGGAACCGGTTTGGTGCTGGTGCTGGAGGCGGCTATGGCTTTGGAGGTGGTGCCGGTAGT<br>GGATTTGGTTTCGGCGGTGGAGCTGGTGGTGGCTTTGGGCTCGGTGGCGGAGCTGGCTTTGGAGGTGGCT<br>TCGGTGGCCCTGGCTTTCCTGTCTGCCCTCCTGGAGGTATCCAAGAGGTCACTGTCAACCAGAGTCTCCT<br>GACTCCCCTCAACCTGCAAATCGACCCCAGCATCCAGAGGGTGAGGACCGAGGAGCGCGAGCAGATCAAG<br>ACCCTCAACAATAAGTTTGCCTCCTTCATCGACAAGGTGCGGTTCCTGGAGCAGCAGAACAAGGTTCTGG<br>ACACCAAGTGGACCCTGCTGCAGGAGCAGGGCACCAAGACTGTGAGGCAGAACCTGGAGCCGTTGTTCGA<br>GCAGTACATCAACAACCTCAGGAGGCAGCTGGACAGCATCGTGGGGGAACGGGGCCGCCTGGACTCAGAG<br>CTGAGAAACATGCAGGACCTGGTGGAAGACTTCAAGAACAAGTATGAGGATGAAATCAACAAGCGTACCA<br>CTGCTGAGAATGAGTTTGTGATGCTGAAGAAGGATGTAGATGCTGCCTACATGAACAAGGTGGAGCTGGA<br>GGCCAAGGTTGATGCACTGATGGATGAGATTAACTTCATGAAGATGTTCTTTGATGCGGAGCTGTCCCAG<br>ATGCAGACGCATGTCTCTGACACCTCAGTGGTCCTCTCCATGGACAACAACCGCAACCTGGACCTGGATA<br>GCATCATCGCTGAGGTCAAGGCCCAGTATGAGGAGATTGCCAACCGCAGCCGGACAGAAGCCGAGTCCTG<br>GTATCAGACCAAGTATGAGGAGCTGCAGCAGACAGCTGGCCGGCATGGCGATGACCTCCGCAACACCAAG<br>CATGAGATCACAGAGATGAACCGGATGATCCAGAGGCTGAGAGCCGAGATTGACAATGTCAAGAAACAGT<br>GCGCCAATCTGCAGAACGCCATTGCGGATGCCGAGCAGCGTGGGGAGCTGGCCCTCAAGGATGCCAGGAA<br>CAAGCTGGCCGAGCTGGAGGAGGCCCTGCAGAAGGCCAAGCAGGACATGGCCCGGCTGCTGCGTGAGTAC<br>CAGGAGCTCATGAACACCAAGCTGGCCCTGGACGTGGAGATCGCCACTTACCGCAAGCTGCTGGAGGGCG<br>AGGAATGCAGACTCAGTGGAGAAGGAGTTGGACCAGTCAACATCTCTGTTGTCACAAGCAGTGTTTCCTC<br>TGGATATGGCAGTGGCAGTGGCTATGGCGGTGGCCTCGGTGGAGGTCTTGGCGGCGGCCTCGGTGGAGGT<br>CTTGCCGGAGGTAGCAGTGGAAGCTACTACTCCAGCAGCAGTGGGGGTGTCGGCCTAGGTGGTGGGCTCA<br>GTGTGGGGGGCTCTGGCTTCAGTGCAAGCAGTGGCCGAGGGCTGGGGGTGGGCTTTGGCAGTGGCGGGGG<br>TAGCAGCTCCAGCGTCAAATTTGTCTCCACCACCTCCTCCTCCCGGAAGAGCTTCAAGAGCTAAGAACCT<br>GCTGCAAGTCACTGCCTTCCAAGTGCAGCAACCCAGCCCATGGAGATTGCCTCTTCTAGGCAGTTGCTCA<br>AGCCATGTTTTATCCTTTTCTGGAGAGTAGTCTAGACCAAGCCAATTGCAGAACCACATTCTTTGGTTCC<br>CAGGAGAGCCCCATTCCCAGCCCCTGGTCTCCCGTGCCGCAGTTCTATATTCTGCTTCAAATCAGCCTTC<br>AGGTTTCCCACAGCATGGCCCCTGCTGACACGAGAACCCAAAGTTTTCCCAAATCTAAATCATCAAAACA<br>GAATCCCCACCCCAATCCCAAATTTTGTTTTGGTTCTAACTACCTCCAGAATGTGTTCAATAAAATGCTT<br>TTATAATAT | 132 |

TABLE 2-continued

| GENBANK ACCESSION NUMBER | SEQUENCE | SEQ ID NO: |
|---|---|---|
| NM_001123066 | GGACGGCCGAGCGGCAGGGCGCTCGCGCGCGCCCACTAGTGGCCGGAGGAGAAGGCTCCCGCGGAGGCCG<br>CGCTGCCCGCCCCCTCCCCTGGGGAGGCTCGCGTTCCCGCTGCTCGCGCCTGCGCCGCCCGCCGGCCTCA<br>GGAACGCGCCCTCTTCGCCGGCGCGCGCCCTCGCAGTCACCGCCACCCACCAGCTCCGGCACCAACAGCA<br>GCGCCGCTGCCACCGCCCACCTTCTGCCGCCGCCACCACAGCCACCTTCTCCTCCTCCGCTGTCCTCTCC<br>CGTCCTCGCCTCTGTCGACTATCAGGTGAACTTTGAACCAGGATGGCTGAGCCCCGCCAGGAGTTCGAAG<br>TGATGGAAGATCACGCTGGGACGTACGGGTTGGGGGACAGGAAAGATCAGGGGGGCTACACCATGCACCA<br>AGACCAAGAGGGTGACACGGACGCTGGCCTGAAAGAATCTCCCCTGCAGACCCCCACTGAGGACGGATCT<br>GAGGAACCGGGCTCTGAAACCTCTGATGCTAAGAGCACTCCAACAGCGGAAGATGTGACAGCACCCTTAG<br>TGGATGAGGGAGCTCCCGGCAAGCAGGCTGCCGCGCAGCCCCACACGGAGATCCCAGAAGGAACCACAGC<br>TGAAGAAGCAGGCATTGGAGACACCCCCAGCCTGGAAGACGAAGCTGCTGGTCACGTGACCCAAGAGCCT<br>GAAAGTGGTAAGGTGGTCCAGGAAGGCTTCCTCCGAGAGCCAGGCCCCCCAGGTCTGAGCCACCAGCTCA<br>TGTCCGGCATGCCTGGGGCTCCCCTCCTGCCTGAGGGCCCCAGAGAGGCCACACGCCAACCTTCGGGGAC<br>AGGACCTGAGGACACAGAGGGCGGCCGCCACGCCCCTGAGCTGCTCAAGCACCAGCTTCTAGGAGACCTG<br>CACCAGGAGGGGCCGCCGCTGAAGGGGGCAGGGGGCAAAGAGAGGCCGGGGAGCAAGGAGGAGGTGGATG<br>AAGACCGCGACGTCGATGAGTCCTCCCCCCAAGACTCCCCTCCCTCCAAGGCCTCCCCAGCCCAAGATGG<br>GCGGCCTCCCCAGACAGCCGCCAGAGAAGCCACCAGCATCCCAGGCTTCCCAGCGGAGGGTGCCATCCCC<br>CTCCCTGTGGATTTCCTCTCCAAAGTTTCCACAGAGATCCCAGCCTCAGAGCCCGACGGGCCCAGTGTAG<br>GGCGGGCCAAAGGGCAGGATGCCCCCCTGGAGTTCACGTTTCACGTGGAAATCACACCCAACGTGCAGAA<br>GGAGCAGGCGCACTCGGAGGAGCATTTGGGAAGGGCTGCATTTCCAGGGGCCCCTGGAGAGGGGCCAGAG<br>GCCCGGGGCCCCTCTTTGGGAGAGGACACAAAGAGGCTGACCTTCCAGAGCCCTCTGAAAAGCAGCCTG<br>CTGCTGCTCCGCGGGGGAAGCCCGTCAGCCGGGTCCCTCAACTCAAAGCTCGCATGGTCAGTAAAAGCAA<br>AGACGGGACTGGAAGCGATGACAAAAAAGCCAAGACATCCACACGTTCCTCTGCTAAAACCTTGAAAAAT<br>AGGCCTTGCCTTAGCCCCAAACACCCCACTCCTGGTAGCTCAGACCCTCTGATCCAACCCTCCAGCCCTG<br>CTGTGTGCCCAGAGCCACCTTCCTCTCCTAAATACGTCTCTTCTGTCACTTCCCGAACTGGCAGTTCTGG<br>AGCAAAGGAGATGAAACTCAAGGGGGCTGATGGTAAAACGAAGATCGCCACACCGCGGGGAGCAGCCCCT<br>CCAGGCCAGAAGGGCCAGGCCAACGCCACCAGGATTCCAGCAAAAACCCCGCCCGCTCCAAAGACACCAC<br>CCAGCTCTGCGACTAAGCAAGTCCAGAGAAGACCACCCCCTGCAGGGCCCAGATCTGAGAGAGGTGAACC<br>TCCAAAATCAGGGGATCGCAGCGGCTACAGCAGCCCCGGCTCCCCAGGCACTCCCGGCAGCCGCTCCCGC<br>ACCCCGTCCCTTCCAACCCCACCCACCCGGGAGCCCAAGAAGGTGGCAGTGGTCCGTACTCCACCCAAGT<br>CGCCGTCTTCCGCCAAGAGCCGCCTGCAGACAGCCCCCGTGCCCATGCCAGACCTGAAGAATGTCAAGTC<br>CAAGATCGGCTCCACTGAGAACCTGAAGCACCAGCCGGGAGGCGGGAAGGTGCAGATAATTAATAAGAAG<br>CTGGATCTTAGCAACGTCCAGTCCAAGTGTGGCTCAAAGGATAATATCAAACACGTCCCGGGAGGCGGCA<br>GTGTGCAAATAGTCTACAAACCAGTTGACCTGAGCAAGGTGACCTCCAAGTGTGGCTCATTAGGCAACAT<br>CCATCATAAACCAGGAGGTGGCCAGGTGGAAGTAAAATCTGAGAAGCTTGACTTCAAGGACAGAGTCCAG<br>TCGAAGATTGGGTCCCTGGACAATATCACCCACGTCCCTGGCGGAGGAAATAAAAAGATTGAAACCCACA<br>AGCTGACCTTCCGCGAGAACGCCAAAGCCAAGACAGACCACGGGGCGGAGATCGTGTACAAGTCGCCAGT<br>GGTGTCTGGGGACACGTCTCCACGGCATCTCAGCAATGTCTCCTCCACCGGCAGCATCGACATGGTAGAC<br>TCGCCCCAGCTCGCCACGCTAGCTGACGAGGTGTCTGCCTCCCTGGCCAAGCAGGGTTTGTGATCAGGCC<br>CCTGGGGCGGTCAATAATTGTGGAGAGGAGAGAATGAGAGAGTGTGGAAAAAAAAAGAATAATGACCCGG<br>CCCCCGCCCTCTGCCCCCAGCTGCTCCTCGCAGTTCGGTTAATTGGTTAATCACTTAACCTGCTTTTGTC<br>ACTCGGCTTTGGCTCGGGACTTCAAAATCAGTGATGGGAGTAAGAGCAAATTTCATCTTTCCAAATTGAT<br>GGGTGGGCTAGTAATAAAATATTTAAAAAAAAACATTCAAAAACATGGCCACATCCAACATTTCCTCAGG<br>CAATTCCTTTTGATTCTTTTTTCTTCCCCCTCCATGTAGAAGAGGGAGAAGGAGAGGCTCTGAAAGCTGC<br>TTCTGGGGGATTTCAAGGGACTGGGGGTGCCAACCACCTCTGGCCCTGTTGTGGGGGTGTCACAGAGGCA<br>GTGGCAGCAACAAAGGATTTGAAACTTGGTGTGTTCGTGGAGCCACAGGCAGACGATGTCAACCTTGTGT<br>GAGTGTGACGGGGGTTGGGGTGGGGCGGGAGGCCACGGGGGAGGCCGAGGCAGGGGCTGGGCAGAGGGGA<br>GAGGAAGCACAAGAAGTGGGAGTGGGAGAGGAAGCCACGTGCTGGAGAGTAGACATCCCCCTCCTTGCCG<br>CTGGGAGAGCCAAGGCCTATGCCACCTGCAGCGTCTGAGCGGCCGCCTGTCCTTGGTGGCCGGGGGTGGG<br>GGCCTGCTGTGGGTCAGTGTGCCACCCTCTGCAGGGCAGCCTGTGGGAGAAGGGACAGCGGGTAAAAAGA<br>GAAGGCAAGCTGGCAGGAGGGTGGCACTTCGTGGATGACCTCCTTAGAAAAGACTGACCTTGATGTCTTG<br>AGAGCGCTGGCCTCTTCCTCCCTCCCTGCAGGGTAGGGGGCCTGAGTTGAGGGGCTTCCCTCTGCTCCAC<br>AGAAACCCTGTTTTATTGAGTTCTGAAGGTTGGAACTGCTGCCATGATTTTGGCCACTTTGCAGACCTGG<br>GACTTTAGGGCTAACCAGTTCTCTTTGTAAGGACTTGTGCCTCTTGGGAGACGTCCACCCGTTTCCAAGC<br>CTGGGCCACTGGCATCTCTGGAGTGTGTGGGGGTCTGGGAGGCAGGTCCCGAGCCCCCTGTCCTTCCCAC<br>GGCCACTGCAGTCACCCCGTCTGCGCCGCTGTGCTGTTGTCTGCCGTGAGAGCCCAATCACTGCCTATAC<br>CCCTCATCACACGTCACAATGTCCCGAATTCCCAGCCTCACCACCCCTTCTCAGTAATGACCCTGGTTGG<br>TTGCAGGAGGTACCTACTCCATACTGAGGGTGAAATTAAGGGAAGGCAAAGTCCAGGCACAAGAGTGGGA<br>CCCCAGCCTCTCACTCTCAGTTCCACTCATCCAACTGGGACCCTCACCACGAATCTCATGATCTGATTCG<br>GTTCCCTGTCTCCTCCTCCCGTCACAGATGTGAGCCAGGGCACTGCTCAGCTGTGACCCTAGGTGTTTCT<br>GCCTTGTTGACATGGAGAGAGCCCTTTCCCCTGAGAAGGCCTGGCCCCTTCCTGTGCTGAGCCCACAGCA<br>GCAGGCTGGGTGTCTTGGTTGTCAGTGGTGGCACCAGGATGGAAGGGCAAGGCACCCAGGGCAGGCCCAC<br>AGTCCCGCTGTCCCCCACTTGCACCCTAGCTTGTAGCTGCCAACCTCCCAGACAGCCCAGCCCGCTGCTC<br>AGCTCCACATGCATAGTATCAGCCCTCCACACCCGACAAAGGGGAACACACCCCCTTGGAAATGGTTCTT<br>TTCCCCCAGTCCCAGCTGGAAGCCATGCTGTCTGTTCTGCTGGAGCAGCTGAACATATACATAGATGTTG<br>CCCTGCCCTCCCCATCTGCACCCTGTTGAGTTGTAGTTGGATTTGTCTGTTTATGCTTGGATTCACCAGA<br>GTGACTATGATAGTGAAAAGAAAAAAAAAAAAAAAAAAGGACGCATGTATCTTGAAATGCTTGTAAAGAG<br>GTTTCTAACCCACCCTCACGAGGTGTCTCTCACCCCCACACTGGGACTCGTGTGGCCTGTGTGGTGCCAC<br>CCTGCTGGGGCCTCCCAAGTTTTGAAAGGCTTTCCTCAGCACCTGGGACCCAACAGAGACCAGCTTCTAG<br>CAGCTAAGGAGGCCGTTCAGCTGTGACGAAGGCCTGAAGCACAGGATTAGGACTGAAGCGATGATGTCCC<br>CTTCCCTACTTCCCCTTGGGGCTCCCTGTGTCAGGGCACAGACTAGGTCTTGTGGCTGGTCTGGCTTGCG<br>GCGCGAGGATGGTTCTCTCTGGTCATAGCCCGAAGTCTCATGGCAGTCCCAAAGGAGGCTTACAACTCCT<br>GCATCACAAGAAAAAGGAAGCCACTGCCAGCTGGGGGGATCTGCAGCTCCCAGAAGCTCCGTGAGCCTCA<br>GCCACCCCTCAGACTGGGTTCCTCTCCAAGCTCGCCCTCTGGAGGGGCAGCGCAGCCTCCCACCAAGGGC<br>CCTGCGACCACAGCAGGGATTGGGATGAATTGCCTGTCCTGGATCTGCTCTAGAGGCCCAAGCTGCCTGC<br>CTGAGGAAGGATGACTTGACAAGTCAGGAGACACTGTTCCCAAAGCCTTGACCAGAGCACCTCAGCCCGC | 133 |

TABLE 2-continued

| GENBANK ACCESSION NUMBER | SEQUENCE | SEQ ID NO: |
|---|---|---|
| | TGACCTTGCACAAACTCCATCTGCTGCCATGAGAAAAGGGAAGCCGCCTTTGCAAAACATTGCTGCCTAA<br>AGAAACTCAGCAGCCTCAGGCCCAATTCTGCCACTTCTGGTTTGGGTACAGTTAAAGGCAACCCTGAGGG<br>ACTTGGCAGTAGAAATCCAGGGCCTCCCCTGGGGCTGGCAGCTTCGTGTGCAGCTAGAGCTTTACCTGAA<br>AGGAAGTCTCTGGGCCCAGAACTCTCCACCAAGAGCCTCCCTGCCGTTCGCTGAGTCCCAGCAATTCTCC<br>TAAGTTGAAGGGATCTGAGAAGGAGAAGGAAATGTGGGGTAGATTTGGTGGTGGTTAGAGATATGCCCCC<br>CTCATTACTGCCAACAGTTTCGGCTGCATTTCTTCACGCACCTCGGTTCCTCTTCCTGAAGTTCTTGTGC<br>CCTGCTCTTCAGCACCATGGGCCTTCTTATACGGAAGGCTCTGGGATCTCCCCCTTGTGGGGCAGGCTCT<br>TGGGGCCAGCCTAAGATCATGGTTTAGGGTGATCAGTGCTGGCAGATAAATTGAAAAGGCACGCTGGCTT<br>GTGATCTTAAATGAGGACAATCCCCCCAGGGCTGGGCACTCCTCCCCTCCCCTCACTTCTCCCACCTGCA<br>GAGCCAGTGTCCTTGGGTGGGCTAGATAGGATATACTGTATGCCGGCTCCTTCAAGCTGCTGACTCACTT<br>TATCAATAGTTCCATTTAAATTGACTTCAGTGGTGAGACTGTATCCTGTTTGCTATTGCTTGTTGTGCTA<br>TGGGGGGAGGGGGGAGGAATGTGTAAGATAGTTAACATGGGCAAAGGGAGATCTTGGGGTGCAGCACTTA<br>AACTGCCTCGTAACCCTTTTCATGATTTCAACCACATTTGCTAGAGGGAGGGAGCAGCCACGGAGTTAGA<br>GGCCCTTGGGGTTTCTCTTTTCCACTGACAGGCTTTCCCAGGCAGCTGGCTAGTTCATTCCCTCCCCAGC<br>CAGGTGCAGGCGTAGGAATATGGACATCTGGTTGCTTTGGCCTGCTGCCCTCTTTCAGGGGTCCTAAGCC<br>CACAATCATGCCTCCCTAAGACCTTGGCATCCTTCCCTCTAAGCCGTTGGCACCTCTGTGCCACCTCTCA<br>CACTGGCTCCAGACACACAGCCTGTGCTTTTGGAGCTGAGATCACTCGCTTCACCCTCCTCATCTTTGTT<br>CTCCAAGTAAAGCCACGAGGTCGGGGCGAGGGCAGAGGTGATCACCTGCGTGTCCCATCTACAGACCTGC<br>AGCTTCATAAAACTTCTGATTTCTCTTCAGCTTTGAAAAGGGTTACCCTGGGCACTGGCCTAGAGCCTCA<br>CCTCCTAATAGACTTAGCCCCATGAGTTTGCCATGTTGAGCAGGACTATTTCTGGCACTTGCAAGTCCCA<br>TGATTTCTTCGGTAATTCTGAGGGTGGGGGGAGGGACATGAAATCATCTTAGCTTAGCTTTCTGTCTGTG<br>AATGTCTATATAGTGTATTGTGTGTTTTAACAAATGATTTACACTGACTGTTGCTGTAAAAGTGAATTTG<br>GAAATAAAGTTATTACTCTGATTAAA | |
| M92424 | GCACCGCGCGAGCTTGGCTGCTTCTGGGGCCTGTGTGGCCCTGTGTGTCGGAAAGATGGAGCAAGAAGCC<br>GAGCCCGAGGGGCGGCCGCGACCCCTCTGACCGAGATCCTGCTGCTTTCGCAGCCAGGAGCACCGTCCCT<br>CCCCGGATTAGTGCGTACGAGCGCCCAGTGCCCTGGCCCGGAGAGTGGAATGATCCCCGAGGCCCAGGGC<br>GTCGTGCTTCCGCAGTAGTCAGTCCCCGTGAAGGAAACTGGGGAGTCTTGAGGGACCCCCGACTCCAAGC<br>GCGAAAACCCCGGATGGTGAGGAGCAGGCAAATGTGCAATACCAACATGTCTGTACCTACTGATGGTGCT<br>GTAACCACCTCACAGATTCCAGCTTCGGAACAAGAGACCCTGGTTAGACCAAAGCCATTGCTTTTGAAGT<br>TATTAAAGTCTGTTGGTGCACAAAAAGACACTTATACTATGAAAGAGGTTCTTTTTTATCTTGGCCAGTA<br>TATTATGACTAAACGATTATATGATGAGAAGCAACAACATATTGTATATTGTTCAAATGATCTTCTAGGA<br>GATTTGTTTGGCGTGCCAAGCTTCTCTGTGAAAGAGCACAGGAAAATATATACCATGATCTACAGGAACT<br>TGGTAGTAGTCAATCAGCAGGAATCATCGGACTCAGGTACATCTGTGAGTGAGAACAGGTGTCACCTTGA<br>AGGTGGGAGTGATCAAAAGGACCTTGTACAAGAGCTTCAGGAAGAGAAACCTTCATCTTCACATTTGGTT<br>TCTAGACCATCTACCTCATCTAGAAGGAGAGCAATTAGTGAGACAGAAGAAAATTCAGATGAATTATCTG<br>GTGAACGACAAAGAAAACGCCACAAATCTGATAGTATTTCCCTTTCCTTTGATGAAAGCCTGGCTCTGTG<br>TGTAATAAGGGAGATATGTTGTGAAAGAAGCAGTAGCAGTGAATCTACAGGGACGCCATCGAATCCGGAT<br>CTTGATGCTGGTGTAAGTGAACATTCAGGTGATTGGTTGGATCAGGATTCAGTTTCAGATCAGTTTAGTG<br>TAGAATTTGAAGTTGAATCTCTCGACTCAGAAGATTATAGCCTTAGTGAAGAAGGACAAGAACTCTCAGA<br>TGAAGATGATGAGGTATATCAAGTTACTGTGTATCAGGCAGGGGAGAGTGATACAGATTCATTTGAAGAA<br>GATCCTGAAATTTCCTTAGCTGACTATTGGAAATGCACTTCATGCAATGAAATGAATCCCCCCCTTCCAT<br>CACATTGCAACAGATGTTGGGCCCTTCGTGAGAATTGGCTTCCTGAAGATAAAGGGAAAGATAAAGGGGA<br>AATCTCTGAGAAAGCCAAACTGGAAAACTCAACACAAGCTGAAGAGGGCTTTGATGTTCCTGATTGTAAA<br>AAAACTATAGTGAATGATTCCAGAGAGTCATGTGTTGAGGAAAATGATGATAAAATTACACAAGCTTCAC<br>AATCACAAGAAAGTGAAGACTATTCTCAGCCATCAACTTCTAGTAGCATTATTTATAGCAGCCAAGAAGA<br>TGTGAAAGAGTTTGAAAGGGAAGAAACCCAAGACAAAGAAGAGAGTGTGGAATCTAGTTTGCCCCTTAAT<br>GCCATTGAACCTTGTGTGATTTGTCAAGGTCGACCTAAAAATGGTTGCATTGTCCATGGCAAAACAGGAC<br>ATCTTATGGCCTGCTTTACATGTGCAAAGAAGCTAAAGAAAAGGAATAAGCCCTGCCCAGTATGTAGACA<br>ACCAATTCAAATGATTGTGCTAACTTATTTCCCCTAGTTGACCTGTCTATAAGAGAATTATATATTTCTA<br>ACTATATAACCCTAGGAATTTAGACAACCTGAAATTTATTCACATATATCAAAGTGAGAAAATGCCTCAA<br>TTCACATAGATTTCTTCTCTTTAGTATAATTGACCTACTTTGGTAGTGGAATAGTGAATACTTACTATAA<br>TTTGACTTGAATATGTAGCTCATCCTTTACACCAACTCCTAATTTTAAATAATTTCTACTCTGTCTTAAA<br>TGAGAAGTACTTGGTTTTTTTTTTCTTAAATATGTATATGACATTTAAATGTAACTTATTATTTTTTTTG<br>AGACCGAGTCTTGCTCTGTTACCCAGGCTGGAGTGCAGTGGGTGATCTTGGCTCACTGCAAGCTCTGCCC<br>TCCCCGGGTTCGCACCATTCTCCTGCCTCAGCCTCCCAATTAGCTTGGCCTACAGTCATCTGCCACCACA<br>CCTGGCTAATTTTTTGTACTTTTAGTAGAGACAGGGTTTCACCGTGTTAGCCAGGATGGTCTCGATCTCC<br>TGACCTCGTGATCCGCCCACCTCGGCCTCCCAAAGTGCTGGGATTACAGGCATGAGCCACCG | 134 |
| NM_014791 | GAGATTTGATTCCCTTGGCGGGCGGAAGCGGCCACAACCCGGCGATCGAAAAGATTCTTAGGAACGCCGT<br>ACCAGCCGCGTCTCTCAGGACAGCAGGCCCCTGTCCTTCTGTCGGGCGCCGCTCAGCCGTGCCCTCCGCC<br>CCTCAGGTTCTTTTTCTAATTCCAAATAAACTTGCAAGAGGACTATGAAAGATTATGATGAACTTCTCAA<br>ATATTATGAATTACATGAAACTATTGGGACAGGTGGCTTTGCAAAGGTCAAACTTGCCTGCCATATCCTT<br>ACTGGAGAGATGGTAGCTATAAAAATCATGGATAAAAACACACTAGGGAGTGATTTGCCCCGGATCAAAA<br>CGGAGATTGAGGCCTTGAAGAACCTGAGACATCAGCATATATGTCAACTCTACCATGTGCTAGAGACAGC<br>CAACAAAATATTCATGGTTCTTGAGTACTGCCCTGGAGGAGAGCTGTTTGACTATATAATTTCCCAGGAT<br>CGCCTGTCAGAAGAGGAGACCCGGGTTGTCTTCCGTCAGATAGTATCTGCTGTTGCTTATGTGCACAGCC<br>AGGGCTATGCTCACAGGGACCTCAAGCCAGAAAATTTGCTGTTTGATGAATATCATAAATTAAAGCTGAT<br>TGACTTTGGTCTCTGTGCAAAACCCAAGGGTAACAAGGATTACCATCTACAGACATGCTGTGGGAGTCTG<br>GCTTATGCAGCACCTGAGTTAATACAAGGCAAATCATATCTTGGATCAGAGGCAGATGTTTGGAGCATGG<br>GCATACTGTTATATGTTCTTATGTGTGGATTTCTACCATTTGATGATGATAATGTAATGGCTTTATACAA<br>GAAGATTATGAGAGGAAAATATGATGTTCCCAAGTGGCTCTCTCCCAGTAGCATTCTGCTTCTTCAACAA<br>ATGCTGCAGGTGGACCCAAAGAAACGGATTTCTATGAAAAATCTATTGAACCATCCCTGGATCATGCAAG<br>ATTACAACTATCCTGTTGAGTGGCAAAGCAAGAATCCTTTTATTCACCTCGATGATGATTGCGTAACAGA<br>ACTTTCTGTACATCACAGAAACAACAGGCAAACAATGGAGGATTTAATTTCACTGTGGCAGTATGATCAC<br>CTCACGGCTACCTATCTTCTGCTTCTAGCCAAGAAGGCTCGGGGAAAACCAGTTCGTTTAAGGCTTTCTT | 135 |

TABLE 2-continued

| GENBANK ACCESSION NUMBER | SEQUENCE | SEQ ID NO: |
|---|---|---|
| | CTTTCTCCTGTGGACAAGCCAGTGCTACCCCATTCACAGACATCAAGTCAAATAATTGGAGTCTGGAAGA<br>TGTGACCGCAAGTGATAAAAATTATGTGGCGGGATTAATAGACTATGATTGGTGTGAAGATGATTTATCA<br>ACAGGTGCTGCTACTCCCCGAACATCACAGTTTACCAAGTACTGGACAGAATCAAATGGGGTGGAATCTA<br>AATCATTAACTCCAGCCTTATGCAGAACACCTGCAAATAAATTAAAGAACAAAGAAAATGTATATACTCC<br>TAAGTCTGCTGTAAAGAATGAAGAGTACTTTATGTTTCCTGAGCCAAAGACTCCAGTTAATAAGAACCAG<br>CATAAGAGAGAAATACTCACTACGCCAAATCGTTACACTACACCCTCAAAAGCTAGAAACCAGTGCCTGA<br>AAGAAACTCCAATTAAAATACCAGTAAATTCAACAGGAACAGACAAGTTAATGACAGGTGTCATTAGCCC<br>TGAGAGGCGGTGCCGCTCAGTGGAATTGGATCTCAACCAAGCACATATGGAGGAGACTCCAAAAAGAAAG<br>GGAGCCAAAGTGTTTGGGAGCCTTGAAAGGGGGTTGGATAAGGTTATCACTGTGCTCACCAGGAGCAAAA<br>GGAAGGGTTCTGCCAGAGACGGGCCCAGAAGACTAAAGCTTCACTATAACGTGACTACAACTAGATTAGT<br>GAATCCAGATCAACTGTTGAATGAAATAATGTCTATTCTTCCAAAGAAGCATGTTGACTTTGTACAAAAG<br>GGTTATACACTGAAGTGTCAAACACAGTCAGATTTTGGGAAAGTGACAATGCAATTTGAATTAGAAGTGT<br>GCCAGCTTCAAAAACCCGATGTGGTGGGTATCAGGAGGCAGCGGCTTAAGGGCGATGCCTGGGTTTACAA<br>AAGATTAGTGGAAGACATCCTATCTAGCTGCAAGGTATAATTGATGGATTCTTCCATCCTGCCGGATGAG<br>TGTGGGTGTGATACAGCCTACATAAAGACTGTTATGATCGCTTTGATTTTAAAGTTCATTGGAACTACCA<br>ACTTGTTTCTAAAGAGCTATCTTAAGACCAATATCTCTTTGTTTTTAAACAAAAGATATTATTTTGTGTA<br>TGAATCTAAATCAAGCCCATCTGTCATTATGTTACTGTCTTTTTTAATCATGTGGTTTTGTATATTAATA<br>ATTGTTGACTTTCTTAGATTCACTTCCATATGTGAATGTAAGCTCTTAACTATGTCTCTTTGTAATGTGT<br>AATTTCTTTCTGAAATAAAACCATTTGTGAATATAG | |
| BG765502 | GCAGCGGAGGAGCCCAGTCCACGATGGCCCGGTCCCTGGTGTGCCTTGGTGTCATCATCTTGCTGTCTGC<br>CTTCTCCGGACCTGGTGTCAGGGGTGGTCCTATGCCCAAGCTGGCTGACCGGAAGCTGTGTGCGGACCAG<br>GAGTGCAGCCACCCTATCTCCATGGCTGTGGCCCTTCAGGACTACATGGCCCCCGACTGCCGATTCCTGA<br>CCATTCACCGGGGCCAAGTGGTGTATGTCTTCTCCAAGCTGAAGGGCCGTGGGCGGCTCTTCTGGGGAGG<br>CAGCGTTCAGGGAGATTACTATGGAGATCTGGCTGCTCGCCTGGGCTATTTCCCCAGTAGCATTGTCCGA<br>GAGGACCAGACCCTGAAACCTGGCAAAGTCGATGTGAAGACAGACAAATGGGATTTCTACTGCCAGTGAG<br>CTCAGCCTACCGCTGGCCCTGCCGTTTCCCCTCCTTGGGTTTATGCAAATACAATCAGCCCAGTGCAAAA<br>AAAAAAAAAAAAAAAAAAACTTCGGAGAAGAGATAGCAACAAAAGGCCGCTTGTGTGAAGGCGCCAAAA<br>GTTTTCGCCCAAGAGACCTTCGGCCTCCCCCAGGGCGCGCGCAAAGGCGCCTTGTTTTGACAACCTCTTG<br>GACAACCGGAGGGGCTACCGCCCGGAGACCCCTGTGGTGGACCCCCCGGGCAACCCGGTGTGACAGGGTA<br>CTCACCCCCACGGCTTTGTCGGGGGTCCCACCAAAGGCCCCAAAGAGGCTCTTTCAAGGCACTATTCCTT<br>GTTGTAGACCTTGTGTGTGCCACAGGCGCCAAAGAAACCTCGGGGGGCTAACAAACGCACGTGCTTGGCA<br>GCTCCGAGAAGGCTCTCTCCCACCCGAGGGGTGGACGCAACAGGGGGAATGGGCCATCATATTGTTGCCC<br>CCGGTGGGCACCAACTCTTTTTCCCCCATAGAGAGGCCTTAGCACACTATGTGGGGCACGTTATTGCCGC<br>CTAGAGAAACCGAGCGCCAGAAAATTTCGAAGGGGGGGGCGCTTCTCATCATTTTGCGCAAAACCCCCTT<br>GTGGGAGTATGCCCCGAACTCCTCTGGAACACACAAGCGACACTTGCGCGGGGTCTGCAAAAAACCTCCT<br>GTTGGGAAGCCGGCTTCACN | |
| NM_002417 | TACCGGGCGGAGGTGAGCGCGGCGCCGGCTCCTCCTGCGGCGGACTTTGGGTGCGACTTGACGAGCGGTG<br>GTTCGACAAGTGGCCTTGCGGGCCGGATCGTCCCAGTGGAAGAGTTGTAAATTTGCTTCTGGCCTTCCCC<br>TACGGATTATACCTGGCCTTCCCCTACGGATTATACTCAACTTACTGTTTAGAAAATGTGGCCCACGAGA<br>CGCCTGGTTACTATCAAAAGGAGCGGGGTCGACGGTCCCCACTTTCCCCTGAGCCTCAGCACCTGCTTGT<br>TTGGAAGGGGTATTGAATGTGACATCCGTATCCAGCTTCCTGTTGTGTCAAAACAACATTGCAAAATTGA<br>AATCCATGAGCAGGAGGCAATATTACATAATTTCAGTTCCACAAATCCAACACAAGTAAATGGGTCTGTT<br>ATTGATGAGCCTGTACGGCTAAAACATGGAGATGTAATAACTATTATTGATCGTTCCTTCAGGTATGAAA<br>ATGAAAGTCTTCAGAATGGAAGGAAGTCAACTGAATTTCCAAGAAAAATACGTGAACAGGAGCCAGCACG<br>TCGTGTCTCAAGATCTAGCTTCTCTTCTGACCCTGATGAGAAAGCTCAAGATTCCAAGGCCTATTCAAAA<br>ATCACTGAAGGAAAAGTTTCAGGAAATCCTCAGGTACATATCAAGAATGTCAAAGAAGACAGTACCGCAG<br>ATGACTCAAAAGACAGTGTTGCTCAGGGAACAACTAATGTTCATTCCTCAGAACATGCTGGACGTAATGG<br>CAGAAATGCAGCTGATCCCATTTCTGGGGATTTTAAAGAAATTTCCAGCGTTAAATTAGTGAGCCGTTAT<br>GGAGAATTGAAGTCTGTTCCCACTACACAATGTCTTGACAATAGCAAAAAAAATGAATCTCCCTTTTGGA<br>AGCTTTATGAGTCAGTGAAGAAAGAGTTGGATGTAAAATCACAAAAAGAAAATGTCCTACAGTATTGTAG<br>AAAATCTGGATTACAAACTGATTACGCAACAGAGAAAGAAAGTGCTGATGGTTTACAGGGGGAGACCCAA<br>CTGTTGGTCTCGCGTAAGTCAAGACCAAAATCTGGTGGGAGCGGCCACGCTGTGGCAGAGCCTGCTTCAC<br>CTGAACAAGAGCTTGACCAGAACAAGGGGAAGGGAAGAGACGTGGAGTCTGTTCAGACTCCCAGCAAGGC<br>TGTGGGCGCCAGCTTTCCTCTCTATGAGCCGGCTAAAATGAAGACCCCTGTACAATATTCACAGCAACAA<br>AATTCTCCACAAAAACATAAGAACAAAGACCTGTATACTACTGGTAGAAGAGAATCTGTGAATCTGGGTA<br>AAAGTGAAGGCTTCAAGGCTGGTGATAAAACTCTTACTCCCAGGAAGCTTTCAACTAGAAATCGAACACC<br>AGCTAAAGTTGAAGATGCAGCTGACTCTGCCACTAAGCCAGAAAATCTCTCTTCCAAAACCAGAGGAAGT<br>ATTCCTACAGATGTGGAAGTTCTGCCTACGGAAACTGAAATTCACAATGAGCCATTTTTAACTCTGTGGC<br>TCACTCAAGTTGAGAGGAAGATCCAAAAGGATTCCCTCAGCAAGCCTGAGAAATTGGGCACTACAGCTGG<br>ACAGATGTGCTCTGGGTTACCTGGTCTTAGTTCAGTTGATATCAACAACTTTGGTGATTCCATTAATGAG<br>AGTGAGGGAATACCTTTGAAAAGAAGGCGTGTGTCCTTTGGTGGGCACCTAAGACCTGAACTATTTGATG<br>AAAACTTGCCTCCTAATACGCCTCTCAAAAGGGGAGAAGCCCCAACCAAAAGAAAGTCTCTGGTAATGCA<br>CACTCCACCTGTCCTGAAGAAAATCATCAAGGAACAGCCTCAACCATCAGGAAAACAAGAGTCAGGTTCA<br>GAAATCCATGTGGAAGTGAAGGCACAAAGCTTGGTTATAAGCCCTCCAGCTCCTAGTCCTAGGAAAACTC<br>CAGTTGCCAGTGATCAACGCCGTAGGTCCTGCAAAACAGCCCCTGCTTCCAGCAGCAAATCTCAGACAGA<br>GGTTCCTAAGAGAGGAGGGAGAAAGAGTGGCAACCTGCCTTCAAAGAGAGTGTCTATCAGCCGAAGTCAA<br>CATGATATTTTACAGATGATATGTTCCAAAAGAAGAAGTGGTGCTTCGGAAGCAAATCTGATTGTTGCAA<br>AATCATGGGCAGATGTAGTAAAACTTGGTGCAAAACAAACACAAACTAAAGTCATAAAACATGGTCCTCA<br>AAGGTCAATGAACAAAAGGCAAAGAAGACCTGCTACTCCAAAGAAGCCTGTGGGCGAAGTTCACAGTCAA<br>TTTAGTACAGGCCACGCAAACTCTCCTTGTACCATAATAATAGGGAAAGCTCATACTGAAAAAGTACATG<br>TGCCTGCTCGACCCTACAGAGTGCTCAACAACTTCATTTCCAACCAAAAAATGGACTTTAAGGAAGATCT<br>TTCAGGAATAGCTGAAATGTTCAAGACCCCAGTGAAGGAGCAACCGCAGTTGACAAGCACATGTCACATC<br>GCTATTTCAAATTCAGAGAATTTGCTTGGAAAACAGTTTCAAGGAACTGATTCAGGAGAAGAACCTCTGC<br>TCCCCACCTCAGAGAGTTTTGGAGGAAATGTGTTCTTCAGTGCACAGAATGCAGCAAAACAGCCATCTGA | 137 |

TABLE 2-continued

| GENBANK ACCESSION NUMBER | SEQUENCE | SEQ ID NO: |
|---|---|---|
| | TAAATGCTCTGCAAGCCCTCCCTTAAGACGGCAGTGTATTAGAGAAAATGGAAACGTAGCAAAAACGCCC | |
| | AGGAACACCTACAAAATGACTTCTCTGGAGACAAAAACTTCAGATACTGAGACAGAGCCTTCAAAAACAG | |
| | TATCCACTGCAAACAGGTCAGGAAGGTCTACAGAGTTCAGGAATATACAGAAGCTACCTGTGGAAAGTAA | |
| | GAGTGAAGAAACAAATACAGAAATTGTTGAGTGCATCCTAAAAAGAGGTCAGAAGGCAACACTACTACAA | |
| | CAAAGGAGAGAAGGAGAGATGAAGGAAATAGAAAGACCTTTTGAGACATATAAGGAAAATATTGAATTAA | |
| | AAGAAAACGATGAAAAGATGAAAGCAATGAAGAGATCAAGAACTTGGGGGCAGAAATGTGCACCAATGTC | |
| | TGACCTGACAGACCTCAAGAGCTTGCCTGATACAGAACTCATGAAAGACACGGCACGTGGCCAGAATCTC | |
| | CTCCAAACCCAAGATCATGCCAAGGCACCAAAGAGTGAGAAAGGCAAAATCACTAAAATGCCCTGCCAGT | |
| | CATTACAACCAGAACCAATAAACACCCCAACACACACAAAACAACAGTTGAAGGCATCCCTGGGGAAAGT | |
| | AGGTGTGAAAGAAGAGCTCCTAGCAGTCGGCAAGTTCACACGGACGTCAGGGGAGACCACGCACACGCAC | |
| | AGAGAGCCAGCAGGAGATGGCAAGAGCATCAGAACGTTTAAGGAGTCTCCAAAGCAGATCCTGGACCCAG | |
| | CAGCCCGTGTAACTGGAATGAAGAAGTGGCCAAGAACGCCTAAGGAAGAGGCCCAGTCACTAGAAGACCT | |
| | GGCTGGCTTCAAAGAGCTCTTCCAGACACCAGGTCCCTCTGAGGAATCAATGACTGATGAGAAAACTACC | |
| | AAAATAGCCTGCAAATCTCCACCACCAGAATCAGTGGACACTCCAACAAGCACAAAGCAATGGCCTAAGA | |
| | GAAGTCTCAGGAAAGCAGATGTAGAGGAAGAATTCTTAGCACTCAGGAAACTAACACCATCAGCAGGGAA | |
| | AGCCATGCTTACGCCCAAACCAGCAGGAGGTGATGAGAAAGACATTAAAGCATTTATGGGAACTCCAGTG | |
| | CAGAAACTGGACCTGGCAGGAACTTTACCTGGCAGCAAAAGACAGCTACAGACTCCTAAGGAAAAGGCCC | |
| | AGGCTCTAGAAGACCTGGCTGGCTTTAAAGAGCTCTTCCAGACTCCTGGTCACACCGAGGAATTAGTGGC | |
| | TGCTGGTAAAACCACTAAAATACCCTGCGACTCTCCACAGTCAGACCCAGTGGACACCCCAACAAGCACA | |
| | AAGCAACGACCCAAGAGAAGTATCAGGAAAGCAGATGTAGAGGGAGAACTCTTAGCGTGCAGGAATCTAA | |
| | TGCCATCAGCAGGCAAAGCCATGCACACGCCTAAACCATCAGTAGGTGAAGAGAAAGACATCATCATATT | |
| | TGTGGGAACTCCAGTGCAGAAACTGGACCTGACAGAGAACTTAACCGGCAGCAAGAGACGGCCACAAACT | |
| | CCTAAGGAAGAGGCCCAGGCTCTGGAAGACCTGACTGGCTTTAAAGAGCTCTTCCAGACCCCTGGTCATA | |
| | CTGAAGAAGCAGTGGCTGCTGGCAAAACTACTAAAATGCCCTGCGAATCTTCTCCACCAGAATCAGCAGA | |
| | CACCCCAACAAGCACAAGAAGGCAGCCCAAGACACCTTTGGAGAAAAGGGACGTACAGAAGGAGCTCTCA | |
| | GCCCTGAAGAAGCTCACACAGACATCAGGGGAAACCACACACACAGATAAAGTACCAGGAGGTGAGGATA | |
| | AAAGCATCAACGCGTTTAGGGAAACTGCAAAACAGAAACTGGACCCAGCAGCAAGTGTAACTGGTAGCAA | |
| | GAGGCACCCAAAAACTAAGGAAAAGGCCCAACCCCTAGAAGACCTGGCTGGCTTGAAAGAGCTCTTCCAG | |
| | ACACCAGTATGCACTGACAAGCCCACGACTCACGAGAAAACTACCAAAATAGCCTGCAGATCACAACCAG | |
| | ACCCAGTGGACACACCAACAAGCTCCAAGCCACAGTCCAAGAGAAGTCTCAGGAAAGTGGACGTAGAAGA | |
| | AGAATTCTTCGCACTCAGGAAACGAACACCATCAGCAGGCAAAGCCATGCACACACCCAAACCAGCAGTA | |
| | AGTGGTGAGAAAAACATCTACGCATTTATGGGAACTCCAGTGCAGAAACTGGACCTGACAGAGAACTTAA | |
| | CTGGCAGCAAGAGACGGCTACAAACTCCTAAGGAAAAGGCCCAGGCTCTAGAAGACCTGGCTGGCTTTAA | |
| | AGAGCTCTTCCAGACACGAGGTCACACTGAGGAATCAATGACTAACGATAAAACTGCCAAAGTAGCCTGC | |
| | AAATCTTCACAACCAGACCCAGACAAAAACCCAGCAAGCTCCAAGCGACGGCTCAAGACATCCCTGGGGA | |
| | AAGTGGGCGTGAAAGAAGAGCTCCTAGCAGTTGGCAAGCTCACACAGACATCAGGAGAGACTACACACAC | |
| | ACACACAGAGCCAACAGGAGATGGTAAGAGCATGAAAGCATTTATGGAGTCTCCAAAGCAGATCTTAGAC | |
| | TCAGCAGCAAGTCTAACTGGCAGCAAGAGGCAGCTGAGAACTCCTAAGGGAAAGTCTGAAGTCCCTGAAG | |
| | ACCTGGCCGGCTTCATCGAGCTCTTCCAGACACCAAGTCACACTAAGGAATCAATGACTAACGAAAAAAC | |
| | TACCAAAGTATCCTACAGAGCTTCACAGCCAGACCTAGTGGACACCCCAACAAGCTCCAAGCCACAGCCC | |
| | AAGAGAAGTCTCAGGAAAGCAGACACTGAAGAAGAATTTTTAGCATTTAGGAAACAAACGCCATCAGCAG | |
| | GCAAAGCCATGCACACACCCAAACCAGCAGTAGGTGAAGAGAAAGACATCAACACGTTTTTGGGAACTCC | |
| | AGTGCAGAAACTGGACCAGCCAGGAAATTTACCTGGCAGCAATAGACGGCTACAAACTCGTAAGGAAAAG | |
| | GCCCAGGCTCTAGAAGAACTGACTGGCTTCAGAGAGCTTTTCCAGACACCATGCACTGATAACCCCACGA | |
| | CTGATGAGAAAACTACCAAAAAAATACTCTGCAAATCTCCGCAATCAGACCCAGCGGACACCCCAACAAA | |
| | CACAAAGCAACGGCCCAAGAGAAGCCTCAAGAAAGCAGACGTAGAGGAAGAATTTTTAGCATTCAGGAAA | |
| | CTAACACCATCAGCAGGCAAAGCCATGCACACGCCTAAAGCAGCAGTAGGTGAAGAGAAAGACATCAACA | |
| | CATTTGTGGGGACTCCAGTGGAGAAACTGGACCTGCTAGGAAATTTACCTGGCAGCAAGAGACGGCCACA | |
| | AACTCCTAAAGAAAAGGCCAAGGCTCTAGAAGATCTGGCTGGCTTCAAAGAGCTCTTCCAGACACCAGGT | |
| | CACACTGAGGAATCAATGACCGATGACAAAATCACAGAAGTATCCTGCAAATCTCCACAACCAGACCCAG | |
| | TCAAAACCCCAACAAGCTCCAAGCAACGACTCAAGATATCCTTGGGGAAAGTAGGTGTGAAAGAAGAGGT | |
| | CCTACCAGTCGGCAAGCTCACACAGACGTCAGGGAAGACCACACAGACACACAGAGAGACAGCAGGAGAT | |
| | GGAAAGAGCATCAAAGCGTTTAAGGAATCTGCAAAGCAGATGCTGGACCCAGCAAACTATGGAACTGGGA | |
| | TGGAGAGGTGGCCAAGAACACCTAAGGAAGAGGCCCAATCACTAGAAGACCTGGCCGGCTTCAAAGAGCT | |
| | CTTCCAGACACCAGACCACACTGAGGAATCAACAACTGATGACAAAACTACCAAAATAGCCTGCAAATCT | |
| | CCACCACCAGAATCAATGGACACTCCAACAAGCACAAGGAGGCGGCCCAAAACACCTTTGGGGAAAAGGG | |
| | ATATAGTGGAAGAGCTCTCAGCCCTGAAGCAGCTCACACAGACCACACACACAGACAAAGTACCAGGAGA | |
| | TGAGGATAAAGGCATCAACGTGTTCAGGGAAACTGCAAAACAGAAACTGGACCCAGCAGCAAGTGTAACT | |
| | GGTAGCAAGAGGCAGCCAAGAACTCCTAAGGGAAAAGCCCAACCCCTAGAAGACTTGGCTGGCTTGAAAG | |
| | AGCTCTTCCAGACACCAATATGCACTGACAAGCCCACGACTCATGAGAAAACTACCAAAATAGCCTGCAG | |
| | ATCTCCACAACCAGACCCAGTGGGTACCCCAACAATCTTCAAGCCACAGTCCAAGAGAAGTCTCAGGAAA | |
| | GCAGACGTAGAGGAAGAATCCTTAGCACTCAGGAAACGAACACCATCAGTAGGGAAAGCTATGGACACAC | |
| | CCAAACCAGCAGGAGGTGATGAGAAAGACATGAAAGCATTTATGGGAACTCCAGTGCAGAAATTGGACCT | |
| | GCCAGGAAATTTACCTGGCAGCAAAAGATGGCCACAAACTCCTAAGGAAAAGGCCCAGGCTCTAGAAGAC | |
| | CTGGCTGGCTTCAAAGAGCTCTTCCAGACACCAGGCACTGACAAGCCCACGACTGATGAGAAAACTACCA | |
| | AAATAGCCTGCAAATCTCCACAACCAGACCCAGTGGACACCCCAGCAAGCACAAAGCAACGGCCCAAGAG | |
| | AAACCTCAGGAAAGCAGACGTAGAGGAAGAATTTTTAGCACTCAGGAAACGAACACCATCAGCAGGCAAA | |
| | GCCATGGACACACCAAAACCAGCAGTAAGTGATGAGAAAAATATCAACACATTTGTGGAAACTCCAGTGC | |
| | AGAAACTGGACCTGCTAGGAAATTTACCTGGCAGCAAGAGACAGCCACAGACTCCTAAGGAAAAGGCTGA | |
| | GGCTCTAGAGGACCTGGTTGGCTTCAAAGAACTCTTCCAGACACCAGGTCACACTGAGGAATCAATGACT | |
| | GATGACAAAATCACAGAAGTATCCTGTAAATCTCCACAGCCAGAGTCATTCAAAACCTCAAGAAGCTCCA | |
| | AGCAAAGGCTCAAGATACCCCTGGTGAAAGTGGACATGAAAGAAGAGCCCCTAGCAGTCAGCAAGCTCAC | |
| | ACGGACATCAGGGGAGACTACGCAAACACACACAGAGCCAACAGGAGATAGTAAGAGCATCAAAGCGTTT | |
| | AAGGAGTCTCCAAAGCAGATCCTGGACCCAGCAGCAAGTGTAACTGGTAGCAGGAGGCAGCTGAGAACTC | |
| | GTAAGGAAAAGGCCCGTGCTCTAGAAGACCTGGTTGACTTCAAAGAGCTCTTCTCAGCACCAGGTCACAC | |
| | TGAAGAGTCAATGACTATTGACAAAAACACAAAAATTCCCTGCAAATCTCCCCCACCAGAACTAACAGAC | |

TABLE 2-continued

| GENBANK ACCESSION NUMBER | SEQUENCE | SEQ ID NO: |
|---|---|---|
| | ACTGCCACGAGCACAAAGAGATGCCCCAAGACACGTCCCAGGAAAGAAGTAAAAGAGGAGCTCTCAGCAG<br>TTGAGAGGCTCACGCAAACATCAGGGCAAAGCACACACACACACAAAGAACCAGCAAGCGGTGATGAGGG<br>CATCAAAGTATTGAAGCAACGTGCAAAGAAGAAACCAAACCCAGTAGAAGAGGAACCCAGCAGGAGAAGG<br>CCAAGAGCACCTAAGGAAAAGGCCCAACCCCTGGAAGACCTGGCCGGCTTCACAGAGCTCTCTGAAACAT<br>CAGGTCACACTCAGGAATCACTGACTGCTGGCAAAGCCACTAAAATACCCTGCGAATCTCCCCCACTAGA<br>AGTGGTAGACACCACAGCAAGCACAAAGAGGCATCTCAGGACACGTGTGCAGAAGGTACAAGTAAAAGAA<br>GAGCCTTCAGCAGTCAAGTTCACACAAACATCAGGGGAAACCACGGATGCAGACAAAGAACCAGCAGGTG<br>AAGATAAAGGCATCAAAGCATTGAAGGAATCTGCAAAACAGACACCGGCTCCAGCAGCAAGTGTAACTGG<br>CAGCAGGAGACGGCCAAGAGCACCCAGGGAAAGTGCCCAAGCCATAGAAGACCTAGCTGGCTTCAAAGAC<br>CCAGCAGCAGGTCACACTGAAGAATCAATGACTGATGACAAAACCACTAAAATACCCTGCAAATCATCAC<br>CAGAACTAGAAGACACCGCAACAAGCTCAAAGAGACGGCCCAGGACACGTGCCCAGAAAGTAGAAGTGAA<br>GGAGGAGCTGTTAGCAGTTGGCAAGCTCACACAAACCTCAGGGGAGACCACGCACACCGACAAAGAGCCG<br>GTAGGTGAGGGCAAAGGCACGAAAGCATTTAAGCAACCTGCAAAGCGGAAGCTGGACGCAGAAGATGTAA<br>TTGGCAGCAGGAGACAGCCAAGAGCACCTAAGGAAAAGGCCCAACCCCTGGAAGATCTGGCCAGCTTCCA<br>AGAGCTCTCTCAAACACCAGGCCACACTGAGGAACTGGCAAATGGTGCTGCTGATAGCTTTACAAGCGCT<br>CCAAAGCAAACACCTGACAGTGGAAAACCTCTAAAAATATCCAGAAGAGTTCTTCGGGCCCCTAAAGTAG<br>AACCCGTGGGAGACGTGGTAAGCACCAGAGACCCTGTAAAATCACAAAGCAAAAGCAACACTTCCCTGCC<br>CCCACTGCCCTTCAAGAGGGGAGGTGGCAAAGATGGAAGCGTCACGGGAACCAAGAGGCTGCGCTGCATG<br>CCAGCACCAGAGGAAATTGTGGAGGAGCTGCCAGCCAGCAAGAAGCAGAGGGTTGCTCCCAGGGCAAGAG<br>GCAAATCATCCGAACCCGTGGTCATCATGAAGAGAAGTTTGAGGACTTCTGCAAAAAGAATTGAACCTGC<br>GGAAGAGCTGAACAGCAACGACATGAAAACCAACAAAGAGGAACACAAATTACAAGACTCGGTCCCTGAA<br>AATAAGGGAATATCCCTGCGCTCCAGACGCCAAAATAAGACTGAGGCAGAACAGCAAATAACTGAGGTCT<br>TTGTATTAGCAGAAAGAATAGAAATAAACAGAAATGAAAAGAAGCCCATGAAGACCTCCCCAGAGATGGA<br>CATTCAGAATCCAGATGATGGAGCCCGGAAACCCATACCTAGAGACAAAGTCACTGAGAACAAAAGGTGC<br>TTGAGGTCTGCTAGACAGAATGAGAGCTCCCAGCCTAAGGTGGCAGAGGAGAGCGGAGGGCAGAAGAGTG<br>CGAAGGTTCTCATGCAGAATCAGAAAGGGAAAGGAGAAGCAGGAAATTCAGACTCCATGTGCCTGAGATC<br>AAGAAAGACAAAAAGCCAGCCTGCAGCAAGCACTTTGGAGAGCAAATCTGTGCAGAGAGTAACGCGGAGT<br>GTCAAGAGGTGTGCAGAAAATCCAAAGAAGGCTGAGGACAATGTGTGTGTCAAGAAAATAAGAACCAGAA<br>GTCATAGGGACAGTGAAGATATTTGACAGAAAAATCGAACTGGGAAAAATATAATAAAGTTAGTTTTGTG<br>ATAAGTTCTAGTGCAGTTTTTGTCATAAATTACAAGTGAATTCTGTAAGTAAGGCTGTCAGTCTGCTTAA<br>GGGAAGAAAACTTTGGATTTGCTGGGTCTGAATCGGCTTCATAAACTCCACTGGGAGCACTGCTGGGCTC<br>CTGGACTGAGAATAGTTGAACACCGGGGGCTTTGTGAAGGAGTCTGGGCCAAGGTTTGCCCTCAGCTTTG<br>CAGAATGAAGCCTTGAGGTCTGTCACCACCCACAGCCACCCTACAGCAGCCTTAACTGTGACACTTGCCA<br>CACTGTGTCGTCGTTTGTTTGCCTATGTCCTCCAGGGCACGGTGGCAGGAACAACTATCCTCGTCTGTCC<br>CAACACTGAGCAGGCACTCGGTAAACACGAATGAATGGATGAGCGCACGGATGAATGGAGCTTACAAGAT<br>CTGTCTTTCCAATGGCCGGGGGCATTTGGTCCCCAAATTAAGGCTATTGGACATCTGCACAGGACAGTCC<br>TATTTTTGATGTCCTTTCCTTTCTGAAAATAAAGTTTTGTGCTTTGGAGAATGACTCGTGAGCACATCTT<br>TAGGGACCAAGAGTGACTTTCTGTAAGGAGTGACTCGTGGCTTGCCTTGGTCTCTTGGGAATACTTTTCT<br>AACTAGGGTTGCTCTCACCTGAGACATTCTCCACCCGCGGAATCTCAGGGTCCCAGGCTGTGGGCCATCA<br>CGACCTCAAACTGGCTCCTAATCTCCAGCTTTCCTGTCATTGAAAGCTTCGGAAGTTTACTGGCTCTGCT<br>CCCGCCTGTTTTCTTTCTGACTCTATCTGGCAGCCCGATGCCACCCAGTACAGGAAGTGACACCAGTACT<br>CTGTAAAGCATCATCATCCTTGGAGAGACTGAGCACTCAGCACCTTCAGCCACGATTTCAGGATCGCTTC<br>CTTGTGAGCCGCTGCCTCCGAAATCTCCTTTGAAGCCCAGACATCTTTCTCCAGCTTCAGACTTGTAGAT<br>ATAACTCGTTCATCTTCATTTACTTTCCACTTTGCCCCCTGTCCTCTCTGTGTTCCCCAAATCAGAGAAT<br>AGCCCGCCATCCCCCAGGTCACCTGTCTGGATTCCTCCCCATTCACCCACCTTGCCAGGTGCAGGTGAGG<br>ATGGTGCACCAGACAGGGTAGCTGTCCCCCAAAATGTGCCCTGTGCGGGCAGTGCCCTGTCTCCACGTTT<br>GTTTCCCCAGTGTCTGGCGGGGAGCCAGGTGACATCATAAATACTTGCTGAATGAATGCAGAAATCAGCG<br>GTACTGACTTGTACTATATTGGCTGCCATGATAGGGTTCTCACAGCGTCATCCATGATCGTAAGGGAGAA<br>TGACATTCTGCTTGAGGGAGGGAATAGAAAGGGGCAGGGAGGGGACATCTGAGGGCTTCACAGGGCTGCA<br>AAGGGTACAGGGATTGCACCAGGGCAGAACAGGGGAGGGTGTTCAAGGAAGAGTGGCTCTTAGCAGAGGC<br>ACTTTGGAAGGTGTGAGGCATAAATGCTTCCTTCTACGTAGGCCAACCTCAAAACTTTCAGTAGGAATGT<br>TGCTATGATCAAGTTGTTCTAACACTTTAGACTTAGTAGTAATTATGAACCTCACATAGAAAAATTTCAT<br>CCAGCCATATGCCTGTGGAGTGGAATATTCTGTTTAGTAGAAAAATCCTTTAGAGTTCAGCTCTAACCAG<br>AAATCTTGCTGAAGTATGTCAGCACCTTTTCTCACCCTGGTAAGTACAGTATTTCAAGAGCACGCTAAGG<br>GTGGTTTTCATTTTACAGGGCTGTTGATGATGGGTTAAAAATGTTCATTTAAGGGCTACCCCCGTGTTTA<br>ATAGATGAACACCACTTCTACACAACCCTCCTTGGTACTGGGGGAGGGAGAGATCTGACAAATACTGCCC<br>ATTCCCCTAGGCTGACTGGATTTGAGAACAAATACCCACCCATTTCCACCATGGTATGGTAACTTCTCTG<br>AGCTTCAGTTTCCAAGTGAATTTCCATGTAATAGGACATTCCCATTAAATACAAGCTGTTTTTACTTTTT<br>CGCCTCCCAGGGCCTGTGGGATCTGGTCCCCCAGCCTCTCTTGGGCTTTCTTACACTAACTCTGTACCTA<br>CCATCTCCTGCCTCCCTTAGGCAGGCACCTCCAACCACCACACACTCCCTGCTGTTTTCCCTGCCTGGAA<br>CTTTCCCTCCTGCCCCACCAAGATCATTTCATCCAGTCCTGAGCTCAGCTTAAGGGAGGCTTCTTGCCTG<br>TGGGTTCCCTCACCCCCATGCCTGTCCTCCAGGCTGGGGCAGGTTCTTAGTTTGCCTGGAATTGTTCTGT<br>ACCTCTTTGTAGCACGTAGTGTTGTGGAAACTAAGCCACTAATTGAGTTTCTGGCTCCCCTCCTGGGGTT<br>GTAAGTTTTGTTCATTCATGAGGGCCGACTGCATTTCCTGGTTACTCTATCCCAGTGACCAGCCACAGGA<br>GATGTCCAATAAAGTATGTGATGAAATGGTCTTAAAAAAAAAAAAAA | |
| NM_024101 | GCGCCGGGACGTGGCCAGTTGCCCGCCTGCCCCGGAGAGCCAGGCGCTAACCAGCCGCTCTGCGCCCCGC<br>GCCCTGCTTGCCCCCATTATCCAGCCTTGCCCCGGCGCCCTGACCTGACGCCCTGGCCTGACGCCCTGCT<br>TCGTCGCCTCCTTTCTCTCCCAGGTGCTGGACCAGGGACTGAGCGTCCCCCGGAGAGGGTCCGGTGTGAC<br>CCCGACAAGAAGCAGAAATGGGGAAGAAACTGGATCTTTCCAAGCTCACTGATGAAGAGGCCCAGCATGT<br>CTTGGAAGTTGTTCAACGAGATTTTGACCTCCGAAGGAAAGAAGAGGAACGGCTAGAGGCGTTGAAGGGC<br>AAGATTAAGAAGGAAAGCTCCAAGAGGGAGCTGCTTTCCGACACTGCCCATCTGAACGAGACCCACTGCG<br>CCCGCTGCCTGCAGCCCTACCAGCTGCTTGTGAATAGCAAAAGGCAGTGCCTGGAATGTGGCCTCTTCAC<br>CTGCAAAAGCTGTGGCCGCGTCCACCCGGAGGAGCAGGGCTGGATCTGTGACCCCTGCCATCTGGCCAGA<br>GTCGTGAAGATCGGCTCACTGGAGTGGTACTATGAGCATGTGAAAGCCCGCTTCAAGAGGTTCGGAAGTG<br>CCAAGGTCATCCGGTCCCTCCACGGGCGGCTGCAGGGTGGAGCTGGGCCTGAACTGATATCTGAAGAGAG | 138 |

TABLE 2-continued

| GENBANK ACCESSION NUMBER | SEQUENCE | SEQ ID NO: |
|---|---|---|
| | AAGTGGAGACAGCGACCAGACAGATGAGGATGGAGAACCTGGCTCAGAGGCCCAGGCCCAGGCCCAGCCC<br>TTTGGCAGCAAAAAAAAGCGCCTCCTCTCCGTCCACGACTTCGACTTCGAGGGAGACTCAGATGACTCCA<br>CTCAGCCTCAAGGTCACTCCCTGCACCTGTCCTCAGTCCCTGAGGCCAGGGACAGCCCACAGTCCCTCAC<br>AGATGAGTCCTGCTCAGAGAAGGCAGCCCCTCACAAGGCTGAGGGCCTGGAGGAGGCTGATACTGGGGCC<br>TCTGGGTGCCACTCCCATCCGGAAGAGCAGCCGACCAGCATCTCACCTTCCAGACACGGCGCCCTGGCTG<br>AGCTCTGCCCGCCTGGAGGCTCCCACAGGATGGCCCTGGGGACTGCTGCTGCACTCGGGTCGAATGTCAT<br>CAGGAATGAGCAGCTGCCCCTGCAGTACTTGGCCGATGTGGACACCTCTGATGAGGAAAGCATCCGGGCT<br>CACGTGATGGCCTCCCACCATTCCAAGCGGAGAGGCCGGGCGTCTTCTGAGAGTCAGATCTTTGAGCTGA<br>ATAAGCATATTTCAGCTGTGGAATGCCTGCTGACCTACCTGGAGAACACAGTTGTGCCTCCCTTGGCCAA<br>GGGTCTAGGTGCTGGAGTGCGCACGGAGGCCGATGTAGAGGAGGAGGCCCTGAGGAGGAAGCTGGAGGAG<br>CTGACCAGCAACGTCAGTGACCAGGAGACCTCGTCCGAGGAGGAGGAAGCCAAGGACGAAAAGGCAGAGC<br>CCAACAGGGACAAATCAGTTGGGCCTCTCCCCCAGGCGGACCCGGAGGTGGGCACGGCTGCCCATCAAAC<br>CAACAGACAGGAAAAAAGCCCCCAGGACCCTGGGGACCCCGTCCAGTACAACAGGACCACAGATGAGGAG<br>CTGTCAGAGCTGGAGGACAGAGTGGCAGTGACGGCCTCAGAAGTCCAGCAGGCAGAGAGCGAGGTTTCAG<br>ACATTGAATCCAGGATTGCAGCCCTGAGGGCCGCAGGGCTCACGGTGAAGCCCTCGGGAAAGCCCCGGAG<br>GAAGTCAAACCTCCCGATATTTCTCCCTCGAGTGGCTGGGAAACTTGGCAAGAGACCAGAGGACCCAAAT<br>GCAGACCCTTCAAGTGAGGCCAAGGCAATGGCTGTGCCCTATCTTCTGAGAAGAAAGTTCAGTAATTCCC<br>TGAAAAGTCAAGGTAAAGATGATGATTCTTTTGATCGGAAATCAGTGTACCGAGGCTCGCTGACACAGAG<br>AAACCCCAACGCGAGGAAAGGAATGGCCAGCCACACCTTCGCGAAACCTGTGGTGGCCCACCAGTCCTAA<br>CGGGACAGGACAGAGAGACAGAGCAGCCCTGCACTGTTTTCCCTCCACCACAGCCATCCTGTCCCTCATT<br>GGCTCTGTGCTTTCCACTATACACAGTCACCGTCCCAATGAGAAACAAGAAGGAGCACCCTCCACATGGA<br>CTCCCACCTGCAAGTGGACAGCGACATTCAGTCCTGCACTGCTCACCTGGGTTTACTGATGACTCCTGGC<br>TGCCCCACCATCCTCTCTGATCTGTGAGAAACAGCTAAGCTGCTGTGACTTCCCTTTAGGACAATGTTGT<br>GTAAATCTTTGAAGGACACACCGAAGACCTTTATACTGTGATCTTTTACCCCTTTCACTCTTGGCTTTCT<br>TATGTTGCTTTCATGAATGGAATGGAAAAAAGATGACTCAGTTAAGGCACCAGCCATATGTGTATTCTTG<br>ATGGTCTATATCGGGGTGTGAGCAGATGTTTGCGTATTTCTTGTGGGTGTGACTGGATATTAGACATCCG<br>GACAAGTGACTGAACTAATGATCTGCTGAATAATGAAGGAGGAATAGACACCCCAGTCCCCACCCTACGT<br>GCACCCGCTCTGCAAGTTCCCATGTGATCTGTAGACCAGGGGAAATTACACTGCGGTCAAGGGCAGAGCC<br>TGCACATGACAGCAAGTGAGCATTTGATAGATGCTCAGATGCTAGTGCAGAGAGCCTGCTGGGAGACGAA<br>GAGACAGCAGGCAGAGCTCCAGATGGGCAAGGAAGAGGCTTGGTTCTAGCCTGGCTCTGCCCCTCACTGC<br>AGTGGATCCAGTGGGGCAGAGGACAGAGGGTCACAACCAATGAGGGATGTCTGCCAAGGATGGGGGTGCA<br>GAGGCCACAGGAGTCAGCTTGCCACTCGCCCATTGGTTACATAGATGATCTCTCAGACAGGCTGGGACTC<br>AGAGTTATTTCCTAGTATCGGTGTGCCCCATCCAGTTTTAAGTGGAGCCCTCCAAGACTCTCCAGAGCTG<br>CCTTTGAACATCCTAACAGTAATCACATCTCACCCTCCCTGAGGTTCACTTTAGACAGGACCCAATGGCT<br>GCACTGCCTTTGTCAGAGGGGGTGCTGAGAGGAGTGGCTTCTTTTAGAATCAAACAGTAGAGACAAGAGT<br>CAAGCCTTGTGTCTTCAAGCATTGACCAAGTTAAGTGTTTCCTTCCCTCTCTCAATAAGACACTTCCAGG<br>AGCTTTCCAATCTCTCACTTAAAACTAAGGTTTGAATCTCAAAGTGTTGCTGGGAGGCTGATACTCCTGC<br>AACTTCAGGAGACCTGTGAGCACACATTAGCAGCTGTTTCTCTGACTCCTTGTGGCATCAGATAAAAACG<br>TGGGAGTTTTTCCATATAATTCCCAGCCTTACTTATAAATTCTATTCTTTGAAAAAATTATTCAGGCTAG<br>GTAAGGTGGCTCATACCTATAATCCCAGCCCTTTGAGAGGCCAAGGTGGGAGAATTGCTTGAGGCCAGGA<br>GTTTGAGACCTCCTGGGCAACATAGTGAGATCCCATCTCTACAAAAAACAAAACAAAAAAATTACCCAAG<br>CATGATGGTATATGCCTGTAGTCGTACCTACTTACTTAGGAGGCTGAGGCAGGAGGATCACTTGAGCCCT<br>GGAGGTTGGGGCTGCAGTGAGCCATGATCGCATCACTATACTCGAGCCTGGGCAACAGAGTGAGACCTTG<br>TCTCTTAAAAAAATTAATAATAAATAAATGAAAATAATTCTTCAGAAAAAAAAAAAAAAAA | |
| NM_005940 | AAGCCCAGCAGCCCCGGGGCGGATGGCTCCGGCCGCCTGGCTCCGCAGCGCGGCCGCGCGCGCCCTCCTG<br>CCCCCGATGCTGCTGCTGCTGCTCCAGCCGCCGCCGCTGCTGGCCCGGGCTCTGCCGCCGGACGCCCACC<br>ACCTCCATGCCGAGAGGAGGGGGCCACAGCCCTGGCATGCAGCCCTGCCCAGTAGCCCGGCACCTGCCCC<br>TGCCACGCAGGAAGCCCCCGGCCTGCCAGCAGCCTCAGGCCTCCCCGCTGTGGCGTGCCCGACCCATCT<br>GATGGGCTGAGTGCCCGCAACCGACAGAAGAGGTTCGTGCTTTCTGGCGGGCGCTGGGAGAAGACGGACC<br>TCACCTACAGGATCCTTCGGTTCCCATGGCAGTTGGTGCAGGAGCAGGTGCGGCAGACGATGGCAGAGGC<br>CCTAAAGGTATGGAGCGATGTGACGCCACTCACCTTTACTGAGGTGCACGAGGGCCGTGCTGACATCATG<br>ATCGACTTCGCCAGGTACTGGCATGGGGACGACCTGCCGTTTGATGGGCCTGGGGGCATCCTGGCCCATG<br>CCTTCTTCCCCAAGACTCACCGAGAAGGGGATGTCCACTTCGACTATGATGAGACCTGGACTATCGGGGA<br>TGACCAGGGCACAGACCTGCTGCAGGTGGCAGCCCATGAATTTGGCCACGTGCTGGGGCTGCAGCACACA<br>ACAGCAGCCAAGGCCCTGATGTCCGCCTTCTACACCTTTCGCTACCCACTGAGTCTCAGCCCAGATGACT<br>GCAGGGGCGTTCAACACCTATATGGCCAGCCCTGGCCCACTGTCACCTCCAGGACCCCAGCCCTGGGCCC<br>CCAGGCTGGGATAGACACCAATGAGATTGCACCGCTGGAGCCAGACGCCCCGCCAGATGCCTGTGAGGCC<br>TCCTTTGACGCGGTCTCCACCATCCGAGGCGAGCTCTTTTTCTTCAAAGCGGGCTTTGTGTGGCGCCTCC<br>GTGGGGGCCAGCTGCAGCCCGGCTACCCAGCATTGGCCTCTCGCCACTGGCAGGGACTGCCCAGCCCTGT<br>GGACGCTGCCTTCGAGGATGCCCAGGGCCACATTTGGTTCTTCCAAGGTGCTCAGTACTGGGTGTACGAC<br>GGTGAAAAGCCAGTCCTGGGCCCCGCACCCCTCACCGAGCTGGGCCTGGTGAGGTTCCCGGTCCATGCTG<br>CCTTGGTCTGGGGTCCCGAGAAGAACAAGATCTACTTCTTCCGAGGCAGGGACTACTGGCGTTTCCACCC<br>CAGCACCCGGCGTGTAGACAGTCCCGTGCCCCGCAGGGCCACTGACTGGAGAGGGGTGCCCTCTGAGATC<br>GACGCTGCCTTCCAGGATGCTGATGGCTATGCCTACTTCCTGCGCGGCCGCCTCTACTGGAAGTTTGACC<br>CTGTGAAGGTGAAGGCTCTGGAAGGCTTCCCCCGTCTCGTGGGTCCTGACTTCTTTGGCTGTGCCGAGCC<br>TGCCAACACTTTCCTCTGACCATGGCTTGGATGCCCTCAGGGGTGCTGACCCCTGCCAGGCCACGAATAT<br>CAGGCTAGAGACCCATGGCCATCTTTGTGGCTGTGGGCACCAGGCATGGGACTGAGCCCATGTCTCCTCA<br>GGGGGATGGGGTGGGGTACAACCACCATGACAACTGCCGGGAGGGCCACGCAGGTCGTGGTCACCTGCCA<br>GCGACTGTCTCAGACTGGGCAGGGAGGCTTTGGCATGACTTAAGAGGAAGGGCAGTCTTGGGCCCGCTAT<br>GCAGGTCCTGGCAAACCTGGCTGCCCTGTCTCCATCCCTGTCCCTCAGGGTAGCACCATGGCAGGACTGG<br>GGGAACTGGAGTGTCCTTGCTGTATCCCTGTTGTGAGGTTCCTTCCAGGGGCTGGCACTGAAGCAAGGGT<br>GCTGGGGCCCCATGGCCTTCAGCCCTGGCTGAGCAACTGGGCTGTAGGGCAGGGCCACTTCCTGAGGTCA<br>GGTCTTGGTAGGTGCCTGCATCTGTCTGCCTTCTGGCTGACAATCCTGGAAATCTGTTCTCCAGAATCCA<br>GGCCAAAAAGTTCACAGTCAAATGGGGAGGGGTATTCTTCATGCAGGAGACCCCAGGCCCTGGAGGCTGC<br>AACATACCTCAATCCTGTCCCAGGCCGGATCCTCCTGAAGCCCTTTTCGCAGCACTGCTATCCTCCAAAG | 139 |

TABLE 2-continued

| GENBANK ACCESSION NUMBER | SEQUENCE | SEQ ID NO: |
|---|---|---|
| | CCATTGTAAATGTGTGTACAGTGTGTATAAACCTTCTTCTTCTTTTTTTTTTTTAAACTGAGGATTGTC | |
| BX647151 | TAGCAGCACACAAGGGTTCGTGTTTGTGGAACCAGGTAGCTTCCTTCAGAGCTGACATTTGCCCACAGCC<br>AGCCTGGCCCAGCCCCATACCACCAGCCCTGGCGCTCTGGGGCGTGAGGTGCCTTTTCTGCCCCCCTGCT<br>CTAGGGCAGGTGGAAATCACCCATGGTGGGTCTACATCTGATAGAAGCATCTTATAGTTCTGCTTCTGGA<br>CCAGACCATCCTGGGTTTTTCTCTGTTCTGCTGAAGGGTTCCCTCCACGTGTCCATCACCTCGGTGAACT<br>CTTGGGAGACCTGGGAAGATGCTGGCCTCACCTCTCGCCTCTCCTTTCCCTCATTGTGCTGCCACCATCC<br>TTCTCACACAGGCTCTCCAGGGAGAGCTGGGCAGGATGGGATCTTCCTGGGTTCCCACCTTGCTCCGTGC<br>CCCCTCTCACTGTTCCTGAAGTGTGGCCACGGACTGCCTTGTTTTCTGGAAAGTCCCAAGTCTGGACCAT<br>GACTGAGCAGCATTCTCGGCTATCTGCCACCTGTCTGGGGCTCCTGGCCCCTCTTAGACTCCCCTCTCCC<br>TTCTGTTTCCCCCGAGCCCCTGACTTGGACCTGCAGGGTGGGGAGAGGGATGGGACGAGAACCTGTGCTG<br>GGGCCAAAGGTCGCACTGGGGGAAGGTGGAGCCAGGGCAGCAGAGTGCCTGGCGTCGGCCCCTATCCTGT<br>CACTAGTTCCCCCGTTCTGGCCCCTGGCAGGTTTGTAACCCCAGATCAGAAGTACTCCATGGACAACACT<br>CCCCACACGCCAACCCCGTTCAAGAACGCCCTGGAGAAGTACGGACCCCTGAAGCCCCTGGTACGTGGTG<br>TGGTCACTGCCGTGGATCTCTGCACAGTGGGATCCCTTCGGTTCATCCAACCATGTTCAGTCCACAGGAC<br>CCTTCCCTCTGAGGTCTCATTTGATTCTTTCTCCTGAGAAGATGCAGAGATCCTGATAATATAAATGGGG<br>AAGCTGAGGCTGCTCTTTGTCACTTCCTCCGACTGCTCCTGAGCACCTGAGTTTGCAAGCACGCGCCGGC<br>TGGTGCTAGAGACATGGTGGTATCCCGTGACACTCAGCCTCAGGATGGGGGAGACTGATGTGAAATACAA<br>ATAACTTAAACACTTTCAGGCAAAGATAAGCACTGGGCCTAGTTCAGAGAAGTGGCAAATTGCTACTCTG<br>GCCTGTCTCTGACCAACTCCCAGTTCTCTACAGAGCACGGGAAAGCCCCTCGGGGACGTCTTTCCTGCAG<br>TGTGCAGGCTGCCCTTCTCCCCTGCTCTTCCCAGTTGATGGGATGGTTGTGTTTTCTCTATGAAAAAAGG<br>AGTTGGCACCTTGGGCTTTCTGAAACACACAGGTGTTTTAGAAATCAGTGGAGGGTGAGAGAAAGGCATG<br>GTTGTGGAGGCACTGGACTGTGAACAAGGTCTGCAGCGGGTCCCCCTGCTGTCTCTCTCTACTGCATGGA<br>GCCTCCTATGAAGCCCAAGGTGGCTGGGGGCTGAGGCTCCCTTGGGCCTGCCATGGAACTGATTCTGAGT<br>CAAGCAGACTTTCCACGGACCATGCTACATGAGCCGAGGTGAGGCACTAGTTAGTGCTCCTTTCCTGTTG<br>CAGTGGAGATTTGGCTCCTCTGTACTAAAATATCTGCATGCTCTCCAAACAGGTGTGAGGGCAAATCACA<br>TGACCTTGGCAGCTGTAATTAAAGTTTGTGGGGGCTTTTCGGATGACTTATGAGGAGTGGCTGTGATTCG<br>CACCTTTCACTCTTAGTAGCACTCGCCCTCCCCTGTTCTCTGTTGCCTGAAGCTGGAGAGGTCCTTGGAA<br>CCCCGAGGCCTGAGAAAGGGAAATGGGTTTGAGAGCCCCCATTAGTGTGGAACAAAGGGTTGAGTGAGCC<br>TGGGCTTTGAGCTGTCGGGGTCCTAATTCAGCAGCTGTGTGACTGTGTGCCAGGCTGTTGATCTCTGAGC<br>TTCTGTTTCTACCTGCTTAAAATGACGGTTACTGCACAGGGCTGTGTGAGGGTTACAGTGCGTCTCTGGG<br>CTGCTCCCAGCCATGGCAGGCCCCTGGGAATCAAGGTCATCAGCTGCTTGTCCAAGGCAGCAGTTAGTGG<br>TTGTGAATGGTGCGTGTGAGATCTGCATCCTGGCGTCAGGCCTCCTTCCTGCCTTACCCAGGACAGCCCA<br>GTTGCAGCTGGGTTGGTCCCACAGTCCCACACACACACAGCCCGAGTGTGGTGCCTCACGTGGGCTGCCC<br>CGTGCCTACCCACAGCCACAGACCCCGCACCTGGAGGAGGACTTGAAGGAGGTGCTGCGTTCTGAGGCTG<br>GCATCGAACTCATCATCGAGGACGACATCAGGCCCGAGAAGCAGAAGAGGAAGCCTGGGCTGCGGCGGAG<br>CCCCATCAAGAAAGTCCGGAAGTCTCTGGCTCTTGACATTGTGGATGAGGATGTGAAGCTGATGATGTCC<br>ACACTGCCCAAGTCTCTATCCTTGCCGACAACTGCCCCTTCAAACTCTTCCAGCCTCACCCTGTCAGGTA<br>TCAAAGAAGACAACAGCTTGCTCAACCAGGGCTTCTTGCAGGCCAAGCCCGAGAAGGCAGCAGTGGCCCA<br>GAAGCCCCGAAGCCACTTCACGACACCTGCCCCTATGTCCAGTGCCTGGAAGACGGTGGCCTGCGGGGGG<br>ACCAGGGACCAGCTTTTCATGCAGGAGAAAGCCCGGCAGCTCCTGGGCCGCCTGAAGCCCAGCCACACAT<br>CTCGGACCCTCATCTTGTCCTGAGGTGTTGAGGGTGTCACGAGCCCATTCACATGTTTACAGGGGTTGTG<br>GGGGCAGAGGGGGTCTGTGAATCTGAGAGTCATTCAGGTGACCTCCTGCAGGGAGCCTTCTGCCACCAGC<br>CCCTCCCCAGACTCTCAGGTGGAGGCAACAGGGCCATGTGCTGCCCTGTTGCCGAGCCCAGCTGTGGGCG<br>GCTCCTGGTGCTAACAACAAAGTTCCACTTCCAGGTCTGCCTGGTTCCCCCCCCAAGGCCACAGGGAGCT<br>CCGTCAGCTTCTCCCAAGCCCACGTCAGGCCTGGCCTCATCTCAGACCCTGCTTAGGATGGGGGATGTGG<br>CCAGGGGTGCTCCTGTGCTCACCCTCTCTTGGTGCATTTTTTTGGAAGAATAAAATTGCCTCTCTCTTTG<br>AAAAAAAAAAAAAAAAA | 140 |
| NM_002467 | GACCCCCGAGCTGTGCTGCTCGCGGCCGCCACCGCCGGGCCCCGGCCGTCCCTGGCTCCCCTCCTGCCTC<br>GAGAAGGGCAGGGCTTCTCAGAGGCTTGGCGGAAAAAGAACGGAGGGAGGGATCGCGCTGAGTATAAAA<br>GCCGGTTTTCGGGGCTTTATCTAACTCGCTGTAGTAATTCCAGCGAGAGGCAGAGGGAGCGAGCGGGCGG<br>CCGGCTAGGGTGGAAGAGCCGGGCGAGCAGAGCTGCGCTGCGGGCGTCCTGGGAAGGGAGATCCGGAGCG<br>AATAGGGGGCTTCGCCTCTGGCCCAGCCCTCCCGCTGATCCCCCAGCCAGCGGTCCGCAACCCTTGCCGC<br>ATCCACGAAACTTTGCCCATAGCAGCGGGCGGGCACTTTGCACTGGAACTTACAACACCCGAGCAAGGAC<br>GCGACTCTCCCGACGCGGGGAGGCTATTCTGCCCATTTGGGGACACTTCCCCGCCGCTGCCAGGACCCGC<br>TTCTCTGAAAGGCTCTCCTTGCAGCTGCTTAGACGCTGGATTTTTTTCGGGTAGTGGAAAACCAGCAGCC<br>TCCCGCGACGATGCCCCTCAACGTTAGCTTCACCAACAGGAACTATGACCTCGACTACGACTCGGTGCAG<br>CCGTATTTCTACTGCGACGAGGAGGAGAACTTCTACCAGCAGCAGCAGCAGAGCGAGCTGCAGCCCCCGG<br>CGCCCAGCGAGGATATCTGGAAGAAATTCGAGCTGCTGCCCACCCCGCCCCTGTCCCCTAGCCGCCGCTC<br>CGGGCTCTGCTCGCCCTCCTACGTTGCGGTCACACCCTTCTCCCTTCGGGGAGACAACGACGGCGGTGGC<br>GGGAGCTTCTCCACGGCCGACCAGCTGGAGATGGTGACCGAGCTGCTGGGAGGAGACATGGTGAACCAGA<br>GTTTCATCTGCGACCCGGACGACGAGACCTTCATCAAAAACATCATCATCCAGGACTGTATGTGGAGCGG<br>CTTCTCGGCCGCCGCCAAGCTCGTCTCAGAGAAGCTGGCCTCCTACCAGGCTGCGCGCAAAGACAGCGGC<br>AGCCCGAACCCCGCCCGCGGCCACAGCGTCTGCTCCACCTCCAGCTTGTACCTGCAGGATCTGAGCGCCG<br>CCGCCTCAGAGTGCATCGACCCCTCGGTGGTCTTCCCCTACCCTCTCAACGACAGCAGCTCGCCCAAGTC<br>CTGCGCCTCGCAAGACTCCAGCGCCTTCTCTCCGTCCTCGGATTCTCTGCTCTCCTCGACGGAGTCCTCC<br>CCGCAGGGCAGCCCCGAGCCCCTGGTGCTCCATGAGGAGACACCGCCCACCACCAGCAGCGACTCTGAGG<br>AGGAACAAGAAGATGAGGAAGAAATCGATGTTGTTTCTGTGGAAAAGAGGCAGGCTCCTGGCAAAAGGTC<br>AGAGTCTGGATCACCTTCTGCTGGAGGCCACAGCAAACCTCCTCACAGCCCACTGGTCCTCAAGAGGTGC<br>CACGTCTCCACACATCAGCACAACTACGCAGCGCCTCCCTCCACTCGGAAGGACTATCCTGCTGCCAAGA<br>GGGTCAAGTTGGACAGTGTCAGAGTCCTGAGACAGATCAGCAACAACCGAAAATGCACCAGCCCCAGGTC<br>CTCGGACACCGAGGAGAATGTCAAGAGGCGAACACACAACGTCTTGGAGCGCCAGAGGAGGAACGAGCTA<br>AAACGGAGCTTTTTTGCCCTGCGTGACCAGATCCCGGAGTTGGAAAACAATGAAAAGGCCCCCAAGGTAG<br>TTATCCTTAAAAAAGCCACAGCATACATCCTGTCCGTCCAAGCAGAGGAGCAAAAGCTCATTTCTGAAGA<br>GGACTTGTTGCGGAAACGACGAGAACAGTTGAAACACAAACTTGAACAGCTACGGAACTCTTGTGCGTAA | 141 |

TABLE 2-continued

| GENBANK ACCESSION NUMBER | SEQUENCE | SEQ ID NO: |
|---|---|---|
| | GGAAAAGTAAGGAAAACGATTCCTTCTAACAGAAATGTCCTGAGCAATCACCTATGAACTTGTTTCAAAT<br>GCATGATCAAATGCAACCTCACAACCTTGGCTGAGTCTTGAGACTGAAAGATTTAGCCATAATGTAAACT<br>GCCTCAAATTGGACTTTGGGCATAAAAGAACTTTTTTATGCTTACCATCTTTTTTTTTTCTTTAACAGAT<br>TTGTATTTAAGAATTGTTTTTAAAAAATTTTAAGATTTACACAATGTTTCTCTGTAAATATTGCCATTAA<br>ATGTAAATAACTTTAATAAAACGTTTATAGCAGTTACACAGAATTTCAATCCTAGTATATAGTACCTAGT<br>ATTATAGGTACTATAAACCCTAATTTTTTTTATTTAAGTACATTTTGCTTTTTAAAGTTGATTTTTTTCT<br>ATTGTTTTTAGAAAAAATAAAATAACTGGCAAATATATCATTGAGCCAAATCTTAAAAAAAAAAAAAAA | |
| BC013732 | GTGGGAGGATTGCATTCAGTCTAGTTCCTGGTTGCCGGCTGAAATAACCTGCTCTCCAAAATGTCCACAA<br>AAGTGACTTAAGTCAGGTTCCCCCAAACCAGACACCAAGACAAGAATCCATGTGTGTGTGACTGAAGGAA<br>GTGCTGGGAGAGCCCCAGCTGCAGCCTGGATGTGAACTGCAACTCCAAAGTGTGTCCAGACTCAAGGCAA<br>GGGCACTAGGCTTTCCAGACCTCCTACTAAGTCATTGATCCAGCACTGCCCTGCCAGGACATAAATCCCT<br>GGCACCTCTTGCTCTCTGCAAAGGAGGGCAAAGCAGCTTCAGGAGCCCTTGGGAGTCCTCCAAAGAGAGT<br>CTAGGGTACAGGTCCGAAAGTAGAAGAACACAGAAGGCAGGCCAGGGGCACTGTGAGATGGTAAAAGAGA<br>TCTGAAGGGATCCAGAATTCAAGCCAGGAAGAAGCAGCAATCTGTCTTCTGGATTAAAACTGAAGATCAA<br>CCTACTTTCAACTTACTAAGAAAGGGGATCATGGACATTGAAGCATATCTTGAAAGAATTGGCTATAAGA<br>AGTCTAGGAACAAATTGGACTTGGAAACATTAACTGATATTCTTCAACACCAGATCCGAGCTGTTCCCTT<br>TGAGAACCTTAACATCCATTGTGGGGATGCCATGGACTTAGGCTTAGAGGCCATTTTTGATCAAGTTGTG<br>AGAAGAAATCGGGGTGGATGGTGTCTCCAGGTCAATCATCTTCTGTACTGGGCTCTGACCACTATTGGTT<br>TTGAGACCACGATGTTGGGAGGGTATGTTTACAGCACTCCAGCCAAAAAATACAGCACTGGCATGATTCA<br>CCTTCTCCTGCAGGTGACCATTGATGGCAGGAACTACATTGTCGATGCTGGGTTTGGACGCTCATACCAG<br>ATGTGGCAGCCTCTGGAGTTAATTTCTGGGAAGGATCAGCCTCAGGTGCCTTGTGTCTTCCGTTTGACGG<br>AAGAGAATGGATTCTGGTATCTAGACCAAATCAGAAGGGAACAGTACATTCCAAATGAAGAATTTCTTCA<br>TTCTGATCTCCTAGAAGACAGCAAATACCGAAAAATCTACTCCTTTACTCTTAAGCCTCGAACAATTGAA<br>GATTTTGAGTCTATGAATACATACCTGCAGACATCTCCATCATCTGTGTTTACTAGTAAATCATTTTGTT<br>CCTTGCAGACCCCAGATGGGGTTCACTGTTTGGTGGGCTTCACCCTCACCCATAGGAGATTCAATTATAA<br>GGACAATACAGATCTAATAGAGTTCAAGACTCTGAGTGAGGAAGAAATAGAAAAAGTGCTGAAAAATATA<br>TTTAATATTTCCTTGCAGAGAAAGCTTGTGCCCAAACATGGTGATAGATTTTTTACTATTTAGAATAAGG<br>AGTAAAACAATCTTGTCTATTTGTCATCCAGCTCACCAGTTATCAACTGACGACCTATCATGTATCTTCT<br>GTACCCTTACCTTATTTTGAAGAAAATCCTAGACATCAAATCATTTCACCTATAAAAATGTCATCATATA<br>TAATTAAACAGCTTTTTAAAGAAACATAACCACAAACCTTTTCAAATAATAATAATAATAATAATAATAA<br>ATGTCTTTTAAAGATGGCCTGTGGTTATCTTGGAAATTGGTGATTTATGCTAGAAAGCTTTTAATGTTGG<br>TTTATTGTTGAATTCCTAGAAAAGTTTTATGGGTAGATGAGTAAATAAAATATTGTAAAAAAACTTATTG<br>TCTATAAAGTATATTAAAACATTGTTGGCTAATATAAAAAAAAAAAAAA | 142 |
| NM_014321 | GCGCGCGGGTTTCGTTGACCCGCGGCGTTCACGGGAATTGTTCGCTTTAGTGCCGGCGCCATGGGGTCGG<br>AGCTGATCGGGCGCCTAGCCCCGCGCCTGGGCCTCGCCGAGCCCGACATGCTGAGGAAAGCAGAGGAGTA<br>CTTGCGCCTGTCCCGGGTGAAGTGTGTCGGCCTCTCCGCACGCACCACGGAGACCAGCAGTGCAGTCATG<br>TGCCTGGACCTTGCAGCTTCCTGGATGAAGTGCCCCTTGGACAGGGCTTATTTAATTAAACTTTCTGGTT<br>TGAACAAGGAGACATATCAGAGCTGTCTTAAATCTTTTGAGTGTTTACTGGGCCTGAATTCAAATATTGG<br>AATAAGAGACCTAGCTGTACAGTTTAGCTGTATAGAAGCAGTGAACATGGCTTCAAAGATACTAAAAAGC<br>TATGAGTCCAGTCTTCCCCAGACACAGCAAGTGGATCTTGACTTATCCAGGCCACTTTTCACTTCTGCTG<br>CACTGCTTTCAGCATGCAAGATTCTAAAGCTGAAAGTGGATAAAAACAAAATGGTAGCCACATCCGGTGT<br>AAAAAAAGCTATATTTGATCGACTGTGTAAACAACTAGAGAAGATTGGACAGCAGGTCGACAGAGAACCT<br>GGAGATGTAGCTACTCCACCACGGAAGAGAAAGAAGATAGTGGTTGAAGCCCCAGCAAAGGAAATGGAGA<br>AGGTAGAGGAGATGCCACATAAACCACAGAAAGATGAAGATCTGACACAGGATTATGAAGAATGGAAAAG<br>AAAAATTTTGGAAAATGCTGCCAGTGCTCAAAAGGCTACAGCAGAGTGATTTCAGCTTCCAAACTGGTAT<br>ACATTCCAAACTGATAGTACATTGCCATCTCCAGGAAGACTTGACGGCTTTGGGATTTTGTTTAAACTTT<br>TATAATAAGGATCCTAAGACTGTTGCCTTTAAATAGCAAAGCAGCCTACCTGGAGGCTAAGTCTGGGCAG<br>TGGGCTGGCCCCTGGTGTGAGCATTAGACCAGCCACAGTGCCTGATTGGTATAGCCTTATGTGCTTTCCT<br>ACAAAATGGAATTGGAGGCCGGGCGCAGTGGCTCACGCCTGTAATCCCAGCACTTTGGGAGGCCAAGGTG<br>GGTGGATCACCTGAGGTCAGGAGCTCGAGACCAGCCTGGCCAACATGGTGAAACCCCATCTCTACTAAAA<br>ATACAAAAATTAGCCAGGTGTGATGGTGCATGCCTGTAATCCCAGCTCCTCAGTAGGCTGAGACAGGAGC<br>ATCACTTGAACGTGGGAGGCAGAGGTTGCAGTGAGCCGAGATTGCACCACCGCACTCCAGCCTGGGTGAC<br>AGAGCGAGACTTATCTCATAAATAAATAGATAGATACTCCAGCCTGGGTGACAGAGCGAGACTTATAGAT<br>AGATAGATAGATAGATGGATAGATAGATAGATAGATAGATAGATAGATAAACGGAATTGGAGCCATTTTG<br>CTTTAAGTGAATGGCAGTCCCTTGTCTTATTCAGAATATAAAATTCAGTCTGAATGGCATCTTACAGATT<br>TTACTTCAATTTTTGTGTACGGTATTTTTTATTTGACTAAATCAATATATTGTACAGCCTAAGTTAATAA<br>ATGTTATTTATATATGCAAAAAAAAAAAAAAAAA | 143 |
| NM_000926 | AGTCCACAGCTGTCACTAATCGGGGTAAGCCTTGTTGTATTTGTGCGTGTGGGTGGCATTCTCAATGAGA<br>ACTAGCTTCACTTGTCATTTGAGTGAAATCTACAACCCGAGGCGGCTAGTGCTCCCGCACTACTGGGATC<br>TGAGATCTTCGGAGATGACTGTCGCCCGCAGTACGGAGCCAGCAGAAGTCCGACCCTTCCTGGGAATGGG<br>CTGTACCGAGAGGTCCGACTAGCCCCAGGGTTTTAGTGAGGGGGCAGTGGAACTCAGCGAGGGACTGAGA<br>GCTTCACAGCATGCACGAGTTTGATGCCAGAGAAAAAGTCGGGAGATAAAGGAGCCGCGTGTCACTAAAT<br>TGCCGTCGCAGCCGCAGCCACTCAAGTGCCGGACTTGTGAGTACTCTGCGTCTCCAGTCCTCGGACAGAA<br>GTTGGAGAACTCTCTTGGAGAACTCCCCGAGTTAGGAGACGAGATCTCCTAACAATTACTACTTTTTCTT<br>GCGCTCCCCACTTGCCGCTCGCTGGGACAAACGACAGCCACAGTTCCCCTGACGACAGGATGGAGGCCAA<br>GGGCAGGAGCTGACCAGCGCCGCCCTCCCCCGCCCCCGACCCAGGAGGTGGAGATCCCTCCGGTCCAGCC<br>ACATTCAACACCCACTTTCTCCTCCCTCTGCCCCTATATTCCCGAAACCCCCTCCTCCTTCCCTTTTCCC<br>TCCTCCTGGAGACGGGGGAGGAGAAAAGGGGAGTCCAGTCGTCATGACTGAGCTGAAGGCAAAGGGTCCC<br>CGGGCTCCCCACGTGGCGGGCGGCCCGCCCTCCCCCGAGGTCGGATCCCCACTGCTGTGTCGCCCAGCCG<br>CAGGTCCGTTCCCGGGGAGCCAGACCTCGGACACCTTGCCTGAAGTTTCGGCCATACCTATCTCCCTGGA<br>CGGGCTACTCTTCCCTCGGCCCTGCCAGGGACAGGACCCCTCCGACGAAAAGACGCAGGACCAGCAGTCG<br>CTGTCGGACGTGGAGGGCGCATATTCCAGAGCTGAAGCTACAAGGGGTGCTGGAGGCAGCAGTTCTAGTC<br>CCCCAGAAAAGGACAGCGGACTGCTGGACAGTGTCTTGGACACTCTGTTGGCGCCCTCAGGTCCCGGGCA | 144 |

TABLE 2-continued

| GENBANK ACCESSION NUMBER | SEQUENCE | SEQ ID NO: |
|---|---|---|
| | GAGCCAACCCAGCCCTCCCGCCTGCGAGGTCACCAGCTCTTGGTGCCTGTTTGGCCCCGAACTTCCCGAA | |
| | GATCCACCGGCTGCCCCCGCCACCCAGCGGGTGTTGTCCCCGCTCATGAGCCGGTCCGGGTGCAAGGTTG | |
| | GAGACAGCTCCGGGACGGCAGCTGCCCATAAAGTGCTGCCCCGGGGCCTGTCACCAGCCCGGCAGCTGCT | |
| | GCTCCCGGCCTCTGAGAGCCCTCACTGGTCCGGGGCCCCAGTGAAGCCGTCTCCGCAGGCCGCTGCGGTG | |
| | GAGGTTGAGGAGGAGGATGGCTCTGAGTCCGAGGAGTCTGCGGGTCCGCTTCTGAAGGGCAAACCTCGGG | |
| | CTCTGGGTGGCGCGGCGGCTGGAGGAGGAGCCGCGGCTGTCCCGCCGGGGGCGGCAGCAGGAGGCGTCGC | |
| | CCTGGTCCCCAAGGAAGATTCCCGCTTCTCAGCGCCCAGGGTCGCCCTGGTGGAGCAGGACGCGCCGATG | |
| | GCGCCCGGGCGCTCCCCGCTGGCCACCACGGTGATGGATTTCATCCACGTGCCTATCCTGCCTCTCAATC | |
| | ACGCCTTATTGGCAGCCCGCACTCGGCAGCTGCTGGAAGACGAAAGTTACGACGGCGGGGCCGGGGCTGC | |
| | CAGCGCCTTTGCCCCGCCGCGGAGTTCACCCTGTGCCTCGTCCACCCCGGTCGCTGTAGGCGACTTCCCC | |
| | GACTGCGCGTACCCGCCCGACGCCGAGCCCAAGGACGACGCGTACCCTCTCTATAGCGACTTCCAGCCGC | |
| | CCGCTCTAAAGATAAAGGAGGAGGAGGAAGGCGCGGAGGCCTCCGCGCGCTCCCCGCGTTCCTACCTTGT | |
| | GGCCGGTGCCAACCCCGCAGCCTTCCCGGATTTCCCGTTGGGGCCACCGCCCCCGCTGCCGCCGCGAGCG | |
| | ACCCCATCCAGACCCGGGGAAGCGGCGGTGACGGCCGCACCCGCCAGTGCCTCAGTCTCGTCTGCGTCCT | |
| | CCTCGGGGTCGACCCTGGAGTGCATCCTGTACAAAGCGGAGGGCGCGCCGCCCCAGCAGGGCCCGTTCGC | |
| | GCCGCCGCCCTGCAAGGCGCCGGGCGCGAGCGGCTGCCTGCTCCCGCGGGACGGCCTGCCCTCCACCTCC | |
| | GCCTCTGCCGCCGCCGCCGGGGCGGCCCCCGCGCTCTACCCTGCACTCGGCCTCAACGGGCTCCCGCAGC | |
| | TCGGCTACCAGGCCGCCGTGCTCAAGGAGGGCCTGCCGCAGGTCTACCCGCCCTATCTCAACTACCTGAG | |
| | GCCGGATTCAGAAGCCAGCCAGAGCCCACAATACAGCTTCGAGTCATTACCTCAGAAGATTTGTTTAATC | |
| | TGTGGGGATGAAGCATCAGGCTGTCATTATGGTGTCCTTACCTGTGGGAGCTGTAAGGTCTTCTTTAAGA | |
| | GGGCAATGGAAGGGCAGCACAACTACTTATGTGCTGGAAGAAATGACTGCATCGTTGATAAAATCCGCAG | |
| | AAAAAACTGCCCAGCATGTCGCCTTAGAAAGTGCTGTCAGGCTGGCATGGTCCTTGGAGGTCGAAAATTT | |
| | AAAAAGTTCAATAAAGTCAGAGTTGTGAGAGCACTGGATGCTGTTGCTCTCCCACAGCCAGTGGGCGTTC | |
| | CAAATGAAAGCCAAGCCCTAAGCCAGAGATTCACTTTTTCACCAGGTCAAGACATACAGTTGATTCCACC | |
| | ACTGATCAACCTGTTAATGAGCATTGAACCAGATGTGATCTATGCAGGACATGACAACACAAAACCTGAC | |
| | ACCTCCAGTTCTTTGCTGACAAGTCTTAATCAACTAGGCGAGAGGCAACTTCTTTCAGTAGTCAAGTGGT | |
| | CTAAATCATTGCCAGGTTTTCGAAACTTACATATTGATGACCAGATAACTCTCATTCAGTATTCTTGGAT | |
| | GAGCTTAATGGTGTTTGGTCTAGGATGGAGATCCTACAAACACGTCAGTGGGCAGATGCTGTATTTTGCA | |
| | CCTGATCTAATACTAAATGAACAGCGGATGAAAGAATCATCATTCTATTCATTATGCCTTACCATGTGGC | |
| | AGATCCCACAGGAGTTTGTCAAGCTTCAAGTTAGCCAAGAAGAGTTCCTCTGTATGAAAGTATTGTTACT | |
| | TCTTAATACAATTCCTTTGGAAGGGCTACGAAGTCAAACCCAGTTTGAGGAGATGAGGTCAAGCTACATT | |
| | AGAGAGCTCATCAAGGCAATTGGTTTGAGGCAAAAAGGAGTTGTGTCGAGCTCACAGCGTTTCTATCAAC | |
| | TTACAAAACTTCTTGATAACTTGCATGATCTTGTCAAACAACTTCATCTGTACTGCTTGAATACATTTAT | |
| | CCAGTCCCGGGCACTGAGTGTTGAATTTCCAGAAATGATGTCTGAAGTTATTGCTGCACAATTACCCAAG | |
| | ATATTGGCAGGGATGGTGAAACCCCTTCTCTTTCATAAAAAGTGAATGTCATCTTTTTCTTTTAAAGAAT | |
| | TAAATTTTGTGGTATGTCTTTTTGTTTTGGTCAGGATTATGAGGTCTTGAGTTTTTATAATGTTCTTCTG | |
| | AAAGCCTTACATTTATAACATCATAGTGTGTAAATTTAAAAGAAAAATTGTGAGGTTCTAATTATTTTCT | |
| | TTTATAAAGTATAATTAGAATGTTTAACTGTTTTGTTTACCCATATTTTCTTGAAGAATTTACAAGATTG | |
| | AAAAAGTACTAAAATTGTTAAAGTAAACTATCTTATCCATATTATTTCATACCATGTAGGTGAGGATTTT | |
| | TAACTTTTGCATCTAACAAATCATCGACTTAAGAGAAAAAATCTTACATGTAATAACACAAAGCTATTAT | |
| | ATGTTATTTCTAGGTAACTCCCTTTGTGTCAATTATATTTCCAAAAATGAACCTTTAAAATGGTATGCAA | |
| | AATTTTGTCTATATATATTTGTGTGAGGAGGAAATTCATAACTTTCCTCAGATTTTCAAAAGTATTTTTA | |
| | ATGCAAAAAATGTAGAAAGAGTTTAAAACCACTAAAATAGATTGATGTTCTTCAAACTAGGCAAAACAAC | |
| | TCATATGTTAAGACCATTTTCCAGATTGGAAACACAAATCTCTTAGGAAGTTAATAAGTAGATTCATATC | |
| | ATTATGCAAATAGTATTGTGGGTTTTGTAGGTTTTAAAATAACCTTTTTGGGGAGAGAATTGTCCTCT | |
| | AATGAGGTATTGCGAGTGGACATAAGAAATCAGAAGATTATGGCCTAACTGTACTCCTTACCAACTGTGG | |
| | CATGCTGAAAGTTAGTCACTCTTACTGATTCTCAATTCTCTCACCTTTGAAAGTAGTAAAATATCTTTCC | |
| | TGCCAATTGCTCCTTTGGGTCAGAGCTTATTAACATCTTTTCAAATCAAAGGAAAGAAGAAAGGGAGAGG | |
| | AGGAGGAGGGAGGTATCAATTCACATACCTTTCTCCTCTTTATCCTCCACTATCATGAATTCATATTATG | |
| | TTTCAGCCATGCAAATCTTTTTACCATGAAATTTCTTCCAGAATTTTCCCCCTTTGACACAAATTCCATG | |
| | CATGTTTCAACCTTCGAGACTCAGCCAAATGTCATTTCTGTAAAATCTTCCCTGAGTCTTCCAAGCAGTA | |
| | ATTTGCCTTCTCCTAGAGTTTACCTGCCATTTTGTGCACATTTGAGTTACAGTAGCATGTTATTTTACAA | |
| | TTGTGACTCTCCTGGGAGTCTGGGAGCCATATAAAGTGGTCAATAGTGTTTGCTGACTGAGAGTTGAATG | |
| | ACATTTTCTCTCTGTCTTGGTATTACTGTAGATTTCGATCATTCTTTGGTTACATTTCTGCATATTTCTG | |
| | TACCCATGACTTTATCACTTTCTTCTCCCATGCTTTATCTCCATCAATTATCTTCATTACTTTTAAATTT | |
| | TCCACCTTTGCTTCCTACTTTGTGAGATCTCTCCCTTTACTGACTATAACATAGAAGAATAGAAGTGTAT | |
| | TTTATGTGTCTTAAGGACAATACTTTAGATTCCTTGTTCTAAGTTTTTAAACTGAATGAATGGAATATTA | |
| | TTTCTCTCCCTAAGCAAAATTCCACAAAACAATTATTTCTTATGTTTATGTAGCCTTAAATTGTTTTGTA | |
| | CTGTAAACCTCAGCATAAAAACTTTCTTCATTTCTAATTTCATTCAACAAATATTGATTGAATACCTGGT | |
| | ATTAGCACAAGAAAAATGTGCTAATAAGCCTTATGAGAATTTGGAGCTGAAGAAAGACATATAACTCAGG | |
| | AAAGTTACAGTCCAGTAGTAGGTATAAATTACAGTGCCTGATAAATAGGCATTTTAATATTTGTACACTC | |
| | AACGTATACTAGGTAGGTGCAAAACATTTACATATAATTTTACTGATACCCATGCAGCACAAAGGTACTA | |
| | ACTTTAAATATTAAATAACACCTTTATGTGTCAGTAATTCATTTGCATTAAATCTTATTGAAAAGGCTTT | |
| | CAATATATTTTCCCCACAAATGTCATCCCAAGAAAAAAGTATTTTTAACATCTCCCAAATATAATAGTTA | |
| | CAGGAAATCTACCTCTGTGAGAGTGACACCTCTCAGAATGAACTGTGTGACACAAGAAAATGAATGTAGG | |
| | TCTATCCAAAAAAAACCCCAAGAAACAAAAACAATATTATTAGCCCTTTATGCTTAAGTGATGGACTCAG | |
| | GGAACAGTTGATGTTGTGATCATTTTATTATCTGATTCTTGTTACTTTGAATTAAACCAATATTTTGATG | |
| | ATATAAATCATTTCCACCAGCATATATTTAATTTCCATAATAACTTTAAAATTTTCTAATTTCACTCAAC | |
| | TATGAGGGAATAGAATGTGGTGGCCACAGGTTTGGCTTTTGTTAAAATGTTTGATATCTTCGATGTTGAT | |
| | CTCTGTCTGCAATGTAGATGTCTAAACACTAGGATTTAATATTTAAGGCTAAGCTTTAAAAATAAAGTAC | |
| | CTTTTTAAAAAGAATATGGCTTCACCAAATGGAAAATACCTAATTTCTAAATCTTTTTCTCTACAAAGTC | |
| | CTATCTACTAATGTCTCCATTACTATTTAGTCATCATAACCATTATCTTCATTTTACATGTCGTGTTCTT | |
| | TCTGGTAGCTCTAAAATGACACTAAATCATAAGAAGACAGGTTACATATCAGGAAATACTTGAAGGTTAC | |
| | TGAAATAGATTCTTGAGTTAATGAAAATATTTTCTGTAAAAAGGTTTGAAAAGCCATTTGAGTCTAAAGC | |
| | ATTATACCTCCATTATCAGTAGTTATGTGACAATTGTGTGTGTGTTTAATGTTTAAAGATGTGGCACTTT | |
| | TTAATAAGGCAATGCTATGCTATTTTTTCCCATTTAACATTAAGATAATTTATTGCTATACAGATGATAT | |

TABLE 2-continued

| GENBANK ACCESSION NUMBER | SEQUENCE | SEQ ID NO: |
| --- | --- | --- |
| | GGAAATATGATGAACAATATTTTTTTTGCCAAAACTATGCCTTGTAAGTAGCCATGGAATGTCAACCTGT<br>AACTTAAATTATCCACAGATAGTCATGTGTTTGATGATGGGCACTGTGGAGATAACTGACATAGGACTGT<br>GCCCCCCTTCTCTGCCACTTACTAGCTGGATGAGATTAAGCAAGTCATTTAACTGCTCTGATTAAACCTG<br>CCTTTCCCAAGTGCTTTGTAATGAATAGAAATGGAAACCAAAAAAAACGTATACAGGCCTTCAGAAATAG<br>TAATTGCTACTATTTTGTTTTCATTAAGCCATAGTTCTGGCTATAATTTTATCAAACTCACCAGCTATAT<br>TCTACAGTGAAAGCAGGATTCTAGAAAGTCTCACTGTTTTATTTATGTCACCATGTGCTATGATATATTT<br>GGTTGAATTCATTTGAAATTAGGGCTGGAAGTATTCAAGTAATTTCTTCTGCTGAAAAAATACAGTGTTT<br>TGAGTTTAGGGCCTGTTTTATCAAAGTTCTAAAGAGCCTATCACTCTTCCATTGTAGACATTTTAAAATA<br>ATGACACTGATTTTAACATTTTTAAGTGTCTTTTTAGAACAGAGAGCCTGACTAGAACACAGCCCCTCCA<br>AAAACCCATGCTCAAATTATTTTTACTATGGCAGCAATTCCACAAAAGGGAACAATGGGTTTAGAAATTA<br>CAATGAAGTCATCAACCCAAAAAACATCCCTATCCCTAAGAAGGTTATGATATAAAATGCCCACAAGAAA<br>TCTATGTCTGCTTTAATCTGTCTTTTATTGCTTTGGAAGGATGGCTATTACATTTTTAGTTTTTGCTGTG<br>AATACCTGAGCAGTTTCTCTCATCCATACTTATCCTTCACACATCAGAAGTCAGGATAGAATATGAATCA<br>TTTTAAAAACTTTTACAACTCCAGAGCCATGTGCATAAGAAGCATTCAAAACTTGCCAAAACATACATTT<br>TTTTTCAAATTTAAAGATACTCTATTTTTGTATTCAATAGCTCAACAACTGTGGTCCCCACTGATAAAGT<br>GAAGTGGACAAGGAGACAAGTAATGGCATAAGTTTGTTTTTCCCAAAGTATGCCTGTTCAATAGCCATTG<br>GATGTGGGAAATTTCTACATCTCTTAAAATTTTACAGAAAATACATAGCCAGATAGTCTAGCAAAAGTTC<br>ACCAAGTCCTAAATTGCTTATCCTTACTTCACTAAGTCATGAAATCATTTTAATGAAAAGAACATCACCT<br>AGGTTTTGTGGTTTCTTTTTTTCTTATTCATGGCTGAGTGAAAACAACAATCTCTGTTTCTCCCTAGCAT<br>CTGTGGACTATTTAATGTACCATTATTCCACACTCTATGGTCCTTACTAAATACAAAATTGAACAAAAAG<br>CAGTAAAACAACTGACTCTTCACCCATATTATAAAATATAATCCAAGCCAGATTAGTCAACATCCATAAG<br>ATGAATCCAAGCTGAACTGGGCCTAGATTATTGAGTTCAGGTTGGATCACATCCCTATTTATTAATAAAC<br>TTAGGAAAGAAGGCCTTACAGACCATCAGTTAGCTGGAGCTAATAGAACCTACACTTCTAAAGTTCGGCC<br>TAGAATCAATGTGGCCTTAAAAGCTGAAAAGAAGCAGGAAAGAACAGTTTTCTTCAATAATTTGTCCACC<br>CTGTCACTGGAGAAAATTTAAGAATTTGGGGGTGTTGGTAGTAAGTTAAACACAGCAGCTGTTCATGGCA<br>GAAATTATTCAATACATACCTTCTCTGAATATCCTATAACCAAAGCAAAGAAAAACACCAAGGGGTTTGT<br>TCTCCTCCTTGGAGTTGACCTCATTCCAAGGCAGAGCTCAGGTCACAGGCACAGGGGCTGCGCCCAAGCT<br>TGTCCGCAGCCTTATGCAGCTGTGGAGTCTGGAAGACTGTTGCAGGACTGCTGGCCTAGTCCCAGAATGT<br>CAGCCTCATTTTCGATTTACTGGCTCTTGTTGCTGTATGTCATGCTGACCTTATTGTTAAACACAGGTTT<br>GTTTGCTTTTTTTCCACTCATGGAGACATGGGAGAGGCATTATTTTTAAGCTGGTTGAAAGCTTTAACCG<br>ATAAAGCATTTTTAGAGAAATGTGAATCAGGCAGCTAAGAAAGCATACTCTGTCCATTACGGTAAAGAAA<br>ATGCACAGATTATTAACTCTGCAGTGTGGCATTAGTGTCCTGGTCAATATTCGGATAGATATGAATAAAA<br>TATTTAAATGGTATTGTAAATAGTTTTCAGGACATATGCTATAGCTTATTTTTATTATCTTTTGAAATTG<br>CTCTTAATACATCAAATCCTGATGTATTCAATTTATCAGATATAAATTATTCTAAATGAAGCCCAGTTAA<br>ATGTTTTTGTCTTGTCAGTTATATGTTAAGTTTCTGATCTCTTTGTCTATGACGTTTACTAATCTGCATT<br>TTTACTGTTATGAATTATTTTAGACAGCAGTGGTTTCAAGCTTTTTGCCACTAAAAATACCTTTTATTTT<br>CTCCTCCCCCAGAAAAGTCTATACCTTGAAGTATCTATCCACCAAACTGTACTTCTATTAAGAAATAGTT<br>ATTGTGTTTTCTTAATGTTTTGTTATTCAAAGACATATCAATGAAAGCTGCTGAGCAGCATGAATAACAA<br>TTATATCCACACAGATTTGATATATTTTGTGCAGCCTTAACTTGATAGTATAAAATGTCATTGCTTTTTA<br>AATAATAGTTAGTCAATGGACTTCTATCATAGCTTTCCTAAACTAGGTTAAGATCCAGAGCTTTGGGGTC<br>ATAATATATTACATACAATTAAGTTATCTTTTTCTAAGGGCTTTAAAATTCATGAGAATAACCAAAAAAG<br>GTATGTGGAGAGTTAATACAAACATACCATATTCTTGTTGAAACAGAGATGTGGCTCTGCTTGTTCTCCA<br>TAAGGTAGAAATACTTTCCAGAATTTGCCTAAACTAGTAAGCCCTGAATTTGCTATGATTAGGGATAGGA<br>AGAGATTTTCACATGGCAGACTTTAGAATTCTTCACTTTAGCCAGTAAAGTATCTCCTTTTGATCTTAGT<br>ATTCTGTGTATTTTAACTTTTCTGAGTTGTGCATGTTTATAAGAAAAATCAGCACAAAGGGTTTAAGTTA<br>AAGCCTTTTTACTGAAATTTGAAAGAAACAGAAGAAAATATCAAAGTTCTTTGTATTTTGAGAGGATTAA<br>ATATGATTTACAAAAGTTACATGGAGGGCTCTCTAAAACATTAAATTAATTATTTTTTGTTGAAAAGTCT<br>TACTTTAGGCATCATTTTATTCCTCAGCAACTAGCTGTGAAGCCTTTACTGTGCTGTATGCCAGTCACTC<br>TGCTAGATTGTGGAGATTACCAGTGTTCCCGTCTTCTCCGAGCTTAGAGTTGGATGGGGAATAAAGACAG<br>GTAAACAGATAGCTACAATATTGTACTGTGAATGCTTATGCTGGAGGAAGTACAGGGAACTATTGGAGCA<br>CCTAAGAGGAGCACCTACCTTGAATTTAGGGGTTAGCAGAGGCATCCTGAAAAAAGTCAAAGCTAAGCCA<br>CAATCTATAAGCAGTTTAGGAATTAGCAGAACGTGCGTGGTGAGGAGATGCCAAAGGCAAGAAGAGAAGA<br>GTATTCCAAACAGGAGGGATTCCAAAGAGAGAAGAGTATCCCAAACAACATTTGCACAAACCTGATGGGG<br>AGAGAGAATGTGGGGTGGGGATGGATGATGAGACTGAAGAAGAAAGCCAGGTCTAGATAATCAGTGGCCT<br>TGTACACCATGTTAAAGAGTGTAGACTTGATTCTGTTGTAAACAGGAAAGCAGCACAATTCATATGAATA<br>TTTTAGAAGACTCCCACTGGAATATGGAGAATAAAGTTGGAGATGACTAATCCTGGAAGCAGGGAGAACA<br>TTTTTGAGGAAGTTGCACTATTTTGGTGAAAATGATGATCATAAACATGAAGAATTGTAGGTGATCATGA<br>CCTCCTCTCTAATTTTCCAGAAGGGTTTTGGAAGATATAACATAGGAACATTGACAGGACTGACGAAAGG<br>AGATGAAATACACCATATAAATTGTCAAACACAAGGCCAGATGTCTAATTATTTTGCTTATGTGTTGAAA<br>TTACAAATTTTTCATCAGGAAACCAAAAACTACAAAACTTAGTTTTCCCAAGTCCCAGAATTCTATCTGT<br>CCAAACAATCTGTACCACTCCACCTATATCCCTACCTTTGCATGTCTGTCCAACCTCAAAGTCCAGGTCT<br>ATACACACGGGTAAGACTAGAGCAGTTCAAGTTTCAGAAAATGAGAAAGAGGAACTGAGTTGTGCTGAAC<br>CCATACAAAATAAACACATTCTTTGTATAGATTCTTGGAACCTCGAGAGGAATTCACCTAACTCATAGGT<br>ATTTGATGGTATGAATCCATGGCTGGGCTCGGCTTTTAAAAAGCCTTATCTGGGATTCCTTCTATGGAAC<br>CAAGTTCCATCAAAGCCCATTTAAAAGCCTACATTAAAAACAAAATTCTTGCTGCATTGTATACAAATAA<br>TGATGTCATGATCAAATAATCAGATGCCATTATCAAGTGGAATTACAAAATGGTATACCCACTCCAAAAA<br>AAAAAAAAAAGCTAAATTCTCAGTAGAACATTGTGACTTCATGAGCCCTCCACAGCCTTGGAGCTGAGGA<br>GGGAGCACTGGTGAGCAGTAGGTTGAAGAGAAAACTTGGCGCTTAATAATCTATCCATGTTTTTTCATCT<br>AAAAGAGCCTTCTTTTTGGATTACCTTATTCAATTTCCATCAAGGAAATTGTTAGTTCCACTAACCAGAC<br>AGCAGCTGGGAAGGCAGAAGCTTACTGTATGTACATGGTAGCTGTGGGAAGGAGGTTTCTTTCTCCAGGT<br>CCTCACTGGCCATACACCAGTCCCTTGTTAGTTATGCCTGGTCATAGACCCCCGTTGCTATCATCTCATA<br>TTTAAGTCTTTGGCTTGTGAATTTATCTATTCTTTCAGCTTCAGCACTGCAGAGTGCTGGGACTTTGCTA<br>ACTTCCATTTCTTGCTGGCTTAGCACATTCCTCATAGGCCCAGCTCTTTTCTCATCTGGCCCTGCTGTGG<br>AGTCACCTTGCCCCTTCAGGAGAGCCATGGCTTACCACTGCCTGCTAAGCCTCCACTCAGCTGCCACCAC<br>ACTAAATCCAAGCTTCTCTAAGATGTTGCAGACTTTACAGGCAAGCATAAAAGGCTTGATCTTCCTGGAC<br>TTCCCTTTACTTGTCTGAATCTCACCTCCTTCAACTTTCAGTCTCAGAATGTAGGCATTTGTCCTCTTTG | |

TABLE 2-continued

| GENBANK ACCESSION NUMBER | SEQUENCE | SEQ ID NO: |
|---|---|---|
| | CCCTACATCTTCCTTCTTCTGAATCATGAAAGCCTCTCACTTCCTCTTGCTATGTGCTGGAGGCTTCTGT<br>CAGGTTTTAGAATGAGTTCTCATCTAGTCCTAGTAGCTTTTGATGCTTAAGTCCACCTTTTAAGGATACC<br>TTTGAGATTTAGACCATGTTTTTCGCTTGAGAAAGCCCTAATCTCCAGACTTGCCTTTCTGTGGATTTCA<br>AAGACCAACTGAGGAAGTCAAAAGCTGAATGTTGACTTTCTTTGAACATTTCCGCTATAACAATTCCAAT<br>TCTCCTCAGAGCAATATGCCTGCCTCCAACTGACCAGGAGAAAGGTCCAGTGCCAAAGAGAAAAACACAA<br>AGATTAATTATTTCAGTTGAGCACATACTTTCAAAGTGGTTTGGGTATTCATATGAGGTTTTCTGTCAAG<br>AGGGTGAGACTCTTCATCTATCCATGTGTGCCTGACAGTTCTCCTGGCACTGGCTGGTAACAGATGCAAA<br>ACTGTAAAAATTAAGTGATCATGTATTTTAACGATATCATCACATACTTATTTTCTATGTAATGTTTTAA<br>ATTTCCCCTAACATACTTTGACTGTTTTGCACATGGTAGATATTCACATTTTTTTGTGTTGAAGTTGATG<br>CAATCTTCAAAGTTATCTACCCCGTTGCTTATTAGTAAAACTAGTGTTAATACTTGGCAAGAGATGCAGG<br>GAATCTTTCTCATGACTCACGCCCTATTTAGTTATTAATGCTACTACCCTATTTTGAGTAAGTAGTAGGT<br>CCCTAAGTACATTGTCCAGAGTTATACTTTTAAAGATATTTAGCCCCATATACTTCTTGAATCTAAAGTC<br>ATACACCTTGCTCCTCATTTCTGAGTGGGAAAGACATTTGAGAGTATGTTGACAATTGTTCTGAAGGTTT<br>TTGCCAAGAAGGTGAAACTGTCCTTTCATCTGTGTATGCCTGGGGCTGGGTCCCTGGCAGTGATGGGGTG<br>ACAATGCAAAGCTGTAAAAACTAGGTGCTAGTGGGCACCTAATATCATCATCATATACTTATTTTCAAGC<br>TAATATGCAAAATCCCATCTCTGTTTTTAAACTAAGTGTAGATTTCAGAGAAAATATTTTGTGGTTCACA<br>TAAGAAAACAGTCTACTCAGCTTGACAAGTGTTTTATGTTAAATTGGCTGGTGGTTTGAAATGAATCATC<br>TTCACATAATGTTTTCTTTAAAAATATTGTGAATTTAACTCTAATTCTTGTTATTCTGTGTGATAATAAA<br>GAATAAACTAATTTCTA | |
| AK093306 | ATTCTATGCTGCAGCCTAAGCATCATTCCTCTTCTCTTCTTAGTGGAGATAAAATTACCCACTGCTCTCC<br>TTACATTTACTTTGTCCATATTTGCTCCTATGCTCTAGGCTCGTGCACAACAAACACAGTGTGGGCCCTT<br>ACCCTAGAAGCCAACTTCTCATGACCTTTCTCTATCTCCAGAATCCATGCAGTGGGAATGAAGGTAAAAG<br>AAGGTTTTCATGGGATCCAGCTGAGAGCTCTACGGGGAAAATGGATCTGAGGAGCCATGTGCTCCATCTC<br>TTTTATTTTACAGGTAGAGACTAGGGGTATAGAGTGAGGTGAATTACCGCAGTGACCCACACATTGTTGG<br>CAGACCTAGGATTAGAACTCTGTCTTCCTGGTTCCCAGCTTGGTGCTTTTGAAAGCATACTTGCTGCTTT<br>CTTACCGGCCTGGTGTCTGCCACTTTGGGACAGAGTGTGGACTTGCTCACCTGCCCCATTTCTTAGGGAT<br>TCTCATTCTGTGTTTGAGCAAGAATATTCTTATTCTGGAAAGAACCACATACCACAGGATTCTGGGTGAG<br>CATAAGGAAGATTGTCTTGGGGATCTGACTTAGCTCACGTATAGTGGCTATGATGAATTCAGTGTCTTAT<br>TTTTTGCATATGTATATTTTTAGTCTAATATTGCCTGGGTGTCTGAGCAAGTCTAGATGAATTTAATTGC<br>TCTCATTTTTCCCCTGCCCCTCTTCCTTTGGTCTCTCTTTTAGGAAATGTTTTTCTTTCAACATTCGTTT<br>CATTCATTATTTACTCATTCGGCCAACCAACATTTATTGAGTGCCTTCCCTGTATCAGGGACAGGGGCTT<br>ACAAAGTAGAATTTGATCCCACCTCTGCCCTCAGTAGCTCAGTGTCTAATGGAGGTAGTGATGTTCATTA<br>AGCGTCGCCAGATACTGTGCTAGGTGCTGTGCCTGTTCTCTCTCGCTTGTTCCTCACACACTTGAGAAGG<br>CCGAAGCTGATTCATAGCTTGGAAGGCAGGGGCCTTGGATTTGAACCCAGGCCTGACCAATGGCAGAACC<br>TATCAGATGTGTGGACAGATGACATTGCCTTTCTTTCTTTGGATATATCAAAATCAGCCAGCAGGCAGGA<br>ACTCCCATTTTGAGCAAGCAATGTGCAGGAATGATAGGGTATACAGAGAGGAACAGGAGATGGCCCCTGA<br>CTTCCAGCATGTGTCTGATGGACATCCAGGCTGCAGGCATCATGGTGCTGTCTAGAGAGATGAGCCAGGT<br>GCCCAGAGCCCATGGGCCAATGCTGCCCTTTCTTGAGCATGCCAAACAAAGCGGTTGGTGTGTTAGAGGC<br>ACAGTCTCCTCCACTCTAAGTAAAAATCAGCATGAGTCCTAGCCCACATTTCCCTAGTGAGTACACCAAA<br>GATATCTATGAACTGGCAGTCATCAGTGACTTCCTAAGGTTCCGGAAATGCATCTCTTACTCAGGAGTAA<br>GCAATGATGTGCCTGCGGCTTTACGAGTTCTCACAGAATGACTTTCTGGACCCAAATGTTTTTTCTGCTT<br>CAGGACTGTGAAGGCCTTATTGTTCGCTCTGCCACCAAGGTGACCGCTGATGTCATCAACGCAGCTGAGA<br>AACTCCAGGTGGTGGGCAGGGCTGGCACAGGTGTGGACAATGTGGATCTGGAGGCCGCAACAAGGAAGGG<br>CATCTTGGTTATGAACACCCCCAATGGGAACAGCCTCAGTGCCGCAGAACTCACTTGTGGAATGATCATG<br>TGCCTGGCCAGGCAGATTCCCCAGGCGACGGCTTCGATGAAGGACGGCAAATGGGAGCGGAAGAAGTTCA<br>TGGGAACAGAGCTGAATGGAAAGACCCTGGGAATTCTTGGCCTGGGCAGGATTGGGAGAGAGGTAGCTAC<br>CCGGATGCAGTCCTTTGGGATGAAGACTATAGGGTATGACCCCATCATTTCCCCAGAGGTCTCGGCCTCC<br>TTTGGTGTTCAGCAGCTGCCCCTGGAGGAGATCTGGCCTCTCTGTGATTTCATCACTGTGCACACTCCTC<br>TCCTGCCCTCCACGACAGGCTTGCTGAATGACAACACCTTTGCCCAGTGCAAGAAGGGGGTGCGTGTGGT<br>GAACTGTGCCCGTGGAGGGATCGTGGACGAAGGCGCCCTGCTCCGGGCCCTGCAGTCTGGCCAGTGTGCC<br>GGGGCTGCACTGGACGTGTTTACGGAAGAGCCGCCACGGGACCGGGCCTTGGTGGACCATGAGAATGTCA<br>TCAGCTGTCCCCACCTGGGTGCCAGCACCAAGGAGGCTCAGAGCCGCTGTGGGGAGGAAATTGCTGTTCA<br>GTTCGTGGACATGGTGAAGGGGAAATCTCTCACGGGGGTTGTGAATGCCCAGGCCCTTACCAGTGCCTTC<br>TCTCCACACACCAAGCCTTGGATTGGTCTGGCAGAAGCTCTGGGGACACTGATGCGAGCCTGGGCTGGGT<br>CCCCCAAAGGGACCATCCAGGTGATAACACAGGGAACATCCCTGAAGAATGCTGGGAACTGCCTAAGCCC<br>CGCAGTCATTGTCGGCCTCCTGAAAGAGGCTTCCAAGCAGGCGGATGTGAACTTGGTGAACGCTAAGCTG<br>CTGGTGAAAGAGGCTGGCCTCAATGTCACCACCTCCCACAGCCCTGCTGCACCAGGGGGGCAAGGCTTCG<br>GGGAATGCCTCCTGGCCGTGGCCCTGGCAGGCGCCCCTTACCAGGCTGTGGGCTTGGTCCAAGGCACTAC<br>ACCTGTACTGCAGGGGCTCAATGGAGCTGTCTTCAGGCCAGAAGTGCCTCTCCGCAGGGACCTGCCCCTG<br>CTCCTATTCCGGACTCAGACCTCTGACCCTGCAATGCTGCCTACCATGATTGGCCTCCTGGCAGAGGCAG<br>GCGTGCGGCTGCTGTCCTACCAGACTTCACTGGTGTCAGATGGGGAGACCTGGCACGTCATGGGCATCTC<br>CTCCTTGCTGCCCAGCCTGGAAGCGTGGAAGCAGCATGTGACTGAAGCCTTCCAGTTCCACTTCTAACCT<br>TGGAGCTCACTGGTCCCTGCCTCTGGGGCTTTTCTGAAGAAACCCACCCACTGTGATCAATAGGGAGAGA<br>AAATCCACATTCTTGGGCTGAACGCGAGCCTCTGACACTGCTTACACTGCACTCTGACCCTGTAGTACAG<br>CAATAACCGTCTAATAAAGAGCCTACCCCC | 145 |
| BE904476 | CAAACAAAAACAGCCAAGCTTTTCTGCCAAAAAGATGACTGAGAAGACTGTTAAAGCAAAAAGCTCTGTT<br>CCTGCCTCAGATGATGCCTATCCAGAAATAGAAAAATTCTTTCCCTTCAATCCTCTAGACTTTGAGAGTT<br>TTGACCTGCCTGAAGAGCACCAGATTGCGCACCTCCCCTTGAGTGGAGTGCCTCTCATGATCCTTGACGA<br>GGAGAGAGAGCTTGAAAAGCTGTTTCAGCTGGGCCCCCCTTCACCTGTGAAGATGCCCTCTCCACCATGG<br>GAATCCAATCTGTTGCAGTCTCCTTCAAGCATTCTGTCGACCCTGGATGTTGAATTGCCACCTGTTTGCT<br>GTGACATAGATATTTAAATTTCTTAGTGCTTCAGAGTCTGTGTGTATTTGTATTAATAAAGCATTCTTTA<br>ACAGAAAAAAAAAAAAAAAAAAAAAAAAAAAAAAAAAAAAAAAAAAAAAGGGGGGGGAGACACAAAAA<br>GAATTCCCCAAGAGGGGGCCACAAGATAATCAGAGGATATCACACAAGATCTCTCGGCGCACCAACGACG<br>GGGGCCCCAAATAAGGGAGAGACCCAGAATCACAACAGCCAAGACACGGTGGACACGACGGAAACAAACA | 146 |

TABLE 2-continued

| GENBANK ACCESSION NUMBER | SEQUENCE | SEQ ID NO: |
|---|---|---|
| | CACAGCCCAGACACGGGGGCAAACACGCGCGCACACCGCGGACACCATGGGACAAAGCAGACACCACCCA<br>CAAAACAACACCGCGGAGGGGGAAGAACAACAAAACAAGTGCGCAAACAGAACACAACCACAGAAAGAGA<br>AAAATTAAAACGGCCCCCAAGACGGCGACAACACAACAAAACAACCACTACAGAGCGCTCAACAGCCGAG<br>TAAAAACACAACAACGGACAACTAACACACAAAGGAATGAAACAAAGCGGGGCCACACACCGACACCGGA<br>AATCCGGCGAACAACTCACACCGAGCGAGGGTCCCAGACAACAAATACACAGACAACGAAACCGAGAAAC<br>AAGACCAGCAAGACGAGCAGGCAAAAGACAAACAAGACAGAGGAGACGACGACGAACGCAAAGGACAAGA<br>GGACACAACGACGCGAGGAGCGAGAGCGAGAGGAAGAGACAACAAAAAGACACAAAAGAACAACAAGCAA<br>GCAGCGAAGAACGACACACAACCACACGAGACAGCAGGAGCAGAGGCGGAGAAAACACAACGAGCAAGCC<br>AAGACCAAGAGAGGAGAACAAAATAAAAAAATACGAGAGCAGGCGGACGAGAGCACGAGACGAACAGACA<br>AACGGGAATCAGAAGCATAACGATCCGCGACGCGAACAACN | |
| AK123010 | GTGCACCCTGTCCCAGCCGTCCTGTCCTGGCTGCTCGCTCTGCTTCGCTGCGCCTCCACTATGCTCTCCC<br>TCCGTGTCCCGCTCGCGCCCATCACGGACCCGCAGCAGCTGCAGCTCTCGCCGCTGAAGGGGCTCAGCTT<br>GGTCGACAAGGAGAACACGCCGCCGGCCCTGAGCGGGACCCGCGTCCTGGCCAGCAAGACCGCGAGGAGG<br>ATCTTCCAGGAGAAAACCCCCGCCGCTTTGTCATCTTCCCCATCGAGTACCATGATATCTGGCAGATGTA<br>TAAGAAGGCAGAGGCTTCCTTTTGGACCGCCGAGGAGGTGGACCTCTCCAAGGACATTCAGCACTGGGAA<br>TCCCTGAAACCCGAGGAGAGATATTTTATATCCCATGTTCTGGCTTTCTTTGCAGCAAGCGATGGCATAG<br>TAAATGAAAACTTGGTGGAGCGATTTAGCCAAGAAGTTCAGATTACAGAAGCCCGCTGTTTCTATGGCTT<br>CCAAATTGCCATGGAAAACATACATTCTGAAATGTATAGTCTTCTTATTGACACTTACATAAAAGATCCC<br>AAAGAAAGGGAATTTCTCTTCAATGCCATTGAAACGATGCCTTGTGTCAAGAAGAAGGCAGACTGGGCCT<br>TGCGCTGGATTGGGGACAAAGAGGCTACCTATGGTGAACGTGTTGTAGCCTTTGCTGCAGTGGAAGGCAT<br>TTTCTTTTCCGGTTCTTTTGCGTCGATATTCTGGCTCAAGAAACGAGGACTGATGCCTGGCCTCACATTT<br>TCTAATGAACTTATTAGCAGAGATGAGGGTTTACACTGTGATTTTGCTTGCCTGATGTTCAAACACCTGG<br>TACACAAACCATCGGAGGAGAGAGTAAGAGAAATAATTATCAATGCTGTTCGGATAGAACAGGAGTTCCT<br>CACTGAGGCCTTGCCTGTGAAGCTCATTGGGATGAATTGCACTCTAATGAAGCAATACATTGAGTTTGTG<br>GCAGACAGACTTATGCTGGAACTGGGTTTTAGCAAGGTTTTCAGAGTAGAGAACCCATTTGACTTTATGG<br>AGAATATTTCACTGGAAGGAAAGACTAACTTCTTTGAGAAGAGAGTAGGCGAGTATCAGAGGATGGGAGT<br>GATGTCAAGTCCAACAGAGAATTCTTTTACCTTGGATGCTGACTTCTAAATGAACTGAAGATGTGCCCTT<br>ACTTGGCTGATTTTTTTTTTTCCATCTCATAAGAAAAATCAGCTGAAGTGTTACCAACTAGCCACACCAT<br>GAATTGTCCGTAATGTTCATTAACAGCATCTTTAAAACTGTGTAGCTACCTCACAACCAGTCCTGTCTGT<br>TTATAGTGCTGGTAGTATCACCTTTTGCCAGAAGGCCTGGCTGGCTGTGACTTACCATAGCAGTGACAAT<br>GGCAGTCTTGGCTTTAAAGTGAGGGGTGACCCTTTAGTGAGCTTAGCACAGCGGGATTAAACAGTCCTTT<br>AACCAGCACAGCCAGTTAAAAGATGCAGCCTCACTGCTTCAACGCAGATTTTAATGTTTACTTAAATATA<br>AACCTGGCACTTTACAAACAAATAAACATTGTTTGTACTCACAAGGCGATAATAGCTTGATTTATTTGGT<br>TTCTACACCAAATACATTCTCCTGACCACTAATGGGAGCCAATTCACAATTCACTAAGTGACTAAAGTAA<br>GTTAAACTTGTGTAGACTAAGCATGTAATTTTTAAGTTTTATTTTAATGAATTAAAATATTTGTTAACCA<br>ACTTTAAAGTCAGTCCTGTGTATACCTAGATATTAGTCAGTTGGTGCCAGATAGAAGACAGGTTGTGTTT<br>TTATCCTGTGGCTTGTGTAGTGTCCTGGGATTCTCTGCCCCCTCTGAGTAGAGTGTTGTGGGATAAAGGA<br>ATCTCTCAGGGCAAGGAGCTTCTTAAGTTAAATCACTAGAAATTTAGGGGTGATCTGGGCCTTCATATGT<br>GTGAGAAGCCGTTTCATTTTATTTCTCACTGTATTTTCCTCAACGTCTGGTTGATGAGAAAAAATTCTTG<br>AAGAGTTTTCATATGTGGGAGCTAAGGTAGTATTGTAAAATTTCAAGTCATCCTTAAACAAAATGATCCA<br>CCTAAGATCTTGCCCCTGTTAAGTGGTGAAATCAACTAGAGGTGGTTCCTACAAGTTGTTCATTCTAGTT<br>TTGTTTGGTGTAAGTAGGTTGTGTGAGTTAATTCATTTATATTTACTATGTCTGTTAAATCAGAAATTTT<br>TTATTATCTATGTTCTTCTAGATTTTACCTGTAGTTCATACTTCAGTCACCCAGTGTCTTATTCTGGCAT<br>TGTCTAAATCTGAGCATTGTCTAGGGGGATCTTAAACTTTAGTAGGAAACCATGAGCTGTTAATACAGTT<br>TCCATTCAAATATTAATTTCAGAATGAAACATAATTTTTTTTTTTTTTTTTGAGATGGAGTCTCGCTCT<br>GTTGCCCAGGCTGGAGTGCAGTGGCGCGATTTTGGCTCACTGTAACCTCCATCTCCTGGGTTCAAGCAAT<br>TCTCCTGTCTCAGCCTCCCTAGTAGCTGGGACTGCAGGTATGTGCTACCACACCTGGCTAATTTTTGTAT<br>TTTTAGTAGAGATGGAGTTTCACCATATTGGTCAGGCTGGTCTTGAACTCCTGACCTCAGGTGATCCACC<br>CACCTCGGCCTCCCAAAGTGCTGGGATTGCAGGCGTGATAAACAAATATTCTTAATAGGGCTACTTTGAA<br>TTAATCTGCCTTTATGTTTGGGAGAAGAAAGCTGAGACATTGCATGAAAGATGATGAGAGATAAATGTTG<br>ATCTTTTGGCCCCATTTGTTAATTGTATTCAGTATTTGAACGTCGTCCTGTTTATTGTTAGTTTTCTTCA<br>TCATTTATTGTATAGACAATTTTTAAATCTCTGTAATATGATACATTTTCCTATCTTTTAAGTTATTGTT<br>ACCTAAAGTTAATCCAGATTATATGGTCCTTATATGTGTACAACATTAAAATGAAAGGCTTTGTCTTGCA<br>TTGTGAGGTACAGGCGGAAGTTGGAATCAGGTTTTAGGATTCTGTCTCTCATTAGCTGAATAATGTGAGG<br>ATTAACTTCTGCCAGCTCAGACCATTTCCTAATCAGTTGAAAGGGAAACAAGTATTTCAGTCTCAAAATT<br>GAATAATGCACAAGTCTTAAGTGATTAAAATAAAACTGTTCTTATGTCAGTTT | 147 |
| BC036503 | AGCGGGGGCACTCCAGCCCTGCAGCCTCCGGAGTCAGTGCCGCGCGCCCGCCGCCCCGCGCCTTCCTGCT<br>CGCCGCACCTCCGGGAGCCGGGGCGCACCCAGCCCGCAGCGCCGCCTCCCCGCCCGCGCCGCCTCCGACC<br>GCAGGCCGAGGGCCGCCACTGGCCGGGGGGACCGGGCAGCAGCTTGCGGCCGCGGAGCCGGGCAACGCTG<br>GGGACTGCGCCTTTTGTCCCCGGAGGTCCCTGGAAGTTTGCGGCAGGACGCGCGCGGGGAGGCGGCGGAG<br>GCAGCCCCGACGTCGCGGAGAACAGGGCGCAGAGCCGGCATGGGCATCGGGCGCAGCGAGGGGGGCCGCC<br>GCGGGGCAGCCCTGGGCGTGCTGCTGGCGCTGGGCGCGGCGCTTCTGGCCGTGGGCTCGGCCAGCGAGTA<br>CGACTACGTGAGCTTCCAGTCGGACATCGGCCCGTACCAGAGCGGGCGCTTCTACACCAAGCCACCTCAG<br>TGCGTGGACATCCCCGCGGACCTGCGGCTGTGCCACAACGTGGGCTACAAGAAGATGGTGCTGCCCAACC<br>TGCTGGAGCACGAGACCATGGCGGAGGTGAAGCAGCAGGCCAGCAGCTGGGTGCCCCTGCTCAACAAGAA<br>CTGCCACGCCGGCACCCAGGTCTTCCTCTGCTCGCTCTTCGCGCCCGTCTGCCTGGACCGGCCCATCTAC<br>CCGTGTCGCTGGCTCTGCGAGGCCGTGCGCGACTCGTGCGAGCCGGTCATGCAGTTCTTCGGCTTCTACT<br>GGCCCGAGATGCTTAAGTGTGACAAGTTCCCCGAGGGGGACGTCTGCATCGCCATGACGCCGCCCAATGC<br>CACCGAAGCCTCCAAGCCCCAAGGCACAACGGTGTGTCCTCCCTGTGACAACGAGTTGAAATCTGAGGCC<br>ATCATTGAACATCTCTGTGCCAGCGAGTTTGCACTGAGGATGAAAATAAAAGAAGTGAAAAAAGAAAATG<br>GCGACAAGAAGATTGTCCCCAAGAAGAAGAAGCCCCTGAAGTTGGGGCCCATCAAGAAGAAGGACCTGAA<br>GAAGCTTGTGCTGTACCTGAAGAATGGGGCTGACTGTCCCTGCCACCAGCTGGACAACCTCAGCCACCAC<br>TTCCTCATCATGGGCCGCAAGGTGAAGAGCCAGTACTTGCTGACGGCCATCCACAAGTGGGACAAGAAAA<br>ACAAGGAGTTCAAAAACTTCATGAAGAAAATGAAAAACCATGAGTGCCCCACCTTTCAGTCCGTGTTTAA | 148 |

TABLE 2-continued

| GENBANK ACCESSION NUMBER | SEQUENCE | SEQ ID NO: |
|---|---|---|
| | GTGATTCTCCCGGGGGCAGGGTGGGGAGGGAGCCTCGGGTGGGGTGGGAGCGGGGGGGACAGTGCCCCGG GAACCCGGTGGGTCACACACACGCACTGCGCCTGTCAGTAGTGGACATTTAATCCAGTCGGCTTGTTCTT GCAGCATTCCCGCTCCCTTCCCTCCATAGCCACGCTCCAAACCCCAGGGTAGCCATGGCCGGGTAAAGCA AGGGCCATTTAGATTAGGAAGGTTTTAAGATCCGCAATGTGGAGCAGCAGCCACTGCACAGGAGGAGGT GACAAACCATTTCCAACAGCAACACAGCCACTAAAACACAAAAAGGGGGATTGGGCGGAAAGTGAGAGCC AGCAGCAAAAACTACATTTTGCAACTTGTTGGTGTGGATCTATTGGCTGATCTATGCCTTTCAACTAGAA AATTCTAATGATTGGCAAGTCACGTTGTTTTCAGGTCCAGAGTAGTTTCTTTCTGTCTGCTTTAAATGGA AACAGACTCATACCACACTTACAATTAAGGTCAAGCCCAGAAAGTGATAAGTGCAGGGAGGAAAAGTGCA AGTCCATTATGTAATAGTGACAGCAAAGGGACCAGGGGAGAGGCATTGCCTTCTCTGCCCACAGTCTTTC CGTGTGATTGTCTTTGAATCTGAATCAGCCAGTCTCAGATGCCCCAAAGTTTCGGTTCCTATGAGCCCGG GGCATGATCTGATCCCCAAGACATGTGGAGGGGCAGCCTGTGCCTGCCTTTGTGTCAGAAAAAGGAAACC ACAGTGAGCCTGAGAGAGACGGCGATTTTCGGGCTGAGAAGGCAGTAGTTTTCAAAACACATAGTTAAAA AAGAAACAAATGAAAAAAATTTTAGAACAGTCCAGCAAATTGCTAGTCAGGGTGAATTGTGAAATTGGGT GAAGAGCTTACGATTCTAATCTCATGTTTTTTCCTTTTCACATTTTTAAAAGAACAATGACAAACACCCA CTTATTTTTCAAGGTTTTAAAACAGTCTACATTGAGCATTTGAAAGGTGTGCTAGAACAAGGTCTCCTGA TCCGTCCGAGGCTGCTTCCCAGAGGAGCAGCTCTCCCCAGGCATTTGCCAAGGGAGGCGGATTTCCCTGG TAGTGTAGCTGTGTGGCTTTCCTTCCTGAAGAGTCCGTGGTTGCCCTAGAACCTAACACCCCCCTAGCAAA ACTCACAGAGCTTTCCGTTTTTTTCTTTCCTGTAAAGAAACATTTCCTTTGAACTTGATTGCCTATGGAT CAAAGAAATTCAGAACAGCCTGCCTGTCCCCCCGCACTTTTTACATATATTTGTTTCATTTCTGCAGATG GAAAGTTGACATGGGTGGGGTGTCCCCATCCAGCGAGAGAGTTTAAAAAGCAAAACATCTCTGCAGTTTT TCCCAAGTGCCCTGAGATACTTCCCAAAGCCCTTATGTTTAATCAGCGATGTATATAAGCCAGTTCACTT AGACAACTTTACCCTTCTTGTCCAATGTACAGGAAGTAGTTCTAAAAAAAATGCATATTAATTTCTTCCC CCAAAGCCGGATTCTTAATTCTCTGCAACACTTTGAGGACATTTATGATTGTCCCTCTGGGCCAATGCTT ATACCCAGTGAGGATGCTGCAGTGAGGCTGTAAAGTGGCCCCCTGCGGCCCTAGCCTGACCCGGAGGAAA GGATGGTAGATTCTGTTAACTCTTGAAGACTCCAGTATGAAAATCAGCATGCCCGCCTAGTTACCTACCG GAGAGTTATCCTGATAAATTAACCTCTCACAGTTAGTGATCCTGTCCTTTTAACACCTTTTTTGTGGGGT TCTCTCTGACCTTTCATCGTAAAGTGCTGGGGACCTTAAGTGATTTGCCTGTAATTTTGGATGATTAAAA AATGTGTATATATATTAGCTAATTAGAAATATTCTACTTCTCTGTTGTCAAACTGAAATTCAGAGCAAGT TCCTGAGTGCGTGGATCTGGGTCTTAGTTCTGGTTGATTCACTCAAGAGTTCAGTGCTCATACGTATCTG CTCATTTTGACAAAGTGCCTCATGCAACCGGGCCCTCTCTCTGCGGCAGAGTCCTTAGTGGAGGGGTTTA CCTGGAACATTAGTAGTTACCACAGAATACGGAAGAGCAGGTGACTGTGCTGTGCAGCTCTCTAAATGGG AATTCTCAGGTAGGAAGCAACAGCTTCAGAAAGAGCTCAAAATAAATTGGAAATGTGAATCGCAGCTGTG GGTTTTACCACCGTCTGTCTCAGAGTCCCAGGACCTTGAGTGTCATTAGTTACTTTATTGAAGGTTTTAG ACCCATAGCAGCTTTGTCTCTGTCACATCAGCAATTTCAGAACCAAAAGGGAGGCTCTCTGTAGGCACAG AGCTGCACTATCACGAGCCTTTGTTTTTCTCCACAAAGTATCTAACAAAACCAATGTGCAGACTGATTGG CCTGGTCATTGGTCTCCGAGAGAGGAGGTTTGCCTGTGATTTCCTAATTATCGCTAGGGCCAAGGTGGGA TTTGTAAAGCTTTACAATAATCATTCTGGATAGAGTCCTGGGAGGTCCTTGGCAGAACTCAGTTAAATCT TTGAAGAATATTTGTAGTTATCTTAGAAGATAGCATGGGAGGTGAGGATTCCAAAAACATTTTATTTTTA AAATATCCTGTGTAACACTTGGCTCTTGGTACCTGTGGGTTAGCATCAAGTTCTCCCCAGGGTAGAATTC AATCAGAGCTCCAGTTTGCATTTGGATGTGTAAATTACAGTAATCCCATTTCCCAAACCTAAAATCTGTT TTTCTCATCAGACTCTGAGTAACTGGTTGCTGTGTCATAACTTCATAGATGCAGGAGGCTCAGGTGATCT GTTTGAGCAGAGCACCCTAGGCAGCCTGCAGGGAATAACATACTGGCCGTTCTGACCTGTTGCCAGCAGA TACACAGGACATGGATGAAATTCCCGTTTCCTCTAGTTTCTTCCTGTAGTACTCCTCTTTTAGATCCTAA GTCTCTTACAAAAGCTTTGAATACTGTGAAAATGTTTTACATTCCATTTCATTTGTGTTGTTTTTTTAAC TGCATTTTACCAGATGTTTTGATGTTATCGCTTATGTTAATAGTAATTCCCGTACGTGTTCATTTTATTT TCATGCTTTTTCAGCCATGTATCAATATTCACTTGACTAAAATCACTCAATTAATCAAAAAAAAAAAAAA AA | |
| NM_012319 | AGTCCTGGGCGAAGGGGGCGGTGGTTCCCCGCGGCGCTGCGCGCGGCGGTAATTAGTGATTGTCTTCCAG CTTCGCGAAGGCTAGGGGCGCGGCTGCCGGGTGGCTGCGCGGCGCTGCCCCCGGACCGAGGGGCAGCCAA CCCAATGAAACCACCGCGTGTTCGCGCCTGGTAGAGATTTCTCGAAGACACCAGTGGGCCCGTTCCGAGC CCTCTGGACCGCCCGTGTGGAACCAAACCTGCGCGCGTGGCCGGGCCGTGGGACAACGAGGCCGCGGAGA CGAAGGCGCAATGGCGAGGAAGTTATCTGTAATCTTGATCCTGACCTTTGCCCTCTCTGTCACAAATCCC CTTCATGAACTAAAAGCAGCTGCTTTCCCCCAGACCACTGAGAAAATTAGTCCGAATTGGGAATCTGGCA TTAATGTTGACTTGGCAATTTCCACACGGCAATATCATCTACAACAGCTTTTCTACCGCTATGGAGAAAA TAATTCTTTGTCAGTTGAAGGGTTCAGAAAATTACTTCAAAATATAGGCATAGATAAGATTAAAAGAATC CATATACACCATGACCACGACCATCACTCAGACCACGAGCATCACTCAGACCATGAGCGTCACTCAGACC ATGAGCATCACTCAGACCACGAGCATCACTCTGACCATGATCATCACTCTCACCATAATCATGCTGCTTC TGGTAAAAATAAGCGAAAAGCTCTTTGCCCAGACCATGACTCAGATAGTTCAGGTAAAGATCCTAGAAAC AGCCAGGGGAAAGGAGCTCACCGACCAGAACATGCCAGTGGTAGAAGGAATGTCAAGGACAGTGTTAGTG CTAGTGAAGTGACCTCAACTGTGTACAACACTGTCTCTGAAGGAACTCACTTTCTAGAGACAATAGAGAC TCCAAGACCTGGAAAACTCTTCCCCAAAGATGTAAGCAGCTCCACTCCACCCAGTGTCACATCAAAGAGC CGGGTGAGCCGGCTGGCTGGTAGGAAAACAAATGAATCTGTGAGTGAGCCCCGAAAAGGCTTTATGTATT CCAGAAACACAAATGAAAATCCTCAGGAGTGTTTCAATGCATCAAAGCTACTGACATCTCATGGCATGGG CATCCAGGTTCCGCTGAATGCAACAGAGTTCAACTATCTCTGTCCAGCCATCATCAACCAAATTGATGCT AGATCTTGTCTGATTCATACAAGTGAAAAGAAGGCTGAAATCCCTCCAAAGACCTATTCATTACAAATAG CCTGGGTTGGTGGTTTTATAGCCATTTCCATCATCAGTTTCCTGTCTCTGCTGGGGGTTATCTTAGTGCC TCTCATGAATCGGGTGTTTTTCAAATTTCTCCTGAGTTTCCTTGTGGCACTGGCCGTTGGGACTTTGAGT GGTGATGCTTTTTTACACCTTCTTCCACATTCTCATGCAAGTCACCACCATAGTCATAGCCATGAAGAAC CAGCAATGGAAATGAAAAGAGGACCACTTTTCAGTCATCTGTCTTCTCAAAACATAGAAGAAAGTGCCTA TTTTGATTCCACGTGGAAGGGTCTAACAGCTCTAGGAGGCCTGTATTTCATGTTTCTTGTTGAACATGTC CTCACATTGATCAAACAATTTAAAGATAAGAAGAAAAAGAATCAGAAGAAACCTGAAAATGATGATGATG TGGAGATTAAGAAGCAGTTGTCCAAGTATGAATCTCAACTTTCAACAAATGAGGAGAAAGTAGATACAGA TGATCGAACTGAAGGCTATTTACGAGCAGACTCACAAGAGCCCTCCCACTTTGATTCTCAGCAGCCTGCA GTCTTGGAAGAAGAAGAGGTCATGATAGCTCATGCTCATCCACAGGAAGTCTACAATGAATATGTACCCA GAGGGTGCAAGAATAAATGCCATTCACATTTCCACGATACACTCGGCCAGTCAGACGATCTCATTCACCA | 149 |

TABLE 2-continued

| GENBANK ACCESSION NUMBER | SEQUENCE | SEQ ID NO: |
|---|---|---|
| | CCATCATGACTACCATCATATTCTCCATCATCACCACCACCAAAACCACCATCCTCACAGTCACAGCCAG<br>CGCTACTCTCGGGAGGAGCTGAAAGATGCCGGCGTCGCCACTCTGGCCTGGATGGTGATAATGGGTGATG<br>GCCTGCACAATTTCAGCGATGGCCTAGCAATTGGTGCTGCTTTTACTGAAGGCTTATCAAGTGGTTTAAG<br>TACTTCTGTTGCTGTGTTCTGTCATGAGTTGCCTCATGAATTAGGTGACTTTGCTGTTCTACTAAAGGCT<br>GGCATGACCGTTAAGCAGGCTGTCCTTTATAATGCATTGTCAGCCATGCTGGCGTATCTTGGAATGGCAA<br>CAGGAATTTTCATTGGTCATTATGCTGAAAATGTTTCTATGTGGATATTTGCACTTACTGCTGGCTTATT<br>CATGTATGTTGCTCTGGTTGATATGGTACCTGAAATGCTGCACAATGATGCTAGTGACCATGGATGTAGC<br>CGCTGGGGGTATTTCTTTTTACAGAATGCTGGGATGCTTTTGGGTTTTGGAATTATGTTACTTATTTCCA<br>TATTTGAACATAAAATCGTGTTTCGTATAAATTTCTAGTTAAGGTTTAAATGCTAGAGTAGCTTAAAAAG<br>TTGTCATAGTTTCAGTAGGTCATAGGGAGATGAGTTTGTATGCTGTACTATGCAGCGTTTAAAGTTAGTG<br>GGTTTTGTGATTTTTGTATTGAATATTGCTGTCTGTTACAAAGTCAGTTAAAGGTACGTTTTAATATTTA<br>AGTTATTCTATCTTGGAGATAAAATCTGTATGTGCAATTCACCGGTATTACCAGTTTATTATGTAAACAA<br>GAGATTTGGCATGACATGTTCTGTATGTTTCAGGGAAAAATGTCTTTAATGCTTTTTCAAGAACTAACAC<br>AGTTATTCCTATACTGGATTTTAGGTCTCTGAAGAACTGCTGGTGTTTAGGAATAAGAATGTGCATGAAG<br>CCTAAAATACCAAGAAAGCTTATACTGAATTTAAGCAAAGAAATAAAGGAGAAAAGAGAAGAATCTGAGA<br>ATTGGGGAGGCATAGATTCTTATAAAAATCACAAAATTTGTTGTAAATTAGAGGGGAGAAATTTAGAATT<br>AAGTATAAAAAGGCAGAATTAGTATAGAGTACATTCATTAAACATTTTTGTCAGGATTATTTCCCGTAAA<br>AACGTAGTGAGCACTTTTCATATACTAATTTAGTTGTACATTTAACTTTGTATAATACAGAAATCTAAAT<br>ATATTTAATGAATTCAAGCAATATATCACTTGACCAAGAAATTGGAATTTCAAAATGTTCGTGCGGGTAT<br>ATACCAGATGAGTACAGTGAGTAGTTTTATGTATCACCAGACTGGGTTATTGCCAAGTTATATATCACCA<br>AAAGCTGTATGACTGGATGTTCTGGTTACCTGGTTTACAAAATTATCAGAGTAGTAAAACTTTGATATAT<br>ATGAGGATATTAAAACTACACTAAGTATCATTTGATTCGATTCAGAAAGTACTTTGATATCTCTCAGTGC<br>TTCAGTGCTATCATTGTGAGCAATTGTCTTTTATATACGGTACTGTAGCCATACTAGGCCTGTCTGTGGC<br>ATTCTCTAGATGTTTCTTTTTTACACAATAAATTCCTTATATCAGCTTGAAAAAAAAAAAAAAAAAA | |
| AK098106 | AACGCACTTGGCGCGCGGCGCGGGCTGCAGACGGCTGCGAGGCGCTGGGCACAGGTGTCCTGATGGCAAA<br>TTTCAAGGGCCACGCGCTTCCAGGGAGTTTCTTCCTGATCATTGGGCTGTGTTGGTCAGTGAAGTACCCG<br>CTGAAGTACTTTAGCCACACGCGGAAGAACAGCCCACTACATTACTATCAGCGTCTCGAGATCGTCGAAG<br>CCGCAATTAGGACTTTGTTTTCCGTCACTGGGATCCTGGCAGAGCAGTTTGTTCCGGATGGGCCCCACCT<br>GCACCTCTACCATGAGAACCACTGGATAAAGTTAATGAATTGGCAGCACAGCACCATGTACCTATTCTTT<br>GCAGTCTCAGGAATTGTTGACATGCTCACCTATCTGGTCAGCCACGTTCCCTTGGGGGTGGACAGACTGG<br>TTATGGCTGTGGCAGTATTCATGGAAGGTTTCCTCTTCTACTACCACGTCCACAACCGGCCTCCGCTGGA<br>CCAGCACATCCACTCACTCCTGCTGTATGCTCTGTTCGGAGGGTGTGTTAGTATCTCCCTAGAGGTGATC<br>TTCCGGGACCACATTGTGCTGGAACTTTTCCGAACCAGTCTCATCATTCTTCAGGGAACCTGGTTCTGGC<br>AGATTGGGTTTGTGCTGTTCCCACCTTTTGGAACACCCGAATGGGACCAGAAGGATGATGCCAACCTCAT<br>GTTCATCACCATGTGCTTCTGCTGGCACTACCTGGCTGCCCTCAGCATTGTGGCCGTCAACTATTCTCTT<br>GTTTACTGCCTTTTGACTCGGATGAAGAGACACGGAAGGGGAGAAATCATTGGAATTCAGAAGCTGAATT<br>CAGATGACACTTACCAGACCGCCCTCTTGAGTGGCTCAGATGAGGAATGAGCCGAGATGCGGAGGGCGCA<br>GATGTCCCACTGCACAGCTGGAATGAATGGAGTTCATCCCCTCCACCTGAATGCCTGCTGTGGTCTGATC<br>TTAAGGGTCTATATATTTGCACCTCCTCATTCAACACAGGGCTGGAGGTTCTACAACAGGAAATCAGGCC<br>TACAGCATCCTGTGTATCTTGCAGTTGGGATTTTTAAACATACTATAAAGTCTGTGTTGGTATAGTACCC<br>TTCATAAGGAAAAATGAAGTAATGCCTATAAGTAGCAGGCCTTTGTGCCTCAGTGTCAAGAGAAATCAAG<br>AGATGCTAAAAGCTTTACAATGGAAGTGGCCTCATGGATGAATCCGGGGTATGAGCCCAGGAGAACGTGC<br>TGCTTTTGGTAACTTATCCCTTTTTCTCTTAAGAAAGCAGGTACTTTCTTATTAGAAATATGTTAGAATG<br>TGTAAGCAAACGACAGTGCCTTTAGAATTACAATTCTAACTTACATATTTTTTGAAAGTAAAATAATTCA<br>CAAGCTTTGGTATTTTAAAATTATTGTTAAACATATCATAACTAATCATACCAGGGTACTGCAATACCAC<br>TGTTTATAAGTGACAAAATTAGGCCAAAGGTGATTTTTTTTTAAATCAGGAAGCTGGTTACTGGCTCTAC<br>TGAGAGTTGGAGCCCTGATGTTCTGATTCTTCAAAGTCACCCTAAAAGAAGATCTGACAGGAAAGCTGTA<br>TAATGAGATAGAAAAACGTCAGGTATGGAAGGCTTTCAGTTTTAATATGGCTGAAAGCAAAGGATAACGA<br>ATTCAGAATTAGTAATGTAAAATCTTGATACCCTAATCTTGCTTCTGGATCTGTTCTTTTTTTAAAAAAA<br>CTTCCTTCACCGCGCCTATAATCCTAGCACTTTGGGAGGCCGAGGCAGGCAGATCACGGGGTCAGGAGAT<br>CAAGACCATCCTGGCTAACATGGTGAAACCCCGTCTCTACTGAAAATACAAAAAATTAGCCGGGTGTGGT<br>GGCGGGCGCCTGTAGTTCCAGCTACTCGGGAGGCTGAGGCAAGAGAATGGCATGAACCCGGTAGGGGAGC<br>TTGCAGTGAGCCCAGATCATGCCACTGTACTCCAGCCTAGGTGACAGAGCAAGACTCTGTCTCAAAAACA<br>AGCAAACAGACTTCCTTCAACAAATATTTATTAAATATCCACTTTGCAACAGCACTGAAATGGCTGTAAG<br>GACTCCTGAGATATGTGTCCAGCAAGGAGTTTACAGTCAAACAGGAGAGACATGCCTGTAGTTACATCCA<br>GTGTGATGGGTGCTGAGAGGCAAGTACAAACCACGATG | 150 |
| BQ056428 | TCCCGCCGCGCCACTTCGCCTGCCTCCGTCCCCCGCCCGCCGCGCCATGCCTGTGGCCGGCTCGGAGCTG<br>CCGCGCCGGCCCTTGCCCCCCGCCGCACAGGAGCGGGACGCCGAGCCGCGTCCGCCGCACGGGGAGCTGC<br>AGTACCTGGGGCAGATCCAACACATCCTCCGCTGCGGCGTCAGGAAGGACGCCCGCCCGGGCACCGGTAC<br>CCTGCCGGTATTCGGCATGCAGGCGCGCTACAGCCTGAGAGATGAATTCCCTCTGCTGACAACCAAACGT<br>GTGTTCTGGAACGGTGCTTCGGAGGAGCTGCTGTGGCTTATCAAGGGATCCACAAACGCTATAGACCTGT<br>CTTCCCCGGCAGCGAAAATCTCGGGATGCCACTGGATCCCGACACTCTCTGGACACCCTGGGATTCTCCA<br>CCAGAGAAGAACGCGACTTGGGCCCAGTTTGTGGCTCTCAGCGGAGGCCTCCTGTGGCAGAATACATACA<br>TTTCCAATCAGATCACTTCCCGGACACGGACCNTGACCAGCCTGCCAAAAAGTGGATTTCCCCCCACCCC<br>AGAACCCANCCCCTGACGCACAGAAACCAACCCATTCGTTGTTGCCGCCTTGCGAACCCCAACCAGAATC<br>TCTCCCCCCTGGCCGGCGCGCCTGCCGCTGCCAATGCCCCTATGGCGGCCTCTTGGCCCGCACCTTCCAA<br>TTGGTCGCCCTGCGCAACCAGCGAGAAAACACTGGCCCGCCCGTCTCCCCCCCGCTCCGCCTACCCCACT<br>TAATGCGCCTCCGTGGCATGACGCACGCGTTTGGTGTCCGCCGCCGTCTCATGTCCGCGCGGTGTGGACC<br>CCCTTTTCTCTCGCGGCACATCCCCCCTATTCCCTTGCCCTTTGGGGGGCACCCCCTCTAGACCCGCGCT<br>TCTCTTCTCGTCCGGTGGGGGACATTGGTTTGCCTGCCGCGGCGGGGGCGNTAAAAATAAAAACAGCCTG<br>TTAGCCCGGCCCAGTACCCCCCCCCGGCCGGGGCCGCCTTNCGTTTGCATTTATACCCCAACCCATAAAG<br>CCGCGCCCCTTTAGCNCCNTAACTTTTGTGGTGTGGCCTCCCCCCTTTTTCCCGGGGAGCAGCAACGGAC<br>ATCTGTACACTAATGCTGGCCCCGACCTTTCCCAAAAACCCCCCGCCCGTGTCCCGTATAAATTTGGTGC<br>CAANCCTGACGNGTTCTCCCCCGCCCTCGCCCCGTTGGCCGCCCGTTTAAAGCCCCCCCGGTGGTTGCGC | 151 |

TABLE 2-continued

| GENBANK ACCESSION NUMBER | SEQUENCE | SEQ ID NO: |
|---|---|---|
| | CGCCCAACGAGTCCACCTATAGTTAANTCCACCAACACCCCCACCTTTTCCTCCCCGCCGCATCTTCCCC<br>ACGTACCCCCTTTTGTCGCGAGATGGCCACTCCCCCCCCCCTGTTTGTTTAAAACAACGAGAATGGTGCT<br>GCCAACGCTGGTCTTTTCCCCCCCCGGACCGCGACCGCCAGGGGGAATACGTACCATAAGCCCCCGCGCC<br>CNCCTTTTTTCCCCCCTCCCCGCCAATCAAGATCCGCCGTCCATTAGACGTATTATTTTTCCCGCGATAC<br>ACGAAAAAACAGGGCCGCCCATTTATAACTAAATTCCCGTCGCCGCCGCGCGGATATGTTTCCCAAAATA<br>CCACCCCCCCCCCCCATTTTCTTTGCCCCCAACTCCTGCGCACCGGTGTTCACCAGCCTCGCGCCGC | |
| BC032677 | GGACGCGTGGGTCGACCCACGCGTCCGGACCCACGCGTCCGGTCGTGTTCTCCGAGTTCCTGTCTCTCTG<br>CCAACGCCGCCCGGATGGCTTCCCAAAACCGCGACCCAGCCGCCACTAGCGTCGCCGCCGCCCGTAAAGG<br>AGCTGAGCCGAGCGGGGGCGCCGCCCGGGGTCCGGTGGGCAAAAGGCTACAGCAGGAGCTGATGACCCTC<br>ATGGTGAGTGATTAAGTGCCCAGAACCCCAGCCTTCCATCCAATTTTCAGTAGCCTCCTTTTTTCCGTCA<br>GCTTTTTTGCTAGACATAGGGGTAATGTAATTTGCTCCCTCCTGGGAAAGAAGTTCATACACCCCACCTA<br>CACCATTTCTTCCAGCAGTCCCTCCTCCCAATTCCATCCCCCCACACGAAGTTATCTCGAACACTTCCCT<br>GAAGTCATACAAGACCCTCCCTATCCAGTGTGTCCCTACTTCCTAGCCCCAACCAAGCTTTACCCACACC<br>CAACTCCCCGCCCTTCTTGGTATTTCTAGCCTATGAATTTGGTTGCTTTATTTTGGATCAGAGTGATGAG<br>ATTAAGGGGAGGCTGGGCGCGGTAGCTCACACCTTATAATCCCAAAGTGCTGGGATTACAGGCGTGAGCC<br>ACCGCGCCCGGCCAGCAACTAATATTCTAATTGAACTAAAGCACAGGATGCCAATTTACAATCCTTAGAC<br>CAAAGAGTCACTGATGTCTCCACCAGATAAGAGGAAAGCATCAGGCTAGGCATAGTGGCTCACACCTGTA<br>ATCTCAGCACTTTGGGAGGCTGAGGCAGGCAGATCACATGAGCCCAGGAGTTTGAGACTGGCCTGGGCAA<br>CATGGTGAAACCCTGTCTCTAAAATAAAAACTAAACTAAAAAAACTTTTTAAAAAGGCAGTGGGGAGCAT<br>CAGAACCAGCTCAACAGTTTGTCTACTGTCCGGTCCCAGAGAAACTCAAGATTCTAGCAAGCCCCTTGTG<br>TGGGGCTTGGGTTGGGACATGAGGCTGCTGCTGGAGCTTACTCTGCAACTGTTTCTCCAAATGCCAGGTA<br>TATGAAGACCTGAGGTATAAGCTCTCGCTAGAGTTCCCCAGTGGCTACCCTTACAATGCGCCCACAGTGA<br>AGTTCCTCACGCCCTGCTATCACCCCAACGTGGACACCCAGGGTAACATATGCCTGGACATCCTGAAGGA<br>AAAGTGGTCTGCCCTGTATGATGTCAGGACCATTCTGCTCTCCATCCAGAGCCTTCTAGGAGAACCCAAC<br>ATTGATAGTCCCTTGAACACACATGCTGCCGAGCTCTGGAAAAACCCCACAGCTTTTAAGAAGTACCTGC<br>AAGAAACCTACTCAAAGCAGGTCACCAGCCAGGAGCCCTGACCCAGGCTGCCCAGCCTGTCCTTGTGTCG<br>TCTTTTTAATTTTTCCTTAGATGGTCTGTCCTTTTTGTGATTTCTGTATAGGACTCTTTATCTTGAGCTG<br>TGGTATTTTTGTTTTGTTTTTGTCTTTTAAATTAAGCCTCGGTTGAGCCCTTGTATATTAAATAAATGCA<br>TTTTTGTCCTTTTTTAAAAAAAAAATAAAAAAAAAAAAAAAAAAAAAAAAAAAAAAAAAAAAAAAAAAAA<br>A | 152 |

FISH analysis or IHC was also performed on samples from patients to classify breast cancers. Samples that showed an amplification ratio of greater than 2.0 for Her2 were classified at Her2+. Because of the multitude of sources of specimens with a wide range of fixatives and processing techniques, a "subtraction scoring" was used. (See Yaziji et al. JAMA 291 (16):1972-1977 (April 2004)). Using this method any visible signal of the non-neoplastic breast epithelium is counted as negative and subtracts the score of the tumor cells from that of the benign cells. When the subtraction score is 2+, the cells were classified as Her2+.

Subjects with breast cancer tumors that fit in the Her-2-E subtype, classified by intrinsic gene analysis, were surprisingly found to have a better prognosis on average when treated with a breast cancer treatment that included an anthracycline. Other subtypes showed no significant difference in prognosis between breast cancer treatment with or without an anthracycline. Subjects that were shown to be Her2+ using FISH analysis or IHC also surprisingly had a better prognosis on average when treated with a breast cancer treatment that includes an anthracycline.

What was also found was that not all tumors classified as Her-2-E were also Her2+. Among samples from patients who were Her-2-E expression subtype but clinical Her2-, there was no significant improvement in prognosis, on average, when subjects were treated with an anthracycline. However, among subjects who had tumors that were both Her-2-E and Her2+, treatment with anthracyclines did show a better prognosis on average. Differentiating the clinical outcome in breast cancer patients with Her-2-E/Her2- cancers from Her-2-E/Her2+ cancers administered a breast cancer treatment including anthracycline when this treatment would not provide increased therapeutic efficacy and be accompanied by worse side effects, improves the clinical outcome and quality of life of thousands of patients.

Definitions

For the purposes of the present disclosure, "breast cancer" includes, for example, those conditions classified by biopsy or histology as malignant pathology. The clinical delineation of breast cancer diagnoses is well known in the medical arts. One of skill in the art will appreciate that breast cancer refers to any malignancy of the breast tissue, including, for example, carcinomas and sarcomas. Particular embodiments of breast cancer include ductal carcinoma in situ (DCIS), lobular carcinoma in situ (LCIS), or mucinous carcinoma. Breast cancer also refers to infiltrating ductal (IDC), lobular neoplasia or infiltrating lobular carcinoma (ILC). In most embodiments of the disclosure, the subject of interest is a human patient suspected of or actually diagnosed with breast cancer.

Breast cancer includes all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructual heterogeneity (e.g., mixed cell types).

A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject.

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

For the purposes of the present disclosure, "anthracyclines" are a class of drugs used in cancer chemotherapy derived from *Streptomyces* bacteria. These drugs are used to treat a wide variety of cancers including breast cancer. However, this class of drugs is extremely toxic and produces significant deleterious side effects including heart damage and vomiting. Anthracyclines include daunorubicin, doxorubicin, epirubicin, idarubicin, valrubicin and mitoxantrone.

For the purposes of the present disclosure, "a breast cancer treatment comprising anthracycline" is a breast cancer treatment that includes an anthracyclines. These treatments can also include other anti-cancer or chemotherapeutic agents.

For the purposes of the present disclosure, "a breast cancer treatment not comprising anthracycline" is a breast cancer treatment that does not include any anthracycline. These treatments contain other anti-cancer or chemotherapeutic agents.

Classes of anti-cancer or chemotherapeutic agents can include alkylating agents, platinum agents, taxanes, vinca agents, anti-estrogen drugs, aromatase inhibitors, ovarian suppression agents, endocrine/hormonal agents, bisphosphonate therapy agents and targeted biological therapy agents.

Specific anti-cancer or chemotherapeutic agents can include cyclophosphamide, fluorouracil (or 5-fluorouracil or 5-FU), methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb or bevacizumab, or combinations thereof Combinational anti-cancer or chemotherapeutic therapies can include AT: Adriamycin® (Doxorubicin) and Taxotere® (Docetaxel); AC: Adriamycin®, Cytoxan® (Cyclophosphamide); AC+Taxol®; AC+Taxotere®; CMF: Cytoxan®, Methotrexate, 5-fluorouracil; CEF: Cytoxan®, Ellence® (Epirubicin), and fluorouracil; EC: Ellence®, Cytoxan®; FAC: 5-fluorouracil, Adriamycin®, and Cytoxan®; GET: Gemzar® (Gemcitabine), Ellence®, and Taxol®; TC: Taxotere®, Cytoxan®; TC: Taxotere®, Paraplatin® (Carboplatin); TAC: Taxotere®, Adriamycin®, Cytoxan® or TCH: Taxotere®, Herceptin® (Trastuzumab), and Paraplatin®. Additional combination chemotherapeutic therapies for metastatic breast cancer can include: Taxol and Xeloda® (Capecitabine); Taxotere and Xeloda®; Taxotere and Paraplatin®; Taxol® and Paraplatin®; Taxol® and Gemzar®; Abraxane® (Protein-bound Paclitaxel) and Xeloda®; Abraxane® and Paraplatin®; Camptosor® (Irinotecan) and Temodar® (Temozolomide); Gemzar® and Paraplatin® or Ixempra® (Ixabepilone) and Xeloda®

Preferably, the anti-cancer or chemotherapeutic agents include cyclophosphamide and 5-fluorouracil or include methotrexate, cyclophosphamide and 5-fluorouracil.

One or more anthracyclines can be administered in the breast cancer treatments described herein. Preferably anthracyclines are administered intravenously, but can be administered by any method known in the art. Anthracyclines can be administered at dosages from 10 mg/m$^2$ to 300 mg/m$^2$ per week. Anthracyclines can be administered at 20-200 mg/m$^2$, 30-100 mg/m$^2$, or 35-75 mg/m$^2$ per week. Preferably, the anthracycline is administered at about 60 mg/m2 per week.

Preferably methotrexate is administered intravenously, but can be administered by any method known in the art. Methotrexate can be administered between 1 mg/m2 and 500 mg/m2. Methotrexate can be administered at 10-200 mg/m$^2$, 20-100 mg/m$^2$ or 30-60 mg/m$^2$ per week. Preferably, methotrexate is administered at about 40 mg/m$^2$ per week.

Preferably 5-fluorouracil is administered intravenously, but can be administered by any method known in the art. 5-fluorouracil can be administered at dosages from 25 mg/m$^2$ to 1000 mg/m$^2$ per week. 5-fluorouracil can be administered at 50-900 mg/m$^2$, 100-800 mg/m$^2$, 300-700 mg/m$^2$ or 450-650 mg/m$^2$ per week. Preferably, 5-fluorouracil is administered at about 500 mg/m$^2$ per week.

Preferably cyclophosphamide is administered orally, but can be administered by any method known in the art. Cyclophosphamide can be administered at dosages from 10 mg/m$^2$ to 300 mg/m$^2$ per day. Cyclophosphamide can be administered at 20-200 mg/m$^2$, 30-100 mg/m$^2$, or 40-80 mg/m$^2$ per day. Preferably, cyclophosphamide is administered at about 75 mg/m$^2$ per day.

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Clinical Variables

The PAM50 classification model described herein may be further combined with information on clinical variables to generate a continuous risk of relapse (ROR) predictor. As described herein, a number of clinical and prognostic breast cancer factors are known in the art and are used to predict treatment outcome and the likelihood of disease recurrence.

Such factors include, for example, lymph node involvement, tumor size, histologic grade, estrogen and progesterone hormone receptor status, HER-2 levels, and tumor ploidy. In one embodiment, risk of relapse (ROR) score is provided for a subject diagnosed with or suspected of having breast cancer. This score uses the PAM50 classification model in combination with clinical factors of lymph node status (N) and tumor size (T). Assessment of clinical variables is based on the American Joint Committee on Cancer (AJCC) standardized system for breast cancer staging. In this system, primary tumor size is categorized on a scale of 0-4 (TO: no evidence of primary tumor; T1: <2 cm; T2: >2 cm-<5 cm; T3: >5 cm; T4: tumor of any size with direct spread to chest wall or skin). Lymph node status is classified as N0-N3 (NO: regional lymph nodes are free of metastasis; N1: metastasis to movable, same-side axillary lymph node(s); N2: metastasis to same-side lymph node(s) fixed to one another or to other structures; N3: metastasis to same-side lymph nodes beneath the breastbone). Methods of identifying breast cancer patients and staging the disease are well known and may include manual examination, biopsy, review of patient's and/or family history, and imaging techniques, such as mammography, magnetic resonance imaging (MRI), and positron emission tomography (PET).

Sample Source

In one embodiment of the present disclosure, breast cancer subtype is assessed through the evaluation of expression patterns, or profiles, of the intrinsic genes listed in Table 1 in one or more subject samples and/or FISH analysis or IHC performed to ascertain the Her-2 status of the cancer. For the purpose of discussion, the term subject, or subject sample, refers to an individual regardless of health and/or disease status. A subject can be a subject, a study participant, a control subject, a screening subject, or any other class of individual from whom a sample is obtained and assessed in the context of the disclosure. Accordingly, a subject can be diagnosed with breast cancer, can present with one or more symptoms of breast cancer, or a predisposing factor, such as a family (genetic) or medical history (medical) factor, for breast cancer, can be undergoing treatment or therapy for breast cancer, or the like. As such, the subject is a subject in need of treatment for breast cancer or detection of breast cancer. Alternatively, a subject can be healthy with respect to any of the aforementioned factors or criteria. It will be appreciated that the term "healthy" as used herein, is relative to breast cancer status, as the term "healthy" cannot be defined to correspond to any absolute evaluation or status. Thus, an individual defined as healthy with reference to any specified disease or disease criterion, can in fact be diagnosed with any other one or more diseases, or exhibit any other one or more disease criterion, including one or more cancers other than breast cancer. However, the healthy controls are preferably free of any cancer.

As used herein, a "subject in need thereof" is a subject having breast cancer or presenting with one or more symptoms of breast cancer, or a subject having an increased risk of developing breast cancer relative to the population at large. Preferably, a subject in need thereof has breast cancer. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

In particular embodiments, the methods for predicting breast cancer intrinsic subtypes or Her-2 status include collecting a biological sample comprising a cancer cell or tissue, such as a breast tissue sample or a primary breast tumor tissue sample. By "biological sample" is intended any sampling of cells, tissues, or bodily fluids in which expression of an intrinsic gene can be detected. Examples of such biological samples include, but are not limited to, biopsies and smears. Bodily fluids useful in the present disclosure include blood, lymph, urine, saliva, nipple aspirates, gynecological fluids, or any other bodily secretion or derivative thereof. Blood can include whole blood, plasma, serum, or any derivative of blood. In some embodiments, the biological sample includes breast cells, particularly breast tissue from a biopsy, such as a breast tumor tissue sample. Biological samples may be obtained from a subject by a variety of techniques including, for example, by scraping or swabbing an area, by using a needle to aspirate cells or bodily fluids, or by removing a tissue sample (i.e., biopsy). Methods for collecting various biological samples are well known in the art. In some embodiments, a breast tissue sample is obtained by, for example, fine needle aspiration biopsy, core needle biopsy, or excisional biopsy. Fixative and staining solutions may be applied to the cells or tissues for preserving the specimen and for facilitating examination. Biological samples, particularly breast tissue samples, may be transferred to a glass slide for viewing under magnification. In one embodiment, the biological sample is a formalin-fixed, paraffin-embedded breast tissue sample, particularly a primary breast tumor sample. In various embodiments, the tissue sample is obtained from a pathologist-guided tissue core sample.

Expression Profiling

In various embodiments, the present disclosure provides methods for classifying, prognosticating, or monitoring breast cancer in subjects. In this embodiment, data obtained from analysis of intrinsic gene expression is evaluated using one or more pattern recognition algorithms. Such analysis methods may be used to form a predictive model, which can be used to classify test data. For example, one convenient and particularly effective method of classification employs multivariate statistical analysis modeling, first to form a model (a "predictive mathematical model") using data ("modeling data") from samples of known subtype (e.g., from subjects known to have a particular breast cancer intrinsic subtype: LumA, LumB, Basal-like, HER2-enriched, or normal-like), and second to classify an unknown sample (e.g., "test sample") according to subtype. Pattern recognition methods have been used widely to characterize many different types of problems ranging, for example, over linguistics, fingerprinting, chemistry and psychology. In the context of the methods described herein, pattern recognition is the use of multivariate statistics, both parametric and non-parametric, to analyze data, and hence to classify samples and to predict the value of some dependent variable based on a range of observed measurements. There are two main approaches. One set of methods is termed "unsupervised" and these simply reduce data complexity in a rational way and also produce display plots which can be interpreted by the human eye. However, this type of approach may not be suitable for developing a clinical assay that can be used to classify samples derived from subjects independent of the initial sample population used to train the prediction algorithm.

The other approach is termed "supervised" whereby a training set of samples with known class or outcome is used to produce a mathematical model which is then evaluated with independent validation data sets. Here, a "training set" of intrinsic gene expression data is used to construct a statistical model that predicts correctly the "subtype" of each sample. This training set is then tested with independent data (referred to as a test or validation set) to determine the robustness of the computer-based model. These models are sometimes termed "expert systems," but may be based on a range of different mathematical procedures. Supervised methods can use a data set with reduced dimensionality (for example, the first few principal components), but typically use unreduced data, with all dimensionality. In all cases the methods allow the quantitative description of the multivariate boundaries that characterize and separate each subtype in terms of its intrinsic gene expression profile. It is also possible to obtain confidence limits on any predictions, for example, a level of probability to be placed on the goodness of fit. The robustness of the predictive models can also be checked using cross-validation, by leaving out selected samples from the analysis.

The PAM50 classification model described herein is based on the gene expression profile for a plurality of subject samples using the intrinsic genes listed in Table 1. The plurality of samples includes a sufficient number of samples derived from subjects belonging to each subtype class. By "sufficient samples" or "representative number" in this context is intended a quantity of samples derived from each subtype that is sufficient for building a classification model that can reliably distinguish each subtype from all others in the group. A supervised prediction algorithm is developed based on the profiles of objectively-selected prototype samples for "training" the algorithm. The samples are selected and subtyped using an expanded intrinsic gene set according to the methods disclosed in U.S. Patent Publication No. 2009/0299640, which is herein incorporated by reference in its entirety. Alternatively, the samples can be subtyped according to any known assay for classifying breast cancer subtypes. After stratifying the training samples according to subtype, a centroid-based prediction algorithm is used to construct centroids based on the expression profile of the intrinsic gene set described in Table 1.

In one embodiment, the prediction algorithm is the nearest centroid methodology related to that described in Narashiman and Chu (2002) PNAS 99:6567-6572, which is herein incorporated by reference in its entirety. In the present disclosure, the method computes a standardized centroid for each subtype. This centroid is the average gene expression for each gene in each subtype (or "class") divided by the within-class standard deviation for that gene. Nearest centroid classification takes the gene expression profile of a new sample, and compares it to each of these class centroids. Subtype prediction is done by calculating the Spearman's rank correlation of each test case to the five centroids, and assigning a sample to a subtype based on the nearest centroid.

Detection of Intrinsic Gene Expression

Any methods available in the art for detecting expression of the intrinsic genes listed in Table 1 are encompassed herein. By "detecting expression" is intended determining the quantity or presence of an RNA transcript or its expression product of an intrinsic gene. Methods for detecting expression of the intrinsic genes of the disclosure, that is, gene expression profiling, include methods based on hybridization analysis of polynucleotides, methods based on sequencing of polynucleotides, immunohistochemistry methods, and proteomics-based methods. The methods generally detect expression products (e.g., mRNA) of the intrinsic genes listed in Table 1. In preferred embodiments, PCR-based methods, such as reverse transcription PCR (RT-PCR) (Weis et al., TIG 8:263-64, 1992), and array-based methods such as microarray (Schena et al., Science 270:467-70, 1995) are used. By "microarray" is intended an ordered arrangement of hybridizable array elements, such as, for example, polynucleotide probes, on a substrate. The term "probe" refers to any molecule that is capable of selectively binding to a specifically intended target biomolecule, for example, a nucleotide transcript or a protein encoded by or corresponding to an intrinsic gene. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Many expression detection methods use isolated RNA. The starting material is typically total RNA isolated from a biological sample, such as a tumor or tumor cell line, and corresponding normal tissue or cell line, respectively. If the source of RNA is a primary tumor, RNA (e.g., mRNA) can be extracted, for example, from frozen or archived paraffin-embedded and fixed (e.g., formalin-fixed) tissue samples (e.g., pathologist-guided tissue core samples).

General methods for RNA extraction are well known in the art and are disclosed in standard textbooks of molecular biology, including Ausubel et al., ed., Current Protocols in Molecular Biology, John Wiley & Sons, New York 1987-1999. Methods for RNA extraction from paraffin embedded tissues are disclosed, for example, in Rupp and Locker, Lab Invest. 56:A67, (1987); and De Andres et al. Biotechniques 18:42-44, (1995). In particular, RNA isolation can be performed using a purification kit, a buffer set and protease from commercial manufacturers, such as Qiagen (Valencia, Calif.), according to the manufacturer's instructions. For example, total RNA from cells in culture can be isolated using Qiagen RNeasy mini-columns. Other commercially available RNA isolation kits include MASTERPURE™ Complete DNA and RNA Purification Kit (Epicentre, Madison, Wis.) and Paraffin Block RNA Isolation Kit (Ambion, Austin, Tex.). Total RNA from tissue samples can be isolated, for example, using RNA Stat-60 (Tel-Test, Friendswood, Tex.). RNA prepared from a tumor can be isolated, for example, by cesium chloride density gradient centrifugation. Additionally, large numbers of tissue samples can readily be processed using techniques well known to those of skill in the art, such as, for example, the single-step RNA isolation process of Chomczynski (U.S. Pat. No. 4,843,155). Isolated RNA can be used in hybridization or amplification assays that include, but are not limited to, PCR analyses and probe arrays. One method for the detection of RNA levels involves contacting the isolated RNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 60, 100, 250, or 500 nucleotides in length and sufficient to specifically hybridize under stringent conditions to an intrinsic gene of the present disclosure, or any derivative DNA or RNA. Hybridization of an mRNA with the probe indicates that the intrinsic gene in question is being expressed. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probes are immobilized on a solid surface and the mRNA is contacted with the probes, for example, in an Agilent gene chip array. A skilled artisan can readily adapt known mRNA detection methods for use in detecting the level of expression of the intrinsic genes of the present disclosure.

An alternative method for determining the level of intrinsic gene expression product in a sample involves the process of nucleic acid amplification, for example, by RT-PCR (U.S. Pat. No. 4,683,202), ligase chain reaction (Barany, PNAS USA 88: 189-93, (1991)), self sustained sequence replication (Guatelli et al., Proc. Natl. Acad. Sci. USA 87: 1874-78, (1990)), transcriptional amplification system (Kwoh et al., Proc. Natl. Acad. ScL USA 86: 1173-77, (1989)), Q-Beta Replicase (Lizardi et al., Bio/Technology 6:1197, (1988)), rolling circle replication (U.S. Pat. No. 5,854,033), or any other nucleic acid amplification method, followed by the detection of the amplified molecules using techniques well known to those of skill in the art. These detection schemes are especially useful for the detection of nucleic acid molecules if such molecules are present in very low numbers.

In particular aspects of the disclosure, intrinsic gene expression is assessed by quantitative RT-PCR. Numerous different PCR or QPCR protocols are known in the art and exemplified herein below and can be directly applied or adapted for use using the presently-described compositions for the detection and/or quantification of the intrinsic genes listed in Table 1. Generally, in PCR, a target polynucleotide sequence is amplified by reaction with at least one oligonucleotide primer or pair of oligonucleotide primers. The primer(s) hybridize to a complementary region of the target nucleic acid and a DNA polymerase extends the primer(s) to amplify the target sequence. Under conditions sufficient to provide polymerase-based nucleic acid amplification products, a nucleic acid fragment of one size dominates the reaction products (the target polynucleotide sequence which is the amplification product). The amplification cycle is repeated to increase the concentration of the single target polynucleotide sequence. The reaction can be performed in any thermocycler commonly used for PCR. However, preferred are cyclers with real time fluorescence measurement capabilities, for example, SMARTCYCLER® (Cepheid, Sunnyvale, Calif.), ABI PRISM 7700® (Applied Biosystems, Foster City, Calif.), ROTOR-GENE™ (Corbett Research, Sydney, Australia), LIGHTCYCLER® (Roche Diagnostics Corp, Indianapolis, Ind.), ICYCLER® (Biorad Laboratories, Hercules, Calif.) and MX4000® (Stratagene, La Jolla, Calif.).

In another embodiment of the disclosure, microarrays are used for expression profiling. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning Hybridization intensities for each probe on the array are determined and converted to a quantitative value representing relative gene expression levels. See, for example, U.S. Pat. Nos. 6,040,138, 5,800,992 and 6,020,135, 6,033,860, and 6,344,316. High-density oligonucleotide arrays are particularly useful for determining the gene expression profile for a large number of RNAs in a sample.

In a preferred embodiment, the nCounter® Analysis system is used to detect intrinsic gene expression. The basis of the nCounter® Analysis system is the unique code assigned to each nucleic acid target to be assayed (U.S. Patent Application Publication No. 2010/0112710 and Geiss et al. Nature Biotechnology. 2008. 26(3): 317-325; the contents of which are each incorporated herein by reference in their entireties). The code is composed of an ordered series of colored fluorescent spots which create a unique barcode for each target to be assayed. A pair of probes is designed for each DNA or RNA target, a biotinylated capture probe and a reporter probe carrying the fluorescent barcode. This system is also referred to, herein, as the nanoreporter code system.

Specific reporter and capture probes are synthesized for each target. Briefly, sequence-specific DNA oligonucleotide probes are attached to code-specific reporter molecules. Capture probes are made by ligating a second sequence-specific DNA oligonucleotide for each target to a universal oligonucleotide containing biotin. Reporter and capture probes are all pooled into a single hybridization mixture, the "probe library".

The relative abundance of each target is measured in a single multiplexed hybridization reaction. The sample is combined with the probe library, and hybridization occurs in solution. After hybridization, the tripartite hybridized complexes are purified in a two-step procedure using magnetic beads linked to oligonucleotides complementary to universal sequences present on the capture and reporter probes. This dual purification process allows the hybridization reaction to be driven to completion with a large excess of target-specific probes, as they are ultimately removed, and, thus, do not interfere with binding and imaging of the sample. All post hybridization steps are handled robotically on a custom liquid-handling robot (Prep Station, NanoString Technologies).

Purified reactions are deposited by the Prep Station into individual flow cells of a sample cartridge, bound to a streptavidin-coated surface via the capture probe, electrophoresed to elongate the reporter probes, and immobilized. After processing, the sample cartridge is transferred to a fully automated imaging and data collection device (Digital Analyzer, NanoString Technologies). The expression level of a target is measured by imaging each sample and counting the number of times the code for that target is detected. For each sample, typically 600 fields-of-view (FOV) are imaged (1376×1024 pixels) representing approximately 10 $mm^2$ of the binding surface. Typical imaging density is 100-1200 counted reporters per field of view depending on the degree of multiplexing, the amount of sample input, and overall target abundance. Data is output in simple spreadsheet format listing the number of counts per target, per sample.

This system can be used along with nanoreporters. Additional disclosure regarding nanoreporters can be found in U.S. Patent Application Publication Nos. 2010/0015607 and 2010/0261026, the contents of which are incorporated herein in their entireties. Further, the term nucleic acid probes and nanoreporters can include the rationally designed (e.g. synthetic sequences) described in U.S. Patent Application Publication No. 2010/0047924, incorporated herein by reference in its entirety.

Data Processing

It is often useful to pre-process gene expression data, for example, by addressing missing data, translation, scaling, normalization, weighting, etc. Multivariate projection methods, such as principal component analysis (PCA) and partial least squares analysis (PLS), are so-called scaling sensitive methods. By using prior knowledge and experience about the type of data studied, the quality of the data prior to multivariate modeling can be enhanced by scaling and/or weighting. Adequate scaling and/or weighting can reveal important and interesting variation hidden within the data, and therefore make subsequent multivariate modeling more efficient. Scaling and weighting may be used to place the data in the correct metric, based on knowledge and experience of the studied system, and therefore reveal patterns already inherently present in the data.

If possible, missing data, for example gaps in column values, should be avoided. However, if necessary, such missing data may replaced or "filled" with, for example, the mean value of a column ("mean fill"); a random value ("random fill"); or a value based on a principal component analysis ("principal component fill").

"Translation" of the descriptor coordinate axes can be useful. Examples of such translation include normalization and mean centering. "Normalization" may be used to remove sample-to-sample variation. For microarray data, the process of normalization aims to remove systematic errors by balancing the fluorescence intensities of the two labeling dyes. The dye bias can come from various sources including differences in dye labeling efficiencies, heat and light sensitivities, as well as scanner settings for scanning two channels. Some commonly used methods for calculating normalization factor include: (i) global normalization that uses all genes on the array; (ii) housekeeping genes normalization that uses constantly expressed housekeeping/invariant genes; and (iii) internal controls normalization that uses known amount of exogenous control genes added during hybridization (Quackenbush Nat. Genet. 32 (Suppl.), 496-501 (2002)). In one embodiment, the intrinsic genes disclosed herein can be normalized to control housekeeping genes. For example, the housekeeping genes described in U.S. Patent Publication 2008/0032293, which is herein incorporated by reference in its entirety, can be used for normalization. Exemplary housekeeping genes include MRPL19, PSMC4, SF3A1, PUM1, ACTB, GAPD, GUSB, RPLPO, and TFRC. It will be understood by one of skill in the art that the methods disclosed herein are not bound by normalization to any particular housekeeping genes, and that any suitable housekeeping gene(s) known in the art can be used.

Many normalization approaches are possible, and they can often be applied at any of several points in the analysis. In one embodiment, microarray data is normalized using the LOWESS method, which is a global locally weighted scatterplot smoothing normalization function. In another embodiment, qPCR data is normalized to the geometric mean of set of multiple housekeeping genes.

"Mean centering" may also be used to simplify interpretation. Usually, for each descriptor, the average value of that descriptor for all samples is subtracted. In this way, the mean of a descriptor coincides with the origin, and all descriptors are "centered" at zero. In "unit variance scaling," data can be scaled to equal variance. Usually, the value of each descriptor is scaled by 1/StDev, where StDev is the standard deviation for that descriptor for all samples. "Pareto scaling" is, in some sense, intermediate between mean centering and unit variance scaling. In pareto scaling, the value of each descriptor is scaled by 1/sqrt(StDev), where StDev is the standard deviation for that descriptor for all samples. In this way, each descriptor has a variance numerically equal to its initial standard deviation. The pareto scaling may be performed, for example, on raw data or mean centered data.

"Logarithmic scaling" may be used to assist interpretation when data have a positive skew and/or when data spans a large range, e.g., several orders of magnitude. Usually, for each descriptor, the value is replaced by the logarithm of that value. In "equal range scaling," each descriptor is divided by the range of that descriptor for all samples. In this way, all descriptors have the same range, that is, 1. However, this method is sensitive to presence of outlier points. In "autoscaling," each data vector is mean centered and unit variance scaled. This technique is a very useful because each descriptor is then weighted equally, and large and small values are treated with equal emphasis. This can be important for genes expressed at very low, but still detectable, levels.

In one embodiment, data is collected for one or more test samples and classified using the PAM50 classification model described herein. When comparing data from multiple analyses (e.g., comparing expression profiles for one or more test samples to the centroids constructed from samples collected and analyzed in an independent study), it will be necessary to normalize data across these data sets. In one embodiment, Distance Weighted Discrimination (DWD) is used to combine these data sets together (Benito et al. (2004) Bioinformatics 20(1): 105-114, incorporated by reference herein in its entirety). DWD is a multivariate analysis tool that is able to identify systematic biases present in separate data sets and then make a global adjustment to compensate for these biases; in essence, each separate data set is a multi-dimensional cloud of data points, and DWD takes two points clouds and shifts one such that it more optimally overlaps the other.

The methods described herein may be implemented and/or the results recorded using any device capable of implementing the methods and/or recording the results. Examples of devices that may be used include but are not limited to electronic computational devices, including computers of all types. When the methods described herein are implemented and/or recorded in a computer, the computer program that may be used to configure the computer to carry out the steps of the methods may be contained in any computer readable medium capable of containing the computer program. Examples of computer readable medium that may be used include but are not limited to diskettes, CD-ROMs, DVDs, ROM, RAM, and other memory and computer storage devices. The computer program that may be used to configure the computer to carry out the steps of the methods and/or record the results may also be provided over an electronic network, for example, over the internet, an intranet, or other network.

Calculation of Risk of Relapse

Provided herein are methods for predicting breast cancer outcome within the context of the intrinsic subtype and optionally other clinical variables. Outcome may refer to overall or disease-specific survival, event-free survival, or outcome in response to a particular treatment or therapy. In particular, the methods may be used to predict the likelihood of long-term, disease-free survival. "Predicting the likelihood of survival of a breast cancer patient" is intended to assess the risk that a patient will die as a result of the underlying breast cancer. "Long-term, disease-free survival" is intended to mean that the patient does not die from or suffer a recurrence of the underlying breast cancer within a period of at least five years, or at least ten or more years, following initial diagnosis or treatment.

In one embodiment, outcome is predicted based on classification of a subject according to subtype. This classification is based on expression profiling using the list of intrinsic genes listed in Table 1. In addition to providing a subtype assignment, the PAM50 bioinformatics model provides a measurement of the similarity of a test sample to all four subtypes which is translated into a Risk of Relapse (ROR) score that can be used in any patient population regardless of disease status and treatment options. The intrinsic subtypes and ROR also have value in the prediction of pathological complete response in women treated with, for example, neoadjuvant taxane and anthracycline chemotherapy (Rouzier et al., J Clin Oncol 23:8331-9 (2005), incorporated herein by reference in its entirety). Thus, in various embodiments of the present disclosure, a risk of relapse (ROR) model is used to predict outcome. Using these risk models, subjects can be stratified into low, medium, and high risk of relapse groups. Calculation of ROR can provide prognostic information to guide treatment decisions and/or monitor response to therapy.

In some embodiments described herein, the prognostic performance of the PAM50-defined intrinsic subtypes and/or other clinical parameters is assessed utilizing a Cox Proportional Hazards Model Analysis, which is a regression method for survival data that provides an estimate of the hazard ratio and its confidence interval. The Cox model is a well-recognized statistical technique for exploring the relationship between the survival of a patient and particular variables. This statistical method permits estimation of the hazard (i.e., risk) of individuals given their prognostic variables (e.g., intrinsic gene expression profile with or without additional clinical factors, as described herein). The "hazard ratio" is the risk of death at any given time point for patients displaying particular prognostic variables. See generally Spruance et al., Antimicrob. Agents & Chemo. 48:2787-92 (2004).

The PAM50 classification model described herein can be trained for risk of relapse using subtype distances (or correlations) alone, or using subtype distances with clinical variables as discussed supra. In one embodiment, the risk score for a test sample is calculated using intrinsic subtype distances alone using the following equation:

ROR=0.05*Basal+0.11*Her2+−0.25*LumA+0.07*LumB+−0.11*Normal, where the variables "Basal," "Her2," "LumA," "LumB," and "Normal" are the distances to the centroid for each respective classifier when the expression profile from a test sample is compared to centroids constructed using the gene expression data deposited with the Gene Expression Omnibus (GEO) as accession number GSE2845.

Risk score can also be calculated using a combination of breast cancer subtype and the clinical variables tumor size (T) and lymph nodes status (N) using the following equation: ROR (full)=0.05*Basal+0.1*Her2+−0.19*LumA+0.05*LumB+−0.09*Normal+0.16*T+0.08*N, again when comparing test expression profiles to centroids constructed using the gene expression data deposited with GEO as accession number GSE2845.

In yet another embodiment, risk score for a test sample is calculated using intrinsic subtype distances alone using the following equation:

ROR-S=0.05*Basal+0.12*Her2+−0.34*LumA+0.0.23*LumB, where the variables "Basal," "Her2," "LumA," and "LumB" are as described supra and the test expression profiles are compared to centroids constructed using the gene expression data deposited with GEO as accession number GSE2845. In yet another embodiment, risk score can also be calculated using a combination of breast cancer subtype and the clinical variable tumor size (T) using the following equation (where the variables are as described supra): ROR-C=0.05*Basal+0.11*Her2+-0.23*LumA+0.09*LumB+0.17*T.

Detection of the Her2+ Subtype

Immunohistochemistry for estrogen (ER), progesterone (PgR), HER2, and Ki67 was performed concurrently on serial sections with the standard streptavidin-biotin complex method with 3,3'-diaminobenzidine as the chromogen. Staining for ER, PgR, and HER2 interpretation can be performed as described previously (Cheang et al., Clin Cancer Res. 2008; 14(5):1368-1376.), however any method known in the art may be used.

For example, a Ki67 antibody (clone SP6; ThermoScientific, Fremont, Calif.) can be applied at a 1:200 dilution for 32 minutes, by following the Ventana Benchmark automated immunostainer (Ventana, Tucson Ariz.) standard Cell Conditioner 1 (CC1, a proprietary buffer) protocol at 98° C. for 30 minutes. An ER antibody (clone SP1; ThermoFisher Scientific, Fremont Calif.) can be used at 1:250 dilution with 10-minute incubation, after an 8-minute microwave antigen retrieval in 10 mM sodium citrate (pH 6.0). Ready-to-use PR antibody (clone 1E2; Ventana) can be used by following the CC1 protocol as above. HER2 staining can be done with a SP3 antibody (ThermoFisher Scientific) at a 1:100 dilution after antigen retrieval in 0.05 M Tris buffer (pH 10.0) with heating to 95° C. in a steamer for 30 minutes. For HER2 fluorescent in situ hybridization (FISH) assay, slides can be hybridized with probes to LSI (locus-specific identifier) HER2/neu and to centromere 17 by use of the PathVysion HER-2 DNA Probe kit (Abbott Molecular, Abbott Park, Ill.) according to manufacturer's instructions, with modifications to pretreatment and hybridization as previously described (Brown L A, Irving J, Parker R, et al. Amplification of EMSY, a novel oncogene on 11q13, in high grade ovarian surface epithelial carcinomas. Gynecol Oncol. 2006; 100(2):264-270). Slides can then be counterstained with 4',6-diamidino-2-phenylindole, stained material was visualized on a Zeiss Axioplan epifluorescent microscope, and signals were analyzed with a Metafer image acquisition system (Metasystems, Altlussheim, Germany). Biomarker expression from immunohistochemistry assays can then be scored by two pathologists, who were blinded to the clinicopathological characteristics and outcome and who used previously established and published criteria for biomarker expression levels that had been developed on other breast cancer cohorts.

Tumors were considered positive for ER or PR if immunostaining was observed in more than 1% of tumor nuclei, as described previously. Tumors were considered positive for HER2 if immunostaining was scored as 3+ according to HercepTest criteria, with an amplification ratio for fluorescent in situ hybridization of 2.0 or more being the cut point that was used to segregate immunohistochemistry equivocal tumors (scored as 2+) (Yaziji, et al., JAMA, 291(16):1972-1977 (2004)). Ki67 was visually scored for percentage of tumor cell nuclei with positive immunostaining above the background level by two pathologists.

Other methods can also be used to detect the Her2+ subtype. These techniques include ELISA, Western blots, Northern blots, or FACS analysis.

Kits

The present disclosure also describes kits useful for classifying breast cancer intrinsic subtypes and/or providing prognostic information to identify breast cancers that are more responsive to anthracyclines. These kits comprise a set of capture probes and/or primers specific for the intrinsic genes listed in Table 1, as well as reagents sufficient to facilitate detection and/or quantitation of Her2, in order to classify cells as Her2+. Preferably, the kit comprises a set of capture probes and/or primers specific for at least 10, at least 15, at least 20, at least 25 of the intrinsic genes or all 50 intrinsic genes listed in Table 1. The kit may further comprise a computer readable medium.

In one embodiment of the present disclosure, the capture probes are immobilized on an array. By "array" is intended a solid support or a substrate with peptide or nucleic acid probes attached to the support or substrate. Arrays typically comprise a plurality of different capture probes that are coupled to a surface of a substrate in different, known locations. The arrays of the disclosure comprise a substrate having a plurality of capture probes that can specifically bind an intrinsic gene expression product. The number of capture probes on the substrate varies with the purpose for which the array is intended. The arrays may be low-density arrays or high-density arrays and may contain 4 or more, 8 or more, 12 or more, 16 or more, 32 or more addresses, but will minimally comprise capture probes for at least 10, at least 15, at least 20, at least 25 of the intrinsic genes or all 50 intrinsic genes listed in Table 1.

Techniques for the synthesis of these arrays using mechanical synthesis methods are described in, e.g., U.S. Pat. No. 5,384,261, incorporated herein by reference in its entirety for all purposes. The array may be fabricated on a surface of virtually any shape or even a multiplicity of surfaces. Arrays may be probes (e.g., nucleic-acid binding probes) on beads, gels, polymeric surfaces, fibers such as fiber optics, glass or any other appropriate substrate, see U.S. Pat. Nos. 5,770,358, 5,789,162, 5,708,153, 6,040,193 and 5,800,992, each of which is hereby incorporated in its entirety for all purposes. Arrays may be packaged in such a manner as to allow for diagnostics or other manipulation on the device. See, for example, U.S. Pat. Nos. 5,856,174 and 5,922,591 herein incorporated by reference.

In another embodiment, the kit comprises a set of oligonucleotide primers sufficient for the detection and/or quantitation of each of the intrinsic genes listed in Table 1. Preferably, the kit comprises a set of oligonucleotide primers sufficient for the detection and/or quantitation of at least 10, at least 15, at least 20, at least 25 of the intrinsic genes or all 50 intrinsic genes listed in Table 1. The oligonucleotide primers may be provided in a lyophilized or reconstituted form, or may be provided as a set of nucleotide sequences. In one embodiment, the primers are provided in a microplate format, where each primer set occupies a well (or multiple wells, as in the case of replicates) in the microplate. The microplate may further comprise primers sufficient for the detection of one or more housekeeping genes as discussed infra. The kit may further comprise reagents and instructions sufficient for the amplification of expression products from the genes listed in Table 1.

In order to facilitate ready access, e.g., for comparison, review, recovery, and/or modification, the molecular signatures/expression profiles are typically recorded in a database. Most typically, the database is a relational database accessible by a computational device, although other formats, e.g., manually accessible indexed files of expression profiles as photographs, analogue or digital imaging readouts, spreadsheets, etc. can be used. Regardless of whether the expression patterns initially recorded are analog or digital in nature, the expression patterns, expression profiles (collective expression patterns), and molecular signatures (correlated expression patterns) are stored digitally and accessed via a database. Typically, the database is compiled and maintained at a central facility, with access being available locally and/or remotely.

In certain embodiments, the kit also includes a substance that is used to find the expression level of Her-2. This substance can be an antibody or a nucleic acid probe. These substances can be used to detect Her-2 using FISH, IHC, ELISA, Western blots, Northern blots, or FACS analysis. Optionally, the kit also includes reagents that allows for the detection of the detecting substance and the quantitation of Her-2 expression in a sample.

EXAMPLES

Example 1

Classification of Tumors Using PAM50 and Immunohistochemistry (IHC) and Fluorescent In Situ Hybridization (FISH)

In this study, the PAM50 gene set was applied to 476 retrospectively collected tumor specimens from a NCIC-CTG MA.5 study, a prospective clinical trial that randomized women with pre-menopausal, node positive breast cancer to adjuvant chemotherapy with CMF vs. CEF.

Materials and Methods

Patients and Treatment Regimens

The MA.5 phase III trial was a randomized, controlled study on 716 premenopausal women with node-positive breast cancers (Levine et al., J Clin Oncol., 16(8):2651-8 (1998); Levine et al. J Clin Oncol., 23(22):5166-70 (2005)). In brief, patients were accrued between 1989 and 1993 and randomized to receive either CEF or CMF treatment regimens. The adjuvant CEF regimen included six cycles of epirubicin 60 mg/m$^2$ and 5-fluorouracil (5-FU) 500 mg/m$^2$, both delivered intravenously on days 1 and 8, and oral cyclophosphamide 75 mg/m$^2$ daily on days 1 through 14. The adjuvant CMF regimen included six cycles of methotrexate 40 mg/m$^2$ and 5-FU 600 mg/m$^2$, both delivered intravenously on days 1 and 8, and oral cyclophosphamide 100 mg/m$^2$ daily on days 1 through 14.

Immunohistochemistry, Fluorescence In Situ Hybridization (FISH) and Tissue Microarray (TMA)

549 archival specimens (77%) were obtained for tissue microarray construction. There were no significant differences in the clinicopathological characteristics between the TMA cohort and the MA.5 study patients. Immunohistochemical staining methods and interpretation of ER, PgR, Her2, Ki-67, EGFR, and CK 5/6 were pre-specified and performed using published methods (Cheang et al., J Natl Cancer Inst., 101(10): 736-50 (2009) and Cheang et al., Clin Cancer Res., 14(5):1368-76 (2008)). Her2/Neu and TOP2A amplifications were measured by fluorescence in-situ hybridization (FISH) as previously described (Pritchard et al., N Engl J Med., 354(20):2103-11 (2006); O'Malley et al., J Natl Cancer Inst., 101(9):644-50 (2009)). To determine Her2 status in this study, FISH data (amplification ratio≥2.0) was used to segregate immunohistochemically-equivocal (2+) results. Missing biomarker data precluded subtype assignment in 38 cases. Biomarker expressions were interpreted by licensed pathologists blinded to clinical outcome.

RNA Preparation, qRT-PCR and Assignment of Intrinsic Subtype 476 tumors (67%) were obtained for qRT-PCR-based PAM50 gene expression test. There were no significant differences in the clinicopathological characteristics between the qRT-PCR cohort and the MA.5 study patients (Table 3). FIG. 1 summarizes the study design as per ReMARK guidelines (McShane et al., Journal of the National Cancer Institute. 2005; 97:1180-4). Patient characteristics stratified by intrinsic subtypes by qRT-PCR PAM50 assay.

TABLE 3

| | All Randomized | Patients with PAM50 | Basal-like | Her2-E | LumA | LumB | Normal |
|---|---|---|---|---|---|---|---|
| All | 716 | 476 | 94 (20%) | 105 (22%) | 146 (31%) | 110 (23%) | 21 (4%) |
| ER (DCC) | | | | | | | |
| Positive (>=10 fmol/mg) | 428 (68%) | 283 (66%) | 8 (10%) | 47 (50%) | 114 (88%) | 100 (96%) | 14 (78%) |
| Negative (<10 fmol/mg) | 201 (32%) | 144 (34%) | 73 (90%) | 47 (50%) | 16 (12%) | 4 (4%) | 4 (22%) |
| Unknown | 87 | 49 | 13 | 11 | 16 | 6 | 3 |
| P-value | 0.6 | | | | 3.2 × 10-41 | | |

TABLE 3-continued

| | All Randomized | Patients with PAM50 | Basal-like | Her2-E | LumA | LumB | Normal |
|---|---|---|---|---|---|---|---|
| ER (IHC) | | | | | | | |
| Positive (>=1%) | | 300 (64%) | 8 (9%) | 46 (44%) | 129 (90%) | 103 (95%) | 14 (67%) |
| Negative | | 168 (36%) | 83 (91%) | 58 (56%) | 15 (10%) | 5 (5%) | 7 (33%) |
| Unknown | | 8 | 3 | 1 | 2 | 2 | 0 |
| P-value | NA | | | | 9.2 x 10-55 | | |
| Nodal status | | | | | | | |
| 1-3 nodes | 436 (61%) | 287 (60%) | 61 (65%) | 64 (61%) | 91 (32%) | 58 (20%) | 13 (5%) |
| 4+ nodes | 280 (39%) | 189 (40%) | 33 (35%) | 41 (39%) | 55 (29%) | 52 (28%) | 8 (4%) |
| P-value | 0.88 | | | | 0.44 | | |
| Age (years) | | | | | | | |
| <50 | 599 (84%) | 396 (83%) | 87 (93%) | 82 (78%) | 118 (81%) | 91 (83%) | 18 (86%) |
| >=50 | 117 (16%) | 80 (17%) | 7 (7%) | 23 (22%) | 28 (19%) | 19 (17%) | 3 (14%) |
| P-value | 0.89 | | | | 0.05 | | |
| Surgery | | | | | | | |
| Lumpectomy | 351 (49%) | 238 (50%) | 51 (54%) | 46 (44%) | 77 (53%) | 58 (53%) | 6 (29%) |
| Mastectomy | 365 (51%) | 238 (50%) | 43 (46%) | 59 (56%) | 69 (47%) | 52 (47%) | 15 (71%) |
| P-value | 0.79 | | | | 0.14 | | |
| T Stage | | | | | | | |
| T1 | 279 (41%) | 180 (41%) | 24 (27%) | 35 (38%) | 68 (50%) | 41 (39%) | 12 (60%) |
| T2 | 352 (53%) | 240 (54%) | 59 (67%) | 53 (57%) | 64 (47%) | 57 (54%) | 7 (35%) |
| T3 | 36 (5%) | 23 (5%) | 5 (6%) | 5 (5%) | 5 (4%) | 7 (7%) | 1 (5%) |
| Unknown | 49 | 33 | 6 | 12 | 9 | 5 | 1 |
| P-value | 0.9 | | | | 0.038 | | |
| Grade | | | | | | | |
| 1 | 77 (12%) | 50 (11%) | 0 | 2 (2%) | 41 (29%) | 3 (3%) | 4 (21%) |
| 2 | 205 (33%) | 140 (30%) | 5 (5%) | 19 (19%) | 79 (55%) | 33 (31%) | 4 (21%) |
| 3 | 344 (55%) | 273 (59%) | 88 (95%) | 80 (79%) | 23 (16%) | 71 (66%) | 11 (58%) |
| Unknown | 90 | 13 | 1 | 4 | 3 | 3 | 2 |
| P-value | 0.4 | | | | 3.2 x 10-37* | | |
| Treatment | | | | | | | |
| CEF | 356 (50%) | 232 (49%) | 45 (48%) | 49 (47%) | 68 (47%) | 59 (54%) | 11 (52%) |
| CMF | 360 (51%) | 244 (51%) | 49 (52%) | 56 (53%) | 78 (53%) | 51 (46%) | 10 (48%) |
| P-value | 0.79 | | | | 0.80 | | |

*Cases with Grade 1 and 2 were combined.

H&E sections from each block were reviewed by a pathologist (T.O.N.). Areas containing representative invasive breast carcinoma were selected and circled on the source block. Using a 1.0-mm punch needle, at least two tumor cores were extracted from the circled area. Details of RNA preparation from paraffin cores, the qRT-PCR assay for the PAM50 panel and reference genes, and tumor samples were classified into luminal A, luminal B, HER2-enriched, basal-like and normal-like subtypes as described previously (Nielsen et al., Clin Cancer Res., 16(21):5222-32 (2010); Parker et al., J. Clin Oncol., 27(8):1160-7 (2009)). ROR-S (ROR based on subtype) risk score assignment was also calculated for each tumor as described previously; ROR-S=(0.05)*Basal-like+(0.12)*HER2-E+(−0.34)*LumA+(0.23)*LumB By pre-specified cutpoints, patients were categorized as low risk if the ROR-S score was less than 23, moderate risk if ROR-S score was between 23-53 and high risk if the ROR-S score was ≥53. All genes expression tests and classifiers were done on all tumor specimens without knowledge of the clinical outcome.

Clinical Correlates of the Intrinsic Subtypes and Risk Classifiers

The intrinsic subtypes, risk classifier and biomarkers data were sent to the NCIC Clinical Trials Group statistical centre for independent analyses of pre-specified hypotheses. Primary outcomes for MA.5 were relapse-free survival (RFS) and overall survival (OS). RFS was defined as time from random assignment to any recurrences including local breast chest wall, regional or distant relapses. OS was defined as any death from any cause. The survival estimates for intrinsic subtypes and risk classifiers were plotted using Kaplan-Meier curves and compared by both log-rank and Wilcoxon tests. Univariable Cox proportional hazard regression models were used to obtain the hazard ratios (HRs) and associated 95% confidence intervals (CIs) of single covariates. Multivariable Cox regression analyses were used with treatments, intrinsic subtypes, and their interaction as covariates, to determine the significance of the interaction between treatment and intrinsic subtypes. These multivariable Cox models were adjusted for age (≥50 years vs. <50 years), number of positive lymph nodes (<4 vs. ≥4), estrogen-receptor level (≥10 vs. <10 fmol/mg), type of surgery (total vs. partial mastectomy) and tumor size (T1, T2, or T3). The association of clinical variables with subtypes was tested using Chi-square test or Fisher's Exact test.

The C-index (concordance index) (Harrell et al., Stat Med., 15(4):361-87 (1996)) is defined as the probability that risk assignments to members of a random pair are accurately ranked according to their prognosis. The number of concordant pairs (order of failure and risk assignment agree), discordant pairs (order of failure and risk assignment disagree), and uninformative pairs are tabulated to calculate the measure. C-indexes for intrinsic subtypes, ROR-S, Her2 status and TOP2A were compared for their predictions in patient outcomes stratified by each treatment arm. The associations of intrinsic subtypes with standard clinicopathological characteristics and biomarkers expressions were determined using Chi-square and Fisher's exact tests.

Results

Using the qRT-PCR-based PAM50 gene expression test, 31% of the 476 tumors were classified as LumA, 23% as LumB, 22% as Her2-E, 20% as Basal-like and 4% as Normal-like subtypes. The clinical ER status was originally determined at accrual using the dextran-coated charcoal (DCC) assay. As expected, 88% of LumA and 96% of LumB tumors were ER positive while 50% of Her2-E and 90% of Basal-like were ER negative (Table 3). According to ER status assessed by IHC, 90% of LumA, 95% of LumB, 44% of HER2-E and 9% of Basal-like were ER positive using a 1% cut off for positivity. ESR1 gene expression levels measured by RT-qPCR and ER by DCC correlated positively (r=0.71, p<0.0001). The LumB, Her2-E and Basal-like subtypes were associated with high grade tumors. There were no significant associations of subtypes with the number of positive lymph nodes, types of surgeries and adjuvant chemotherapy regimens respectively.

Example 2

Association of Intrinsic Subtypes by qRT-PCR PAM50 with Survival and Subset Analysis When analyzed on the entire cohort, intrinsic subtypes were significantly associated with different relapse-free and overall survival estimates (Table 4).

TABLE 4

Survival by intrinsic subtypes by PAM50 in all patients.

| | # of patients | 5-Year RFS (95% CI) | RFS P-values | 5-Year OS (95% CI) | OS P-values |
|---|---|---|---|---|---|
| Subtype | | | | | |
| Basal-like | 94 | 57.2% (47.1%-67.2%) | Log-rank | 58.5% (48.5%-68.4%) | Log-rank |
| Her2-E | 105 | 44.2% (34.7%-53.8%) | 0.0005 | 52.9% (43.3%-62.5%) | <0.0001 |
| LumA | 146 | 70.5% (63.2%-77.9%) | Wilcoxon | 91.8% (87.3%-96.2%) | Wilcoxon |
| LumB | 110 | 56.8% (47.5%-66.1%) | <0.0001 | 75.8% (67.7%-83.9%) | <0.0001 |
| ROR-S | | | | | |
| High | 174 | 50.6% (43.2%-58.1%) | Log-rank | 53.4% (45.9%-60.9%) | Log-rank |
| Med | 202 | 58.7% (51.9%-65.5%) | 0.008 | 79.6% (74.0%-85.2%) | <0.0001 |
| Low | 79 | 74.7% (65.1%-84.3%) | Wilcoxon | 93.7% (88.3%-99.0%) | Wilcoxon |
| | | | 0.0002 | | <0.0001 |

These results confirmed the prognostic values of subtypes among patients treated with adjuvant chemotherapy, regardless of the types of regimens. In this study, the ROR-S low-risk group (n=79) were all classified as LumA. For the ROR-S moderate-risk group (n=202), 33% were LumA, 39% LumB, 21% HER2-E and 7% were classified as Basal-like. Within the ROR-S high-risk group (n=174), 36% were classified as HER2-E, 46% as Basal-like and 18% as LumB. The ROR-S risk classifier was significantly associated with distinct survival differences (Log-rank p<0.0001): the low-risk group (75% RFS and 94% OS at 5-yr) had the most favorable clinical outcome, when compared to the moderate-risk group (59% RFS and 80% OS at 5-yr) and high-risk group (51% RFS and 53% OS at 5-yr) respectively (Table 4).

Figure 2A:
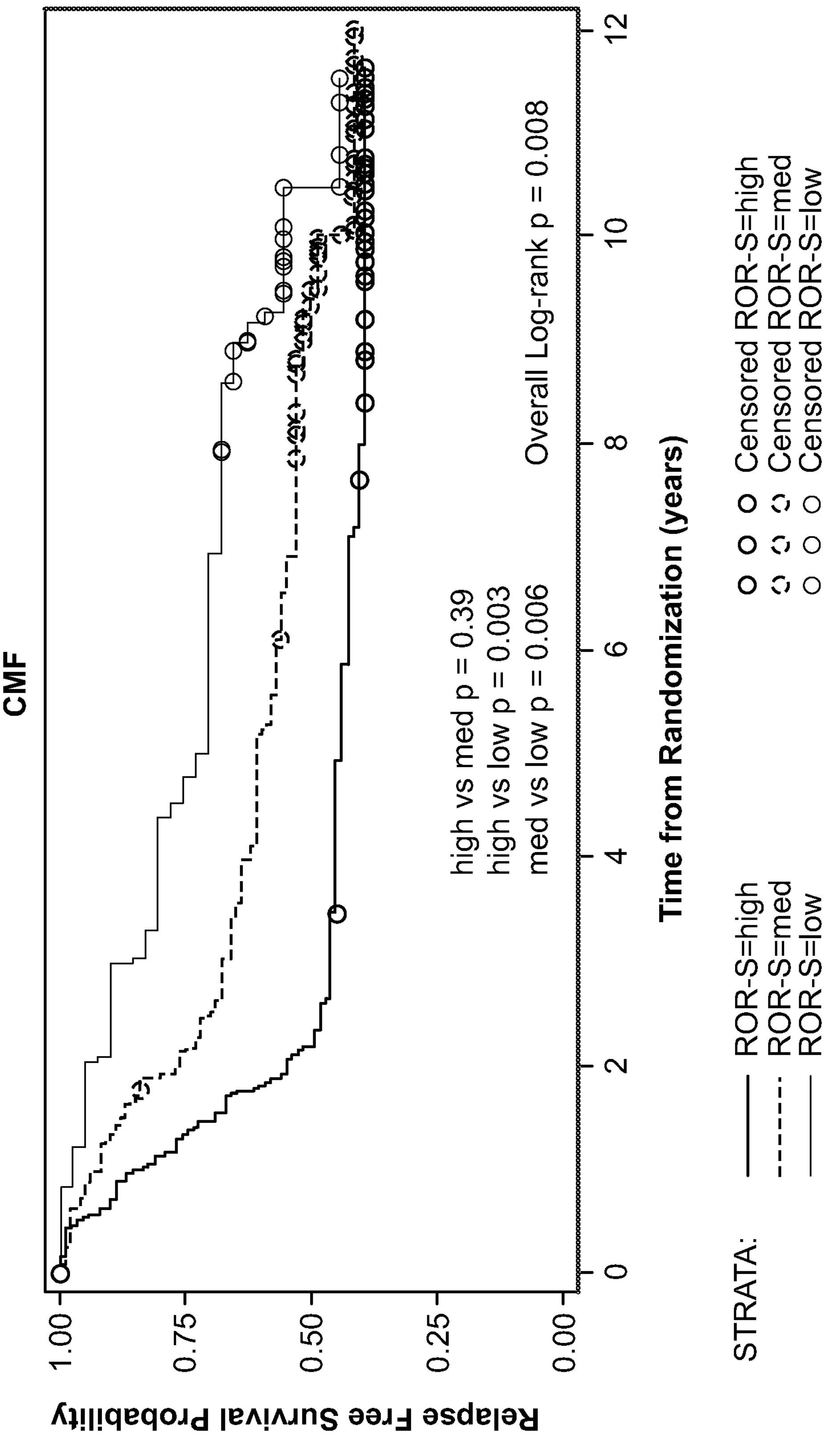
FIG. 2A is a line graph showing a Kaplan-Meier (K-M) curve of relapse-free survival of risk classifier risk of relapse score (ROR-S) identified using the PAM50 intrinsic genes in patients that received a cyclophosphamide, methotrexate and 5-fluorouracil (CMF) treatment regimen.
Figure 2B:
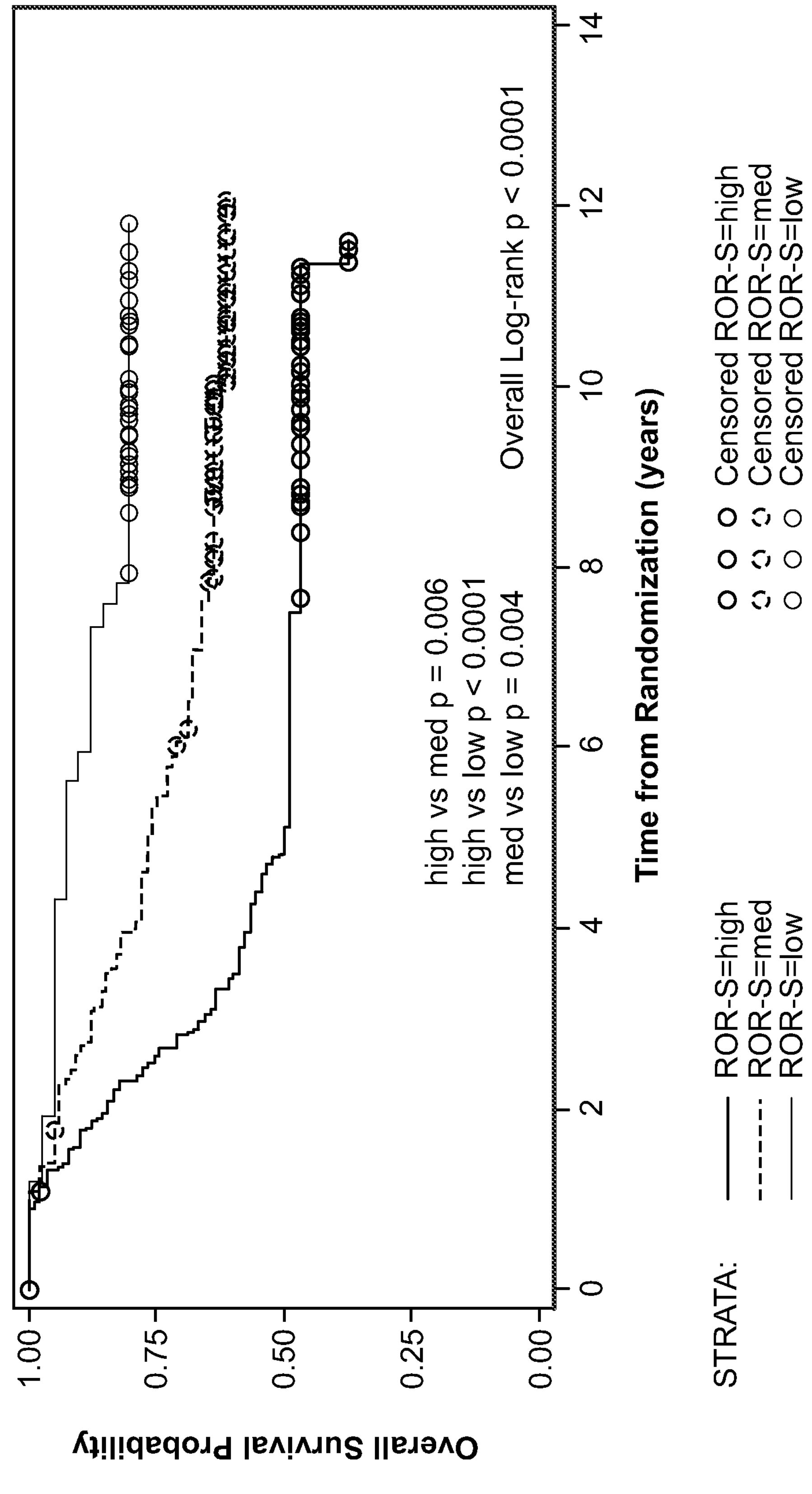
FIG. 2B is a line graph showing a K-M curve of overall survival of risk classifier ROR-S identified using the PAM50 intrinsic genes in patients that received the CMF treatment regimen.

Within the CMF treated cohort, intrinsic subtypes were associated with significant distinct RFS and OS (Log-rank P<0.0001, Table 5). Patients with HER2-E tumors had the poorest clinical outcome, significantly worse than each of the other subtypes (Table 5). Patients with HER2-E tumors even had a significantly worse outcome when compared to the Basal-like group, with a hazard ratio of 2.08 to develop relapses and 1.69 to any death (Table 6). In contrast, the Basal-like subtype did not have statistically significant differences in relapse-free survival when compared to patient with LumA or LumB tumors in this non-anthracycline, CMF-treated arm. Comparing the two ER positive subtypes, LumB tumors had a worse prognosis than LumA, having hazard ratios of 2.0 to develop any relapses and 2.44 to any death (Table 6). The three survival risk groups defined by the pre-specified ROR-S risk classifier were significantly associated with distinct RFS and OS estimates (FIG. 2*a*-2*b*). The low risk group (n=41) had absolute 12% higher 5-yr RFS and 16% higher 5-yr OS when compared to the moderate-risk group (n=101), and 29% higher 5-yr RFS and 43% higher 5-yr OS when compared to the high-risk group (n=92).

Figure 2C:
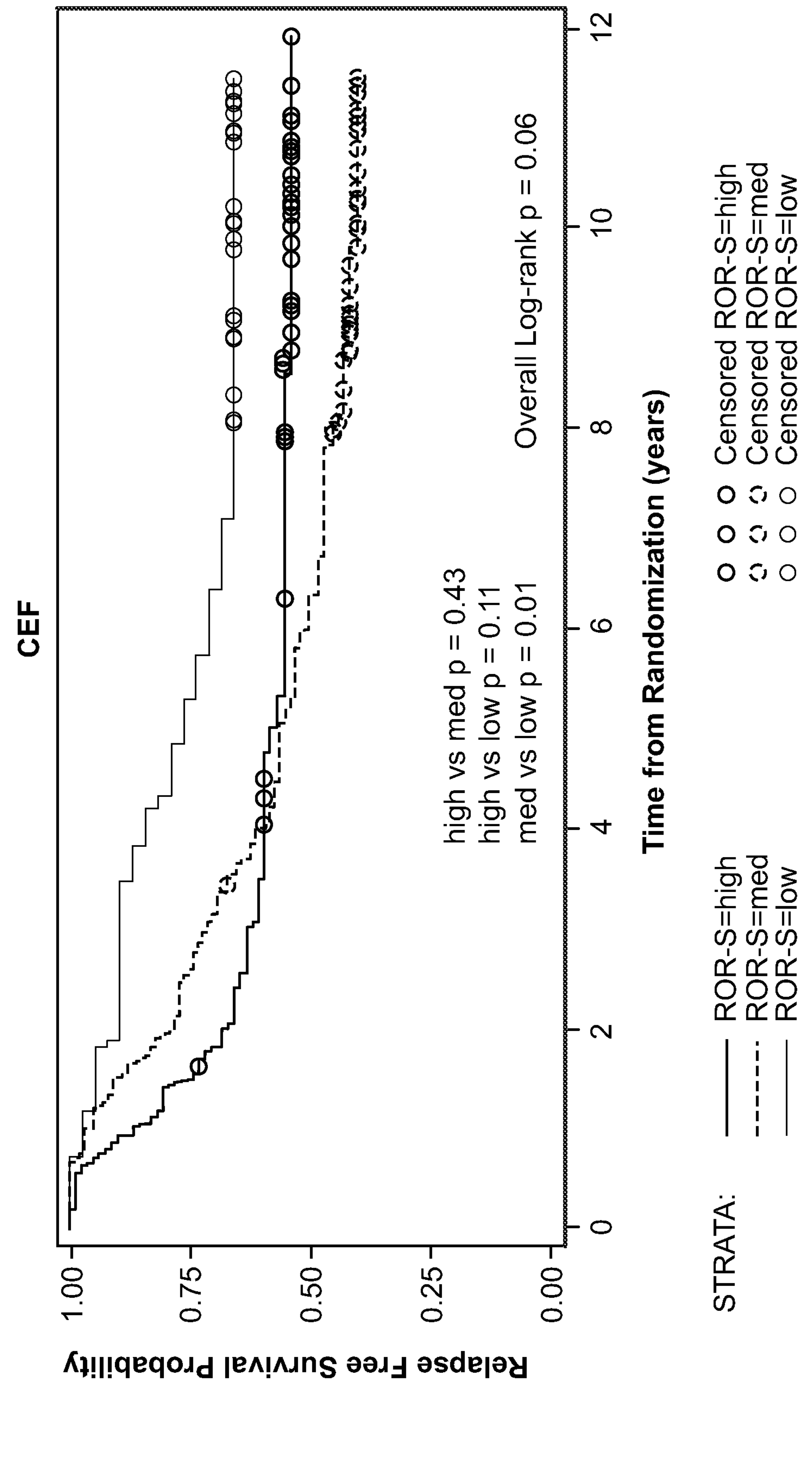
FIG. 2C is a line graph showing a K-M curve of relapse-free survival of risk classifier ROR-S identified using the PAM50 intrinsic genes in patients that received a cyclophosphamide, epirubicin and 5-fluorouracil (CEF) treatment regimen.
Figure 2D:
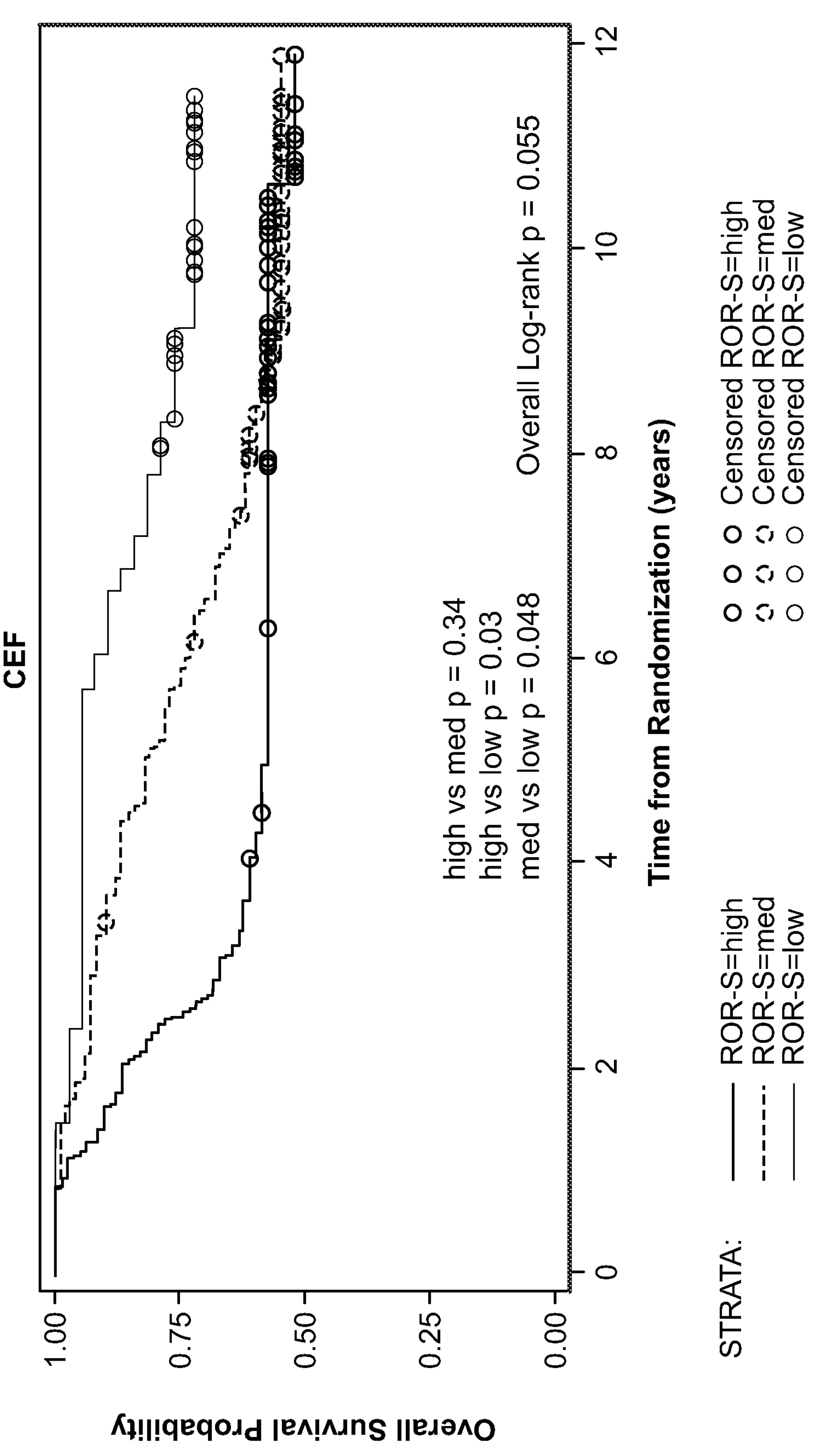
FIG. 2D is a line graph showing a K-M curve of overall survival of risk classifier ROR-S identified using the PAM50 intrinsic genes in patients that received the CEF treatment regimen.

In the CEF treated arm, intrinsic subtypes showed less distinct differences for both endpoints (Log-rank p=0.64 for RFS and p=0.09 for OS, Table 5). Patients with HER2-E, Basal-like and LumB subtypes had comparably poor clinical outcomes, whereas those with the LumA subtype had the best prognosis (Table 5). By log-rank test, only the Basal-like subtype had a statistically significantly poorer prognosis than LumA, evident for the OS endpoint (Table 6). In this CEF arm, the ROR-S defined risk groups had significantly different survival (FIG. 2*c*-2*d*). The low risk group (n=38) had absolute 20% higher 5-yr RFS and 13% higher 5-yr OS when compared to the moderate risk group (n=101), and 18% higher 5-yr RFS and 38% higher 5-yr OS when compared with the high risk group (n=82). Almost all events in the high-risk group occurred within 5 years, and differences between the moderate and high-risk groups did not reach statistical significance.

TABLE 5

Survival by PAM50-determined intrinsic subtypes, stratified by adjuvant treatment arms: CMF and CEF respectively.

| Subtype | # of patients | 5-Year RFS (95% CI) | RFS P-values | 5-Year OS (95% CI) | OS P-values |
|---|---|---|---|---|---|
| CMF | | | | | |
| HER2-E | 56 | 34.5% (22.0%, 47.1%) | Log-rank | 43.6% (30.5%, 56.7%) | Log-rank |
| Basal-like | 49 | 59.1% (45.3%, 72.9%) | <0.0001 | 63.3% (49.8%, 76.8%) | <0.0001 |
| LumB | 51 | 52.2% (38.4%, 66.1%) | Wilcoxon | 71.5% (58.8%, 84.1%) | Wilcoxon |
| LumA | 78 | 73.1% (63.2%, 82.9%) | <0.0001 | 89.7% (83.0%, 96.5%) | <0.0001 |
| CEF | | | | | |
| HER2-E | 49 | 55.1% (41.2%, 69.0%) | Log-rank | 63.3% (49.8%, 76.8%) | Log-rank |
| Basal-like | 45 | <55.1% (40.8%, 69.8%) | 0.64 | 53.1% (38.5%, 67.8%) | 0.09 |
| LumB | 59 | 60.6% (48.0%, 73.2%) | Wilcoxon | 79.4% (69.1%, 89.8%) | Wilcoxon |
| LumA | 68 | 67.6% (56.5%, 78.8%) | 0.25 | 94.1% (88.5%, 99.7%) | 0.005 |

TABLE 6

Pairwise comparison of survival by PAM50-determined intrinsic subtypes, stratified by adjuvant treatment arms: CMF and CEF respectively.

| | | RFS | | | OS | | |
|---|---|---|---|---|---|---|---|
| | | Unadjusted Hazard Ratio | P-value Log-rank | P-value Wilcoxon | Unadjusted Hazard Ratio | P-value Log-rank | P-value Wilcoxon |
| CMF | | | | | | | |
| Subtype | Overall | — | <0.0001 | <0.0001 | — | <0.0001 | <0.0001 |
| | Her2-E vs. Basal-like | 2.08 | 0.006 | 0.03 | 1.69 | 0.06 | 0.14 |
| | Her2-E vs. LumB | 1.48 | 0.09 | 0.02 | 1.93 | 0.01 | 0.006 |
| | Her2-E vs. LumA | 2.87 | <0.0001 | <0.0001 | 4.61 | <0.0001 | <0.0001 |
| | Basal-like vs. LumB | 0.64 | 0.11 | 0.53 | 1.04 | 0.09 | 0.57 |
| | Basal-like vs. LumA | 1.13 | 0.67 | 0.14 | 2.32 | 0.009 | 0.006 |
| | LumB vs. LumA | 2.00 | 0.005 | 0.001 | 2.44 | 0.005 | 0.005 |
| CEF | | | | | | | |
| Subtype | Overall | — | 0.64 | 0.25 | — | 0.09 | 0.005 |
| | Her2-E vs. Basal-like | 1.05 | 0.85 | 0.86 | 0.85 | 0.59 | 0.41 |
| | Her2-E vs. LumB | 1.01 | 0.97 | 0.4 | 1.35 | 0.32 | 0.12 |
| | Her2-E vs. LumA | 1.35 | 0.27 | 0.12 | 1.65 | 0.09 | 0.02 |
| | Basal-like vs. LumB | 0.98 | 0.93 | 0.29 | 1.66 | 0.09 | 0.01 |
| | Basal-like vs. LumA | 1.27 | 0.41 | 0.1 | 1.94 | 0.02 | 0.002 |
| | LumB vs. LumA | 1.35 | 0.22 | 0.32 | 1.33 | 0.33 | 0.19 |

Example 3

Selective Treatment Benefits Across Intrinsic Subtypes

Figure 3A:
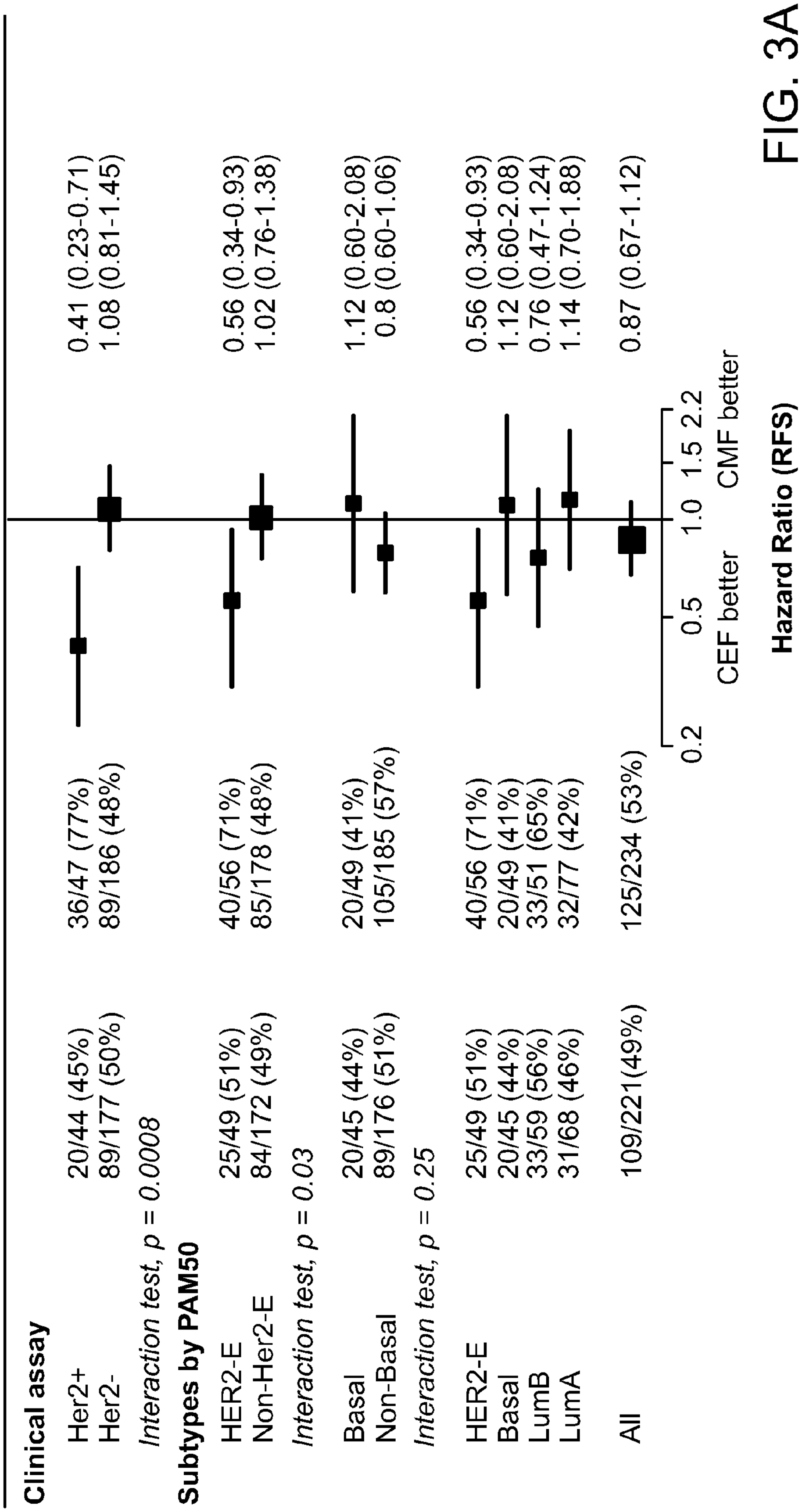
FIG. 3A shows a multivariable Cox regression analysis adjusted relapse free survival (RFS) hazard ratio plots by PAM50 intrinsic subtype, adjusted for clinicopathological variables.
Figure 3B:
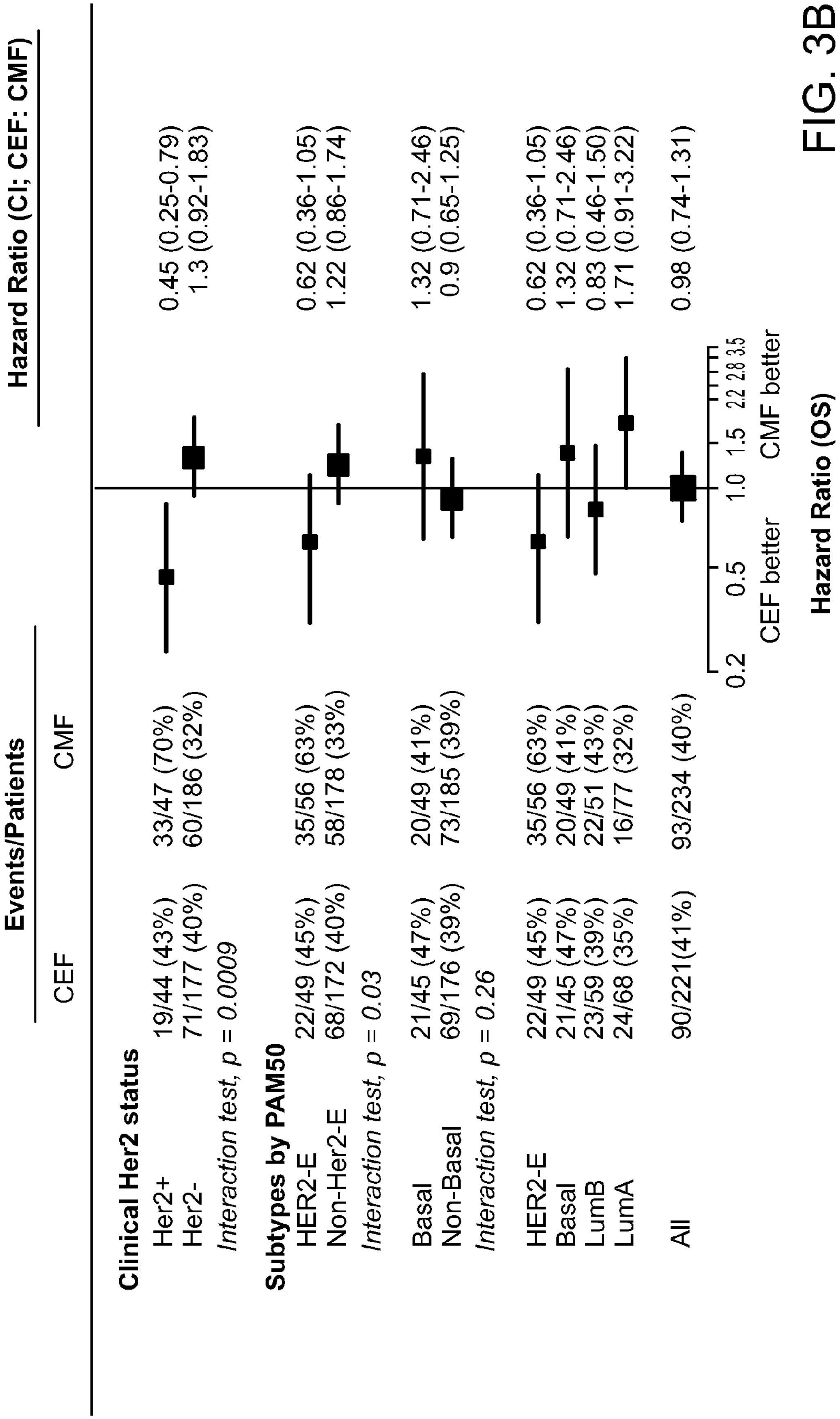
FIG. 3B shows a multivariable Cox regression analysis adjusted overall survival (OS) hazard ratio plots by PAM50 intrinsic subtype, adjusted for clinicopathological variables.
Figure 4A:
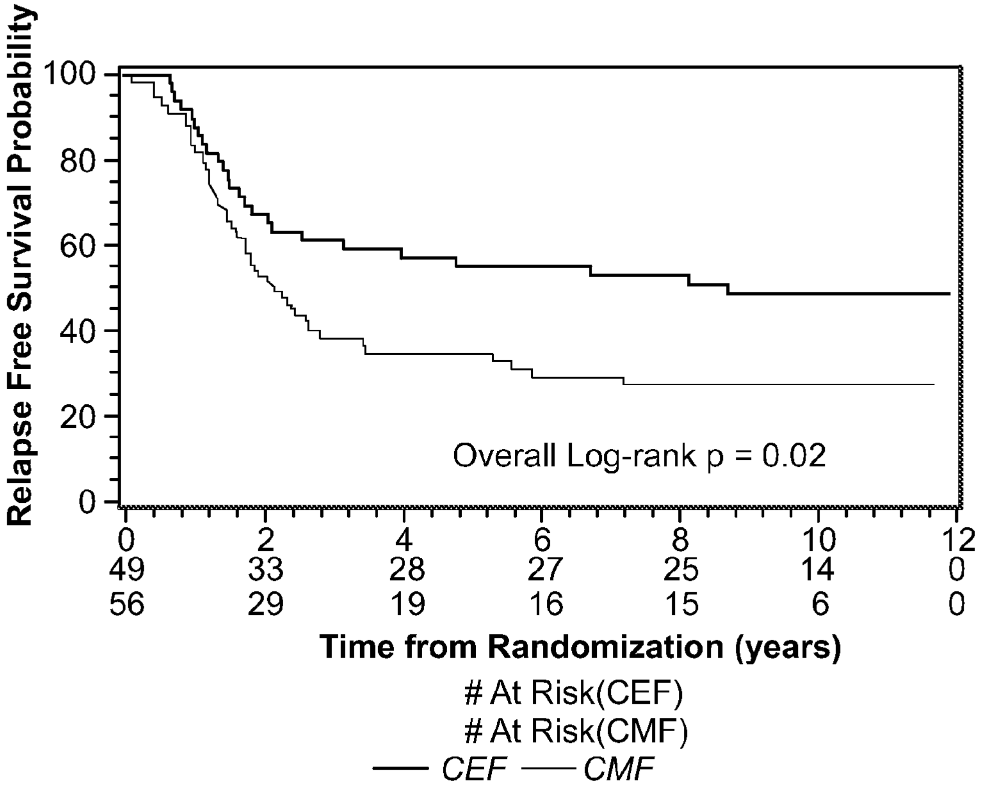
FIG. 4A a line graph showing a K-M curve of relapse-free survival of treatment arms, CEF vs. CMF, in the HER2-E subtype.
Figure 4B:
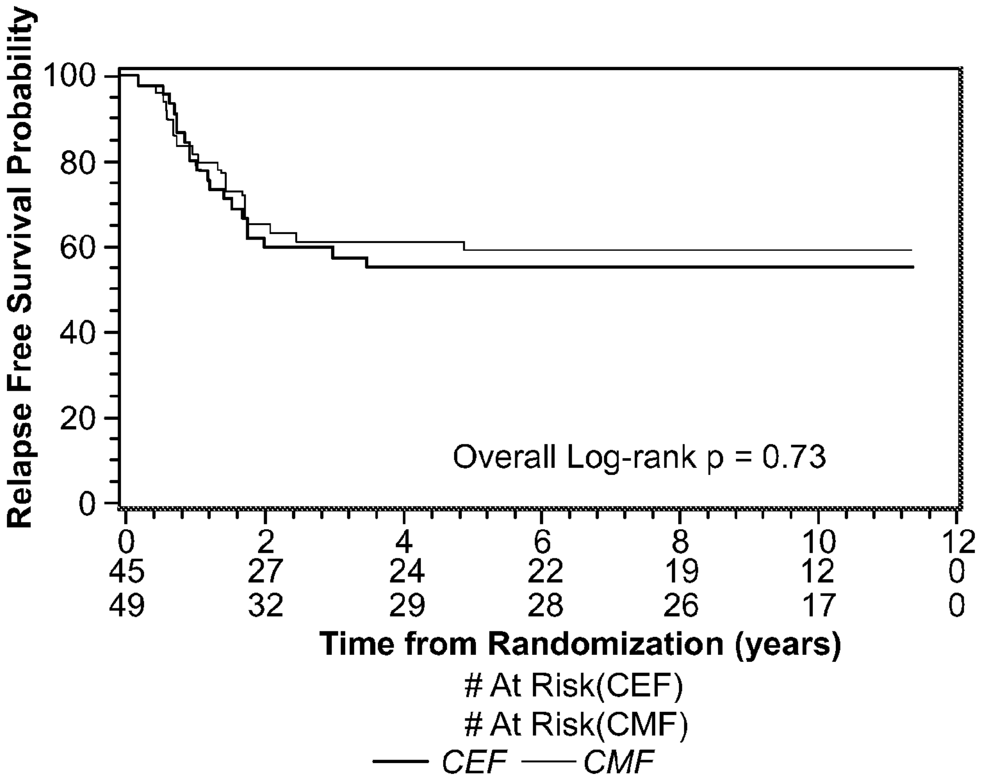
FIG. 4B a line graph showing a K-M curve of relapse-free survival of treatment arms, CEF vs. CMF, in the basal-like subtype.
Figure 4C:
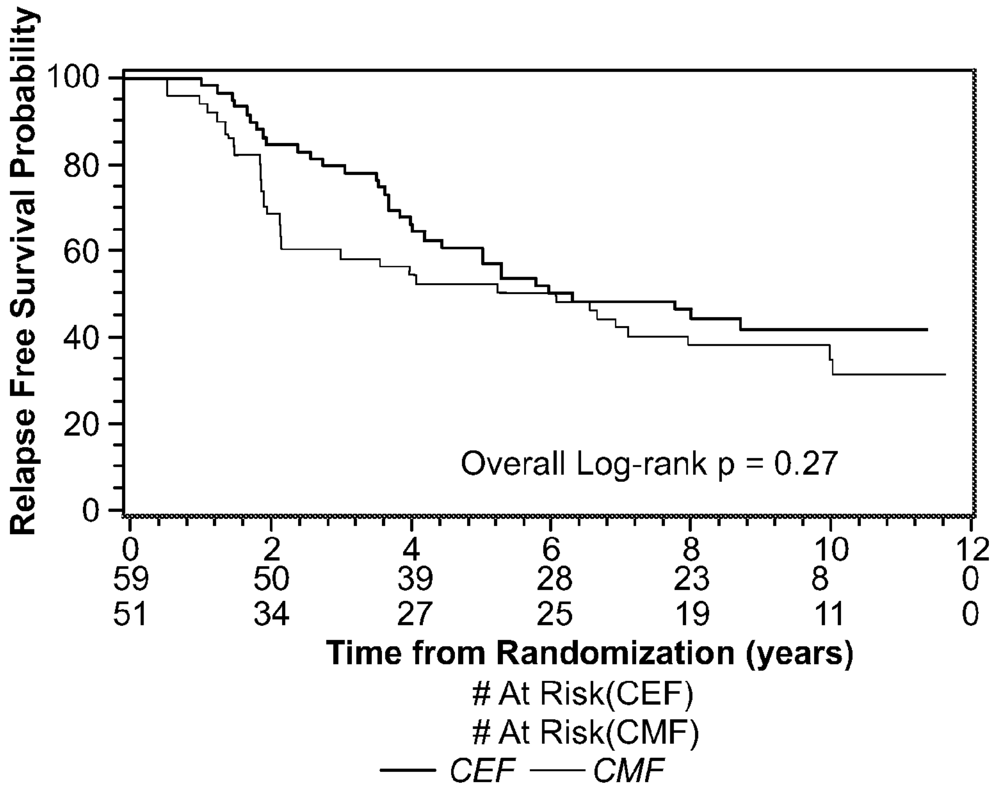
FIG. 4C a line graph showing a K-M curve of relapse-free survival of treatment arms, CEF vs. CMF, in the LumB subtype.
Figure 4D:
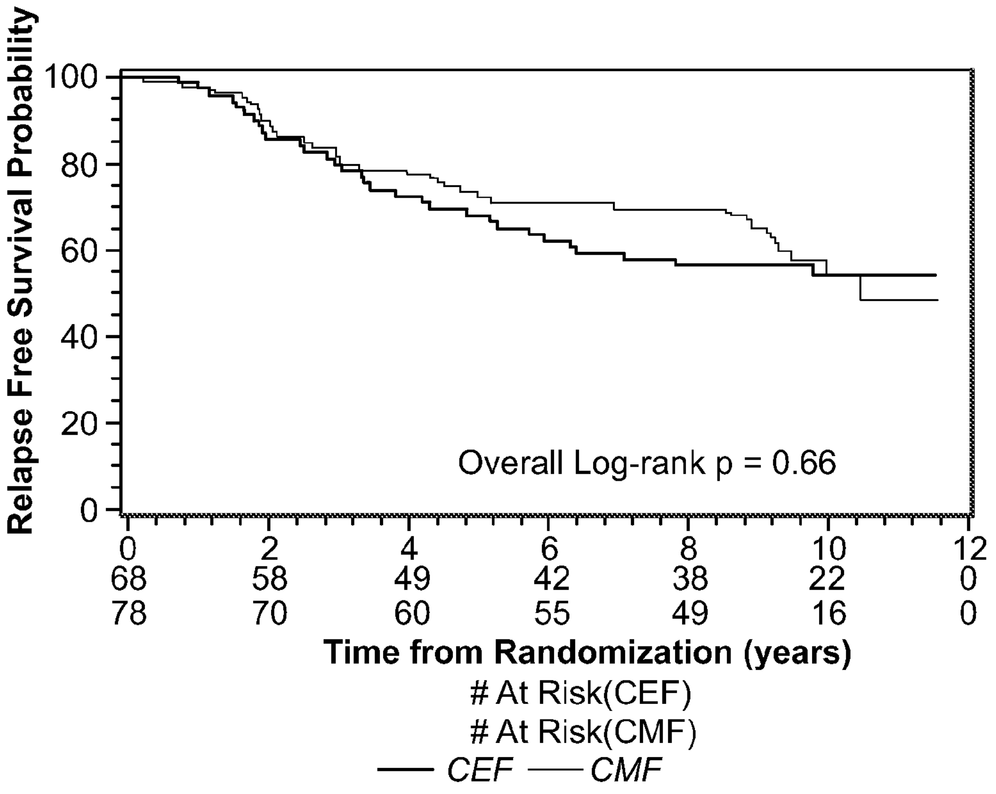
FIG. 4D a line graph showing a K-M curve of relapse-free survival of treatment arms, CEF vs. CMF, in the LumA subtype.
Figure 4E:
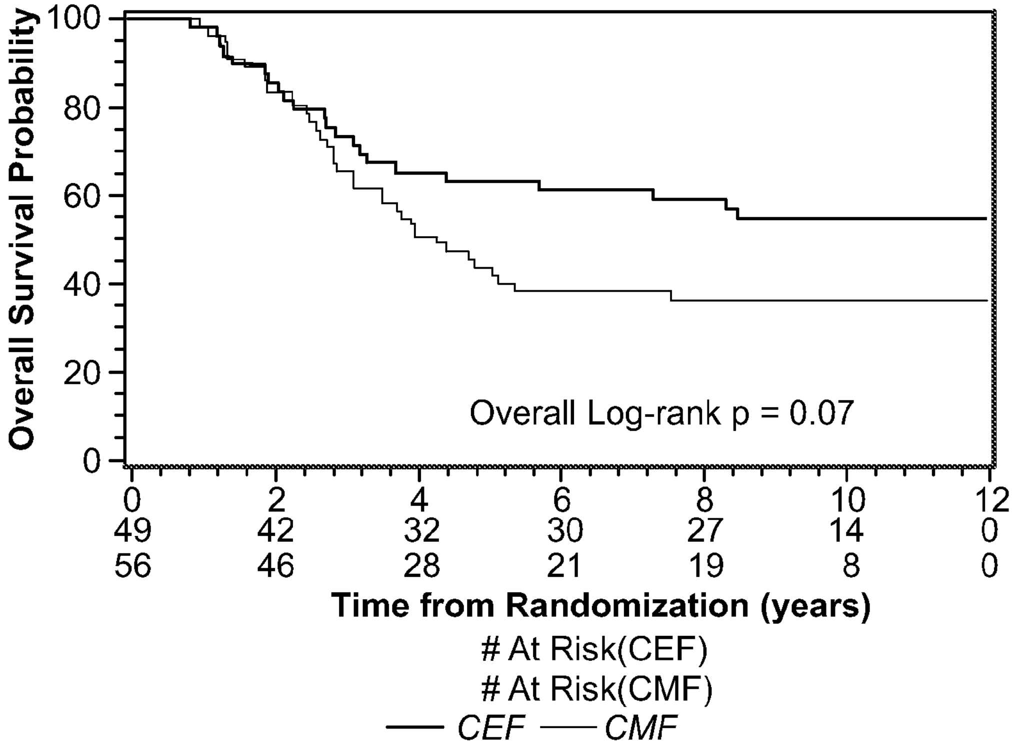
FIG. 4E a line graph showing a K-M curve of overall survival of treatment arms, CEF vs. CMF, in the HER2-E subtype.
Figure 4F:
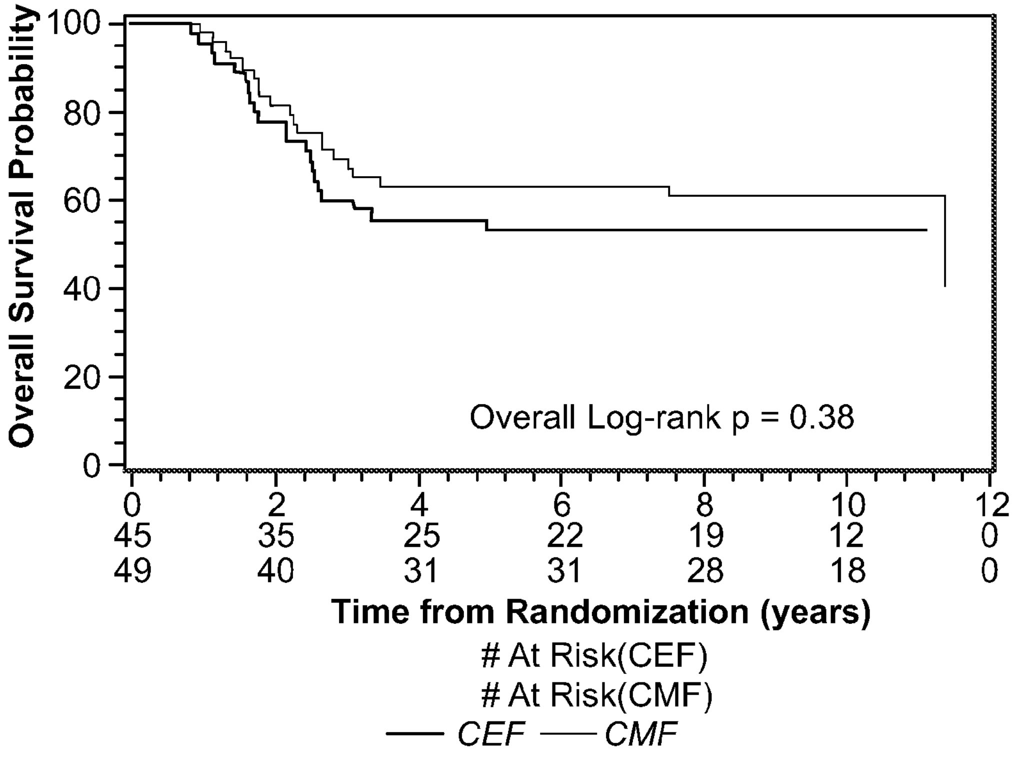
FIG. 4F a line graph showing a K-M curve of overall survival of treatment arms, CEF vs. CMF, in the basal-like subtype.
Figure 4G:
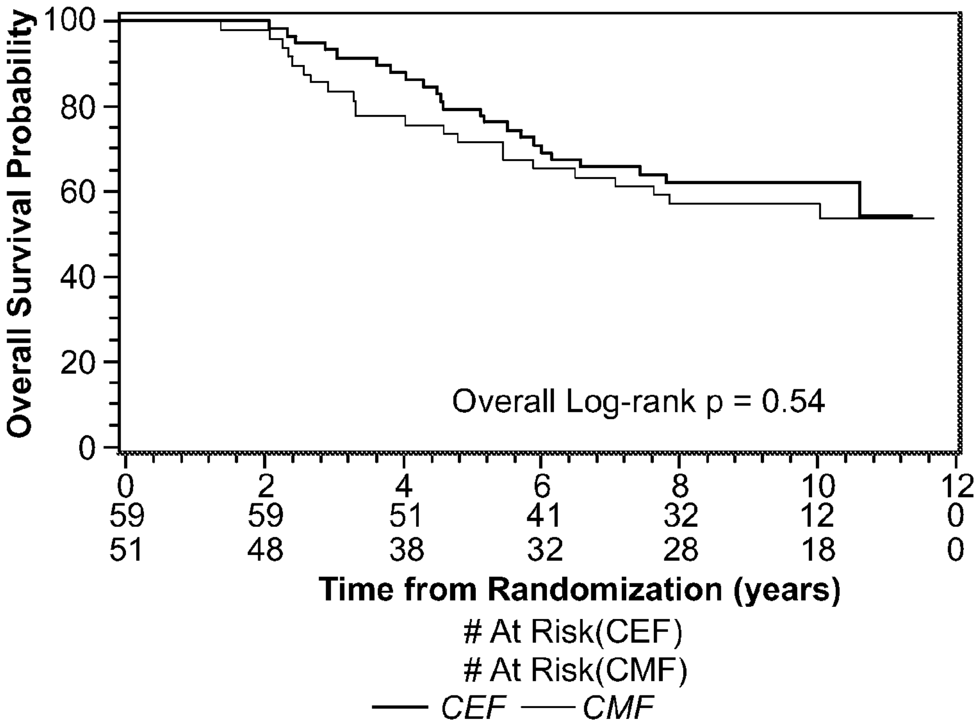
FIG. 4G a line graph showing a K-M curve of overall survival of treatment arms, CEF vs. CMF, in the LumB subtype.
Figure 4H:
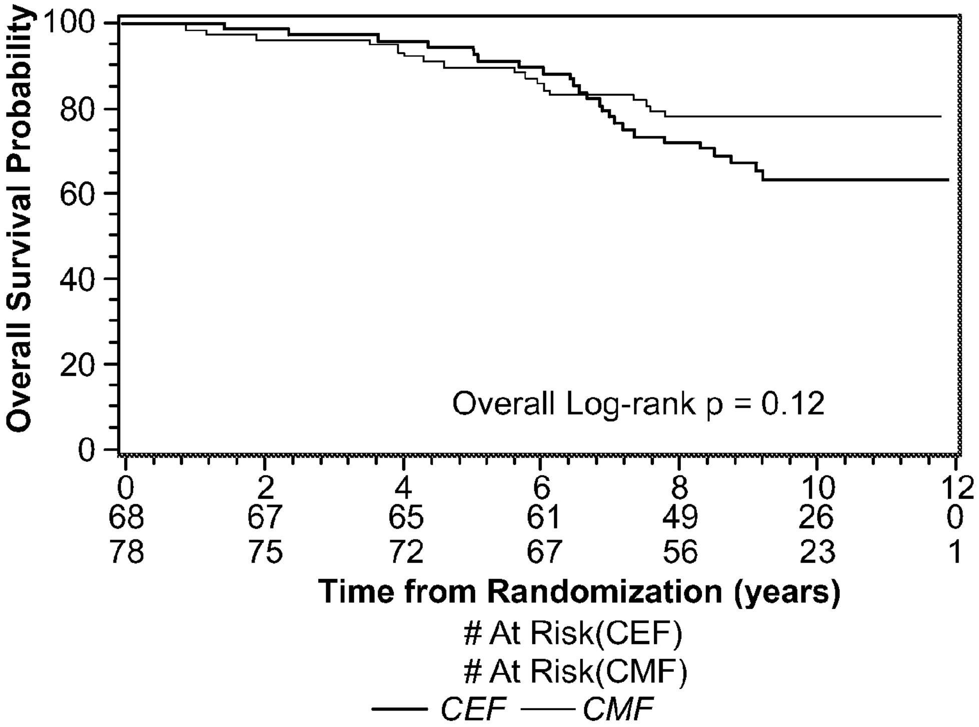
FIG. 4H a line graph showing a K-M curve of overall survival of treatment arms, CEF vs. CMF, in the LumA subtype.

In the MA.5 study subset with paraffin blocks available for this study, there was a trend for survival improvement for the anthracycline-containing regimen over the non-anthracycline, methotrexate containing control arm (FIGS. 3A and 3B) comparable in magnitude to that previously reported for the trial as a whole. HER2-E tumors demonstrated the greatest benefit from CEF versus CMF (FIGS. 3A and 3B), with an observed 21% gain in 5-yr RFS and 20% gain in 5-yr OS (FIGS. 4A and 4E). The interaction between HER2-E subtype and anthracycline sensitivity was significant for both endpoints (FIGS. 3A and 3B, p=0.03). In contrast, Basal-like tumors achieved no survival advantage for CEF over CMF, with a reverse trend having an observed 10% higher 5-yr OS for the CMF arm (FIG. 4*f*). The treatment effect differences between the two Luminal subtypes, which differ markedly in expression of proliferation genes, were also compared. Results from the multivariable Cox regression analysis suggested that patients with LumB tumors had a trend for better survival when treated with CEF, whereas LumA tumors trended to better survival when treated with CMF (FIGS. 3A and 3B and FIGS. 4C-4D and 4*g*-4*h*). However, the interaction test for treatment by LumA and LumB subtypes was not significant (RFS p=0.25; OS p=0.11).

Thus, the relative observed relapse-free and overall survival risk reduction associated with CEF vs. CMF was 44% and 38% for HER2-E, and 24% and 17% for LumB respectively. On the other hand, the relative observed relapse-free and overall survival risk reduction associated with CMF vs. CEF (i.e. the opposite pattern of drug sensitivity, favoring CMF) was 11% and 24% for Basal-like, and 12% and 42% for LumA. Differences only reached statistical significance for the HER2-E group.

Example 4

Her2-E Subtype Versus Clinical Her2 Status in Predicting for Anthracyclines Sensitivity The HER2-E subtype by PAM50 was significantly associated with clinical Her2 positivity (p<0.001). Sixty-eight percent (71/105) of the HER2-E subtype tumors were clinically Her2 positive by IHC/FISH analyses. For the other subtypes, 6% (9/145) of LumA, 7% (8/110) of LumB, and 2% (2/94) of Basal-like were Her2 positive by IHC/FISH.

Clinical Her2 status was previously shown to be a significant predictor of improved survival for CEF over CMF in MA.5 (Pritchard et al., N Engl J Med. 2006; 354:2103-11), a result also observed in this study subset (Table 7).

TABLE 7

Predictive analysis of clinical Her2 status with RFS and OS endpoint among patients subjected to PAM50 assay.

| Clinical HER2 Status and treatments | | # of patients (# of events) | | P-value | Hazard Ratio (95% CI) | HER2-treatment Interaction P-value |
|---|---|---|---|---|---|---|
| | | | 5-Year RFS (95% CI) | | | |
| HER2 over-expressed/ amplified | CEF | 44 (20) | 56.7% (42.1%-71.4%) | Log-rank 0.0010 | 0.406 | 0.0008 |
| | CMF | 47 (36) | 24.8% (12.2%-37.5%) | Wilcoxon 0.0028 | (0.234-0.706) | |
| Her2 negative/weak | CEF | 177 (89) | 61.3% (54.1%-68.5%) | Log-rank 0.5988 | 1.082 | |
| | CMF | 186 (89) | 64.5% (57.6%-71.4%) | Wilcoxon 0.6083 | (0.807-1.452) | |
| | | | 5-Year OS (95% CI) | | | |
| HER2 over-expressed/ amplified | CEF | 44 (19) | 63.6% (49.4%-77.9%) | Log-rank 0.0045 | 0.447 | 0.0009 |
| | CMF | 47 (33) | 33.5% (19.7%-47.3%) | Wilcoxon 0.0139 | (0.253-0.790) | |
| HER2 negative/weak | CEF | 177 (71) | 77.9% (71.8%-84.0%) | Log-rank 0.1348 | 1.300 | |
| | CMF | 186 (60) | 77.8% (71.9%-83.8%) | Wilcoxon 0.2466 | (0.921-1.834) | |

Therefore the accuracy and significance of the PAM50-based HER2-E subtype and clinical Her2 status was compared as biomarkers to predict patient outcome. Using multivariable Cox regression analysis, the treatment interactions observed in the HER2-E subtype remained significantly independent when adjusted with the clinical Her2 status (Table 8). The treatment interactions in clinical Her2 status also remained independent when adjusted with the HER2-E subtype status. These results suggest that clinical Her2 status and gene expression HER2-E subtype, although correlated, are not equivalent, and moreover that defining patients as HER2-E subtype by gene expression provides independent information of potential clinical value beyond that obtained by Her2 testing alone.

TABLE 8

Multivariable Cox Regression analysis analyses of clinical Her2 status and Her2-E subtypes to predict anthracyclines sensitivity based on RFS and OS endpoints. All MVA models included the standard clinicopathological variables.

| | Interatction Term | P-value | Adjusted for |
|---|---|---|---|
| RFS | Her2-E by PAM50 × Treatment | 0.016 | Clinical Her2 status |
| | Clinical Her2 × Treatment | 0.0007 | Her2-E by PAM50 |

TABLE 8-continued

Multivariable Cox Regression analysis analyses of clinical Her2 status and Her2-E subtypes to predict anthracyclines sensitivity based on RFS and OS endpoints. All MVA models included the standard clinicopathological variables.

| | Interatction Term | P-value | Adjusted for |
|---|---|---|---|
| OS | Her2E by PAM50 × Treatment | 0.012 | Clinical Her2 status |
| | Clinical Her2 × Treatment | 0.0008 | Her2-E by PAM50 |

Figure 5A:
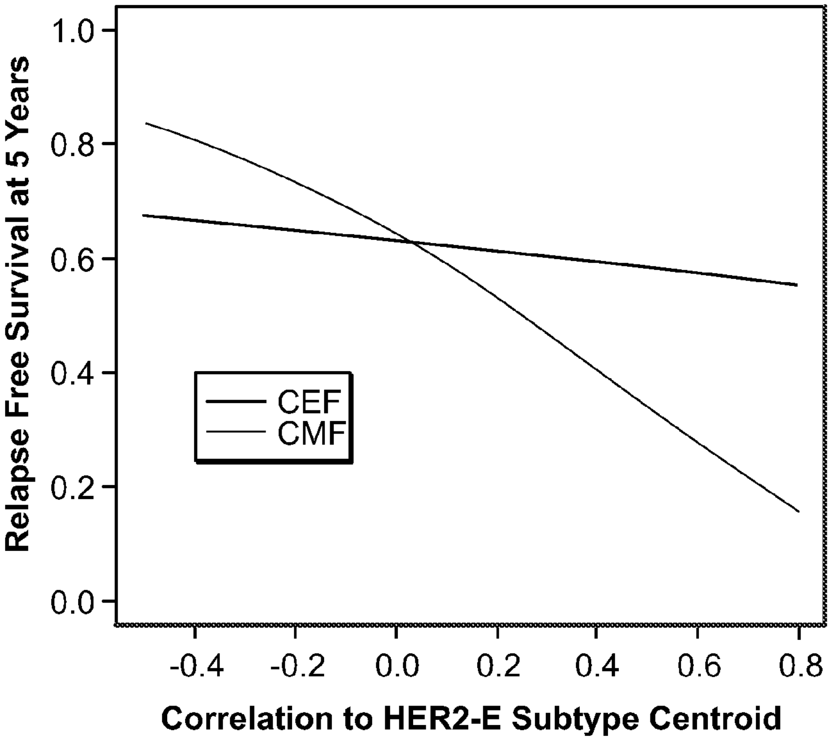
FIG. 5A is a line graph showing the predicted rate of relapse-free survival as a continuous function of the correlation to HER2-E subtype centroid stratified by adjuvant CEF and CMF treatment.
Figure 5B:
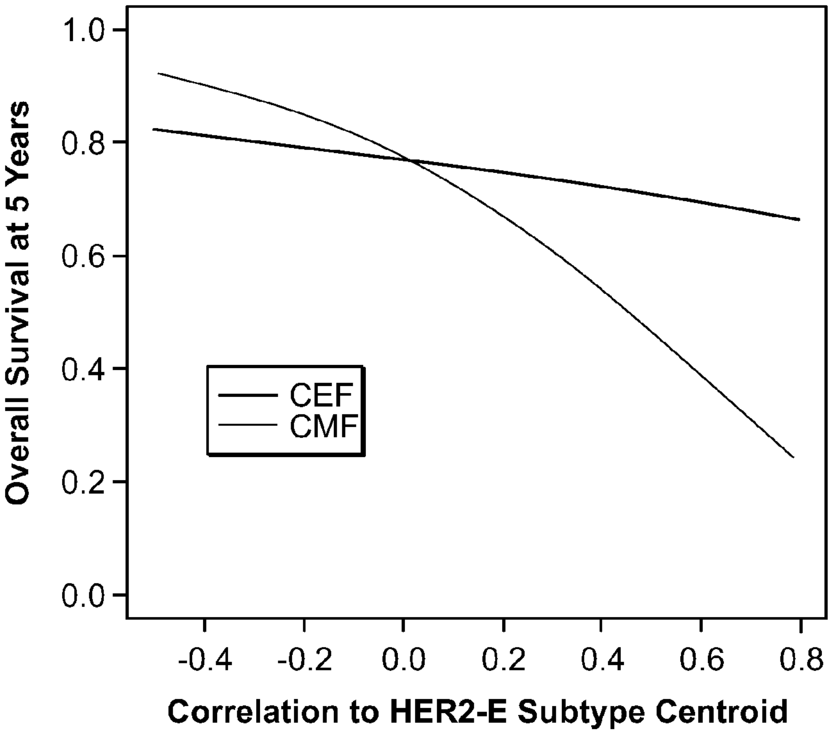
FIG. 5B is a line graph showing the predicted rate of overall survival as a continuous function of the correlation to HER2-E subtype centroid stratified by adjuvant CEF and CMF treatment. The continuous function was generated from a multivariable Cox model including standard clinicopathological variables and HER2-E centroid. X-axis shows the correlation of a tumor to HER2-E centroid; i.e., the higher the positive correlation value, the higher HER2-E subtype component within that sample. The Y-axis shows the predicted relapse-free and overall survival at 5-years for individual patients

The post hoc hypothesis was developed that the anthracycline-benefit would be mostly conferred within Her2+ tumors by those also assigned as HER2-E by PAM50. Consistent with this hypothesis, the Her2+ HER2-E tumor subset treated with CEF had especially large benefits in relapse-free (an absolute 40% gain in 5-yr RFS) and overall survival (an absolute 35% gain in 5-yr OS) when compared with those randomized to CMF (Table 9). Among the clinical Her2 negative/weak tumors, patients with HER2-E tumors by PAM50 did not appear to gain benefit from CEF over CMF (Table 9). Although study numbers are small, these data suggest that positive clinical Her2 combined with assignment to HER2-E PAM50 subtype could be the best predictor for survival benefit of anthracycline substitution for methotrexate. An exploratory analysis was carried out to examine further if there was a linear relationship between a tumor's correlation to the HER2-E subtype and survival in each study arm. FIGS. 5A and 5B illustrate the relationship between benefit of CEF over CMF with the tumor's relation to the prototypical HER2-E centroid as a continuous predictor. 5-year predicted relapse free survival and overall survival were estimated from a Cox model including the HER2-E component of a tumor (i.e. the higher the HER2-E content present in a tumor, the higher the HER2-E centroid value). This analysis demonstrates a slight benefit of CMF over CEF when a tumor anti-correlates with the HER2-E centroid, and a more striking benefit of CEF over CMF when a tumor positively correlates with the HER2-E centroid. The higher the content of HER2-E in a tumor, the lower the 5-yr RFS and OS rate when treated with CMF.

TABLE 9

Exploratory analysis on predictive values of Her2-E among clinical Her2 positive tumors (overexpressed/amplified) and Her2 negative tumors.

| | | # of patients (# of events) | | P-value | Her2-PAM50/Treatment interaction test |
|---|---|---|---|---|---|
| **Clinical Her2 positive** | | | | | |
| | | | 5-Year RFS (95% CI) | | |
| HER2-E by PAM50 | CEF | 34 (13) | 61.8% (45.4%, 78.1%) | Log-rank: 0.0006 | 0.09 |
| | CMF | 38 (30) | 21.6% (8.36%, 34.9%) | Wilcoxon: 0.003 | |
| Non-HER2-E by PAM50 | CEF | 10 (7) | 37.5% (6.03%, 69.0%) | Log-rank: 0.88 | |
| | CMF | 9 (6) | 38.1% (4.34%, 71.8%) | Wilcoxon: 0.86 | |
| | | | 5-Year OS (95% CI) | | |
| HER2-E by PAM50 | CEF | 34 (13) | 64.7% (48.6%, 80.8%) | Log-rank: 0.005 | 0.27 |
| | CMF | 38 (27) | 29.7% (15.0%, 44.5%) | Wilcoxon: 0.01 | |
| Non-HER2-E by PAM50 | CEF | 10 (6) | 60.0% (29.6%, 90.4%) | Log-rank: 0.59 | |
| | CMF | 9 (6) | 50.8% (16.2%, 85.4%) | Wilcoxon: 0.86 | |
| **Clinical Her2 negative** | | | | | |
| | | | 5-Year RFS (95% CI) | | |
| HER2-E by PAM50 | CEF | 15 (12) | 40.0% (15.2%, 64.8%) | Log-rank: 0.23 | 0.28 |
| | CMF | 18 (10) | 61.1% (38.6%, 83.6%) | Wilcoxon: 0.35 | |
| Non-HER2-E by PAM50 | CEF | 162 (77) | 63.3% (55.9%, 70.8%) | Log-rank: 0.85 | |
| | CMF | 168 (79) | 64.8% (57.6%, 72.1%) | Wilcoxon: 0.81 | |
| | | | 5-Year OS (95% CI) | | |
| HER2-E by PAM50 | CEF | 15 (9) | 60.0% 35.2%, 84.8%) | Log--rank: 0.27 | 0.59 |
| | CMF | 18 (8) | 72.2% (51.5%, 92.9%) | Wilcoxon: 0.20 | |
| Non-HER2-E by PAM50 | CEF | 162 (62) | 79.5% (73.3%, 85.8%) | Log-rank: 0.19 | |
| | | | | Wilcoxon: 0.35 | |

Discussion

In this study, the predictive value of intrinsic subtypes was tested in a cohort of patients randomized to anthracycline vs. non-anthracycline chemotherapy. It was found that intrinsic subtypes, identified using the PAM50 assay, particularly Her2-E subtype, provide significant additional predictive value to select patients who may benefit the most from adjuvant anthracycline-based chemotherapy. The ER positive tumors were also subset into their component intrinsic subtypes, including Luminal A and Luminal B, and were unable to detect any statistically significant survival gain in these subgroups when treated with CEF.

Anthracycline-based chemotherapy is probably the most common conventional adjuvant regimen for early stage breast cancers despite of their significant association with long-term cardiotoxicities (Doyle et al., J Clin Oncol., 23(34):8597-605 (2005)). This favored choice of treatment in clinical practice is mostly sustained by a meta-analysis of data from randomized trials showing a marginal gain of 4% in overall and disease-free survival rates of anthracycline-based chemotherapy over non-anthracycline-based chemotherapy (EBCTCG, Lancet, 365(9472):1687-717 (2005)). To date, there is no report if there are selective treatments benefits across the intrinsic subtypes for anthracycline-based over non-anthracycline-based chemotherapy.

Here, the analysis of the MA.5 trial showed that a Spearman correlation to the HER2-E centroid (i.e. a quantitative measurement of similarity to the average expression profiles of a typical HER2-E tumor) is a useful tool to estimate the tumor sensitivity for adjuvant CMF or CEF. The data demonstrated that the relative sensitivity of anthracyclines remained fairly constant across the spectrum of HER2-E subtype centroid similarity. On the other hand, it appeared that there was a negative correlating relationship between adjuvant CMF benefit with the HER2-E subtype centroid. Thus, the data demonstrates the predictive value of the HER2-E subtype centroid, as a quantitative measurement, to identify anthracycline sensitive tumors in addition to the standard clinical assays such as Her2 status.

Basal-like breast cancers represent a particular clinical challenge as they are both hormone receptor and Her2 negative and therefore not sensitive to existing targeted therapies. Studies of neoadjuvant chemotherapy in breast cancer demonstrate that clinical and pathological response rates tend to be high in Basal-like cancers (Rouzier et al., Clin Cancer Res. 2005; 11:5678-85, Carey et al., Clin Cancer Res. 2007; 13:2329-34, Liedtke et al., J Clin Oncol. 2008; 26:1275-81), supporting sensitivity of these tumors to conventional chemotherapy. The results provided herein indicated that anthracyclines may not be an essential component of chemotherapy for the treatment of Basal-like breast cancers. Patients with these tumors who received CEF had a 32% relative increase in mortality compared to those who received CMF. The 95% confidence interval on the hazard ratio ranged from 0.7 to 2.5. Data indicate that CMF is likely equal to or better than CEF for these tumors, although it is possible that CEF could be anywhere from 30% better than CMF to 50% worse for basal-like tumors.

Luminal B breast cancers are highly proliferative ER positive tumors which carry a significantly worse prognosis than their counterpart ER positive/Luminal A tumors (Cheang et al., Journal of the National Cancer Institute. 2009; 101:736-50). These Luminal B tumors are chemosensitive and generally respond to cytotoxic drugs. Paik et al. reported that the Oncotype Dx® high risk group had a large benefit from additional adjuvant CMF with an absolute decrease of 28% in distant relapse risk when compared to the tamoxifen only arm in the NSABP-B20 trial (Paik et al., Journal of clinical oncology: official journal of the American Society of Clinical Oncology. 2006; 24:3726-34). The date provided herein shows that there was no major survival difference between adjuvant anthracycline-containing vs. non-anthracycline adjuvant chemotherapy regimens among Luminal B tumors, although there was a trend to better survival on CEF. Luminal A tumors, representing 31% of patients in this study, do appear to represent another large subset of patients in whom anthracycline based treatment may be dispensed with.

The present invention also provides for the assessment of prognostic value of ROR-S risk classifier for adjuvant CMF and CEF regimens respectively. The ROR-S classifiers were previously developed and defined based on the biology of intrinsic subtypes using an independent cohort of node negative, untreated patients (Parker et al., Journal of clinical oncology: official journal of the American Society of Clinical Oncology. 2009; 27:1160-7).The data validated that the three pre-defined risk groups were significantly associated with survival differences for both treatment arms, most distinct within the 5 years. Although ROR-S risk groups were highly associated with intrinsic subtype classifiers, the data demonstrated that ROR-S could also provide prognostic information for clinicians to estimate the survival rates of a patient for adjuvant CMF and CEF.

The invention demonstrates that intrinsic subtypes provide independent predictive value to anthracycline vs. non-anthracycline chemotherapy beyond clinical Her2 status. The data show that the benefit of CEF over CMF is directed to patients with the HER2-E gene expression pattern and Her2+ IHC/FISH status. Chemotherapy-sensitive Basal-like tumors showed no added benefit of CEF vs. CMF, indicating that non-anthracycline regimens are adequate in this subtype.

What is claimed is:

1. A method of treating breast cancer in a subject in need thereof comprising:

(a) providing a biological sample from the subject;

(b) assaying the biological sample to determine whether the biological sample is classified as a Her2+ subtype;

(c) assaying the biological sample to determine whether the biological sample is classified as a Her-2-E subtype;

(d) providing an assessment of the likelihood of effectiveness of a breast cancer treatment comprising an anthracycline in the subject, wherein if the biological sample is classified as both a Her2+ subtype and a Her-2-E subtype, the breast cancer treatment comprising the anthracycline is more likely to be effective in the subject and wherein if the biological sample is classified as a Her-2-E subtype and is classified as not a Her2+ subtype, the breast cancer treatment comprising the anthracycline is less likely to be effective in the subject; and (e) administering a breast cancer treatment comprising anthracycline to the subject subsequent to said assessment if the biological sample is classified as both a Her2+ subtype and a Her-2-E subtype and administering a breast cancer treatment not comprising anthracycline to the subject subsequent to said assessment if the biological sample is classified as a Her-2-E subtype and classified as not a Her2+ subtype, thereby treating breast cancer in the subject.

2. The method of claim 1, wherein assaying the biological sample to determine whether the biological sample is classified as a Her2+ subtype is performed using fluorescence in situ hybridization (FISH) or immunohistochemistry (IHC).

3. The method of claim 1, wherein assaying the biological sample to determine whether the biological sample is classified as a Her-2-E subtype is performed by detecting the expression levels of a combination of at least 40 genes selected from Table 1, wherein at least 25 of the at least 40 genes comprise FOXA1, MLPH, ESR1, FOXC1, CDC20, ANLN, MAPT, ORC6L, CEP55, MKI67, UBE2C, KNTC2, EXO1, PTTG1, MELK, BIRC5, GPR160, RRM2, SRFP1, MYBL2, NAT1, KIF2C, CXXC5, MIA and BCL2.

4. The method of claim 1, wherein the anthracycline is selected from the group consisting of daunorubicin, doxorubicin, epirubicin, idarubicin, valrubicin and mitoxantrone.

5. The method of claim 4, wherein the anthracycline is epirubicin.

6. The method of claim 1, wherein the breast cancer treatment comprising anthracycline further comprises one or more anti-cancer agents selected from the group consisting of cyclophosphamide, fluorouracil (or 5-fluorouracil or 5-FU), methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb or bevacizumab, or combinations thereof.

7. The method of claim 1, wherein the breast cancer treatment comprising anthracycline further comprises one or more anti-cancer agents selected from the group consisting of cyclophosphamide and 5-fluorouracil.

8. The method of claim 1, wherein the breast cancer treatment not comprising anthracycline further comprises one or more anti-cancer agents selected from the group consisting of cyclophosphamide, fluorouracil (or 5-fluorouracil or 5-FU), methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb or bevacizumab, or combinations thereof.

9. The method of claim 1, wherein the breast cancer treatment not comprising an anthracycline comprises one or more anti-cancer agents of the group consisting of cyclophosphamide, 5-fluorouracil and methotrexate.

10. The method of claim 1, wherein the biological sample is selected from the group consisting of a cell, tissue and bodily fluid.

11. The method of claim 10, wherein the tissue is obtained from a biopsy.

12. The method of claim 10, wherein the bodily fluid is selected from the group consisting of blood, lymph, urine, saliva and nipple aspirate.

* * * * *